United States Patent
Li et al.

(10) Patent No.: US 7,642,267 B2
(45) Date of Patent: Jan. 5, 2010

(54) BENZIMIDAZOLE AND PYRIDYLIMIDAZOLE DERIVATIVES

(75) Inventors: Guiying Li, Branford, CT (US); Pamela Albaugh, Carmel, IN (US); Kevin S. Currie, North Branford, CT (US); Guolin Cai, Thousand Oaks, CA (US); Linda M. Gustavson, Guilford, CT (US); Kyungae Lee, Guilford, CT (US); Alan Hutchison, Madison, CT (US); George D. Maynard, Clinton, CT (US); Jun Yuan, Guilford, CT (US); Ling Hong Xie, Guilford, CT (US); Manuka Ghosh, Branford, CT (US); Nian Liu, North Branford, CT (US); George P. Luke, Clinton, CT (US); Scott Mitchell, East Haven, CT (US); Martin Patrick Allen, North Stonington, CT (US); Spiros Liras, Stonington, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 11/942,480

(22) Filed: Nov. 19, 2007

(65) Prior Publication Data

US 2008/0227793 A1    Sep. 18, 2008

Related U.S. Application Data

(62) Division of application No. 11/179,458, filed on Jul. 12, 2005, now Pat. No. 7,300,945, which is a division of application No. 10/038,069, filed on Dec. 21, 2001, now Pat. No. 6,916,819.

(60) Provisional application No. 60/257,492, filed on Dec. 21, 2000.

(51) Int. Cl.
*C07D 471/04*    (2006.01)
*A61K 31/437*    (2006.01)

(52) U.S. Cl. .................... 514/262.1; 544/262; 544/264; 544/265; 544/277; 514/263.2

(58) Field of Classification Search ................ 544/262, 544/264, 265, 277; 514/262.1, 263.2
See application file for complete search history.

(56) References Cited

U.S. PATENT DOCUMENTS 4,654,350 A * 3/1987 Irmscher et al. ............. 514/303

* cited by examiner

*Primary Examiner*—Kahsay T Habte
(74) *Attorney, Agent, or Firm*—McDonnell Boehnen Hulbert & Berghoff LLP

(57) ABSTRACT

This invention relates to benzimidazoles, pyridylimidazoles and related bicyclic heteroaryl compounds, all of which may be described by of Formula I. The invention is particularly related to such compounds that bind with high selectivity and high affinity to the benzodiazepine site of $GABA_A$ receptors. This invention also relates to pharmaceutical compositions comprising such compounds and to the use of such compounds in treatment of certain central nervous system (CNS) diseases. Novel processes for preparing compounds of Formula I are disclosed. This invention also relates to the use of benzimidazoles, pyridylimidazoles and related bicyclic heteroaryl compounds of Formula I in combination with one or more other CNS agents to potentiate

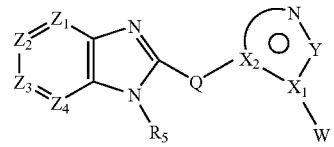

Formula I the effects of the other CNS agents. Additionally this invention relates to the use such compounds as probes for the localization of $GABA_A$ receptors in tissue sections.

21 Claims, No Drawings

BENZIMIDAZOLE AND PYRIDYLIMIDAZOLE DERIVATIVES

BACKGROUND OF THE INVENTION

1. Field of the Invention

This invention relates to benzimidazole and pyridylimidazole derivatives, and, more specifically, to such derivatives that bind with high selectively and/or high affinity to the benzodiazepine site of $GABA_A$ receptors. This invention also relates to pharmaceutical compositions comprising such compounds and to the use of such compounds in the treatment of central nervous system (CNS) diseases.

2. Description of the Related Art

The $GABA_A$ receptor superfamily represents one of the classes of receptors through which the major inhibitory neurotransmitter, γ-aminobutyric acid, or GABA, acts. Widely, although unequally, distributed throughout the mammalian brain, GABA mediates many of its actions through a complex of proteins called the $GABA_A$ receptor, which causes alteration in chloride conductance and membrane polarization. In addition to being the site of neurotransmitter action, a number of drugs including the anxiolytic and sedating benzodiazepines bind to this receptor. The $GABA_A$ receptor comprises a chloride channel that generally, but not invariably, opens in response to GABA, allowing chloride to enter the cell. This, in turn, effects a slowing of neuronal activity through hyperpolarization of the cell membrane potential.

$GABA_A$ receptors are composed of five protein subunits. A number of cDNAs for these $GABA_A$ receptor subunits have been cloned and their primary structures determined. While these subunits share a basic motif of 4 membrane-spanning helices, there is sufficient sequence diversity to classify them into several groups. To date at least 6α, 3β, 3γ, 1ε, 1δ and 2ρ subunits have been identified. Native $GABA_A$ receptors are typically composed of 2α, 2β, and 1γ. Various lines of evidence (such as message distribution, genome localization and biochemical study results) suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$ (Mohler et al. *Neuroch. Res.* 1995; 20(S):631-36).

The $GABA_A$ receptor binding sites for GABA (2 per receptor complex) are formed by amino acids from the α and β subunits. Amino acids from the α and γ subunits together form one benzodiazepine site per receptor. Benzodiazepines exert their pharmacological actions by interacting with the benzodiazepine binding sites associated with the $GABA_A$ receptor. In addition to the benzodiazepine site (sometimes referred to as the benzodiazepine or BDZ receptor), the $GABA_A$ receptor contains sites of interaction for several other classes of drugs. These include a steroid binding site, a picrotoxin site, and a barbiturate site. The benzodiazepine site of the $GABA_A$ receptor is a distinct site on the receptor complex that does not overlap with the site of interaction for other classes of drugs that bind to the receptor or for GABA (see, e.g., Cooper, et al., The Biochemical Basis of Neuropharmacology, $6^{th}$ ed., 1991, pp. 145-148, Oxford University Press, New York).

In a classic allosteric mechanism, the binding of a drug to the benzodiazepine site increases the affinity of the GABA receptor for GABA. Benzodiazepines and related drugs that enhance the ability of GABA to open $GABA_A$ receptor channels are known as agonists or partial agonists depending on the level of GABA enhancement. Other classes of drugs, such as β-carboline derivatives, that occupy the same site and negatively modulate the action of GABA are called inverse agonists. A third class of compounds exists which occupy the same site as both the agonists and inverse agonists and yet have little or no effect on GABA activity. These compounds will, however, block the action of agonists or inverse agonists and are thus referred to as $GABA_A$ receptor antagonists.

The important allosteric modulatory effects of drugs acting at the benzodiazepine site were recognized early, and the distribution of activities at different subtype receptors has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have enjoyed long pharmaceutical use as anxiolytics, these compounds are known to exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of certain other CNS active compounds. For example, there is evidence that selective serotonin reuptake inhibitors (SSRIs) may show greater antidepressant activity when used in combination with $GABA_A$ selective ligands than when used alone.

SUMMARY OF THE INVENTION

This invention provides benzimidazole and pyridylimidazole derivatives that bind to the benzodiazepine site of $GABA_A$ receptors, including human $GABA_A$ receptors. Preferred compounds of the invention bind with high selectivity and/or high affinity to $GABA_A$ receptors. Preferred compounds act as agonists, antagonists or inverse agonists of such receptors. As such, they are useful in the treatment of various CNS disorders.

The invention provides compounds of Formula I (shown below), and pharmaceutical compositions comprising compounds of Formula I.

The invention provides methods for synthesizing compounds of Formula I.

The invention further provides methods of treating patients suffering from certain CNS disorders with an effective amount of a compound of the invention. The patient may be a human or other mammal. Treatment of humans, domesticated companion animals (pets) or livestock animals suffering from certain CNS disorders with an effective amount of a compound of the invention is encompassed by the invention.

In a separate aspect, the invention provides methods of potentiating the actions of other CNS active compounds. These methods comprise administering an effective amount of a compound of the invention in conjunction with the administration of another CNS active compound.

Additionally this invention relates to the use of compounds of Formula I as probes for the localization of $GABA_A$ receptors in tissue sections.

In a first aspect, the invention provides compounds of Formula I

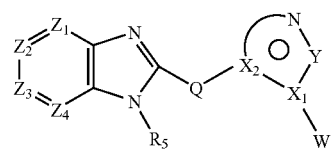

and the pharmaceutically acceptable salts thereof.

In this aspect, $Z_1$ is nitrogen or $CR_1$; $Z_2$ is nitrogen or $CR_2$; $Z_3$ is nitrogen or $CR_3$; and $Z_4$ is nitrogen or $CR_4$; provided that no more than two of $Z_1$, $Z_2$, $Z_3$, and $Z_4$ are nitrogen. Further in Formula I, $R_1$, $R_2$, $R_3$, and $R_4$ are independently selected from i) hydrogen, halogen, hydroxy, nitro, cyano, amino, haloalkyl, and haloalkoxy, ii) alkyl, alkoxy, cycloalkyl, alkenyl, alkynyl, (cycloalkyl)alkyl, —NH($R_{10}$), —N($R_{10}$)($R_{11}$), hydroxyalkyl, aminoalkyl, ($R_{10}$)NHalkyl-, ($R_{10}$)($R_{11}$)Nalkyl-; alkanoyl, alkoxycarbonyl, (heterocycloalkyl)alkyl, alkylsulfonyl, alkylthio, mono- or dialkylaminocarbonyl, heterocycloalkyl, aryl, and heteroaryl, each of which is optionally substituted with 1, 2, 3, or 4 of $R_{20}$, wherein $R_{10}$ and $R_{11}$, are independently selected from the group consisting of alkyl, alkenyl, alkynyl, alkoxy, cycloalkyl, (cycloalkyl)alkyl, aryl, arylalkyl, alkanoyl, and mono and dialkylaminoalkyl; and iii) a group of the formula:

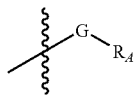

where G is a bond, alkyl, —O—, —C(=O)—, or —CH$_2$C(=O)—, and $R_A$ is a saturated, partially unsaturated, or aromatic carbocycle, consisting of 1 ring or 2 fused, pendant, or spiro rings, each ring containing 0, 1, or 2 heteroatoms independently chosen from N, S, and O, said saturated, partially unsaturated, or aromatic carbocycle is optionally substituted with 1, 2, 3, or 4 of $R_{20}$, iv) a group of the formula

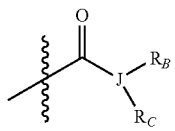

where J is N, CH, or C-alkyl, and $R_B$ and $R_C$ are independently selected from the group consisting of hydrogen, alkyl, alkenyl, alkynyl, alkoxy, cycloalkyl, (cycloalkyl)alkyl, heterocycloalkyl, aryl, arylalkyl, alkanoyl, heteroaryl, and mono and dialkylaminoalkyl, each of which is optionally substituted by 1 or 2 substituents independently chosen from halogen, hydroxy, cyano, amino, nitro, alkoxy, and alkyl, $R_B$ and $R_C$ and the atom to which they are attached form a 4- to 10-membered monocyclic or bicyclic ring, which may contain:

a) one or more double bonds, b) one or more of oxo, O, S, SO, SO$_2$, or N—$R_D$ wherein $R_D$ is hydrogen, Ar$_1$, alkyl, cycloalkyl, heterocycloalkyl, or Ar$_1$alkyl; wherein Ar$_1$ is aryl or heteroaryl, each of which is optionally substituted by 1 or 2 substituents independently chosen from halogen, hydroxy, cyano, amino, nitro, alkoxy, and alkyl, c) one or more substituents $R_{20}$;

v) —OC(=O)$R_E$, —C(=O)O$R_E$, —C(=O)NH$_2$, —C(=O)NHR$_E$, —C(=O)NR$_E$R$_F$, —S(O)$_n$R$_E$, —S(O)$_n$NH$_2$, —S(O)$_n$NHR$_E$, —S(O)$_n$NR$_E$R$_F$, —NHC(=O)R$_E$, —C(=NR$_E$)R$_F$, —HC=N—OH, —HC=N(alkoxy), —HC=N(alkyl), —NR$_E$C(=O)R$_F$, —NHS(O)$_n$R$_E$, and —NR$_E$S(O)$_m$R$_F$, where m is 0, 1 or 2, and $R_E$ and $R_F$ are independently selected at each occurrence from alkyl, cycloalkyl, heterocycloalkyl, alkoxy, mono- or dialkylamino, aryl, or heteroaryl each of which is optionally substituted by 1, 2, or 3 of $R_{30}$.

$R_{20}$, in this aspect of the invention, is independently selected at each occurrence from the group consisting of: halogen; hydroxy; nitro; cyano; amino; alkyl; alkoxy optionally substituted with amino or mono- or dialkylamino; cycloalkyl; cycloalkylalkyl; cycloalkylalkoxy; alkenyl; alkynyl; haloalkyl; oxo; haloalkoxy; mono- and dialkylamino; aminoalkyl; and mono- and dialkylaminoalkyl.

$R_{30}$ is independently selected at each occurrence from halogen, hydroxy, nitro, cyano, amino, alkyl, alkoxy optionally substituted with amino or mono- or dialkylamino, cycloalkyl, cycloalkylalkyl, cycloalkylalkoxy, heterocycloalkyl, alkenyl, alkynyl, haloalkyl, haloalkoxy, oxo, mono- and dialkylamino, aminoalkyl, and mono- and dialkylaminoalkyl.

$R_5$ represents hydrogen or haloalkyl; or $R_5$ represents alkyl, cycloalkyl, or (cycloalkyl)alkyl, each of which may contain one or more double or triple bonds, and each of which is optionally substituted with 1, 2, or 3 of $R_{30}$, or $R_5$ represents aryl, arylalkyl, heteroaryl, or heteroarylalkyl each of which is optionally substituted with 1, 2, or 3 substituents selected from the group consisting of haloalkyl, amino, —NH($R_{10}$), —N($R_{10}$)($R_{11}$), carboxamido, ($R_{10}$)NHcarbonyl, ($R_{10}$)($R_{11}$)Ncarbonyl, halogen, hydroxy, nitro, cyano, amino, alkyl, alkoxy optionally substituted with amino or mono- or dialkylamino, cycloalkyl, cycloalkylalkyl, cycloalkylalkoxy, heterocycloalkyl, alkenyl, alkynyl, haloalkyl, haloalkoxy, aminoalkyl, and mono- and dialkylaminoalkyl.

Q represents —C($R_6$)($R_7$) or oxygen, with the proviso that Q is not oxygen when $X_2$ is nitrogen.

$R_6$ and $R_7$ independently represent hydrogen, fluorine, or alkyl.

The group:

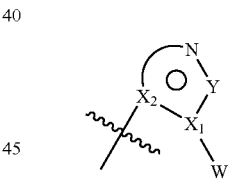

represents a 5 to 7 membered heteroaryl or heterocycloalkyl ring containing up to 4 heteroatoms selected from nitrogen, sulfur, and oxygen, said 5 to 7 membered heteroaryl or heterocycloalkyl ring is substituted at each carbon atom by R, and substituted at each nitrogen atom available for substitution by R'.

R is independently chosen at each occurrence from hydrogen, halogen, amino, alkyl, alkenyl, alkynyl, alkoxy, cycloalkyl, (cycloalkyl)alkyl, haloalkyl, haloalkoxy, carboxamido, and 3- to 7-membered carbocyclic or heterocyclic groups which are saturated, unsaturated, or aromatic, which may be further substituted with one or more substituents independently selected from halogen, oxo, hydroxy, alkyl, and alkoxy.

R' is independently chosen at each occurrence from alkyl, hydrogen, cycloalkyl, cycloalkyl(alkyl), and 3- to 7-membered carbocyclic or heterocyclic groups which are saturated, unsaturated, or aromatic, which 3- to 7-membered carbocyclic or heterocyclic groups are optionally substituted with one or more substituents independently selected from halogen, oxo, hydroxy, alkyl, and alkoxy.

$X_1$ and $X_2$ independently represent nitrogen, carbon or CH.

Y is nitrogen, oxygen, carbon, —CH—, —CH$_2$—, or absent.

W represents aryl or heteroaryl, wherein the aryl or heteroaryl group is optionally substituted with up to 4 groups independently selected from $R_{30}$, —CO$_2$H, —C(=O)OR$_E$, —C(=O)NHR$_E$, —C(=O)NR$_E$R$_F$, —C(O)R$_E$, and —S(O)$_m$R$_E$, —OR$_E$, where $R_{30}$ and $R_E$ are as defined above and m is 0, 1, or 2.

DETAILED DESCRIPTION

In addition to the compounds and salts of Formula I, described above, the invention further provides compounds of Formula I wherein $R_1$, $R_2$, $R_3$, and $R_4$ are independently selected from i) hydrogen, halogen, hydroxy, nitro, cyano, amino, halo (C$_1$-C$_6$)alkyl, and halo(C$_1$-C$_6$)alkoxy, ii) (C$_1$-C$_6$)alkyl, (C$_1$-C$_6$)alkoxy, (C$_3$-C$_8$)cycloalkyl, (C$_2$-C$_6$)alkenyl, alkynyl, ((C$_3$-C$_8$)cycloalkyl) (C$_1$-C$_4$)alkyl, —NH(R$_{10}$), —N(R$_{10}$)(R$_{11}$), hydroxy(C$_1$-C$_6$)alkyl, amino (C$_1$-C$_6$)alkyl, (R$_{10}$)NH(C$_1$-C$_6$)alkyl, (R$_{10}$)(R$_{11}$)N(C$_3$-C$_6$)alkyl, (C$_1$-C$_6$)alkanoyl, (C$_1$-C$_6$)alkoxycarbonyl, (C$_1$-C$_6$)alkylsulfonyl, (C$_1$-C$_6$)alkylthio, mono- or di(C$_1$-C$_6$)alkylaminocarbonyl, heterocycloalkyl, (heterocycloalkyl)C$_1$-C$_4$alkyl, aryl, and heteroaryl, each of which is optionally substituted with 1, 2, 3, or 4 of $R_{20}$, wherein $R_{10}$ and $R_{11}$ are independently selected from the group consisting of (C$_1$-C$_6$)alkyl, (C$_2$-C$_6$)alkenyl, (C$_1$-C$_6$)alkoxy, (C$_3$-C$_8$)cycloalkyl, (C$_3$-C$_8$)cycloalkylalkyl, aryl, aryl(C$_1$-C$_6$)alkyl, (C$_1$-C$_6$)alkanoyl, and mono and di(C$_1$-C$_6$)alkylaminoalkyl;

iii) a group of the formula:

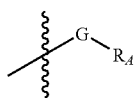

where G is (C$_1$-C$_6$)alkyl, —O—, —C(=O)—, or —CH$_2$C(=O)—, and $R_A$ is a saturated, partially unsaturated, or aromatic carbocycle, consisting of 1 ring or 2 fused, pendant, or spiro rings, each ring consisting of from 3 to 8 ring atoms, and each ring containing 0, 1, or 2 heteroatoms independently chosen from N, S, and O; said saturated, partially unsaturated, or aromatic carbocycle is optionally substituted with 1, 2, 3, or 4 of $R_{20}$, iv) a group of the formula

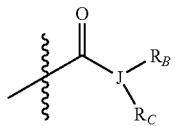

where J is N, CH, or C—(C$_1$-C$_6$)alkyl and $R_B$ and $R_C$ are independently selected from the group consisting of hydrogen, (C$_1$-C$_6$)alkyl, (C$_2$-C$_6$)alkenyl, (C$_2$-C$_6$)alkynyl, (C$_1$-C$_6$)alkoxy, (C$_3$-C$_8$)cycloalkyl, (C$_3$-C$_8$cycloalkyl) (C$_1$-C$_4$)alkyl, heterocycloalkyl, aryl, aryl(C$_1$-C$_4$)alkyl, (C$_1$-C$_6$)alkanoyl, heteroaryl, and mono and di(C$_1$-C$_6$)alkylamino(C$_1$-C$_6$)alkyl, each of which is optionally substituted by 1 or 2 substituents independently chosen from halogen, hydroxy, cyano, amino, nitro, C$_1$-C$_6$alkoxy, and C$_1$-C$_6$alkyl; or $R_B$ and $R_C$ and the atom to which they are attached form a 4- to 10-membered monocyclic or bicyclic ring, which may contain a) one or more double bonds b) one or more of oxo, O, S, SO, SO$_2$, and N—R$_D$ wherein R$_D$ is hydrogen, Ar$_1$, (C$_1$-C$_6$)alkyl, (C$_3$-C$_8$)cycloalkyl, heterocycloalkyl, or Ar$_1$(C$_1$-C$_5$)alkyl; wherein Ar$_1$ is aryl or heteroaryl, each of which is optionally substituted by 1 or 2 substituents independently chosen from halogen, hydroxy, cyano, amino, nitro, C$_1$-C$_6$alkoxy, and C$_1$-C$_6$alkyl;

c) one or more substituents $R_{20}$;

v) —OC(=O)R$_E$, —C(=O)OR$_E$, —C(=O)NH$_2$, —C(=O)NHR$_E$, —C(=O)NR$_E$R$_F$, —S(O)$_n$R$_E$, —S(O)$_n$NH$_2$, —S(O)$_n$NHR$_E$, —S(O)$_n$NR$_E$R$_F$, —NHC(=O)R$_E$, —C(=NR$_E$)R$_F$, —HC=N—OH, —HC=N(C$_1$-C$_6$alkoxy), —HC=N(C$_1$-C$_6$alkyl) —NR$_E$C(=O)R$_F$, —NHS(O)R$_E$, and —NR$_E$S(O)$_m$R$_F$, where m is 0, 1 or 2, and R$_E$ and R$_F$ are independently selected at each occurrence from (C$_1$-C$_6$)alkyl, (C$_3$-C$_8$)cycloalkyl, heterocycloalkyl, (C$_1$-C$_6$)alkoxy, mono- and di(C$_1$-C$_6$)alkylamino, aryl, and heteroaryl each of which is optionally substituted by 1, 2, or 3 of R$_{30}$.

$R_{20}$ is independently selected at each occurrence from the group consisting of halogen; hydroxy; nitro; cyano; amino; (C$_1$-C$_6$)alkyl; (C$_1$-C$_6$)alkoxy optionally substituted with amino or mono- or di(C$_1$-C$_6$)alkylamino; (C$_3$-C$_8$)cycloalkyl; (C$_3$-C$_8$)cycloalkyl(C$_1$-C$_4$)alkyl; (C$_3$-C$_8$)cycloalkyl(C$_1$-C$_4$)alkoxy; (C$_2$-C$_6$)alkenyl; (C$_2$-C$_6$)alkynyl; halo(C$_1$-C$_6$)alkyl; halo(C$_1$-C$_6$)alkoxy; oxo; mono- and di(C$_1$-C$_6$)alkylamino; amino(C$_1$-C$_6$)alkyl; and mono- and di(C$_1$-C$_6$)alkylamino (C$_1$-C$_6$)alkyl.

$R_{30}$ is independently selected at each occurrence from halogen, hydroxy, nitro, cyano, amino, (C$_1$-C$_6$)alkyl, (C$_1$-C$_6$)alkoxy optionally substituted with amino or mono- or di(C$_1$-C$_6$)alkylamino, (C$_3$-C$_8$)cycloalkyl, (C$_3$-C$_8$)cycloalkyl(C$_1$-C$_4$)alkyl, (C$_3$-C$_8$)cycloalkyl(C$_1$-C$_4$)alkoxy, heterocycloalkyl, (C$_2$-C$_6$)alkenyl, (C$_2$-C$_6$)alkynyl, halo(C$_1$-C$_6$)alkyl, halo(C$_1$-C$_{10}$)alkoxy, oxo, mono- and di(C$_1$-C$_6$)alkylamino, amino(C$_1$-C$_6$)alkyl, and mono- and di(C$_1$-C$_6$)alkylamino(C$_1$-C$_6$)alkyl.

$R_5$ represents hydrogen or halo(C$_1$-C$_6$)alkyl; or $R_5$ represents (C$_1$-C$_6$)alkyl, (C$_3$-C$_8$)cycloalkyl, or (C$_3$-C$_8$cycloalkyl) (C$_1$-C$_4$)alkyl, each of which may contain one or more double or triple bonds, and each of which is optionally substituted with 1, 2, or 3 of R$_{30}$, or $R_5$ represents aryl, aryl(C$_1$-C$_4$)alkyl, heteroaryl, or heteroaryl(C$_1$-C$_4$)alkyl each of which is optionally substituted with 1, 2, or 3 substituents selected from the group consisting of: halo(C$_1$-C$_6$)alkyl, amino, NH(R$_{10}$), N(R$_{10}$)(R$_{11}$), carboxamido, NH(R$_{10}$)carbonyl, N(R$_{10}$)(R$_{11}$)carbonyl, halogen, hydroxy, nitro, cyano, amino, (C$_1$-C$_6$)alkyl, (C$_1$-C$_8$)alkoxy optionally substituted with amino or mono- or di(C$_1$-C$_{10}$)alkylamino, (C$_3$-C$_{10}$)cycloalkyl, (C$_3$-C$_8$)cycloalkyl(C$_1$-C$_4$)alkyl, (C$_3$-C$_{10}$)cycloalkyl(C$_1$-C$_4$)alkoxy, heterocyclo(C$_1$-C$_4$)alkyl, (C$_2$-C$_6$)alkenyl, (C$_2$-C$_6$)alkynyl, halo(C$_1$-C$_6$)alkyl, halo(C$_1$-C$_6$)alkoxy, amino(C$_1$-C$_6$)alkyl, and mono- and di(C$_1$-C$_{10}$)alkylamino(C$_1$-C$_6$)alkyl;

Q represents —C(R$_6$)(R$_7$) or oxygen, with the proviso that Q is not oxygen when $X_2$ is nitrogen;

$R_6$ and $R_7$ independently represent hydrogen, fluorine, or C$_1$-C$_6$alkyl; and the group:

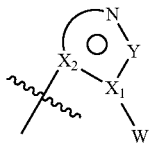

represents a 5 to 7 membered heteroaryl or heterocycloalkyl ring containing up to 4 heteroatoms selected from nitrogen, sulfur, and oxygen, said 5 to 7 membered heteroaryl or heterocycloalkyl ring is substituted at each carbon atom by R, and is substituted at each nitrogen atom available for substitution by R';

R is independently chosen at each occurrence from hydrogen, halogen, amino, $C_1$-$C_6$alkyl, $(C_2$-$C_6)$alkenyl, $(C_2$-$C_6)$alkynyl, $C_1$-$C_6$alkoxy, $(C_3$-$C_8)$cycloalkyl, $(C_3$-$C_8$cycloalkyl)$(C_1$-$C_4)$alkyl, halo($C_1$-$C_6$)alkyl, haloalkoxy, carboxamido, and 3- to 7-membered carbocyclic or heterocyclic groups which are saturated, unsaturated, or aromatic, which may be further substituted with one or more substituents independently selected from halogen, oxo, hydroxy, $C_{1-4}$alkyl, and —O($C_{1-4}$alkyl);

R' is independently chosen at each occurrence from hydrogen, $C_1$-$C_6$alkyl, $C_3$-$C_8$cycloalkyl, $C_3$-$C_8$cycloalkyl($C_1$-$C_4$alkyl), and 3- to 7-membered carbocyclic or heterocyclic groups which are saturated, unsaturated, or aromatic, which 3- to 7-membered carbocyclic or heterocyclic groups are optionally substituted with one or more substituents independently selected from halogen, oxo, hydroxy, $C_{1-4}$alkyl, and —O($C_{1-4}$alkyl); and $X_1$, $X_2$, W, and Y are as defined for Formula I, above.

Such compounds will be referred to as compounds of Formula IA.

A particular aspect of the invention is directed to compounds and pharmaceutically acceptable salts of Formula II

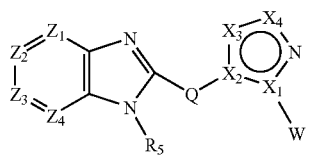

Formula II

In Formula II, the variables $Z_1$, $Z_2$, $Z_3$, $Z_4$, $R_5$, Q, $X_1$, $X_2$, and W carry the definition set forth for Formula I, or more preferably, for Formula IA;

$X_3$ and $X_4$ are independently selected from the group consisting of carbon, CR, N, O, S, NH, and N($C_1$-$C_6$)alkyl; provided that at least one of $X_1$, $X_2$, $X_3$, and $X_4$ is carbon or CR; and R is independently chosen at each occurrence from hydrogen, halogen, amino, $(C_1$-$C_6)$alkyl, $(C_1$-$C_6)$alkoxy, $(C_3$-$C_8)$cycloalkyl, $(C_3$-$C_8)$cycloalkyl($C_1$-$C_6)$alkyl, $(C_2$-$C_6)$alkenyl, $(C_2$-$C_6)$alkynyl, halo($C_1$-$C_6$)alkyl, halo($C_1$-$C_6$)alkoxy, carboxamido, and 3- to 7-membered carbocyclic or heterocyclic groups which are saturated, unsaturated, or aromatic, which may be further substituted with one or more substituents independently selected from halogen, oxo, hydroxy, $C_{1-4}$alkyl, and —O($C_{1-4}$alkyl).

The invention is particularly directed to compounds of Formula I, Formula IA, and Formula II, in which $Z_1$ is $CR_1$, $Z_2$ is $CR_2$, $Z_3$ is $CR_3$, and $Z_4$ is $CR_4$.

The invention is also directed to compounds of Formula I, Formula IA, and Formula II, in which one, and only one, of $Z_1$, $Z_2$, $Z_3$, and $Z_4$ is nitrogen.

Another particular aspect of the invention provides compounds of Formula I, Formula IA, and Formula II, in which $Z_1$ is $CR_1$, $Z_4$ is $CR_4$, and only one, of $Z_2$ and $Z_3$ is nitrogen.

The invention is further directed to compounds of Formula I, Formula IA, and Formula II wherein:

i) $X_2$ is carbon; and Q is oxygen;
ii) $X_2$ is N; and Q is $C(R_6)(R_7)$
iii) $X_2$ is carbon; and Q is $C(R_6)(R_7)$;
iv) $X_1$ is carbon; $X_2$ is N; and Q is $C(R_6)(R_7)$
v) $X_1$ is nitrogen; $X_2$ is carbon; and Q is $C(R_6)(R_7)$; or wherein
vi) Q is $C(R_6)(R_7)$ For each of i) through vi) preferred compounds are those where $Z_1$ is $CR_1$, $Z_2$ is $CR_2$, $Z_3$ is $CR_3$, and $Z_4$ is $CR_4$. For each of i) through vi) preferred compounds are those in which one, and only one, of $Z_1$, $Z_2$, $Z_3$, and $Z_4$ is nitrogen. For each of i) through vi) compounds in which $Z_1$ is $CR_1$, and only one, of $Z_2$ and $Z_3$ is nitrogen are particularly preferred.

In another aspect, the invention provides compounds of Formula III and Formula IV:

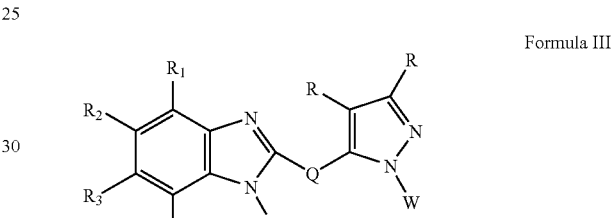

Formula III

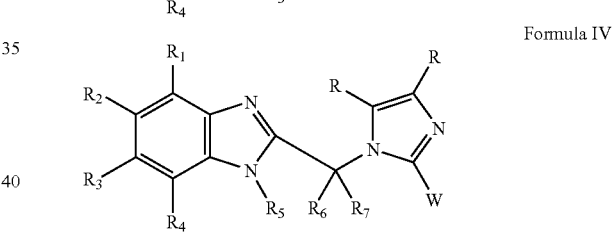

Formula IV wherein R, $R_1$, $R_2$, $R_3$, $R_4$, $R_5$, Q, and W carry the definitions set forth for Formula I, or more preferably for Formula IA.

Particular compounds of Formula III included in the invention are those wherein Q is $C(R_6)(R_7)$.

Preferred compounds of Formula IV include those where $R_6$ and $R_7$ are hydrogen, methyl or fluoro and the other is ethyl, or where one of $R_6$ and $R_7$ is hydrogen, methyl or fluoro and the other is ethyl.

Other compounds of the invention include compounds of Formula III or Formula IV, wherein R is independently selected at each occurrence from the group consisting of:

i) hydrogen, halogen, $(C_1$-$C_6)$alkyl, $(C_3$-$C_8)$cycloalkyl, $(C_3$-$C_8)$cycloalkyl($C_1$-$C_6)$alkyl, $(C_1$-$C_6)$alkoxy, halo($C_1$-$C_6$)alkyl, halo($C_1$-$C_6$)alkoxy, and ii) phenyl and pyridyl each of which is optionally substituted with up to 3 substituents independently chosen from halogen, hydroxy, $C_{1-4}$alkyl, and —O($C_{1-4}$alkyl).

Q (in Formula III) is $C(R_6)(R_7)$.

In Formula III and IV, $R_1$, $R_2$, $R_3$, and $R_4$ are independently selected from hydrogen, halogen, hydroxy, nitro, cyano, amino, $(C_1$-$C_6)$alkyl, $(C_1$-$C_6)$alkoxy, $(C_3$-$C_8)$cycloalkyl, $(C_3$-$C_8)$cycloalkyl($C_1$-$C_6)$alkyl, $(C_2$-$C_6)$alkenyl, $(C_2$-$C_6)$alkynyl, heterocycloalkyl, halo($C_1$-$C_6$)alkyl, halo($C_1$-$C_6$)alkoxy, mono or di($C_1$-$C_6$)alkylamino, amino($C_1$-$C_6$)alkyl, and mono- and di($C_1$-$C_6$)alkylamino($C_1$-$C_6$)alkyl;

$R_5$ represents hydrogen, ($C_1$-$C_6$)alkyl, ($C_3$-$C_8$)cycloalkyl, ($C_3$-$C_8$)cycloalkyl($C_1$-$C_6$)alkyl, phenyl, benzyl, thiophenyl, thiazoyl, pyridyl, imidazolyl, pyrazolyl, or pyrimidinyl;

$R_6$ and $R_7$ independently represent hydrogen, fluorine, or $C_1$-$C_6$ alkyl; and W represents phenyl, thienyl, thiazoyl, pyridyl, imidazolyl, oxazolyl, triazolyl, tetrazolyl, pyrazolyl, isoxazolyl, or pyrimidinyl, each of which is optionally substituted with up to 4 $R_{30}$ groups, where $R_{30}$ carries the definition set forth for Formula I, or more preferably $R_{30}$ carries the definition set forth for Formula IA.

Particularly included in the invention are compounds of Formula III and Formula IV in which wherein R, $R_1$, $R_2$, $R_3$, $R_4$, $R_5$, Q, and W carry the definition set forth for Formula I, or more preferably for Formula IA, and W represents a 6-membered aryl or heteroaryl groups, wherein the 6-membered aryl or heteroaryl group is optionally substituted with up to 4 groups independently selected from $R_{30}$, —$CO_2H$, —C(=O)$OR_E$, —C(=O)$NHR_E$, —C(=O)$NR_ER_F$, —C(O)$R_E$, —S(O)$_mR_E$, and —$OR_E$ or wherein W represents a 5-membered heteroaryl group, wherein the 5-membered heteroaryl group is optionally substituted with up to 4 groups independently selected from $R_{30}$, —$CO_2H$, —C(=O)$OR_E$, —C(=O)$NHR_E$, —C(=O)$NR_ER_F$, —C(O) $R_E$, —S(O)$_nR_E$, and —$OR_E$.

In these embodiments of the invention m is 0, 1, or 2, and $R_E$ carries the definition set forth for Formula I, or more preferably $R_E$ carries the definition set forth for Formula IA and $R_{30}$ carries the definition set forth above with respect to Formula IA.

In another aspect, the compounds of Formula III or Formula IV are those in which one of $R_2$ or $R_3$ carries the definition set forth for Formula I, or more preferably for Formula IA.

In this aspect of the invention,

R is independently selected at each occurrence from the group consisting of hydrogen, halogen, and ($C_1$-$C_2$)alkyl;

$R_1$, $R_4$, and the other of $R_2$ and $R_3$ are independently selected from hydrogen, halogen, hydroxy, nitro, cyano, amino, ($C_1$-$C_6$)alkyl, ($C_1$-$C_6$)alkoxy, ($C_3$-$C_8$)cycloalkyl, ($C_3$-$C_8$)cycloalkyl($C_1$-$C_6$)alkyl, halo($C_1$-$C_6$)alkyl, halo($C_1$-$C_6$) alkoxy, mono or di($C_1$-$C_6$)alkylamino, amino($C_1$-$C_6$)alkyl, and mono- and di($C_1$-$C_6$)alkylamino($C_1$-$C_6$)alkyl;

$R_5$ represents ($C_1$-$C_6$)alkyl; and

Q (in Formula III) is $CH_2$, and $R_6$ and $R_7$ in Formula IV are hydrogen; and W represents phenyl, furanyl, thienyl, thiazoyl, pyridyl, imidazolyl, oxazolyl, triazolyl, tetrazolyl, pyrazolyl, isoxazolyl, pyrimidinyl, benzimidazolyl, quinolinyl, isoquinolinyl each of which is optionally substituted with up to 4 $R_{30}$ groups, where $R_{30}$ carries the definition set forth for Formula I, or more preferably $R_{30}$ carries the definition set forth for Formula IA.

Still other preferred W groups are 4-pyrimidinyl, 5-halo-2-pyrimidinyl, 3,6-dihalopyrimidin-2-yl, and 2,6-, 4,6-, and 5,6-dihalopyridin-2-yl. Other preferred W groups are phenyl substituted with one or two independently selected $C_1$-$C_2$ alkyl, $C_1$-$C_2$ alkoxy, amino, halogen, trifluoromethyl, or cyano groups. Still other preferred W groups are 2-thiazolyl groups carrying one or two independently selected $C_1$-$C_2$ alkyl, amino, ($C_1$-$C_3$) alkyl, hydroxy, ($C_1$-$C_3$)alkyl, or trifluoromethyl groups.

Another aspect of the invention includes compounds of Formula III or Formula IV wherein R is independently selected at each occurrence from the group consisting of hydrogen, halogen, and ($C_1$-$C_2$)alkyl;

$R_1$, $R_4$, and one of $R_2$ and $R_3$ are independently selected from hydrogen, halogen, trifluoromethyl, $C_1$-$C_2$ alkyl, and cyano;

the other of $R_2$ and $R_3$ carries the definition set forth for Formula I, or more preferably for Formula IA; and $R_5$ represents ($C_1$-$C_6$)alkyl, and preferably $C_2$-$C_4$ alkyl. Preferably $R_1$ and $R_4$ are hydrogen;

Preferred R groups are independently selected from hydrogen and $C_1$-$C_3$ alkyl, more preferably hydrogen and methyl, and most preferably are hydrogen.

More preferred $R_5$ groups are ethyl and n-propyl.

In this aspect,

Q (in Formula III) is $CH_2$, and $R_6$ and $R_7$ in Formula IV are hydrogen; and W, is phenyl, pyridyl, or thiazolyl, each which is optionally substituted by one or more substituents independently chosen from halogen, cyano, hydroxy, oxo, $C_1$-$C_2$haloalkyl, $C_1$-$C_2$alkyl, and $C_1$-$C_2$ alkoxy, or more preferably W is 2-thiazolyl, 2-pyrimidinyl, 3-fluorophenyl, or 6-fluoro-2-pyridinyl. Such compounds will be referred to as compounds of Formula III-A and Formula IV-A.

A particular aspect of the invention provides compounds of Formula III-A and Formula IV-A, wherein:

one of $R_2$ and $R_3$ is chosen from hydrogen, halogen, hydroxy, nitro, cyano, amino, ($C_1$-$C_6$)alkyl, ($C_1$-$C_6$)alkoxy, ($C_3$-$C_8$)cycloalkyl, ($C_3$-$C_8$)cycloalkyl($C_1$-$C_6$)alkyl, halo($C_1$-$C_6$)alkyl, halo($C_1$-$C_6$)alkoxy, mono or di($C_1$-$C_6$)alkylamino, amino($C_1$-$C_6$)alkyl, and mono- and di($C_1$-$C_6$)alkylamino ($C_1$-$C_6$)alkyl;

the other of $R_2$ and $R_3$ is chosen from i) hydrogen, halogen, hydroxy, nitro, cyano, amino, halo($C_1$-$C_6$)alkyl, and halo($C_1$-$C_6$)alkoxy, and ii) $C_1$-$C_6$alkyl, $C_1$-$C_6$alkoxy, $C_3$-$C_8$cycloalkyl, $C_2$-$C_6$alkenyl, $C_2$-$C_6$alkynyl, ($C_3$-$C_8$cycloalkyl)$C_1$-$C_4$alkyl, —NH($R_{10}$), —N($R_{10}$)($R_{11}$) ($R_{10}$)NH($C_1$-$C_6$)alkyl, ($R_{10}$)($R_{11}$)N($C_1$-$C_6$)alkyl, (heterocycloalkyl)alkyl, and heterocycloalkyl, each of which is optionally substituted with 1, 2, 3, or 4 of $R_{20}$; and $R_{20}$ carries the definition set forth for Formula I, or more preferably $R_{20}$ carries the definition set forth with respect to Formula IA.

In this aspect, preferred compounds of Formula III-A and IV-A include those where one of $R_2$ and $R_3$ is hydrogen, halogen, hydroxy, nitro, cyano, amino, $C_1$-$C_3$ alkyl, $C_1$-$C_2$ alkoxy, cyclopropyl, cyclopropylmethyl, trifluoromethyl, or mono- or di($C_1$-$C_2$)alkylamino, and the other is hydrogen, halogen, or $C_1$-$C_3$ alkyl, preferably hydrogen or methyl. More preferred compounds of Formula IV-A include those where $R_2$ is hydrogen, halogen, more preferably fluoro or chloro, cyano, amino, $C_1$-$C_2$ alkyl or $C_1$-$C_2$ alkoxy and $R_3$ is hydrogen or methyl. Other more preferred compounds of Formula IV-A include those where $R_2$ is hydrogen, methyl, or ethyl, and $R_3$ is hydrogen, halogen, preferably fluoro or chloro, cyano, amino, or $C_1$-$C_3$ alkoxy.

Another aspect of the invention provides compounds of Formula III-A and Formula IV-A, wherein:

one of $R_2$ and $R_3$ is chosen from hydrogen, halogen, hydroxy, nitro, cyano, amino, ($C_1$-$C_6$)alkyl, ($C_1$-$C_6$)alkoxy, ($C_3$-$C_8$)cycloalkyl, ($C_3$-$C_8$)cycloalkyl($C_1$-$C_6$)alkyl, halo($C_1$-$C_6$)alkyl, halo($C_1$-$C_6$)alkoxy, mono or di($C_1$-$C_6$)alkylamino, amino($C_1$-$C_6$)alkyl, and mono- and di($C_1$-$C_6$)alkylamino ($C_1$-$C_6$)alkyl;

the other of $R_2$ and $R_3$ is chosen from

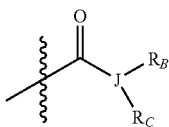

where J is N, CH, or C—($C_1$-$C_6$)alkyl and
$R_B$ and $R_C$ are independently selected from the group consisting of hydrogen, ($C_1$-$C_6$)alkyl, ($C_2$-$C_6$)alkenyl, ($C_2$-$C_6$) alkynyl, $C_3$-$C_8$ cycloalkyl, and ($C_3$-$C_8$ cycloalkyl)($C_1$-$C_4$) alkyl; or
$R_B$ and $R_C$ and the atom to which they are attached form a 4- to 10-membered monocyclic or bicyclic ring, which may contain
a) one or more double bonds,
b) one or more of oxo, O, S, SO, $SO_2$, and N—$R_D$ wherein $R_D$ is hydrogen or ($C_1$-$C_6$)alkyl;
c) one or more of $R_{20}$; and
$R_{20}$ carries the definition set forth with respect to Formula I, or more preferably $R_{20}$ carries the definition set forth for $R_{20}$ Formula IA.

The invention also provides compounds of Formula III-A and Formula IV-A, wherein:
one of $R_2$ and $R_3$ is chosen from hydrogen, halogen, hydroxy, nitro, cyano, amino, ($C_1$-$C_6$)alkyl, ($C_1$-$C_6$)alkoxy, ($C_3$-$C_8$)cycloalkyl, ($C_3$-$C_8$)cycloalkyl($C_1$-$C_6$)alkyl, halo($C_1$-$C_6$)alkyl, halo($C_1$-$C_6$)alkoxy, mono or di($C_1$-$C_6$)alkylamino, amino($C_1$-$C_6$)alkyl, and mono- and di($C_1$-$C_6$)alkylamino ($C_1$-$C_6$)alkyl;
the other of $R_2$ and $R_3$ is a group of the formula:

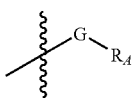

where G is a bond or $C_1$-$C_2$alkyl;
$R_A$ is a saturated, partially unsaturated, or aromatic carbocycle, consisting of 1 ring or 2 fused, pendant, or spiro rings, each ring containing 0, 1, or 2 heteroatoms independently chosen from N, S, and O, said saturated, partially unsaturated, or aromatic carbocycle is optionally substituted with 1, 2, 3, or 4 of $R_{20}$; and
$R_{20}$ carries the definition set forth for $R_a$ in Formula I, or more preferably $R_{20}$ carries the definition set forth for $R_{20}$ in Formula IA $R_{20}$.

Preferably $R_A$ is chosen from phenyl, pyrrolyl, pyrazolyl, thiazolyl, isoxazolyl, triazolyl, tetrazolyl, oxadiazolyl, and oxazolyl each of which is optionally substituted with 1, 2, 3, or 4 of $R_{20}$.

Other compounds of the invention are compounds of Formula III-A and Formula IV-A, wherein:
one of $R_2$ and $R_3$ is chosen from hydrogen, halogen, hydroxy, nitro, cyano, amino, ($C_1$-$C_6$)alkyl, ($C_1$-$C_5$)alkoxy, ($C_3$-$C_8$)cycloalkyl, ($C_3$-$C_8$)cycloalkyl($C_1$-$C_6$)alkyl, halo($C_1$-$C_6$)alkyl, halo($C_1$-$C_6$)alkoxy, mono or di($C_1$-$C_6$)alkylamino, amino($C_1$-$C_6$)alkyl, and mono- and di($C_1$-$C_6$)alkylamino ($C_1$-$C_6$)alkyl; and
the other of $R_2$ and $R_3$ is —HC=N—OH or —HC=N($C_1$-$C_6$alkoxy).

Another aspect of the invention is directed to compounds of Formula I, Formula IA and Formula II wherein
one and only one of $Z_1$ is $CR_1$, $Z_4$ is $CR_4$, either $Z_2$ or $Z_3$ is nitrogen; and
i) W represents a 5-membered heteroaryl group, and the 5-membered heteroaryl group is optionally substituted with up to 4 groups independently selected from $R_{30}$, —$CO_2H$, —C(=O)$OR_E$, —C(=O)$NHR_E$, —C(=O)$NR_ER_F$, —C(O)$R_E$, and —S(O)$_nR_E$, —$OR_E$; or
ii) W represents a 6-membered aryl or heteroaryl group, wherein the 6-membered aryl or heteroaryl group is optionally substituted with up to 4 groups independently selected from $R_{30}$, —$CO_2H$, —C(=O)$OR_E$, —C(=O)$NHR_E$, —C(=O)$NR_ER_F$, —C(O)$R_E$, and —S(O)$_nR_E$, —$OR_E$; where
$R_{30}$ and $R_E$ carry the definitions set forth for those groups in Formula I, or preferably for Formula IA, and m is 0, 1, or 2.

Thus, the invention includes compounds represented by Formula V and Formula VI

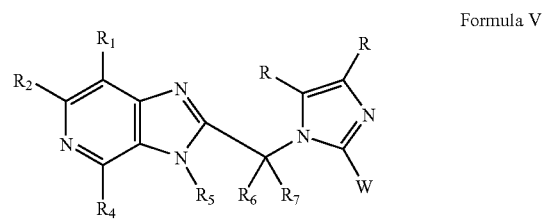

Formula V

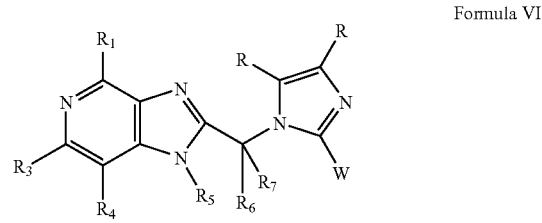

Formula VI wherein R, $R_1$, $R_2$, $R_3$, $R_4$, $R_5$, and Q carry the definitions set forth for Formula I, or more preferably for Formula IA, and W is a 5-membered heteroaryl group as described above.

The invention further includes compounds of Formula V and Formula VI wherein
R is independently selected at each occurrence from the group consisting of
i) hydrogen, halogen, ($C_1$-$C_6$)alkyl, ($C_3$-$C_8$)cycloalkyl, ($C_3$-$C_8$)cycloalkyl($C_1$-$C_6$)alkyl, ($C_1$-$C_6$)alkoxy, halo($C_3$-$C_8$) alkyl, halo($C_1$-$C_6$)alkoxy, and
ii) phenyl and pyridyl each of which is optionally substituted with up to 3 substituents independently chosen from halogen, hydroxy, $C_{1-4}$alkyl, and —O($C_{1-4}$alkyl);
$R_1$, $R_2$, $R_3$, and $R_4$, are independently selected from hydrogen, halogen, hydroxy, nitro, cyano, amino, ($C_1$-$C_6$)alkyl, ($C_1$-$C_6$)alkoxy, ($C_3$-$C_8$)cycloalkyl, ($C_3$-$C_8$)cycloalkyl($C_1$-$C_6$)alkyl, ($C_2$-$C_6$)alkenyl, ($C_2$-$C_6$)alkynyl, heterocycloalkyl, halo($C_1$-$C_6$)alkyl, halo($C_1$-$C_6$)alkoxy, mono or di($C_1$-$C_6$) alkylamino, amino($C_1$-$C_6$)alkyl, and mono- and di($C_1$-$C_6$) alkylamino($C_1$-$C_6$)alkyl;
$R_5$ represents hydrogen, ($C_1$-$C_6$)alkyl, ($C_3$-$C_8$)cycloalkyl, ($C_3$-$C_8$)cycloalkyl($C_1$-$C_6$)alkyl, phenyl, benzyl, thiophenyl, thiazoyl, pyridyl, imidazolyl, pyrazolyl, or pyrimidinyl;
$R_6$ and $R_7$ independently represent hydrogen, fluorine, or $C_1$-$C_6$ alkyl;
W represents either a 5-membered heteroaryl group chosen from thienyl, thiazolyl, imidazolyl, oxazolyl, triazolyl, tetrazolyl, pyrazolyl, or isoxazolyl each of which is optionally substituted with up to 4 $R_{30}$ groups; or W represents a 6-membered aryl or heteroaryl group chosen from phenyl, pyrimidinyl, pyridyl, pyridizinyl, or pyrazinyl, each of which is optionally substituted with up to 4 $R_{30}$ groups; and $R_{30}$ is as defined for Formula I, or preferably as defined for Formula IA.

Preferred compounds of Formula V an VI include those where $R_2$ and $R_3$ independently represent hydrogen, halogen, preferably fluoro or chloro, $C_1$-$C_3$ alkyl, cyclopropyl, cyclopropylmethyl, $C_1$-$C_3$ alkoxy, trifluoromethyl, nitro, cyano, amino, or mono- or di($C_1$-$C_3$)alkylamino. Other preferred $R_2$ and $R_3$ groups are mono- or di($C_1$-$C_3$)alkylamino($C_2$-$C_3$) alkoxy, morpholinyl($C_2$-$C_3$)alkoxy, piperidin-1-yl($C_2$-$C_3$) alkoxy, and piperazin-1-yl($C_2$-$C_3$)alkoxy.

In another aspect, the invention is directed to compounds of Formula V and Formula VI wherein:

R is independently selected at each occurrence from the group consisting of hydrogen, halogen, and ($C_1$-$C_2$)alkyl; and $R_1$ and $R_4$ are independently selected from hydrogen, halogen, hydroxy, nitro, cyano, amino, ($C_1$-$C_8$)alkyl, ($C_1$-$C_6$) alkoxy, ($C_3$-$C_8$)cycloalkyl, ($C_3$-$C_8$)cycloalkyl($C_1$-$C_6$)alkyl, halo($C_1$-$C_6$)alkyl, halo($C_1$-$C_6$)alkoxy, mono or di($C_1$-$C_6$) alkylamino, amino($C_1$-$C_6$)alkyl, and mono- and di($C_1$-$C_6$) alkylamino($C_1$-$C_6$)alkyl.

In this aspect of the invention, $R_2$ (Formula V) and $R_3$ (Formula VI) carry the definitions set forth with respect to Formula I, or more preferably for Formula IA;

$R_5$ represents ($C_1$-$C_{10}$)alkyl, preferably ethyl or n-propyl;

$R_6$ and $R_7$ are hydrogen;

W represents a 5-membered heteroaryl group chosen from furanyl, thienyl, thiazoyl, imidazolyl, oxazolyl, triazolyl, tetrazolyl, pyrazolyl, or isoxazolyl, each of which is optionally substituted with up to 4 $R_{30}$ groups, or W represents a 6-membered aryl or heteroaryl group chosen from phenyl, pyrimidinyl, pyridyl, pyridizinyl, or pyrazinyl each of which is optionally substituted with up to 4 $R_{30}$ groups; and $R_{30}$ is as defined for Formula I, or more preferably for Formula IA.

Compounds of this aspect of the invention will be referred to as compounds of Formula V-A and Formula VI-A.

Preferred R groups are hydrogen and $C_1$-$C_3$ alkyl, more preferably hydrogen and methyl, and most preferably hydrogen.

Preferred $R_1$ and $R_4$ groups for this aspect of the invention include hydrogen, halogen, trifluoromethyl, $C_1$-$C_2$ alkyl, and cyano. Preferably $R_1$ and $R_4$ are hydrogen. More preferably R, $R_1$, and $R_4$ are all hydrogen.

Preferred compounds of this aspect of the invention in which W is a 5-membered heteroaryl group include those wherein W is thiazolyl which is optionally substituted by one or more substituents independently chosen from halogen, cyano, hydroxy, oxo, $C_1$-$C_2$haloalkyl, $C_1$-$C_2$alkyl, and $C_1$-$C_2$ alkoxy. Other preferred compounds are those wherein W is 2-thiazolyl.

Preferred compounds of this aspect in which W is a 6-membered heteroaryl group include those wherein W is phenyl or pyridyl, each of which is optionally substituted by one or more substituents independently chosen from halogen, cyano, hydroxy, oxo, $C_1$-$C_2$haloalkyl, $C_1$-$C_2$alkyl, and $C_1$-$C_2$ alkoxy. Also preferred are compounds wherein W is 2-pyrimidinyl, 3-fluorophenyl, or 6-fluoro-2-pyridinyl.

Still other preferred W groups are 4-pyrimidinyl, 5-halo-2-pyrimidinyl, 3,6-dihalopyrimidin-2-yl, and 2,6-, 4,6-, and 5,6-dihalopyridin-2-yl. Other preferred W groups are phenyl substituted with one or two independently selected $C_1$-$C_2$ alkyl, $C_1$-$C_2$ alkoxy, amino, halogen, trifluoromethyl, or cyano groups. Still other preferred W groups are 2-thiazolyl groups carrying one or two independently selected $C_1$-$C_2$ alkyl, amino, ($C_1$-$C_3$) alkyl, hydroxy, ($C_1$-$C_3$)alkyl, or trifluoromethyl groups.

Other aspects of the invention include compounds of Formula V-A and Formula VI-A wherein $R_2$ (for Formula V-A) or $R_3$ (for Formula VI-A) is chosen from i) hydrogen, halogen, hydroxy, nitro, cyano, amino, halo ($C_1$-$C_6$)alkyl, and halo($C_1$-$C_6$)alkoxy, ii) $C_1$-$C_6$alkyl, $C_1$-$C_6$alkoxy, $C_3$-$C_8$cycloalkyl, $C_2$-$C_6$alkenyl, $C_1$-$C_6$alkynyl, ($C_3$-$C_8$cycloalkyl)$C_1$-$C_4$alkyl, —NH($R_{10}$), —N($R_{10}$)($R_{11}$), ($R_{10}$)NH($C_1$-$C_6$)alkyl, ($R_{10}$)($R_{11}$)N($C_1$-$C_6$)alkyl, (heterocycloalkyl) $C_1$-$C_4$alkyl, and heterocycloalkyl, each of which is optionally substituted with 1, 2, 3, or 4 of $R_{20}$, where $R_{20}$ carries the definition set forth for compounds of Formula I, or preferably for compounds of Formula IA.

Another aspect of the invention is directed to compounds of Formula V-A and Formula VI-A wherein $R_2$ (for Formula V-A) or $R_3$ (for Formula VI-A) is chosen from hydrogen, halogen, hydroxy, nitro, cyano, amino, halo($C_1$-$C_6$)alkyl, and halo($C_1$-$C_6$)alkoxy.

Further aspects of the invention include compounds of Formula V-A and Formula VI-A wherein $R_2$ (for Formula V-A) or $R_3$ (for Formula VI-A) is a group of the formula

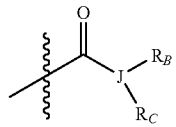

where J is N, CH, or C—($C_1$-$C_{10}$)alkyl and $R_B$ and $R_C$ are independently selected from the group consisting of hydrogen, ($C_1$-$C_6$)alkyl, ($C_2$-$C_6$)alkenyl, ($C_2$-$C_6$) alkynyl, $C_3$-$C_8$)cycloalkyl, and ($C_3$-$C_8$cycloalkyl) ($C_1$-$C_4$) alkyl; or $R_B$ and $R_C$ and the atom to which they are attached form a 4- to 10-membered monocyclic or bicyclic ring, which may contain a) one or more double bonds, b) one or more of oxo, O, S, SO, $SO_2$, and N—$R_D$ wherein $R_D$ is hydrogen or ($C_1$-$C_6$)alkyl; and/or c) one or more substituents $R_{20}$, where $R_{20}$ carries the definition set forth for compounds of Formula I, or more preferably that set forth for compounds of Formula IA.

Also provided by the invention are compounds of Formula V-A and Formula VI-A wherein $R_2$ (for Formula V-A) or $R_3$ (for Formula VI-A) is a group of the formula

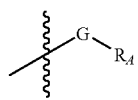

where G is a bond or $C_1$-$C_2$alkyl; and $R_A$ is a saturated, partially unsaturated, or aromatic carbocycle consisting of 1 ring or 2 fused, pendant, or spiro rings, each ring containing 0, 1, or 2 heteroatoms independently selected from N, S, and O, where the saturated, partially unsaturated, or aromatic carbocycle is optionally substituted with 1, 2, 3, or 4 of $R_{20}$. Preferred compounds of this class are those where $R_A$ is chosen from phenyl, pyrrolyl, pyrazolyl, thiazolyl, isoxazolyl, triazolyl, tetrazolyl, oxadiazolyl, and oxazolyl each of which is optionally substituted with 1, 2, 3, or 4 of $R_{20}$. $R_{20}$ carries the definition set forth for compounds of Formula I, or more preferably that set forth for compounds of Formula IA.

The invention also includes compounds of Formula V-A and Formula VI-A wherein $R_2$ (for Formula V-A) or $R_3$ (for Formula VI-A) is —HC=N—OH or —HC=N($C_1$-$C_6$alkoxy).

Other benzimidazole and pyridylimidazole compounds of the invention are represented by Formula X-Formula XVIII, below.

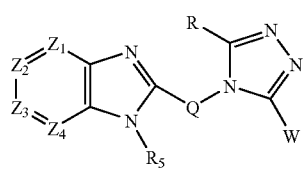

Formula X

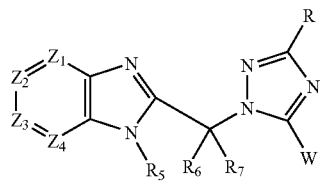

Formula XI

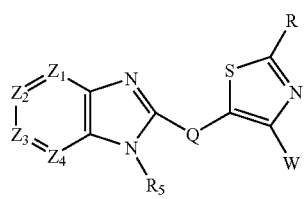

Formula XII

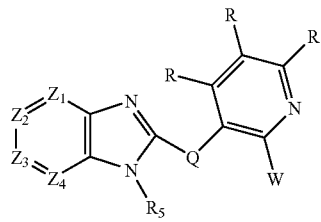

Formula XIII

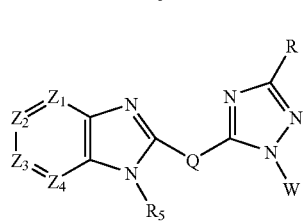

Formula XIV

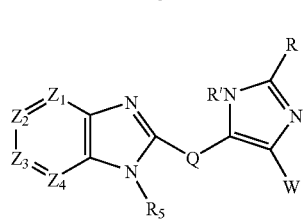

Formula XV where R' is H or $C_1$-$C_6$alkyl

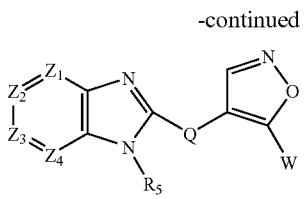

Formula XVI

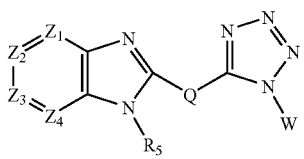

Formula XVII

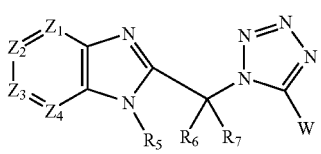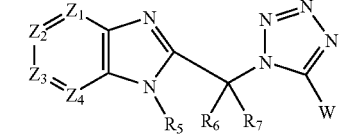

Formula XVIII

The variables $Z_1$, $Z_2$, $Z_3$, $Z_4$, R, Q, and W, which appear in Formulae X-XVIII carry the definition set forth for Formula I, or more preferably for Formula IA.

Compounds of Formulae X-XVIII wherein $Z_1$ is $CR_1$, $Z_2$ is $CR_2$, $Z_3$ is $CR_3$, and $Z_4$ is $OR_4$ are preferred. Compounds of Formulae X-XVIII wherein one and only one $Z_1$, $Z_2$, $Z_3$, $Z_4$ is nitrogen are also preferred. Compounds of Formulae X-XVIII wherein one and only one $Z_1$, $Z_2$, $Z_3$, $Z_4$ is nitrogen, and either $Z_2$ or $Z_3$ is nitrogen are particularly preferred.

Particularly embodied in the invention are compounds of Formulae X-XVIII wherein Q (when present) is $C(R_6)(R_7)$. Preferably $R_6$ and $R_7$ are hydrogen.

Other embodiments of the invention are directed to compounds of Formulae X-XVIII wherein w represents a 5-membered heteroaryl group, and the 5-membered heteroaryl group is optionally substituted with up to 4 groups independently selected from $R_{30}$, —$CO_2H$, —C(=O)$OR_E$, —C(=O)$NHR_E$, —C(=O)$NR_ER_F$, —C(O)$R_E$, and —S(O)$_n R_E$, —$OR_E$, where $R_{30}$ and $R_E$ are as defined above and m is 0, 1, or 2. Preferred compounds of this class are compounds wherein wherein $Z_1$ is $CR_1$, $Z_2$ is $CR_2$, $Z_3$ is $CR_3$, and $Z_4$ is $CR_4$ or wherein one and only one $Z_1$, $Z_2$, $Z_3$, $Z_4$ is nitrogen are also preferred; compounds of this class wherein one and only one $Z_1$, $Z_2$, $Z_3$, $Z_4$ is nitrogen, and either $Z_2$ or $Z_3$ is nitrogen are particularly preferred.

This invention provides benzimidazole and pyridylimidazole derivatives, preferred examples of which bind with high affinity to the benzodiazepine site of $GABA_A$ receptors, including human $GABA_A$ receptors. The affinity of compounds of Formula I for the benzodiazepine site may be determined using a $GABA_A$ receptor binding assay, such as the assay presented in Example 53. Preferred compounds of Formula I that bind with high affinity to the benzodiazepine site of the $GABA_A$ receptor exhibit $K_i$ values of less than 1 µM in that assay, Very high affinity compounds of the invention exhibit $K_i$ values of less than 100 nM or more preferably less than 10 nM in the assay presented in Example 53. Without wishing to be bound to any particular theory, it is believed that the interaction of the compounds of Formula I with the benzodiazepine site results in the pharmaceutical utility of these compounds.

Benzimidazole and pyridylimidazole derivatives that bind with high selectivity to the benzodiazepine site of $GABA_A$ receptors, including human $GABA_A$ receptors, are also included in this invention. Preferred compounds of Formula I which exhibit high selectivity (or high specificity) exhibit affinity for the benzodiazepine site of the GABA receptor that is at least 10-fold greater, and preferably 100-fold greater, than the affinity exhibited at any other membrane-bound receptor which is a known drug target. More preferred compounds of Formula I do not exhibit a binding affinity at any other membrane-bound receptor which is a known drug target that is less than 1 micromolar. Membrane-bound receptors that are known drug targets include, but are not limited to dopamine receptors, CRF receptors, bradykinin receptors, NPY receptors, beta-adrenergic receptors, capsaicin receptors, galanin receptors, MCH receptors, melanocortin receptors, and neurokinin receptors. Binding affinities for membrane-bound receptors which are known drug targets may be determined via radioligand binding assays which are generally well known in the art.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as inverse agonists at the $\alpha_5\beta_3\gamma_2$ are particularly useful in treating cognitive disorders through the enhancement of memory, and particularly short-term memory, in memory-impaired patients. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, memory impairment, short-term memory impairment, Alzheimer's disease, Parkinson's disease, mild cognitive impairment (MC1), age-related cognitive decline (ARCD), stroke, traumatic brain injury, AIDS associated dementia, and dementia associated with depression, anxiety or psychosis.

Attention Deficit Disorder, e.g. attention deficit disorder (ADD), and attention deficit and hyperactivity disorder (ADHD).

Speech disorders, e.g. stuttering, including motor tic, clonic stuttering, dysfluency, speech blockage, dysarthria, Tourete syndrome or logospasm.

Psychosis e.g. schizophrenia, hallucinatory disorders

The invention also provides pharmaceutical compositions comprising one or more compounds of the invention together with a pharmaceutically acceptable carrier or excipient, for treating disorders responsive to $GABA_A$ receptor modulation, e.g., treatment of anxiety, depression, sleep disorders or cognitive impairment by $GABA_A$ receptor modulation. Pharmaceutical compositions include packaged pharmaceutical compositions comprising a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5\text{-HT}_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211-218; Smith, et al., *Am. J. Psychiatry* (1998) 155(10) 1339-45; or Le, et al., *Alcohol and Alcoholism* (1996) 31 Suppl. 127-132. Also see, the discussion of the use of the $GABA_A$ receptor ligand 3-(5-methylisoxazol-3-yl)-6-(1-methyl-1,2,3-triazol-4-yl)methyloxy-1,2,4-triazolo[3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The present invention also pertains to methods of inhibiting the binding of benzodiazepine compounds, such as Ro15-1788, or GABA to the $GABA_A$ receptors which methods involve contacting a solution containing compound of the invention with cells expressing $GABA_A$ receptors, wherein the compound is present at a concentration sufficient to inhibit benzodiazepine binding or GABA binding to $GABA_A$ receptors in vitro. This method includes inhibiting the binding of benzodiazepine compounds to $GABA_A$ receptors in vivo, e.g., in a patient given an amount of a compound of Formula I that would be sufficient to inhibit the binding of benzodiazepine compounds or GABA to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via a $GABA_A$ receptor binding assay, such as the assay described in Example 53. The $GABA_A$ receptors used to determine in vitro binding may be obtained from a variety of sources, for example from preparations of rat cortex or from cells expressing cloned human $GABA_A$ receptors.

The invention also provides methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given an amount of a compound of Formula I that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 54. The cells expressing the GABA receptors in vivo may be, but are not limited to, neuronal cells or brain cells. Such cells may be contacted with compounds of the invention through contact with a body fluid containing the compound, for example through contact with cerebrospinal fluid. Alteration of the signal-transducing activity of $GABA_A$ receptors in vitro may be determined from a detectable change in the electrophysiology of cells expressing $GABA_A$ receptors, when such cells are contacted with an compound of the invention in the presence of GABA. For example, a change in the electrophysiology of cells expressing $GABA_A$ receptors may be detected using a voltage-clamp assay performed on oocytes injected with $GABA_A$ receptor mRNA. Such an assay is shown in Example 54.

Intracellular recording or patch-clamp recording may be used to quantitate changes in electrophysiology of cells. A reproducible change in behavior of an animal given a compound of the invention may also be used to indicate that changes in the electrophysiology of the animal's cells expressing $GABA_A$ receptors has occurred.

The $GABA_A$ receptor ligands provided by this invention and labeled derivatives thereof are also useful as standards and reagents in determining the ability of a potential pharmaceutical to bind to the $GABA_A$ receptor. Radiolabeled derivatives the $GABA_A$ receptor ligands provided by this invention are also useful as radiotracers for positron emission tomography (PET) imaging or for single photon emission computerized tomography (SPECT).

More particularly compounds of the invention may be used for demonstrating the presence of $GABA_A$ receptors in cell or tissue samples. This may be done by preparing a plurality of matched cell or tissue samples, at least one of which is prepared as an experimental sample and at least one of which is prepared as a control sample. The experimental sample is prepared by contacting (under conditions that permit binding of RO15-1788 to $GABA_A$ receptors within cell and tissue samples) at least one of the matched cell or tissue samples that has not previously been contacted with any compound or salt of the invention with an experimental solution comprising the detectably-labeled preparation of the selected compound or salt at the first measured molar concentration. The control sample is prepared in the same manner as the experimental sample and also contains an unlabelled preparation of the same compound or salt of the invention at a greater molar concentration.

The experimental and control samples are then washed to remove unbound detectably-labeled compound. The amount of remaining bound detectably-labeled compound is then measured and the amount of detectably-labeled compound in the experimental and control samples is compared. A comparison that indicates the detection of a greater amount of detectable label in the at least one washed experimental sample than is detected in any of control samples demonstrates the presence of $GABA_A$ receptors in that experimental sample.

The detectably-labeled compound used in this procedure may be labeled with a radioactive label or a directly or indirectly luminescent label. When tissue sections are used in this procedure and the detectably-labeled compound is radiolabeled, the bound, labeled compound may be detected autoradiographically to generate an autoradiogram. The amount of detectable label in an experimental or control sample may be measured by viewing the autoradiograms and comparing the exposure density of the autoradiograms.

The invention provides a method for preparing a compound of Formula A

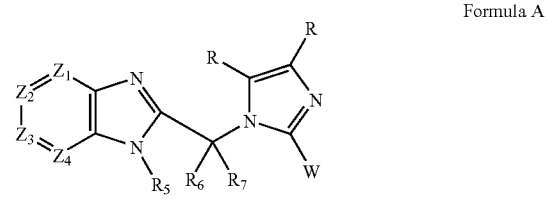

Formula A which comprises reacting a compound of Formula B

Formula B with a compound of Formula C

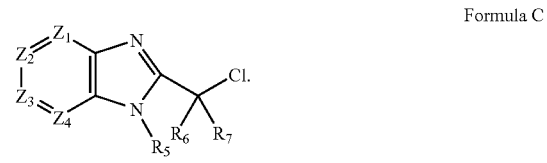

Formula C

In Formula A and C, above $Z_1$, $Z_2$, $Z_3$, $Z_4$, and $R_5$ carry the definitions forth for Formula I, or more preferably $Z_1$, $Z_2$, $Z_3$, $Z_4$, and $R_5$ carry the definitions forth for Formula Ia.

$R_6$ and $R_7$ independently represent hydrogen, fluorine, or alkyl.

R in Formula B, above, is independently chosen at each occurrence from hydrogen, halogen, amino, $C_1$-$C_6$alkyl, ($C_2$-$C_6$)alkenyl, ($C_2$-$C_6$)alkynyl, $C_1$-$C_6$alkoxy, ($C_3$-$C_8$)cycloalkyl, ($C_3$-$C_8$cycloalkyl) ($C_1$-$C_4$)alkyl, halo($C_1$-$C_6$)alkyl, haloalkoxy, carboxamido, and 3- to 7-membered carbocyclic or heterocyclic groups which are saturated, unsaturated, or aromatic, which may be further substituted with one or more substituents independently selected from halogen, oxo, hydroxy, $C_{1-4}$alkyl, and —O($C_{1-4}$alkyl).

W in Formula B represents aryl or heteroaryl, wherein the aryl or heteroaryl group is optionally substituted with up to 4 groups independently selected from $R_{30}$, —$CO_2H$, $C(=O)$$OR_E$, —$C(=O)NHR_E$, —$C(=O)NR_ER_F$, —$C(O)R_E$, and —$S(O)_mR_E$, —$OR_E$, where $R_{30}$ and $R_E$ are as for Formula I or preferably as defined for Formula Ia and m is 0, 1, or 2. This process will be referred to as Process 1.

In particular embodiments the invention includes a process of preparing a compound of Formula A as described above wherein: $Z_1$ is $CR_1$, $Z_2$ is $CR_2$, $Z_3$ is $CR_3$, and $Z_4$ is $CR_4$.

R is independently selected at each occurrence from the group consisting of hydrogen, halogen, and ($C_1$-$C_2$)alkyl;

$R_1$, $R_4$, and one of $R_2$ and $R_3$ are independently selected from hydrogen, halogen, hydroxy, nitro, cyano, amino, ($C_1$-$C_5$)alkyl, ($C_1$-$C_6$)alkoxy, ($C_3$-$C_8$)cycloalkyl, ($C_3$-$C_8$)cycloalkyl($C_1$-$C_6$)alkyl, halo($C_1$-$C_6$)alkyl, halo($C_1$-$C_6$)alkoxy, mono or di($C_1$-$C_6$)alkylamino, amino($C_1$-$C_6$)alkyl, and mono- and di($C_3$-$C_6$)alkylamino($C_1$-$C_6$)alkyl.

The other of $R_2$ and $R_3$ carries the definition set forth for Formula I, or preferably that set forth for Formula Ia, or in certain preferred embodiments this group is chosen from
i) hydrogen, halogen, hydroxy, nitro, cyano, amino, halo($C_1$-$C_6$)alkyl, and halo($C_1$-$C_6$)alkoxy,
ii) $C_1$-$C_6$alkyl, $C_1$-$C_6$alkoxy, $C_3$-$C_8$cycloalkyl, $C_2$-$C_6$alkenyl, $C_2$-$C_6$alkynyl, ($C_3$-$C_8$cycloalkyl) $C_1$-$C_4$alkyl, —$NH(R_{10})$, —$N(R_{10})(R_{11})$, $(R_{10})NH(C_1$-$C_6)$alkyl, $(R_{10})(R_{11})N(C_1$-$C_6)$alkyl, (heterocycloalkyl)$C_1$-$C_4$alkyl, and heterocycloalkyl, each of which is optionally substituted with 1, 2, 3, or 4 of $R_{20}$.

In certain preferred embodiments R, $R_1$, and $R_4$ are all hydrogen.

$R_5$ represents ($C_1$-$C_6$)alkyl. Preferred definitions of $R_5$ include ethyl and n-propyl.

$R_6$ and $R_7$ are hydrogen.

W represents phenyl, furanyl, thienyl, thiazolyl, imidazolyl, oxazolyl, triazolyl, tetrazolyl, pyrazolyl, isoxazolyl, pyrimidinyl, benzimidazolyl, quinolinyl, isoquinolinyl each of which is optionally substituted with up to 4 $R_{30}$ groups, where $R_{30}$ is as defined in the above process. Preferred W groups include, 2-thiazolyl, 2-pyrimidinyl, 3-fluorophenyl, or 6-fluoro-2-pyridinyl.

In other preferred embodiments the invention is directed to a process, as described as for Process 1, wherein $Z_1$ is $CR_1$; one and only one of $Z_2$ or $Z_2$ is nitrogen; $Z_4$ is $CR_4$.

$R_1$ and $R_4$ may carry the definition set forth in Process 1. Preferred definitions of $R_1$ and $R_4$ include hydrogen, halogen, trifluoromethyl, $C_1$-$C_2$ alkyl, and cyano.

In certain preferred embodiments R, $R_1$, and $R_4$ are all hydrogen.

$R_2$ or $R_3$ (for whichever one of $Z_2$ or $Z_3$ is $CR_2$ or $CR_3$) is chosen from
i) hydrogen, halogen, hydroxy, nitro, cyano, amino, halo ($C_1$-$C_6$)alkyl, and halo($C_1$-$C_6$)alkoxy,
ii) $C_1$-$C_6$alkyl, $C_1$-$C_6$alkoxy, $C_3$-$C_8$cycloalkyl, $C_2$-$C_6$alkenyl, $C_2$-$C_6$alkynyl, ($C_3$-$C_8$cycloalkyl) $C_1$-$C_4$alkyl, —$NH(R_{10})$, —$N(R_{10})(R_{11})$ $(R_{10})NH(C_1$-$C_6)$alkyl, $(R_{10})(R_{11})N(C_3$-$C_6)$alkyl, (heterocycloalkyl)$C_1$-$C_4$alkyl, and heterocycloalkyl, each of which is optionally substituted with 1, 2, 3, or 4 of $R_{20}$.

$R_5$ represents ($C_1$-$C_6$)alkyl. Preferred definitions of $R_5$ include ethyl and n-propyl.

$R_6$ and $R_7$ are hydrogen.

W represents a 5-membered heteroaryl group, the 5-membered heteroaryl group is optionally substituted with up to 4 groups independently selected from $R_{30}$, —$CO_2H$, —$C(=O)$$OR_E$, —$C(=O)NHR_E$, —$C(=O)NR_ER_F$, —$C(O)R_E$, and —$S(O)_mR_E$, —$OR_E$, where $R_{30}$ and $R_E$ are as defined above and m is 0, 1, or 2; or W represents a 6-membered aryl or heteroaryl group, wherein the 6-membered aryl or heteroaryl group is optionally substituted with up to 4 groups independently selected from $R_{30}$, —$CO_2H$, —$C(=O)OR_E$, —$C(=O)NHR_E$, —$C(=O)NR_ER_F$, —$C(O)R_E$, and —$S(O)_mR_E$, —$OR_E$, where $R_{30}$ and $R_E$ are as defined above and m is 0, 1, or 2.

When W represents a 5-membered heteroaryl group W is preferably thiazolyl, thienyl, imidazolyl, oxazolyl, triazolyl, tetrazolyl, pyrazolyl, or isoxazolyl, each of which is optionally substituted by one or more substituents independently chosen from halogen, cyano, hydroxy, oxo, $C_1$-$C_2$haloalkyl, $C_1$-$C_2$alkyl, and $C_1$-$C_2$ alkoxy. Unsubstituted 2-thiazolyl is a particularly preferred W group.

When W represents a 6-membered aryl or heteroaryl group, W is preferably phenyl, pyrimidinyl, pyridyl, pyrazinyl, or pyridizinyl, each of which is optionally substituted by one or more substituents independently chosen from halogen, cyano, hydroxy, oxo, $C_1$-$C_2$haloalkyl, $C_1$-$C_2$alkyl, and $C_1$-$C_2$ alkoxy. Particularly preferred W groups include 2-pyrimidinyl, 3-fluorophenyl, or 6-fluoro-2-pyridinyl.

In this process the reactants B and C are generally combined in a polar aprotic solvent, such as THF, DMF, or 1,4-dioxane, at temperatures ranging from 0-100 degrees C. A reducing agent such as NaH or other base, for example sodium hydroxide, potassium butoxide, potassium carbonate, or cesium carbonate, is then added, and the reaction is allowed to proceed. Choice of solvent, reaction temperature, and reducing agent will depend on the identity of the reactants B and C, but will be readily determined by a worker of ordinary skill in the art of chemical synthesis. Scheme I, step 4, provides further illustration of this process.

Chemical Description and Terminology

Formula I includes, but is not limited to the subformulae exemplified as Formula Ia, Formulae II-VI and Formulae X-XVIII and their pharmaceutically acceptable acid and base addition salts.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. As used herein, "pharmaceutically acceptable salts" refer to derivatives of the disclosed compounds wherein the parent compound is modified by making acid or base salts thereof. Those skilled in the art will recognize a wide variety of non-toxic pharmaceutically acceptable addition salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, hydroiodic, sulfuric, sulfamic, sulfinic, phosphoric, nitric and the like; and the salts prepared from organic acids such as alkanoic such as acetic, HOOC—$(CH_2)_n$-ACOOH where n is 0-4, and the like, tartaric, maleic, propionic, succinic, glycolic, stearic, lactic, malic, tartaric, citric, ascorbic, pamoic, malefic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985).

The invention includes hydrates of compounds of Formula I.

The invention includes all crystalline forms of the compounds of Formula I. Certain crystalline forms may be preferred.

The present invention also encompasses the acylated prodrugs of the compounds of Formula I. Those skilled in the art will recognize various synthetic methodologies that may be employed to prepare non-toxic pharmaceutically acceptable addition salts and acylated prodrugs of the compounds encompassed by Formula I. The invention further encompasses all enantiomers and diastereomers of the disclosed compounds. Those of ordinary skill in the art will readily recognize methods by which mixtures of enantiomers and diasteromers may be resolved. The definition of Formula I as used in herein include possible isomers, such as tautomers and rotamers.

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

When any variable occurs more than one time in any constituent or formula for a compound, its definition at each occurrence is independent of its definition at every other occurrence. Thus, for example, if a group is shown to be substituted with 0 to 3 R*, (where R* indicates any variable group such as R) then said group may optionally be substituted with up to three R* groups and R* at each occurrence is selected independently from the definition of R*. Also, combinations of substituents and/or variables are permissible only if such combinations result in stable compounds.

When any group, such as an aryl group, heteroaryl group, carbocyclic group, heterocyclic group, or monocylic or bicyclic ring is said to be "optionally substituted by one or more substituents" that group may contain 0 or from 1 to the maximum number of substituents allowable without exceeding the valency of the atoms of the substituted group. Preferably such groups are substituted with 0 or from 1 to 4 substituents, and more preferably such groups are substituted with 0 or from 1 to 3 substituents. Preferably such groups are not substituted with more that one oxo substituent.

A dash "—" that is not between two letters or symbols is used to indicate a point of attachment for a substituent. For example —C(=O)NH$_2$ is attached through the carbon atom.

As used herein, "alkyl" is intended to include both branched and straight-chain aliphatic hydrocarbon groups, having the specified number of carbon atoms. Alkyl groups of 2 or more carbon atoms may contain double or triple bonds. Examples of alkyl include, but are not limited to, methyl, ethyl, n-propyl, i-propyl, n-butyl, s-butyl, t-butyl, n-pentyl, and s-pentyl. Preferred alkyl groups are $C_1$-$C_6$ alkyl groups. "$C_1$-$C_6$ alkyl" indicates alkyl groups having from 1 to about 6 carbon atoms.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. "$C_1$-$C_6$ alkoxy" indicates alkoxy groups having from 1 to about 6 carbon atoms.

"Alkenyl" is intended to include hydrocarbon chains of either a straight or branched configuration comprising one or more unsaturated carbon-carbon bonds which may occur in any stable point along the chain, such as ethenyl and propenyl. Alkenyl groups typically will have 2 to about 8 carbon atoms, more typically 2 to about 6 carbon atoms.

"Alkynyl" is intended to include hydrocarbon chains of either a straight or branched configuration comprising one or more triple carbon-carbon bonds which may occur in any stable point along the chain, such as ethynyl and propynyl. Alkynyl groups typically will have 2 to about 8 carbon atoms, more typically 2 to about 6 carbon atoms.

"Aryl" refers to aromatic groups having 1 or more rings, wherein the members of the aromatic ring or rings are carbon. When indicated such groups may be substituted. Preferred aryl groups include optionally substituted phenyl and optionally substituted naphthyl.

The term "Cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "(cycloalkyl)alkyl", Cycloalkyl and alkyl are as defined above and the point of attachment is on the alkyl group. This term encompasses, but is not limited to, cyclopropylmethyl, cyclohexylmethyl, cyclohexylmethyl.

As used herein, "haloalkyl" is intended to include both branched and straight-chain saturated aliphatic hydrocarbon groups having the specified number of carbon atoms, substituted with 1 or more halogen atoms (for example —$C_vF_w$ where v=1 to 3 and w=1 to (2v+1). Examples of haloalkyl include, but are not limited to, trifluoromethyl, difluoromethyl, trichloromethyl, pentafluoroethyl, and pentachloroethyl.

As used herein, "haloalkoxy" indicates a haloalkyl group as defined above with the indicated number of carbon atoms attached through an oxygen bridge. Examples of haloalkoxy groups include, but are not limited to, trifluoromethoxy and trichloromethoxy.

As used herein the term "heteroaryl" is intended to mean a stable 5- to 7-membered monocyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the heteroaryl group is not more than 1.

Examples of heteroaryl groups include, but are not limited to, pyrimidinyl, pyridyl, quinolinyl, benzothienyl, indolyl, pryidazinyl, pyazinyl, isoindolyl, isoquinolyl, quinazolinyl, quinoxalinyl, phthalazinyl, imidazolyl, isoxazolyl, pyrazolyl, oxazolyl, thienyl, thiazolyl, indolizinyl, indazolyl, benzothiazolyl, benzimidazolyl, benzofuranyl, benzoisoxolyl, dihydro-benzodioxinyl, furanyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide.

Preferred heteroaryl groups include imidazolyl, pyrrolyl, pyridyl, thiazolyl, pyrazolyl, thiazolyl, isoxazolyl, triazolyl, tetrazolyl, oxadiazolyl, pyrimidinyl, and oxazolyl.

The term "heterocycloalkyl" is intended to include saturated ring groups having at least 1 heteroatom. Heterocycloalkyl groups typically include 3 to 8 ring atoms, preferably 5 to 7 ring atoms. Heterocycloalkyl groups typically have from 1 to 3 heteroatoms selected from N, S, and O with remaining ring atoms being carbon. Preferably not more than one S atom and one O atom is present in a heterocycloalkyl group. Preferred heterocycloalkyl groups include morpholinyl, piperidinyl, piperazinyl, thiomorpholinyl, and pyrrolidinyl.

The phrase "monocyclic or bicyclic ring" refers to saturated, partially unsaturated, or aromatic rings or ring systems, which optionally contain from 1 to 4 heteroatoms independently chosen from N, S, and O with remaining ring members being carbon. Preferred monocyclic and bicyclic rings are saturated and partially unsaturated rings or ring systems.

The term "oxo" indicates a carbonyl group. When an oxo group appears as a substituent the allowed valence of the substituted position is not exceeded.

Pharmaceutical Compositions

The compounds of general Formulas I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formulas I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formulas I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to high solubility (preferably 500 ng/ml or more) in aqueous solutions, oral bioavailability, low toxicity, low serum protein binding, lack of clinically relevant EKG effects, and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1-27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120-1127).

EXAMPLES

Preparation of Compounds

Representative procedures suitable for the preparation of compounds of Formula I are outlined in Schemes I-X, which are not to be construed as limiting the invention in scope or spirit to the specific reagents and conditions shown in them. Those having skill in the art will recognize that the reagents and conditions may be varied and additional steps employed to produce compounds encompassed by the present invention. In some cases, protection of reactive functionalities may be necessary to achieve the desired transformations. In general, such need for protecting groups, as well as the conditions necessary to attach and remove such groups, will be apparent to those skilled in the art of organic synthesis. Unless otherwise stated in the schemes below, the variables, e.g., $Z_1$, $Z_2$, $Z_3$, $Z_4$, $R_5$, $R_2$, $R_3$ and W, are as defined in Formula I.

Scheme I

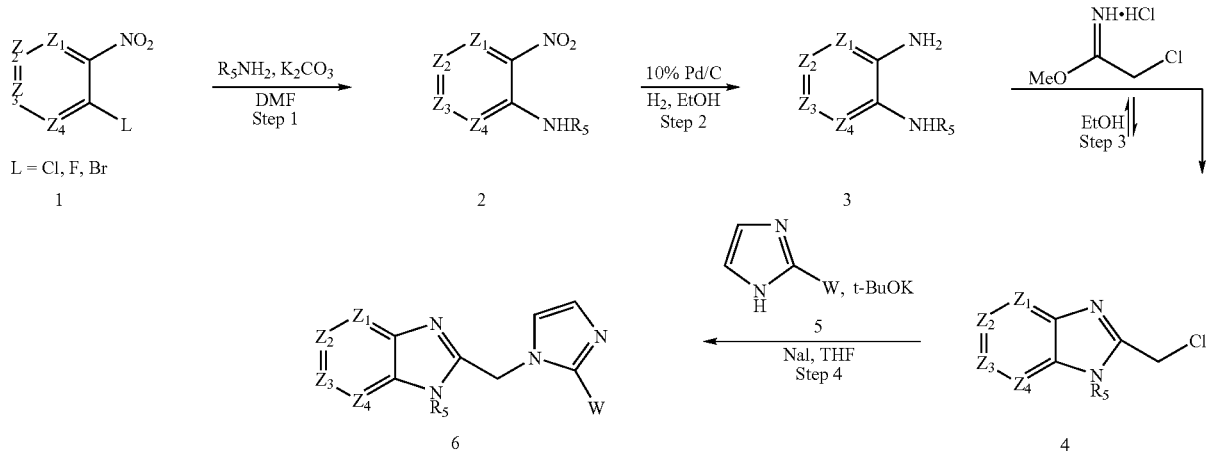

Scheme I illustrates a route to selected compounds of Formula 6 via coupling of chloromethyl compounds 4 and aryl imidazoles 5. In Step 1, aryl and heteroaryl halides of formula 1 are reacted with appropriate amines in the presence of base to obtain amino adducts of formula 2. In Step 2, reduction of the nitro group in compounds of formula 2 yields diamines 3. In Step 3, diamines of formula 3 are reacted with 2-chloroacetimidic acid methyl ester hydrochloride or a similar electrophile such as 2-chloro-1,1,1-trimethoxy-ethane or chloroacetic acid anhydride. In Step 4, chloromethyl compounds of formula 4 are reacted with aryl and heteroaryl imidazoles of formula 5 in the presence of base and solvent to obtain compounds of formula 6. Depending on the particular nature of 5, a stronger or weaker base may be selected to facilitate the reaction in Step 4.

Scheme II illustrates the synthesis of compounds of formula 10 from diamines 3. In Step 1, reaction of malonyl dichloride with ethyl vinyl ether provides 7. In Step 2, treatment of 7 with triethyl orthoformate in the presence of acid yields 8. Compound 8 is reacted in Step 3 with a variety of aryl and heteroaryl hydrazines to obtain compounds of formula 9 as a mixture with the undesired regioisomer. As illustrated in Steps 4 and 5, compounds of formula 9 can be hydrolyzed to the corresponding acids and coupled with compounds of formula 3 to obtain, following cyclization in refluxing acetic acid, compounds of formula 10. As described in subsequent schemes and examples, compounds of formula 9 may also be directly coupled to compounds of formula 3 in the presence of trimethylaluminum. Depending on the particular example Scheme II

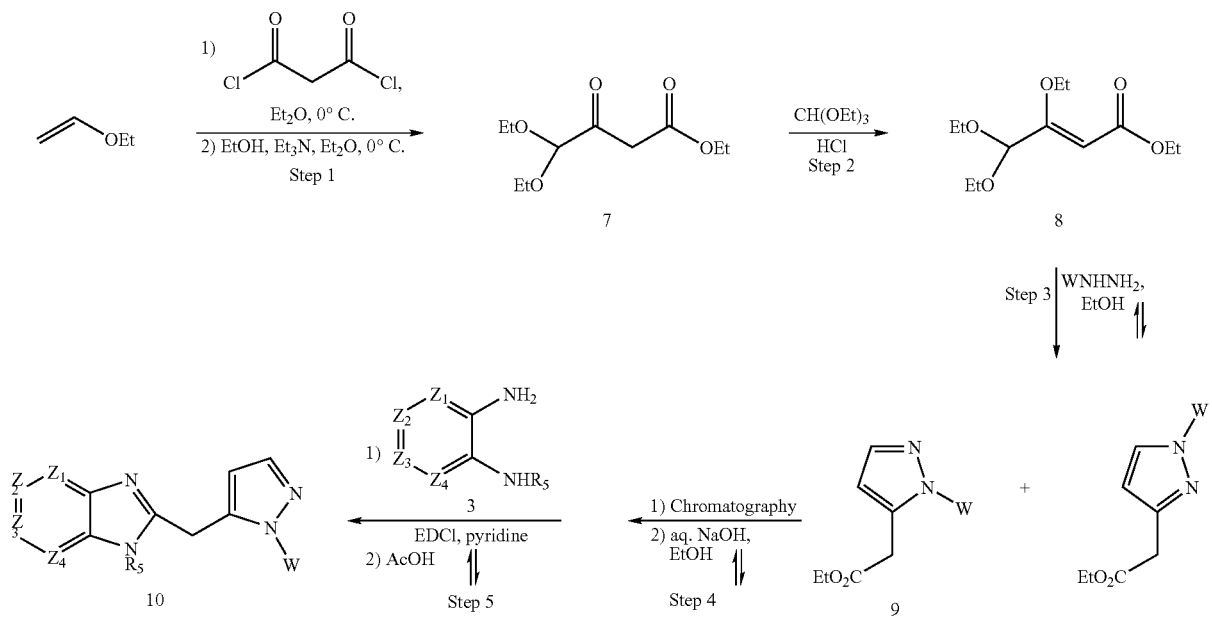

Scheme III

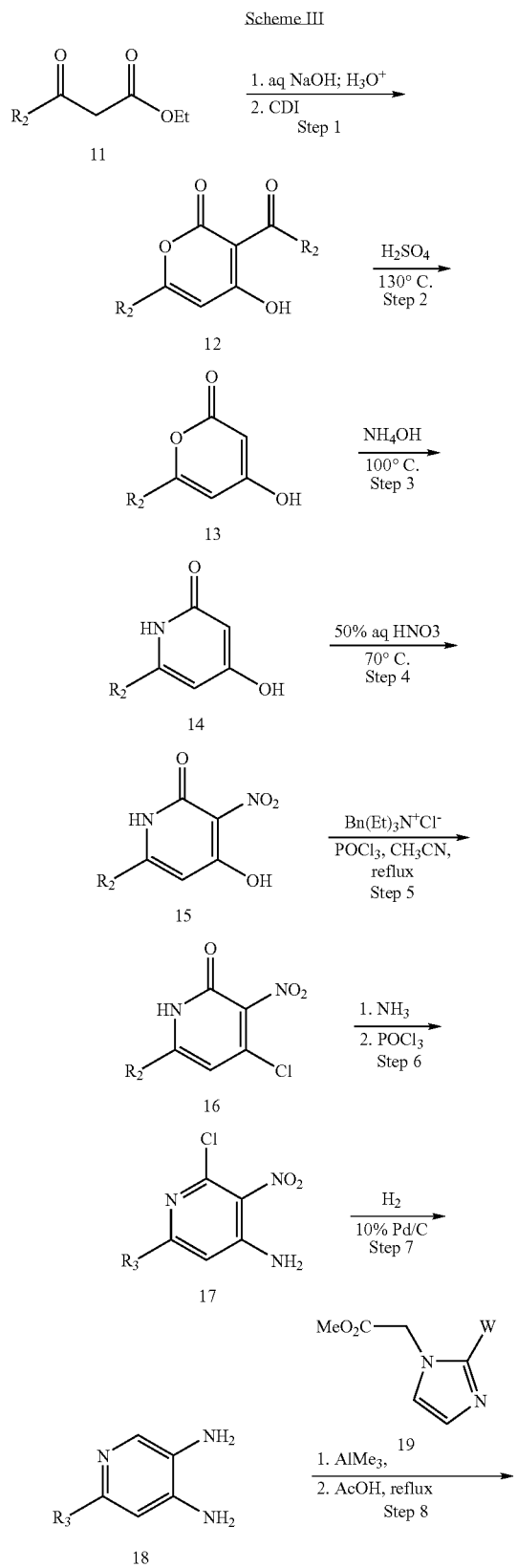

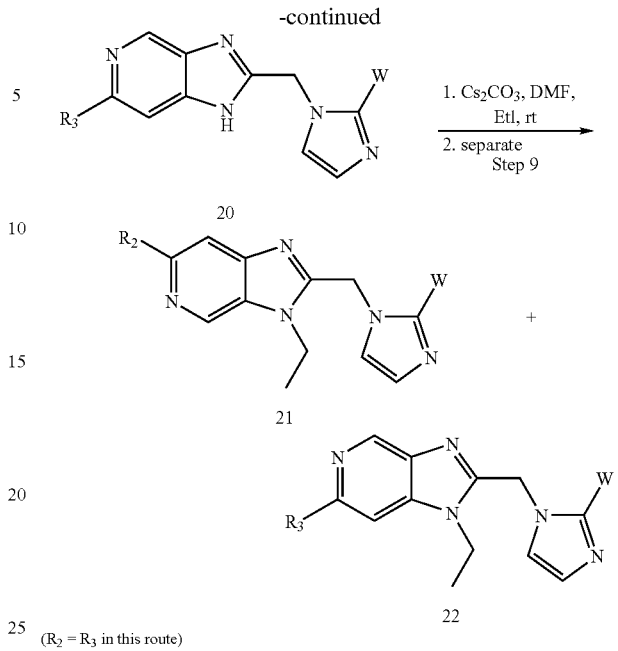

($R_2 = R_3$ in this route)

Scheme III illustrates a method for preparing compounds of formula 21 and 22. Step 1 encompasses hydrolysis of compounds of formula 11 to the corresponding acids followed by dimerization in the presence of a suitable coupling reagent such as 1,1'-carbonyldiimidazole to form compounds of formula 12. In Step 2, deacylation of compounds of formula 12 is accomplished by heating with concentrated sulfuric acid to obtain compounds of formula 13. Heating of compounds of formula 13 with ammonium hydroxide in Step 3 results in formation of compounds of formula 14. Nitration of compounds of formula 14 in Step 4 is accomplished using nitric acid to obtain compounds of formula 15. Compounds of formula 15 are converted to the corresponding chlorides 16 in Step 5 by heating with phosphorous oxychloride. In Step 6, chlorides 16 are reacted with ammonia followed by heating with phosphorous oxychloride to obtain 2-chloropyridines 17, which are subsequently reduced to diamines 18 in Step 7. In Step 8, diamines 18 are reacted with esters of formula 19 in the presence of trimethylaluminum followed by heating in acetic acid to obtain compounds of formula 20. Depending on the particular example and reaction conditions selected, cyclization may occur without need for heating in acetic acid. Step 9 illustrates alkylation of compounds of formula 20 with ethyl iodide in the presence of base to obtain a mixture of compounds of formula 21 and 22. Those skilled in the art will realize that alternate alkylating agents may be employed to obtain similar compounds bearing different $R_5$ groups.

Scheme IV

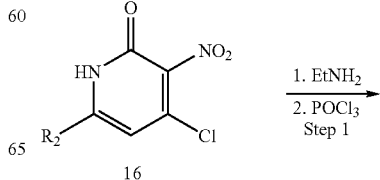

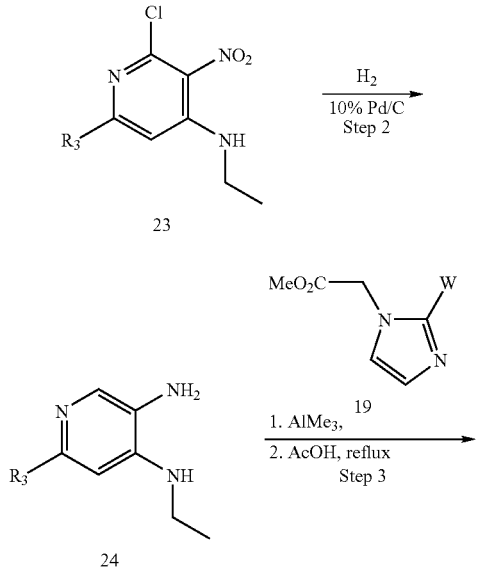

Scheme IV illustrates a variation of Scheme III for specifically preparing compounds of formula 22. In Step 1, compounds of formula 16 are reacted with ethyl amine to form the amino adducts which are subsequently converted to 2-chloropyridines 23 by reaction with phosphorous oxychloride. Those skilled in the art will realize that numerous other suitable amines of formula $R_5NH_2$ may be employed in Step 1 to yield other variants of Formula I. In Steps 2 and 3, hydrogenation of compounds of formula 23 to diamines of formula 24 followed by trimethylaluminum-facilitated coupling and cyclization in acetic acid provides compounds of formula 22. Depending on the particular example and reaction conditions selected, cyclization may occur without need for heating in acetic acid Scheme V

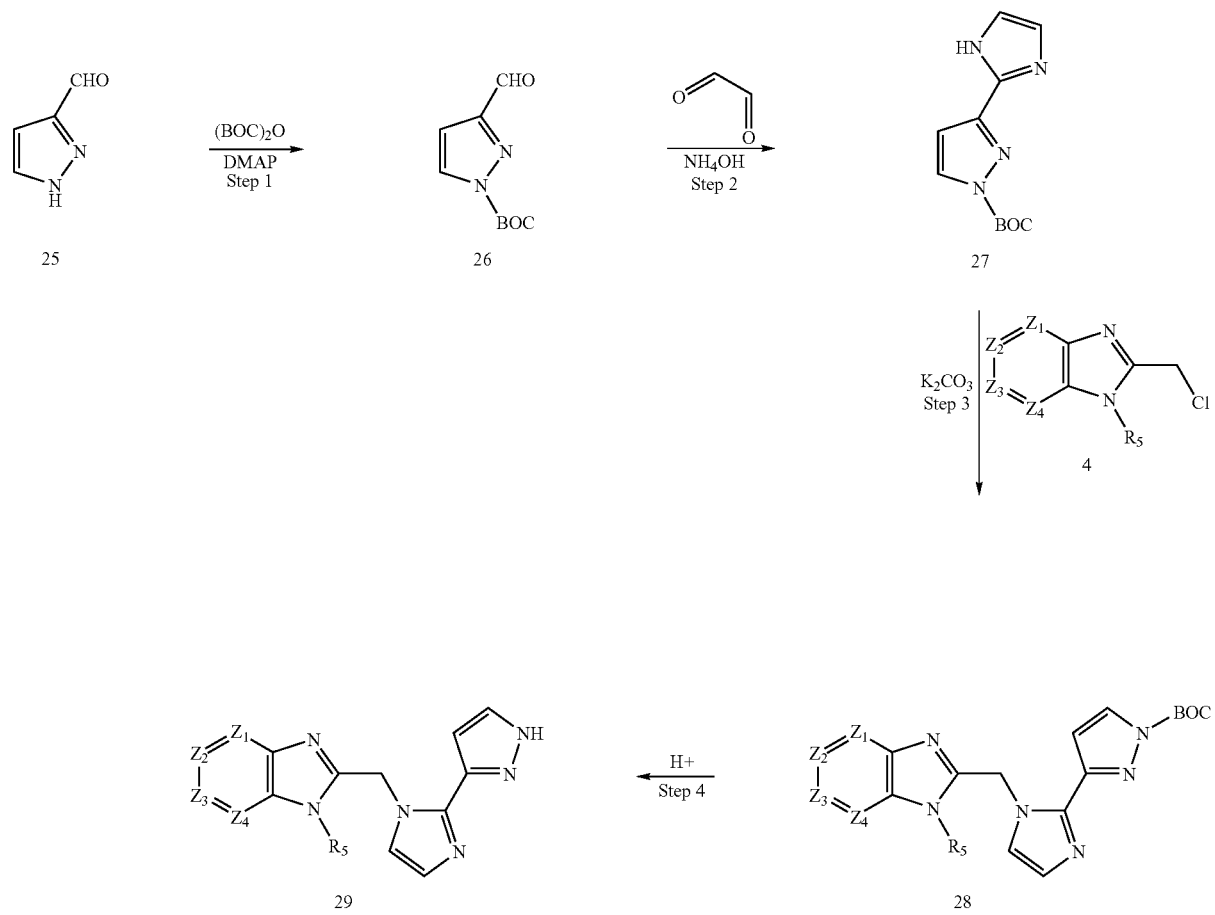

Scheme V illustrates a route employing a protecting group strategy for preparing pyrazole compounds of formula 29. In Step 1, pyrazole 25 is reacted with di-tert-butyldicarbonate in the presence of 4-dimethylaminopyridine to obtain 26. Reaction with glyoxal and ammonium hydroxide provides 27. Reaction of 27 with chloromethyl compounds of formula 4 in the presence of base provides compounds of formula 28. Deprotection of compounds of formula 28 with acid in Step 4 provides pyrazoles of formula 29.

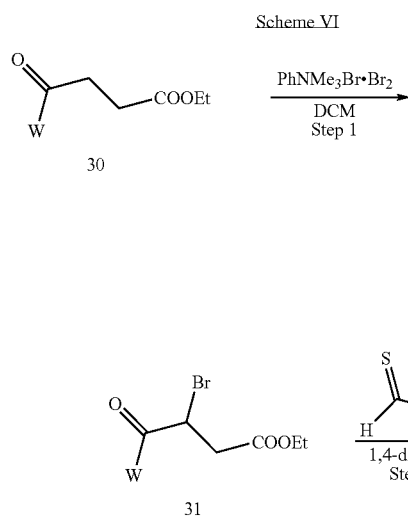

Scheme VI

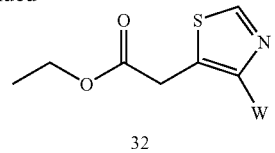

32

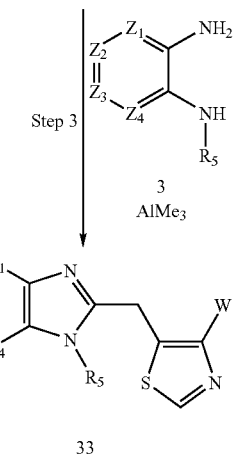

Scheme VI provides a route for preparing thiazole compounds of formula 33. Step 1 involves bromination of ketoesters of formula 30 to form α-bromoketones of formula 31. In Step 2, compounds of formula 31 are reacted with thioformamide to obtain thiazoles of formula 32. Condensation of 32 with 3 in Step 3 in the presence of trimethylaluminum provides compounds of formula 33. Depending on the particular reactants and conditions employed in Step 3, the product mixture may require heating in a suitable solvent such as acetic acid to enhance formation of 33.

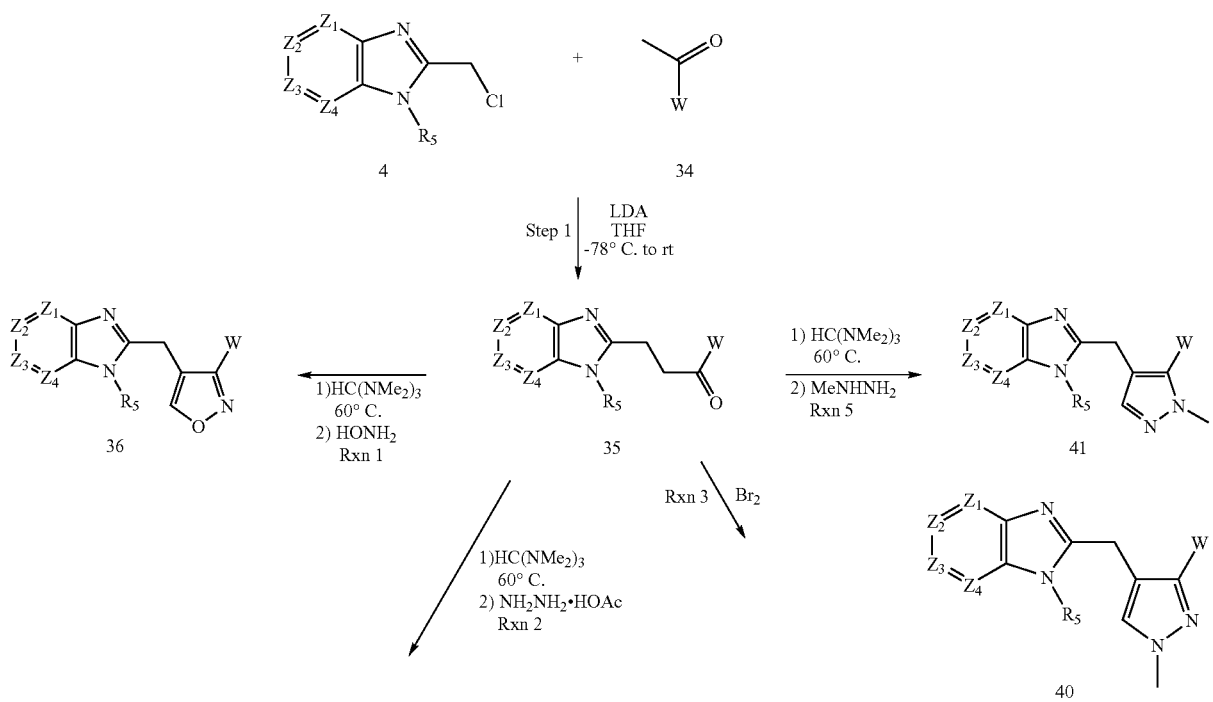

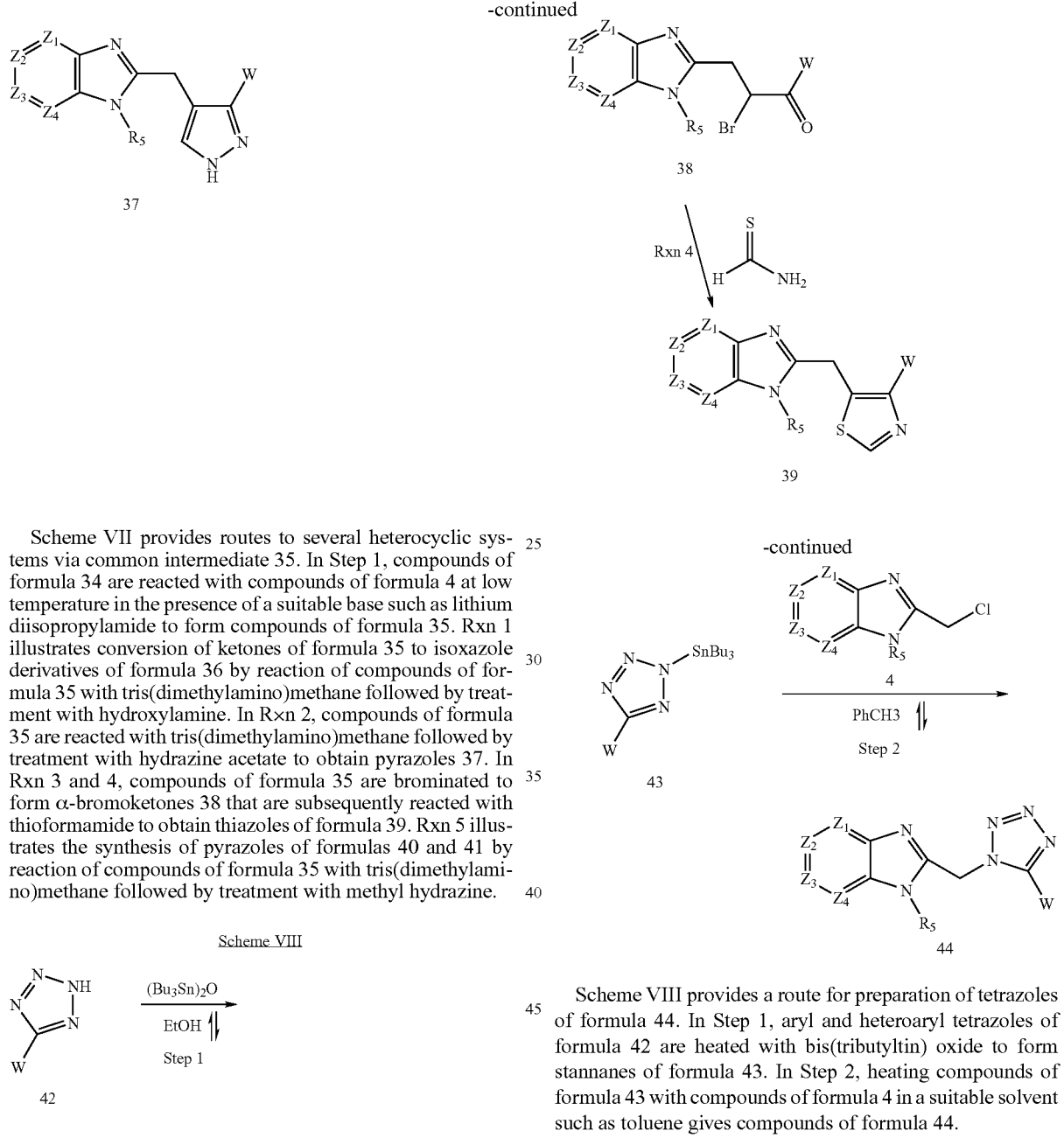

Scheme VII provides routes to several heterocyclic systems via common intermediate 35. In Step 1, compounds of formula 34 are reacted with compounds of formula 4 at low temperature in the presence of a suitable base such as lithium diisopropylamide to form compounds of formula 35. Rxn 1 illustrates conversion of ketones of formula 35 to isoxazole derivatives of formula 36 by reaction of compounds of formula 35 with tris(dimethylamino)methane followed by treatment with hydroxylamine. In Rxn 2, compounds of formula 35 are reacted with tris(dimethylamino)methane followed by treatment with hydrazine acetate to obtain pyrazoles 37. In Rxn 3 and 4, compounds of formula 35 are brominated to form α-bromoketones 38 that are subsequently reacted with thioformamide to obtain thiazoles of formula 39. Rxn 5 illustrates the synthesis of pyrazoles of formulas 40 and 41 by reaction of compounds of formula 35 with tris(dimethylamino)methane followed by treatment with methyl hydrazine.

Scheme VIII provides a route for preparation of tetrazoles of formula 44. In Step 1, aryl and heteroaryl tetrazoles of formula 42 are heated with bis(tributyltin) oxide to form stannanes of formula 43. In Step 2, heating compounds of formula 43 with compounds of formula 4 in a suitable solvent such as toluene gives compounds of formula 44.

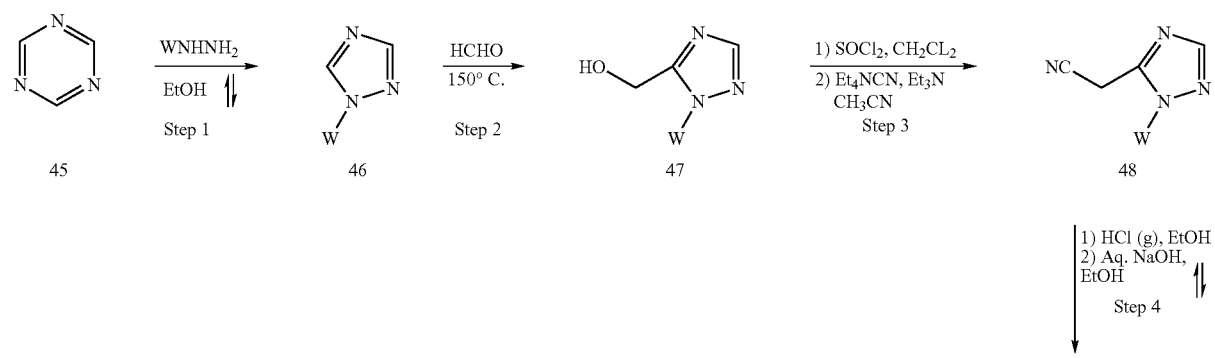

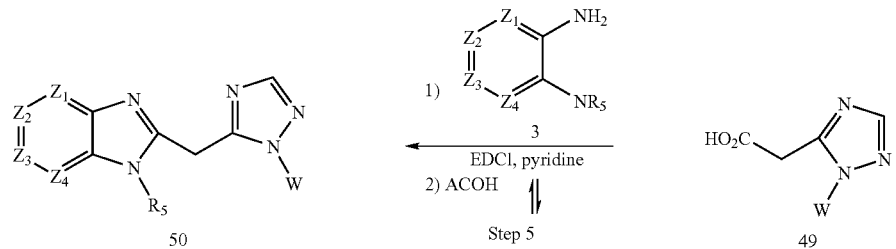

Scheme IX illustrates the synthesis of triazoles of formula 50. In Step 1, aryl and heteroaryl hydrazines are reacted with 1,3,5-triazine 45 to obtain triazoles of formula 46. In Step 2, heating compounds of formula 46 with formaldehyde provides alcohols of formula 47. In Step 3 alcohols of formula 47 are converted to the corresponding chlorides by treatment with thionyl chloride. The chlorides are subsequently converted to nitriles 48 by the action of tetraethyl ammonium cyanide. Cyanides 48 are hydrolyzed in Step 4 to carboxylic acids 49. In Step 5, carboxylic acids of formula 49 are coupled with diamines 3 in the presence of EDCI [1-(3-dimethylaminopropyl)-3-ethylcarbodiimide hydrochloride] or other suitable coupling reagents followed by heating in acetic acid to complete cyclization of the intermediate amino amides to compounds of formula 50.

compounds of formula 55. Subsequent treatment of compounds of formula 55 with acid in Step 3' provides compounds of formula 52.

The invention is illustrated further by the following examples, which are not to be construed as limiting the invention in scope or spirit to the specific procedures described in them. Additional compounds encompassed by this invention beyond the accompanying Examples may be prepared using methods known to those skilled in the art of chemical synthesis. Those having skill in the art will recognize that the starting materials may be varied and additional steps employed to produce compounds encompassed by the present inventions, as demonstrated by the following examples. In some cases, protection of reactive functionalities may be necessary to achieve some the desired transformations. In general, such

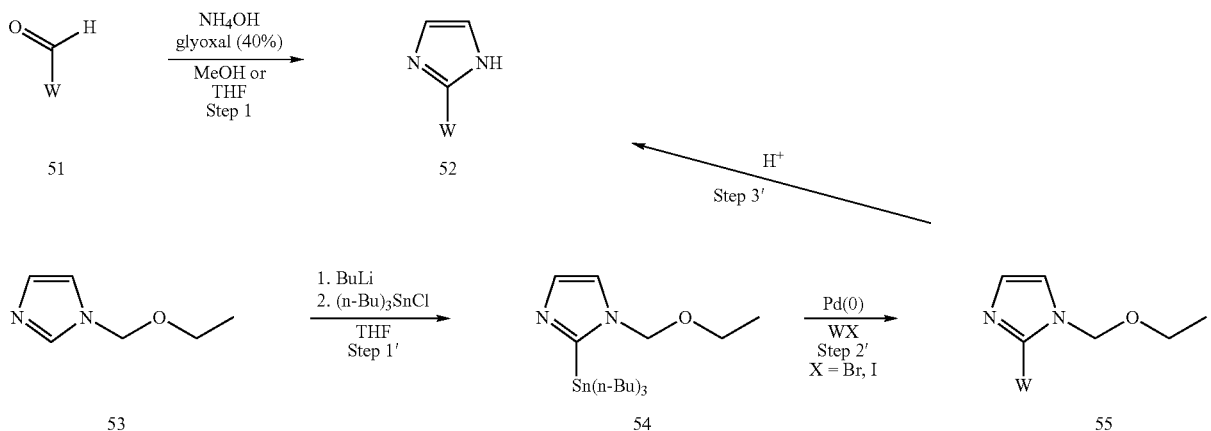

Scheme X illustrates two routes for the synthesis of imidazoles of formula 52, which are intermediates in the synthesis of selected compounds of Formula I. In Step 1, aryl and heteroaryl aldehydes are treated with glyoxal and ammonium hydroxide to form imidazoles of formula 52. In Step 1', imidazole 53 is treated with butyl lithium followed by tri-n-butyltin chloride to obtain compounds of formula 54, which must be handled with care to avoid decomposition. In Step 2', compounds of formula 54 are utilized in palladium cross-coupling reactions with aryl and heteroaryl halides to obtain need for protecting groups, as well as the conditions necessary to attach and remove such groups, will be apparent to those skilled in the art of organic synthesis.

Preparation of Starting Materials and Intermediates

The starting materials and various intermediates may be obtained from commercial sources, prepared from commercially available organic compounds, or prepared using known synthetic methods. Representative examples of methods suitable for preparing intermediates of the invention are set forth below.

Example 1

Synthesis of 1-Propyl-2-{[2-(2-fluoropyrid-6-yl)-1H-imidazol-1-yl]methyl}-5-cyano-1H-benzimidazole

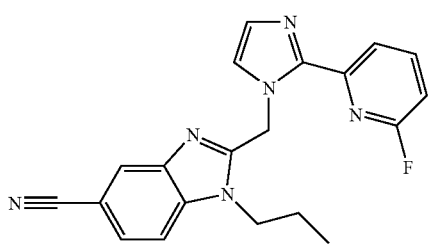

1. Preparation of 4-n-Propylamino-3-nitrobenzonitrile

To a stirring suspension of 4-chloro-3-nitrobenzonitrile (7.30 g, 40 mmol) in isopropanol (30 mL) is added n-propylamine (9.87 mL, 120 mmol). The mixture is stirred at room temperature for 5 h, and the solid is then collected by filtration to give 4-n-propylamino-3-nitrobenzonitrile as a yellow solid. $^1$H NMR (CDCl$_3$) δ 8.51 (1H, q), 8.42 (1H, br s), 7.60 (1H, m), 6.91 (1H, d), 3.33 (2H, q), 1.84-1.74 (2H, m), 1.07 (3H, t). LRMS 206.3 (MH+).

2. Preparation of 3-Amino-4-n-propylaminobenzonitrile

To a Parr bottle containing 4-n-propylamino-3-nitrobenzonitrile (7.63 g, 37.2 mmol) in ethyl acetate (38 mL) is added 5% Pd/C (50% wet, 633 mg). The Parr bottle is sealed in a mechanical shaker, evacuated, and then purged with nitrogen followed by hydrogen. The system is pressurized to 50 PSI of hydrogen at room temperature and mechanical shaking engaged. After 2 hours, shaking is stopped, and the system purged with nitrogen prior to opening the vessel. The reaction mixture is filtered through celite, concentrated in vacuo, and the obtained solid recrystallized by dissolving in ethyl acetate (15 mL), heating, and adding hexanes (15 mL), to give 3-Amino-4-n-propylaminobenzonitrile as gray crystals. $^1$H NMR (CDCl$_3$) δ 7.14 (1H, dd), 6.92 (1H, d), 6.56 (1H, d), 3.98 (1H, br s), 3.30 (2H, br s), 3.12 (2H, t), 1.75-1.65 (2H, m), 1.03 (3H, t). LRMS calcd 175.23, found 176.2 (MH+).

3. Preparation of 1-Propyl-2-{[2-(2-fluoropyrid-6-yl)-1H-imidazol-1-yl]methyl}-5-cyano-1H-benzimidazole Method A (A) Preparation of 1-n-Propyl-2-chloromethyl-5-cyanobenzimidazole hydrochloride i) A solution of 3-amino-4-n-propylaminobenzonitrile (7.38 g, 42.1 mmol) and ethyl chloroacetimidate hydrochloride (9.92 g, 63.2 mmol) in ethanol (100 mL) is heated at reflux for 17 h, then cooled and concentrated to give 1-n-Propyl-2-chloromethyl-5-cyanobenzimidazole hydrochloride. Prior to use in the next step, this material is converted to free base by adding aqueous bicarbonate and extracting with dichloromethane, drying (Na$_2$SO$_4$), and concentrating.

ii) Alternatively, chloroacetylchloride rather than ethyl chloroacetimidate can by used: To a solution of 3-amino-4-n-propylaminobenzonitrile (5.15 g, 29.4 mmol) and triethylamine (4.51 mL) in ethyl acetate (52 mL) at room temperature, chloroacetyl chloride (2.57 mL) is added slowly. After stirring the reaction mixture for 30 minutes at room temperature, acetic acid (5 mL) is added and the reaction mixture heated to reflux. After heating for 20 h, the reaction mixture is cooled to room temperature and diluted with water (50 mL). The organic solution is washed twice with 1.0 M sodium hydroxide (2×50 mL), then washed with an aqueous solution of 0.25 M KH$_2$PO$_4$ (50 mL), followed by brine (50 mL). The organic layer is dried (sodium sulfate), concentrated in vacuo, and the solid recrystallized by heating in ethyl acetate (20 mL), adding hexane (40 mL) and cooling to room temperature with stirring to afford 1-n-Propyl-2-chloromethyl-5-cyanobenzimidazole as brown crystals. $^1$H NMR (CDCl$_3$): δ 8.08 (d, J=0.8 Hz, 1H), 7.57 (dd, J=1.65, 8.52 Hz, 1H), 7.45 (d, J=8.24 Hz, 1H), 7.26 (s, 1H), 4.84 (s, 2H) 4.24 (t, J=7.6 Hz, 2H), 1.94 (pentet, J=7.4. 7.6 Hz, 2H), 1.03 (t, S=7.4 Hz, 3H).

(B) Preparation of 1-Propyl-2-{[2-(2-fluoropyrid-6-yl)-1H-imidazol-1-yl]methyl}-5-cyano-1H-benzimidazole To a stirring suspension of sodium hydride (2.25 g of 60% in oil) in DMF (10 mL) at 0° a solution of 2-Fluoro-6-(1H-imidazol-2-yl)-pyridine (7.7 g, 47.2 mmol) in DMF (20 mL) is added. After stirring for 5 minutes, a solution of 1-n-Propyl-2-chloromethyl-5-cyanobenzimidazole (11 g, 47.2 mmol) and sodium iodide (20 mg) in DMF (80 mL) is added. The reaction mixture is stirred for 6 h, gradually warmed to room temperature. The reaction mixture is cooled, water added, the solid collected, rinsed with water and dried to afford the title compound, 1-Propyl-2-{[2-(2-fluoropyrid-6-yl)-1H-imidazol-1-yl]methyl}-5-cyano-1H-benzimidazole.

Method B

Trimethylaluminum (0.54 mL of 2.0M in toluene, 1.09 mmol) is added dropwise to a solution of 3-Amino-4-propylaminobenzonitrile (152 mg; 0.87 mmol) in dichloromethane (10 mL), and the mixture was stirred at room temperature for 1 hr. A solution of [2-(2-Fluoropyridin-6-yl)-imidazol-1-yl] acetic acid methyl ester (102 mg; 0.43 mmol) in dichloromethane (5 mL) is added all at once, and the mixture heated at reflux for 16 hr. The brown solution is cooled to room temperature and treated dropwise with methanol (1 mL) then water (2 mL) and stirred at room temperature for 15 min. Anhydrous sodium sulfate is added until the gel becomes solid, the mixture is diluted with dichloromethane (100 mL) and filtered through celite. The filtrate is concentrated to give a brown oil which is dissolved in acetic acid (7 mL) and heated at 100° for 72 hr. The mixture is cooled to room temperature and concentrated. The residue is dissolved in ethyl acetate (15 mL), washed with saturated aqueous NaHCO$_3$ (1×50 mL), then brine (1×50 mL), dried (MgSO$_4$), and concentrated, and the residue purified by preparative thin layer chromatography to give 1-n-Propyl-2-{[2-(2-fluoropyrid-6-yl)-1H-imidazol-1-yl]methyl}-5-cyano-1H-benzimidazole as a light brown semi-solid (57 mg).

Method C

A solution of [2-(6-Fluoropyridin-2-yl)-imidazol-1-yl] acetic acid hydrochloride (274 mg; 1.06 mmol) and triethylamine (0.15 mL; 1.06 mmol) in dichloromethane (10 mL) is treated dropwise with oxalyl chloride (0.64 mL of a 2M solution in dichloromethane; 1.27 mmol), and the resulting suspension stirred at room temperature for 2 hr.

The mixture is concentrated and the residue suspended in dichloromethane (10 mL). A solution of 3-Amino-4-propylaminobenzonitrile (185 mg; 1.06 mmol) in dichloromethane (5 mL) is added and the mixture stirred at room temperature for 16 hr, then concentrated. The residue is dissolved in acetic acid (10 mL) and heated at 100° for 1 hr. The mixture is cooled to room temperature, concentrated, taken up in ethyl acetate (150 mL), washed with saturated aqueous NaHCO$_3$ (50 mL) and then washed with brine (50 mL), dried (MgSO$_4$), and concentrated to give the crude product as a waxy brown solid (338 mg). This crude product is slurried with diethyl ether (ca. 4 mL) and a few drops of methanol, then filtered to give 1-n-Propyl-2-{[2-(2-fluoropyrid-6-yl)-1H-imidazol-1-yl]methyl}-5-cyano-1H-benzimidazole as a pale brown solid (230 mg).

$^1$H NMR (399.96 MHz, CDCl$_3$): δ 8.17 (dd, J=2.0, 7.6 Hz, 1H, H-18), 8.05 (s, 1H, H-4), 7.88 (q, J=8.0 Hz, 1H, H-19), 7.52 (d, J=8.4 Hz, 1H, H-6), 7.41 (d, J=8.4 Hz, 1H, H-7), 7.21 (s, 1H, H-14), 7.18 (s, 1H, H-15), 6.28 (s, 2H, H-13), 4.28 (t, J=7.6 Hz, 2H, H-10), 1.68 (dt, J=7.6 Hz, 2H, H-11), 0.84 (t, J=7.6 Hz, 3H, H-12).

$^{13}$C NMR (100.57 MHz, CDCl$_3$, $^1$H decoupled at 399.957 MHz): δ, 162.36 (d, J$_{C-F}$=239.6 Hz), 152.53, 148.69 (d, J$_{C-F}$=13.0 Hz), 142.36 (d, J$_{C-F}$=7.6 Hz), 142.31, 142.28, 138.42, 129.96, 126.55, 125.31, 124.23, 120.27 (d, J$_{C-F}$=3.8 Hz), 119.96, 111.23, 108.52 (d, J$_{C-F}$=35.9 Hz), 105.70, 46.10, 44.57, 23.43, 11.27.

Example 2

Synthesis of 1-Ethyl-2-{[2-(3-fluorophenyl)-pyrazol-3-yl]methyl}-5-cyano-1H-benzimidazole

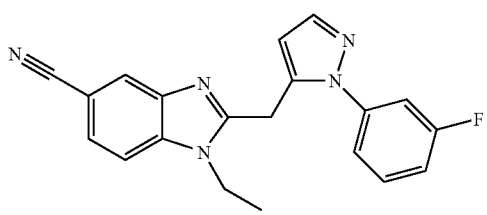

1. Preparation of 1-(3-Fluorophenyl)-5-carboxymethylpyrazole

To a stirring solution of ethyl vinyl ether (340 ml, 3.55 mol) in diethyl ether (200 mL), cooled in an ice bath, is added dropwise a solution of malonyl dichloride (69 mL, 0.71 mol) in ether (20 mL). Stirring is continued at 0° C. for 2 h, then a solution of triethylamine (196 mL) and ethanol (350 mL) in ether (210 mL) is added with cooling. More ether is added to further precipitate triethylamine hydrochloride, the mixture is then filtered, and the filtrate concentrated. The residue is taken up in ethanol (710 mL), then triethyl orthoformate (177 mL, 1.07 mol) and concentrated HCl (5 mL) is added. The mixture is stirred overnight then concentrated. To the residue is added ethanol (500 mm) and 3-Fluorophenylhydrazine hydrochloride (27.6 g, 0.17 mol). The mixture is heated at reflux for 2 h, then cooled and concentrated. Ethyl acetate is added, the mixture is washed with aqueous bicarbonate, then with water, dried (Na$_2$SO$_4$), concentrated, and the residue purified by silica gel chromatography. Ethanol (20 mL) and 1 N NaOH (100 mL) are added, and heated at reflux for 1 h. The mixture is cooled and washed with ethyl acetate. The aqueous layer is cooled and acidified, the solid collected by filtration, rinsed well with water and dried to give 1-(3-Fluorophenyl)-5-carboxymethylpyrazole as a gold solid. $^1$H NMR (CDCl$_3$): δ 7.68 (d, J=1.8 Hz, 1H), 7.41-7.48 (m, 1H), 7.10-7.26 (m, 3H), 6.44 (d, J=2.1 Hz, 1H), 3.77 (s, 2H). LCMS: 221.2 (MH$^+$), 219.2 (MH$^-$).

2. Preparation of 1-Ethyl-2-{[2-(3-fluorophenyl)-pyrazol-3-yl]methyl}-5-cyano-1H-benzimidazole To a stirring solution of 3-amino-4-ethylaminobenzonitrile (887 mg, 5.5 mmol) and 1-(3-Fluorophenyl)-5-carboxymethylpyrazole (1.10 g, 5 mmol) in pyridine (5 mL) is added 1-(3-dimethylaminopropyl)-3-ethylcarbodiimide hydrochloride (1.15 g, 6 mmol). The mixture is stirred at room temperature for 17.5 h, then concentrated. The residue is cooled in an ice bath, aqueous HCl is added with stirring, the precipitate is collected by filtration, rinsed well with water and dried. The solid is added to acetic acid (75 mL) and heated at reflux for 5.5 h. The mixture is cooled, concentrated, and purified by silica gel chromatography to give 1-Ethyl-2-{[2-(3-fluorophenyl)-pyrazol-3-yl]methyl}-5-cyano-1H-benzimidazole. The product is converted to the mesylate salt in acetone. $^1$H NMR (CDCl$_3$): δ 8.17 (s, 1H), 7.89 (d, J=8.52 Hz, 1H), 7.68-7.75 (m 1H), 7.44-7.54 (m, 2H), 7.37-7.40 (m, 1H), 7.21-7.28 (m, 1H), 6.35 (d, J=1.65 Hz, 1H), 4.65 (s, 2H), 4.29 (q, J=7.14 Hz, 2H), 2.34 (s, 3H), 1.19 (t, J=7.14 Hz, 3H). LCMS 346.0 (MH$^+$), 344.4 (MH$^-$).

Example 3

Synthesis of 1-Ethyl-2-{[1-(3-fluorophenyl)-1,2,4-triazol-5-yl]methyl}-5-cyano-1H-benzimidazole

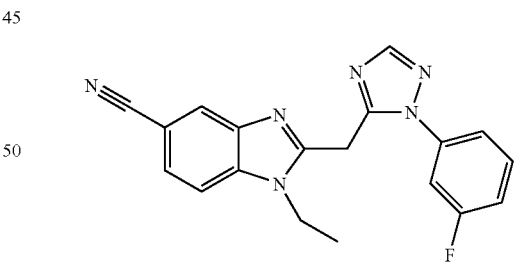

1. Preparation of 1-(3-Fluorophenyl)-1,2,4-triazole

A mixture of 1,3,5-triazine (1 g, 12.3 mmol) and 3-Fluorophenylhydrazine hydrochloride (2 g, 12.3 mmol) in ethanol (20 mL) is heated at reflux overnight. After concentrating, ethyl acetate is added, the mixture is washed with aqueous bicarbonate followed by saturated aqueous sodium chloride, dried (MgSO$_4$), and concentrated to give 1.8 g of crude 1-(3-Fluorophenyl)-1,2,4-triazole. $^1$H NMR (CDCl$_3$): δ 8.57 (s, 1H), 8.12 (s, 1H), 7.46-7.51 (m, 3H), 7.08-7.15 (m, 1H). LCMS 164.1 (MH$^+$).

2. Preparation of 1-(3-Fluorophenyl)-5-hydroxymethyl-1,2,4-triazole

A mixture of the crude 1-(3-Fluorophenyl)-1,2,4-triazole and formaldehyde (10 mL of 37 wt % in water) is heated at 150° C. in a sealed tube for 48 h. After cooling the reaction vessel, the reaction mixture is extracted with dichloromethane, dried (MgSO$_4$), concentrated, and the residue purified using silica gel chromatography to afford 1-(3-Fluorophenyl)-5-hydroxymethyl 1,2,4-triazole. $^1$H NMR (CDCl$_3$): δ 8.02 (s, 1H), 7.42-7.53 (m, 3H), 7.22-7.29 (m, 1H), 4.81 (s, 2H). LCMS 194.2 (MH$^-$).

3. Preparation of 1-(3-Fluorophenyl)-5-cyanomethyl-1,2,4-triazole 1-(3-Fluorophenyl)-5-hydroxymethyl-1,2,4-triazole (1.7 g) is treated with thionyl chloride (10 mL) in dichloromethane (20 mL) at room temperature overnight. The solvent is then removed. To the residue is added acetonitrile (20 mL), tetraethylammonium cyanide (2.75 g, 17.6 mmol), and triethylamine (2.5 mL, 17.6 mmol). The mixture is stirred at room temperature for 2 h. The mixture is diluted with ethyl acetate, washed with aqueous bicarbonate, and then with saturated aqueous sodium chloride, dried (Na$_2$SO$_4$), concentrated and the residue purified by silica gel chromatography to give crude 1-(3-Fluorophenyl)-5-cyanomethyl-1,2,4-triazole. $^1$H NMR (CDCl$_3$): δ 8.06 (s, 1H), 7.52-7.62 (m, 1H), 7.20-7.30 (m, 3H), 3.98 (s, 2H). LCMS 203.0 (MH$^+$), 201.2 (MH$^-$).

4. Preparation of 1-(3-Fluorophenyl)-5-carboxymethyl-1,2,4-triazole

Crude 1-(3-Fluorophenyl)-5-cyanomethyl-1,2,4-triazole (0.9 g) is taken up in ethanol (50 mL) and cooled in an ice bath. HCl gas is bubbled through for 0.5 h. Water (10 mL) is added and the mixture heated at 65° C. for 2 h. After cooling, most of the ethanol is removed on a roto-evaporator, 3 N NaOH (25 mL) and ethanol (25 mL) are then added. The solution is heated at reflux for 2 h, cooled, and then extracted with diethyl ether (3×). The aqueous layer is acidified to pH 2, extracted with ethyl acetate. The organic layer is washed with saturated aqueous sodium chloride, dried (Na$_2$SO$_4$), and concentrated to give 1-(3-Fluorophenyl)-5-carboxymethyl-1,2,4-triazole. $^1$H NMR (CDCl$_3$): δ 8.08 (s, 1H), 7.50-7.57 (m, 1H), 7.22-7.32 (m, 3H), 4.01 (s, 2H).

5. Preparation of 1-Ethyl-2-{[1(3-fluorophenyl)-1,2,4-triazol-5-yl]methyl}-5-cyano-1H-benzimidazole Using the procedure described in Example 2, Step 2, 1-(3-fluorophenyl)-5-carboxymethyl-1,2,4-triazole is converted to 1-Ethyl-2-{[1-(3-fluorophenyl)-1,2,4-triazol-5-yl]methyl}-5-cyano-1H-benzimidazole. $^1$H NMR (CDCl$_3$): δ 8.03 (s, 1H); 8.01 (s, 1H); 7.42-7.56 (m, 5H); 7.22 (m, 1H); 4.51 (s, 2H); 4.43 (q, 2H); 1.45 (t, 3H). LCMS 347.3 (MH$^+$).

Example 4

Synthesis of 1-Propyl-2-[(5-phenyl-1H-tetrazol-1-yl)methyl]-1H-benzimidazole

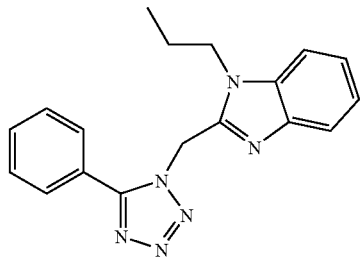

1. Preparation of 2-(Tri-n-butyltin)-5-phenyl-1h-tetrazole

A mixture of 5-phenyl-1H-tetrazole (200 mg, 1.22 mmol) and bis(tri-n-butyltin)oxide (0.31 mL, 0.61 mmol) in ethanol (2 mL) is heated at reflux for 10 minutes. The mixture is cooled, concentrated, and the crude 2-(Tri-n-butyltin)-5-phenyl-1H-tetrazole used directly.

2. Preparation of 1-Propyl-2-[5-phenyl-1H-tetrazol-1-yl)methyl]-1H-benzimidazole Crude 2-(tri-n-butyltin)-5-phenyl-1H-tetrazole (2.09 g, 4.8 mmol) and 1-propyl-2-chloromethylbenzimidazole (1.0 g, 4.8 mmol) are heated in toluene (5 mL) at reflux overnight. The solvent is removed in vacuo, the residue washed with hexane, and then purified by preparative chromatography to give 1-Propyl-2-[(5-phenyl-1H-tetrazol-1-yl)methyl]-1H-benzimidazole as the minor isomer. $^1$H NMR (CDCl$_3$): δ 8.05-8.12 (m, 2H); 7.77 (m, 1H); 7.58-7.62 (m, 2H); 7.29-7.43 (m, 3H); 5.86 (5, 2H); 4.40 (t, 2 h); 1.85 (m, 2H); 1.01 (t, 3H).

Example 5

Synthesis of 1-Ethyl-2-{[2-(3-fluorophenyl)-pyrazol-3-yl]methyl}-5-acetyl-1H-benzimidazole

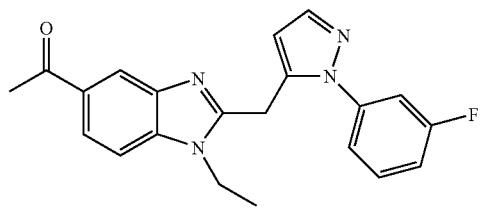

A mixture of 1-Ethyl-2-{[2-(3-fluorophenyl)-pyrazol-3-yl]methyl}-5-bromo-1H-benzimidazole (200 mg, 0.5 mmol), tributyl(1-ethoxyvinyl)tin (0.34 ml, 1.0 mmol), and tetrakis(triphenylphosphine)palladium(0) (29 mg) in toluene (10 mL) is heated at reflux for 1 h under argon. The solvent is removed in vacuo, the residue is then dissolved in 10% HCl (5 mL) and THF (5 mL). The mixture is stirred at room temperature for 0.5 h, then extracted with ethyl acetate. The aqueous layer is adjusted to pH 9, extracted with dichloromethane, and the organic layer dried (Na$_2$SO$_4$), concentrated, and the residue purified by preparative silica gel chromatography to give 1-Ethyl-2-{[2-(3-fluorophenyl)-pyrazol-3-yl]methyl}-5-acetyl-1H-benzimidazole. $^1$H NMR (CDCl$_3$): δ 8.36 (d, 1H); 7.99 (dd, 1H); 7.645 (d, 1H); 7.25-7.49 (m, 4H); 7.14 (m, 1H); 6.21 (d, 1 h); 4.36 (s, 2H); 4.02 (g, 2H); 2.68 (s, 3H); 1.24 (t, 3H).

Example 6

Synthesis of 1-Ethyl-2-{[2-(3-fluorophenyl)-pyrazol-3-yl]methyl}-5-[1-(methoxyimino)ethyl]-1H-benzimidazole

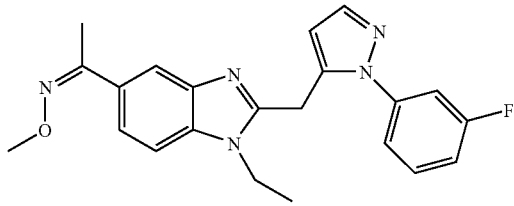

A mixture of 1-Ethyl-2-{[2-(3-fluorophenyl)-pyrazol-3-yl]methyl}-5-acetyl-1H-benzimidazole (23 mg), methoxylamine hydrochloride (15 mg, 3 eq.), and sodium acetate (15 mg, 3 eq.) in methanol (1 mL) is stirred at room temperature overnight. The solvent is removed in vacuo and aqueous sodium bicarbonate added to pH 9, then extracted with ethyl acetate. The organic layer is dried (Na$_2$SO$_4$) and concentrated to give 1-Ethyl-2-{[2-(3-fluorophenyl)-pyrazol-3-yl]methyl}-5-[1-(methoxyimino)ethyl]-1H-benzimidazole. $^1$H NMR (CDCl$_3$): δ 7.94 (d, 1H); 7.73 (dd 1H); 7.73 (dd, 1H); 7.63 (d, 1H); 7.52 (m, 1H); 7.38-7.40 (m, 3H); 7.27 (m, 1H); 6.19 (d, 1H); 4.32 (s, 2H); 3.87-4.10 (m, 5H); 2.30 (s, 3H); 1.22 (t, 3H).

Example 7

Synthesis of 1-Ethyl-2-{[2-(2,5-difluorophenyl)-pyrazol-3-yl]methyl}-5-[5-(4-fluorophenyl)-1,3,4-oxadiazol-2-yl]-1H-benzimidazole

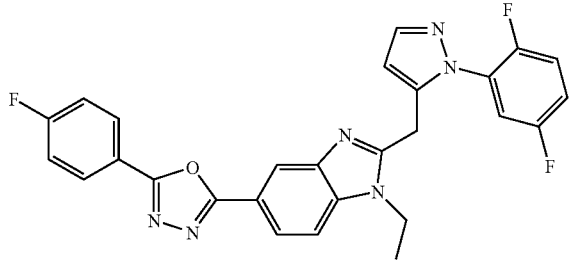

A mixture of 1-Ethyl-2-{[2-(2,5-difluorophenyl)-pyrazol-3-yl]methyl}-1H-benzimadol-5-carboxylate (152 mg) and 4-fluorobenzhydrazide (1.05 eq.) in phosphorous oxychloride (6 mL) is heated at reflux for 1.5 h. The mixture is cooled and concentrated, and then water (5 mL) is added to the residue. After adjusting to pH >7 with saturated aqueous bicarbonate, the solution is extracted with ethyl acetate (3×), and the combined organic layers are washed with water (2×) then with saturated aqueous sodium chloride, dried (MgSO$_4$), concentrated, and the residue purified by preparative silica gel chromatography to give 1-Ethyl-2-{[2-(2,5-difluorophenyl)-pyrazol-3-yl]methyl}-5-[5-(4-fluorophenyl)-1,3,4-oxadiazol-2-yl]-1H-benzimidazole. LCMS MH$^+$ 501.068.

Example 8

Synthesis of 1-Ethyl-2-{[2-(3-fluorophenyl)-1H-imidazol-1-yl]methyl}-5-(1,3,4-oxadiazol-2-yl)-1H-benzimidazole

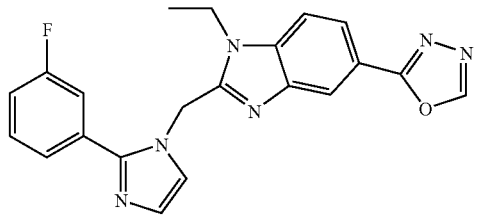

A mixture of 1-ethyl-2-{[2-(3-fluorophenyl)-1H-imidazol-1-yl]methyl}-1H-benzimadol-5-hydrazide (177 my), triethylorthoformate (8 mL) and acetic acid (2 mL) is heated at reflux for 5 h. The reaction is cooled, concentrated, and the residue purified by preparative silica gel chromatography to give 1-Ethyl-2-{[2-(3-fluorophenyl)-1H-imidazol-1-yl]methyl}-5-(1,3,4-oxadiazol-2-yl)-1H-benzimidazole, which was converted to the hydrochloride salt in ethyl acetate. $^1$H NMR (d6 DMSO): δ 9.32 (s, 1H), 8.19 (s, 1H), 8.03 (d, 1H), 7.97-7.95 (m, 2Hm), 7.87 (d, 1H), 7.72 (m, 1H), 7.66-7.60 (m, 2H), 7.54-7.50 (m, 1H), 5.99 (s, 2H), 4.34 (q, 2H), 1.31 (t, 3H), LCMS MH$^+$ 389.4

Example 9

Synthesis of 1-Ethyl-2-{[2-(2,5-difluorophenyl)-1H-imidazol-1-yl]methyl}-5-amino-1H-benzimidazole

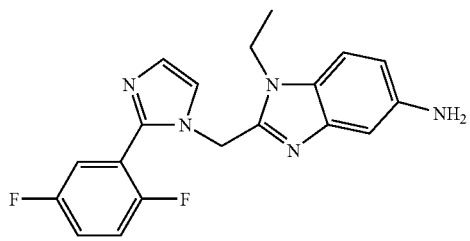

1. Preparation of 4-Fluoro-3-nitroacetanilide

4-Fluoro-3-nitroaniline (5.2 g) is treated with acetic anhydride (1.1 eq.) in dichloromethane at room temperature for 1 h. The reaction is concentrated, the residue taken up in dichloromethane and washed with aqueous sodium bicarbonate (2×) then with saturated aqueous sodium chloride, dried (MgSO$_4$), and concentrated to give 4.7 g of crude 4-Fluoro-3-nitroacetanilide.

2. Preparation of 3-Nitro-4-(ethylamino)acetanilide

A mixture of crude 4-Fluoro-3-nitroacetanilide (4.6 g), ethylamine (23 mL of 2M in THF), and potassium carbonate (3.5 g) in DMF (100 mL) is stirred at room temperature for 4 h, then heated at 60° C. for 5 h. The reaction is allowed to cool, water (150 mL) is added, and extracted with ethyl acetate (3×). The combined organic extracts are washed with water (3×), then washed with saturated aqueous sodium chloride, dried (MgSO$_4$), and concentrated to give crude 3-Nitro-4-(ethylamino)acetanilide.

3. Preparation of N-[3-Amino-4-(ethylamino)phenyl]acetamide

Crude 3-Nitro-4-(ethylamino)acetanilide (4.8 g), 10% Pd/C (0.5 g), methanol (50 mL) and ethyl acetate (200 mL) are placed in a Paar apparatus under hydrogen at 50 psi for 5 h. The mixture is filtered through Celite and concentrated to give 4 g of crude N-[3-Amino-4-(ethylamino)phenyl]acetamide

4. Preparation of N-{2-{[2-(2,5-Difluorophenyl)-1H-imidazol-1-yl]methyl}-1-ethyl-1H-benzimidazol-5-yl}acetamide Using the procedure described in Example 1 Method A, crude N-[3-amino-4-(ethylamino)phenyl]acetamide is converted to N-{2-{[2-(2,5-Difluorophenyl)-1H-imidazol-1-yl]methyl}-1-ethyl-1H-benzimidazol-5-yl}acetamide.

5. Preparation of 1-Ethyl-2-({[2-(2,5-difluorophenyl)-1H-imidazol-1-yl]methyl}-5-amino-1H-benzimidazole Crude N-{1-Ethyl-2-{[2-(2,5-difluorophenyl)-1H-imidazol-1-yl]methyl}-1H-benzimidazol-5-yl}acetamide is treated with 10% aqueous HCl (20 mL) in methanol (10 mL) at reflux for 1.5 h. After cooling, the methanol is removed in vacuo, and the aqueous layer washed with ethyl acetate. The aqueous layer is adjusted to pH 10 with 3 N NaOH, then extracted with ethyl acetate (3×), and the combined organic extracts washed with water (2×) then saturated aqueous sodium chloride, dried (MgSO$_4$) and concentrated to give 1-Ethyl-2-{[2-(2,5-difluorophenyl)-1H-imidazol-1-yl]methyl}-5-amino-1H-benzimidazole. LCMS MH$^+$ 354.4.

Example 10

Synthesis of 1-Ethyl-2-{[2-(3-fluorophenyl)-pyrazol-3-yl]methyl}-5-(1,2,4-triazol-1-yl)-1H-benzimidazole

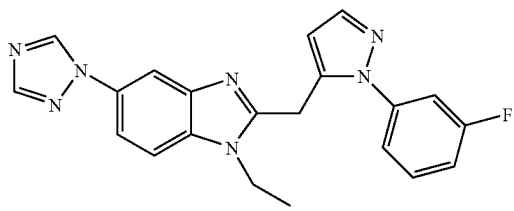

1-Ethyl-2-{[2-(3-fluorophenyl)-pyrazol-3-yl]methyl}-5-amino-1H-benzimidazole (274 mg) is treated with N,N-dimethylformamide azine hydrochloride (1 eq) in toluene (10 mL) and methoxyethanol (10 mL) and refluxed for 6 h. After cooling and concentrating, the residue is treated with water and extracted with dichloromethane (2×). The aqueous layer is adjusted to pH 8 with aqueous sodium bicarbonate and extracted with dichloromethane (2×). The combined organic extracts are washed with saturated aqueous sodium chloride, dried (MgSO$_4$), concentrated, purified by preparative silica gel chromatography, and triturated with ether to afford 1-Ethyl-2-{[2-(3-fluorophenyl)-pyrazol-3-yl]methyl}-5-(1,2,4-triazol-1-yl)-1H-benzimidazole, which is converted to the hydrochloride salt in ethyl acetate. LCMS MH$^+$ 406.2.

Example 11

Synthesis of 1-ethyl-2-{[2-(2,5-difluorophenyl)-1H-imidazol-1-yl]methyl}-5-(1,2,3-triazol-1-yl-4-carboxylate)-1H-benzimidazole

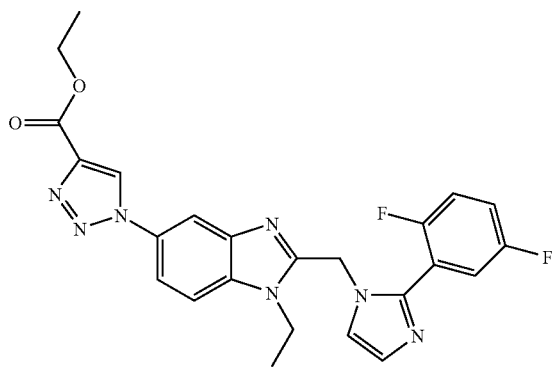

1. Preparation of 1-Ethyl-2-{[2-(2,5-difluorophenyl)-1H-imidazol-1-yl]methyl}-5-azido-1H-benzimidazole To an ice-cold solution of 1-ethyl-2-{[2-(2,5-difluorophenyl)-1H-imidazol-1-yl]methyl}-5-amino-1H-benzimidazole (466 mg) in acetic acid (8 mL) a solution of sodium nitrite (1.1 eq) in water (4 mL) is added dropwise. After stirring at 0° C. for 1 h, a solution of sodium azide (1.3 eq) in water (5 mL) is added dropwise. Stirring is continued for 0.5 h at 0° C., and then at room temperature for 0.5 h. The reaction mixture is concentrated to ⅓ volume, water (10 mL) is added and then mixture is then extracted with ethyl acetate (3×). The combined organic layers are washed with aqueous sodium bicarbonate (2×), then washed with saturated aqueous sodium chloride, dried (MgSO$_4$), and concentrated to give 641 mg of crude 1-Ethyl-2-{[2-(2,5-difluorophenyl)-1H-imidazol-1-yl]methyl}-5-azido-1H-benzimidazole.

2. Preparation of 1-{2-[2-(2,5-Difluoro-phenyl)-imidazol-1-ylmethyl]-1-ethyl-1H-benzoimidazol-5-yl}-1H-[1,2,3]triazole-4-carboxylic acid ethyl ester A mixture of crude 1-ethyl-2-{[2-(2,5-difluorophenyl)-1H-imidazol-1-yl]methyl}-5-azido-1H-benzimidazole (143 mg) and ethyl propiolate (1 eq.) in ethanol (10 mL) is heated at reflux for 6 h. The mixture is cooled, concentrated, and the residue purified by preparative silica gel chromatography to give 1-{2-[2-(2,5-Difluoro-phenyl)-imidazol-1-ylmethyl]-1-ethyl-1H-benzoimidazol-5-yl}-1H-[1,2,3]triazole-4-carboxylic acid ethyl ester. $^1$H NMR (CDCl$_3$): δ 8.51 s, (1H), 8.05 (s, 1H), 7.74 (m, 1H), 7.50-7.39 (m, 4H), 7.21-7.17 (m, 2H), 7.06 (s, 1H), 5.54 (s, 2H), 4.47 (q, 2H), 3.86 (q, 2H), 1.43 (t, 3H), 1.04 (t, 3H), LCMS MH+ 460.6.

Example 12

Synthesis of 1-ethyl-2-{[2-(2,5-difluorophenyl)-pyrazol-3-yl]methyl}-5-(1,2,3,4-tetrazol-1-yl)-1H-benzimidazole

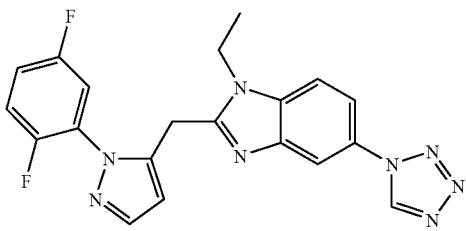

1-Ethyl-2-{[2-(2,5-difluorophenyl)-pyrazol-3-yl]methyl}-5-amino-1H-benzimidazole (104 mg) is treated with triethylorthoformate (4 eq) in acetic acid (10 mL) at reflux for 4 h. After concentrating the solution, acetic acid is re-added, sodium azide (4 eq) added, and the mixture heated at 70° C. for 3 h. After cooling, water (15 mL) is added and the mixture concentrated. The residue is taken up in ethyl acetate, washed with aqueous sodium bicarbonate (2×) then saturated aqueous sodium chloride, dried (MgSO$_4$), concentrated, and purified by preparative silica gel chromatography to give 1-ethyl-2-{[2-(2,5-difluorophenyl)-pyrazol-3-yl]methyl}-5-(1,2,3,4-tetrazol-1-yl)-1H-benzimidazole, which is converted to the hydrochloride salt in ethyl acetate. LCMS MH+ 395.018

Example 13

Synthesis of 1-Ethyl-2-{[2-(2,5-difluorophenyl)-pyrazol-3-yl]methyl}-5-(5-methyl-oxazol-2-yl)-1H-benzimidazole

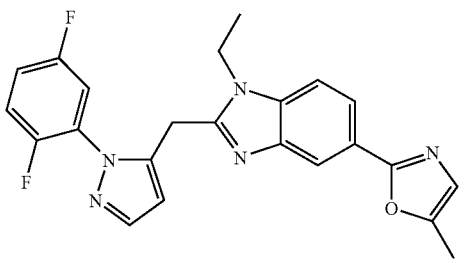

1. Preparation of N-propargyl 1-ethyl-2-{[2-(2,5-difluorophenyl)-pyrazol-3-yl]methyl}-1H-benzimidazole-5-carboxamide Oxalyl chloride (2.5 eq of 2M in dichloromethane) is added dropwise to a solution of 1-ethyl-2-{[2-(2,5-difluorophenyl)-pyrazol-3-yl]methyl}-1H-benzimidazole-5-carboxylate (368 mg) in DMF (5 drops) and dichlormethane (30 mL) at 0° C. The mixture is stirred at 0° C. for 0.5 h, then at room temperature for 1 h. The solution is concentrated, the residue taken up in DMF (30 ml), excess propargylamine added, and the mixture stirred for 6 h. Dilute aqueous sodium bicarbonate is added then extracted with dichloromethane (3×), the combined organic layers washed with saturated aqueous sodium chloride, dried (MgSO$_4$), and concentrated to give 462 my of crude N-propargyl 1-ethyl-2-{[2-(2,5-difluorophenyl)-pyrazol-3-yl]methyl}-1H-benzimidazole-5-carboxamide.

2. Preparation of 1-Ethyl-2-{[2-(2,5-difluorophenyl)-pyrazol-3-yl]methyl}-5-(5-methyl-oxazol-2-yl)-1H-benzimidazole A mixture of crude N-propargyl 1-ethyl-2-{[2-(2,5-difluorophenyl)-pyrazol-3-yl]methyl}-1H-benzimidazole-5-carboxamide (450 mg) and mercury(II) acetate (1 eq) is heated at reflux in acetic acid (15 mL) for 6 h. The mixture is concentrated, saturated aqueous potassium carbonate added and extracted with ethyl acetate (3×). The combined organic layers were washed with water then with saturated aqueous sodium chloride, dried (MgSO$_4$), concentrated, and triturated with ether to give 1-ethyl-2-{[2-(2,5-difluorophenyl)-pyrazol-3-yl]methyl}-5-(5-methyl-oxazol-2-yl)-1H-benzimidazole, which is converted to the hydrochloride salt in ethyl acetate. $^1$H NMR (d6 DMSO): δ 8.16 (s, 1H), 8.09-9.01 m. (2H), 7.78 (m, 1H), 7.62 (m, 1H), 7.49-7.45 (m, 3H), 7.04 (m, 1H), 6.56 (s, 1H), 4.70 (s, 2H), 4.36 (q, 2H), 2.41 (s, 3H), 1.21 (t, 3H). LCMS MH+ 420.5.

Example 14

Synthesis of 2-{[2-(3-Fluorophenyl)-1H-imidazol-1-yl]methyl}-1-ethyl-5-(1,2,4-oxadiazol-3-yl)-1H-benzimidazole

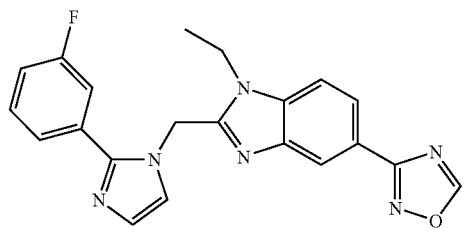

1. Preparation of 1-Ethyl-2-{[2-(2,5-difluorophenyl)-1H-imidazol-1-yl]methyl-1H-benzimidazol}-5-carboxamide oxime 1-Ethyl-2-{[2-(3-fluorophenyl)-1H-imidazol-1-yl]methyl}-5-cyano-1H-benzimidazole (340 mg) is added to a solution of hydroxylamine hydrochloride (137 mg, 2 eq) and triethylamine (0.3 mL, 2.2 eq) in methanol (3 mL), then heated at reflux for 2.5 h. The reaction is cooled, concentrated, water added, the solid collected and rinsed well with water and dried to give 305 mg of 1-Ethyl-2-{[2-(2,5-difluorophenyl)-1H-imidazol-1-yl]methyl-1H-benzimidazol}-5-carboxamide oxime.

2. Preparation of 1-Ethyl-2-{[2-(2,5-difluorophenyl)-1H-imidazol-1-yl]methyl-1H-benzimidazol}-5-carboxamide oxime 1-Ethyl-2-{[2-(3-fluorophenyl)-1H-imidazol-1-yl]methyl-1H-benzimidazol}-5-carboxamide oxime (161 mg) is treated with triethylorthoformate (3 mL) and boron trifluoride-THF complex (0.1 mL) at 100° C. for 2.5 h. 1N HCl (0.5 mL) is added to the hot mixture; the reaction is then cooled and concentrated. After cooling in an ice bath, aqueous sodium hydroxide is added. The solid is collected, rinsed with water, then ether and dried to give 1-Ethyl-2-{[2-(2,5-difluorophenyl)-1H-imidazol-1-yl]methyl-1H-benzimidazol}-5-carboxamide oxime, which is converted to the methanesulfonate salt in acetone. Mp 183-186° C.

Example 15

Synthesis of 4-amino-3-ethylaminobenzonitrile

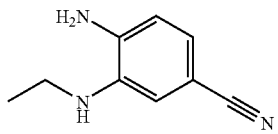

1. 4-nitro-3-chlorobenzonitrile

To an ice cold solution of 4-amino-3-chlorobenzonitrile (1 g, 6.6 mmol) in concentrated HCl (2.5 mL) plus water (2.5 mL) a chilled solution of sodium nitrite (0.74 g, 1.62 eq) in water (3.6 mL) is added dropwise to maintain the reaction temperature <0° C. After stirring at 0° C. for 10 min, the mixture is added portion-wise to an ice cold solution of sodium nitrite (3.29 g, 7.22 eq) and copper(I) oxide (349 mg, 0.37 eq) in water 14.5 mL). Stirring is continued at 0° C. for 40 min, and then at room temperature for 0.5 h. The reaction mixture is extracted with dichloromethane (2×), the combined organic layers washed with saturated aqueous sodium chloride, dried (MgSO₄), concentrated, and purified by silica gel chromatography to give 4-nitro-3-chlorobenzonitrile. $^1$H NMR (CDCl₃): δ 7.96 (d, J=8.24 Hz, 1 h), 7.88 (d, T=1.65 Hz, 1H), 7.63 (dd, J=1.65, 8.24 Hz, 1H.

2. Preparation of 4-Ethylamino-3-chloro benzonitrile

A mixture of 4-nitro-3-chlorobenzonitrile (0.74 g, 4.1 mmol), potassium carbonate (1.68 g, 12.2 mmol), and ethylamine (4 mL, 2M in THF) in DMF (2 mL) is stirred at ambient temperature for 3 h. Additional ethylamine (2.1 mL, 2M in THF) is added, the flask stoppered, and stirring continued an additional 15.5 h. Water (50 mL) is added and extracted 2× with ethyl acetate (50 mL), and the combined organic layers are washed with water, then brine, dried (MgSO₄), and concentrated to give a mixture of 3-Ethylamine-4-nitrobenzonitrile and 4-Ethylamino-3-chloro benzonitrile which was carried forward without purification.

3. Preparation of 4-Amino-3-ethylaminobenzonitrile

To a suspension of crude 4-ethylamino-3-chloro benzonitrile (above) in conc. HCl (4 mL) tin(II) chloride dihydrate (3.16 g) is added. After stirring at ambient temperature for 1.5 h, the mixture is poured onto ice and the solution mad alkaline with 10 N aq. NaOH. The aqueous solution is extracted 2× with dichloromethane, and the combined organic layers washed with brine, dried (MgSO₄), and concentrated. Trituration with ether affords 4-Amino-3-ethylaminobenzonitrile as a white solid. $^1$H NMR (CDCl₃): δ 7.00 (dd, J=1.65, 7.97 Hz, 1H), 6.83 (d, J=1.65 Hz, 1H), 6.67 (d, J=7.97 Hz, 1 h), 3.13 (q, J=7.14 Hz, 1.31 (t, J=7.14 Hz, 3H).

Example 16

Synthesis of 2-Fluoro-6-(1H-imidazol-2-yl)-pyridine

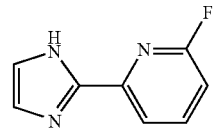

1. Preparation of 2-Fluoropyridine-6-carboxaldehyde

Method A

2-Fluoro-6-methylpyridine (14.4 g, 0.13 mol) and tert-butoxybis(dimethylamino)methane (Bredereck's reagent; 34.9 g, 0.20 mol) are heated at 140° C. for 24 h. The reaction is cooled and diluted with THF (100 mL). Sodium periodate (75 g) in water (400 mL) is added at 0-5° C., and the reaction mixture is then stirred for 24 h at room temperature. The precipitate is filtered through celite, and the filtrate extracted 5× with diethyl ether. The combined ether layers are washed with water, brine, and dried (MgSO₄). Most of the solvent is removed by concentration at 0° C. (by keeping ice in the bath) to provide 2-Fluoropyridine-6-carboxaldehyde.

Method B

2-Fluoropyridine-6-carboxaldehyde can also be prepared as follows: To a solution of diisopropylamine (6.54 mL, 1.2 equiv) in 30 mL of THF at 0° C. a solution of n-butyllithium (17.1 mL, 2.5M in hexanes) is added dropwise. Stirring is continued for 15 minutes at 0° C., the reaction is then cooled to −78° C. 2-Fluoro-6-methylpyridine (4.00 mL, 38.9 mmol) is added dropwise to the cold solution. The reaction mixture is stirred at −78° C. for 1 h and then quenched with DMF (4.52 mL, 1.5 equiv). The reaction is maintained at −78° C. for 30 minutes and then warmed to 0° C. The cold solution is added to a mixture of sodium periodate (24.9 g) in 120 mL of water at 0° C. The reaction mixture is allowed to gradually warm to room temperature over 1 h and then stirred at room temperature for 24 h. The reaction mixture is filtered through a plug of celite to remove the precipitate and the plug is washed with ether. The organic layer is separated, washed with aqueous sodium bicarbonate (1×40 mL), then with 0.25M KH₂PO₄ (1×40 mL) and then brine (1×40 mL). The organic solution is dried (NaSO₄) and concentrated in vacuo.

2. Preparation of 2-Fluoro-6-(1H-imidazol-2-yl)-pyridine

To a solution of the crude aldehyde from step 1, Method B (above) in methanol (12 mL) aqueous glyoxal (6.21 mL, 40 wt. % in water) is added dropwise. The solution is cooled to 0° C. and aqueous ammonium hydroxide (6.0 mL, 28 wt. % in water) is added. The reaction is allowed to warm to room temperature gradually over about an hour and then stirred another 3 h at room temperature. Most of the methanol is removed in vacuo, the reaction mixture diluted with water (10 mL) and extracted with ethyl acetate (30 mL). The organic layer is washed with brine (20 mL), diluted with hexanes (15 mL), passed through a plug of silica gel (¼ inch deep×1¼ inch diameter), and the plug washed with more 2:1 ethyl acetate/hexanes (20 mL). The combined eluents are concentrated in vacuo to yield crude 2-Fluoro-6-(1H-imidazol-2-yl)-pyridine.

Example 17

Synthesis of 2-Fluoro-6-(1H-imidazol-2-yl)-pyridine acetic acid

1. Preparation of [2-(6-fluoropyridin-2-yl)-imidazol-1-yl]acetic acid tert-butyl ester A mixture of 2-Fluoro-6-(1H-imidazol-2-yl)pyridine (410 mg; 2.51 mmol), tert-butyl bromoacetate (539 mg; 2.76 mmol), potassium carbonate (520 mg; 3.77 mmol), and N,N-dimethylformamide (20 mL) is stirred at room temperature for 16 h. Water (60 mL) is added and the mixture extracted with ethyl acetate (3×70 mL). The organic extracts are washed with water (3×40 mL) and brine (1×40 mL), dried (MgSO$_4$), and concentrated to give [2-(6-Fluoropyridin-2-yl)-imidazol-1-yl]acetic acid tert-butyl ester as an orange oil (630 mg). $^1$H NMR (CDCl$_3$) δ 8.12 (dd, 1H), 7.82 (q, 1H), 7.16 (s, 1H), 6.98 (s, 1H), 6.81 (dd, 1H), 5.14 (s, 2H), 1.44 s, (9H), LCMS: 276.1 (M$^-$).

2. Preparation of 2-Fluoro-6-(1H-imidazol-2-yl)-pyridine acetic acid

A solution of [2-(6-fluoropyridin-2-yl)-imidazol-1-yl]acetic acid tert-butyl ester (630 mg; 2.27 mmol) and trifluoroacetic acid (4 mL) in dichloromethane (4 mL) is stirred at room temperature for 5 hr. The reaction mixture is concentrated. The residue is treated with 3M HCl in ethyl acetate (10 mL) and the suspension stirred at room temperature for 1 hr. The precipitate is collected, washed with ethyl acetate, and dried to give 2-Fluoro-6-(1H-imidazol-2-yl)-pyridine acetic acid as a tan solid (581 mg), $^1$H NMR (d$_6$DMSO) δ 8.35-8.26 (m, 2H) 7.83 (s, 1H), 7.76 (s, 1H), 7.44-7.41 (m. 1H) 5.40 (s, 2H). LCMS: 222.1 (MH$^+$).

Example 18

Synthesis of 2-{[2-(2,5-di-fluorophenyl)-1H-imidazol-1-yl]methyl}-ethyl-1H-imidazo[4,5-b]pyridine

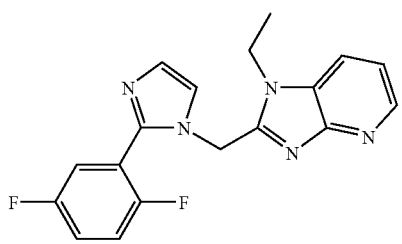

1. Preparation of 3-ethylamino-2-nitro-pyridine

Ice cold ethylamine (0.55 mL) was added to a solution of 3-fluoro-2-nitropyridine (400 mg, 2.8 mmol; prepared according to N. Plé and G. Queguiner, *J. Heterocyclic Chem*, 1989, 26, 475-476) in 2:1 DMF:THF (6 mL) at ambient temperature, and the mixture stirred for 0.75 h. Water was added, then extracted 2× with ethyl acetate. The combined organic layers were washed with water then with saturated aqueous sodium chloride, dried (MgSO$_4$), and concentrated to give 3-ethylamino-2-nitro-pyridine as a gold solid. $^1$H NMR (CDCl$_3$): δ 7.87 (d, 1 h0, 7.43 (dd, 1H), 7.35 (d, 1H), 3.38 (pentet, 2H), 1.4 (t, 3H). LCMS: 121.1 (MH$^+$—NO$_2$).

2. Preparation of 2-Amino-3-ethylaminopyridine

A mixture of 3-ethylamino-2-nitro-pyridine (400 mg), 10% palladium on carbon (40 mg) and 1:1 ethyl acetate: methanol (30 mL) were placed in a Parr apparatus under hydrogen (50 psi) for 50 min. The mixture was filtered through Celite, concentrated, and the product triturated with hexane to give 2-Amino-3-ethylaminopyridine as a brown solid. More material was recovered from the filtrate. $^1$H NMR (CDCl$_3$): δ 7.59 (d, J=4.94 Hz, 1H), 6.81 (d, J=6.32 Hz, 1H), 6.71 (dd, J=4.94, 7.69 Hz, 1H), 3.12 (q, J=7.14 Hz, 2 h), 1.31 (t, J=7.14 Hz, 3H).

3. Preparation of 2-{[2-(2,5-Difluorophenyl)-1H-imidazol-1-yl]methyl}-1-ethyl-1H-imidazo[4,5-b]pyridine 2-Amino-3-ethylaminopyridine (60 mg, 0.43 mmol) and methyl 1-carboxymethyl-2-(2,5-difluorophenyl)-imidazole (193 mg, 0.76 mmol) were used according to Example 1 Method B to prepare 2-{[2-(2,5-Difluorophenyl)-1H-imidazol-1-yl]methyl}-1-ethyl-1H-imidazo[4,5-b]pyridine, which is converted to the hydrochloride salt in ethyl acetate. m.p. 214-216° C. LCMS MH$^+$ 322.2, MH$^-$ 320.3.

Example 19

Synthesis of 2-{[2-(3-Fluorophenyl)-1H-imidazol-1-yl]methyl}-1-ethyl-3H-imidazo[4,5-c]pyridine

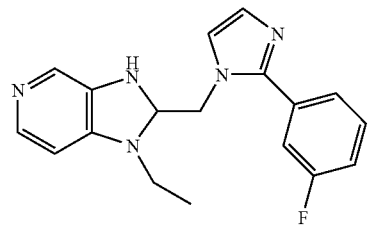

1. Preparation of 3-Chloro-4-nitropyridine N-oxide

Aqueous hydrogen peroxide (30 mL of 30%) is added dropwise to an ice cold mixture of 3-chloropyridine (6.0 g, 53 mmol) in acetic anhydride (30 mL). The mixture is allowed to stir at ambient temperature for 24 h, water is then added and the mixture concentrated. The residue is taken up in concentrated sulfuric acid (10 mL) and fuming sulfuric acid (5 mL), and then cooled to 0° C. Concentrated nitric acid (24 mL) is added slowly, and the ice bath removed. The reaction is then heated at reflux for 2 h, cooled, and poured into ice water. Ammonium bicarbonate is added carefully until pH 8 is achieved, the solution is then extracted with dichloromethane. The organic layer is washed with water, dried (NaSO$_4$), and concentrated to give 3-Chloro-4-nitropyridine N-oxide as a yellow solid. $^1$H NMR (CDCl$_3$). δ 8.47 (d, J=4 Hz, H), 8.35 (dd, J=5, 12 Hz, 1H), 7.73 (ddd, J=4, 9, 12 Hz, 1H).

2. Preparation of 3-Ethylamino-4-nitro-3-pyridine N-oxide

To an ice cold solution of 3-chloro-4-nitropyridine N-oxide (2.93 g, 16.8 mmol) in ethanol (30 mL) ethylamine (25 mL of 2M in THF) is added. The mixture is allowed to stir overnight at ambient temperature, then concentrated in vacuo to afford crude 3-Ethylamino-4-nitro-3-pyridine N-oxide as a yellow oil. $^1$H NMR (CDCl$_3$): δ 8.01 (d, J=7 Hz, H), 7.91 (s, 1H), 7.45 (d, J=7 Hz, 1H), 3.31 (q, J=7 Hz, 2H), 1.40 (t, J=7 Hz, 3H).

3. Preparation of 3-Ethylamino-4-aminopyridine

Crude 3-ethylamino-4-nitro-3-pyridine N-oxide and 10% palladium on carbon (1 g) in methanol (30 mL) are placed in a Parr apparatus under hydrogen (60 psi) for 2 days. Additional 10% palladium on carbon (880 mg) is added and returned under hydrogen (60 psi) for 2 days. The mixture was filtered through Celite, concentrated, and the product triturated with hexane-ether to afford 1.3 g of 3-Ethylamino-4-aminopyridine. $^1$H NMR (d6-DMSO): δ 7.63 (d, J=6 Hz, 1H), 7.47 (s, 1H), 6.57 (d, J=6 Hz, 1H), 3.05 (q, J=7 Hz, 2H), 1.21 (t, J=7 Hz, 3H).

4. Preparation of 2-{[2-(3-Fluorophenyl)-1H-imidazol-1-yl]methyl}-1-ethyl-3H-imidazo[4,5-c]pyridine 3-Ethylamino-4-aminopyridine (548 mg, 3.99 mmol) and methyl 1-carboxymethyl-2-(3-fluorophenyl)-imidazole (467 mg, 1.99 mmol) were used according to Example 1 Method B to prepare 2-{[2-(3-Fluorophenyl)-1H-imidazol-1-yl]methyl}-1-ethyl-3H-imidazo[4,5-c]pyridine. $^1$H NMR (CDCl$_3$): δ 1.08 (t, J=7 Hz, 3H), 3.89 (q, J=7 Hz, 2H), 5.52 (s, 2H), 7.04 (s, 1H), 7.16-7.20 (m, 2H), 7.37-7.50 (m, 3H), 7.68 (d, J=6 Hz, 1H), 8.47 (d, J=6 Hz, 1H), 8.78 (s, 1H).

Example 20

Synthesis of 3-fluoro-(1H-imidazol-2-yl)benzene

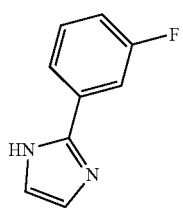

Saturated ammonium hydroxide solution (30 mL) is slowly added to a solution of 3-fluorobenzaldehyde (12.4 g, 100 mmol) and glyoxal (17.5 mL of 40% wt in water, 120 mmol) in methanol (100 mL) at ambient temperature. After stirring for 24 h, most of the solvent is removed at reduced pressure. Benzene is added and evaporated to remove residual water. The resulting dark oil is purified by chromatography on silica gel (2% MeOH/CH$_2$Cl$_2$) to obtain a tan solid. Trituration with ether/hexane provides 3-fluoro-(1H-imidazol-2-yl)benzene as a white solid. LRMS m/z (M+1) 163.2.

Example 21

Synthesis of 3-chloro-4-fluoro-(1H-imidazol-2-yl)benzene

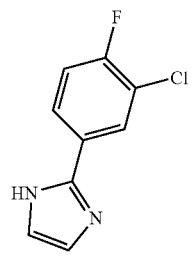

A mixture of 3-chloro-4-fluoro-benzaldehyde (0.032 mol), glyoxal (40% in water, 0.038 mol) and ammonium hydroxide (28% in water, 0.16 mol) in MeOH (60 mL) is stirred at room temperature overnight. Solvent is removed in vacuo and the residue is partitioned between water and CH$_2$Cl$_2$. The organic layer is washed with brine, dried (Na$_2$SO$_4$), and concentrated. The residue is purified by column chromatography on silica gel eluting with CH$_2$Cl$_2$/MeOH (95/5) to afford 3-chloro-4-fluoro-(1H-imidazol-2-yl)benzene as a yellow solid. $^1$H NMR (CDCl$_3$) δ 7.88 (dd, 1H), 7.70 (m, 1H), 7.19 (t, 1H), 7.17 (s, 2H). LRMS m/z (M+1) 197.0.

Example 22

Synthesis of 2,3,4-trifluoro-(1H-imidazol-2-yl)benzene

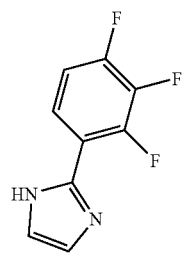

Saturated ammonium hydroxide solution (26 mL) is slowly added to a solution of 2,3,4-trifluorobenzaldehyde (5.0 g, 31.2 mmol) and glyoxal (10.75 mL of 40% wt in water, 93.7 mmol) in methanol (100 mL) at ambient temperature. After stirring for 24 h, most of the solvent is removed at reduced pressure. Benzene is added and evaporated to remove residual water. The resulting dark oil is purified by chromatography on silica gel (5% MeOH/CH$_2$Cl$_2$) to obtain a tan solid. Trituration with ether/hexane provides 2,3,4-trifluoro-(1H-imidazol-2-yl)benzene as a white solid. LRMS m/z (M+1) 199.10.

Example 23

Synthesis of 2-(1H-imidazol-2-yl)-thiazole

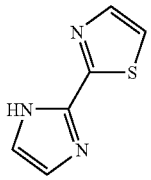

1. Preparation of 1-ethoxymethyl-2-tributylstannanyl-1H-imidazole

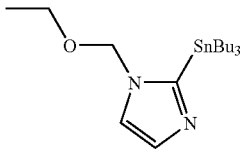

1.6 M n-BuLi (12.0 mL, 19.2 mmol) is slowly added to a solution of 1-ethoxymethyl-1H-imidazole [available via the procedure outlined in Tang, C. C.; Davalian, D.; Huang, P.; Breslow, R. *J. Am. Chem. Soc.* 1978, 100, 3918] (2.20 g, 17.4 mmol) in THF (30 mL) at −78° C. under $N_2$. The reaction mixture is stirred at −78° C. for 20 min. whereupon tributyltin chloride (5.7 mL, 20.9 mmol) is slowly added. The reaction mixture is stirred at −78° C. for 10 min. and then warmed to room temperature. After stirring at room temperature for 1.5 h, the reaction mixture is concentrated in vacuo. The residue is triturated with hexanes and filtered, and the filtrate is concentrated in vacuo. The residue is again triturated with hexanes and filtered, and the filtrate concentrated in vacuo. The $^1$H NMR of the resulting oil indicates a 2:1 mixture of 1-ethoxymethyl-2-tributylstannanyl-1H-imidazole: 1-ethoxymethyl-1H-imidazole. This material is used in the next reaction without further purification. Selected $^1$H NMR resonances (400 MHz, CDCl$_3$) δ 7.21 (s, 1H), 7.14 (s, 1H), 5.24 (s, 2H) ppm.

2. Preparation of 2-(1-ethoxymethyl-1H-imidazol-2-yl)-thiazole

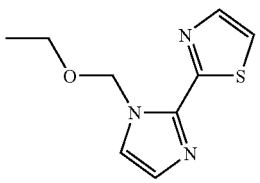

A solution of crude 1-ethoxymethyl-2-tributylstannanyl-1H-imidazole (previous experimental), 2-bromothiazole (1.05 mL, 11.6 mmol, 1.0 eq based on integration of $^1$H NMR of crude 1-ethoxymethyl-2-tributylstannanyl-1H-imidazole), and Pd(PPh$_3$)$_4$ (0.67 g, 0.58 mmol) in toluene (20 mL) is stirred at 80° C. for 18 h. After cooling to room temperature, the reaction mixture is poured into saturated aqueous NaHCO$_3$ and extracted twice with CH$_2$Cl$_2$. The combined extracts are dried over Na$_2$SO$_4$ and concentrated in vacuo. The residue is purified by flash chromatography on silica gel, eluting with 2:1 hexanes-EtOAc (+0.5% Et$_3$N). Fractions containing product are concentrated and resubjected to flash chromatography on silica gel. Elution with 2:1 hexanes-EtOAc (+0.5% Et$_3$N) affords (26%) of 2-(1-ethoxymethyl-1H-imidazol-2-yl)-thiazole as a bright yellow oil. $^1$H NMR (400 MHz, CDCl$_3$) δ 7.82 (d, J=3.2 Hz, 1H), 7.33 (d, J=3.2 Hz, 1H), 7.20 (d, J=1.2 Hz, 1H), 7.15 (d, J=1.2 Hz, 1H), 6.03 (s, 2H), 3.56 (q, J=7.2 Hz, 2H), 1.17 (t, J=7.2 Hz, 3H) ppm.

3. Preparation of 2-(1H-imidazol-2-yl)-thiazole

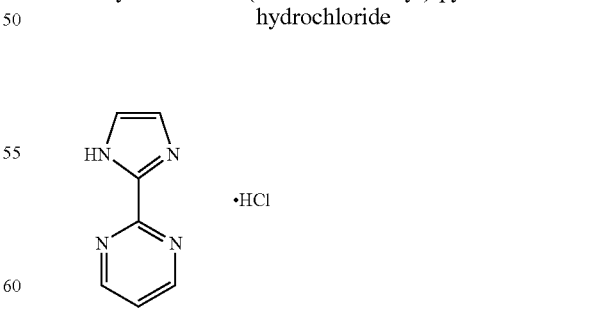

Concentrated HCl (10 ml) is added to a solution of 2-(1-ethoxymethyl-1H-imidazol-2-yl)-thiazole (940 mg, 4.49 mmol) in 24 mL of 1:1 EtOH—H$_2$O at room temperature. The solution is stirred at reflux for 3 h. The reaction mixture is then cooled to 0° C. and made basic by the addition of about 12 mL of 10 N aqueous NaOH. The mixture is back titrated to approximately pH 4 using concentrated HCl. Solid NaHCO$_3$ is added to the point of saturation and approximately pH 8. The mixture is then extracted twice using a mixture of THF and EtOAc. The combined extracts are dried over Na$_2$SO$_4$ and concentrated to an oily solid, which is triturated with a small amount of CH$_2$Cl$_2$. The solid is collected by filtration. The filtrate is concentrated, and the oily solid triturated once more with CH$_2$Cl$_2$. The second resultant solid is collected by filtration and combined with the solid first obtained. The product, 2-(1H-imidazol-2-yl)-thiazole, is obtained as a slightly off-white solid. $^1$H NMR (400 MHz, DMSO-d$_6$) δ 13.04 (br, 1H), 7.87 (d, J=3.2 Hz, 1H), 7.70 (d, J=3.2 Hz, 1H), 7.14 (br, 2H) ppm.

The compound of this example can be prepared essentially according to the procedures described in Example 21.

Example 24

Synthesis of 2-(1H-Imidazol-2-yl)-pyrimidine hydrochloride

A mixture of 2-Cyanopyrimidine (8.0 g, 76 mmol, prepared according to *Liebigs Ann. Chem.* 2, 1981, 333-341) and Aminoacetaldehyde dimethyl acetal (8 g, 76 mmol) is heated at 100° C. for 4 hours, cooled, and 100 mL of MeOH and 5 mL of concentrated HCl are added. The mixture is heated at reflux with stirring for 30 hours, cooled and evaporated to dryness in vacuo. 50 mL of i-ProH is added to the residue and the mixture is heated at reflux with stirring for 30 minutes and cooled. The crystals are collected by filtration, washed with ether, and dried to give the title compound. $^1$H NMR (DMSO): δ 9.08 (d, 2H), 7.87 (s, 2H), 7.75 (t, 1H). LRMS calcd 146. found 147 (MH+).

Example 25

Synthesis of 2-(1H-Imidazol-2-yl)-thiazole-4-carbonitrile

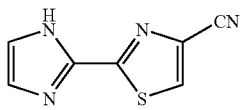

1) Preparation of 1-Dimethylsulfamoyl-1H-imidazole-2-carbothioic acid methoxymethyl-amide To a solution of 1-Dimethylsulfamoyl-1-imidazole (2.0 g, 11.4 mmol) in 10 mL of anhydrous THF at −78° C. is added a solution of n-BuLi in Hexane (2.5 M, 4.6 mL) dropwise under N$_2$. After the mixture is stirred at the same temperature for about one hour, Methoxymethyl isocyanate (1.2 g, 11.4 mmol) is added dropwise at −78° C. The reaction mixture is stirred at −78° C. for about 6 hours and slowly warmed to room temperature. After quenched with a saturated aqueous NH$_4$Cl solution (20 mL), the mixture is extracted with Ethyl acetate (20 mL×2). The extract is washed with water, dried and concentrated. The residue is purified on a silica gel column with 3% MeOH in CH$_2$Cl$_2$ as eluent to give the title compound. $^1$H NMR (CDCl$_3$): δ 8.60 (br, 1H), 7.32 (d, 1H), 7.01 (d, 1H), 5.22 (d, 2H), 3.51 (s, 3H), 3.00 (d, 6H). LRMS calcd 278. found 279 (MH+).

2) Preparation of 1H-Imidazole-2-carbothioic acid amide

A solution of 1-Dimethylsulfamoyl-1H-imidazole-2-carbothioic acid methoxymethyl-amide (1.0 g, 3.6 mmol) in Acetic acid (10 mL) and water (2 mL) is stirred at 50° C. overnight. After the volatiles are evaporated in vacuo, the residue is partitioned between Ethyl acetate (40 mL) and aqueous NaHCO$_3$ (10 mL). The organic layer is separated, washed with water, dried and concentrated in vacuo to a solid (250 mg). $^1$H NMR (DMSO): δ 12.7 (s, 1H), 9.65 (s, 1H), 9.42 (s, 1H), 7.24 (s, 1H), 7.15 (s, 1H.

3) Preparation of 2-(1H-Imidazole-2-yl)-thiazole-4-carboxylic acid ethyl ester A mixture of 1H-Imidazole-2-carbothioic acid amide (200 mg, 1.57 mmol) and Ethyl bromopyruvate (340 mg, 1.57 mmol) is heated at 75° C. for about 5 hours. After the volatiles are evaporated in vacuo, the residue is partitioned between Ethyl acetate (40 mL) and aqueous NaHCO$_3$ (10 mL). The organic layer is separated, washed with water, dried and concentrated. The residue is purified on a silica gel column with 3% MeOH in CH$_2$Cl$_2$ as eluent to give 200 mg of the titled compound. $^1$H NMR (CDCl$_3$): δ 8.15 (s, 1H), 7.20 (br, 1H), 7.10 (br, 1H), 4.33 (q, 2H), 1.23 (t, 3H). LRMS calcd 223. found 224 (MH+).

4) Preparation of 2-(1H-Imidazole-2-yl)-thiazole-4-carboxylic acid amide

A solution of 2-(1H-Imidazole-2-yl)-thiazole-4-carboxylic acid ethyl ester (190 mg) in 5 mL of MeOH is saturated with NH$_3$ gas, and heated at 60° C. in a sealed tube overnight. After cooled, the reaction mixture is transferred to a round bottle flask and evaporated in vacuo to a solid. LRMS calcd 194. found 195 (MH+).

5) Preparation of 2-(H-Imidazole-2-yl)-thiazole-4-carbonitrile

To a solution of 2-(1H-Imidazole-2-yl)-thiazole-4-carboxylic acid amide (120 mg) in 2 mL of anhydrous pyridine is added 0.25 mL of POCl$_3$ dropwise at 0° C. The reaction mixture is stirred at the same temperature for 2 hours, poured into ice water, neutralized with solid NaHCO$_3$, and extracted with 5% MeOH in CH$_2$Cl$_2$. The extract is washed with brine, dried and concentrated to a solid. $^1$H NMR (DMSO): δ 13.45 (br, 1H), 8.82 (s, 1H), 7.38 (s, 1H), 7.12 (s, 1H). LRMS calcd 176. found 177 (MH+).

Example 26

Synthesis of 2-[2-(6-fluoro-pyridin-2-yl)-imidazol-1-ylmethyl]-1-propyl-1-H-imidazo[4,5-c]pyridine

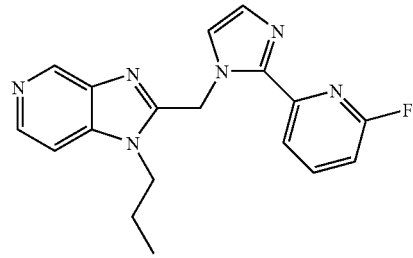

1. Preparation of (3-nitro-pyridin-4-yl)-propyl-amine

To a solution of 4-chloro-3-nitro-pyridine (18.0 g, 114 mmol) in EtOH(300 ml) is added n-propylamine (46.9 ml, 568 mmol) slowly at 0° C. and the resulting yellow mixture is warmed to room temp. After stirring for 2 h, the reaction is concentrated in vacuo. The residue is purified by flash chromatography (eluent 50% Hex/EtOAc) to give (3-nitro-pyridin-4-yl)-propyl-amine as a yellow solid. $^1$H NMR (CDCl$_3$) δ 9.16 (s, 1H), 8.25 (d, J=6 Hz, 1H), 8.15 (br s, 1H), 6.68 (d, J=6 Hz, 1H), 3.29 (q, J=6.8 Hz, 2H), 1.74 (sextet, J=7.2 Hz, 2H), 1.02 (t, J=7.6 Hz, 3H). LRMS calcd 181.19. found 182.5 (MH+).

2. Preparation of N-propyl-pyridine-3,4-diamine

A solution of (3-nitro-pyridin-4-yl)-propyl-amine (19.7 g, 109 mmol) in abs. MeOH(150 ml) is hydrogenated at room temp. and 50 psi in the presence of 10% palladium on carbon (1.9 g) for 15 h. Removal of catalyst, concentration of filtrate, and recrystallization the residue in dichloromethae-hexane yields N-propyl-pyridine-3,4-diamine as a tan solid. $^1$H NMR (DMSO-d$_6$) δ 7.59 (s, 1H), 7.55 (d, J=5.4 Hz, 1H), 6.30 (d, J=5.4 Hz, 1H), 5.26 (br s, 1H), 4.55 (br s, 2H), 3.02 (q, J=6.6 Hz, 2H), 1.56 (sextet, J=7.1 Hz, 2H), 0.92 (t, 7.2 Hz, 3H). LRMS calcd 151.21. found 152.4 (MH+).

3. Preparation of 2-[2-(6-fluoro-pyridin-2-yl)-imidazol-1-ylmethyl]-1-propyl-1-H-imidazo[4,5-c]pyridine Trimethylaluminum (11 ml of 2.0M in toluene, 22.4 mmol) is added dropwise to a solution of N-propyl-pyridine-3,4-diamine (1.70 g, 11.2 mmol) in dichloromethane (50 ml), and the mixture is stirred for 30 minutes at room temperature. To this is added a solution of [2-(6-fluoro-pyridin-2-yl)-imidazol-1-yl]-acetic acid methyl ester (1.32 g, 5.61 mmol) in dichloromethane (10 ml) The mixture is heated at reflux for 18 hours. The resulting brown mixture is poured into ice-water and filtered through celite. The filtrate is extracted with dichloromethane and the combined extracts are washed with saturated brine, dried over anhydrous Na$_2$SO$_4$, filtered, concentrated in vacuo, and chromatographed on silica gel to afford 2-[2-(6-fluoro-pyridin-2-yl)-imidazol-1-ylmethyl]-1-propyl-1-H-imidazo[4,5-c]pyridine as a pale yellow solid. $^1$H NMR (CDCl$_3$) δ 9.06 (s, 1H), 8.42 (d, J=5.6 Hz, 1H), 8.18 (dd, J=2.1, 7.6 Hz, 1H), 7.88 (dd, J=7.6, 8.4 Hz, 1H), 7.29 (d, J=5.6 Hz, 1H), 7.22 (s, 1H), 7.18 (s, 1H), 6.88 (dd, J=2.4, 8.4 Hz, 1H), 6.29 (s, 2H), 4.26 (t, J=7.6 Hz, 2H), 1.68 (sextet, J=7.2 Hz, 2H), 0.84 (t, J=7.2 Hz, 3H). LRMS calcd 336.37. found 337.6 (MH+).

Example 27

Synthesis of 3-Ethyl-2-{[2-(1,3-thiazol-2-yl)-1H-imidazol-1-yl]methyl}-3H-imidazo[4,5-c]pyridine

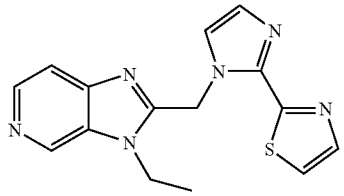

1. Preparation of 3-Chloro-4-nitro-pyridine-1-oxide

Aqueous 30% H$_2$O$_2$ (60 mL) is added dropwise to a magnetically stirred solution of 3-chloro-pyridine (12 g, 105 mmol) in acetic anhydride (60 mL) under cold conditions (0 to 10° C.). The resulting mixture is allowed to warm up to room temperature slowly and then stirred overnight at room temperature. The reaction mixture is quenched with water (50 mL), diluted with toluene and concentrated to obtain the crude N-oxide as an oil in near quantitative yield.

Fuming H$_2$SO$_4$ (25 mL) is added dropwise to a solution of crude 3-chloro-pyridine-1-oxide in concentrated H$_2$SO$_4$ (25 mL) under cold conditions (0° C.) with stirring. HNO$_3$ (fuming, 90%, 60 mL) is added carefully to the above mixture with caution to keep the offset of any exotherm under control, and then allowed to warm to room temperature slowly. The resulting mixture is then heated at 120° C. for 4 h with stirring, cooled, poured into ice-cold water, and extracted with CHCl$_3$. The combined organic phase is washed successively with saturated aqueous NaHCO$_3$, water, brine, dried over Na$_2$SO$_4$, and concentrated in vacuo to afford 3-Chloro-4-nitro-pyridine-1-oxide as an yellow solid. $^1$H NMR (300 MHz, CDCl$_3$): δ 8.31 (d, J=1.5 Hz, 1H), 8.13 (dd, J=1.5, 5.4 Hz, 1H), 7.95 (d, J=7.2 Hz, 1H).

2. Preparation of 3-Ethylamino-4-nitro-pyridine-1-oxide

Anhydrous K$_2$CO$_3$ (19 g, 144.5 mmol) is suspended in a solution of 3-Chloro-4-nitro-pyridine-1-oxide (10 g, 57.8 mmol) in anhydrous acetonitrile (100 mL). Excess diethyl amine (2.0 M) in THF is added to the above suspension under cold conditions (ice-bath). After complete addition of diethyl amine, the reaction mixture is allowed to warm to room temperature and left stirring overnight. The reaction mixture is filtered to remove K$_2$CO$_3$ and the filtrate evaporated under reduced pressure to remove volatile solvents. The organic residue is subjected to chromatography, eluting with 30% EtOAc-hexanes to afford 3-Ethylamino-4-nitro-pyridine-1-oxide as an orange solid. $^1$H NMR (300 MHz, CDCl$_3$): δ8.0 1 (d, J=7.5 Hz, 1H), 7.91 (s, 1H), 7.8 (brs, NH), 7.44 (d, J=7.2 Hz, 1H), 3.30 (t, J=7.2 Hz, 2H), 1.39 (t, J=7.2 Hz, 3H), m/z 184 [M+1]

3. Preparation of N$^3$-Ethyl-pyridine-3,4-diamine

A solution of 3-ethylamino-4-nitro-pyridine 1-oxide (1.5 g, 8.19 mmol), in methanol (30 mL) is hydrogenated over 10% Pd—C (1.5 g) at 50-60 psi for 48 h. The catalyst is removed by filtration through a pad of celite, and the solvent is evaporated under vacuum to afford N$^3$-Ethyl-pyridine-3,4-diamine as an white solid. 1H NMR (300 MHz, CDCl$_3$): δ 7.59 (s, 1H), 7.57 (d, J=2.4 Hz, 1H), 6.56 (d, J=5.4 Hz, 1H), 3.20 (t, J=7.2 Hz, 2H), 1.29 (t, J=7.2 Hz, 3H), m/z 138 [M+1]

4. Preparation of N-(3-Ethylamino-pyridin-4-yl)-2-(2-thiazol-2-yl-imidazol-1-yl)-acetamide A solution (2.0 M) of Me$_3$Al (4.8 mL, 9.6 mmol) in toluene is added to a solution of the N$^3$-ethyl-pyridine-3,4-diamine (1.06 g, 7.70 mmol) in anhydrous dichloromethane (40 mL) slowly under nitrogen, and the resulting mixture is stirred at room temperature for 1 h. (2-Thiazol-2-yl-imidazol-1-yl)-acetic acid methyl ester (860 mg, 3.85 mmol) is added to the above reaction mixture. The resulting suspension is refluxed overnight and then cooled to room temperature. The reaction mixture is decomposed with a few drops of MeOH. The resulting brown precipitate is suspended in 15% MeOH in CH$_2$Cl$_2$ (200 mL), subjected to sonication for 25 min, filtered through a pad of celite, and concentrated to afford a mixture of 3-Ethyl-2-{[2-(1,3-thiazol-2-yl)-1H-imidazol-1-yl]methyl}-3H-imidazo[4,5-c]pyridine and N-(3-ethylamino-pyridin-4-yl)-2-(2-thiazol-2-yl-imidazol-1-yl)-acetamide in a 2:1 ratio which is carried over to the next step without further purification. A portion of the crude residue chromatographed over silica gel eluting with 7% MeOH—CH$_2$Cl$_2$ containing few drops of NH$_4$OH to obtain an analytical sample of N-(3-ethylamino-pyridin-4-yl)-2-(2-thiazol-2-yl-imidazol-1-yl)-acetamide for characterization purposes. $^1$H NMR (300 MHz, CD$_3$OD): δ 7.95 (s, 1H) 7.87 (d, J=3.3 Hz, 1H), 7.79 (d, J=5.4 Hz, 1H), 7.61 (d, J=3.3 Hz, 1H), 7.42 (d, J=5.1 Hz, 1H), 7.33 (d, J=1.5 Hz, 1H), 7.12 (d, J=1.2 Hz, 1H), 5.51 (s, 2H), 3.2o (t, J=6.9 Hz, 2H) 1.23 (t, J=6.9 Hz, 3H); LRMS Calcd 328.38. found 329

5. Preparation of 3-Ethyl-2-{[2-(1,3-thiazol-2-yl)-1H-imidazol-1-yl]methyl}-3H-imidazo[4,5-c]pyridine The mixture (2:1) of the cyclized 3-Ethyl-2-{[2-(1,3-thiazol-2-yl)-1H-imidazol-1-yl]methyl}-3H-imidazo[4,5-c]pyridine and the intermediate N-(3-ethylamino-pyridin-4-yl)-2-(2-thiazol-2-yl-imidazol-1-yl)-acetamide obtained from the above Me$_3$Al-mediated coupling conditions is dissolved in 30 mL of acetic acid and heated at 115° C. overnight with stirring. The next day, most of the AcOH is evaporated off under reduced pressure. The residue is diluted with 100 mL of CH$_2$Cl$_2$, washed with NaHCO$_3$, water, brine, dried over Na$_2$SO$_4$, and concentrated. The crude product is purified by chromatography, eluting with 3% MeOH—CH$_2$Cl$_2$ containing few drops of NH$_4$OH to afford 3-ethyl-2-{[2-(1,3-thiazol-2-yl)-1H-imidazol-1-yl]methyl}-3H-imidazo[4,5-c]pyridine as an white solid. $^1$H NMR (300 MHz, CD$_3$OD) δ 8.87 (s, 1H), 8.30 (d, J=5.7 Hz, 1H), 7.75 (d, J=3.3 Hz, 1H), 7.57 (d, J=4.8 Hz, 1H), 7.52 (d, J=3.3 Hz, 1H), 7.39 (d, J=1.5 Hz, 1H), 7.18 (d, J=1.5 Hz, 1H), 6.29 (s, 2H), 4.52 (q, J=7.5 Hz, 2H), 1.44 (t, J=7.5 Hz, 3H); LRMS Calcd 310.38 found 311; Anal. Calcd for CHNS: C, 58.05; H, 4.55; N, 27.08. Found C, 57.79; H, 4.38; N, 27.04.

Example 28

Synthesis of 3-ethyl-6-isopropyl-2-{[2-(1,3-thiazol-2-yl)-H-imidazol-1-yl]methyl}-3H-imidazo[4,5-c]pyridine and 1-ethyl-6-isopropyl-2-{[2-(1,3-thiazol-2-yl)-1H-imidazol-1-yl]methyl}-1H-imidazo[4,5-c]pyridine

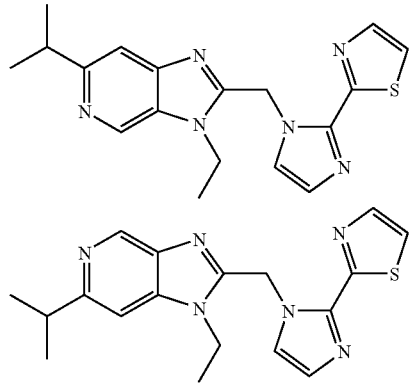

1. Preparation of isobutyrylacetic acid

A mixture of ethyl isobutyrylacetate (20.47 g, 129 mmol) and 1.5 M aq NaOH (250 mL) is stirred at room temperature overnight. The solution is then cooled to 0° C. and acidified to pH 1-2 by the slow addition of conc. HCl (~35 mL). The solution is then saturated with NaCl and extracted thrice with EtOAc and once with CHCl$_3$. The combined extracts are dried over Na$_2$SO$_4$ and concentrated to 14.46 g (86%) of isobutyrylacetic acid as an oil. $^1$H NMR (CDCl$_3$, 300 MHz) reveals a mixture of keto and enol forms (~4:1), in favor of the keto form. Keto form: δ 3.57 (s, 2H), 2.73 (sept, J=6.9 Hz, 1H), 1.16 (d, J=6.9 Hz, 6H) ppm. Enol form: 11.85 (s, 1H), 5.03 (s, 1H), 2.44 (sept, J=6.9 Hz, 1H) 1.10 (d, J=6.9 Hz, 6H) ppm.

2. Preparation of 4-hydroxy-3-isobutyryl-6-isopropyl-pyran-2-one

To a solution of the isobutyrylacetic acid (14.45 g, 111 mmol) in THF (200 mL) at room temperature under N$_2$ is added CDI (19.8 g, 122 mmol) in one portion. The yellow solution is stirred at room temperature for 20 h and then concentrated in vacuo. The residue is dissolved in CH$_2$Cl$_2$ and washed with 10% aq HCl (100 mL) followed by H$_2$O (50 mL). The aqueous washes are reextracted once with CH$_2$Cl$_2$, and the combined extracts are dried over Na$_2$SO$_4$ and concentrated to provide 4-hydroxy-3-isobutyryl-6-isopropyl-pyran-2-one as a yellow oil. This material is sufficiently pure to be used without further purification in the next reaction. $^1$H NMR (CDCl$_3$, 300 MHz) δ 17.02 (s, 1H), 5.92 (s, 1H), 3.94 (sept, J=6.9 Hz, 1H), 2.72 (sept, J=6.9 Hz, 1H), 1.25 (d, J=6.9 Hz, 6H), 1.16 (d, J=6.9 Hz, 6H) ppm.

3. Preparation of 4-hydroxy-6-isopropyl-pyran-2-one

A solution of 4-hydroxy-3-isobutyryl-6-isopropyl-pyran-2-one (10.26 g, 45.8 mmol) in conc. H$_2$SO$_4$ (40 mL) is stirred at 130° C. for 15 min. The dark reaction mixture is then cooled to 0° C., and crushed ice (~200 g) is added with stirring. The resulting solution is extracted thrice with Et$_2$O, and the combined extracts are dried over Na$_2$SO$_4$ and concentrated. The crude material is purified by flash chromatography on silica gel. Gradient elution with 3:2 hexanes-EtOAc, 1:1 EtOAc-hexanes, 2:1 EtOAc-hexanes, and 3:1 EtOAc-hexanes affords 4-hydroxy-6-isopropyl-pyran-2-one as a light yellow solid. $^1$H NMR (CDCl$_3$, 300 MHz) δ 11.2 (br, 1H), 6.00 (d, J=1.8 Hz, 1H), 5.58 (d, J=1.8 Hz, 1H), 2.73 (sept, J=6.9 Hz, 1H), 1.22 (d, J=6.9 Hz, 1H) ppm.

4. Preparation of 4-hydroxy-6-isopropyl-1H-pyridin-2-one

A mixture of 4-hydroxy-6-isopropyl-pyran-2-one (4.82 g, 31.3 mmol) in conc. NH$_4$OH (15 mL) is stirred at 100° C. in a sealed tube for 4 h. The solution is then transferred to a recovery flask and concentrated in vacuo. Toluene is used to azeotropically remove any remaining water. 4-Hydroxy-6-isopropyl-1H-pyridin-2-one is obtained as a tan powder. $^1$H NMR (DMSO-d$_6$, 300 MHz) δ 10.96 (br s, 1H), 10.36 (br s, 1H), 5.59 (d, J=2.1 Hz, 1H), 5.33 (d, J=2.1 Hz, 1H), 2.64 (sept, J=6.9 Hz, 1H), 1.11 (d, J=6.9 Hz, 6H) ppm.

5. Preparation of 4-hydroxy-6-isopropyl-3-nitro-1H-pyridin-2-one

A solution of 4-hydroxy-6-isopropyl-1H-pyridin-2-one (1.76 g, 11.5 mmol) in 55-60 mL of 50% aq HNO$_3$ is stirred at 70° C. for 2.5 h. After cooling, the reaction mixture is poured into ice-cold H$_2$O (~100 mL). The resulting solution is allowed to sit in the refrigerator for 3.5 days. The solid that precipitates is collected by filtration, washed with water, and dried to afford 4-hydroxy-6-isopropyl-3-nitro-1H-pyridin-2-one as yellow crystals. $^1$H NMR (DMSO-d$_6$, 300 MHz) δ 12.30 (br s, 1H), 11.82 (br s, 1H), 5.82 (d, J=1.2 Hz, 1H), 2.71 (sept, J=6.9 Hz, 1H), 1.13 (d, J=6.9 Hz, 6H) ppm.

6. Preparation of 4-chloro-6-isopropyl-3-nitro-1H-pyridin-2-one

To a suspension of 4-hydroxy-6-isopropyl-3-nitro-1H-pyridin-2-one (3.02 g, 15.2 mmol) in CH$_3$CN (60 mL) at room temperature is added benzyltriethylammonium chloride (13.88 g, 61.0 mmol). The mixture is stirred at room temperature for 5-10 min, and then POCl$_3$ (6.25 mL, 67.1 mmol) is added. The reaction mixture is stirred at room temperature for 15 min and then at reflux for 1 h. After cooling, the reaction mixture is concentrated in vacuo. The flask is then placed in an ice bath, and the residue treated with H$_2$O (~60 mL). The mixture is stirred for 4 h while slowly warming to rt. The solid that forms over this period of time is collected by filtration and then washed with H$_2$O and a small amount of hexanes. 4-Chloro-6-isopropyl-3-nitro-1H-pyridin-2-one is obtained as a yellow solid. $^1$H NMR (CDCl$_3$, 300 MHz) δ 13.13 (br s, 1H), 6.24 (s, 1H), 2.89 (sept, J=6.9 Hz, 1H), 1.31 (d, J=6.9 Hz, 6H) ppm.

7. Preparation of 4-amino-6-isopropyl-3-nitro-1H-pyridin-2-one

A mixture of 4-chloro-6-isopropyl-3-nitro-1H-pyridin-2-one (700 mg, 3.23 mmol) in 6-7 µL of 7 N NH$_3$ in MeOH is stirred at 100° C. in a sealed tube for 1.5 h. After cooling, the reaction mixture is concentrated in vacuo. The residue is suspended in H$_2$O, filtered, washed with H$_2$O, and dried, yielding 4-amino-6-isopropyl-3-nitro-1H-pyridin-2-one. $^1$H NMR (DMSO-d$_6$, 300 MHz) δ 10.96 (br s, 1H), 8.15 (br s, 2H), 5.70 (d, J=0.9 Hz, 1H), 2.58 (sept, J=6.9 Hz, 1H), 1.11 (d, J=6.9 Hz, 6H) ppm.

8. Preparation of 2-chloro-6-isopropyl-pyridin-4-ylamine

A mixture of 4-amino-6-isopropyl-3-nitro-1H-pyridin-2-one (555 mg, 2.81 mmol) in POCl$_3$ (10 mL) is stirred at reflux under N$_2$ for 1.5 h. After cooling, the solution is concentrated in vacuo. The reaction flask is then placed in an ice bath, and crushed ice (~20 g) is added to the residue. The mixture is swirled vigorously for several minutes and then stirred at room temperature for 30 min. The mixture is then extracted with EtOAc. The extract is washed with an additional 20 mL of H$_2$O. The aqueous washes are reextracted once with EtOAc, and the combined extracts are dried over Na$_2$SO$_4$ and concentrated, yielding 2-chloro-6-isopropyl-pyridin-4-ylamine as an orange oil. This material is used without further purification. $^1$H NMR (DMSO-d$_6$, 300 MHz) δ 7.27 (br s, 2H), 6.65 (s, 1H), 2.77 (sept, J=6.9 Hz, 1H), 1.13 (d, J=6.9 Hz, 6H) ppm.

9. Preparation of 6-isopropyl-pyridine-3,4-diamine hydrochloride

A solution of 2-chloro-6-isopropyl-pyridin-4-ylamine (684 mg, 3.17 mmol) in MeOH (10-15 mL) containing 10% Pd/C (~70 mg) is stirred under an atmosphere of H$_2$ (double stuffed balloon) for 5 h. The reaction mixture is then filtered through a pad of Celite using MeOH, and the filtrate is concentrated in vacuo. The residue is dissolved in a small amount of MeOH and further diluted with toluene. The solution is then concentrated in vacuo. This is repeated once more, affording 6-isopropyl-pyridine-3,4-diamine hydrochloride as an orange-yellow solid. $^1$H NMR (DMSO-d$_6$, 300 MHz) δ 13.26 (br, 1H), 7.45, 7.40 (br m, 3H), 6.59 (s, 1H), 5.48 (br, 2H), 2.94 (sept, J=6.9 Hz, 1H), 1.19 (d, J=6.9 Hz, 6H) ppm.

10. Preparation of 6-isopropyl-2-(2-thiazol-2-yl-imidazol-1-ylmethyl)-1H-imidazo[4,5-c]pyridine To a mixture of 6-isopropyl-pyridine-3,4-diamine hydrochloride (265 mg, 1.41 mmol) in 1,2-dichloroethane (10 mL) at room temperature under N$_2$ is added 2.0 M AlMe$_3$ in toluene (2.12 mL, 4.24 mmol). The mixture is stirred at room temperature for 45 min and then treated with a solution of (2-thiazol-2-yl-imidazol-1-yl)-acetic acid methyl ester (252 mg, 1.13 mmol) in 1,2-dichloroethane (2 mL) via cannula, followed by a 1 mL rinse. The reaction mixture is then stirred at reflux for 20 h. After cooling, the reaction mixture is diluted with some MeOH (~2 mL), followed by some water and then saturated aq NaHCO$_3$. The resulting mixture is stirred vigorously for 15 min. The mixture is then extracted thrice with CHCl$_3$ containing some (~5) MeOH. The combined extracts are dried over Na$_2$SO$_4$ and concentrated. The crude residue is then triturated with CHCl$_3$, and the resulting mixture filtered. The solid is washed with a small amount of CHCl$_3$ and dried, affording N-(4-amino-6-isopropyl-pyridin-3-yl)-2-(2-thiazol-2-yl-imidazol-1-yl)-acetamide as an off-white solid. $^1$H NMR (DMSO-d$_6$, 300 MHz) δ 9.52 (s, 1H), 7.86 (s, 1H), 7.85 (d, J=3.3 Hz, 1H), 7.75 (d, J=3.6 Hz, 1H)/, 7.39 (s, 1H), 7.04 (d, J=0.9 Hz, 1H), 6.45 (s, 1H), 5.65 (s, 2H), 5.38 (s, 2H), 2.74 (sept, J=6.9 Hz, 1H), 1.13 (d, J=6.9 Hz, 6H) ppm. The filtrate is concentrated and further purified by flash chromatography on silica gel. Elution with 20:1 CHCl$_3$-MeOH followed by 15:1 CHCl$_3$-MeOH affords 6-isopropyl-2-(2-thiazol-2-yl-imidazol-1-ylmethyl)-1H-imidazo[4,5-c]pyridine (160 mg, 44%). $^1$H NMR (CDCl$_3$, 300 MHz) δ 12.23 (br, 1H), 8.97 (br, 1H), 7.94 (d, J=2.7 Hz, 1H), 7.43 (d, J=3.3 Hz, 1H), 7.23 (br, 1H), 7.20 (d, J=0.9 Hz, 1H), 7.04 (s, 1H), 5.82 (s, 2H), 3.14 (sept, J=6.9 Hz, 1H), 1.30 (d, J=6.9 Hz, 6H) ppm.

11. Preparation of 3-ethyl-6-isopropyl-2-{[2-(1,3-thiazol-2-yl)-1H-imidazol-1-yl]methyl}-3H-imidazo[4,5-c]pyridine and 1-ethyl-6-isopropyl-2-{[2-(1,3-thiazol-2-yl)-1H-imidazol-1-yl]methyl}-1H-imidazo[4,5-c]pyridine To a solution of 6-isopropyl-2-(2-thiazol-2-yl-imidazol-1-ylmethyl)-1H-imidazo[4,5-c]pyridine (160 mg, 0.493 mmol) in DMF (1.0 mL) at room temperature under N$_2$ is added Cs$_2$CO$_3$ (168 mg, 0.518 mmol) followed by iodoethane (0.047 mL, 0.592 mmol). The mixture is stirred at room temperature for 1 h and then diluted with water and extracted twice with CH$_2$Cl$_2$. The combined extracts are dried over K$_2$CO$_3$ and concentrated. The residue is purified by preparative TLC, developing with 15:1 CHCl$_3$-MeOH (+0.5% Et$_3$N). The less polar (top) band affords 3-ethyl-6-isopropyl-2-{[2-(1,3-thiazol-2-yl)-1H-imidazol-1-yl]methyl}-3H-imidazo[4,5-c]pyridine. $^1$H NMR (CDCl$_3$, 300 MHz) δ 8.70 (d, J=1.2 Hz, 1H), 7.83 (d, J=3.0 Hz, 1H), 7.53 (d, J=0.9 Hz, 1H), 7.39 (d, J=3.0 Hz, 1H), 7.18 (d, J=0.9 Hz, 1H), 7.14 (d, J=0.9 Hz, 1H), 6.32 (s, 2H), 4.32 (q, J=7.2 Hz, 2H), 3.18 (sept, J=6.9 Hz, 1H), 1.34 (d, J=6.9 Hz, 6H), 1.17 (t, J=7.2 Hz, 3H) ppm. The more polar (bottom) band affords 74 mg (43%) of 1-ethyl-6-isopropyl-2-{[2-(1,3-thiazol-2-yl)-1H-imidazol-1-yl]methyl}-1H-imidazo[4,5-c]pyridine. $^1$H NMR (CDCl$_3$, 300 MHz) δ 9.01 (s, 1H), 7.83 (d, J=3.2 Hz, 1H), 7.38 (d, J=3.2 Hz, 1H), 7.15 (s, 1H), 7.12 (s, 1H), 7.09 (s, 1H), 6.32 (s, 2H), 4.21 (q, J=7.2 Hz, 2H), 3.17 (sept, J=6.8 Hz, 1H), 1.34 (d, J=6.8 Hz, 6H), 1.10 (t, J=7.2 Hz, 3H) ppm.

Example 29

Synthesis of 1-ethyl-6-isopropyl-2-{[2-(1,3-thiazol-2-yl)-1H-imidazol-1-yl]methyl}-1H-imidazo[4,5-c]pyridine

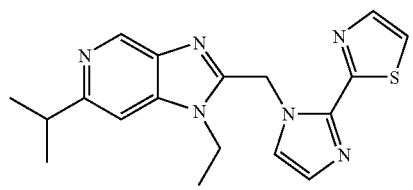

1. Preparation of 4-ethylamino-6-isopropyl-3-nitro-1H-pyridin-2-one

To a mixture of 4-chloro-6-isopropyl-3-nitro-1H-pyridin-2-one (Example 28, step 6) (500 mg, 2.31 mmol) in $CH_3CN$ at room temperature is added $EtNH_2 \cdot HCl$ (565 mg, 6.92 mmol) followed by $Et_3N$ (1.29 mL, 9.23 mmol). The reaction mixture is then stirred in a sealed tube at 100° C. for 1.5 h. After cooling, the reaction mixture is diluted with $CH_2Cl_2$ and washed with $H_2O$ (2×25 mL). The aqueous washes are reextracted once with $CH_2Cl_2$, and the combined extracts are dried over $Na_2SO_4$ and concentrated to provide 4-ethylamino-6-isopropyl-3-nitro-1H-pyridin-2-one as a yellow-orange solid. The material is sufficiently pure to be used without further purification. $^1H$ NMR (DMSO-$d_6$, 400 MHz) δ 11.1 (br, 1H), 8.93 (m, 1H), 5.73 (s, 1H), 3.37 (dq, J=7.4, 6.8 Hz, 2H), 2.67 (sept, J=6.8 Hz, 1H), 1.17 (t, J=7.4 Hz, 3H), 1.15 (d, J=6.8 Hz, 6H) ppm.

2. Preparation of (2-chloro-6-isopropyl-3-nitro-pyridin-4-yl)-ethyl-amine

A mixture of 4-ethylamino-6-isopropyl-3-nitro-1H-pyridin-2-one (520 mg, 2.31 mmol) in $POCl_3$ is stirred at reflux for 1.5 h. After cooling, the solution is concentrated in vacuo. The reaction flask is then placed in an ice bath and crushed ice is added to the residue. The mixture is swirled vigorously for a few minutes and then stirred at 0° C. for 1 h. The mixture is then extracted with EtOAc. The extract is washed with additional $H_2O$ (20 mL) and brine (20 mL). The extract is dried over $Na_2SO_4$ and concentrated to afford (2-chloro-6-isopropyl-3-nitro-pyridin-4-yl)-ethyl-amine as a yellow solid. The material is sufficiently pure to be used without further purification. $^1H$ NMR ($CDCl_2$, 400 MHz) δ 6.62 (br, 1H), 6.44 (s, 1H), 3.31 (m, 2H), 2.91 (sept, J=6.8 Hz, 1H), 1.33 (t, J=7.4 Hz, 3H), 1.26 (d, J=6.8 Hz, 6H) ppm.

3. Preparation of $N^4$-ethyl-6-isopropyl-pyridine-3,4-diamine hydrochloride A solution of (2-chloro-6-isopropyl-3-nitro-pyridin-4-yl)-ethyl-amine (0.56 g, 2.30 mmol) in MeOH (20 mL) containing 10% Pd/C (~50 mg) is stirred under and atmosphere of 12 for 3.5 h. The reaction mixture is then filtered through a pad of Celite using MeOH. The filtrate is concentrated in vacuo. Toluene is added to the residue and then removed in vacuo. This is repeated once more, yielding $N^4$-ethyl-6-isopropyl-pyridine-3,4-diamine hydrochloride as a dark solid. $^1H$ NMR ($CD_3OD$, 400 MHz) δ 7.46 (s, 1H), 6.60 (s, 1H), 3.43 (q, J=7.4 Hz, 2H), 3.03 (sept, J=6.8 Hz, 1H), 1.35 (t, J=7.4 Hz, 3H), 1.33 (d, J=6.8 Hz, 6H) ppm.

4. Preparation of 1-ethyl-6-isopropyl-2-{[2-(1,3-thiazol-2-yl)-1H-imidazol-1-yl]methyl}-1H-imidazo[4,5-c]pyridine To a suspension of $N^4$-ethyl-6-isopropyl-pyridine-3,4-diamine hydrochloride (126 mg, 0.582 mmol) in $CH_2Cl_2$ (5 mL) at room temperature under $N_2$ is added 2.0 M $AlMe_3$ in toluene (0.35 mL, 0.728 mmol). The dark solution is then stirred at room temperature for 45 min. Next, a solution of (2-Thiazol-2-yl-imidazol-1-yl)-acetic acid methyl ester (65 mg, 0.291 mmol) in $CH_2Cl_2$ (2 mL) is added via cannula followed by a 1 mL rinse. The reaction mixture is stirred at reflux overnight. After cooling, it is treated with MeOH (~0.5 mL) and then diluted with 0.5 N NaOH and additional $CH_2Cl_2$. The mixture is stirred vigorously for 15 min and then extracted thrice with $CH_2Cl_2$ containing some (~5%) MeOH. The combined extracts are dried over $K_2CO_3$ and concentrated to 156 mg of a crude mixture of the desired 1-ethyl-6-isopropyl-2-{[2-(1,3-thiazol-2-yl)-1H-imidazol-1-yl]methyl}-1H-imidazo[4,5-c]pyridine and N-(4-amino-6-isopropyl-pyridin-3-yl)-2-(2-thiazol-2-yl-imidazol-1-yl)-acetamide. This material is then dissolved in AcOH (6 mL), and the resulting solution is stirred at reflux for 5 h. After cooling, the reaction mixture is concentrated in vacuo. The residue is dissolved in $CH_2Cl_2$ and washed with 0.5 N NaOH. The aqueous layer is reextracted twice with $CH_2Cl_2$, and the combined extracts are dried over $K_2CO_3$ and concentrated. The crude material is purified by preparative TLC. Developing with 15:1 $CHCl_3$ yields 1-ethyl-6-isopropyl-2-{[2-(1,3-thiazol-2-yl)-1H-imidazol-1-yl]methyl}-1H-imidazo[4,5-c]pyridine. $^1H$ NMR ($CDCl_3$, 400 MHz) δ 9.01 (s, 1H), 7.83 (d, J=3.2 Hz, 1H), 7.38 (d, J=3.2 Hz, 1H), 7.15 (s, 1H), 7.12 (s, 1H), 7.09 (s, 1H), 6.32 (s, 2H), 4.21 (q, J=7.2 Hz, 2H), 3.17 (sept, J=6.8 Hz, 1H), 1.34 (d, J=6.8 Hz, 6H), 1.10 (t, J=7.2 Hz, 3H) ppm.

Example 30

Synthesis of 1-ethyl-2-{[2-(1,3-thiazol-2-yl)-4-(trifluoromethyl)-1H-imidazol-1-yl]methyl}-1H-imidazo[4,5-c]pyridine

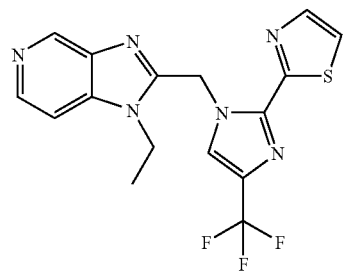

1. Preparation of 2-(4-trifluoromethyl-1H-imidazol-2-yl)-thiazole

Analogous to the published procedure (*J. Med. Chem.* 2000, 43, 2165-2175), 1,1-dibromo-3,3,3-trifluoroacetone (4.47 g, 16.6 mmol) is added to a solution of NaOAc (2.72 g, 33.1 mmol) in $H_2O$ (15 mL). The resulting solution is stirred at 100° C. for 30 min and then allowed to cool to rt. Next, a solution of 2-thiazolecarboxaldehyde (1.5 g, 13.3 mmol) in MeOH (15 mL), containing conc. NH$_4$OH (5 mL), is added. The reaction mixture is then stirred at room temperature for 20 h. It is then filtered, the solid washed with H$_2$O, and dried. 2-(4-Trifluoromethyl-1H-imidazol-2-yl)-thiazole is obtained as an off-white fluffy solid. $^1$H NMR (DMSO-d$_6$, 400 MHz) δ 13.81 (br, 1H), 7.97 (d, J=3.2 Hz, 1H), 7.94 (s, 1H), 7.87 (d, J=3.2 Hz, 1H) ppm.

2. Preparation of (2-thiazol-2-yl-4-trifluoromethyl-imidazol-1-yl)-acetic acid methyl ester To a suspension of NaH (109 mg of a 60% dispersion in mineral oil, 2.74 mmol) in THF (10 mL) at 0° C. under N$_2$ is added a solution of 2-(4-trifluoromethyl-1H-imidazol-2-yl)-thiazole (500 mg, 2.28 mmol) in THF (4 mL) via cannula, followed by a 1 mL rinse. The mixture is stirred at 0° C. for 30 min and then treated with methyl bromoacetate (0.28 mL, 2.97 mmol). The reaction mixture is stirred overnight while slowly warming to rt. It is then diluted with H$_2$O (10 mL) and the resulting mixture stirred vigorously for 5 min. The mixture is further diluted with some brine and then extracted twice with EtOAc. The combined extracts are dried over Na$_2$SO$_4$ and concentrated. The crude material is purified by flash chromatography on silica gel. Elution with 4:1 hexanes-EtOAc followed by 3:1 hexanes-EtOAc affords unreacted 2-(4-trifluoromethyl-1H-imidazol-2-yl)-thiazole as well as (2-thiazol-2-yl-4-trifluoromethyl-imidazol-1-yl)-acetic acid methyl ester. $^1$H NMR (CDCl$_3$, 400 MHz) δ 7.82 (d, J=3.2 Hz, 1H), 7.40 (d, J=3.2 Hz, 1H), 7.35 (s, 1H), 5.41 (s, 2H), 3.77 (s, 3H) ppm.

3. Preparation of 1-ethyl-2-[{2-(1,3-thiazol-2-yl)-4-(trifluoromethyl)-1H-imidazol-1-yl]methyl}-1H-imidazo[4,5-c]pyridine To a mixture of N$^4$-ethyl-pyridine-3,4-diamine (94 mg, 0.687 mmol) in CH$_2$Cl$_2$ (5 mL) at room temperature under N$_2$ is added 2.0 M AlMe$_3$ in toluene (0.43 mL, 0.858 mmol), and the resulting mixture is stirred at room temperature for 1 h. Next, a solution of (2-thiazol-2-yl-4-trifluoromethyl-imidazol-1-yl)-acetic acid methyl ester (100 mg, 0.343 mmol) in CH$_2$Cl$_2$ is added via cannula. The reaction mixture is then stirred at reflux overnight. After cooling to rt, it is treated with MeOH (~1 mL). The mixture is further diluted with 0.5 N aq NaOH (10 mL) and then stirred vigorously for 30 min. The mixture is then extracted thrice with CH$_2$Cl$_2$ containing some (~5%) MeOH, and the combined extracts are dried over K$_2$CO$_3$ and concentrated. The crude mixture of 1-ethyl-2-{[2-(1,3-thiazol-2-yl)-4-(trifluoromethyl)-1H-imidazol-1-yl]methyl}-1H-imidazo[4,5-c]pyridine and N-(4-amino-pyridin-3-yl)-2-(2-thiazol-2-yl-4-trifluoromethyl-imidazol-1-yl)-acetamide is dissolved in AcOH (6 mL), and the resulting solution stirred at reflux overnight. The reaction mixture is then concentrated, and the residue is dissolved in CH$_2$Cl$_2$ and washed with 0.5 N aq NaOH. The aqueous layer is reextracted once with CH$_2$Cl$_2$, and the combined extracts are dried over K$_2$CO$_3$ and concentrated. The crude residue is purified by preparative TLC. Developing with 15:1 CHCl$_3$-MeOH affords 1-ethyl-2-{[2-(1,3-thiazol-2-yl)-4-(trifluoromethyl)-1H-imidazol-1-yl]methyl}-1H-imidazo[4,5-c]pyridine. $^1$H NMR (CDCl$_3$, 400 MHz) δ 9.10 (s, 1H), 8.47 (d, J=6.0 Hz, 1H), 7.88 (d, J=3.2 Hz, 1H), 7.58 (s, 1H), 7.48 (d, J=3.2 Hz, 1H), 7.31 (d, J=5.6 Hz, 1H), 6.37 (s, 2H), 4.31 (q, J=7.2 Hz, 2H), 1.24 (t, J=7.2 Hz, 3H) ppm.

Example 31

Synthesis of 3-ethyl-2-{[2-(6-fluoropyridin-2-yl)-1H-imidazol-1-yl]methyl}-6-propyl-3H-imidazo[4,5-c]pyridine

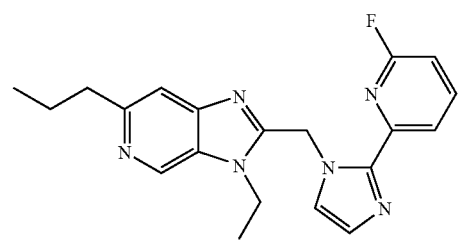

1. Preparation of N-(4-amino-6-propyl-pyridin-3-yl)-acetamide

To a mixture of 6-propyl-pyridine-3,4-diamine hydrochloride (prepared from ethyl butyrylacetate as described in Example 28, steps 1-9) (187 mg, 1.00 mmol) in CH$_2$Cl$_2$ (4 mL) at 0° C. under N$_2$ is added pyridine (0.24 mL, 3.00 mmol) followed by DMF (2 mL) (for solubility). Next, AC20 (0.104 mL, 1.1 mmol) is added. The reaction mixture is stirred for 3 h while slowly warming to rt. It is then poured into saturated aq NaHCO$_3$ and extracted thrice with CH$_2$Cl$_2$. The combined extracts are dried over K$_2$CO$_3$ and concentrated to 114 mg of crude N-(4-amino-6-propyl-pyridin-3-yl)-acetamide, which was used without further purification. $^1$H NMR (CDCl$_3$, 300 MHz) δ 8.73 (br, 1H), 8.00 (s, 1H), 8.43 (s, 1H), 4.63 (br, 2H), 2.54 (m, 2H), 2.13 (s, 3H), 1.63 (sextet, J=7.2 Hz, 2H), 0.89 (t, J=7.2 Hz, 3H) ppm. Electrospray MS: m/z 194 [M+1].

2. Preparation of N$^3$-ethyl-6-propyl-pyridine-3,4-diamine

A solution of the crude N-(4-amino-6-propyl-pyridin-3-yl)-acetamide (114 mg, 0.59 mmol) in THF (2.5 mL) at 0° C. under N$_2$ is treated with 0.5 M EtNMe$_2$.AlH$_3$ in toluene (2.4 mL, 1.18 mmol). The reaction mixture is stirred for 4 h while slowly warming to rt, whereupon it is treated with additional 0.5 M EtNMe$_2$.AlH$_3$ in toluene (2.4 mL, 1.18 mmol). After stirring at room temperature overnight, the reaction mixture is cooled to 0° C. and treated with moist Na$_2$CO$_3$. The mixture is diluted with CH$_2$Cl$_2$ and stirred vigorously for 15 min. It is then filtered through a pad of Celite, and the filtrate concentrated. The crude material is partially purified by preparative thin layer chromatography, developing with 15:1 CHCl$_3$-MeOH (+1% Et$_3$N). The band containing the desired N$^3$-ethyl-6-propyl-pyridine-3,4-diamine does not separate well from the approximately 10% of the slightly more polar, unreacted N-(4-amino-6-propyl-pyridin-3-yl)-acetamide. Both bands are collected, and the mixture is carried into the next reaction. $^1$H NMR (CDCl$_3$, 300 MHz) δ 7.74 (s, 1H), 6.42 (s, 1H), 4.10 (br, 1H), 3.67 (m, 1H), 3.10 (q, J=7.2 Hz, 2H), 2.56 (m, 2H), 1.67 (sextet, J=7.2 Hz, 2H), 1.25 (t, J=7.2 Hz, 3H), 0.91 (t, J=7.2 Hz, 3H) ppm. Electrospray MS: m/z 180 [M+1].

3. Preparation of 3-ethyl-2-{[2-(6-fluoropyridin-2-yl)-1H-imidazol-1-yl]methyl}-6-propyl-3H-imidazo[4,5-c]pyridine A solution of $N^3$-ethyl-6-propyl-pyridine-3,4-diamine (82 mg, ~0.45 mmol, contaminated with ~10% of N-(4-amino-6-propyl-pyridin-3-yl)-acetamide) in 1,2-dichloroethane (4 mL) at room temperature under $N_2$ is treated with 2.0 M AlMe$_3$ (0.69 mL, 1.37 mmol). The resulting solution is stirred at room temperature for 30 min and then treated with a solution of [2-(6-fluoro-pyridin-2-yl)-imidazol-1-yl]-acetic acid methyl ester (97 mg, 0.41 mmol) in 1,2-dichloroethane via cannula, followed by a 1 ml rinse. The reaction mixture is then stirred at reflux overnight. After cooling, it is treated with MeOH (~2 mL) and then further diluted with saturated aq NaHCO$_3$ (~10 mL) and some H$_2$O. The mixture is stirred vigorously for 15 min and then extracted thrice with CHCl$_3$ containing some (~5%) MeOH. The combined extracts are dried over K$_2$CO$_3$ and concentrated. The crude material is purified by preparative thin layer chromatography. Developing with 15:1 CHCl$_3$-MeOH yields 3-ethyl-2-{[2-(6-fluoropyridin-2-yl)-1H-imidazol-1-yl]methyl}-6-propyl-3H-imidazo[4,5-c]pyridine as an off-white solid. $^1$H NMR (CDCl$_3$, 300 MHz) δ 8.70 (d, J=0.9 Hz, 1H), 8.17 (dd, J=8.0, 2.6 Hz, 1H), 7.89 (q, J=7.8 Hz, 1H), 7.47 (s, 1H), 7.22 (d, J=0.9 Hz, 1H), 7.18 (d, J=1.5 Hz, 1H), 6.88 (dd, J=8.6, 2.9 Hz, 1H), 6.27 (s, 2H), 4.42 (q, J=7.2 Hz, 2H), 2.86 (m, 2H), 1.78 (sextet, J=7.2 Hz, 2H), 1.30 (t, J=7.2 Hz, 3H), 0.97 (t, J=7.2 Hz, 3H) ppm. Electrospray MS: m/z 365 [M+1].

Example 32

Synthesis of 1-ethyl-2-{[2-(1,3-thiazol-2-yl)-1H-imidazol-1-yl]methyl}-6-(trifluoromethyl)-1H-imidazo[4,5-c]pyridine

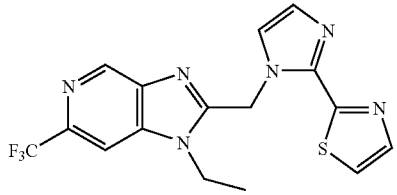

1. Preparation of 5-Nitro-2-trifluoromethyl-pyridin-4-ol 25 mL of fuming H$_2$SO$_4$ under cold conditions (0° C.) is added dropwise to a stirred solution of 4-hydroxy-2-trifluoromethylpyridine [*Chemistry of Heterocyclic Compounds* 1997, 33, 995-996] (4 g, 24.5 mmol) in concentrated H$_2$SO$_4$ (10 mL). HNO$_3$ (fuming, 90%, 25 mL) is added carefully to the above mixture with caution to keep the offset of any exotherm under control, and the reaction is allowed to warm to room temperature slowly. After heating at 120° C. for 6 h with stirring, the resulting mixture is cooled to room temperature, poured into ice-cold water maintaining the pH around 1 with the addition of 10N NaOH solution, and then extracted with CHCl$_3$. The combined organic phase is washed successively with saturated aqueous NaHCO$_3$, water, brine, dried over Na$_2$SO$_4$, and concentrated in vacuo to afford 5-nitro-2-trifluoromethyl-pyridin-4-ol as an yellow solid. $^1$H NMR (300 MHz, CDCl$_3$) δ 9.33 (s, 1H), 7.50 (s, 1H).

2. Preparation of 4-Chloro-5-nitro-2-trifluoromethyl-pyridine

The crude 5-nitro-2-trifluoromethyl-pyridin-4-ol (3.4 g, 16.3 mmol) was treated with PCl$_5$ (5.2 g, 24.97 mmol) and POCl$_3$ (7 mL, 24.49 mmol). The resulting mixture is heated at 80° C. for 18 h, cooled and poured into ice-cold water, and extracted with CH$_2$Cl$_2$. The combined organic phase is washed successively with saturated aqueous NaHCO$_3$, water, brine, dried over Na$_2$SO$_4$, and concentrated in vacuo to afford 4-Chloro-5-nitro-2-trifluoromethyl-pyridine as an yellow oil. $^1$H NMR (300 MHz, CDCl$_3$): δ 9.17 (s, 1H) 7.9 (s, 1H).

3. Preparation of Ethyl-(5-nitro-2-trifluoromethyl-pyridin-4-yl)-amine

K$_2$CO$_3$ (4.15 g, 30.01 mmol), and 2.0 M solution of EtNH$_2$ (15 mL, 30.01 mmol) in THF are added to a solution of 4-chloro-5-nitro-2-trifluoromethyl-pyridine (3.4 g, 15.0 mmol) in acetonitrile (30 mL) under cold conditions. The reaction is complete after stirring at 0° C. for 2 h. Usual work up affords ethyl-(5-nitro-2-trifluoromethyl-pyridin-4-yl)-amine as an yellow-orange viscous oil. $^1$H NMR (300 MHz, CDCl$_3$) δ 9.24 (s, 1H) 7.09 (s, 1H), 3.45 (t, J=7.2 Hz, 2H), 1.42 (t, J=7.2 Hz, 3H).

4. Preparation of $N^4$-Ethyl-6-trifluoromethyl-pyridine-3,4-diamine

Ethyl-(5-nitro-2-trifluoromethyl-pyridin-4-yl)-amine is hydrogenated under usual conditions to afford N-ethyl-6-trifluoromethyl-pyridine-3,4-diamine. $^1$H NMR (300 MHz, CD$_3$OD): δ 7.71 (s, 1H), 6.75 (s, 1H), 3.28 (t, J=6.9 Hz, 2H), 1.31 (t, J=6.9 Hz, 3H).

5. Preparation of 2-Chloromethyl-1-ethyl-6-trifluoromethyl-1H-imidazo[4,5-c]pyridine The HCl salt of ethyl 2-chloro-acetimidate (3.90 g, 24.58 mmol) is added to a solution of N-ethyl-6-trifluoromethyl-pyridine-3,4-diamine (1.44 g, 7.02 mmol) in EtOH (20 mL) and refluxed for 3 h. The reaction mixture is cooled to room temperature and concentrated under reduced pressure. The residue is diluted with CH$_2$Cl$_2$, washed with NaHCO$_3$ solution, dried over Na$_2$SO$_4$, and concentrated to obtain 2-chloromethyl-1-ethyl-6-trifluoromethyl-1H-imidazo[4,5-c]pyridine. $^1$H NMR (300 MHz, CDCl$_3$): δ 9.14 (s, 1H), 7.66 (s, 1H), 7.26 (s, 1H), 4.87 (s, 2H), 4.40 (t, J=7.5 Hz, 2H), 1.58 (t, J=7.5 Hz, 3H).

6. Preparation of 1-ethyl-2-{[2-(1,3-thiazol-2-yl)-1H-imidazol-1-yl]methyl}-6-(trifluoromethyl)-1H-imidazo[4,5-c]pyridine A solution of 2-Chloromethyl-1-ethyl-6-trifluoromethyl-1H imidazo[4,5-c]pyridine (1 g, 3.8 mmol) in anhydrous DMF (15 mL) were added K$_2$CO$_3$ (2.68 g, 19 mmol), and 2-(1H-imidazol-2-yl)-thiazole (555 mg, 3.8 mmol) and stirred at room temperature for 48 h. The crude residue after usual work up was purified eluting with 5% MeOH—CH$_2$Cl$_2$ containing few drops of NH$_4$OH to afford 1-ethyl-2-{[2-(1,3-thiazol-2-yl)-1H-imidazol-1-yl]methyl}-6-(trifluoromethyl)-1H-imidazo[4,5-c]pyridine (800 mg, 80%); $^1$H NMR (CD$_3$OD): δ 8.83 (s, 1H), 8.14 (s, 1H), 7.71 (d, J=2.7 Hz, 1H), 7.53 (d, J=2.7 Hz, 1H), 7.45 (d, J=0.9 Hz, 1H), 7.19 (d, J=0.9 Hz, 1H), 6.30 (s, 2H), 4.54 (q, J=5.4 Hz, 2H), 1.46 (t, J=5.4 Hz, 3H); m/z 379 [M+1]

Example 33

Synthesis of 3-ethyl-2-{[2-(1,3-thiazol-2-yl)-1H-imidazol-1-yl]methyl}-6-(trifluoromethyl)-3H-imidazo[4,5-c]pyridine

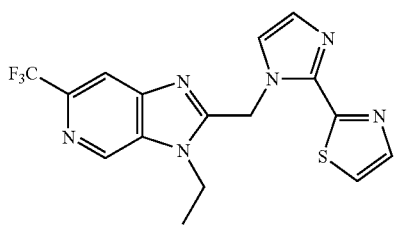

1. Preparation of 5-Nitro-2-trifluoromethyl-pyridin-4-ylamine

Ammonia gas is bubbled through a solution of 2-trifluoromethyl-4-chloro-5-nitro-pyridine (4.12 g, 18.23 mmol) in anhydrous THF at room temperature for 3 h. Removal of solvent under reduced pressure affords 5-nitro-2-trifluoromethyl-pyridin-4-ylamine (3.6 g, 96%); $^1$H NMR (300 MHz, CDCl$_3$) δ 7.15 (s, 1H), 9.15 (s, 1H).

2. Preparation of 6-Trifluoromethyl-pyridine-3,4-diamine

Hyrogenation as described in the previous examples provides 6-trifluoromethyl-pyridine-3,4-diamine. $^1$H NMR (300 MHz, CDCl$_3$) δ 6.95 (s, 1H), 8.01 (s, 1H).

3. Preparation of N$^3$-ethyl-6-trifluoromethyl-pyridine-3,4-diamine

Cesium carbonate (3.1 g, 26.88 mmol) and ethyl iodide (1.76 g, 10.75 mmol) is added to a solution of 6-trifluoromethyl-pyridine-3,4-diamine (1.05 g, 8.96 mmol) in anhydrous DMF (12 mL). The mixture is heated in a sealed tube for 18 h, then cooled to room temperature, and diluted with EtOAc and water. Usual work up and purification by column chromatography, eluting with EtOAc-hexanes provides pure N-Ethyl-6-trifluoromethyl-pyridine-3,4-diamine. $^1$H NMR (300 MHz, CDCl$_3$) δ 7.95 (s, 1H); 6.95 (s, 1H), 3.21 (q, J=5.4 Hz, 2H), 1.35 (t, J=5.4 Hz, 3H).

4. Preparation of 2-Chloromethyl-3-ethyl-6-trifluoromethyl-3H-imidazo[4,5-c]pyridine 2-Chloromethyl-3-ethyl-6-trifluoromethyl-3H-imidazo[4,5-c]pyridine is made from N$^3$-Ethyl 6-Trifluoromethyl-pyridine-3,4-diamine following the procedure described previously for the preparation of 2-Chloromethyl-1-ethyl-6-trifluoromethyl-1H-imidazo[4,5-c]pyridine. $^1$H NMR (300 MHz, CDCl$_3$) δ 8.89 (s, 1H), 8.04 (s, 1H), 4.87 (s, 2H), 4.45 (t, J=7.2 Hz, 2H), 1.59 (t, J=7.2 Hz, 3H)

5. Preparation of 3-ethyl-2-{[2-(1,3-thiazol-2-yl)-1H-imidazol-1-yl]methyl}-6-(trifluoromethyl)-3H-imidazo[4,5-c]pyridine As described previously for the preparation of 1-Ethyl-2-(2-thiazol-2-yl-imidazol-1-ylmethyl)-6-trifluoromethyl-1H-imidazo[4,5-c]pyridine, nucleophilic displacement of the 2-chloromethyl-3-ethyl-6-trifluoromethyl-3H-imidazo[4,5-c]pyridine with the same 2-(1H-imidazol-2-yl)-thiazole followed by usual work provides 3-ethyl-2-{[2-(1,3-thiazol-2-yl)-1H-imidazol-1-yl]methyl}-6-(trifluoromethyl)-3H-imidazo[4,5-c]pyridine. $^1$H NMR (CD$_3$OD) δ 9.02 (s, 1H), 7.89 (s, 1H), 7.70 (d, J=3 Hz, 1H), 7.52 (d, J=3.3 Hz, 1H), 7.46 (d, J=1.5 Hz, 1H), 7.19 (d, J=1.5 Hz, 1H), 6.29 (s, 2H), 4.56 (q, J=7.5 Hz, 2H), 1.52 (t, J=7.5 Hz, 3H) m/z 379 [M+1]

Example 34

Synthesis of 3-ethyl-2-[(2-pyrimidin-2-yl-1H-imidazol-1-yl)methyl]-3H-imidazo[4,5-c]pyridine-4-carbonitrile

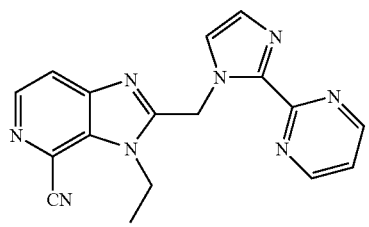

1. Preparation of 3-Ethylamino-4-nitro-pyridine-2-carbonitrile

TMSCN (1.1 ml, 8.33 mmol) and dimethyl amino carbamoyl chloride (0.76 mL, 8.33 mmoL) are added to a solution of 3-ethylamino-4-nitro-pyridine-1-oxide (1 g, 6.94 mmol) in anhydrous DMF (10 mL) were added. The reaction mixture is stirred overnight at 80° C., cooled to room temperature, and diluted with CH$_2$Cl$_2$ and water. The combined organic layer is washed with water, brine, dried over Na$_2$SO$_4$, and concentrated. The residue is chromatographed eluting with 40% EtOAc-hexanes to afford 3-ethylamino-4-nitro-pyridine-2-carbonitrile as a yellow solid. $^1$H NMR (300 MHz, CD$_3$OD): δ 7.82 (d, J=4.5 Hz, 1H), 7.50 (d, J=4.5 Hz, 1H), 3.70 (q, J=7.2 Hz, 2H), 1.39 (t, J=7.2 Hz, 3H).

2. Preparation of 4-Amino-3-ethylamino-pyridine-2-carbonitrile

Hydrogenaton of 3-Ethylamino-4-nitro-pyridine-2-carbonitrile under conditions previously described provides 4-Amino-3-ethylamino-pyridine-2-carbonitrile. $^1$H NMR (300 MHz, CD$_3$OD): δ 7.75 (d, J=5.4 Hz, 1H), 6.66 (d, J=5.4 Hz, 1H), 3.35 (q, J=7.2 Hz, 2H), 1.29 (t, J=7.2 Hz, 3H).

3. Preparation of 2-Chloromethyl-3-ethyl-3H-imidazo[4,5-c]pyridine-4-carbonitrile 2-Chloromethyl-3-ethyl-3H-imidazo[4,5-c]pyridine-4-carbonitrile is prepared from the reaction of 4-amino-3-ethylamino-pyridine-2-carbonitrile and 2-chloro acetimidate following the previously described procedure. $^1$H NMR (300 MHz, CDCl$_3$) δ 8.55 (d, J=5.4 Hz, 1H), 7.84 (d, J=5.4 Hz, 1H), 4.98 (s, 2H), 3.41 (q, J=7.5 Hz, 2H), 1.23 (t, J=7.5 Hz, 3H).

4. Preparation of 3-ethyl-2-[(2-pyrimidin-2-yl-1H-imidazol-1-yl)methyl]-3H-imidazo[4,5-c]pyridine-4-carbonitrile 3-ethyl-2-[(2-pyrimidin-2-yl-1H-imidazol-1-yl)methyl]-3H-imidazo[4,5-c]pyridine-4-carbonitrile is obtained from 2-chloromethyl-3-ethyl-3H-imidazo[4,5-c]pyridine-4-carbonitrile by nucleophilic displacement with 2-(1H-Imidazol-2-yl)-pyrimidine, as described previously, followed by usual work up. $^1$H NMR (300 MHz, CD$_3$OD): δ 8.70 (d, J=5.1 Hz, 2H), 8.41 (d, J=5.4 Hz, 1H), 7.73 (d, J=5.1 Hz, 1H), 7.52 (d, J=1.2 Hz, 1H), 7.31 (d, J=1.2 Hz, 1H), 7.27 (t, J=4.5 Hz, 1H), 6.35 (s, 2H), 4.75 (q, J=7.5 Hz, 2H), 1.63 (t, J=7.2 Hz, 3H); m/z 331 [M+1].

Example 35

Synthesis of 1-(2-{[2-(6-fluoropyridin-2-yl)-1H-imidazol-1-yl]methyl}-1-propyl-1H-imidazo[4,5-c]pyridin-4-yl)ethanone

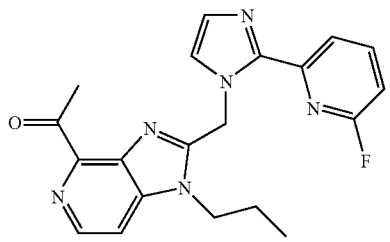

To the mixture of H$_2$O (5 mL) and CH$_2$Cl$_2$ (5 mL) is added 1-Propyl-2-{[2-(2-fluoropyrid-6-yl)-1H-imidazol-1-yl]methyl}-5-aza-1H-benzimidazole (168 mg, 0.5 mmol), pyruvic acid (132 mg, 1.5 mmol), silver nitrate (7 mg, 0.04 mmol), (NH$_4$)$_2$S$_2$O$_8$ (342 mg, 1.5 mmol), and sulfuric acid (98%, 100 mg, 1.0 mmol). The mixture is heated to 40° C. for 2 hr, then cooled to room temperature. The aqueous solution is neutralized to pH 8 with saturated sodium bicarbonate solution and extracted with CH$_2$Cl$_2$. The combined organic layers are dried over Na$_2$SO$_4$ and solvent is removed to give a brown solid. Purification by preparative TLC provides 1-(2-({[2-(6-fluoropyridin-2-yl)-1H-imidazol-1-yl]methyl}-1-propyl-1H-imidazo[4,5-c]pyridin-4-yl)ethanone as white solid. $^1$H NMR (CDCl$_3$) δ 8.48 (d, 1H), 8.12 (dd, 1H), 7.88 (q, 1H), 7.44 (d, 1H), 7.23 (d, 1H), 7.11 (d, 1H), 6.88 (dd, 1H), 6.40 (s, 2H), 4.22 (q, 2H), 2.84 (s, 3H), 1.58 (m, 2H), 0.74 (t, 3H).

Example 36

Synthesis of 1-(3-ethyl-2-{[2-(1,3-thiazol-2-yl)-1H-imidazol-1-yl]methyl}-3H-imidazo[4,5-c]pyridin-6-yl)ethanone

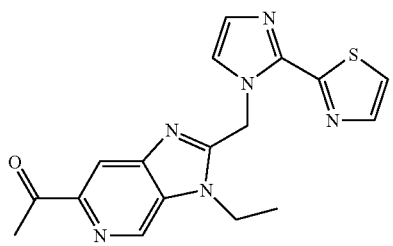

1. Preparation of 2,5-Dichloro-pyridine 1-oxide

A mixture of 2,5-Dichlropyridine (30 g, 0.2 mmol) and 3-Chloroperoxybenzoic acid (70%, 50 g, 0.2 mmol) in 500 mL of Dichloroethane is heated at 50° C. overnight. After cooling to −30° C., NH$_3$ gas is bubbled into the reaction mixture for 5 minutes. The mixture is filtered, the solid is washed with dichloroethane (50 mL), and the filtrate is concentrated to a solid. The solid is mixed with 200 mL of Hexane and heated at reflux for 30 minutes. After cooling, the precipitate is collected by filtration, and dried to give the titled compound as a tan solid. $^1$H NMR (CDCl$_3$): δ 8.40 (d, 1H), 7.44 (d, 1H), 7.22 (t, 1H).

2. Preparation of 2,5-dichloro-4-nitro-pyridine 1-oxide

At 0° C., 30% oleum (13 mL) is added slowly to fuming HNO$_3$ (22 mL) and the resulting mixture is added slowly to the solution of 2,5-dichloro-pyridine 1-oxide (5.2 g, 31 mmol) in concentrated H$_2$SO$_4$. After addition, the reaction mixture is warmed to room temperature over 1 hr, then heated to 80° C. for 2 hr. After cooling to room temperature, the mixture is poured into ice (120 g) and precipitate is formed gradually. The solid is collected by filtration and washed with water. The product is obtained as yellow solid. $^1$H NMR (CDCl$_3$) δ 8.46 (s, 1H), 8.25 (s, 1).

3. Preparation of (6-Chloro-4-nitro-1-oxy-pyridin-3-yl)-ethylamine

To a solution of 2,5-Dichloro-4-nitro-pyridine 1-oxide (7 g, 33 mmol) in 100 mL of THF is added a solution of Ethylamine (2M, 50 mL) dropwise at ° C. The reaction mixture is warmed to room temperature and stirred overnight. The volatiles are evaporated in vacuo. The residue is purified on a silica gel column with 1% CH$_2$Cl$_2$ as eluent to give the title compound as an orange solid. $^1$H NMR (CDCl$_3$): δ 8.24 (s, 1H), 8.06 (s, 1H), 7.62 (br, 1H), 3.25 (q, 2H), 1.38 (t, 3H).

4. Preparation of 1-(5-ethylamino-4-nitro-pyridin-2-yl)-ethanone (6-Chloro-4-nitro-1-oxy-pyridin-3-yl)ethyl-amine (700 mg, 3.2 mmol), tributyl-(1-ethoxy-vinyl)-stannane (1.75 g, 4.9 mmol), PdCl$_2$(PPh$_3$)$_2$ (350 mg, 0.5 mmol), and toluene (35 mL)o are added to a sealed tube; the mixture is degassed for 30 min. The reaction is heated to 75° C. for 16 hr and then cooled to room temperature. 6N HCl solution (20 mL) is added to the mixture is added and the reaction is stirred at room temperature for 1 hr. The reaction mixture is filtered through celite and the aqueous layer is neutralized to basic with saturated NaHCO$_3$. The aqueous layer is extracted with ethyl acetate and the combined organic layers are dried over Na$_2$SO$_4$. The solvent is removed in vacuo. Purification by flash column provides the product as orange solid. $^1$H NMR (CDCl$_3$) δ 8.70 (s, 1H), 8.48 (s, 1H), 7.96 (br, 1H), 3.55 (m, 2H), 2.65 (s, 3H), 0.92 (t, 3H). LRMS 210.1 (MH+).

5. Preparation of 1-(4-amino-5-ethylamino-pyridin-2-yl)-ethanone

A mixture of 1-(5-ethylamino-4-nitro-pyridin-2-yl)-ethanone (310 mg, 1.5 mmol) and 10% Pd/C (50 mg) in ethanol (10 mL) is stirred under hydrogen for 1 hr. The mixture is filtered through Celite and concentrated in vacuo to give the product as yellow solid. $^1$H NMR (CD$_3$OD) δ 7.61 (s, 1H), 7.30 (s, 1H), 3.26 (q, 2H), 2.53 (s, 3H), 0.90 (t, 3H). LRMS 180.5 (MH+).

6. Preparation of 1-(3-ethyl-2-{[2-(1,3-thiazol-2-yl)-1H-imidazol-1-yl]methyl}-3H-imidazo[4,5-c]pyridin-6-yl)ethanone A mixture of 1-(4-amino-5-ethylamino-pyridin-2-yl)-ethanone (54 mg, 0.3 mmol), (2-thiazol-2-yl-imidazol-1-yl)-acetic acid (61 mg, 0.3 mmol), EDCI (60 mg, 0.3 mmol) and pyridine (2 mL) is stirred at room temperature for 72 hr and then poured into water. The aqueous layer is extracted with ethyl acetate and the combined organic layers are dried over Na$_2$SO$_4$. Solvent is evaporated in vacuo and the residue is taken up in acetic acid (5 mL). The mixture is heated to reflux for 16 hr and saturated NaHCO$_3$ solution is added to neutralize the reaction. The aqueous solution is extracted with ethyl acetate and the combined organic layers are dried over Na$_2$SO$_4$. Solvent is removed in vacuo and purification by preparative TLC provides the product as white solid. $^1$H NMR (CDCl$_3$) δ 8.79 (d, 2H), 8.47 (d, 1H), 7.83 (d, 1H), 7.40 (d, 1H), 7.19 (d, 1H), 7.15 (d, 1H), 6.39 (s, 2H), 4.02 (q, 2H), 2.77 (s, 3H), 1.86 (t, 3H). LRMS 353.2 (MH+).

Example 37

Synthesis of 1-Ethyl-2-(2-thiazol-2-yl-2H-pyrazol-3-ylmethyl)-1H-imidazo[4,5-c]pyridine

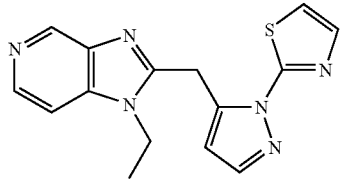

1. Preparation of (2-Thiazol-2-yl-2H-pyrazol-3-yl)-acetic acid ethyl ester

A mixture of thiazol-2-ylhydrazine (2.2 g, 19.1 mmol) and 3,5,5-triethoxy-pent-2-enoic acid ethyl ester (70% purity, 7.1 g, 19.1 mmol) is refluxed in acetic acid overnight. Acetic acid is removed. To the residue is added NaHCO$_3$ (aq.) (40 mL) and ethyl acetate (100 mL). The insoluble material is filtered. The organic layer is dried and solvent removed. The crude is subjected to column separation (hexane/ethyl acetate 3:1) to give (2-thiazol-2-yl-2H-pyrazol-3-yl)-acetic acid ethyl ester as an oil.

2. Preparation of 1-Ethyl-2-(2-thiazol-2-yl-2H-pyrazol-3-ylmethyl)-1H-imidazo[4,5-c]pyridine Trimethylaluminum (2M in toluene) (1.4 mL, 2.85 mmol) is added dropwise under N$_2$ to a solution of N$^4$-Ethyl-pyridine-3,4-diamine (156 mg, 1.14 mmol) in DCM (5 mL). The mixture is stirred at room temperature for 1 hour. A solution of thiazol-2-yl-2H-pyrazol-3-yl)-acetic acid ethyl ester (270 mg, 1.14 mmol) in DCM (2 mL) is added. The mixture is reluxed for 25 hours. On cooling, the reaction is quenched with water added dropwise and DCM (20 mL) is added. The organic layer is separated and the aqueous layer is extracted with DCM (3×30 mL). The combined organic layers are dried and solvent removed. Acetic acid (10 ml) is added to the residue. The solution is refluxed for 3.5 h. Acetic acid is removed in vacuo and the residue is purified by PTLC (10% methanol in DCM) to give 1-Ethyl-2-(2-thiazol-2-yl-2H-pyrazol-3-ylmethyl)-1H-imidazo[4,5-c]pyridine as a solid. $^1$H NMR (CDCl$_3$) δ 9.00 (s, 1H), 8.43 (d, 1H), 7.63 (d, 1H), 7.43 (d, 1H), 7.15 (d, 1H) 7.06 (d, 1H), 6.25 (d, 1H), 4.99 (s, 2H), 4.25 (q, 2H), 1.36 (t, 3H).

Example 38

Synthesis of 1-Ethyl-2-[1-(2-thiazol-2-yl-2H-pyrazol-3-yl)-ethyl]-1H-imidazo[4,5-c]pyridine

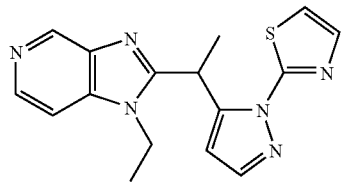

1. Preparation of 2-(2-Thiazol-2-yl-2H-pyrazol-3-yl)-propionic acid ethyl ester A mixture of (2-thiazol-2-yl-2H-pyrazol-3-yl)-acetic acid ethyl ester (100 mg, 0.42 mmol), methyl iodide (66 mg, 0.46 mmol) and cesium carbonate (151 mg, 0.46 mmol) in DMF (6 mL) is stirred at room temperature overnight. The reaction is quenched with NH$_4$Cl (aq.) (6 mL) and ethyl acetate (30 mL). The organic layer is separated and the aqueous layer is extracted with ethyl acetate (3×30 mL). The combined organic layers are dried and the solvent removed. The crude is purified by PTLC (hexane/ethyl acetate 3:1) to give 2-(2-thiazol-2-yl-2H-pyrazol-3-yl)-propionic acid ethyl ester as an oil.

2. Preparation of 1-Ethyl-2-[1-(2-thiazol-2-yl-2H-pyrazol-3-yl)-ethyl]-1H-imidazo[4,5-c]pyridine Trimethylaluminum (2N in toluene)(0.5 mL, 1 mmol)) is added dropwise under N$_2$ to a solution of N$^4$-Ethyl-pyridine-3,4-diamine (44 mg, 0.32 mmol) in DCM (5 mL). The mixture is stirred at room temperature for 1 hour. A solution of thiazol-2-yl-2H-pyrazol-3-yl)-propionic acid ethyl ester in DCM (2 mL) is added. The mixture is reluxed for 3 days. On cooling, the reaction is quenched with water added dropwise and DCM (20 mL) is added. The organic layer is separated and the aqueous layer is extracted with DCM (3×30 mL). The combined organic layers are dried and the solvent removed. The residue is purified by PTLC (10% methanol in DCM) to give 1-ethyl-2-[1-(2-thiazol-2-yl-2H-pyrazol-3-yl)-ethyl]-1H-imidazo[4,5-c]pyridine as a solid. $^1$H NMR (CDCl$_3$) δ 9.05 (s, 1H), 8.39 (d, 1H), 7.59 (d, 1H), 7.49 (d, 1H), 7.25 (d, 1H), 7.09 (d, 1H), 6.28 (d, 1H), 5.85 (q, 1H), 4.19 (q, 2H), 1.85 (d, 3H), 1.29 (t, 3H).

Example 39

Synthesis of 2-[2,4']Bithiazolyl-5'-ylmethyl-1-ethyl-1H-imidazo[4,5-c]pyridine

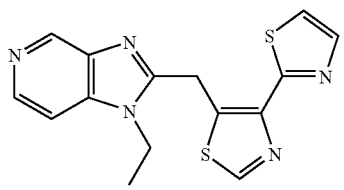

1. Preparation of 4-Oxo-4-thiazol-2-yl-butyric acid ethyl ester

To a stirred solution of 2-trimethylsilanyl-thiazole (2.6 g, 16.53 mmol) in DCM (30 mL) is added a solution of 3-chlorocarbonyl-propionic acid ethyl ester (5.4 g, 32.81 mmol) in DCM (10 mL). The mixture is stirred overnight at room temperature. To the mixture is added 5% NaHCO$_3$ (30 mL) and mixture is stirred at room temperature for 20 minutes. The organic layer is separated and the aqueous lay is extracted with DCM (2×50 mL). The combined organic layers are dried and the solvent removed. The residue is separated by column (methylene chloride) to give 4-oxo-4-thiazol-2-yl-butyric acid ethyl ester.

2. Preparation of 3-Bromo-4-oxo-4-thiazol-2-yl-butyric acid ethyl ester

Phenyltrimethylammonium tribromide (3.4 g, 8.91 mmol) in DCM (20 mL) is added dropwise to a solution of 4-oxo-4-thiazol-2-yl-butyric acid ethyl ester (1.9 g, 8.91 mmol) in DCM (30 mL. The mixture is stirred overnight at room temperature. 5% NaHCO$_3$ (40 mL) is added to the mixture. The organic layer is separated and the aqueous layer is extracted with DCM (2×40 mL). The combined organic layers are dried and solvent removed. The residue is purified by column (hexanes/ethyl acetate 3:1) to give 3-bromo-4-oxo-4-thiazol-2-yl-butyric acid ethyl ester.

3. Preparation of [2,4']Bithiazolyl-5'-yl-acetic acid ethyl ester

To a solution of 3-bromo-4-oxo-4-thiazol-2-yl-butyric acid ethyl ester (2.2 g, 7.53 mmol) in 1,4-dioxane (40 mL) is added thioformamide (freshly made from formamide and P$_2$S$_5$ in 1,4-dioxane) (22.59 mmol). The mixture is refluxed overnight. The solvent is removed and NaHCO$_3$ (aq.) (40 mL) and DCM (100 mL) are added to the residue. The organic layer is separated and the aqueous layer is extracted with DCM (2×40 mL). The combined organic layers are dried and solvent removed. The crude is purified by column (1% methanol n DCM) to give [2,4']bithiazolyl-5'-yl-acetic acid ethyl ester.

4. Preparation of 2-[2,4']Bithiazolyl-5'-ylmethyl-1-ethyl-1H-imidazo[4,5-c]pyridine Trimethylaluminum (2M in toluene)(2.2 mL, 4.4 mmol) is added dropwise under N$_2$ yo a solution of N$^4$-Ethyl-pyridine-3,4-diamine (237 mg, 1.73 mmol) in DCM (5 mL). The mixture is stirred at room temperature for 1 hour. A solution of [2,4']bithiazolyl-5'-yl-acetic acid ethyl ester (440 mg, 1.73 mmol) in DCM (2 mL) is added. The mixture is reluxed for 3 days. On cooling, the reaction is quenched with water added dropwise and DCM (40 mL) is added. The organic layer is separated and the aqueous layer is extracted with DCM (3×30 mL). The combined organic layers are dried and solvent removed. The residue is purified by PTLC (10% methanol in DCM) to give 2-[2,4']bithiazolyl-5'-ylmethyl-1-ethyl-1H-imidazo[4,5-c]pyridine as a solid. $^1$H NMR (CDCl$_3$) δ 9.05 (s, 1H0), 8.76 (s, 1H), 8.41 (d, 1H), 7.88 (d, 1H), 7.41 (d, 1H), 7.25 (d, 1H), 5.35 (s, 2H), 4.26 (q, 2H), 1.25 (t, 3H).

Example 40

Synthesis of 5-Bromo-1-ethyl-2-[3-(3-fluoro-phenyl)-isoxazol-4-ylmethyl]-1-benzoimidazole

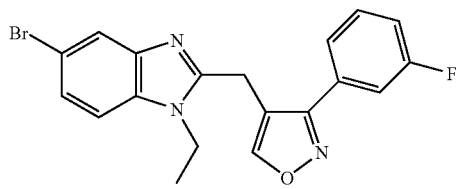

1. Preparation of 3-(5-Bromo-1-ethyl-1H-benzoimidazol-2-yl)-1-(3-fluoro-phenyl)-propan-1-one To a solution of 1-(3-fluoro-phenyl)-ethanone (0.55 g, 4.0 mmol) in THF (30 mL) at −78° C. under N$_2$ is added LDA (2M in hexanes, 2.0 mL, 4.0 mmol). After 10 minutes, 5-bromo-2-chloromethyl-1-ethyl-1H-benzoimidazole (1 g, 3.65 mmol) in THF (5 mL) is added. The mixture is stirred at this temperature for an additional 1 hour and is gradually warmed to room temperature. The reaction is then quenched with saturated NH$_4$Cl. The mixture is extracted with ethyl acetate (3×50 mL). Upon drying, the organic solvent is removed to give 3-(5-Bromo-1-ethyl-1H-benzoimidazol-2-yl)-1-(3-fluoro-phenyl)-propan-1-one as a yellow oil.

2. Preparation of 5-Bromo-1-ethyl-2-[3-(3-fluoro-phenyl)-isoxazol-4-ylmethyl]-1H-benzoimidazole A mixture of 3-(5-Bromo-1-ethyl-1H-benzoimidazol-2-yl)-1-(3-fluoro-phenyl)-propan-1-one (0.1 g, 0.27 mmol) and tris(dimethylamino)methane (0.077 g, 0.54 mmol) is heated at 60° C. in a sealed tube for 6 hours. The volatile material is removed in vacuo. To the residue is added EtOH (5 mL) and hydroxylamine (1.1 mmol). The mixture is heated at 120° C. for 2 hours. The solvent is removed. To the residue is added NaHCO$_3$ (aq.) (10 mL) and DCM (30 mL). The organic layer is separated and the aqueous layer is extracted with DCM (2×15 mL). The combined organic layers are dried and the solvent removed. The crude is purified by PTLC (ethyl acetate/Hexanes 1:1) to give 5-Bromo-1-ethyl-2-[3-(3-fluoro-phenyl)-isoxazol-4-ylmethyl]-1H-benzoimidazole as a solid. $^1$H NMR (CDCl$_3$) δ 8.40 (s, 1H), 7.88 (s, 1H), 7.31-7.52 (m, 4H), 7.18-7.22 (m, 2H), 4.14 (s, 2H), 4.04 (q, 2H), 1.18 (t, 3H).

Example 41

Synthesis of 5-Bromo-1-ethyl-2-[3-(3-fluoro-phenyl)-1H-pyrazol-4-ylmethyl]-1H-benzoimidazole

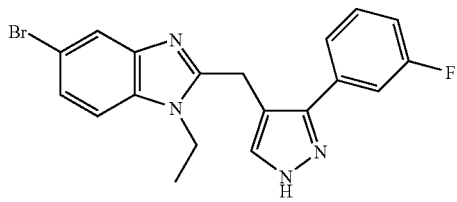

A mixture of 3-(5-Bromo-1-ethyl-1H-benzoimidazol-2-yl)-1-(3-fluoro-phenyl)-propan-1-one (0.1 g, 0.27 mmol) and tris(dimethylamino)methane (0.077 g, 0.54 mmol) is heated at 60° C. in a sealed tube for 6 hours. The volatile material is removed in vacuo. EtOH (5 mL) and hydrazine acetate (1.1 mmol) are added to the residue. The mixture is heated at 120° C. for 2 hours. The solvent is removed. NaHCO$_3$ (aq.) (10 mL) and DCM (30 mL) are added to the residue. The organic layer is separated and the aqueous layer is extracted with DCM (2×15 mL). The combined organic layers are dried and the solvent removed. The crude is purified by PTLC (ethyl acetate/Hexanes 1:1) to give 5-bromo-1-ethyl-2-[3-(3-fluoro-phenyl)-1H-pyrazol-4-ylmethyl]-1H-benzoimidazole as a solid. LRMS: calcd 399.3. found [M+1] 401.0.

Example 42

Synthesis of 5-Bromo-1-ethyl-2-[3-(3-fluoro-phenyl)-1-methyl-1H-pyrazol-4-ylmethyl]-1H-benzoimidazole and 5-Bromo-1-ethyl-2-[5-(3-fluoro-phenyl)-1-methyl-1H-pyrazol-4-ylmethyl]-1H-benzoimidazole

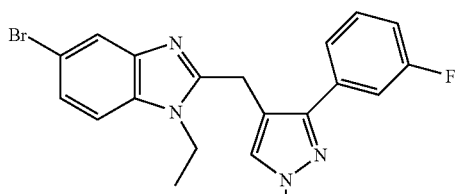

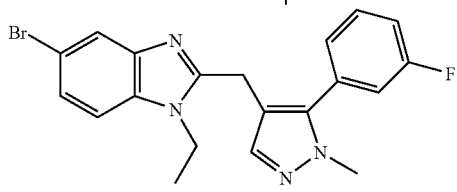

A mixture of 3-(5-Bromo-1-ethyl-1H-benzoimidazol-2-yl)-1-(3-fluoro-phenyl)-propan-1-one (0.1 g, 0.27 mmol) and tris(dimethylamino)methane (0.077 g, 0.54 mmol) is heated at 60° C. in a sealed tube for 6 hours. The volatile material is removed in vacuo. EtOR (5 mL) and methyl hydrazine (1.1 mmol) are added to the residue. The mixture is heated at 120° C. for 2 hours. The solvent is removed. NaHCO$_3$ (aq.) (10 mL) and DCM (30 mL) are added to the residue. The organic layer is separated and the aqueous layer is extracted with DCM (2×15 mL). The combined organic layers are dried and the solvent removed. The crude is purified by PTLC (ethyl acetate/Hexanes 1:1) to give 5-bromo-1-ethyl-2-[3-(3-fluoro-phenyl)-1-methyl-1H-pyrazol-4-ylmethyl]-1H-benzoimidazole and 5-bromo-1-ethyl-2-[5-(3-fluoro-phenyl)-1-methyl-1H-pyrazol-4-ylmethyl]-1H-benzoimidazole.
5-bromo-1-ethyl-2-[3-(3-fluoro-phenyl)-1-methyl-1H-pyrazol-4-ylmethyl]-1H-benzoimidazole: $^1$H NMR (CDCl$_3$) δ 7.88 (s, 1H), 7.27-7.42 (m, 4H), 7.00-7.20 (m, 3H), 4.21 (s, 2H), 3.95 (t, 2H), 3.83 (s, 3H), 1.15 (t, 3H). 5-bromo-1-ethyl-2-[5-(3-fluoro-phenyl)-1-methyl-1H-pyrazol-4-ylmethyl]-1H-benzoimidazole: $^1$H NMR (CDCl$_3$) δ 7.81 (s, 1H), 7.38-7.45 (m, 2H), 7.32 (dd, 1H), 7.00-7.18 (m, 4H), 4.00 (s, 2H), 3.90 (q, 2H), 3.78 (s, 3H), 1.15 (t, 3H).

Example 43

Synthesis of 5-Bromo-1-ethyl-2-[4-(3-fluoro-phenyl)-thiazol-5-ylmethyl]-1H-benzoimidazole

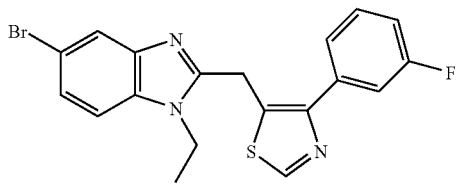

A mixture of 3-(5-bromo-1-ethyl-1H-benzoimidazol-2-yl)-1-(3-fluoro-phenyl)-propan-1-one (0.2 g, 0.53 mmol) and bromine (0.1 g, 0.62 mmol) is refluxed in 1,4-dioxane for 2 hours. Thioformamide (freshly made from formamide and P$_2$S$_5$ in 1,4-dioxane) (1.3 mmol) are added to the solution. The mixture is refluxed overnight. The solvent is removed and NaHCO$_3$ (aq.) (15 mL) and DCM (40 mL) are added to the residue. The organic layer is separated and the aqueous layer is extracted with DCM (2×30 mL). The combined organic layers are dried and solvent removed. The crude is purified by PTLC (5% methanol in DCM) to give 5-bromo-1-ethyl-2-[4-(3-fluoro-phenyl)-thiazol-5-ylmethyl]-1H-benzoimidazole.
$^1$H NMR (CDCl$_3$) δ 8.78 (s, 1H), 7.91 (s, 1H), 7.38-7.48 (m, 4H), 7.11-7.19 (m, 2H), 4.59 (s, 2H), 3.90 (q, 2H), 1.12 (t, 3H).

Example 44

Synthesis of 1-[3-Ethyl-2-(2-thiazol-2-yl-imidazol-1-ylmethyl)-3H-benzoimidazol-5-yl]-ethanone

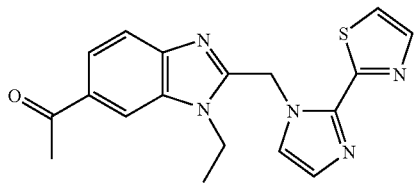

1. Preparation of (5-Chloro-2-nitro-phenyl)-ethyl-amine

A mixture of 4-cloro-2-fluoronitrobenzene (5 g, 28.48 mmol), ethylamine (2M in THF, 24 mL, 48 mmol), and K₂CO₃ (7.9 g, 57 mmol) in acetonitrile (30 mL) is stirred at room temperature overnight. Solvent is removed. Ethyl acetate (80 mL) and brine (40 mL) are added to the residue. The organic layer is separated and the aqueous layer is extracted with ethyl acetate (2×50 mL). The combined organic layers are dried and solvent removed to give 5-chloro-2-nitro-phenyl)-ethyl-amine.

2. Preparation of 1-(3-Ethylamino-4-nitro-phenyl)-ethanone

A mixture of 5-chloro-2-nitro-phenyl)-ethyl-amine (1 g, 4.98 mmol), tributyl-(1-ethoxyvinyl)stannane (2.7 g, 7.48 mmol) and dichlorobis(triphenylphosphine)palladium (II) (175 mg, 0.25 mmol) in toluene (80 mL) is heated at 100° C. in a sealed tube for 5 hours. On cooling, water (30 mL) and HCl (con. 30 mL) are added and the mixture is stirred at room temperature for 2 hours. The mixture is neutralized with NaOH (2 N) and extracted with DCM (3×50 ml). The combined organic layers are dried and solvent removed. The residue is purified by column (hexanes/ethyl acetate 3:1) to give 1-(3-ethylamino-4-nitro-phenyl)-ethanone.

3. Preparation of 1-(4-Amino-3-ethylamino-phenyl)-ethanone

10% Pd/C (100 mg) is added to a Parr bottle containing 1-(3-ethylamino-4-nitro-phenyl)-ethanone (0.98 g, 4.7 mmol) in ethanol (40 mL). The Parr bottle is sealed in a mechanical shaker, evacuated, and then purged with nitrogen followed by hydrogen. The system is pressurized to 50 PSI of hydrogen at room temperature and mechanical shaking engaged. After 2 hours, shaking is stopped, and the system purged with nitrogen prior to opening the vessel. The reaction mixture is filtered through celite, concentrated in vacuo, to give 1-(4-amino-3-ethylamino-phenyl)-ethanone.

4. Preparation of 1-(2-Chloromethyl-3-ethyl-3H-benzoimidazol-5-yl)-ethanone

A mixture of 1-(4-amino-3-ethylamino-phenyl)-ethanone (300 mg, 1.69 mmol) and 2-chloroacetamidine hydrochloride (804 mg, 5.1 mmol) in acetonitrile (20 mL) is refluxed for 3 hours. Solvent is removed and the residue is treated with NaHCO₃ (5%, 20 mL) and DCM (50 mL). The organic layer is separated and the aqueous layer is extracted with DCM (2×40 mL). The combined organic layers are dried and solvent removed to give 1-(2-Chloromethyl-3-ethyl-3H-benzoimidazol-5-yl)-ethanone.

5. Preparation of 1-[3-Ethyl-2-(2-thiazol-2-yl-imidazol-1-ylmethyl)-3H-benzoimidazol-5-yl]-ethanone A mixture of 1-(2-Chloromethyl-3-ethyl-3H-benzoimidazol-5-yl)-ethanone (150 mg, 0.63 mmol), 2-(1H-Imidazol-2-yl)-thiazole (95 mg, 0.63 mmol) and K₂CO₃ (262 mg, 1.9 mmol) in DMF (10 mL) is stirred at room temperature for 48 hours. Brine (6 mL) and DCM (20 mL) are added. The organic layer is separated and the aqueous layer is extracted with DCM (3×29 mL). The combined organic layers are dried and solvent removed. The residue is purified by PTLC (10% methanol in DCM) to give 1-[3-Ethyl-2-(2-thiazol-2-yl-imidazol-1-ylmethyl)-3H-benzoimidazol-5-yl]-ethanone as a solid. ¹H NMR (CDCl₃) δ 8.05 (d, 1H), 7.92 (dd, 1H), 7.87 (dd, 1H), 7.81 (dd, 1H), 7.40 (d, 1H), 7.20 (d, 1H), 7.14 (d, 1H), 6.17 (s, 2H), 4.3.3 (q, 2H), 2.67 (s, 3H), 1.13 (t, 3H).

Example 45

Synthesis of 1-Ethyl-2-[(2-(1H-pyrazol-3-yl)-imidazol-1-ylmethyl]-1H-benzoimidazole-5-carbonitrile

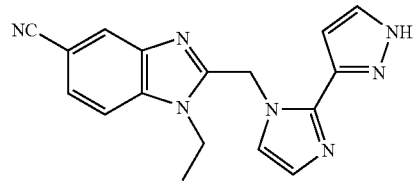

1. Preparation of 3-(H-Imidazol-2-yl)-pyrazole-1-carboxylic acid tert-butyl ester A mixture of 1H-Pyrazole-3-carbaldehyde (1 g, 10.4 mmol) di-tert-butyl dicarbonate (11.4 mmol) and N,N-dimethylpyridine (20 mg) in DCM (15 mL) and methanol (5 mL) is stirred at room temperature overnight. Solvent is removed. Glyoxal (6 mL) and ammonium hydroxid (8 mL) are added to the residue and the mixture is stirred at room temperature for 1.5 hours. Acetic acid is added dropwise to the mixture to pH ~7. Solvent is removed and DCM (50 mL) and brine (30 mL) are added to the residue. The organic layer is separated and the aqueous layer is extracted with DCM (2×40 mL). The combined organic layers are dried and solvent removed to give 3-(1H-imidazol-2-yl)-pyrazole-1-carboxylic acid tert-butyl ester.

2. Preparation of 1-Ethyl-2-[2-(1H-pyrazol-3-yl)-imidazol-1-ylmethyl]-1H-benzoimidazole-5-carbonitrile As described previously, nucleophilic displacement of 2-Chloromethyl-1-ethyl-1H-benzoimidazole-5-carbonitrile with 3-(1H-Imidazol-2-yl)-pyrazole-1-carboxylic acid tert-butyl ester followed by usual work-up provides 1-Ethyl-2-[2-(1H-pyrazol-3-yl)-imidazol-1-ylmethyl]-1H-benzoimidazole-5-carbonitrile; ¹H NMR (CD₃OD) δ 7.97 (s, 1H), 7.53 (brs, 1H), 7.46 (d, J=8.7 Hz, 1H), 7.35 (d, J=8.1 Hz, 1H), 6.97 (d, J=6.3 Hz, 2H), 6.79 (br s, 1H), 6.10 (, 2H), 4.22 (q, J=7.2 Hz, 2H), 0.88 (t, J=7.2 Hz, 3H); m/z 318 [M+1].

Example 46

Synthesis of 4-(1-ethyl-2-{[2-(1,3-thiazol-2-yl)-1H-imidazol-1-yl]methyl}-1H-benzimidazol-5-yl)-2-methylbutan-2-ol

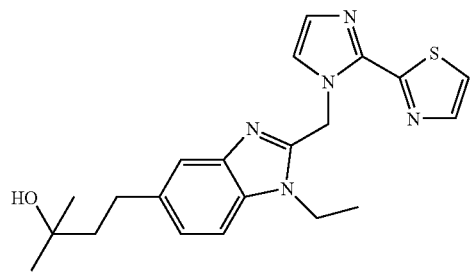

1. Preparation of 4-(1-ethyl-2-{[2-(1,3-thiazol-2-yl)-1H-imidazol-1-yl]methyl}-1H-benzimidazol-5-yl)-2-methyl-1-but-3-yn-2-ol Pd (PPh₃)₄ (15 mg, 0.013 mmol), CuI (5 mg, 0.026 mmol), and 2-methyl-but-3-yn-2-ol (250 μL, 2.6 mmol) are added to the solution of 1-ethyl-5-bromo-2-{[2-(1,3-thiazol-2-yl)-1H-imidazol-1-yl]methyl}-1H-benzimidazole (100 mg, 0.26 mmol) in i-Pr₂NH (5 mL). The resulting mixture is heated to 100° C. for 20 hr, and then diluted with water. The aqueous layer is extracted with ethyl acetate. The combined organic layers are dried over Na₂SO₄ and solvent is removed to give a brown oil. Purification by preparative TLC provides 40 mg of product as yellow solid. LCMS 392.37 (MH+).

2. Preparation of 4-(1-ethyl-2-{[2-(1,3-thiazol-2-yl)-1H-imidazol-1-yl]methyl}-1H-benzimidazol-5-yl)-2-methylbutan-2-ol To a Parr bottle containing 4-(1-ethyl-2-{[2-(1,3-thiazol-2-yl)-1H-imidazol-1-yl]methyl}-1H-benzimidazol-5-yl)-2-methyl-1-but-3-yn-2-ol (40 mg, 0.1 mmol) in ethanol (10 mL) is added 10% Pd/C (50 mg). The Parr bottle is sealed in a mechanical shaker, evacuated, and then purged with nitrogen followed by hydrogen. The system is pressurized to 40 PSI of hydrogen at room temperature and mechanical shaking engaged. After 2 hours, shaking is stopped, and the system purged with nitrogen prior to opening the vessel. The reaction mixture is filtered through celite and concentrated in vacuo. The product is obtained as white solid. ¹H NMR (CDCl₃) δ 7.85 (d, 1H), 7.60 (s, 1H), 7.38 (d, 1H), 7.22 (m, 1H) 7.15 (m, 2H), 7.09 (s, 1H), 6.31 (s, 2H), 4.17 (q, 2H), 2.80 (m, 2H), 1.81 (m, 2H), 1.22 (d, 6H), 1.01 (t, 3H). LCMS 396.38 (MH+).

Example 47

Synthesis of 1-(1-ethyl-2-{[2-(1,3-thiazol-2-yl)-1H-imidazol-1yl]methyl}-1H-benzimidazol-5-yl)-4-hydroxypentan-1-one

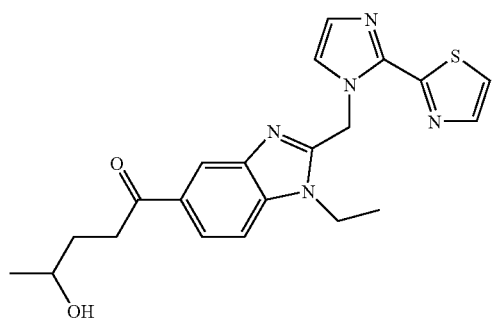

To the bi-layer system of 3 N HCl (5 mL) and CH₂Cl₂ is added 5-(1-ethyl-2-{[2-(1,3-thiazol-2-yl)-1H-imidazol-1-yl]methyl}-1H-benzimidazol-5-yl)-pent-4-yn-2-ol (107 mg, 0.27 mmol), PdCl₂ (5 mg, 0.028 mmol), and n-Bu₄NCl (17 mg, 0.056 mmol). The resulting mixture is stirred at room temperature for 72 hr, and then poured into saturated NaHCO₃ solution. The aqueous layer is extracted with CH₂Cl₂ and the combined organic layers are dried over Na₂SO₄. Solvent is removed and purification by preparative TLC provides the product as white solid. ¹H NMR (CDCl₃) δ 8.44 (d, 1H), 7.80 (dd, 1H), 7.85 (d, 1H), 7.40 (d, 1H), 7.36 (d, 1H), 7.18 (d, 1H), 7.14 (d, 1H), 6.36 (s, 2H), 4.27 (q, 2H), 3.86 (m, 1H), 3.19 (t, 2H), 1.93 (m, 2H), 1.25 (d, 3H), 1.09 (t, 3H). LCMS 410.2 (MH+).

Example 48

Synthesis of 8-{[2-(6-Fluoropyridin-2-yl)-1H-imidazol-1-yl]methyl}-2,9-dimethyl-9H-purine

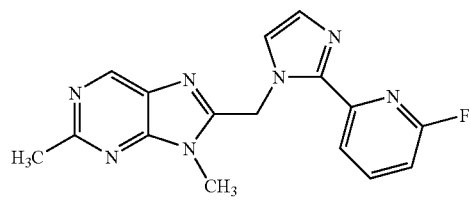

1) Preparation of 6-Amino-4-chloro-2,N-dimethyl-5-nitropyrimidine

A solution of Methylamine (15.4 mL 1M in THF, diluted with 10 mL of hexane) is added dropwise to a solution of 4,6-Dichloro-2-methyl-5-nitropyrimidine (3.2 g, 15.4 mmol) in Hexane (30 mL). After addition, the reaction mixture is stirred at room temperature for one hour, and concentrated in vacuo to a solid. After the solid is dissolved in 50 mL of CH₂Cl₂, the resultant solution is washed with 0.1 N HCl (20 mL) and water (20 mL), dried over Na₂SO₄ and concentrated to a yellow solid. ¹H NMR (CDCl₃): δ 7.7 (bs, 1H), 3.10 (d, 3H), 2.55 (s, 5H).

2) Preparation of 2,N-Dimethyl-4,5-diaminopyrimidine

A mixture of 6-Amino-4-chloro-2,N-dimethyl-5-nitropyrimidine (1.0 g, 0.5 mmol), NaOH (40 mg, 1 mmol) and 1.0 g 10% Pd/C in 50 mL of 2% aqueous THF is hydrogenated at 50 PSI of hydrogen at room temperature overnight. The reaction mixture is filtered through celite, concentrated in vacuo, and the obtained solid is purified on a silica gel column eluting with 10/1/0.1 CH₂Cl₂/MeOH/NH₄OH to give the title compound. ¹H NMR (CDCl₃) δ 7.64 (s, 1H), 4.95 (bs, 1H), 3.02 (d, 3H), 2.45 (s, 3H), 1.90 (bs, 2H).

3) Preparation of 8-chloromethyl-2,9-dimethyl-9H-purine

A solution of 2,N-Dimethyl-4,5-diaminopyrimidine (180 mg, 1.3 mmol) and ethyl chloroacetimidate hydrochloride (310 g, 2.0 mmol) in dichloroethane (10 mL) is heated at reflux for 17 h and cooled. The mixture is washed with aqueous NaHCO₃, water, dried and concentrated to give 8-Chloromethyl-2,9-dimethyl-9H-purine.

4) Preparation 8-{[2-(6-fluoropyridin-2-yl)-1H-imidazol-1-yl]methyl}-2,9-dimethyl-9H-purine A mixture of 8-Chloromethyl-2,9-dimethyl-9H-purine (40 mg, 0.2 mmol), 2-Fluoro-6-(1H-imidazol-2-yl)-pyridine (40 mg, 0.25 mmol) and K₂CO₃ (55 mg, 0.4 mmol) in 2 mL of DMF is stirred at room temperature for four hours. The mixture is diluted with water (10 mL), and extracted with ethyl acetate three times. The combined extract is washed with brine, dried and concentrated. The residue is purified by preparative thin layer chromatography to give the title compound. $^1$H NMR (CDCl$_3$): δ 8.92 (s, 1H), 8.18 (dd, 1H), 7.88 (q, 1H), 7.25 (s, 1H), 7.20 (s, 1H), 7.11 (s, 1H), 6.83 (dd, 1H), 6.22 (s, 2H), 3.89 (s, 3H), 2.8 (s, 3H). LRMS calcd 323. found 324 (MH+).

Example 49

The following compounds are prepared essentially according to the procedures in the previous examples.
a) 3-Methyl-2-(2-oxazol-2-yl-imidazol-1-ylmethyl)-3H-imidazo[4,5-c]pyridine
b) 3-Ethyl-2-(2-[1,3,4]oxadiazol-2-yl-imidazol-1-ylmethyl)-3H-imidazo[4,5-c]pyridine
c) 3-Ethyl-2-[2-(3-methyl-pyridin-2-yl)-imidazol-1-ylmethyl]-3H-imidazo[4,5-c]pyridine

Example 50

The compounds listed in tables 1-8 are prepared essentially according to the procedures set forth above in Schemes I-X and the preceding examples.

In tables 1-5 the designations $X_1$, $X_2$, $W_1$, $X_5$, $W_6$, etc., on the substituents WI, $R_5$, etc., indicate the point of attachment of the substituent to the parent structural formula. For example, $R_5$ in compound number (hereinafter "Cmp. #") 112 is an ethyl group; $R_5$ in compound 134 is a cyclopropylmethyl group; and $W_1$ in compound 132 is a 3-chlorophenyl group.

LC-MS data is provided for a number of the compounds in tables 1-5. The following HPLC method was used to obtain this data: YMC-pack pro C$_{18}$ column, 33×4.6 mm(L×ID) 5 µm particle size. 3 min gradient from 5% to 95% B with 0.5 min hold at 95% B. Solvent A: 95% H$_2$O-5% MeOH-0.05% TFA; Solvent B: 95% MeOH-5% H$_2$O-0.05% TFA). Flow rate=2.0 ml/min. Injection volume=1 µl. MS (ES$^+$) m/e 360 [MH]$^+$. The LC data is given as HPLC retention times.

TABLE 1

| Cmp. # | R5 | W1 | MW | RT | Mass | GC/FID or LC/MS |
|---|---|---|---|---|---|---|
| 100 | X5–CH2–CH3 | X1–phenyl | 302.3792 | 1.60 | 303.1 | LC/MS |
| 101 | (H3C)2CH–X5 | X1–phenyl | 316.406 | 1.80 | 317.1 | LC/MS |
| 102 | H3C–CH2–CH2–X5 | X1–phenyl | 316.406 | 1.80 | 317.1 | LC/MS |
| 103 | X5–CH2–CH3 | X1–(2-F-phenyl) | 320.3693 | 5.06 | | GC/FID |
| 104 | (H3C)2CH–X5 | X1–(2-F-phenyl) | 334.3961 | 5.07 | | GC/FID |
| 105 | H3C–CH2–CH2–X5 | X1–(2-F-phenyl) | 334.3961 | 5.17 | | GC/FID |

TABLE 1-continued

| Cmp. # | R5 | W1 | MW | RT | Mass | GC/FID or LC/MS |
|---|---|---|---|---|---|---|
| 106 | H3C—X5 | 3-F-C6H4—X1 | 306.3425 | 5.12 | | GC/FID |
| 107 | CH3CH2—X5 | 3-F-C6H4—X1 | 320.3693 | 5.11 | | GC/FID |
| 108 | (H3C)2CH—X5 | 3-F-C6H4—X1 | 334.3961 | 5.10 | | GC/FID |
| 109 | H3C-CH2CH2—X5 | 3-F-C6H4—X1 | 334.3961 | 5.20 | | GC/FID |
| 110 | H3C-CH2CH2—X5 | 4-F-C6H4—X1 | 334.3961 | 5.21 | | GC/FID |
| 111 | H3C—X5 | 2,5-F2-C6H3—X1 | 324.3326 | 4.95 | | GC/FID |
| 112 | CH3CH2—X5 | 2,5-F2-C6H3—X1 | 338.3594 | 4.95 | | GC/FID |
| 113 | (H3C)2CH—X5 | 2,5-F2-C6H3—X1 | 352.3862 | 4.95 | | GC/FID |
| 114 | H3C-CH2CH2—X5 | 2,5-F2-C6H3—X1 | 352.3862 | 5.05 | | GC/FID |

TABLE 1-continued

| Cmp. # | R5 | W1 | MW | RT | Mass | GC/FID or LC/MS |
|---|---|---|---|---|---|---|
| 115 | ethyl-X5 | 3-Cl-4-F-phenyl-X1 | 354.8144 | 5.43 | | GC/FID |
| 116 | isopropyl-X5 | 4-F-3-Cl-phenyl-X1 | 368.8412 | 5.42 | | GC/FID |
| 117 | n-propyl-X5 | 4-F-3-Cl-phenyl-X1 | 368.8412 | 5.51 | | GC/FID |
| 118 | ethyl-X5 | 3-thienyl-X1 | 308.4074 | 5.27 | | GC/FID |
| 119 | isopropyl-X5 | 3-thienyl-X1 | 322.4342 | 5.26 | | GC/FID |
| 120 | n-propyl-X5 | 3-thienyl-X1 | 322.4342 | 5.37 | | GC/FID |
| 121 | CH3-X5 | 3-CF3-phenyl-X1 | 356.3495 | 4.99 | | GC/FID |
| 122 | ethyl-X5 | 3-CF3-phenyl-X1 | 370.3763 | 4.98 | | GC/FID |
| 123 | isopropyl-X5 | 3-CF3-phenyl-X1 | 384.4031 | 4.98 | | GC/FID |

TABLE 1-continued
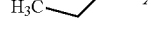
| Cmp. # | R5 | W1 | MW | RT | Mass | GC/FID or LC/MS |
|---|---|---|---|---|---|---|
| 124 | 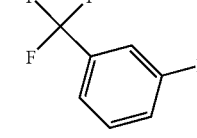 |  | 384.4031 | 5.07 | | GC/FID |
| 125 | 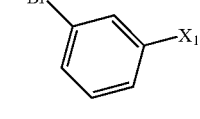 | 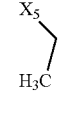 | 367.2485 | 5.68 | | GC/FID |
| 126 | 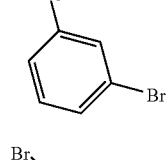 | 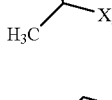 | 351.2753 | 5.67 | | GC/FID |
| 127 | 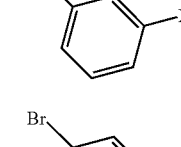 |  | 395.3021 | 5.65 | | GC/FID |
| 128 | 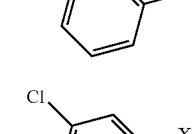 |  | 395.3021 | 5.74 | | GC/FID |
| 129 | 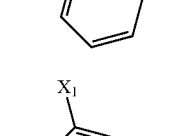 |  | 322.7975 | 1.67 | 323.1 | LC/MS |
| 130 | 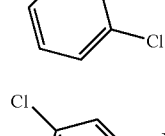 | 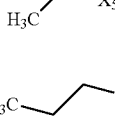 | 336.8243 | 1.87 | 337.3 | LC/MS |
| 131 | 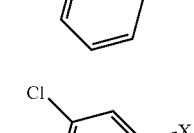 |  | 350.8511 | 2.00 | 351.1 | LC/MS |
| 132 | 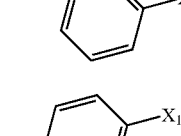 |  | 350.8511 | 2.07 | 351.3 | LC/MS |
| 133 | 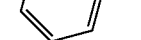 |  | 330.4328 | 2.00 | 331.3 | LC/MS |

TABLE 1-continued
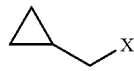
| Cmp. # | R5 | W1 | MW | RT | Mass | GC/FID or LC/MS |
|---|---|---|---|---|---|---|
| 134 | 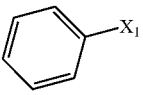 | 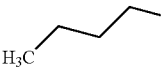 | 328.417 | 1.87 | 329.2 | LC/MS |
| 135 | 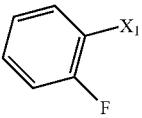 | 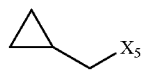 | 348.4229 | 5.15 | | GC/FID |
| 136 | 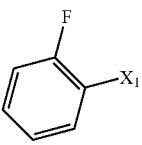 | 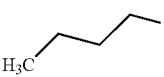 | 346.4071 | 5.28 | | GC/FID |
| 137 | 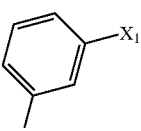 | 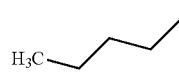 | 348.4229 | 5.18 | | GC/FID |
| 138 | 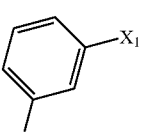 |  | 362.4497 | 5.32 | | GC/FID |
| 139 | 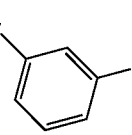 | 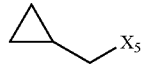 | 346.4071 | 5.31 | | GC/FID |
| 140 | 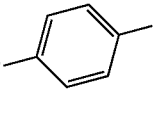 | 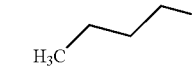 | 346.4071 | 5.31 | | GC/FID |
| 141 | 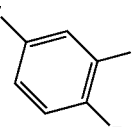 |  | 366.413 | 5.04 | | GC/FID |
| 142 | 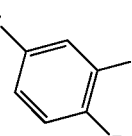 | | 380.4398 | 5.18 | | GC/FID |

TABLE 1-continued
| Cmp. # | R5 | W1 | MW | RT | Mass | GC/FID or LC/MS |
|---|---|---|---|---|---|---|
| 143 | 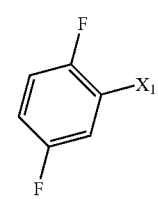 |  | 364.3972 | 5.16 | | GC/FID |
| 144 | 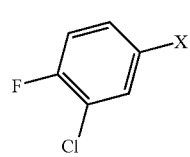 |  | 382.868 | 5.47 | | GC/FID |
| 145 | 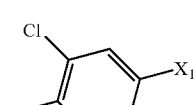 | 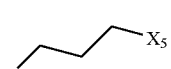 | 380.8522 | 5.59 | | GC/FID |
| 146 | 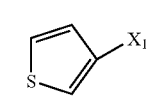 |  | 336.461 | 5.33 | | GC/FID |
| 147 | 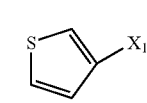 |  | 334.4452 | 5.46 | | GC/FID |
| 148 | 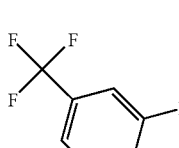 | 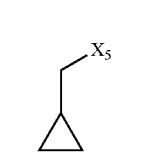 | 398.4299 | 5.04 | | GC/FID |
| 149 | 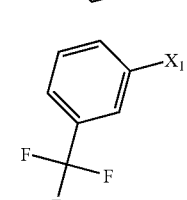 |  | 396.4141 | 5.17 | | GC/FID |
| 150 | 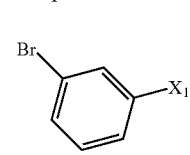 | 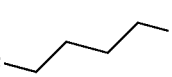 | 409.3289 | 5.68 | | GC/FID |
| 151 | 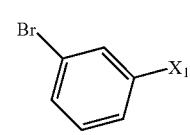 |  | 423.3557 | 5.80 | | GC/FID |

TABLE 1-continued
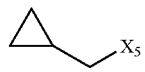
| Cmp. # | R5 | W1 | MW | RT | Mass | GC/FID or LC/MS |
|---|---|---|---|---|---|---|
| 152 | 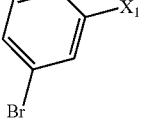 | 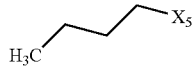 | 407.3131 | 5.81 | | GC/FID |
| 153 | 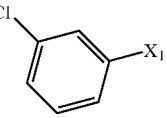 | 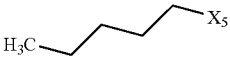 | 364.8779 | 2.20 | 365.2 | LC/MS |
| 154 | 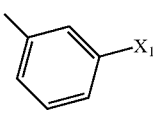 | 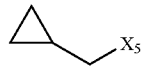 | 378.9047 | 2.40 | 379.3 | LC/MS |
| 155 | 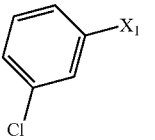 | 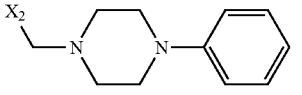 | 362.8621 | 2.07 | 363.3 | LC/MS |
TABLE 2
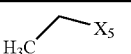
| Cmp. # | R2 | R5 | W6 | RT | GC/FID or LC/MS |
|---|---|---|---|---|---|
| 156 | 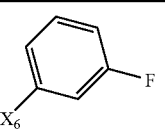 | 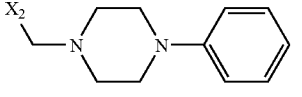 |  | 9.18 | GC/FID |
| 157 | 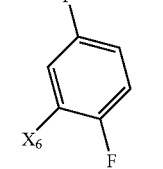 | 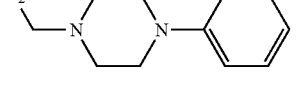 |  | 8.67 | GC/FID |
| 158 |  | | | 10.56 | GC/FID |

TABLE 2-continued
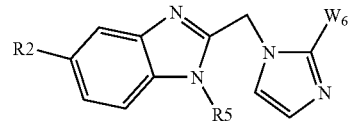
| Cmp. # | R2 | R5 | W6 | RT | GC/FID or LC/MS |
|---|---|---|---|---|---|
| 159 | 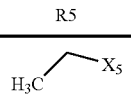 | 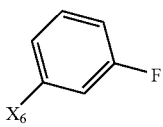 | 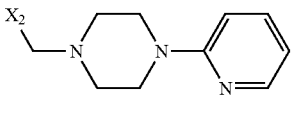 | 9.39 | GC/FID |
| 160 | 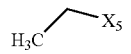 | 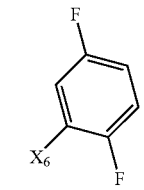 | 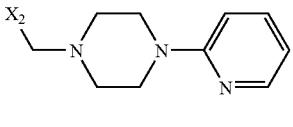 | 8.87 | GC/FID |
| 161 | 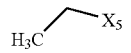 | 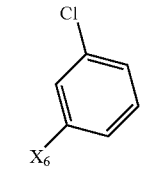 | 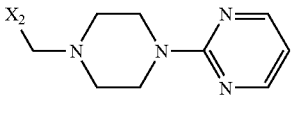 | 10.91 | GC/FID |
| 162 | 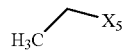 | 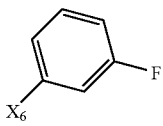 | 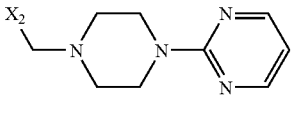 | 9.12 | GC/FID |
| 163 | 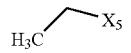 | 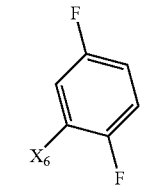 | 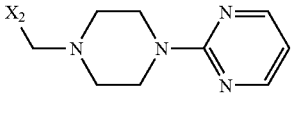 | 8.61 | LC/MS |
| 164 | 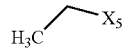 | 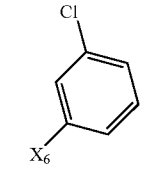 | 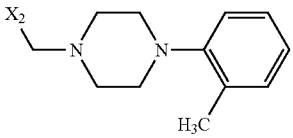 | 10.46 | GC/FID |
| 165 | 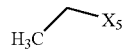 | 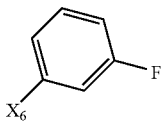 | 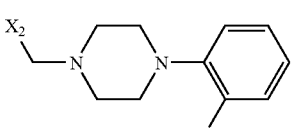 | 8.98 | GC/FID |
| 166 | 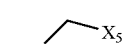 | 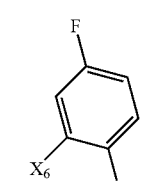 | | 8.49 | GC/FID |

TABLE 2-continued

| Cmp. # | R2 | R5 | W6 | RT | GC/FID or LC/MS |
|---|---|---|---|---|---|
| 167 | X₂–CH₂–N(piperazine)N–(2-methylphenyl) | H₃C–X₅ (ethyl) | 3-Cl-phenyl (X₆) | 10.28 | GC/FID |
| 168 | X₂–CH₂–N(piperazine)N–(4-methylphenyl) | H₃C–X₅ | 3-F-phenyl (X₆) | 9.77 | GC/FID |
| 169 | X₂–CH₂–N(piperazine)N–(4-methylphenyl) | H₃C–X₅ | 2,5-F₂-phenyl (X₆) | 9.17 | GC/FID |
| 170 | X₂–CH₂–N(piperazine)N–(4-methylphenyl) | H₃C–X₅ | 3-Cl-phenyl (X₆) | 11.41 | LC/MS |
| 171 | X₂–CH₂–N(piperazine)N–(2-fluorophenyl) | H₃C–X₅ | 3-F-phenyl (X₆) | 8.75 | GC/FID |
| 172 | X₂–CH₂–N(piperazine)N–(2-fluorophenyl) | H₃C–X₅ | 2,5-F₂-phenyl (X₆) | 8.31 | GC/FID |
| 173 | X₂–CH₂–N(piperazine)N–(2-fluorophenyl) | H₃C–X₅ | 3-Cl-phenyl (X₆) | 9.97 | GC/FID |
| 174 | X₂–CH₂–N(piperazine)N–(4-fluorophenyl) | H₃C–X₅ | 3-F-phenyl (X₆) | 9.04 | GC/FID |

TABLE 2-continued
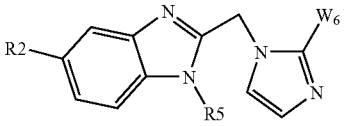
| Cmp. # | R2 | R5 | W6 | RT | GC/FID or LC/MS |
|---|---|---|---|---|---|
| 175 | 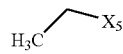 | 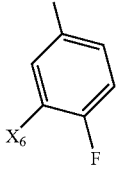 | 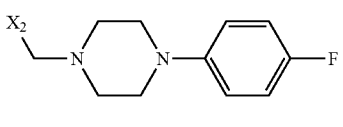 | 8.55 | GC/FID |
| 176 | 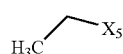 | 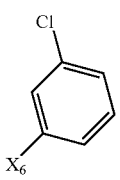 | 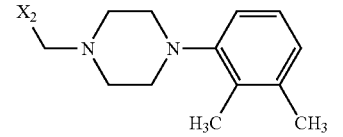 | 10.36 | GC/FID |
| 177 | 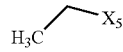 | 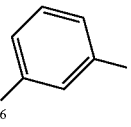 | 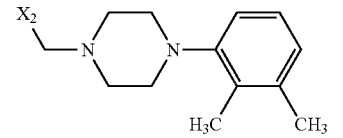 | 9.81 | GC/FID |
| 178 | 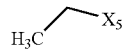 | 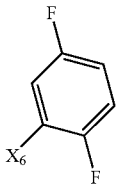 | 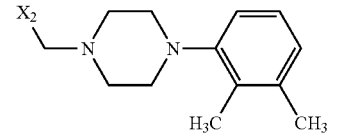 | 9.21 | GC/FID |
| 179 | 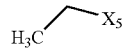 | 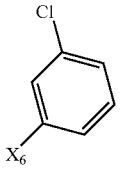 | 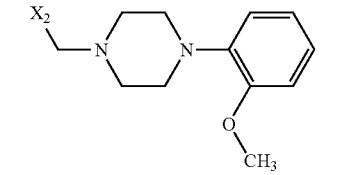 | 11.49 | GC/FID |
| 180 | 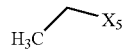 | 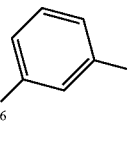 | 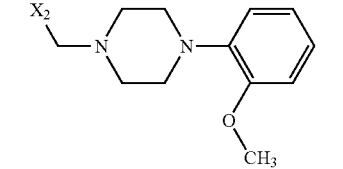 | 9.64 | GC/FID |
| 181 | 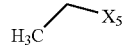 | 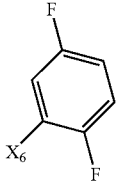 |  | 9.05 | GC/FID |

TABLE 2-continued

| Cmp. # | R2 | R5 | W6 | RT | GC/FID or LC/MS |
|---|---|---|---|---|---|
| 182 | X₂–CH₂–N(piperazine)N–(2-methoxyphenyl) | H₃C–CH₂–X₅ | 3-Cl-phenyl (X₆) | 11.22 | LC/MS |
| 183 | X₂–CH₂–N(piperazine)N–(4-methoxyphenyl) | H₃C–CH₂–X₅ | 3-F-phenyl (X₆) | 10.86 | GC/FID |
| 184 | X₂–CH₂–N(piperazine)N–(4-methoxyphenyl) | H₃C–CH₂–X₅ | 2,5-diF-phenyl (X₆) | 10.08 | GC/FID |
| 185 | X₂–CH₂–N(piperazine)N–(4-methoxyphenyl) | H₃C–CH₂–X₅ | 3-Cl-phenyl (X₆) | 12.97 | GC/FID |
| 186 | X₂–CH₂–N(piperazine)N–(2-chlorophenyl) | H₃C–CH₂–X₅ | 3-F-phenyl (X₆) | 9.85 | GC/FID |
| 187 | X₂–CH₂–N(piperazine)N–(2-chlorophenyl) | H₃C–CH₂–X₅ | 2,5-diF-phenyl (X₆) | 9.23 | GC/FID |
| 188 | X₂–CH₂–N(piperazine)N–(2-chlorophenyl) | H₃C–CH₂–X₅ | 3-Cl-phenyl (X₆) | 11.52 | GC/FID |

TABLE 3

| Cpd. # | R2 | R5 | W1 | RT | GC/FID or LC/MS |
|---|---|---|---|---|---|
| 189 | X2-CH2-pyrrolidine | H3C-CH2-X5 | 3-F-phenyl (X1) | 6.17 | GC/FID |
| 190 | X2-CH2-pyrrolidine | H3C-CH2-X5 | 2,4-diF-phenyl (X1) | 6.02 | GC/FID |
| 191 | X2-CH2-piperidine | H3C-CH2-X5 | 3-F-phenyl (X1) | 6.32 | GC/FID |
| 192 | X2-CH2-piperidine | H3C-CH2-X5 | 2,4-diF-phenyl (X1) | 6.15 | GC/FID |
| 193 | X2-CH2-morpholine | H3C-CH2-X5 | 3-F-phenyl (X1) | 6.37 | GC/FID |
| 194 | X2-CH2-morpholine | H3C-CH2-X5 | 2,4-diF-phenyl (X1) | 6.20 | GC/FID |
| 195 | X2-CH2-(4-methylpiperidine) | H3C-CH2-X5 | 3-F-phenyl (X1) | 6.40 | GC/FID |
| 196 | X2-CH2-(4-methylpiperidine) | H3C-CH2-X5 | 2,4-diF-phenyl (X1) | 1.32 | LC/MS |
| 197 | X2-CH2-azepane | H3C-CH2-X5 | 3-F-phenyl (X1) | 6.52 | GC/FID |
| 198 | X2-CH2-azepane | H3C-CH2-X5 | 2,4-diF-phenyl (X1) | 6.36 | GC/FID |

TABLE 3-continued
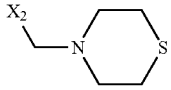
| Cpd. # | R2 | R5 | W1 | RT | GC/FID or LC/MS |
|---|---|---|---|---|---|
| 199 | 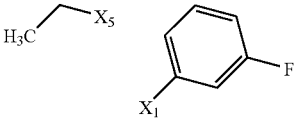 | 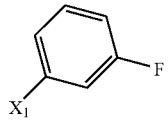 | 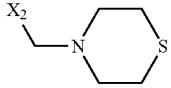 | 6.77 | GC/FID |
| 200 | 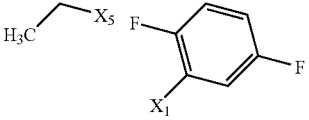 | 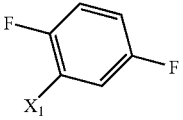 | 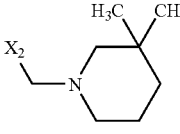 | 6.60 | GC/FID |
| 201 | 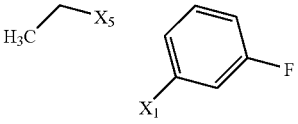 | 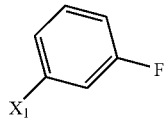 | 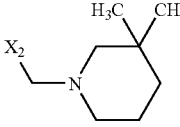 | 6.37 | GC/FID |
| 202 | 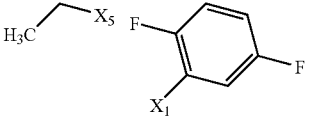 | 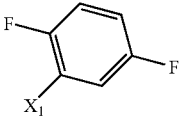 | 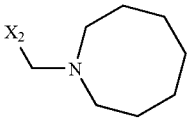 | 6.22 | GC/FID |
| 203 | 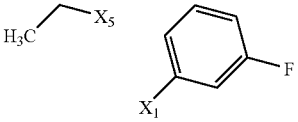 | 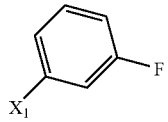 | 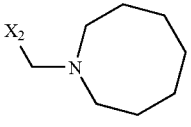 | 1.40 | LC/MS |
| 204 | 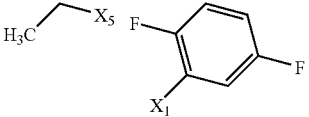 | 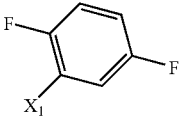 | 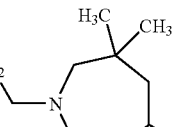 | 6.50 | GC/FID |
| 205 | 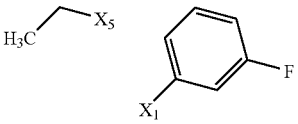 | 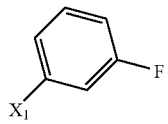 | 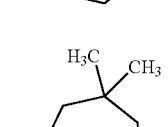 | 6.66 | GC/FID |
| 206 | 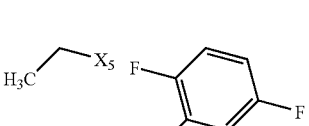 | 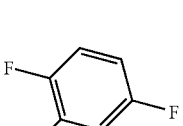 | 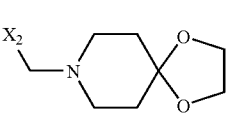 | 6.51 | GC/FID |
| 207 | 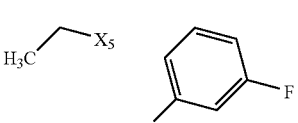 | 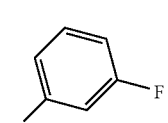 | | 7.15 | GC/FID |

TABLE 3-continued

| Cpd. # | R2 | R5 | W1 | RT | GC/FID or LC/MS |
|---|---|---|---|---|---|
| 208 | X₂–CH₂–N(piperidine-4-spiro-1,3-dioxolane) | H₃C–CH₂–X₅ | 2,4-difluorophenyl (X₁) | 6.91 | GC/FID |
| 209 | X₂–CH₂–N(decahydroquinolinyl) | H₃C–CH₂–X₅ | 3-fluorophenyl (X₁) | 7.13 | GC/FID |
| 210 | X₂–CH₂–N(decahydroquinolinyl) | H₃C–CH₂–X₅ | 2,4-difluorophenyl (X₁) | 6.91 | GC/FID |
| 211 | X₂–CH₂–N(CH₃)₂ | H₃C–CH₂–X₅ | 3-fluorophenyl (X₁) | 5.64 | GC/FID |
| 212 | X₂–CH₂–N(CH₃)₂ | H₃C–CH₂–X₅ | 2,4-difluorophenyl (X₁) | 5.47 | GC/FID |
| 213 | X₂–CH₂–N(CH₃)(CH₂CH=CH₂) | H₃C–CH₂–X₅ | 3-fluorophenyl (X₁) | 5.92 | GC/FID |
| 214 | X₂–CH₂–N(CH₃)(CH₂CH=CH₂) | H₃C–CH₂–X₅ | 2,4-difluorophenyl (X₁) | 5.75 | GC/FID |
| 215 | X₂–CH₂CH₂–N(CH₂CH₃)₂ | H₃C–CH₂–X₅ | 3-fluorophenyl (X₁) | 1.13 | LC/MS |
| 216 | X₂–CH₂–N(CH₂CH₃)₂ | H₃C–CH₂–X₅ | 2,4-difluorophenyl (X₁) | 5.71 | GC/FID |

TABLE 3-continued
| Cpd. # | R2 | R5 | W1 | RT | GC/FID or LC/MS |
|---|---|---|---|---|---|
| 217 | 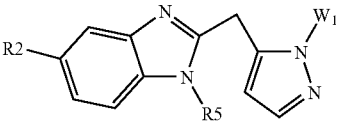 | 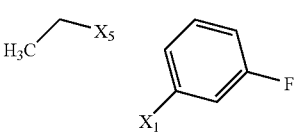 | 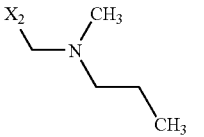 | 5.91 | GC/FID |
| 218 | 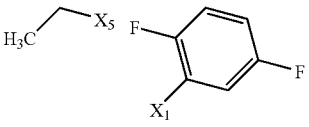 | 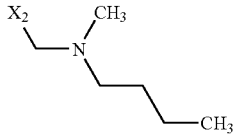 | 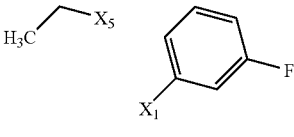 | 5.74 | GC/FID |
| 219 | 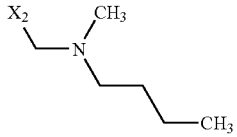 | 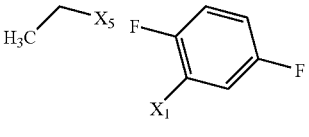 | 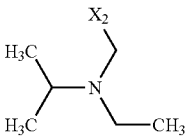 | 6.05 | GC/FID |
| 220 | 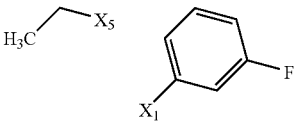 | 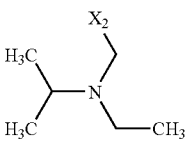 | 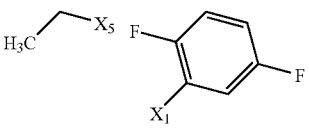 | 5.89 | GC/FID |
| 221 | 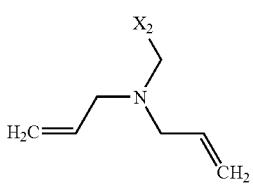 | 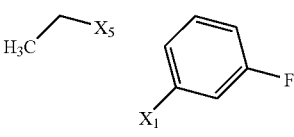 | 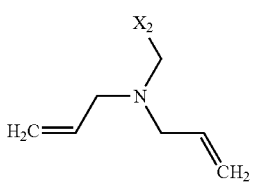 | 5.99 | GC/FID |
| 222 | 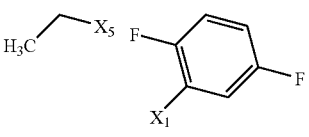 | | | 5.82 | GC/FID |
| 223 | | | | 6.11 | GC/FID |
| 224 | | | | 5.96 | GC/FID |

TABLE 3-continued

| Cpd. # | R2 | R5 | W1 | RT | GC/FID or LC/MS |
|---|---|---|---|---|---|
| 225 | X₂-CH₂-N(CH₂CH₂CH₃)(CH₂CH₂CH₃) | H₃C-X₅ | 3-F-C₆H₄-X₁ | 6.09 | GC/FID |
| 226 | X₂-CH₂-N(CH₂CH₂CH₃)(CH₂CH₂CH₃) | H₃C-X₅ | 2,5-diF-C₆H₃-X₁ | 5.94 | GC/FID |
| 227 | X₂-CH₂-N(CH₂CH₂CH₂CH₃)(CH₂CH₂CH₃) | H₃C-X₅ | 3-F-C₆H₄-X₁ | 6.11 | GC/FID |
| 228 | X₂-CH₂-N(CH₂CH₂CH₂CH₃)(CH₂CH₂CH₃) | H₃C-X₅ | 2,5-diF-C₆H₃-X₁ | 5.96 | GC/FID |
| 229 | (cyclopropyl)CH₂-N(CH₂X₂)(CH₂CH₂CH₃) | H₃C-X₅ | 3-F-C₆H₄-X₁ | 6.33 | GC/FID |
| 230 | (cyclopropyl)CH₂-N(CH₂X₂)(CH₂CH₂CH₃) | H₃C-X₅ | 2,5-diF-C₆H₃-X₁ | 6.18 | GC/FID |
| 231 | X₂-CH₂-N(CH₃)(CH₂CH₂CH₂CH₂CH₃) | H₃C-X₅ | 3-F-C₆H₄-X₁ | 6.33 | GC/FID |

TABLE 3-continued

| Cpd. # | R2 | R5 | W1 | RT | GC/FID or LC/MS |
|---|---|---|---|---|---|
| 232 | X₂–CH₂–N(CH₃)–(CH₂)₄–CH₃ | H₃C–CH₂–X₅ | 2,5-difluoro (X₁ at 2-position) | 6.19 | GC/FID |
| 233 | X₂–CH₂–N(CH₂CH₂CH₂CH₃)₂ | H₃C–CH₂–X₅ | 3-fluoro (X₁) | 6.21 | GC/FID |
| 234 | X₂–CH₂–N(CH₂CH₂CH₂CH₃)₂ | H₃C–CH₂–X₅ | 2,5-difluoro (X₁) | 6.07 | GC/FID |
| 235 | X₂–CH₂–N(CH₃)(CH(CH₃)₂) | H₃C–CH₂–X₅ | 3-fluoro (X₁) | 5.81 | GC/FID |
| 236 | X₂–CH₂–N(CH₃)(CH(CH₃)₂) | H₃C–CH₂–X₅ | 2,5-difluoro (X₁) | 5.64 | GC/FID |
| 237 | X₂–CH₂–(2-methylpiperidin-1-yl) | H₃C–CH₂–X₅ | 3-fluoro (X₁) | 6.29 | GC/FID |
| 238 | X₂–CH₂–(2-methylpiperidin-1-yl) | H₃C–CH₂–X₅ | 2,5-difluoro (X₁) | 6.13 | GC/FID |
| 239 | X₂–CH₂–N(CH₂CH₃)(CH₂–C(CH₃)=CH₂) | H₃C–CH₂–X₅ | 3-fluoro (X₁) | 5.97 | GC/FID |

TABLE 3-continued
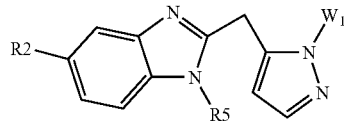
| Cpd. # | R2 | R5 | W1 | RT | GC/FID or LC/MS |
|---|---|---|---|---|---|
| 240 | 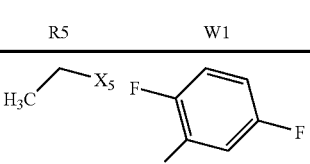 | 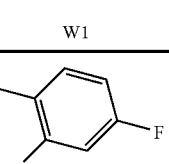 | 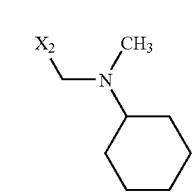 | 5.82 | GC/FID |
| 241 | 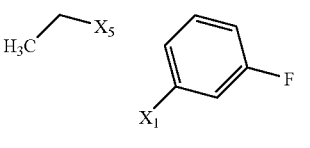 | 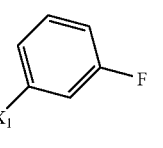 | 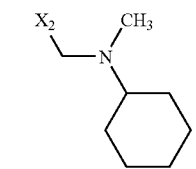 | 6.51 | GC/FID |
| 242 | 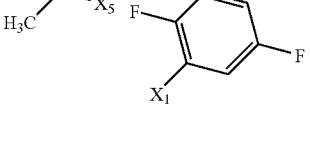 | 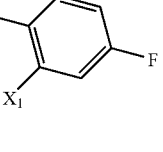 | 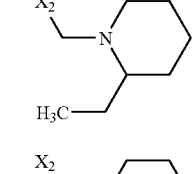 | 6.36 | GC/FID |
| 243 | 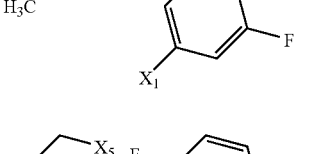 | 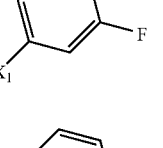 | 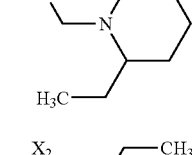 | 6.42 | GC/FID |
| 244 | 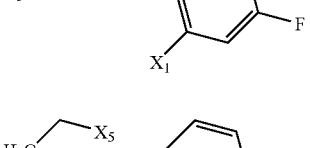 | 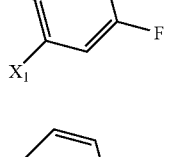 | 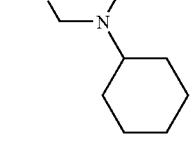 | 6.26 | GC/FID |
| 245 | 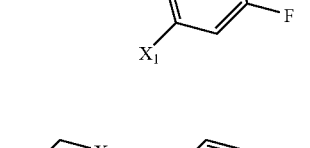 | 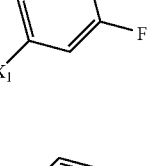 | 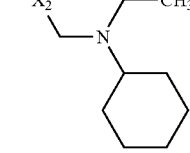 | 6.52 | GC/FID |
| 246 | 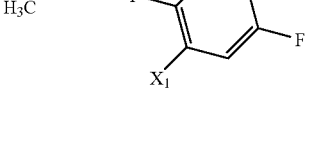 | 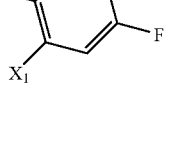 | 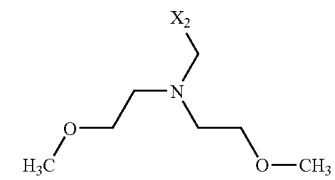 | 6.38 | GC/FID |
| 247 | 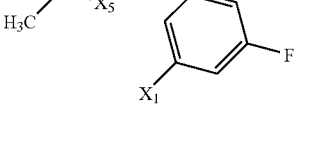 | 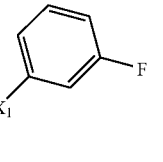 | | 6.34 | GC/FID |

TABLE 3-continued

| Cpd. # | R2 | R5 | W1 | RT | GC/FID or LC/MS |
|---|---|---|---|---|---|
| 248 | X₂-CH₂-N(CH₂CH₂OCH₃)₂ | H₃C-X₅ | 2,5-difluorophenyl (X₁) | 6.19 | GC/FID |
| 249 | X₂-CH₂-N(pentyl)(pentyl) | H₃C-X₅ | 3-fluorophenyl (X₁) | 6.45 | GC/FID |
| 250 | X₂-CH₂-N(pentyl)(pentyl) | H₃C-X₅ | 2,5-difluorophenyl (X₁) | 6.32 | GC/FID |
| 251 | X₂-CH₂-N(hexyl)(hexyl) | H₃C-X₅ | 3-fluorophenyl (X₁) | 6.71 | GC/FID |
| 252 | X₂-CH₂-N(hexyl)(hexyl) | H₃C-X₅ | 2,5-difluorophenyl (X₁) | 2.18 | LC/MS |
| 253 | X₂-CH₂-(3,5-dimethylpiperidin-1-yl) | H₃C-X₅ | 3-fluorophenyl (X₁) | 6.28 | GC/FID |

TABLE 3-continued

| Cpd. # | R2 | R5 | W1 | RT | GC/FID or LC/MS |
|---|---|---|---|---|---|
| 254 | X₂-CH₂-N(3,5-dimethylpiperidine) | H₃C-CH₂-X₅ | 2,4-difluorophenyl (X₁) | 6.12 | GC/FID |
| 255 | X₂-CH₂-N(4-cyclopentylpiperazine) | H₃C-CH₂-X₅ | 3-fluorophenyl (X₁) | 7.38 | GC/FID |
| 256 | X₂-CH₂-N(4-cyclopentylpiperazine) | H₃C-CH₂-X₅ | 2,4-difluorophenyl (X₁) | 7.11 | GC/FID |
| 257 | X₂-CH₂-N(4-cycloheptylpiperazine) | H₃C-CH₂-X₅ | 3-fluorophenyl (X₁) | 1.48 | LC/MS |
| 258 | X₂-CH₂-N(4-cycloheptylpiperazine) | H₃C-CH₂-X₅ | 2,4-difluorophenyl (X₁) | 7.95 | GC/FID |
| 259 | X₂-CH₂-N(4-methylpiperazine) | H₃C-CH₂-X₅ | 3-fluorophenyl (X₁) | 6.34 | GC/FID |
| 260 | X₂-CH₂-N(4-methylpiperazine) | H₃C-CH₂-X₅ | 2,4-difluorophenyl (X₁) | 6.18 | GC/FID |
| 261 | X₂-CH₂-N(4-ethylpiperazine) | H₃C-CH₂-X₅ | 3-fluorophenyl (X₁) | 6.47 | GC/FID |
| 262 | X₂-CH₂-N(4-ethylpiperazine) | H₃C-CH₂-X₅ | 2,4-difluorophenyl (X₁) | 6.32 | GC/FID |

TABLE 3-continued

| Cpd. # | R2 | R5 | W1 | RT | GC/FID or LC/MS |
|---|---|---|---|---|---|
| 263 | X₂–CH₂–N(CH₃)–CH₂CH₂–N(CH₃)(CH₃) | H₃C–X₅ | 3-F-phenyl | 6.10 | GC/FID |
| 264 | X₂–CH₂–N(CH₃)–CH₂CH₂–N(CH₃)(CH₃) | H₃C–X₅ | 2,5-diF-phenyl | 5.95 | GC/FID |
| 265 | (CH₃)(CH₃)N–CH₂CH₂–N(CH₃)–CH₂–X₂ | H₃C–X₅ | 3-F-phenyl | 6.15 | GC/FID |
| 266 | (CH₃)(CH₃)N–CH₂CH₂–N(CH₃)–CH₂–X₂ | H₃C–X₅ | 2,5-diF-phenyl | 6.00 | GC/FID |
| 267 | X₂–CH₂–(4-pyrrolidin-1-yl-piperidin-1-yl) | H₃C–X₅ | 3-F-phenyl | 7.43 | GC/FID |
| 268 | X₂–CH₂–(4-pyrrolidin-1-yl-piperidin-1-yl) | H₃C–X₅ | 2,5-diF-phenyl | 7.15 | GC/FID |
| 269 | X₂–CH₂–(4-piperidin-1-yl-piperidin-1-yl) | H₃C–X₅ | 3-F-phenyl | 7.74 | GC/FID |
| 270 | X₂–CH₂–(4-piperidin-1-yl-piperidin-1-yl) | H₃C–X₅ | 2,5-diF-phenyl | 7.41 | GC/FID |

TABLE 3-continued

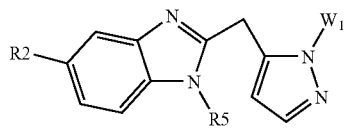

| Cpd. # | R2 | R5 | W1 | RT | GC/FID or LC/MS |
|---|---|---|---|---|---|
| 271 | X₂–CH₂–N(CH₃)–(1-methylpiperidin-4-yl) | H₃C–CH₂–X₅ | 3-fluorophenyl (X₁) | 6.65 | GC/FID |
| 272 | X₂–CH₂–N(CH₃)–(1-methylpiperidin-4-yl) | H₃C–CH₂–X₅ | 2,4-difluorophenyl (X₁) | 6.50 | GC/FID |
| 273 | X₂–CH₂–N(CH₃)–CH₂CH₂CH₂–N(CH₃)₂ | H₃C–CH₂–X₅ | 3-fluorophenyl (X₁) | 6.23 | GC/FID |
| 274 | X₂–CH₂–N(CH₃)–CH₂CH₂CH₂–N(CH₃)₂ | H₃C–CH₂–X₅ | 2,4-difluorophenyl (X₁) | 6.08 | GC/FID |
| 275 | X₂–CH₂–N(CH₃)–CH₂CH₂–N(CH₂CH₃)₂ | H₃C–CH₂–X₅ | 3-fluorophenyl (X₁) | 6.30 | GC/FID |
| 276 | X₂–CH₂–N(CH₃)–CH₂CH₂–N(CH₂CH₃)₂ | H₃C–CH₂–X₅ | 2,4-difluorophenyl (X₁) | 6.15 | GC/FID |

TABLE 4
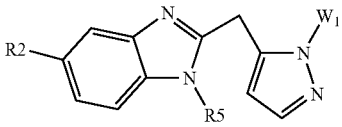
| Cmp. # | R2 | R5 | W1 | RT | Mass | GC/FID or LC/MS |
|---|---|---|---|---|---|---|
| 277 | 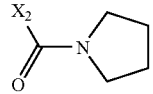 | 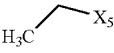 | 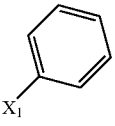 | 7.12 | | GC/FID |
| 278 | 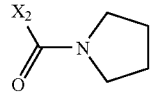 |  | 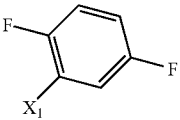 | 6.77 | | GC/FID |
| 279 | 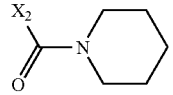 | 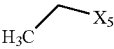 | 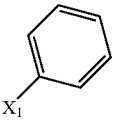 | 7.17 | | GC/FID |
| 280 | 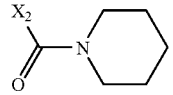 | 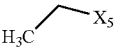 | 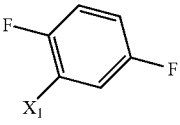 | 6.82 | | GC/FID |
| 281 | 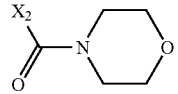 |  | 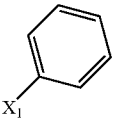 | 7.10 | | GC/FID |
| 282 | 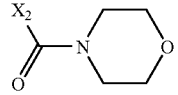 | 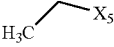 | 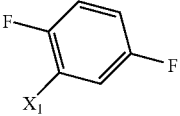 | 6.77 | | GC/FID |
| 283 | 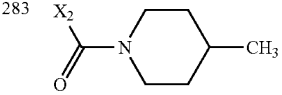 | 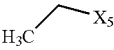 | 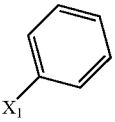 | 7.30 | | GC/FID |
| 284 | 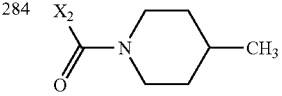 | 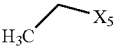 | 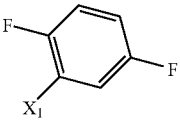 | 6.92 | | GC/FID |
| 285 | 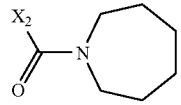 | 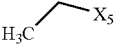 | 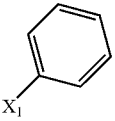 | 7.53 | | GC/FID |
| 286 | 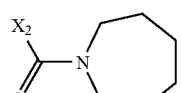 | 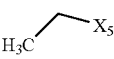 | 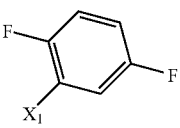 | 7.07 | | GC/FID |

TABLE 4-continued
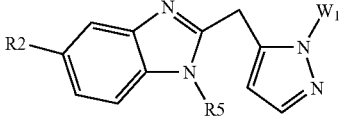
| Cmp. # | R2 | R5 | W1 | RT | Mass | GC/FID or LC/MS |
|---|---|---|---|---|---|---|
| 287 | 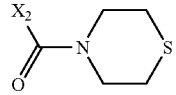 | 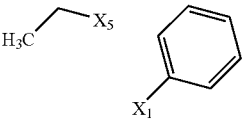 | 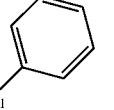 | 7.79 | | GC/FID |
| 288 | 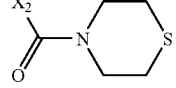 | 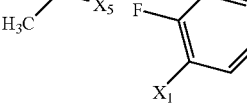 | 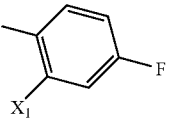 | 7.28 | | GC/FID |
| 289 | 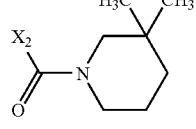 | 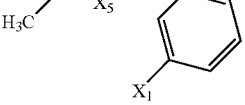 | 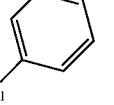 | 7.29 | | GC/FID |
| 290 | 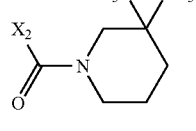 | 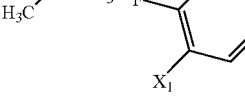 | 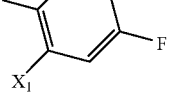 | 6.92 | | GC/FID |
| 291 | 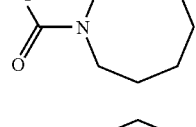 | 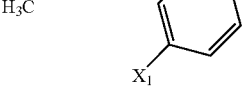 | 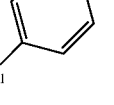 | 7.86 | | GC/FID |
| 292 | 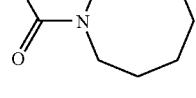 | 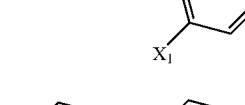 | 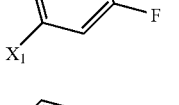 | 7.34 | | GC/FID |
| 293 | 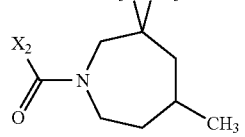 | 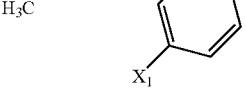 | 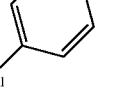 | 7.77 | | GC/FID |
| 294 | 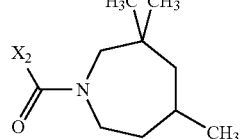 | 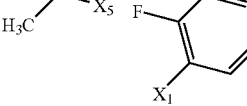 | 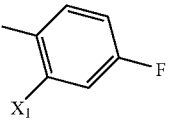 | 7.29 | | GC/FID |
| 295 | 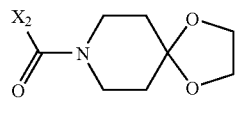 | 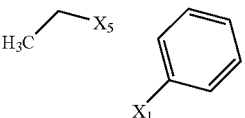 | 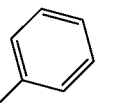 | 1.44 | 472.4 | LC/MS |

TABLE 4-continued

| Cmp. # | R2 | R5 | W1 | RT | Mass | GC/FID or LC/MS |
|---|---|---|---|---|---|---|
| 296 | X2-C(O)-N(spiro dioxolane piperidine) | H3C-CH2-X5 | 2,5-difluorophenyl (X1) | 1.56 | 508.4 | LC/MS |
| 297 | X2-C(O)-N(decahydroquinoline) | H3C-CH2-X5 | phenyl (X1) | 2.02 | 468.5 | LC/MS |
| 298 | X2-C(O)-N(decahydroquinoline) | H3C-CH2-X5 | 2,5-difluorophenyl (X1) | 7.84 | | GC/FID |
| 299 | X2-C(O)-N(CH3)2 | H3C-CH2-X5 | phenyl (X1) | 6.41 | | GC/FID |
| 300 | X2-C(O)-N(CH3)2 | H3C-CH2-X5 | 2,5-difluorophenyl (X1) | 1.32 | 410.3 | LC/MS |
| 301 | X2-C(O)-N(CH3)(CH2CH=CH2) | H3C-CH2-X5 | phenyl (X1) | 6.59 | | GC/FID |
| 302 | X2-C(O)-N(CH3)(CH2CH=CH2) | H3C-CH2-X5 | 2,5-difluorophenyl (X1) | 6.35 | | GC/FID |
| 303 | X2-C(O)-N(CH2CH3)2 | H3C-CH2-X5 | phenyl (X1) | 6.54 | | GC/FID |
| 304 | X2-C(O)-N(CH2CH3)2 | H3C-CH2-X5 | 2,5-difluorophenyl (X1) | 6.29 | | GC/FID |

TABLE 4-continued

| Cmp. # | R2 | R5 | W1 | RT | Mass | GC/FID or LC/MS |
|---|---|---|---|---|---|---|
| 305 | X2-C(O)-N(CH3)-propyl | H3C-CH2-X5 | phenyl (X1) | 6.61 | | GC/FID |
| 306 | X2-C(O)-N(CH3)-propyl | H3C-CH2-X5 | 2,5-difluorophenyl (X1) | 6.37 | | GC/FID |
| 307 | X2-C(O)-N(CH3)-butyl | H3C-CH2-X5 | phenyl (X1) | 6.76 | | GC/FID |
| 308 | X2-C(O)-N(CH3)-butyl | H3C-CH2-X5 | 2,5-difluorophenyl (X1) | 6.50 | | GC/FID |
| 309 | X2-C(O)-N(ethyl)(isopropyl) | H3C-CH2-X5 | phenyl (X1) | 6.58 | | GC/FID |
| 310 | X2-C(O)-N(ethyl)(isopropyl) | H3C-CH2-X5 | 2,5-difluorophenyl (X1) | 6.34 | | GC/FID |
| 311 | X2-C(O)-N(allyl)2 | H3C-CH2-X5 | phenyl (X1) | 6.72 | | GC/FID |
| 312 | X2-C(O)-N(allyl)2 | H3C-CH2-X5 | 2,5-difluorophenyl (X1) | 6.47 | | GC/FID |

TABLE 4-continued

| Cmp. # | R2 | R5 | W1 | RT | Mass | GC/FID or LC/MS |
|---|---|---|---|---|---|---|
| 313 | H3C-CH2-N(CH2CH3)-C(=O)-X2 (N,N-dipropyl carbamoyl) | H3C-CH2-X5 | phenyl (X1) | 6.74 | | GC/FID |
| 314 | H3C-CH2-N(CH2CH3)-C(=O)-X2 | H3C-CH2-X5 | 2,5-difluorophenyl (X1) | 6.50 | | GC/FID |
| 315 | X2-C(=O)-N(CH2CH3)(CH2CH2CH2CH3) | H3C-CH2-X5 | phenyl (X1) | 6.78 | | GC/FID |
| 316 | X2-C(=O)-N(CH2CH3)(CH2CH2CH2CH3) | H3C-CH2-X5 | 2,5-difluorophenyl (X1) | 6.52 | | GC/FID |
| 317 | cyclopropylmethyl-N(CH2CH2CH3)-C(=O)-X2 | X5-CH2-CH3 | phenyl (X1) | 7.05 | | GC/FID |
| 318 | cyclopropylmethyl-N(CH2CH2CH3)-C(=O)-X2 | X5-CH2-CH3 | 2,5-difluorophenyl (X1) | 6.74 | | GC/FID |
| 319 | X2-C(=O)-N(CH3)(CH2CH2CH2CH2CH2CH3) | H3C-CH2-X5 | phenyl (X1) | 7.13 | | GC/FID |

TABLE 4-continued
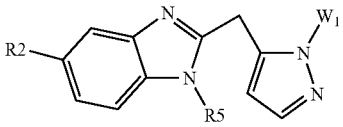
| Cmp. # | R2 | R5 | W1 | RT | Mass | GC/FID or LC/MS |
|---|---|---|---|---|---|---|
| 320 | 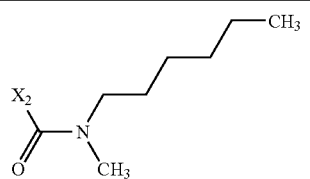 | 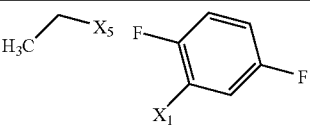 | 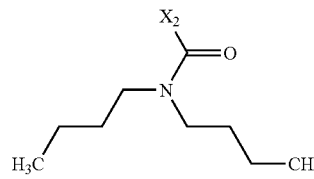 | 2.14 | 480.5 | LC/MS |
| 321 | 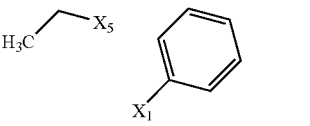 | 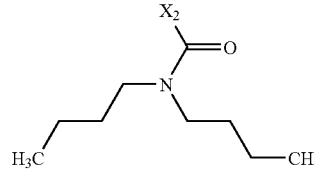 | 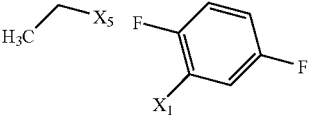 | 6.96 | | GC/FID |
| 322 | 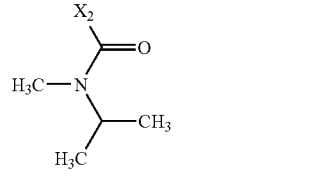 | 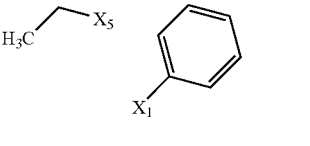 | 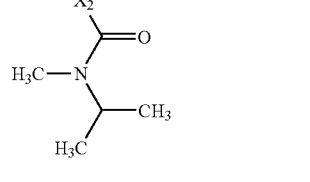 | 6.67 | | GC/FID |
| 323 | 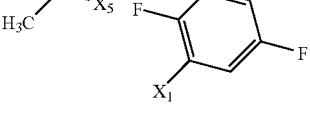 | | | 6.49 | | GC/FID |
| 324 | 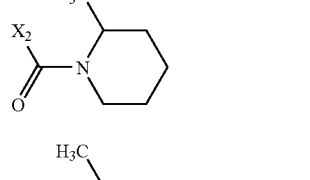 | | | 6.26 | | GC/FID |
| 325 | 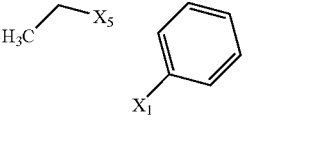 | | | 7.13 | | GC/FID |
| 326 | 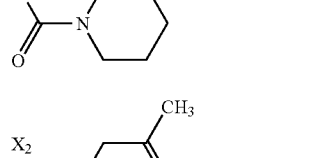 | | 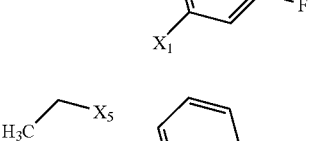 | 6.77 | | GC/FID |
| 327 | 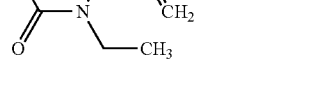 | 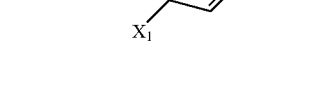 | | 6.65 | | GC/FID |

TABLE 4-continued
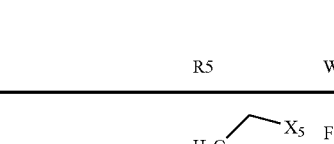
| Cmp. # | R2 | R5 | W1 | RT | Mass | GC/FID or LC/MS |
|---|---|---|---|---|---|---|
| 328 |  | 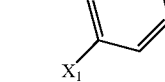 | 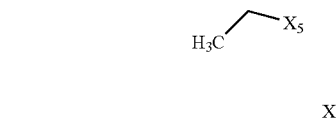 | 6.42 | | GC/FID |
| 329 |  | 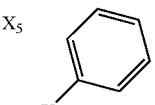 | 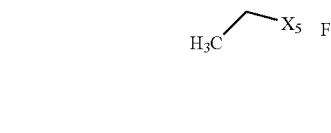 | 7.39 | | GC/FID |
| 330 |  | 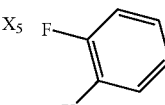 | 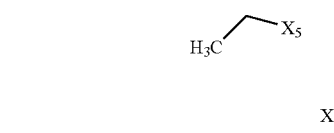 | 7.00 | | GC/FID |
| 331 |  | 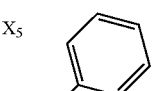 | 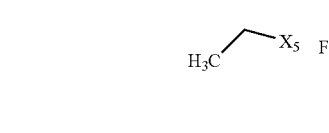 | 7.26 | | GC/FID |
| 332 |  | 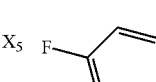 | 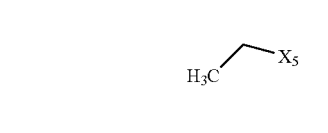 | 6.90 | | GC/FID |
| 333 |  | 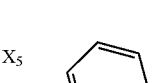 | 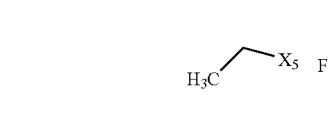 | 1.99 | 456.5 | LC/MS |
| 334 |  | | 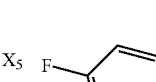 | 2.06 | 492.5 | LC/MS |

TABLE 4-continued

| Cmp. # | R2 | R5 | W1 | RT | Mass | GC/FID or LC/MS |
|---|---|---|---|---|---|---|
| 335 | X₂–C(=O)–N(CH₂CH₂OCH₃)₂ | H₃C–X₅ | phenyl (X₁) | 7.00 | | GC/FID |
| 336 | X₂–C(=O)–N(CH₂CH₂OCH₃)₂ | H₃C–X₅ | 2,5-difluorophenyl (X₁) | 6.71 | | GC/FID |
| 337 | X₂–C(=O)–N(n-pentyl)₂ | H₃C–X₅ | phenyl (X₁) | 7.31 | | GC/FID |
| 338 | X₂–C(=O)–N(n-pentyl)₂ | H₃C–X₅ | 2,5-difluorophenyl (X₁) | 2.45 | 545.6 | LC/MS |
| 339 | X₂–C(=O)–N(n-hexyl)₂ | H₃C–X₅ | phenyl (X₁) | 7.86 | | GC/FID |
| 340 | X₂–C(=O)–N(n-hexyl)₂ | H₃C–X₅ | 2,5-difluorophenyl (X₁) | 2.65 | 550.7 | LC/MS |

TABLE 4-continued
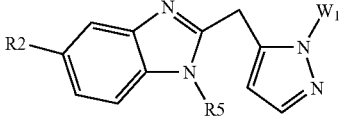
| Cmp. # | R2 | R5 | W1 | RT | Mass | GC/FID or LC/MS |
|---|---|---|---|---|---|---|
| 341 | 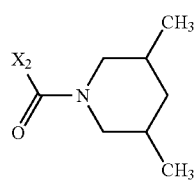 | 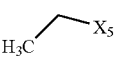 | 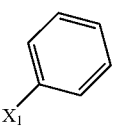 | 7.14 | | GC/FID |
| 342 | 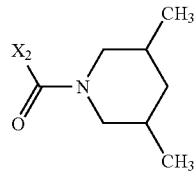 | 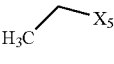 | 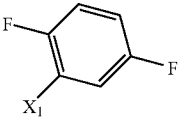 | 6.81 | | GC/FID |
| 343 | 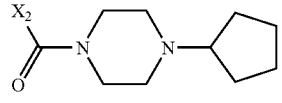 | 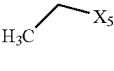 | 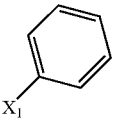 | 9.51 | | GC/FID |
| 344 | 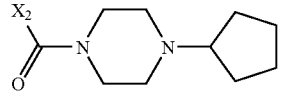 | 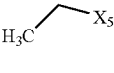 | 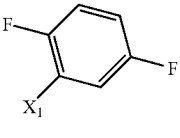 | 8.54 | | GC/FID |
| 345 | 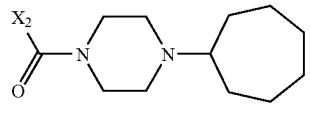 | 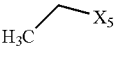 | 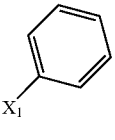 | 11.94 | | GC/FID |
| 346 | 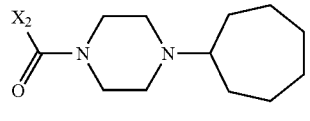 | 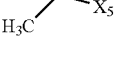 | 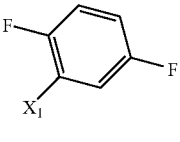 | 1.48 | 547.7 | LC/MS |
| 347 | 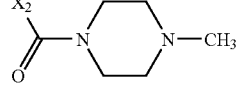 | 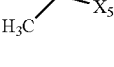 | 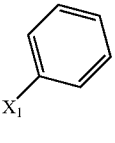 | 7.22 | | GC/FID |
| 348 | 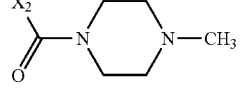 | 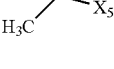 | 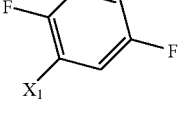 | 6.83 | | GC/FID |
| 349 | 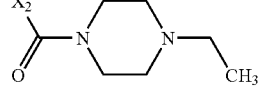 | 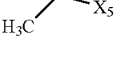 | 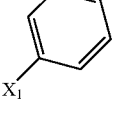 | 7.44 | | GC/FID |

TABLE 4-continued
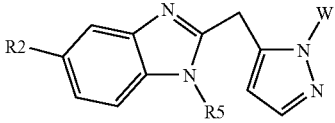
| Cmp. # | R2 | R5 | W1 | RT | Mass | GC/FID or LC/MS |
|---|---|---|---|---|---|---|
| 350 | 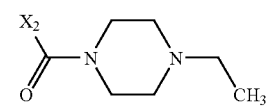 | 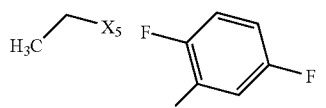 |  | 7.04 | | GC/FID |
| 351 | 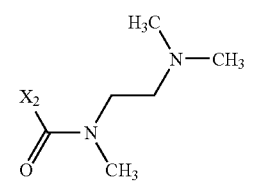 | 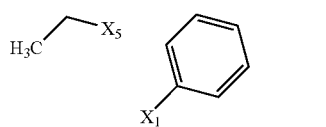 |  | 6.83 | | GC/FID |
| 352 | 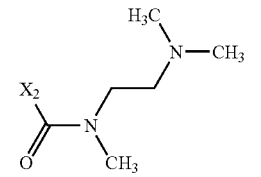 | 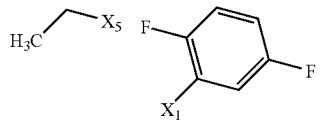 |  | 6.56 | | GC/FID |
| 353 | 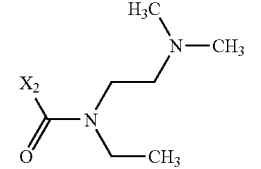 | 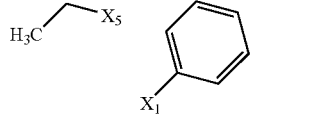 |  | 6.84 | | GC/FID |
| 354 | 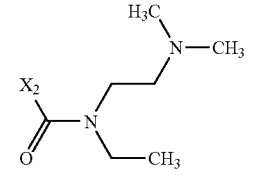 | 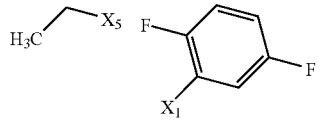 |  | 6.58 | | GC/FID |
| 355 | 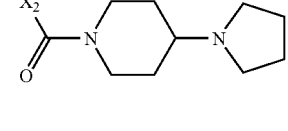 | 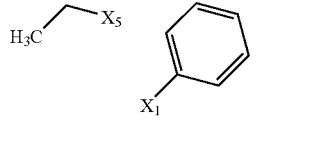 |  | 9.63 | | GC/FID |
| 356 | 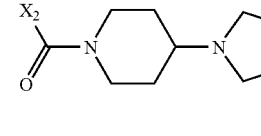 | 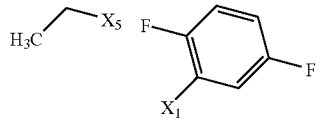 |  | 8.64 | | GC/FID |
| 357 | 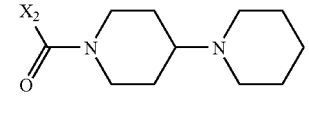 | 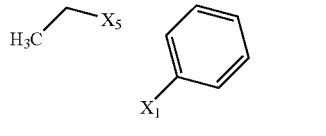 |  | 1.05 | 497.6 | LC/MS |

TABLE 4-continued

| Cmp. # | R2 | R5 | W1 | RT | Mass | GC/FID or LC/MS |
|---|---|---|---|---|---|---|
| 358 | X2–C(O)–N(piperidine-4-yl-piperidine) | H3C–CH2–X5 | 2,5-difluorophenyl (X1) | 9.16 | | GC/FID |
| 359 | X2–C(O)–N(CH3)(1-methylpiperidin-4-yl) | H3C–CH2–X5 | phenyl (X1) | 7.61 | | GC/FID |
| 360 | X2–C(O)–N(CH3)(1-methylpiperidin-4-yl) | H3C–CH2–X5 | 2,5-difluorophenyl (X1) | 7.17 | | GC/FID |
| 361 | X2–C(O)–N(CH3)CH2CH2CH2N(CH3)2 | H3C–CH2–X5 | phenyl (X1) | 7.02 | | GC/FID |
| 362 | X2–C(O)–N(CH3)CH2CH2CH2N(CH3)2 | H3C–CH2–X5 | 2,5-difluorophenyl (X1) | 6.72 | | GC/FID |
| 363 | X2–C(O)–N(CH3)CH2CH2N(CH2CH3)2 | H3C–CH2–X5 | phenyl (X1) | 1.05 | 459.5 | LC/MS |
| 364 | X2–C(O)–N(CH3)CH2CH2N(CH2CH3)2 | H3C–CH2–X5 | 2,5-difluorophenyl (X1) | 6.79 | | GC/FID |

TABLE 5
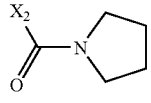
| Cpd. # | R2 | R5 | W1 | MW | RT | Mass | GC/FID or LC/MS |
|---|---|---|---|---|---|---|---|
| 365 | 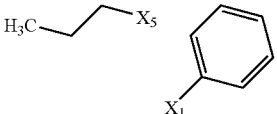 |  | 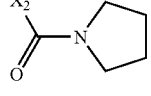 | 413.5223 | NA | | |
| 366 | 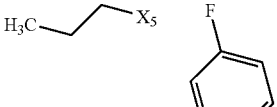 | 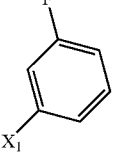 | 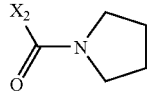 | 431.5124 | 1.73 | 432.1 | LC/MS |
| 367 | 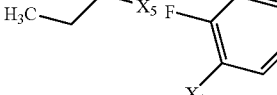 | 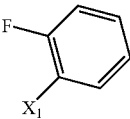 | 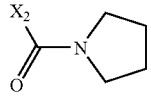 | 449.5025 | 1.67 | 450.4 | LC/MS |
| 368 | 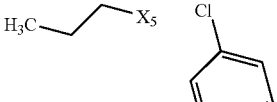 | 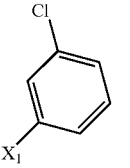 | 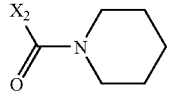 | 447.9674 | 1.87 | 448.3 | LC/MS |
| 369 | 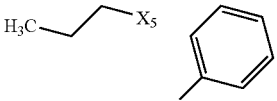 | 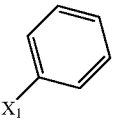 | 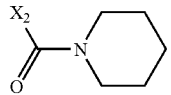 | 427.5491 | 1.87 | 428.4 | LC/MS |
| 370 | 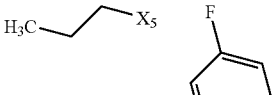 | 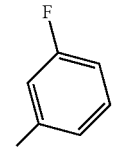 | 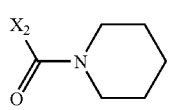 | 445.5392 | 1.94 | 446.4 | LC/MS |
| 371 | 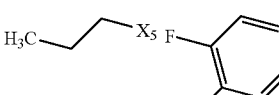 | 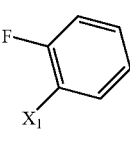 | 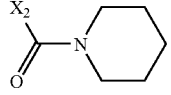 | 463.5293 | 1.87 | 464.4 | LC/MS |
| 372 | 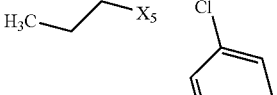 | | 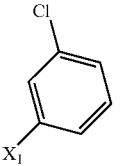 | 461.9942 | 2.07 | 462.4 | LC/MS |

TABLE 5-continued

| Cpd. # | R2 | R5 | W1 | MW | RT | Mass | GC/FID or LC/MS |
|---|---|---|---|---|---|---|---|
| 373 | X₂-C(O)-N-morpholine | H₃C-propyl-X₅ | phenyl-X₁ | 429.5213 | 2.87 | 430 | LC/MS |
| 374 | X₂-C(O)-N-morpholine | H₃C-propyl-X₅ | 3-F-phenyl-X₁ | 447.5114 | 1.53 | 448.3 | LC/MS |
| 375 | X₂-C(O)-N-morpholine | H₃C-propyl-X₅ | 2,4-diF-phenyl-X₁ | 465.5015 | 1.47 | 466.5 | LC/MS |
| 376 | X₂-C(O)-N-morpholine | H₃C-propyl-X₅ | 3-Cl-phenyl-X₁ | 463.9664 | 1.67 | 464.4 | LC/MS |
| 377 | X₂-C(O)-N(4-Me-piperidine) | H₃C-propyl-X₅ | phenyl-X₁ | 441.5759 | 2.07 | 442.6 | LC/MS |
| 378 | X₂-C(O)-N(4-Me-piperidine) | H₃C-propyl-X₅ | 3-F-phenyl-X₁ | 459.566 | 2.13 | 460.3 | LC/MS |
| 379 | X₂-C(O)-N(4-Me-piperidine) | H₃C-propyl-X₅ | 2,4-diF-phenyl-X₁ | 477.5561 | NA | | |
| 380 | X₂-C(O)-N(azepane) | H₃C-propyl-X₅ | phenyl-X₁ | 441.5759 | 2.00 | 442.6 | LC/MS |

TABLE 5-continued

| Cpd. # | R2 | R5 | W1 | MW | RT | Mass | GC/FID or LC/MS |
|---|---|---|---|---|---|---|---|
| 381 | X₂–C(O)–N(azepane) | H₃C–CH₂–CH₂–X₅ | 3-F-phenyl-X₁ | 459.566 | 2.07 | 460.3 | LC/MS |
| 382 | X₂–C(O)–N(thiomorpholine) | H₃C–CH₂–CH₂–X₅ | phenyl-X₁ | 445.5883 | 1.73 | 446.4 | LC/MS |
| 383 | X₂–C(O)–N(thiomorpholine) | H₃C–CH₂–CH₂–X₅ | 3-F-phenyl-X₁ | 463.5784 | 1.80 | 464.4 | LC/MS |
| 384 | X₂–C(O)–N(thiomorpholine) | H₃C–CH₂–CH₂–X₅ | 2,4-diF-phenyl-X₁ | 481.5685 | 1.73 | 482.2 | LC/MS |
| 385 | X₂–C(O)–N(thiomorpholine) | H₃C–CH₂–CH₂–X₅ | 3-Cl-phenyl-X₁ | 480.0334 | NA | | |
| 386 | X₂–C(O)–N(3,3-diMe-piperidine) | H₃C–CH₂–CH₂–X₅ | phenyl-X₁ | 455.6027 | 2.13 | 456.4 | LC/MS |
| 387 | X₂–C(O)–N(3,3-diMe-piperidine) | H₃C–CH₂–CH₂–X₅ | 3-F-phenyl-X₁ | 473.5928 | NA | | |
| 388 | X₂–C(O)–N(3,3-diMe-piperidine) | H₃C–CH₂–CH₂–X₅ | 2,4-diF-phenyl-X₁ | 491.5829 | 2.13 | 492.4 | LC/MS |

TABLE 5-continued
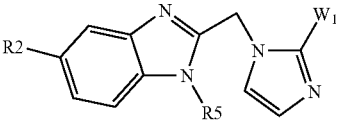
| Cpd. # | R2 | R5 | W1 | MW | RT | Mass | GC/FID or LC/MS |
|---|---|---|---|---|---|---|---|
| 389 | 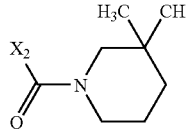 | 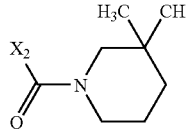 | 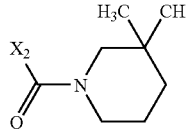 | 490.0478 | 2.27 | 490.3 | LC/MS |
| 390 | 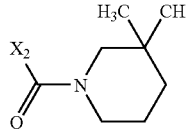 | 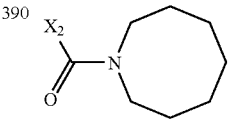 | 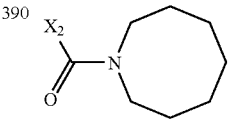 | 455.6027 | 2.13 | 456.4 | LC/MS |
| 391 | 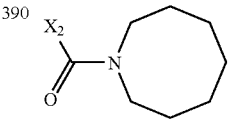 | 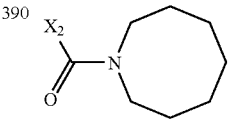 | 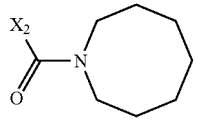 | 473.5928 | NA | | |
| 392 | 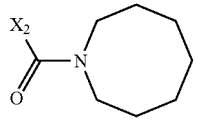 | 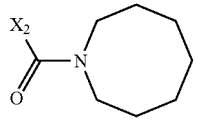 | 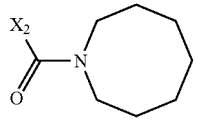 | 491.5829 | 2.13 | 492.4 | LC/MS |
| 393 | 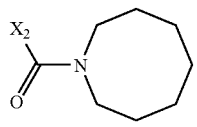 | 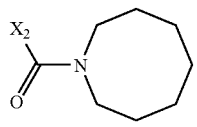 | 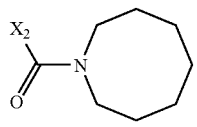 | 490.0478 | 2.27 | 490.5 | LC/MS |
| 394 | 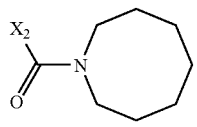 | 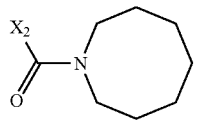 | 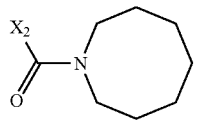 | 483.6563 | 2.40 | 484.5 | LC/MS |
| 395 | 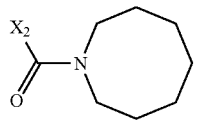 | 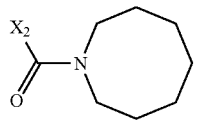 | 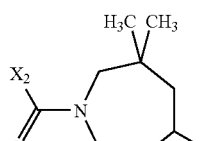 | 501.6464 | 2.47 | 502.3 | LC/MS |
| 396 | 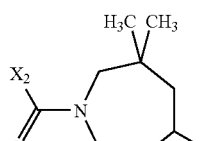 | 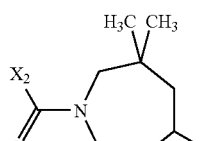 | 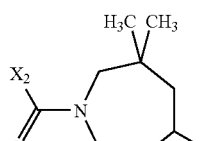 | 519.6365 | NA | | |

TABLE 5-continued

[Structure: benzimidazole with R2 substituent, N-R5, linked via CH2 to imidazole bearing W1]

| Cpd. # | R2 | R5 | W1 | MW | RT | Mass | GC/FID or LC/MS |
|---|---|---|---|---|---|---|---|
| 397 | X2—C(O)—N(3,3-dimethyl-6-methyl-azepane) | H3C—/—X5 (propyl) | 3-Cl-phenyl (X1) | 518.1014 | NA | | |
| 398 | X2—C(O)—N(1,4-dioxa-8-azaspiro[4.5]decane) | H3C—/—X5 | phenyl (X1) | 485.5849 | 1.73 | 486.3 | LC/MS |
| 399 | X2—C(O)—N(1,4-dioxa-8-azaspiro[4.5]decane) | H3C—/—X5 | 3-F-phenyl (X1) | 503.575 | 1.73 | 504.3 | LC/MS |
| 400 | X2—C(O)—N(1,4-dioxa-8-azaspiro[4.5]decane) | H3C—/—X5 | 2,4-difluoro-phenyl (X1) | 521.5651 | NA | | |
| 401 | X2—C(O)—N(1,4-dioxa-8-azaspiro[4.5]decane) | H3C—/—X5 | 3-Cl-phenyl (X1) | 520.03 | 1.87 | 520.2 | LC/MS |
| 402 | X2—C(O)—N(decahydroquinoline) | H3C—/—X5 | phenyl (X1) | 481.6405 | 2.34 | 482.5 | LC/MS |
| 403 | X2—C(O)—N(decahydroquinoline) | H3C—/—X5 | 3-F-phenyl (X1) | 499.6306 | 2.40 | 500.4 | LC/MS |
| 404 | X2—C(O)—N(decahydroquinoline) | H3C—/—X5 | 2,4-difluoro-phenyl (X1) | 517.6207 | 2.34 | 518 | LC/MS |

TABLE 5-continued

| Cpd. # | R2 | R5 | W1 | MW | RT | Mass | GC/FID or LC/MS |
|---|---|---|---|---|---|---|---|
| 405 | X2-C(O)-N(decahydroquinoline) | H3C-CH2-CH2-X5 | 3-Cl-C6H4-X1 | 516.0856 | 2.47 | 516.4 | LC/MS |
| 406 | X2-C(O)-N(CH3)2 | H3C-CH2-CH2-X5 | C6H5-X1 | 387.4845 | 1.47 | 388.5 | LC/MS |
| 407 | X2-C(O)-N(CH3)2 | H3C-CH2-CH2-X5 | 3-F-C6H4-X1 | 405.4746 | 1.53 | 406.3 | LC/MS |
| 408 | X2-C(O)-N(CH3)2 | H3C-CH2-CH2-X5 | 2,4-F2-C6H3-X1 | 423.4647 | 1.47 | 424.2 | LC/MS |
| 409 | X2-C(O)-N(CH3)(CH2CH=CH2) | H3C-CH2-CH2-X5 | C6H5-X1 | 413.5223 | 1.80 | 414.4 | LC/MS |
| 410 | X2-C(O)-N(CH3)(CH2CH=CH2) | H3C-CH2-CH2-X5 | 3-F-C6H4-X1 | 431.5124 | 1.87 | 432.1 | LC/MS |
| 411 | X2-C(O)-N(CH3)(CH2CH=CH2) | H3C-CH2-CH2-X5 | 2,4-F2-C6H3-X1 | 449.5025 | 1.73 | 450.3 | LC/MS |
| 412 | X2-C(O)-N(CH3)(CH2CH=CH2) | H3C-CH2-CH2-X5 | 3-Cl-C6H4-X1 | 447.9674 | 1.93 | 448.5 | LC/MS |

TABLE 5-continued
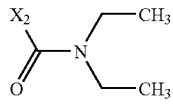
| Cpd. # | R2 | R5 | W1 | MW | RT | Mass | GC/FID or LC/MS |
|---|---|---|---|---|---|---|---|
| 413 | 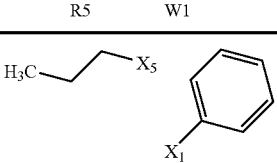 | 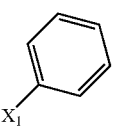 | 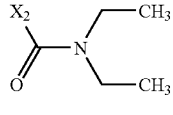 | 415.5381 | 1.80 | 416.4 | LC/MS |
| 414 | 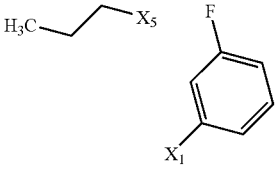 | 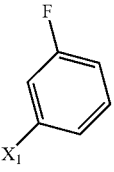 | 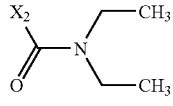 | 433.5282 | 1.87 | 434.5 | LC/MS |
| 415 | 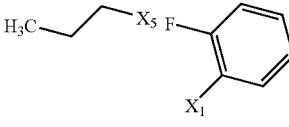 | 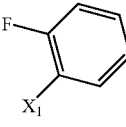 | 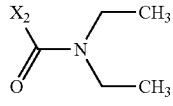 | 451.5183 | 1.80 | 452.4 | LC/MS |
| 416 | 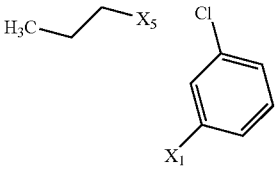 | 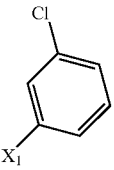 | 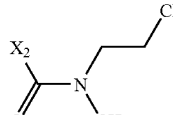 | 449.9832 | 2.00 | 450.3 | LC/MS |
| 417 | 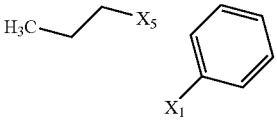 | 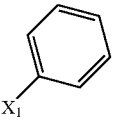 | 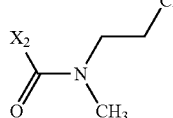 | 415.5381 | 1.80 | 416.4 | LC/MS |
| 418 | 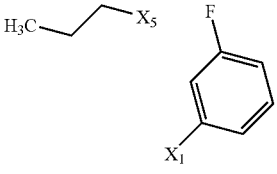 | 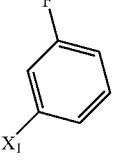 | 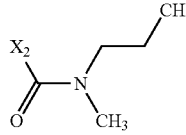 | 433.5282 | 1.87 | 434.5 | LC/MS |
| 419 | 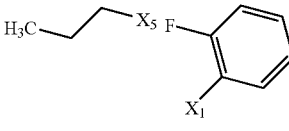 | 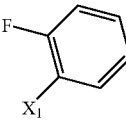 | 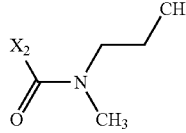 | 451.5183 | 1.80 | 452.4 | LC/MS |
| 420 | 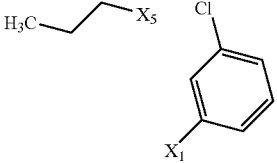 | 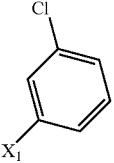 | | 449.9832 | 2.00 | 450.3 | LC/MS |

TABLE 5-continued

| Cpd. # | R2 | R5 | W1 | MW | RT | Mass | GC/FID or LC/MS |
|---|---|---|---|---|---|---|---|
| 421 | X2–C(O)–N(CH3)–CH2CH2CH2CH3 | H3C–CH2CH2–X5 | phenyl (X1) | 429.5649 | 2.00 | 430.2 | LC/MS |
| 422 | X2–C(O)–N(CH3)–CH2CH2CH2CH3 | H3C–CH2CH2–X5 | 3-F-phenyl (X1) | 447.555 | 2.07 | 448.6 | LC/MS |
| 423 | X2–C(O)–N(CH3)–CH2CH2CH2CH3 | H3C–CH2CH2–X5 | 2,4-F2-phenyl (X1) | 465.5451 | 2.00 | 466.3 | LC/MS |
| 424 | X2–C(O)–N(CH3)–CH2CH2CH2CH3 | H3C–CH2CH2–X5 | 3-Cl-phenyl (X1) | 464.01 | 2.20 | 464.4 | LC/MS |
| 425 | X2–C(O)–N(Et)–CH(CH3)2 | H3C–CH2CH2–X5 | phenyl (X1) | 429.5649 | 1.93 | 430.2 | LC/MS |
| 426 | X2–C(O)–N(Et)–CH(CH3)2 | H3C–CH2CH2–X5 | 3-F-phenyl (X1) | 447.555 | 2.00 | 448.6 | LC/MS |
| 427 | X2–C(O)–N(Et)–CH(CH3)2 | H3C–CH2CH2–X5 | 2,4-F2-phenyl (X1) | 465.5451 | 1.93 | 466.3 | LC/MS |
| 428 | X2–C(O)–N(Et)–CH(CH3)2 | H3C–CH2CH2–X5 | 3-Cl-phenyl (X1) | 464.01 | 2.13 | 464.4 | LC/MS |

TABLE 5-continued

| Cpd. # | R2 | R5 | W1 | MW | RT | Mass | GC/FID or LC/MS |
|---|---|---|---|---|---|---|---|
| 429 | X2-C(=O)-N(CH2CH=CH2)2 | H3C-CH2-CH2-X5 | phenyl-X1 | 439.5601 | 2.00 | 440.7 | LC/MS |
| 430 | X2-C(=O)-N(CH2CH=CH2)2 | H3C-CH2-CH2-X5 | 3-F-phenyl-X1 | 457.5502 | 2.07 | 458.4 | LC/MS |
| 431 | X2-C(=O)-N(CH2CH=CH2)2 | H3C-CH2-CH2-X5 | 2,5-diF-phenyl-X1 | 475.5403 | NA | | |
| 432 | X2-C(=O)-N(CH2CH=CH2)2 | H3C-CH2-CH2-X5 | 3-Cl-phenyl-X1 | 474.0052 | NA | | |
| 433 | X2-C(=O)-N(CH2CH2CH3)2 | H3C-CH2-CH2-X5 | phenyl-X1 | 443.5917 | 2.13 | 444.6 | LC/MS |
| 434 | X2-C(=O)-N(CH2CH2CH3)2 | H3C-CH2-CH2-X5 | 3-F-phenyl-X1 | 461.5818 | 2.20 | 462.4 | LC/MS |
| 435 | X2-C(=O)-N(CH2CH2CH3)2 | H3C-CH2-CH2-X5 | 2,5-diF-phenyl-X1 | 479.5719 | NA | | |

TABLE 5-continued

| Cpd. # | R2 | R5 | W1 | MW | RT | Mass | GC/FID or LC/MS |
|---|---|---|---|---|---|---|---|
| 436 | X₂–C(=O)–N(CH₂CH₂CH₃)(CH₂CH₂CH₃) | H₃C–CH₂–CH₂–X₅ | 3-Cl-phenyl (X₁) | 478.0368 | NA | | |
| 437 | X₂–C(=O)–N(CH₂CH₃)(CH₂CH₂CH₂CH₃) | H₃C–CH₂–CH₂–X₅ | phenyl (X₁) | 443.5917 | 2.13 | 444.6 | LC/MS |
| 438 | X₂–C(=O)–N(CH₂CH₃)(CH₂CH₂CH₂CH₃) | H₃C–CH₂–CH₂–X₅ | 3-F-phenyl (X₁) | 461.5818 | 2.20 | 462.4 | LC/MS |
| 439 | X₂–C(=O)–N(CH₂CH₃)(CH₂CH₂CH₂CH₃) | H₃C–CH₂–CH₂–X₅ | 2,4-diF-phenyl (X₁) | 479.5719 | NA | | |
| 440 | X₂–C(=O)–N(CH₂CH₃)(CH₂CH₂CH₂CH₃) | H₃C–CH₂–CH₂–X₅ | 3-Cl-phenyl (X₁) | 478.0368 | NA | | |
| 441 | (cyclopropyl-CH₂)N(CH₂CH₂CH₃)–C(=O)–X₂ | X₅–CH₂–CH₂–CH₃ | phenyl (X₁) | 455.6027 | 2.20 | 456.4 | LC/MS |
| 442 | (cyclopropyl-CH₂)N(CH₂CH₂CH₃)–C(=O)–X₂ | X₅–CH₂–CH₂–CH₃ | 3-F-phenyl (X₁) | 473.5928 | NA | | |

TABLE 5-continued
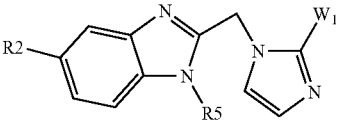
| Cpd. # | R2 | R5 | W1 | MW | RT | Mass | GC/FID or LC/MS |
|---|---|---|---|---|---|---|---|
| 443 | 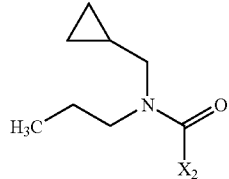 | X$_5$—CH$_2$—CH$_3$ | 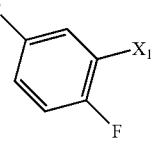 | 491.5829 | NA | | |
| 444 | 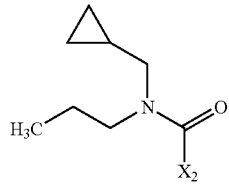 | X$_5$—CH$_2$—CH$_3$ | 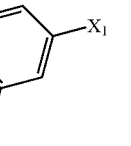 | 490.0478 | 2.34 | 490.3 | LC/MS |
| 445 | 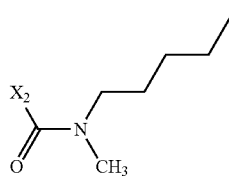 | H$_3$C—CH$_2$—X$_5$ | 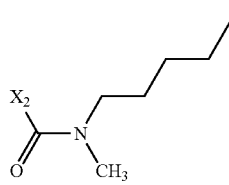 | 457.6185 | 2.34 | 458.4 | LC/MS |
| 446 | 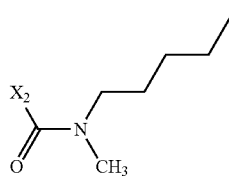 | H$_3$C—CH$_2$—X$_5$ | 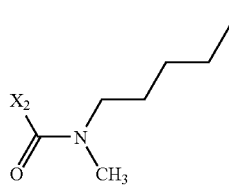 | 475.6086 | NA | | |
| 447 | 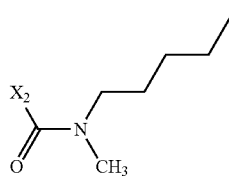 | H$_3$C—CH$_2$—X$_5$ | 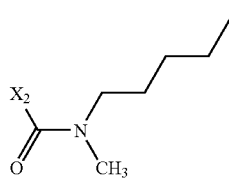 | 493.5987 | 2.34 | 494.5 | LC/MS |
| 448 | 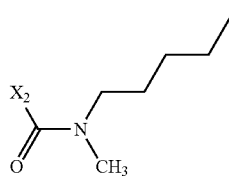 | H$_3$C—CH$_2$—X$_5$ | 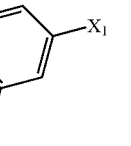 | 492.0636 | 2.47 | 492.4 | LC/MS |

TABLE 6

| Cpd # | STRUCTURE | IUPAC NAME | NMR | MS (m/z) |
|---|---|---|---|---|
| 449 | 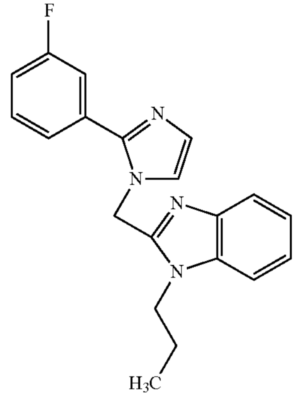 | 2-{[2-(3-fluorophenyl)-1H-imidazol-1-yl]methyl}-1-propyl-1H-benzimidazole | 1H NMR (CDCl3): 7.80 (m, 1H), 7.41-7.53 (m, 3H), 7.29-7.31 (m, 3H), 7.14-7.22 (m, 2H), 7.06 (d, 1H), 5.51 (s, 2H), 3.69 (t, 2H), 1.43 (m, 2H), 0.74 (t, 3H) | |
| 450 | 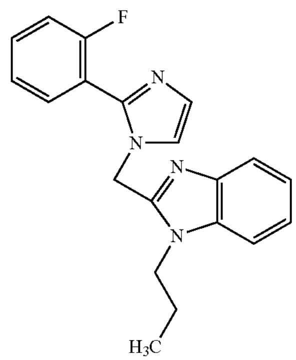 | 2-{[2-(2-fluorophenyl)-1H-imidazol-1-yl]methyl}-1-propyl-1H-benzimidazole | 7.78 (m, 1H), 7.66 (m, 1H), 7.51 (m, 1H), 7.23-7.37 (m, 5H), 7.17 (d, 1H), 7.03 (d, 1H), 5.35 (s, 2H), 3.68 (t, 2H), 1.40 (m, 2H), 0.72 (t, 3H) | |

TABLE 6-continued

| Cpd # | STRUCTURE | IUPAC NAME | NMR | MS (m/z) |
|---|---|---|---|---|
| 451 | 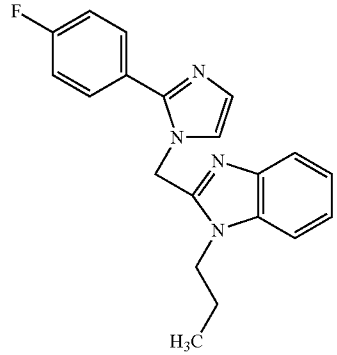 | 2-{[2-(4-fluorophenyl)-1H-imidazol-1-yl]methyl}-1-propyl-1H-benzimidazole | 1H NMR (CDCl3): 7.80 (m, 1H), 7.65-7.69 (m, 2H), 7.18-7.32 (m, 5H), 7.13 (d, 1H), 7.04 (d, 1H), 5.47 (s, 2H), 3.68 (t, 2H,), 1.42 (m, 2H), 0.74 (t, 3H) | |
| 452 | 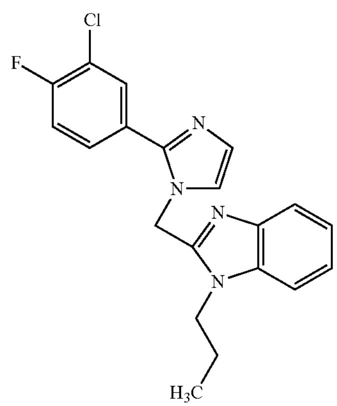 | 2-{[2-(3-chloro-4-fluorophenyl)-1H-imidazol-1-yl]methyl}-1-propyl-1H-benzimidazole | 1H NMR (CDCl3): 7.76-7.81 (m, 2H), 7.56 (m, 1H), 7.25-7.32 (m, 4H), 7.14 (d, 1H), 7.05 (d, 1H), 5.46 (s, 2H), 3.74 (t, 2H,), 1.47 (m, 2H), 0.78 (t, 3H) | |

TABLE 6-continued

| Cpd # | STRUCTURE | IUPAC NAME | NMR | MS (m/z) |
|---|---|---|---|---|
| 453 | 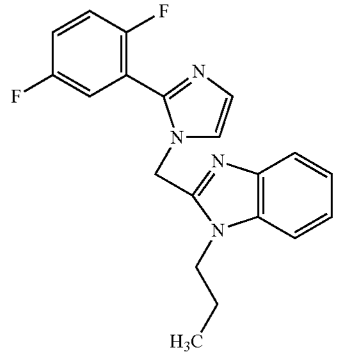 | 2-{[2-(2,5-difluorophenyl)-1H-imidazol-1-yl]methyl}-1-propyl-1H-benzimidazole | 7.78 (m, 1H), 7.38 (m, 1H), 7.17-7.31 (m, 6H), 7.03 (d, 1H), 5.36 (s, 2H), 3.73 (t, 2H), 1.44 (m, 2H), 0.76 (t, 3H) | |
| 454 | 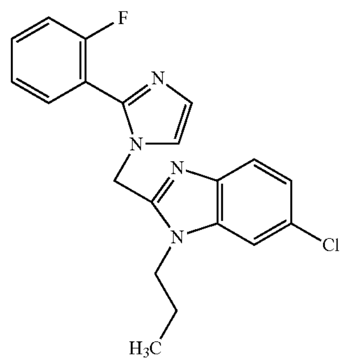 | 6-chloro-2-{[2-(2-fluorophenyl)-1H-imidazol-1-yl]methyl}-1-propyl-1H-benzimidazole | 1H NMR (CDCl3): 7.62-7.69 (m, 2H), 7.51 (m, 1H), 7.22-7.34 (m, 4H), 7.18 (d, 1H), 7.02 (d, 1H), 5.34 (s, 2H), 3.64 (t, 2H), 1.40 (m, 2H), 0.73 (t, 3H) | |

TABLE 6-continued

| Cpd # | STRUCTURE | IUPAC NAME | NMR | MS (m/z) |
|---|---|---|---|---|
| 455 | (structure) | 6-chloro-2-{[2-(3-fluorophenyl)-1H-imidazol-1-yl]methyl}-1-propyl-1H-benzimidazole | 1H NMR (CDCl3): 7.69 (d, 1H), 7.38-7.52 (m, 3H), 7.15-7.29 (m, 4H), 7.04 (d, 1H), 5.48 (s, 2H), 3.65 (t, 2H), 1.42 (m, 2H), 0.75 (t, 3H) | |
| 456 | (structure) | 6-chloro-2-{[2-(4-fluorophenyl)-1H-imidazol-1-yl]methyl}-1-propyl-1H-benzimidazole | 1H NMR (CDCl3): 7.62-7.70 (m, 3H), 7.13-7.28 (m, 5H), 7.02 (d, 1H), 3.64 (t, 2H), 1.41 (m, 2H), 0.75 (t, 3H) | |

| Cpd # | STRUCTURE | IUPAC NAME | NMR | MS (m/z) |
|---|---|---|---|---|
| 457 | 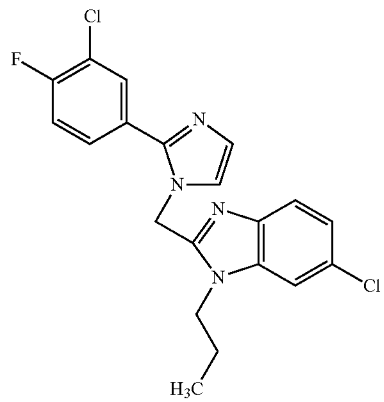 | 6-chloro-2-{[2-(3-chloro-4-fluorophenyl)-1H-imidazol-1-yl]methyl}-1-propyl-1H-benzimidazole | 1H NMR (CDCl3): 7.75 (dd, 1H), 7.69 (dd, 1H), 7.55 (m, 1H), 7.24-7.30 (m, 3H), 7.15 (d, 1H), 7.03 (d, 1H), 5.43 (s, 2H), 3.71 (t, 2H), 1.47 (m, 2H), 0.79 (t, 3H) | |
| 458 | 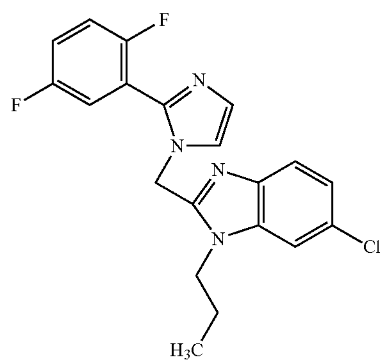 | 6-chloro-2-{[2-(2,5-difluorophenyl)-1H-imidazol-1-yl]methyl}-1-propyl-1H-benzimidazole | 1H NMR (CDCl3): 7.67 (d, 1H), 7.37 (m, 1H), 7.17-7.29 (m, 5H), 7.02 (d, 1H), 5.34 (s, 2H), 3.69 (t, 2H), 1.43 (m, 2H), 0.77 (t, 3H) | |

| Cpd # | STRUCTURE | IUPAC NAME | NMR | MS (m/z) |
|---|---|---|---|---|
| 459 | 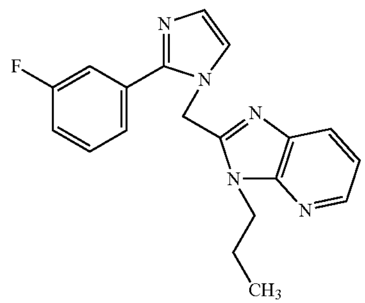 | 2-{[2-(3-fluorophenyl)-1H-imidazol-1-yl]methyl}-3-propyl-3H-imidazo[4,5-b]pyridine | 1H NMR (CDCl3): 8.40 (dd, 1H), 8.06 (dd, 1H), 7.39-7.50 (m, 3H), 7.15-7.29 (m, 3H), 7.08 (d, 1H), 5.52 (s, 2H), 3.88 (t, 2H), 1.51 (m, 2H), 0.77 (t, 3H) | |
| 460 | 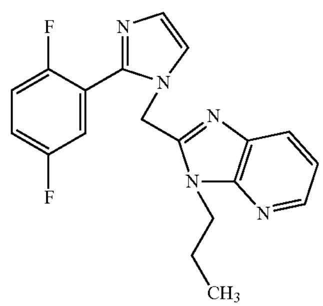 | 2-{[2-(2,5-difluorophenyl)-1H-imidazol-1-yl]methyl}-3-propyl-3H-imidazo[4,5-b]pyridine | 1H NMR (CDCl3): 8.40 (dd, 1H), 8.05 (dd, 1H), 7.38 (m, 1H), 7.17-7.28 (m, 4H), 7.08 (d, 1H), 5.39 (s, 2H), 3.89 (t, 2H), 1.50 (m, 2H), 0.79 (t, 3H) | |
| 461 | 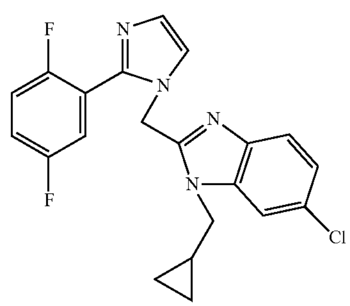 | 6-chloro-1-(cyclopropylmethyl)-2-{[2-(2,5-difluorophenyl)-1H-imidazol-1-yl]methyl}-1H-benzimidazole | 1H NMR (CDCl3): 7.68 (d, 1H), 7.38 (m, 1H), 7.32 (d, 1H), 7.19-7.28 (m, 4H), 7.04 (d, 1H), 5.36 (d, 2H), 3.62 (d, 2H), 0.65 (m, 1H), 0.46-0.51 (m, 2H), 0.07-0.11 (m, 2H) | |

TABLE 6-continued

| Cpd # | STRUCTURE | IUPAC NAME | NMR | MS (m/z) |
|---|---|---|---|---|
| 462 | 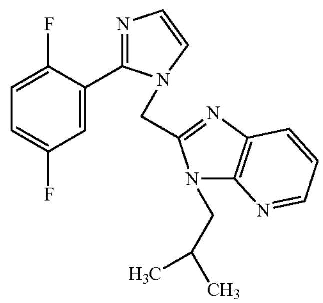 | 2-{[2-(2,5-difluorophenyl)-1H-imidazol-1-yl]methyl}-1-isobutyl-3H-imidazo[4,5-b]pyridine | 1H NMR (CDCl3): 8.38 (dd, 1H), 8.04 (dd, 1H), 7.38 (m, 1H), 7.16-7.27 (m, 4H), 7.09 (d, 1H), 5.38 (s, 2H), 3.73 (d, 2H), 1.98 (m, 1H), 0.72 (d, 6H) | |
| 463 | 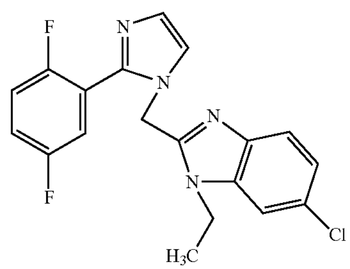 | 6-chloro-2-{[2-(2,5-difluorophenyl)-1H-imidazol-1-yl]methyl}-1-ethyl-1H-benzimidazole | 1H NMR (CDCl3): 7.67 (d, 1H), 7.37 (m, 1H), 7.17-7.30 (m, 5H), 7.01 (d, 1H), 5.35 (s, 2H), 3.79 (q, 2H), 0.99 (t, 3H) | |
| 464 | 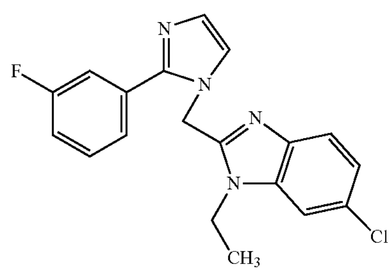 | 6-chloro-1-ethyl-2-{[2-(3-fluorophenyl)-1H-imidazol-1-yl]methyl}-1H-benzimidazole | 1H NMR (CDCl3): 7.69 (d, 1H), 7.39-7.51 (m, 3H), 7.16-7.30 (m, 4H), 7.03 (d, 1H), 5.49 (s, 2H), 3.75 (q, 2H), 0.98 (t, 3H) | |

TABLE 6-continued

| Cpd # | STRUCTURE | IUPAC NAME | NMR | MS (m/z) |
|---|---|---|---|---|
| 465 | 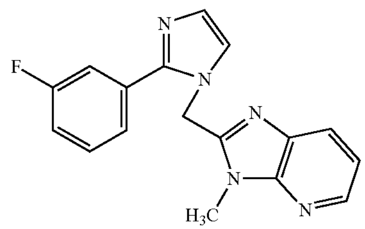 | 2-{[2-(3-fluorophenyl)-1H-imidazol-1-yl]methyl}-3-methyl-3H-imidazo[4,5-b]pyridine | 1H NMR (CDCl3): 8.40 (dd, 1H), 8.05 (dd, 1H), 7.40-7.51 (m, 3H), 7.13-7.29 (m, 3H), 7.02 (d, 1H), 5.53 (s, 2H), 3.51 (s, 3H) | |
| 466 | 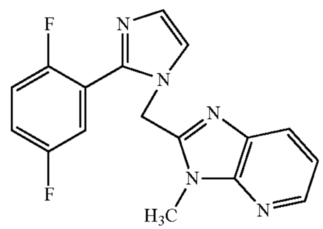 | 2-{[2-(2,5-difluorophenyl)-1H-imidazol-1-yl]methyl}-3-methyl-3H-imidazo[4,5-b]pyridine | 1H NMR (CDCl3): 8.40 (dd, 1H), 8.03 (dd, 1H), 7.36 (m, 1H), 7.15-7.27 (m, 4H), 7.03 (d, 1H), 5.41 (s, 2H), 3.51 (s, 3H) | |
| 467 | 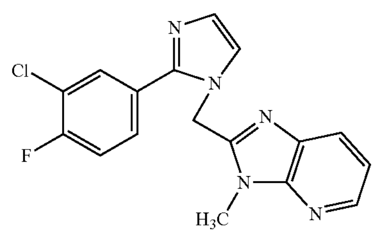 | 2-{[2-(3-chloro-4-fluorophenyl)-1H-imidazol-1-yl]methyl}-3-methyl-3H-imidazo[4,5-b]pyridine | | |
| 468 | 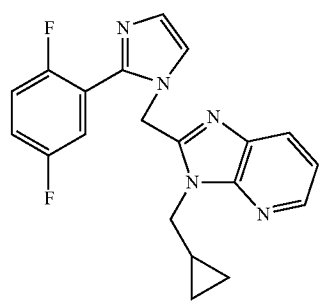 | 3-(cyclopropylmethyl)-2-{[2-(2,5-difluorophenyl)-1H-imidazol-1-yl]methyl}-3H-imidazo[4,5-b]pyridine | 1H NMR (CDCl3): 8.37 (dd, 1H), 8.04 (dd, 1H), 7.38 (m, 1H), 7.09-7.28 (m, 4H), 7.09 (d, 1H), 5.42 (s, 2H), 3.83 (d, 2H), 0.68 (m, 1H), 0.38-0.43 (m, 2H), 0.24-0.29 (m, 2H) | |

TABLE 6-continued

| Cpd # | STRUCTURE | IUPAC NAME | NMR | MS (m/z) |
|---|---|---|---|---|
| 469 | 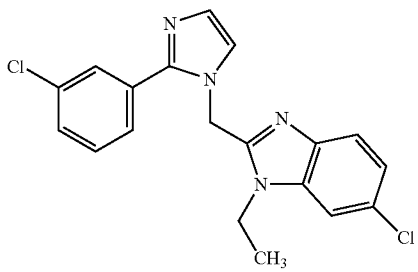 | 6-chloro-2-{[2-(3-chlorophenyl)-1H-imidazol-1-yl]methyl}-1-ethyl-1H-benzimidazole | 1H NMR (CDCl3): 7.67-7.71 (m, 2H), 7.45-7.56 (m, 3H), 7.24-7.30 (m, 2H), 7.16 (d, 2H), 7.04 (d, 1H), 5.47 (s, 2H), 3.76 (q, 2H), 0.99 (t, 3H) | |
| 470 | 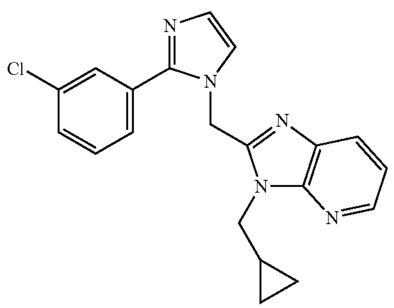 | 2-{[2-(3-chlorophenyl)-1H-imidazol-1-yl]methyl}-3-(cyclopropylmethyl)-3H-imidazo[4,5-b]pyridine | 1H NMR (CDCl3): 8.39 (dd, 1H), 8.06 (dd, 1H), 7.68 (m, 1H), 7.40-7.68 (m, 3H), 7.27 (m, 1H), 7.18 (d, 1H), 7.10 (d, 1H), 5.53 (s, 2H), 3.83 (d, 2H), 0.73 (m, 1H), 0.40-0.46 (m, 2H), 0.24-0.28 (m, 2H) | |
| 471 | 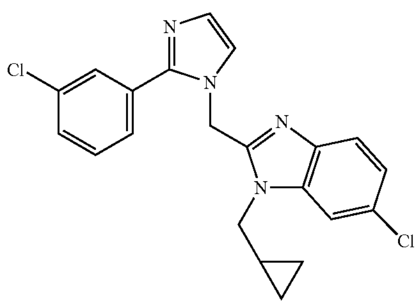 | 6-chloro-2-{[2-(3-chlorophenyl)-1H-imidazol-1-yl]methyl}-1-(cyclopropylmethyl)-1H-benzimidazole | 1H NMR (CDCl3): 7.67-7.71 (m, 2H), 7.42-7.56 (m, 3H), 7.24-7.33 (m, 2H), 7.15 (d, 1H), 7.06 (d, 1H), 5.47 (s, 2H), 3.58 (d, 2H), 0.69 (m, 1H), 0.47-0.53 (m, 2H), 0.03-0.09 (m, 2H) | |

| Cpd # | STRUCTURE | IUPAC NAME | NMR | MS (m/z) |
|---|---|---|---|---|
| 472 | 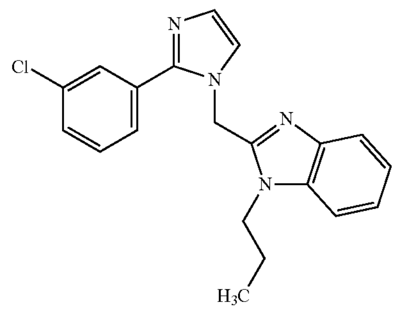 | 2-{[2-(3-chlorophenyl)-1H-imidazol-1-yl]methyl}-1-propyl-1H benzimidazole | 1H NMR (CDCl3): 7.79 (m, 1H), 7.69 (m, 1H), 7.44-7.58 (m, 3H), 7.27-7.30 (m, 3H), 7.14 (d, 1H), 7.07 (d, 1H), 5.49 (s, 2H), 3.69 (t, 2H), 1.42 (m, 2H), 0.75 (t, 3H) | |
| 473 | 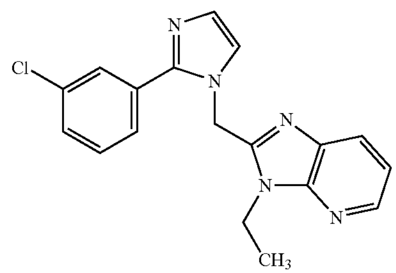 | 2-{[2-(3-chlorophenyl)-1H-imidazol-1-yl]methyl}-3-ethyl-3H-imidazo[4,5-b]pyridine | 1H NMR (CDCl3): 8.40 (dd, 1H), 8.06 (dd, 1H), 7.67 (m, 1H), 7.43-7.57 (m, 3H), 7.26 (m, 1H), 7.19 (d, 1H), 7.08 (d, 1H), 5.51 (s, 2H), 4.00 (q, 2H), 1.09 (t, 3H) | |
| 474 | 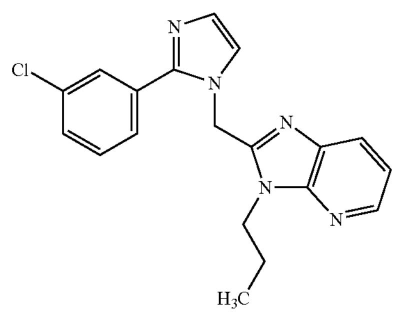 | 2-{[2-(3-chlorophenyl)-1H-imidazol-1-yl]methyl}-3-propyl-3H-imidazo[4,5-b]pyridine | 1H NMR (CDCl3): 8.40 (dd, 1H), 8.06 (dd, 1H), 7.68 (m, 1H), 7.43-7.56 (m, 3H), 7.26 (m, 1H), 7.18 (d, 1H), 7.09 (d, 1H), 5.50 (s, 2H), 3.89 (t, 2H), 1.52 (m, 2H), 0.79 (t, 3H) | |

TABLE 6-continued

| Cpd # | STRUCTURE | IUPAC NAME | NMR | MS (m/z) |
|---|---|---|---|---|
| 475 | 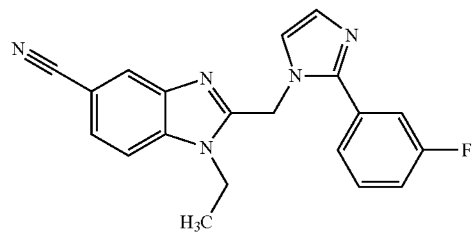 | 1-ethyl-2-{[2-(3-fluorophenyl)-1H-imidazol-1-yl]methyl}-1H-benzimidazole-5-carbonitrile | | 346.3 [M + 1]; 344.2 [M − 1] |
| 476 | 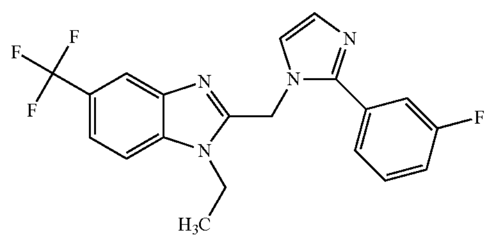 | 1-ethyl-2-{[2-(3-fluorophenyl)-1H-imidazol-1-yl]methyl}-5-(trifluoromethyl)-1H-benzimidazole | | 389.2 [M + 1] |
| 477 | 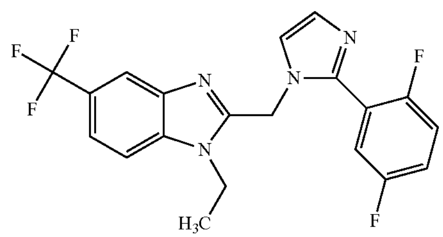 | 2-{[2-(2,5-difluorophenyl)-1H-imidazol-1-yl]methyl}-1-ethyl-5-(trifluoromethyl)-1H-benzimidazole | | 407.3 [M + 1] |
| 478 | 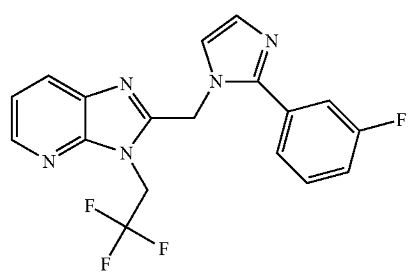 | 2-{[2-(3-fluorophenyl)-1H-imidazol-1-yl]methyl}-3-(2,2,2-trifluoroethyl)-3H-imidazo[4,5-b]pyridine | | 376.2 [M + 1] |

TABLE 6-continued

| Cpd # | STRUCTURE | IUPAC NAME | NMR | MS (m/z) |
|---|---|---|---|---|
| 479 | 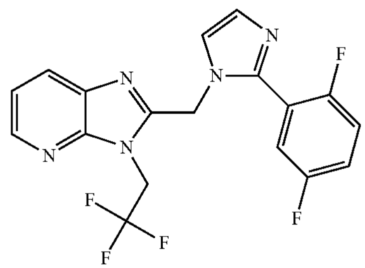 | 2-{[2-(2,5-trifluorophenyl)-1H-imidazol-1-yl]methyl}-3-(2,2,2-trifluoroethyl)-3H-imidazo[4,5-b]pyridine | | 394.2 [M + 1] |
| 480 | 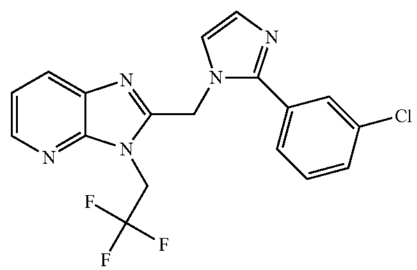 | 2-{[2-(3-chlorophenyl)-1H-imidazol-1-yl]methyl}-3-(2,2,2-trifluoroethyl)-3H-imidazo[4,5-b]pyridine | | 392.2 [M + 1] |
| 481 | 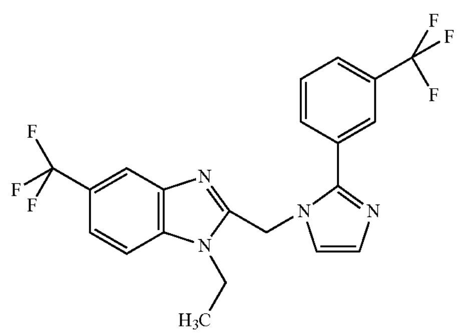 | 1-ethyl-5-(trifluoromethyl)-2-({2-[3-(trifluoromethyl)phenyl]-1H-imidazol-1-yl}methyl)-1H-benzimidazole | 1H NMR (CDCl3): 8.09 (d, 1H), 7.37-7.95 (m, 6H), 7.19 (d, 1H), 7.05 (d, 1H), 5.49 (s, 2H), 3.85 (q, 2H), 1.02 (t, 3H) | |

TABLE 6-continued

| Cpd # | STRUCTURE | IUPAC NAME | NMR | MS (m/z) |
|---|---|---|---|---|
| 482 | 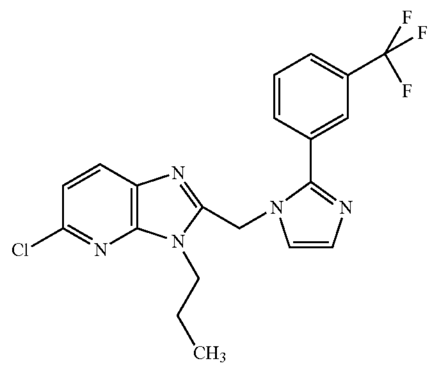 | 5-chloro-3-propyl-2-({2-[3-(trifluoromethyl)phenyl]-1H-imidazol-1-yl}methyl)-3H-imidazo[4,5-b]pyridine | 1H NMR (CDCl3): 7.60-7.97 (m, 5H), 7.22-7.27 (m, 2H), 7.09 (d, 1H), 5.45 (s, 2H), 3.85 (t, 2H), 1.51 (m, 2H), 0.76 (t, 3H) | |
| 483 | 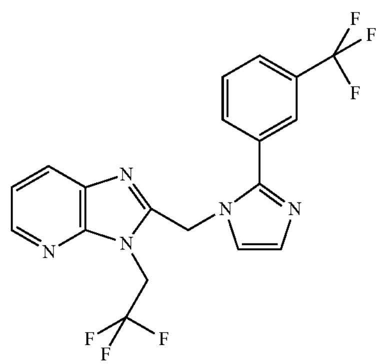 | 3-(2,2,2-trifluoroethyl)-2-({2-[3-(trifluoromethyl)phenyl]-1H-imidazol-1-yl}methyl)-3H-imidazo[4,5-b]pyridine | 1H NMR (CDCl3): 8.44 (dd, 1H), 8.07 (dd, 1H), 7.54-7.89 (m, 4H), 7.24-7.34 (m, 2H), 7.12 (d, 1H), 5.51 (s, 2H), 4.51 (q, 2H) | |

TABLE 6-continued

| Cpd # | STRUCTURE | IUPAC NAME | NMR | MS (m/z) |
|---|---|---|---|---|
| 484 | 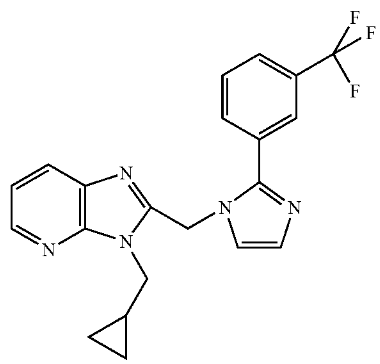 | 3-(cyclopropylmethyl)-2-({2-[3-(trifluoromethyl)phenyl]-1H-imidazol-1-yl}methyl)-3H-imidazo[4,5-b]pyridine | 1H NMR (CDCl3): 8.39 (dd, 1H), 7.60-8.03 (m, 5H), 7.21-7.26 (m, 2H), 7.11 (d, 1H), 5.51 (s, 2H), 3.84 (d, 2H), 0.70 (m, 1H), 0.44 (m, 2H), 0.24 (m, 2H) | |
| 485 | 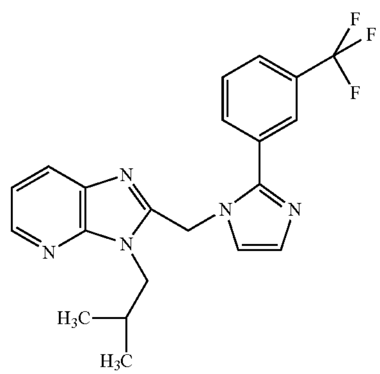 | 3-isobutyl-2-({2-[3-(trifluoromethyl)phenyl]-1H-imidazol-1-yl}methyl)-3H-imidazo[4,5-b]pyridine | 1H NMR (CDCl3): 8.39 (dd, 1H), 7.60-8.07 (m, 5H), 7.21-7.26 (m, 2H), 7.12 (d, 1H), 5.49 (s, 2H), 3.71 (d, 2H), 1.98 (m, 1H), 0.69 (d, 6H) | |

TABLE 6-continued
| Cpd # | STRUCTURE | IUPAC NAME | NMR | MS (m/z) |
|---|---|---|---|---|
| 486 | 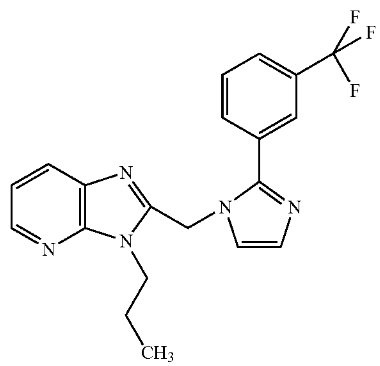 | 3-propyl-2-({2-[3-(trifluoromethyl)phenyl]-1H-imidazol-1-yl}methyl)-3H-imidazo[4,5-b]pyridine | 1H NMR (CDCl3): 8.40 (dd, 1H), 7.60-8.07 (m, 5H), 7.21-7.26 (m, 2H), 7.11 (d, 1H), 5.49 (s, 2H), 3.89 (t, 2H), 1.51 (m, 2H), 0.76 (t, 3H) | |
| 487 | 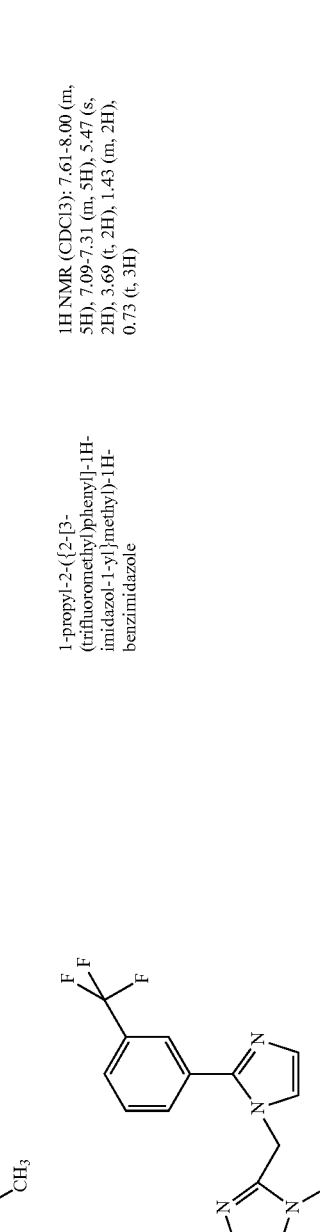 | 1-propyl-2-({2-[3-(trifluoromethyl)phenyl]-1H-imidazol-1-yl}methyl)-1H-benzimidazole | 1H NMR (CDCl3): 7.61-8.00 (m, 5H), 7.09-7.31 (m, 5H), 5.47 (s, 2H), 3.69 (t, 2H), 1.43 (m, 2H), 0.73 (t, 3H) | |

TABLE 6-continued

| Cpd # | STRUCTURE | IUPAC NAME | NMR | MS (m/z) |
|---|---|---|---|---|
| 488 | 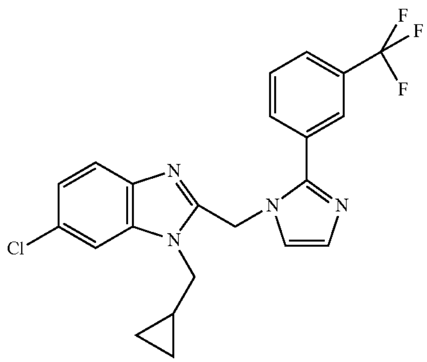 | 6-chloro-1-(cyclopropylmethyl)-2-({2-[3-(trifluoromethyl)phenyl]-1H-imidazol-1-yl}methyl)-1H-benzimidazole | 1H NMR (CDCl3): 7.60-7.96 (m, 5H), 7.05-7.31 (m, 4H), 5.45 (s, 2H), 3.58 (d, 2H), 0.65 (m, 1H), 0.47 (m, 2H), 0.05 (m, 2H) | |
| 489 | 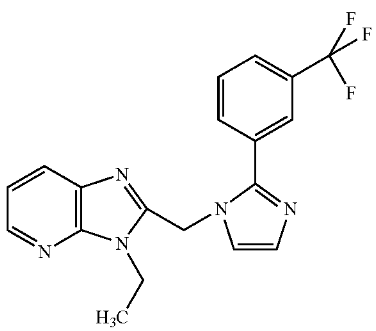 | 3-ethyl-2-({2-[3-(trifluoromethyl)phenyl]-1H-imidazol-1-yl}methyl)-3H-imidazo[4,5-b]pyridine | 1H NMR (CDCl3): 8.40 (dd, 1H), 7.60-8.06 (m 5H), 7.21-7.28 (m, 2H), 7.09 (d, 1H), 5.49 (s, 2H), 4.01 (q, 2H), 1.09 (t, 3H) | |
| 490 | 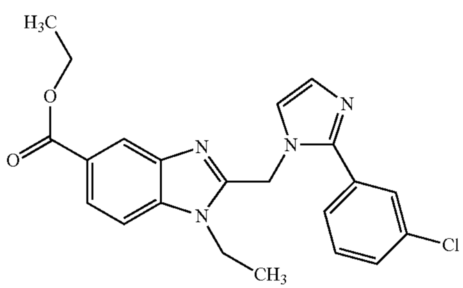 | ethyl 2-{[2-(3-chlorophenyl)-1H-imidazol-1-yl]methyl}-1-ethyl-1H-benzimidazole-5-carboxylate | | |

TABLE 6-continued

| Cpd # | STRUCTURE | IUPAC NAME | NMR | MS (m/z) |
|---|---|---|---|---|
| 491 | 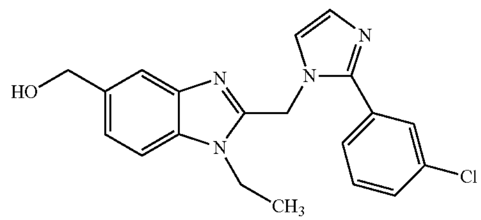 | (2-{[2-(3-chlorophenyl)-1H-imidazol-1-yl]methyl}-1-ethyl-1H-benzimidazol-5-yl)methanol | | |
| 492 | 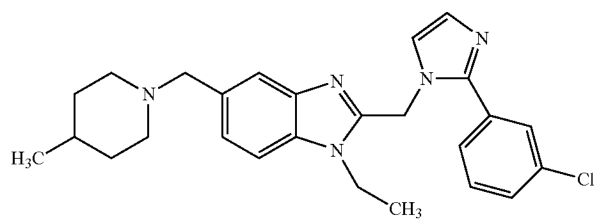 | 2-{[2-(3-chlorophenyl)-1H-imidazol-1-yl]methyl}-1-ethyl-5-[(4-methylpiperidin-1-yl)methyl]-1H-benzimidazole | | |
| 493 | 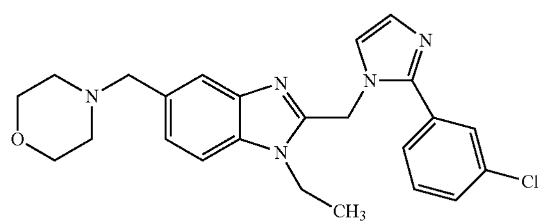 | 2-{[2-(3-chlorophenyl)-1H-imidazol-1-yl]methyl}-1-ethyl-5-(morpholin-4-ylmethyl)-1H-benzimidazole | | |
| 494 | 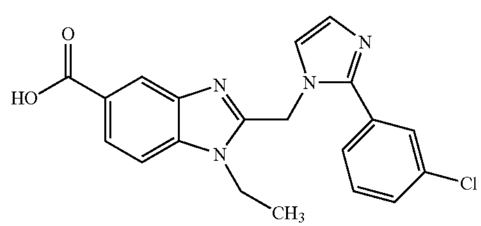 | 2-{[2-(3-chlorophenyl)-1H-imidazol-1-yl]methyl}-1-ethyl-1H-benzimidazole-5-carboxylic acid | | |

TABLE 6-continued

| Cpd # | STRUCTURE | IUPAC NAME | NMR | MS (m/z) |
|---|---|---|---|---|
| 495 | 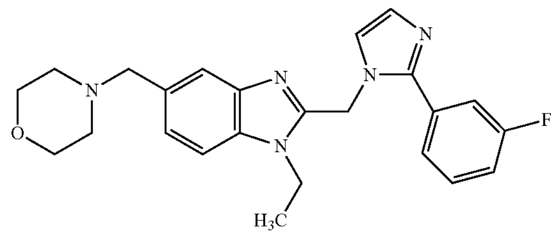 | 1-ethyl-2-{[2-(3-fluorophenyl)-1H-imidazol-1-yl]methyl}-5-(morpholin-4-ylmethyl)-1H-benzimidazole | | 420.4 [M + 1]; 418.2 [M − 1] |
| 496 | 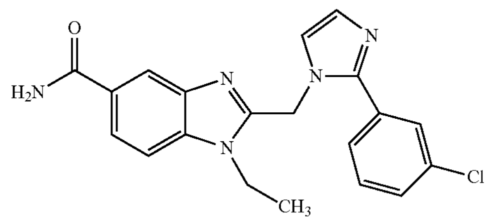 | 2-{[2-(3-chlorophenyl)-1H-imidazol-1-yl]methyl}-1-ethyl-1H-benzimidazole-5-carboxamide | | |
| 497 | 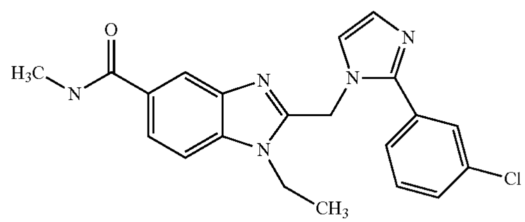 | 2-{[2-(3-chlorophenyl)-1H-imidazol-1-yl]methyl}-1-ethyl-N-methyl-1H-benzimidazole-5-carboxamide | | |
| 498 | 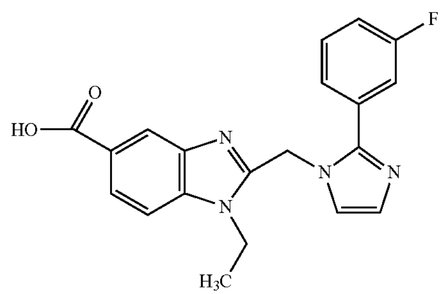 | 1-ethyl-2-{[2-(3-fluorophenyl)-1H-imidazol-1-yl]methyl}-1H-benzimidazole-5-carboxylic acid | | 365.1 [M + 1] |

TABLE 6-continued

| Cpd # | STRUCTURE | IUPAC NAME | NMR | MS (m/z) |
|---|---|---|---|---|
| 499 | 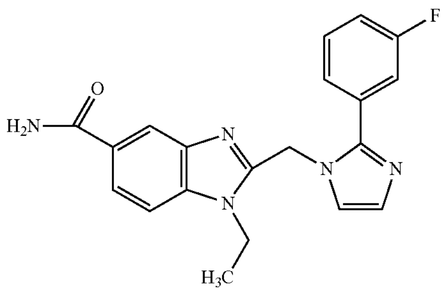 | 1-ethyl-2-{[2-(3-fluorophenyl)-1H-imidazol-1-yl]methyl}-1H-benzimidazole-5-carboxamide | | |
| 500 | 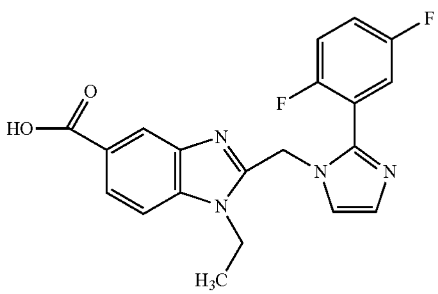 | 2-{[2-(2,5-difluorophenyl)-1H-imidazol-1-yl]methyl}-1-ethyl-1H-benzimidazole-5-carboxylic acid | | 383.2 [M + 1] |
| 501 | 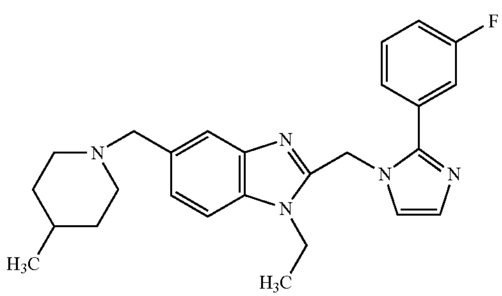 | 1-ethyl-2-{[2-(3-fluorophenyl)-1H-imidazol-1-yl]methyl}-5-[(4-methylpiperidin-1-yl)methyl]-1H-benzimidazole | | 432.4 [M + 1] |

TABLE 6-continued

| Cpd # | STRUCTURE | IUPAC NAME | NMR | MS (m/z) |
|---|---|---|---|---|
| 502 | 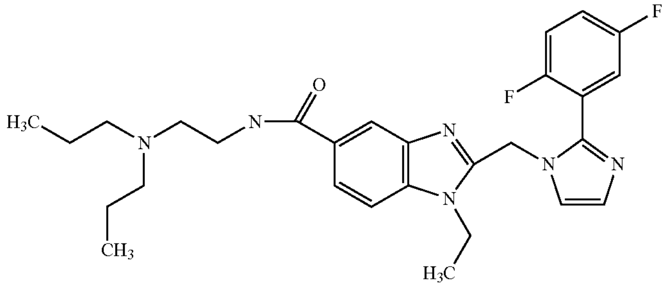 | 2-{[2-(2,5-difluorophenyl)-1H-imidazol-1-yl]methyl}-N-[2-(dipropylamino)ethyl]-1-ethyl-1H-benzimidazole-5-carboxamide | | 509.5 [M + 1] |
| 503 | 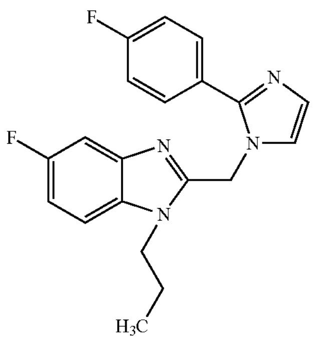 | 5-fluoro-2-{[2-(4-fluorophenyl)-1H-imidazol-1-yl]methyl}-1-propyl-1H-benzimidazole | 1H NMR (CDCl3): 7.65-7.71 (m, 2H), 7.47 (d, 1H), 7.03-7.23 (m, 6H), 5.47 (s, 2H), 3.65 (t, 2H), 1.41 (h, 2H), 0.71 (t, 3H) | |
| 504 | 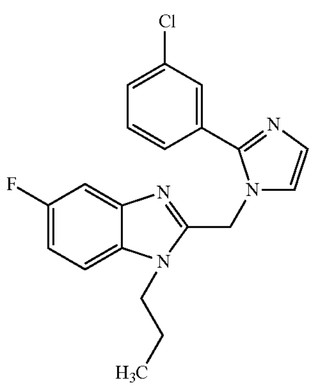 | 2-{[2-(3-chlorophenyl)-1H-imidazol-1-yl]methyl}-5-fluoro-1-propyl-1H-benzimidazole | 1H NMR (CDCl3): 7.65 (s, 1H), 7.41-7.53 (m, 3H), 7.06-7.24 (m, 5H), 5.47 (s, 2H), 3.65 (t, 2H), 1.47 (h, 2H), 0.71 (t, 3H) | |

TABLE 6-continued

| Cpd # | STRUCTURE | IUPAC NAME | NMR | MS (m/z) |
|---|---|---|---|---|
| 505 | 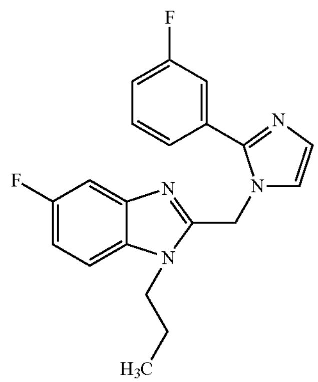 | 5-fluoro-2-{[2-(3-fluorophenyl)-1H-imidazol-1-yl]methyl}-1-propyl-1H-benzimidazole | 1H NMR (CDCl3): 7.35-7.47 (m, 4H), 7.0-7.1 (m, 5H), 5.47 (s, 2H), 3.65 (t, 2H), 1.35 (h, 2H), 0.71 (t, 3H) | |
| 506 | 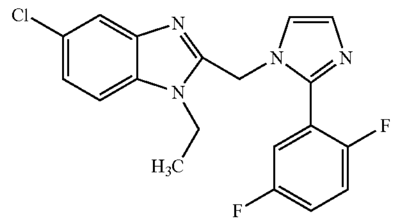 | 5-chloro-2-{[2-(2,5-difluorophenyl)-1H-imidazol-1-yl]methyl}-1-ethyl-1H-benzimidazole | 1H NMR (CDCl3): 7.75 (d, 1H), 7.37 (m, 1H), 7.20-7.27 (m, 5H), 7.02 (d, 1H), 5.36 (s, 2H), [0.99 T, 3H], 3.82 (q, 2H) | |
| 507 | 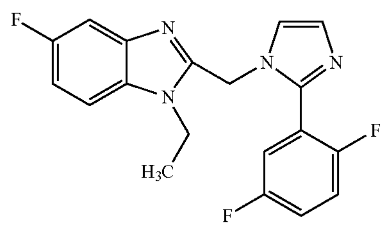 | 2-{[2-(2,5-difluorophenyl)-1H-imidazol-1-yl]methyl}-1-ethyl-5-fluoro-1H-benzimidazole | 1H NMR (CDCl3): 7.43 (m, 1H), 7.37 (m, 1H), 7.19-7.25 (m, 4H), 7.03-7.10 (m, 2H), 5.35 (s, 2H), 3.82 (q, 2H), 1.00 (t, 3H) | |

TABLE 6-continued

| Cpd # | STRUCTURE | IUPAC NAME | NMR | MS (m/z) |
|---|---|---|---|---|
| 508 | 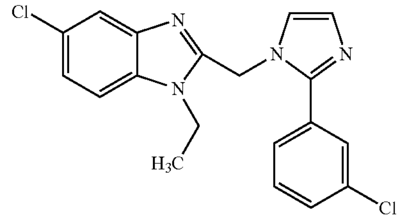 | 5-chloro-2-{[2-(3-chlorophenyl)-1H-imidazol-1-yl]methyl}-1-ethyl-1H-benzimidazole | (L)-Tartrate salt 1H NMR (CD3OD): 7.24-7.59 (m, 9H), 5.66 (s, 2H), 4.51 (s, 2H), 4.12 (q, 2H), 1.28 (t, 3H) | |
| 509 | 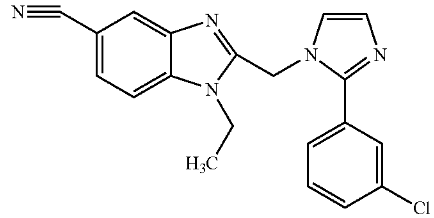 | 2-{[2-(3-chlorophenyl)-1H-imidazol-1-yl]methyl}-1-ethyl-1H-benzimidazole-5-carbonitrile | 8.00 (s, 1H), 7.38-7.72 (m, 7H), 7.24 (s, 1H), 5.71 (s, 2H), 4.50 (s, 2H), 4.20 (q, 2H), 1.22 (t, 3H) | |
| 510 | 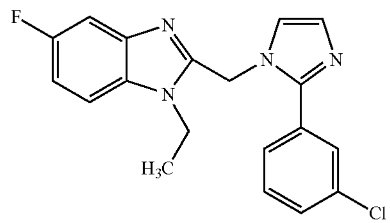 | 2-{[2-(3-chlorophenyl)-1H-imidazol-1-yl]methyl}-1-ethyl-5-fluoro-1H-benzimidazole | (L)-Tartrate salt 1H NMR (CD3OD): 7.08-7.60 (m, 9H), 5.66 (s, 2H), 4.51 (s, 2H), 4.12 (s, 2H), 1.18 (t, 3H) | |
| 511 | 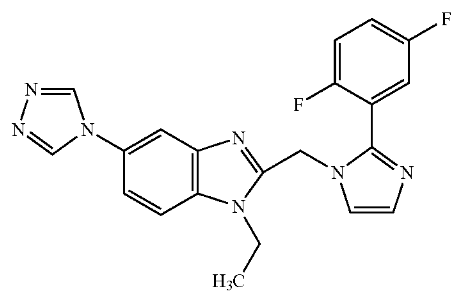 | 2-{[2-(2,5-difluorophenyl)-1H-imidazol-1-yl]methyl}-1-ethyl-5-(4H-1,2,4-triazol-4-yl)-1H-benzimidazole | Hydrochloride 1H NMR (d6 DMSO): 9.57 (2H, s), 8.11 (1H, m), 8.01-7.99 (1H, m), 7.86 (1H, d), 7.78-7.74 (1H, m), 7.66-7.52 (3H, m), 5.95 (2H, s), 4.31 (2H, q), 1.26 (3H, t) | 406.5 [M + 1] |

TABLE 6-continued

| Cpd # | STRUCTURE | IUPAC NAME | NMR | MS (m/z) |
|---|---|---|---|---|
| 512 | 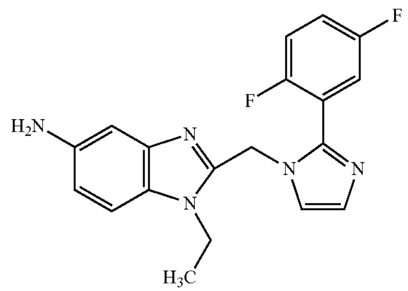 | 2-{[2-(2,5-difluorophenyl)-1H-imidazol-1-yl]methyl}-1-ethyl-1H-benzimidazol-5-amine | | 354.4 [M + 1] |
| 513 | 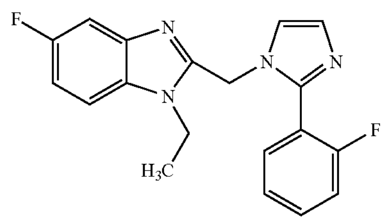 | 1-ethyl-5-fluoro-2-{[2-(2-fluorophenyl)-1H-imidazol-1-yl]methyl}-1H-benzimidazole | (L)-Tartrate salt 1H NMR (CD3OD): 7.07-7.58 (m, 9H), 5.53 (s, 2H), 4.51 (s, 2H), 4.03 (q, 2H), 1.07 (t, 3H) | |
| 514 | 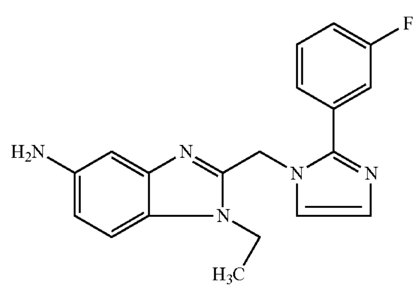 | 1-ethyl-2-{[2-(3-fluorophenyl)-1H-imidazol-1-yl]methyl}-1H-benzimidazol-5-amine | 1H NMR (CDCl3): 7.38-7.5 (m, 4h), 7.15 (t, 3H), 7.1 (s, 1H), 7.05 (t, 2H), 6.7 (d, 1H), 5.4 (s, 2H), 3.70 (q, 2H), 0.9 (t, 3H) | |

TABLE 6-continued

| Cpd # | STRUCTURE | IUPAC NAME | NMR | MS (m/z) |
|---|---|---|---|---|
| 515 | 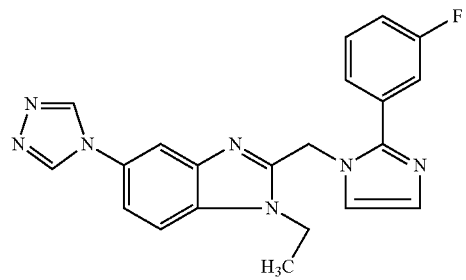 | 1-ethyl-2-{[2-(3-fluorophenyl)-1H-imidazol-1-yl]methyl}-5-(4H-1,2,4-triazol-4-yl)-1H-benzimidazole | | 388.2 [M + 1] |
| 516 | 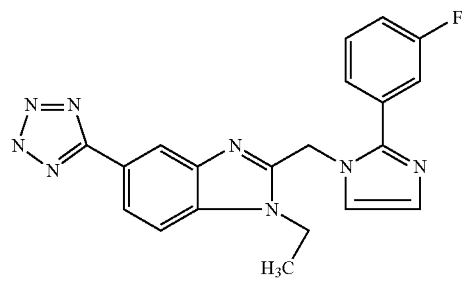 | 1-ethyl-2-{[2-(3-fluorophenyl)-1H-imidazol-1-yl]methyl}-5-(2H-tetraazol-5-yl)-1H-benzimidazole | | 389.2 [M + 1] |
| 517 | 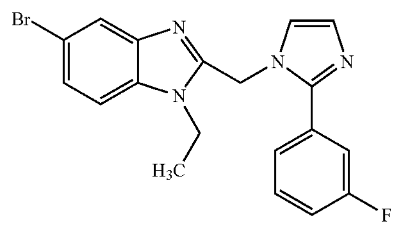 | 5-bromo-1-ethyl-2-{[2-(3-fluorophenyl)-1H-imidazol-1-yl]methyl}-1H-benzimidazole | 1H NMR (CDCl3): 7.93 (d, 1H), 7.39-7.52 (m, 4H), 7.15-7.22 (m, 3H), 7.025 (d, 1H), 5.49 (s, 2H), 3.76 (q, 2H), 0.97 (t, 3H) | |
| 518 | 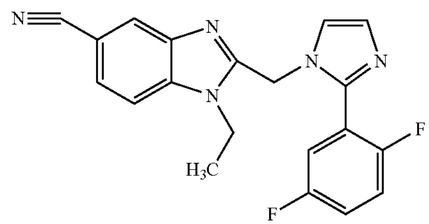 | 2-{[2-(2,5-difluorophenyl)-1H-imidazol-1-yl]methyl}-1-ethyl-1H-benzimidazole-5-carbonitrile | 1H NMR (CDCl3): 8.09 (d, 1H), 7.56 (m, 1H), 7.33-7.40 (m, 2H), 7.16-7.24 (m, 3H), 7.04 (d, 1H), 5.41 (s, 2H), 3.89 (q, 2H), 1.03 (t, 3H) | |

TABLE 6-continued

| Cpd # | STRUCTURE | IUPAC NAME | NMR | MS (m/z) |
|---|---|---|---|---|
| 519 | 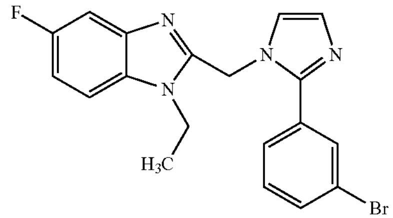 | 2-{[2-(3-bromophenyl)-1H-imidazol-1-yl]methyl}-1-ethyl-5-fluoro-1H-benzimidazole | Hydrochloride 1H NMR (d6-DMSO): 7.41-8.00 (m, 8H), 7.18 (m, 1H), 5.92 (s, 2H), 4.28 (q, 2H), 1.27 (t, 3H) | |
| 520 | 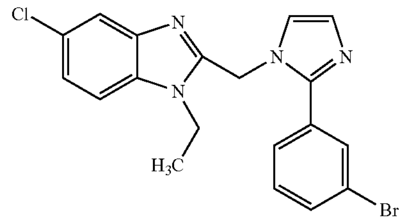 | 2-{[2-(3-bromophenyl)-1H-imidazol-1-yl]methyl}-5-chloro-1-ethyl-1H-benzimidazole | Hydrochloride 1H NMR (d6-DMSO): 7.32-8.00 (m, 9H), 5.95 (s, 2H), 4.29 (q, 2H), 1.27 (t, 3H) | |
| 521 | 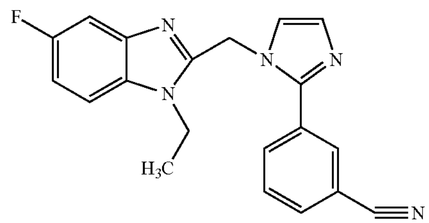 | 3-{1-[(1-ethyl-5-fluoro-1H-benzimidazol-2-yl)methyl]-1H-imidazol-2-yl}benzonitrile | | 346.11 [M + 1] |
| 522 | 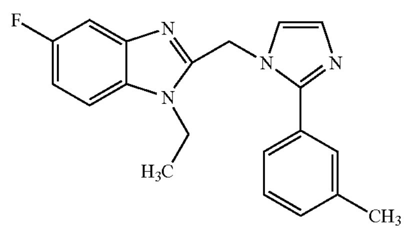 | 1-ethyl-5-fluoro-2-{[2-(3-methylphenyl)-1H-imidazol-1-yl]methyl}-1H-benzimidazole | | |

TABLE 6-continued

| Cpd # | STRUCTURE | IUPAC NAME | NMR | MS (m/z) |
|---|---|---|---|---|
| 523 | (structure) | 1-ethyl-5-fluoro-2-{[2-(3-methoxyphenyl)-1H-imidazol-1-yl]methyl}-1H-benzimidazole | | 351.15 [M + 1] |
| 524 | (structure) | 4-{1-[(1-ethyl-5-fluoro-1H-benzimidazol-2-yl)methyl]-1H-imidazol-2-yl}-fluorophenol | | 355.12 [M + 1] |
| 525 | (structure) | 2-{[2-(3-bromophenyl)-1H-imidazol-1-yl]methyl}-1-ethyl-1H-benzimidazole-5-carbonitrile | 1H NMR (CDCl3): 8.11 (d, 1H), 7.81 (s, 1H), 7.55-7.67 (m, 3H), 7.35-7.41 (m, 2H), 7.19 (m, 1H), 7.04 (d, 1H), 5.51 (s, 2H), 3.84 (q, 2H), 1.04 (t, 3H) | |
| 526 | (structure) | 2-{[2-(3-fluorophenyl)-1H-imidazol-1-yl]methyl}-1-propyl-1H-benzimidazole-5-carbonitrile | | 360.2 [M + 1]; 358.2 [M − 1] |

TABLE 6-continued

| Cpd # | STRUCTURE | IUPAC NAME | NMR | MS (m/z) |
|---|---|---|---|---|
| 527 | 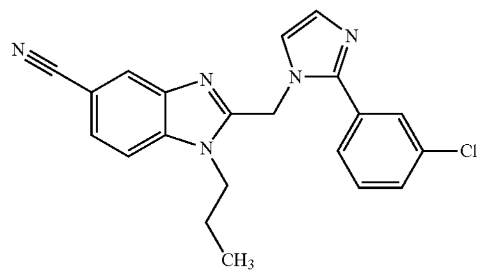 | 2-{[2-(3-chlorophenyl)-1H-imidazol-1-yl]methyl}-1-propyl-1H-benzimidazole-5-carbonitrile | | 376.2 [M + 1]; 374.2 [M − 1] |
| 528 | 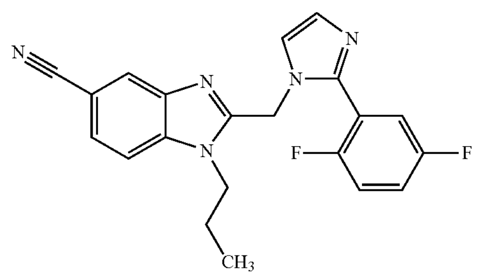 | 2-{[2-(2,5-difluorophenyl)-1H-imidazol-1-yl]methyl}-1-propyl-1H-benzimidazole-8-carbonitrile | | 378.2 [M + 1] |
| 529 | 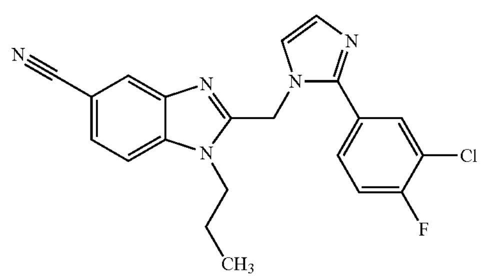 | 2-{[2-(3-chloro-4-fluorophenyl)-1H-imidazol-1-yl]methyl}-1-propyl-1H-benzimidazole-5-carbonitrile | | 394.4 [M + 1]; 392.1 [M − 1] |

TABLE 6-continued

| Cpd # | STRUCTURE | IUPAC NAME | NMR | MS (m/z) |
|---|---|---|---|---|
| 530 | 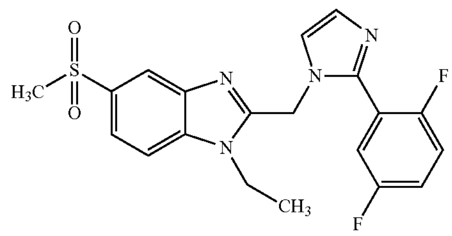 | 2-{[2-(2,5-difluorophenyl)-1H-imidazol-1-yl]methyl}-1-ethyl-5-(methylsulfonyl)-1H-benzimidazole | | |
| 531 | 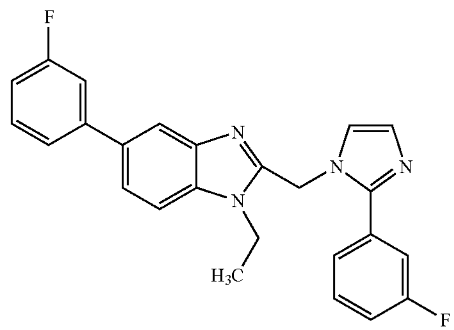 | 1-ethyl-5-(3-fluorophenyl)-2-{[2-(3-fluorophenyl)-1H-imidazol-1-yl]methyl}-1H-benzimidazole | 1H NMR (CDCl3): 7.98 (m, 1H), 7.27-7.54 (m, 8H), 7.16-7.22 (m, 2H), 7.01-7.07 (m, 2H), 5.53 (s, 2H), 3.82 (q, 2H), 1.02 (t, 3H) | |
| 532 | 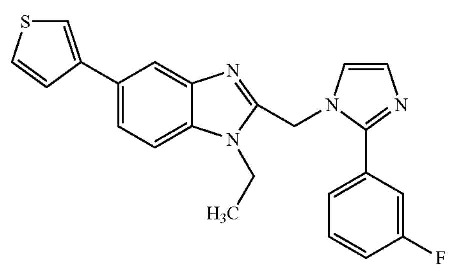 | 1-ethyl-2-{[2-(3-fluorophenyl)-1H-imidazol-1-yl]methyl}-5-thien-3-yl-1H-benzimidazole | 1H NMR (CDCl3): 8.0 (m, 1H), 7.16-7.59 (m, 10H), 7.07 (d, 1H), 5.52 (s, 2H), 3.81 (q, 2H), 1.01 (t, 3H) | |

TABLE 6-continued

| Cpd # | STRUCTURE | IUPAC NAME | NMR | MS (m/z) |
|---|---|---|---|---|
| 533 | 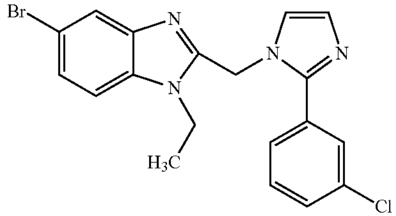 | 5-bromo-2-{[2-(3-chlorophenyl)-1H-imidazol-1-yl]methyl}-1-ethyl-1H-benzimidazole | 1H NMR (CDCl3): 7.93 (d, 1H), 7.68 (m, 1H), 7.40-7.57 (m, 2H), 7.15-7.19 (m, 2H), 7.03 (d, 1H), 5.48 (s, 2H), 3.77 (q, 2H), 0.98 (t, 3H) | |
| 534 | 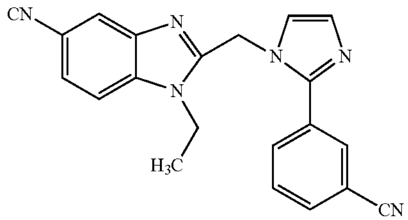 | 2-{[2-(3-cyanophenyl)-1H-imidazol-1-yl]methyl}-1-ethyl-1H-benzimidazole-5-carbonitrile | | 353.15 [M + 1] |
| 535 | 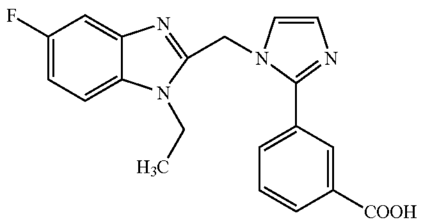 | 3-{1-[(1-ethyl-5-fluoro-1H-benzimidazol-2-yl)methyl]-1H-imidazol-2-yl}benzoic acid | | 364.10 [M + 1] |
| 536 | 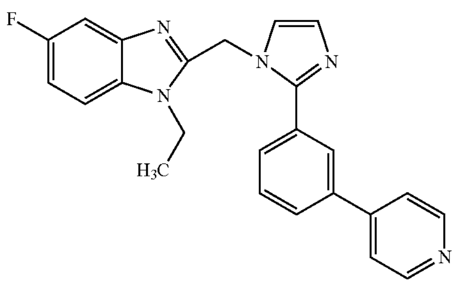 | 1-ethyl-5-fluoro-2-{[2-(3-pyridin-4-yl)phenyl)-1H-imidazol-1-yl]methyl})-1H-benzimidazole | | 398.18 [M + 1] |

TABLE 6-continued

| Cpd # | STRUCTURE | IUPAC NAME | NMR | MS (m/z) |
|---|---|---|---|---|
| 537 | 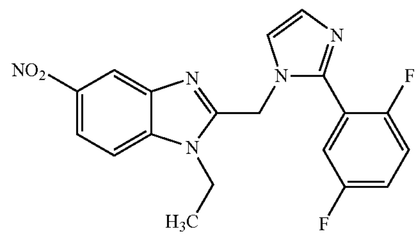 | 2-{[2-(2,5-difluorophenyl)-1H-imidazol-1-yl]methyl}-1-ethyl-5-nitro-1H-benzimidazole | Hydrochloride 1H NMR (d6 DMSO): 8.42 (1H, d), 8.17 (1H, dd), 8.00 (1H, s), 7.90 (1H, s), 7.85 (1H, d), 7.70 (1H, m), 7.56-7.51 (2H, m), 5.90 (2H, s), 4.31 (2H, q), 1.24 (3H, t) | 384.1 [M + 1] |
| 538 | 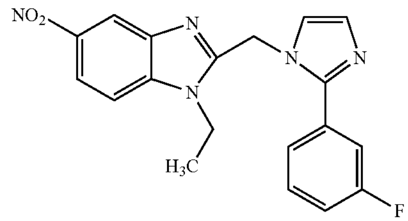 | 1-ethyl-2-{[2-(3-fluorophenyl)-1H-imidazol-1-yl]methyl}-5-nitro-1H-benzimidazole | 1H NMR (dO DMSO): 8.47 (1H, d), 8.19 (1H, dd), 8.00 (1H, m), 7.96 (1H, m), 7.88 (1H, d), 7.71-7.50 (4H, m), 5.98 (2H, s), 4.35 (2H, q), 1.30 (3H, t) | 366.2 [M + 1] |
| 539 | 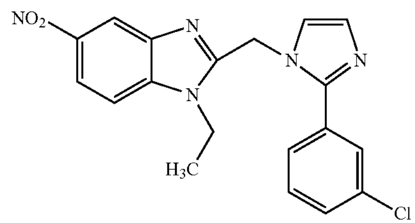 | 2-{[2-(3-chlorophenyl)-1H-imidazol-1-yl]methyl}-1-ethyl-5-nitro-1H-benzimidazole | | 381.95 [M + 1] |
| 540 | 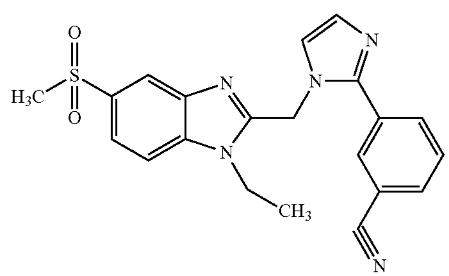 | 3-(1-{[1-ethyl-5-(methylsulfonyl)-1H-benzimidazol-2-yl]methyl}-1H-imidazol-2-yl)benzonitrile | | 406.3 [M + 1]; 404.3 [M − 1] |

TABLE 6-continued

| Cpd # | STRUCTURE | IUPAC NAME | NMR | MS (m/z) |
|---|---|---|---|---|
| 541 | 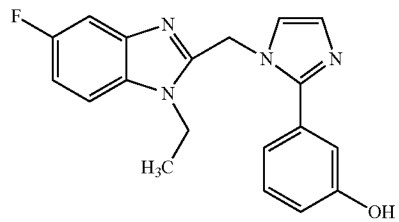 | 3-{1-[(1-ethyl-5-fluoro-1H-benzimidazol-2-yl)methyl]-1H-imidazol-2-yl}phenol | | 337.01 [M + 1] |
| 542 | 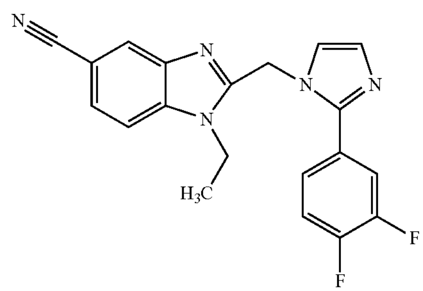 | 2-{[2-(3,4-difluorophenyl)-1H-imidazol-1-yl]methyl}-1-ethyl-1H-benzimidazole-5-carbonitrile | | 379.11 [M + 1] |
| 543 | 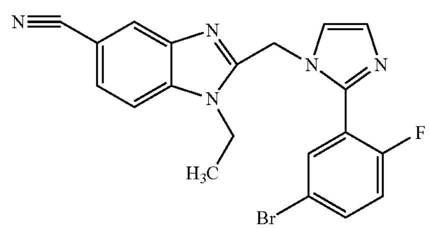 | 2-{[2-(5-bromo-2-fluorophenyl)-1H-imidazol-1-yl]methyl}-1-ethyl-1H-benzimidazole-5-carbonitrile | | 425.98 [M + 1] |
| 544 | 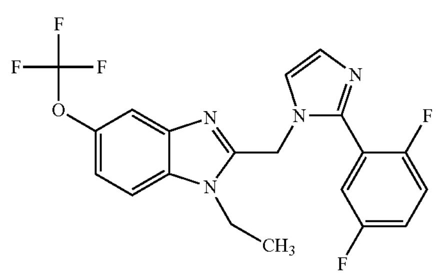 | 2-{[2-(2,5-difluorophenyl)-1H-imidazol-1-yl]methyl}-1-ethyl-5-(trifluoromethoxy)-1H-benzimidazole | 1H NMR (CDCl3): 7.65 (s, 1H), 7.18-7.41 (m, 6H), 7.06 (s, 1H), 5.35 (s, 2H), 3.82 (q, 2H), 1.0 (t, 3H) | |

TABLE 6-continued

| Cpd # | STRUCTURE | IUPAC NAME | NMR | MS (m/z) |
|---|---|---|---|---|
| 545 | 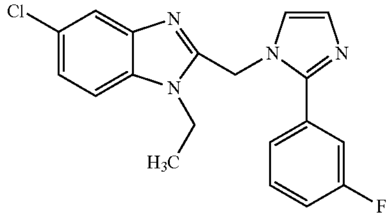 | 5-chloro-1-ethyl-2-{[2-(3-fluorophenyl)-1H-imidazol-1-yl]methyl}-1H-benzimidazole | 1H NMR (CDCl3): 7.22-7.60 (m, 9H), 5.67 (s, 2H), 4.49 (s, 2H), 4.11 (q, 2H), 1.16 (t, 3H) | |
| 546 | 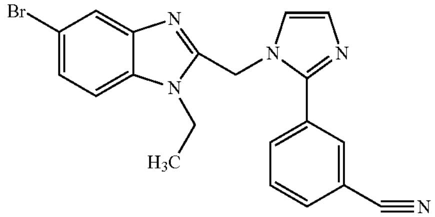 | 3-{1-[(5-bromo-1-ethyl-1H-benzimidazol-2-yl)methyl]-1H-imidazol-2-yl}benzonitrile | Hydrochloride 1H NMR (CD3OD): 7.71-8.25 (m, 9H), 6.18 (s, 2H), 4.50 (br s, 2H), 1.50 (br s, 3H) | |
| 547 | 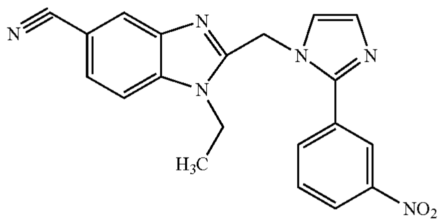 | 1-ethyl-2-{[2-(3-nitrophenyl)-1H-imidazol-1-yl]methyl}-1H-benzimidazole-5-carbonitrile | | 373.15 [M + 1] |
| 548 | 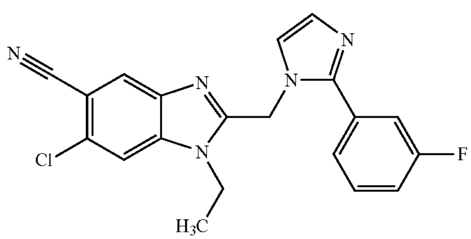 | 6-chloro-1-ethyl-2-{[2-(3-fluorophenyl)-1H-imidazol-1-yl]methyl}-1H-benzimidazol-5-carbonitrile | | 380.4 [M + 1]; 378.2 [M − 1] |

TABLE 6-continued

| Cpd # | STRUCTURE | IUPAC NAME | NMR | MS (m/z) |
|---|---|---|---|---|
| 549 | 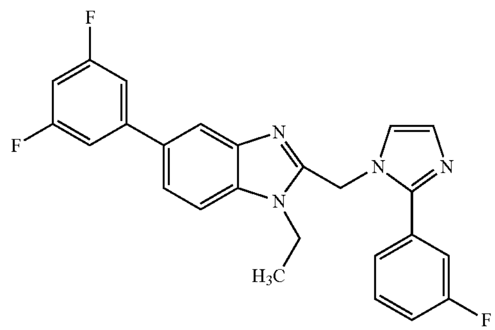 | 5-(3,5-difluoropheny)-1-ethyl-2-{[2-(3-fluorophenyl)-1H-imidazol-1-yl]methyl}-1H-benzimidazole | 1H NMR (CDCl3): 7.96 (d, 1H), 7.35-7.70 (m, 6H), 7.06-7.23 (m, 4H), 6.78 (m, 1H), 5.52 (s, 2H), 3.81 (q, 2H), 1.00 (t, 3H) | |
| 550 | 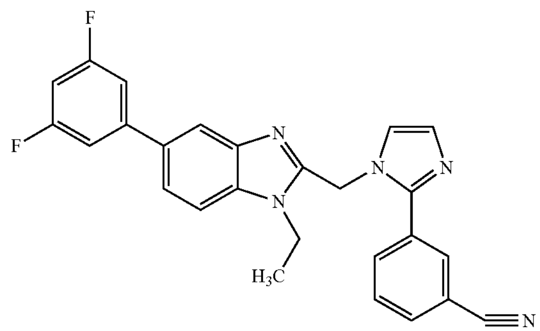 | 3-(1-{[5-(3,5-difluorophenyl)-1-ethyl-1H-benzimidazol-2-yl]methyl}-1H-imidazol-2-yl)benzonitrile | 1H NMR (CDCl3): 7.93-8.02 (m, 2H), 7.37-7.77 (m, 6H), 7.08-7.19 (m, 3H), 6.77 (m, 1H), 5.49 (s, 2H), 3.89 (q, 2H), 1.10 (t, 3H) | |
| 551 | 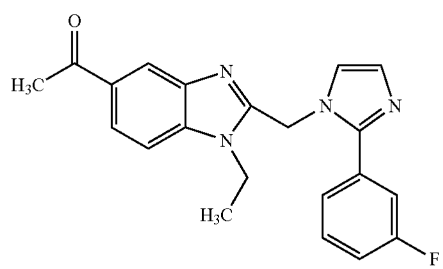 | 1-(1-ethyl-2-{[2-(3-fluorophenyl)-1H-imidazol-1-yl]methyl}-1H-benzimidazol-5-yl)ethanone | 1H NMR (CDCl3): 8.40 (s, 1H), 8.00 (dd, 1H), 7.33-7.53 (m, 4H), 7.17-7.22 (m, 2H), 7.05 (d, 1H), 5.53 (s, 2H), 3.82 (q, 2H), 2.67 (s, 3H), 1.01 (t, 3H) | |

TABLE 6-continued

| Cpd # | STRUCTURE | IUPAC NAME | NMR | MS (m/z) |
|---|---|---|---|---|
| 552 | 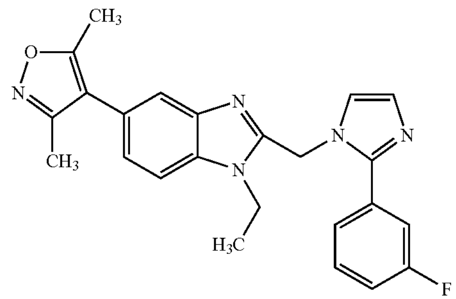 | 5-(3,5-dimethylisoxazol-4-yl)-1-ethyl-2-{[2-(3-fluorophenyl)-1H-imidazol-1-yl]methyl}-1H-benzimidazole | 1H NMR (CDCl3): 7.66 (d, 1H), 7.34-7.54 (m, 4H), 7.15-7.22 (m, 3H), 7.05 (d, 1H), 5.52 (s, 2H), 3.83 (q, 2H), 2.41 (s, 3H), 2.28 (s, 3H), 1.02 (s, 3H) | |
| 553 | 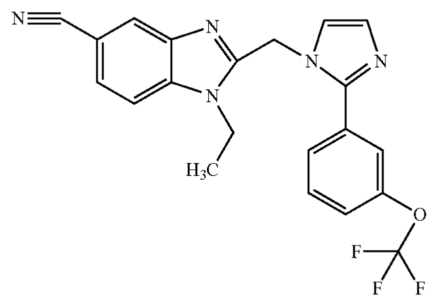 | 1-ethyl-2-({2-[3-(trifluoromethoxy)phenyl]-1H-imidazol-1-yl}methyl)-1H-benzimidazole-5-carbonitrile | | 411.96 [M + 1] |
| 554 | 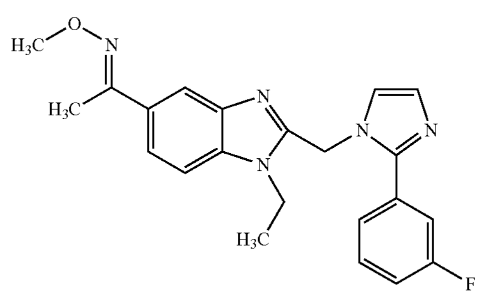 | (1E)-1-(1-ethyl-2-{[2-(3-fluorophenyl)-1H-imidazol-1-yl]methyl}-1H-benzimidazol-5-yl)ethanone O-methyloxime | Syn and anti 1H NMR (CDCl3): 7.98 (d, 1H), 7.94 (d, 1H1), 7.75 (dd, 1H + H1), 7.14-7.22 (m, 2H + H1), 7.32-7.52 (m, 4H + H1), [7.03 (d, 1H), 7.01 (d, 1H1)], 5.49 (s, 2H), [4.00 (s, 2H), 3.86 (s, 2H1)], 3.79 (q, 2H + H1), [2.30 (s, 3H), 2.26 (s, 3H1)], 0.98 (t, 3H + H1) | |

TABLE 6-continued

| Cpd # | STRUCTURE | IUPAC NAME | NMR | MS (m/z) |
|---|---|---|---|---|
| 555 | 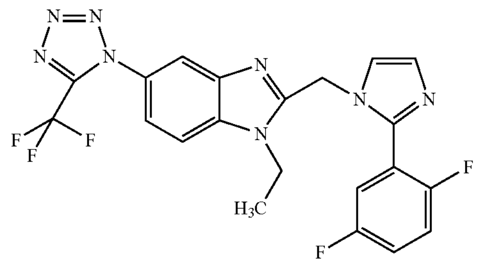 | 2-{[2-(2,5-difluorophenyl)-1H-imidazol-1-yl]methyl}-1-ethyl-5-[5-(trifluoromethyl)-1H-tetraazol-1-yl]-1H-benzimidazole | | 475.1 [M + 1] |
| 556 | 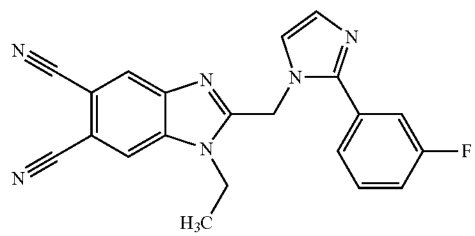 | 1-ethyl-2-{[2-(3-fluorophenyl)-1H-imidazol-1-yl]methyl}-1H-benzimidazole-5,6-dicarbonitrile | | 371.0 [M + 1] |
| 557 | 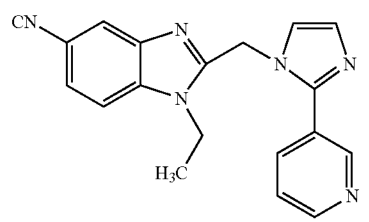 | 1-ethyl-2-{[2-(pyridin-3-yl-1H-imidazol-1-yl]methyl}-1H-benzimidazole-5-carbonitrile | Dihydrochloride 1H NMR (d6 DMSO): 8.96 (1H, s), 8.82 (1H, d), 8.24 (1H, d), 8.14 (1H, s), 8.05 (1H, d), 7.98 (1H, d), 7.85 (1H, d), 7.69-7.65 (2H, m), 6.01 (2H, s), 4.33 (2H, q), 1.29 (3H, t) | |
| 558 | 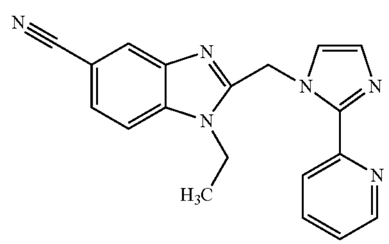 | 1-ethyl-2-{[2-(pyridin-2-yl-1H-imidazol-1-yl]methyl}-1H-benzimidazole-5-carbonitrile | Dihydrochloride 1H NMR (d6 DMSO): 8.55 (1H, d), 8.41 (1H, d), 8.10-7.98 (4H, m), 7.85 (1H, d), 7.64 (1H, d), 7.54-7.51 (1H, m), 6.39 (2H, s), 4.45 (2H, q), 1.41 (3H, t) | 329.4 [M + 1] |

TABLE 6-continued

| Cpd # | STRUCTURE | IUPAC NAME | NMR | MS (m/z) |
|---|---|---|---|---|
| 559 | 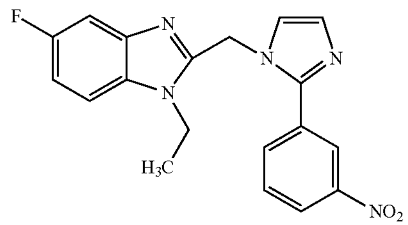 | 1-ethyl-5-fluoro-2-{[2-(3-nitrophenyl)-1H-imidazol-1-yl]methyl}-1H-benzimidazole | | 365.99 [M + 1] |
| 560 | 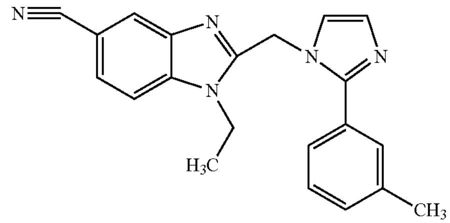 | 1-ethyl-2-{[2-(3-methylphenyl)-1H-imidazol-1-yl]methyl}-1H-benzimidazole-5-carbonitrile | | 343.06 [M + 1] |
| 561 | 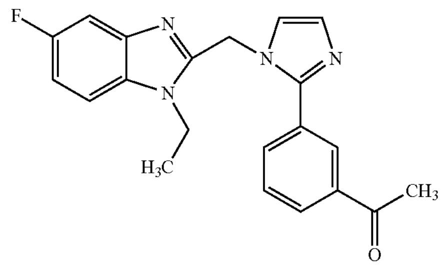 | 1-(3-{1-[(1-ethyl-5-fluoro-1H-benzimidazol-2-yl)methyl]-1H-imidazol-2-yl}phenyl)ethanone | | 363.05 [M + 1] |
| 562 | 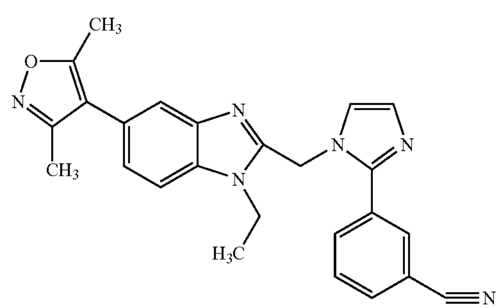 | 3-(1-{[5-(3,5-dimethylisoxazol-4-yl)-1-ethyl-1H-benzimidazol-2-yl]methyl}-1H-imidazol-2-yl)benzonitrile | 1H NMR (CDCl3): 7.94-8.01 (m, 2H), 7.75 (m, 1H), 7.61-7.66 (m, 2H), 7.38 (dd, 1H), 7.18-7.22 (m, 2H), 7.10 (d, 1H), 5.49 (s, 2H), 3.90 (q, 2H), 2.42 (s, 3H), 2.29 (s, 3H), 1.12 (t, 3H) | |

TABLE 6-continued

| Cpd # | STRUCTURE | IUPAC NAME | NMR | MS (m/z) |
|---|---|---|---|---|
| 563 | 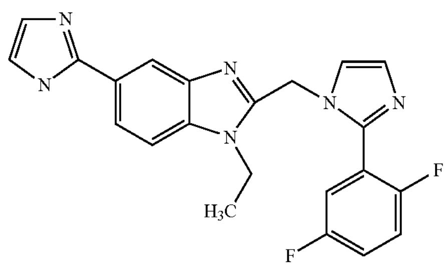 | 2-{[2-(2,5-difluorophenyl)-1H-imidazol-1-yl]methyl}-1-ethyl-5-(1H-imidazol-2-yl)-1H-benzimidazole | . Dihydrochloride 1H NMR (d6 DMSO): 8.43 (1H, s), 8.13-8.11 (2H, m), 7.99 (1H, d), 7.89 (1H, d), 7.79-7.75 (3H, m), 7.60-7.51 (3H, m), 5.95 (2H, s), 4.31 (2H, q), 1.26 (3H, t) | 405.3 [M + 1] |
| 564 | 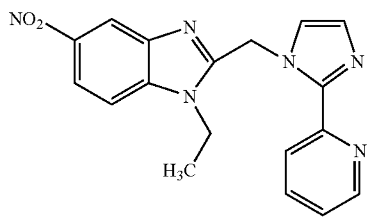 | 1-ethyl-5-nitro-2-[(2-pyridin-2-yl-1H-imidazol-1-yl)methyl]-1H-benzimidazole | | 349.1 [M + 1] |
| 565 | 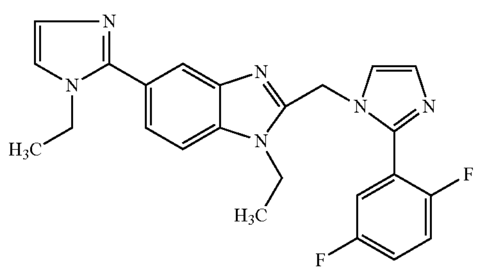 | 2-{[2-(2,5-difluorophenyl)-1H-imidazol-1-yl]methyl}-1-ethyl-5-(1-ethyl-1H-imidazol-2-yl)-1H-benzimidazole | | 433.2 [M + 1] |
| 566 | 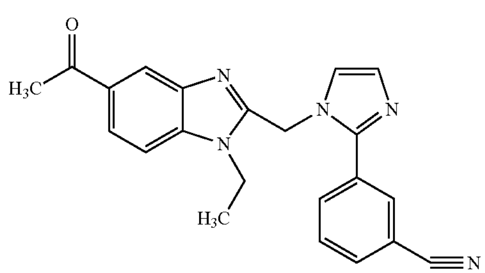 | 3-{1-[(5-acetyl-1-ethyl-1H-benzimidazol-2-yl)methyl]-1H-imidazol-2-yl}benzonitrile | 1H NMR (CDCl3): 8.40 (d, 1H), 7.93-8.05 (m, 3H), 7.76 (m, 1H), 7.63 (m, 1H), 7.37 (dd, 1H), 7.21 (d, 1H), 7.09 (d, 1H), 5.50 (s, 2H), 3.91 (q, 2H), 2.68 (s, 3H), 1.11 (t, 3H) | |

TABLE 6-continued

| Cpd # | STRUCTURE | IUPAC NAME | NMR | MS (m/z) |
|---|---|---|---|---|
| 567 | 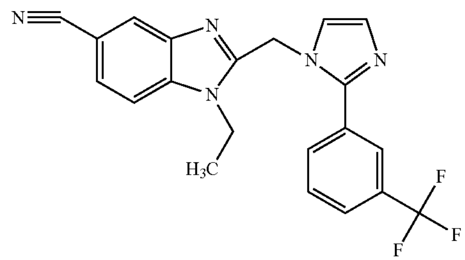 | 1-ethyl-2-({2-[3-(trifluoromethyl)phenyl]-1H-imidazol-1-yl}methyl)-1H-benzimidazole-5-carbonitrile | | 396.06 [M + 1] |
| 568 | 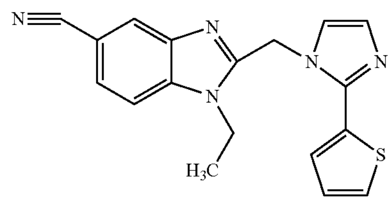 | 1-ethyl-2-[(2-thien-2-yl-1H-imidazol-1-yl)methyl]-1H-benzimidazole-5-carbonitrile | | 334.04 [M + 1] |
| 569 | 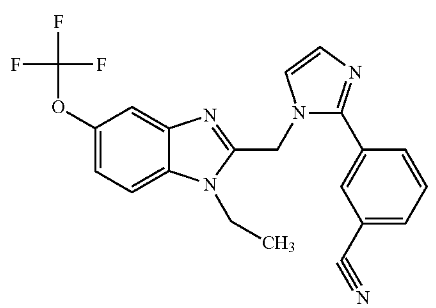 | 3-(1-{[1-ethyl-5-(trifluoromethoxy)-1H-benzimidazol-2-yl]methyl}-1H-imidazol-2-yl)benzonitrile | | 412.2 [M + 1]; 410.2 [M − 1] |
| 570 | 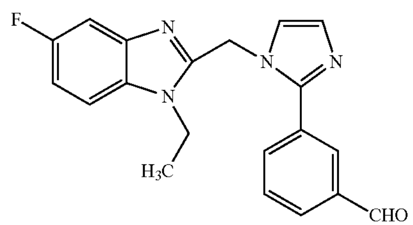 | 3-{1-[(1-ethyl-5-fluoro-1H-benzimidazol-2-yl)methyl]-1H-imidazol-2-yl}benzaldehyde | | 349.17 [M + 1] |

TABLE 6-continued

| Cpd # | STRUCTURE | IUPAC NAME | NMR | MS (m/z) |
|---|---|---|---|---|
| 571 | 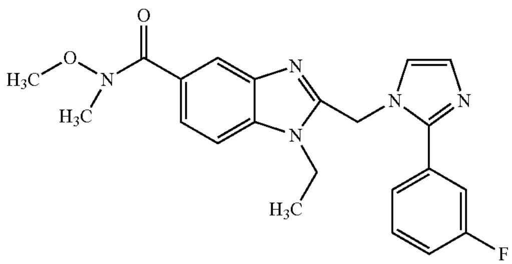 | 1-ethyl-2-{[2-(3-fluorophenyl)-1H-imidazol-1-yl]methyl}-N-methoxy-N-methyl-1H-benzimidazole-5-carboxamide | 1H NMR (CDCl3): 8.19 (d, 1H), 7.71 (dd, 1H), 7.40-7.55 (m, 3H), 7.32 (dd, 1H), 7.16-7.23 (m, 2H), 7.05 (d, 1H), 5.53 (s, 2H), 3.80 (q, 2H), 3.59 (s, 3H), 3.41 (s, 3H), 1.00 (t, 3H) | |
| 572 | 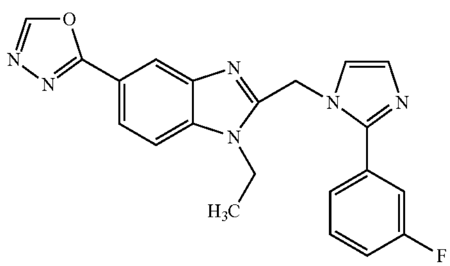 | 1-ethyl-2-{[2-(3-fluorophenyl)-1H-imidazol-1-yl]methyl}-5-(1,3,4-oxadiazol-2-yl)-1H-benzimidazole | | |
| 573 | 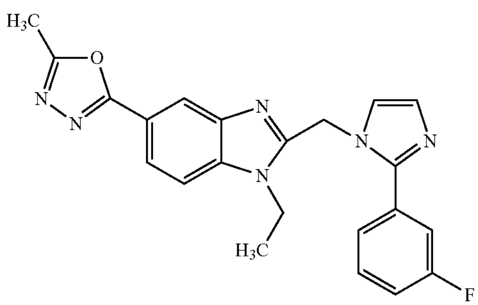 | 1-ethyl-2-{[2-(3-fluorophenyl)-1H-imidazol-1-yl]methyl}-5-(5-methyl-1,3,4-oxadiazol-2-yl)-1H-benzimidazole | Hydrochloride 1H NMR (d6 DMSO): 8.11 (1H, s), 8.00 (1H, d), 7.95 (1H, d), 7.90-7.82 (2H, m), 7.74-7.72 (1H, m), 7.64-7.58 (2H, m), 7.53-7.49 (1H, m), 5.96 (2H, s), 4.329 (2H, q), 2.56 (3H, s), 1.30 (3H, t) | 403.3 [M + 1] |

TABLE 6-continued

| Cpd # | STRUCTURE | IUPAC NAME | NMR | MS (m/z) |
|---|---|---|---|---|
| 574 | 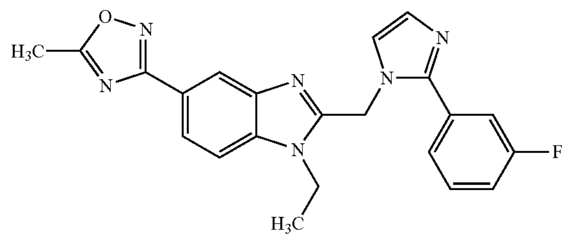 | 1-ethyl-2-{[2-(3-fluorophenyl)-1H-imidazol-1-yl]methyl}-5-(5-methyl-1,2,4-oxadiazol-3-yl)-1H-benzimidazole | | 403.8 [M + 1]; 401.4 [M − 1] |
| 575 | 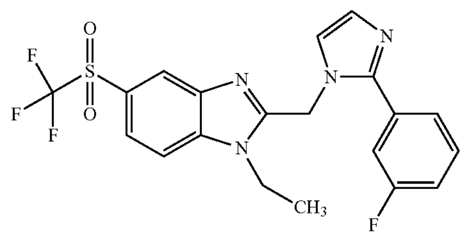 | 1-ethyl-2-{[2-(3-fluorophenyl)-1H-imidazol-1-yl]methyl}-5-[(trifluoromethyl)sulfonyl]-1H-benzimidazole | | 453.8 [M + 1]; 451.2 [M − 1] |
| 576 | 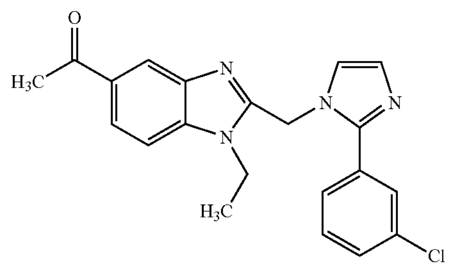 | 1-(2-{[2-(3-chlorophenyl)-1H-imidazol-1-yl]methyl}-1-ethyl-1H-benzimidazol-5-yl)ethanone | 1H NMR (CDCl3): (8.40 (d, 1H), 8.01 (dd, 1H), 7.68 (m, 1H), 7.55 (m, 1H), 7.45-7.52 (m, 2H), 7.35 (d, 1H), 7.17 (d, 1H), 7.06 (d, 1H), 5.52 (s, 2H), 3.85 (q, 2H), 2.68 (s, 3H), 1.03 (t, 3H) | |
| 577 | 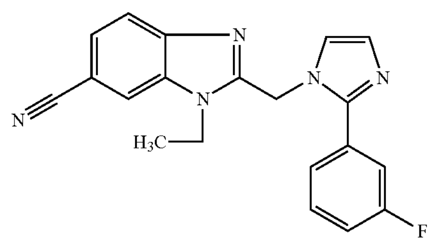 | 1-ethyl-2-{[2-(3-fluorophenyl)-1H-imidazol-1-yl]methyl}-1H-benzimidazole-6-carbonitrile | | 346.2 [M + 1]; 344.3 [M − 1] |

TABLE 6-continued

| Cpd # | STRUCTURE | IUPAC NAME | NMR | MS (m/z) |
|---|---|---|---|---|
| 578 | 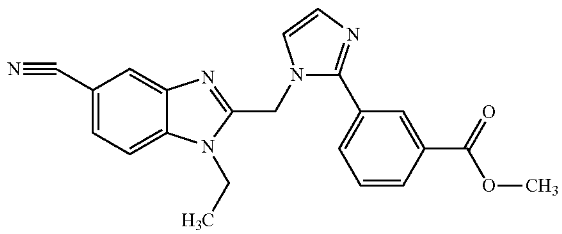 | methyl 3-{1-[(5-cyano-1-ethyl-1H-benzimidazol-2-yl)methyl]-1H-imidazol-2-yl}benzoate | | 386.17 [M + 1] |
| 579 | 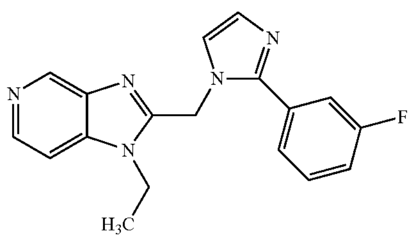 | 1-ethyl-2-{[2-(3-fluorophenyl)-1H-imidazol-1-yl]methyl}-1H-imidazo[4,5-c]pyridine | 1H NMR (CDCl3): 9.10 (s, 1H), 8.44 (d, 1H), 7.38-7.52 (m, 3H), 7.18-7.20 (m, 2H), 7.16 (s, 1H), 7.04 (d, 1H), 5.53 (s, 2H), 3.79 (q, 2H), 1.00 (t, 3H) | |
| 580 | 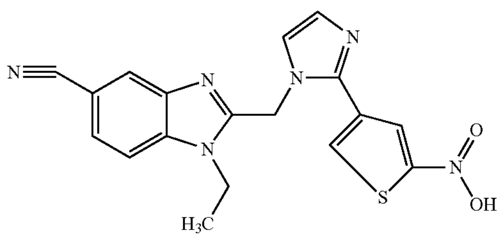 | 1-ethyl-2-{[2-(5-nitrothien-3-yl)-1H-imidazol-1-yl]methyl}-1H-benzimidazole-5-carbonitrile | | 379.05 [M + 1] |
| 581 | 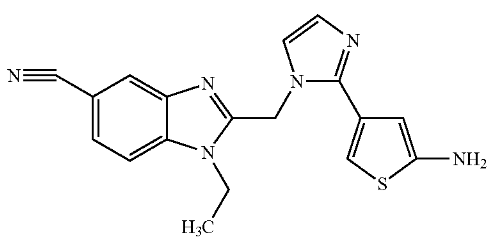 | 2-{[2-(5-aminothien-3-yl)-1H-imidazol-1-yl]methyl}-1-ethyl-1H-benzimidazole-5-carbonitrile | | 397.12 [M + 1] |

TABLE 6-continued

| Cpd # | STRUCTURE | IUPAC NAME | NMR | MS (m/z) |
|---|---|---|---|---|
| 582 | 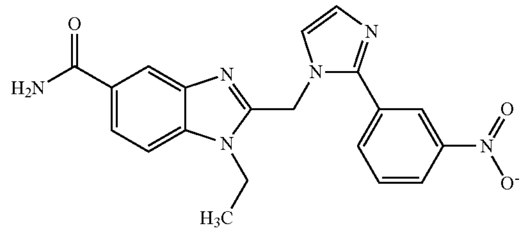 | 1-ethyl-2-{[2-(3-nitrophenyl)-1H-imidazol-1-yl]methyl}-1H-benzimidazole-5-carboxamide | | 391.17 [M + 1] |
| 583 | 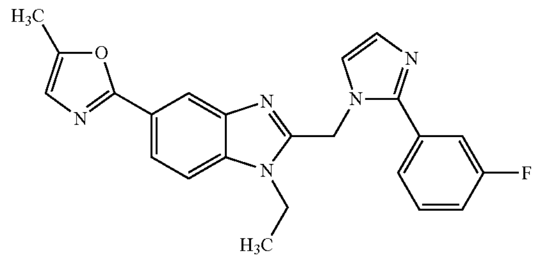 | 1-ethyl-2-{[2-(3-fluorophenyl)-1H-imidazol-1-yl]methyl}-5-(5-methyl-1,3-oxazol-2-yl)-1H-benzimidazole | Hydrochloride 1H NMR (d6 DMSO): 8.05 (1H, s), 7.99 (1H, d), 7.97 (1H, s), 7.88-7.86 (1H, m), 7.76-7.72 (2H, m), 7.65-7.59 (2H, m), 7.54-7.51 (1H, m), 6.99 (1H, s), 5.9392H, s), 4.31 (2H, q), 2.36 (3H, s), 1.29 (3H, t). | 402.5 [M + 1] |
| 584 | 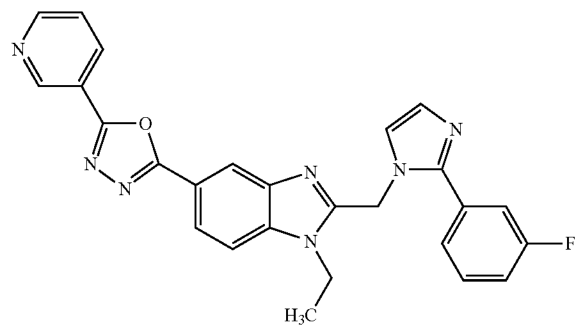 | 1-ethyl-2-{[2-(3-fluorophenyl)-1H-imidazol-1-yl]methyl}-5-(5-pyridin-3-yl-1,3,4-oxadiazol-2-yl)-1H-benzimidazole | Hydrochloride 1H NMR (d6 DMSO): 9.36 (1H, d), 6.84 (1H, dd), 8.57 (1H, m), 8.44 (1H, s), 8.10 (1H, dd), 8.03 (1H, d) 7.98 (1H, d), 7.90 (1H, d), 7.75-7.51 (5H, m), 5.99 (2H, s), 4.35 (2H, q), 1.33 (3H, t). | 466.5 [M + 1] |

TABLE 6-continued

| Cpd # | STRUCTURE | IUPAC NAME | NMR | MS (m/z) |
|---|---|---|---|---|
| 585 | 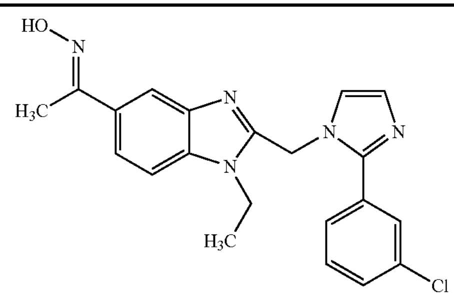 | (1E)-1-(2-{[2-(3-chlorophenyl)-1H-imidazol-1-yl]methyl}-1-ethyl-1H-benzimidazol-5-yl)ethanone | 1H NMR (CDCl3): 11.03 (s, 1H), 7.81 (s, 1H), 7.52-7.67 (m, 4H), 7.40-7.45 (m, 2H), 7.31 (s, 1H), 7.07 (s, 1H), 5.67 (s, 2H), 4.17 (q, 2H), 2.18 (s, 3H), 1.16 (t, 3H) | |
| 586 | 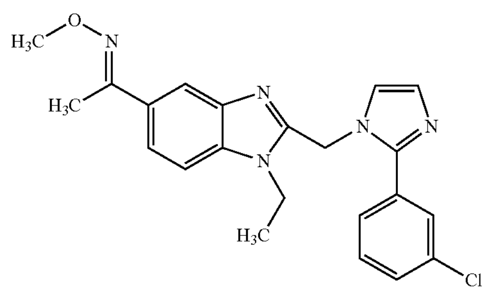 | (1E)-1-(2-{[2-(3-chlorophenyl)-1H-imidazol-1-yl]methyl}-1-ethyl-1H-benzimidazol-5-yl)ethanone O-methyloxime | Syn and anti 1H NMR (CDCl3): 7.99 (dd, 1H), 7.95 (dd, 1H1), 7.76 (dd, 1H + H1), 7.65 (m, 1H + H1), 7.44-7.57 (m, 3H + H1), 7.27 (d, 1H + H1), 7.16 (d, 1H + H1), 7.04 (d, 1H + H1), 5.49 (s, 2H + H1), 4.01 (s, 3H), 3.87 (s, 3H1), 3.80 (q, 2H + H1), [2.30 (s, 3H), 2.27 (s, 3H1)], 1.00 (t, 3H + H1) | |
| 587 | 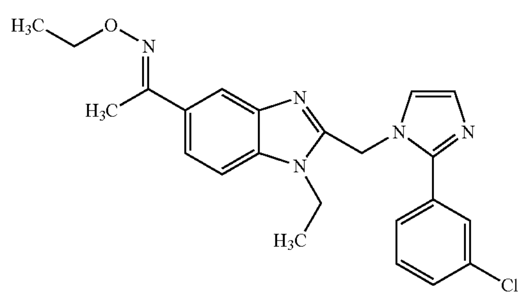 | (1E)-1-(2-{[2-(3-chlorophenyl)-1H-imidazol-1-yl]methyl}-1-ethyl-1H-benzimidazol-5-yl)ethanone O-ethyloxime | Syn and anti 1H NMR (CDCl3): 8.00 (dd, 1H + H1), 7.76 (dd, 1H + H1), 7.69 (m, 1H + H1), 7.44-7.57 (m, 3H + H1), 7.27 (dd, 1H + H1), 7.15 (d, 1H + H1), 7.04 (d, 1H), 7.03 (d, 1H), 5.49 (s, 2H + H1), 4.26 (q, 2H), 4.13 (q, 2H1), 3.80 (q, 2H + H1), 2.27 (s, 3H1), 1.34 (t, 3H), 1.25 (t, 3H1), 1.00 (t, 3H + H1) | |

TABLE 6-continued

| Cpd # | STRUCTURE | IUPAC NAME | NMR | MS (m/z) |
|---|---|---|---|---|
| 588 | 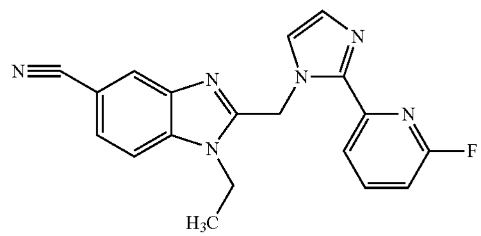 | 1-ethyl-2-{[2-(6-fluoropyridin-2-yl)-1H-imidazol-1-yl]methyl}-1H-benzimidazole-5-carbonitrile | | 347.07 [M + 1] |
| 589 | 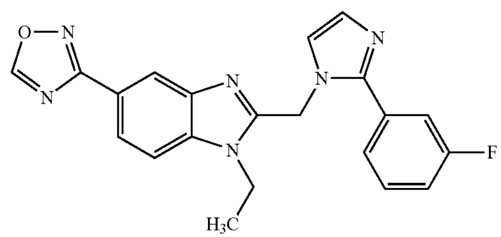 | 1-ethyl-2-{[2-(3-fluorophenyl)-1H-imidazol-1-yl]methyl}-5-(1,2,4-oxadiazol-3-yl)-1H-benzimidazole | | |
| 590 | 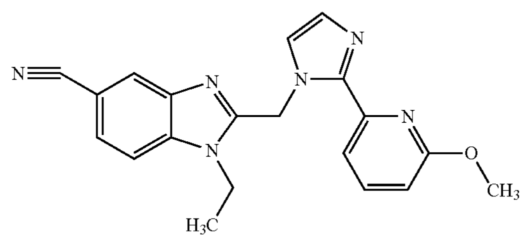 | 1-ethyl-2-{[2-(6-methoxypyridin-2-yl)-1H-imidazol-1-yl]methyl}-1H-benzimidazole-5-carbonitrile | | 359.08 [M + 1] |
| 591 | 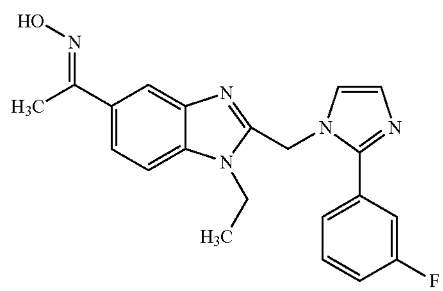 | (1E)-1-(1-ethyl-2-{[2-(3-fluorophenyl)-1H-imidazol-1-yl]methyl}-1H-benzimidazol-5-yl)ethanone oxime | Hydrochloride 1H NMR (d6-DMSO): 11.10 s, 1H), 7.52-7.99 (m, 9H + H1), 5.923 (s, 2H + H1); 4.30 (q, 2H + H1), 2.18 (s, 3H), 2.14 (s, 3H), 1.29 (t, 3H + H1) | |

TABLE 6-continued

| Cpd # | STRUCTURE | IUPAC NAME | NMR | MS (m/z) |
|---|---|---|---|---|
| 592 | 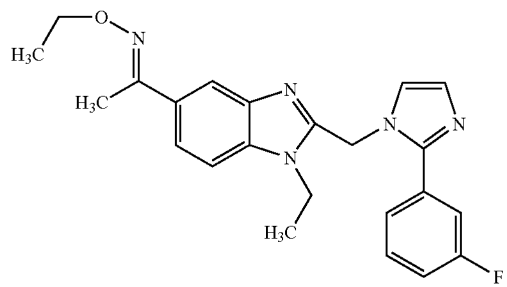 | (1E)-1-(1-ethyl-2-{[2-(3-fluorophenyl)-1H-imidazol-1-yl]methyl}-1H-benzimidazol-5-yl)ethanone O-ethyloxime | Hydrochloride 1H NMR (d6-DMSO): 7.52-7.99 (m, 9H), 5.93 (s, 2H), 4.28 (q, 2H), 4.14 (q, 2H), 2.20 (s, 3H), 1.23-1.29 (m, 6H) | |
| 593 | 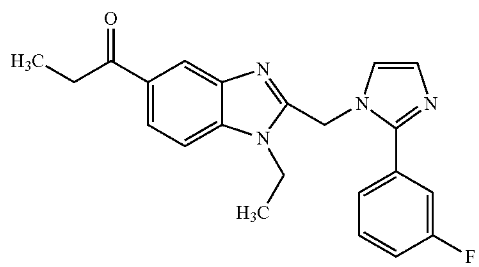 | 1-(1-ethyl-2-{[2-(3-fluorophenyl)-1H-imidazol-1-yl]methyl}-1H-benzimidazol-5-yl)propan-1-one | 1H NMR (CDCl3): 8.42 (d, 1H), 8.02 (dd, 1H), 7.32-7.54 (m, 4H), 7.17-7.24 (m, 2H), 7.06 (d, 1H), 5.53 (s, 2H), 3.83 (q, 2H), 3.09 (q, 2H), 1.27 (t, 3H), 1.02 (t, 3H) | |
| 594 | 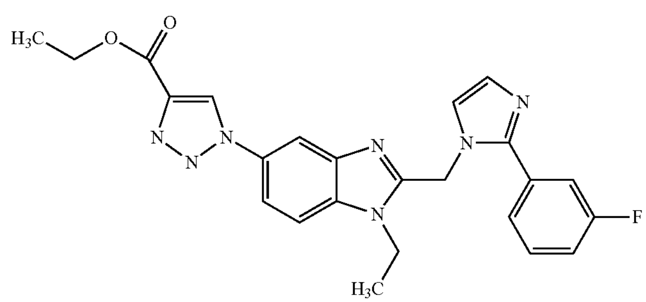 | ethyl 1-(1-ethyl-2-{[2-(3-fluorophenyl)-1H-imidazol-1-yl]methyl}-1H-benzimidazol-5-yl)-1H-1,2,3-triazole-4-carboxylate | | |

TABLE 6-continued

| Cpd # | STRUCTURE | IUPAC NAME | NMR | MS (m/z) |
|---|---|---|---|---|
| 595 | 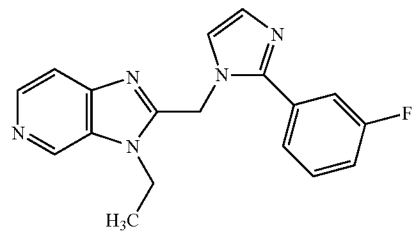 | 3-ethyl-2-{[2-(3-fluorophenyl)-1H-imidazol-1-yl]methyl}-3H-imidazo[4,5-c]pyridine | | |
| 596 | 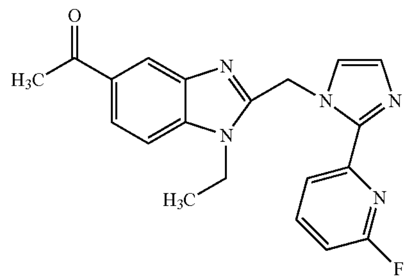 | 1-(1-ethyl-2-{[2-(6-fluoropyridin-2-yl)-1H-imidazol-1-yl]methyl}-1H-benzimidazol-5-yl)ethanone | | 364.2 [M + 1]; 362.6 [M − 1] |
| 597 | 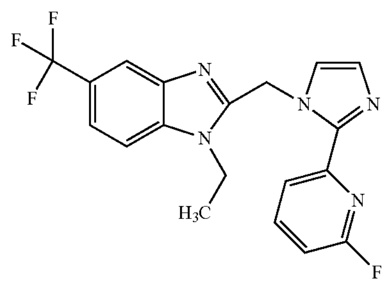 | 1-ethyl-2-{[2-(6-fluoropyridin-2-yl)-1H-imidazol-1-yl]methyl}-5-(trifluoromethyl)-1H-benzimidazole | | 390.2 [M + 1]; 388.2 [M − 1] |
| 598 | 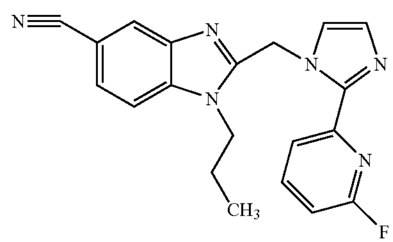 | 2-{[2-(6-fluoropyridin-2-yl)-1H-imidazol-1-yl]methyl}-1-propyl-1H-benzimidazole-5-carbonitrile | 1H NMR (399.96 MHz, CDCl3): d 8.17 (dd, J = 2.0, 7.6Hz, 1H), 8.05 (s, 1H), 7.88 (q, J = 8.0 Hz, 1H), 7.52 (d, J = 8.4Hz, 1H), 7.41 (d, J = 8.4Hz, 1H), 7.21 (s, 1H), 7.18 (s, 1H), 6.28 (s, 2H), 4.28 (t, J = 7.6Hz, 2H), 1.68 (dt, J = 7.6Hz, 2H), 0.84 (t, J = 7.6 Hz, 3H) | 361.2 [M + 1]; 359.2 [M − 1] |

TABLE 6-continued

| Cpd # | STRUCTURE | IUPAC NAME | NMR | MS (m/z) |
|---|---|---|---|---|
| 599 | 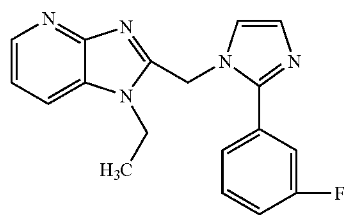 | 1-ethyl-2-{[2-(3-fluorophenyl)-1H-imidazol-1-yl]methyl}-1H-imidazo[4,5-b]pyridine | | 322.2 [M + 1]; 320.3 [M − 1] |
| 600 | 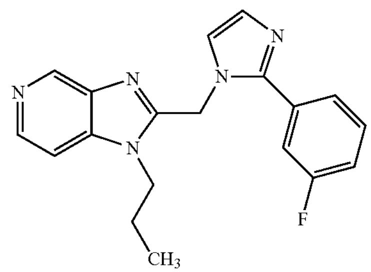 | 2-{[2-(3-fluorophenyl)-1H-imidazol-1-yl]methyl}-1-propyl-1H-imidazo[4,5-c]pyridine | 1H NMR (CDCl3): 9.11 (s, 1H), 8.45 (d, 1H), 7.38-7.52 (m, 3H), 7.16-7.26 (m, 3H) 7.06 (s, 1H), 5.53 (s, 2H), 3.71 (t, 2H), 1.43 (q, 2H), 0.75 (t, 3H) | |
| 601 | 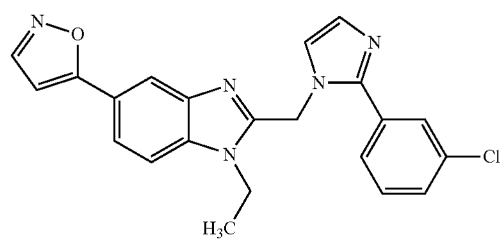 | 2-{[2-(3-chlorophenyl)-1H-imidazol-1-yl]methyl}-1-ethyl-5-isoxazol-5-yl-1H-benzimidazole | 1H NMR (CDCl3): 8.30 (d, 1H), 8.21 (dd, 1H), 7.78 (dd, 1H), 7.69 (m, 1H), 7.56 (m, 1H), 7.45-7.48 (m, 2H), 7.39 (dd, 1H), 7.17 (d, 1H), 7.07 (d, 1H), 6.53 (d, 1H), 5.52 (s, 2H), 3.83 (q, 2H), 1.03 (t, 3H) | |
| 602 | 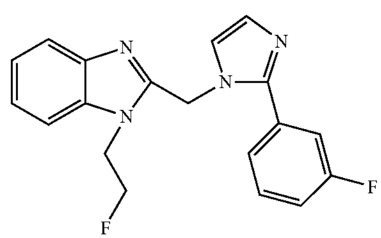 | 1-(2-fluoroethyl)-2-{[2-(3-fluorophenyl)-1H-imidazol-1-yl]methyl}-1H-benzimidazole | | 339.2 [M + 1] |

TABLE 6-continued

| Cpd # | STRUCTURE | IUPAC NAME | NMR | MS (m/z) |
|---|---|---|---|---|
| 603 | 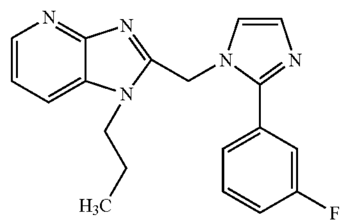 | 2-{[2-(3-fluorophenyl)-1H-imidazol-1-yl]methyl}-1-propyl-1H-imidazo[4,5-b]pyridine | | 336.2 [M + 1]; 334.2 [M − 1] |
| 604 | 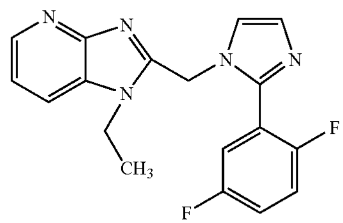 | 2-{[2-(2,5-difluorophenyl)-1H-imidazol-1-yl]methyl}-1-ethyl-1H-imidazo[4,5-b]pyridine | | |
| 605 | 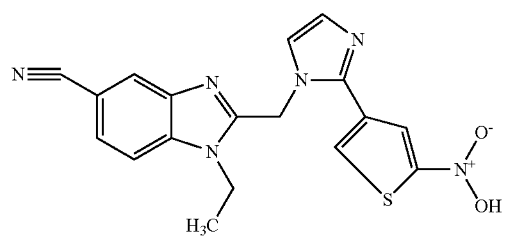 | 1-ethyl-2-[(2-{5-[hydroxy(oxido)amino]thien-3-yl}-1H-imidazol-1-yl)methyl]-1H-benzimidazole-5-carbonitrile | | |
| 606 | 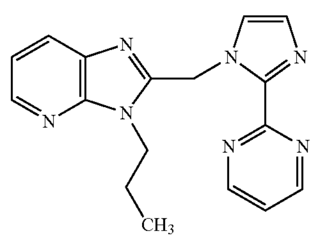 | 3-propyl-2-{[2-(2-pyrimidin-2-yl-1H-imidazol-1-yl)methyl]-3H-imidazo[4,5-b]pyridine | (CDCl3) 8.46 (d, 1H), 8.39 (dd, 1H), 8.03 (dd, 1H), 7.27 (m, 5H), 6.37 (s, 2H), 4.27 (t, 2H), 1.70 (p, 2H), 0.82 (t, 3H) | 320.4 [M + 1] |

TABLE 6-continued

| Cpd # | STRUCTURE | IUPAC NAME | NMR | MS (m/z) |
|---|---|---|---|---|
| 607 | 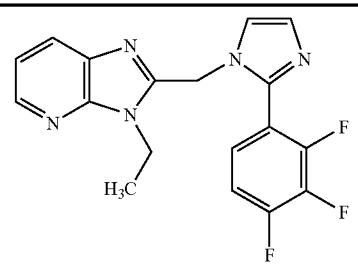 | 3-ethyl-2-{[2-(2,3,4-trifluorophenyl)-1H-imidazol-1-yl]methyl}-3H-imidazo[4,5-b]pyridine | (CDCl3) 8.40 (dd, 1H), 8.02 (dd, 1H), 7.36 (dq, 1H), 7.25 (dd, 1H), 7.22 (d, 1H), 7.01 (m, 2H), 5.38 (s, 2H), 4.03 (q, 2H), 1.10 (t, 3H) | 358.2 [M + 1] |
| 608 | 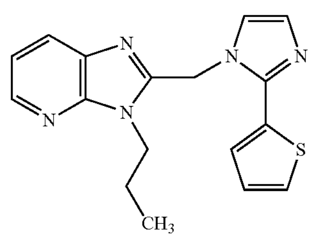 | 3-propyl-2-{[2-(2-thien-2-yl)-1H-imidazol-1-yl)methyl]-3H-imidazo[4,5-b]pyridine | (CDCl3) 8.40 (dd, 1H), 8.05 (dd, 1H), 7.46 (dd, 1H), 7.25 (dd, 1H), 7.15 (m, 2H), 7.03 (d, 1H), 5.61 (s, 2H), 3.96 (t, 2H), 1.55 (p, 2H), 0.80 (t, 3H) | 324.3 [M + 1] |
| 609 | 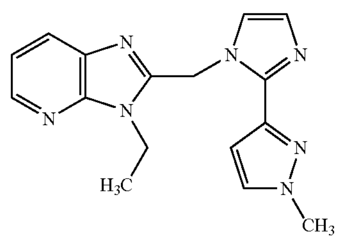 | 3-ethyl-2-{[2-(1-methyl-1H-pyrazol-3-yl)-1H-imidazol-1-yl]methyl}-3H-imidazo[4,5-b]pyridine | (CDCl3) 8.39 (dd, 1H), 8.05 (dd, 1H), 7.43 (dd, 1H), 7.23 (dd, 1H), 7.10 (dd, 1H), 7.04 (dd, 1H), 6.91 (dd, 1H), 6.21 (s, 2H), 4.33 (q, 2H), 3.97 (s, 3H), 1.13 (t, 3H) | m/z 308.3 [M + 1] |
| 610 | 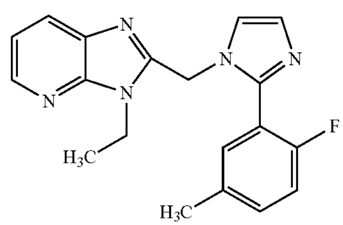 | 3-ethyl-2-{[2-(2-fluoro-5-methylphenyl)-1H-imidazol-1-yl]methyl}-3H-imidazo[4,5-b]pyridine | (CDCl3) 8.39 (dd, J = 4.8, 1.5 Hz, 1H), 8.05 (dd, J = 8.4, 1.5 Hz, 1H), 7.44 (dd, J = 6.6, 2.1 Hz, 1H), 7.25-7.30 (m, 2H), 7.19 (d, J = 1.5Hz, 1H), 7.12 (dd, J = 9.9, 8.7Hz, 1H), 7.04 (d, J = 1.5 Hz, 1H), 5.38 (s, 2H), 3.96 (q, J = 7.2Hz, 2H), 2.37 (s, 3H), 1.03 (t, J = 7.2Hz, 3H) | 336.2 [M + 1] |

TABLE 6-continued

| Cpd # | STRUCTURE | IUPAC NAME | NMR | MS (m/z) |
|---|---|---|---|---|
| 611 | 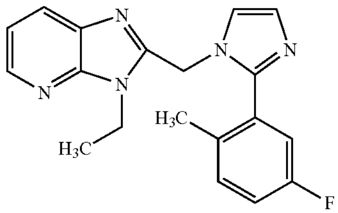 | 3-ethyl-2-{[2-(5-fluoro-2-methylphenyl)-1H-imidazol-1-yl]methyl}-3H-imidazo[4,5-b]pyridine | (CDCl3) 8.39 (dd, J = 4.6, 1.5 Hz, 1H), 8.04 (dd, J = 8.0, 1.5 Hz, 1H), 7.19-7.32 (m, 3H), 7.07-7.13 (m, 3H), 5.26 (s, 2H), 3.98 (q, J = 7.2Hz, 2H), 2.24 (s, 3H), 1.11 (t, J = 7.2Hz, 3H) | m/z 336.2 [M + 1] |
| 612 | 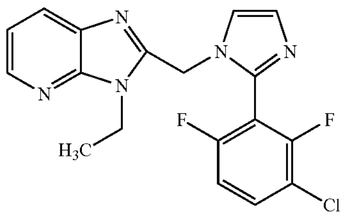 | 2-{[2-(3-chloro-2,6-difluorophenyl)-1H-imidazol-1-yl]methyl}-3-ethyl-3H-imidazo[4,5-b]pyridine | (CDCl3) 8.40 (dd, J = 4.7, 1.5 Hz, 1H), 8.01 (dd, J = 8.0, 1.5 Hz, 1H), 7.52 (m, 1H), 7.23-7.30 (m, 2H), 7.11 (d, J = 1.5Hz, 1H), 7.03 (m, 1H), 5.34 (s, 2H), 4.03 (q, J = 7.2Hz, 2H), 1.10 (t, J = 7.2Hz, 3H) | m/z 374.2 [M + 1] |
| 613 | 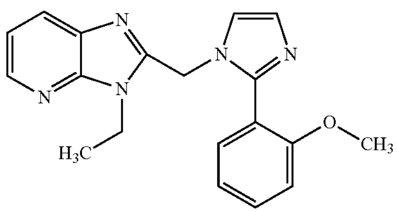 | 3-ethyl-2-{[2-(2-methoxyphenyl)-1H-imidazol-1-yl]methyl}-3H-imidazo[4,5-b]pyridine | (CDCl3) 8.38 (dd, J = 4.8, 1.5 Hz, 1H), 8.03 (dd, J = 8.1, 1.5 Hz, 1H), 7.46-7.57 (m, 2H), 7.25 (m, 1H), 7.16 (d, J = 1.2Hz, 1H), 7.13 (dt, J = 7.5, 1.2Hz, 1H), 7.04 (d, J = 8.4Hz, 1H), 7.00 (d, J = 1.2Hz, 1H), 5.29 (s, 2H), 3.90 (q, J = 7.2 Hz, 2H), 3.84 (s, 3H), 0.98 (t, J = 7.2Hz, 3H) | m/z 334.2 [M + 1] |
| 614 | 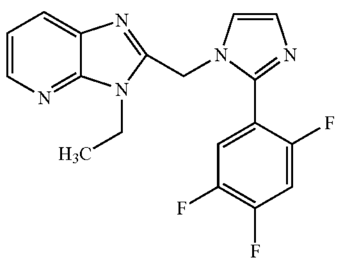 | 3-ethyl-2-{[2-(2,4,5-trifluorophenyl)-1H-imidazol-1-yl]methyl}-3H-imidazo[4,5-b]pyridine | (CDCl3) 8.40 (dd, J = 4.6, 1.4 Hz, 1H), 8.04 (dd, J = 8.2, 1.5 Hz, 1H), 7.50 (m, 1H), 7.25 (dd, J = 7.8, 5.1Hz, 1H), 7.21 (d, J = 1.5Hz, 1H), 7.14 (m, 1H), 7.06 (d, J = 1.5Hz, 1H), 5.37 (s, 2H), 4.02 (q, J = 7.2Hz, 2H), 1.11 (t, J = 7.2Hz, 3H) | m/z 358.2 [M + 1] |

TABLE 6-continued

| Cpd # | STRUCTURE | IUPAC NAME | NMR | MS (m/z) |
|---|---|---|---|---|
| 615 | 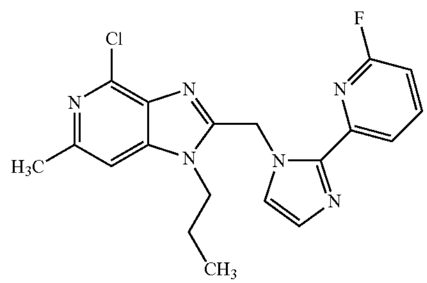 | 4-chloro-2-{[2-(6-fluoropyridin-2-yl)-1H-imidazol-1-yl]methyl}-6-methyl-1-propyl-1H-imidazo[4,5-c]pyridine | (CDCl3) 8.19 (dd, J = 6, 1.2Hz, 1H), 7.93 (q, J = 6Hz, 1H), 7.21 (d, J = 1Hz, 1H), 7.14 (d, J = 1Hz, 1H), 7.05 (s, 1H), 6.93 (dd, J = 6, 2Hz, 1H), 6.38 (s, 2H), 4.18 (t, J = 5.6Hz, 2H), 2.63 (s, 3H), 1.57 (sextet, J = 5.4Hz, 2H), 0.77 (t, J = 5.4Hz, 3H) | m/z 385 [M + 1] |
| 616 | 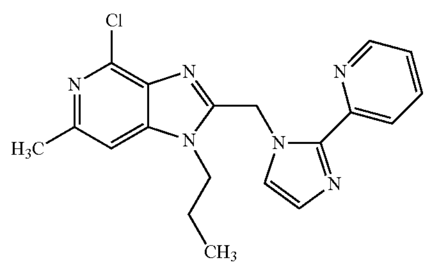 | 4-chloro-6-methyl-1-propyl-2-[(2-pyridin-2-yl-1H-imidazol-1-yl)methyl]-1H-imidazo[4,5-c]pyridine | (CD3OD) 8.02-7.98 (m, 3H), 7.34 (d, J = 2Hz, 1H), 7.14 (d, J = 1.8Hz, 1H), 6.47 (s, 1H), 6.12 (s, 2H), 4.21 (t, J = 5.2Hz, 2H), 2.33 (s, 3H), 1.68 (sextet, J = 5.4Hz, 2H), 0.86 (t, J = 5.4Hz, 3H) | m/z 367 [M + 1] |
| 617 | 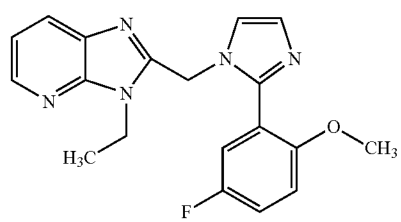 | 3-ethyl-2-{[2-(5-fluoro-2-methoxyphenyl)-1H-imidazol-1-yl]methyl}-3H-imidazo[4,5-b]pyridine | (CDCl3) 8.39 (dd, J = 4.6, 1.4 Hz, 1H), 8.04 (dd, J = 8.0, 1.4 Hz, 1H), 7.15-7.32 (m, 4H), 7.01 (d, J = 1.5Hz, 1H), 6.96 (d, J = 9.0, 4.5Hz, 1H), 5.30 (s, 2H), 3.95 (q, J = 7.2Hz, 2H), 3.80 (s, 3H), 1.02 (t, J = 7.2Hz, 3H) | m/z 352.3 [M + 1] |
| 618 | 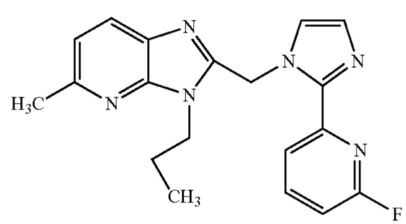 | 2-{[2-(6-fluoropyridin-2-yl)-1H-imidazol-1-yl]methyl}-5-methyl-3-propyl-3H-imidazo[4,5-b]pyridine | (CDCl3) 8-18 (dd, J = 7.8, 2.1 Hz, 1H), 7.84-7.92 (m, 2H), 7.21 (d, J = 1.2Hz, 1H), 7.18 (d, J = 1.2Hz 1H), 7.06 (d, J = 7.8Hz, 1H), 6.89 (dd, J = 8.1, 2.7Hz, 1H), 6.29 (s, 2H), 4.29 (t, J = 7.5 Hz, 2H), 2.64 (s, 3H), 1.72 (m, 2H), 0.83 (t, J = 7.5Hz, 3H) | |

TABLE 6-continued

| Cpd # | STRUCTURE | IUPAC NAME | NMR | MS (m/z) |
|---|---|---|---|---|
| 619 | 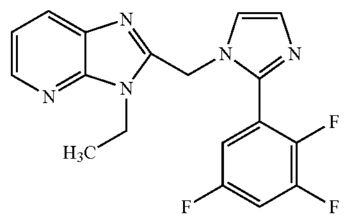 | 3-ethyl-2-{[2-(2,3,5-trifluorophenyl)-1H-imidazol-1-yl]methyl}-3H-imidazo[4,5-b]pyridine | (CDCl3) 8.40 (dd, J = 4.8, 1.2 Hz, 1H), 8.04 (dd, J = 7.8, 1.2 Hz, 1H), 7.05-7.28 (m, 5H), 5.40 (s, 2H), 4.04 (q, J = 7.3Hz, 2H), 1.10 (t, J = 7.3Hz, 3H) | |
| 620 | 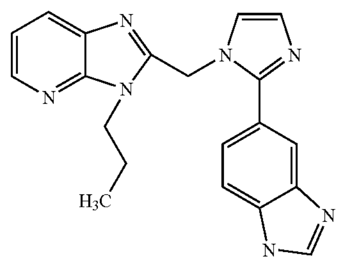 | 2-{[2-(1H-benzimidazol-5-yl)-1H-imidazol-1-yl]methyl}-3-propyl-3H-imidazo[4,5-b]pyridine | (CDCl3): 8.38 (d, 1H), 8.02 (m, 2H), 7.96 (s, 1H), 7.66 (s, 1H), 7.42 (d, 1H), 7.25 (m, 2H), 5.56 (s, 2H), 5.29 (1H), 3.87 (t, 2H), 1.48 (m, 2H), 0.68 (t, 3H) | m/z 358 [M + 1] |
| 621 | 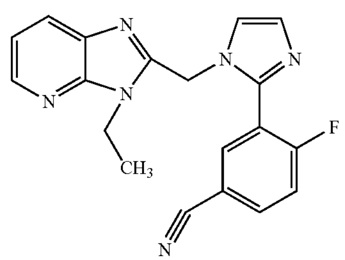 | 3-{1-(3-ethyl-3H-imidazo[4,5-b]pyridin-2-yl)methyl]-1H-imidazol-2-yl}-4-fluorobenzonitrile | (CDCl3): 8.40 (d, 1H), 7.96 (m, 2H), 7.75 (m, 1H), 7.31 (m, 3H), 7.10 (s, 1H), 5.38 (s, 2H), 4.03 (q, 2H), 1.11 (t, 3H) | |
| 622 | 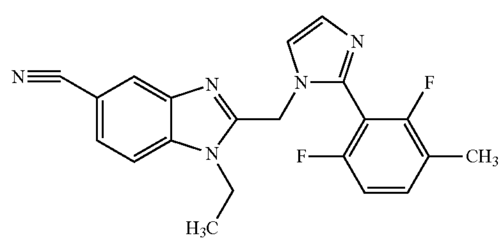 | 2-{[2-(2,6-difluoro-3-methylphenyl)-1H-imidazol-1-yl]methyl}-1-ethyl-1H-benzimidazole-5-carbonitrile | (CDCl3) 8.06 (s, 1H), 7.55 (m, 1H), 7.37 (dd, J = 8.0, 1.2Hz, 1H), 7.32-7.26 (m, 2H), 7.04 (s, 1H), 6.94 (t, J = 8.8Hz, 1H), 5.34 (s, 2H), 3.88 (q, J = 7.1Hz, 2H), 2.25 (S, 3H), 1.03 (t, J = 7.1Hz, 3H) | m/z 378 [M + 1] |

TABLE 6-continued

| Cpd # | STRUCTURE | IUPAC NAME | NMR | MS (m/z) |
|---|---|---|---|---|
| 623 | 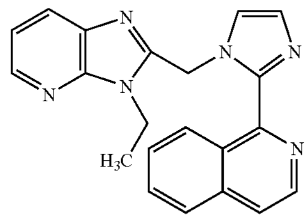 | 1-(1-[(3-ethyl-3H-imidazo[4,5-b]pyridin-2-yl)methyl]-1H-imidazol-2-yl)isoquinoline | (CDCl3) 9.11 (d, 1H), 8.58 (d, 1H), 8.37 (dd, 1H), 8.02 (dd, 1H), 7.86 (dd, 1H), 7.51 (m, 3H), 7.32 (d, 1H), 7.22 (m, 2H), 6.11 (s, 2H), 4.36 (q, 2H), 1.11 (t, 3H) | m/z 355.2 [M + 1] |
| 624 | 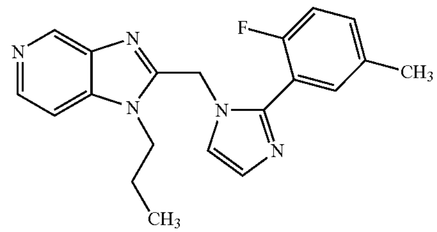 | 2-[[2-(2-fluoro-5-methylphenyl)-1H-imidazol-1-yl]methyl]-1-propyl-1H-imidazo[4,5-c]pyridine | (CDCl3) 9.01 (s, 1H), 8.41 (d, J = 4.5Hz, 1H), 8.12 (dd, J = 5.1, 1.5 Hz, 1H), 7.28-7.24 (m, 2H), 7.21 (d, J = 4.2Hz, 1H), 7.10 (t, J = 6.6Hz, 1H), 7.01 (s, 1H), 5.37 (s, 2H), 3.69 (t, J = 5.7Hz, 2H), 2.34 (s, 3H), 1.40 (sextet, J = 5.7Hz, 2H), 0.74 (t, J = 5.7Hz, 3H) | m/z 350 [M + 1] |
| 625 | 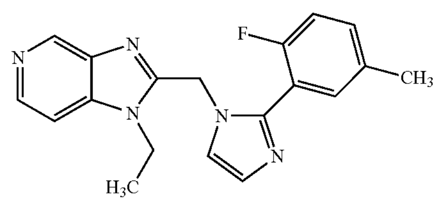 | 1-ethyl-2-[[2-(2-fluoro-5-methylphenyl)-1H-imidazol-1-yl]methyl]-1H-imidazo[4,5-c]pyridine | (CDCl3) 9.09 (s, 1H), 8.44 (d, J = 4.8Hz, 1H), 7.42 (d, J = 5.0 Hz, 1H), 7.29-7.23 (m, 3H), 7.12 (t, J = 6.3Hz, 1H), 7.00 (s, 1H), 5.39 (s, 2H), 3.81 (q, J = 5.4Hz, 2H), 2.36 (s, 3H), 0.99 (t, J = 5.1Hz, 3H) | m/z 336 [M + 1] |
| 626 | 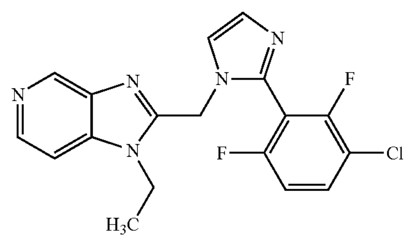 | 2-[[2-(3-chloro-2,6-difluorophenyl)-1H-imidazol-1-yl]methyl]-1-ethyl-1H-imidazo[4,5-c]pyridine | D6dmso) 9.42 (s, 1H), 8.69 (d, J = 6.4Hz, 1H), 8.36 (d, J = 6.4Hz, 1H), 7.99-7.91 (m, 2H), 7.75 (s, 1H), 7.39 (t, J = 8Hz, 1H), 5.95 (s, 2H), 4.43 (q, J = 7.2Hz, 2H), 1.25 (t, J = 7.2Hz, 3H) | m/z 374 [M + 1] |

| Cpd # | STRUCTURE | IUPAC NAME | NMR | MS (m/z) |
|---|---|---|---|---|
| 627 | 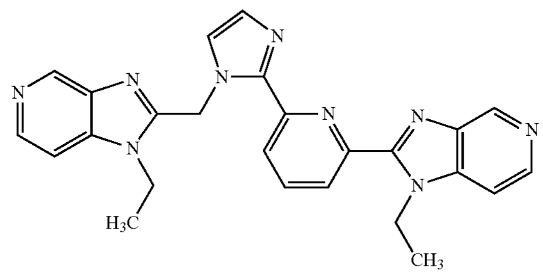 | 1-ethyl-2-(6-{[1-(1-ethyl-1H-imidazo[4,5-c]pyridin-2-yl)methyl]1H-imidazol-2-yl}pyridin-2-yl)-1H-imidazo[4,5-c]pyridine | (D6dmso) 9.57 (s, 1H), 9.34 (s, 1H), 8.74 (d, J = 6.8Hz, 1H), 8.63 (d, J = 6.4Hz, 1H), 8.42 (d, J = 6.8Hz, 1H), 8.33 (d, J = 6.4Hz, 1H), 8.25 (t, J = 8Hz, 1H), 8.17 (d, J = 6.8Hz, 1H), 8.07 (d, J = 7.6Hz, 1H), 7.70 (s, 1H), 7.46 (s, 1H), 6.32 (s, 2H), 4.24-4.16 (m, 4H), 0.97 (t, J = 7.2Hz, 3H), 0.89 (t, J = 7.2Hz, 3H) | |
| 628 | 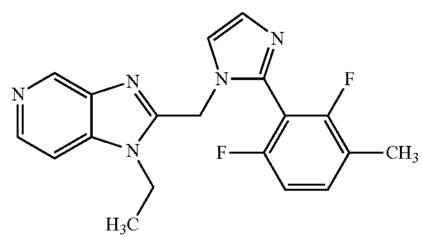 | 2-{[2-(2,6-difluoro-3-methylphenyl)-1H-imidazol-1-yl]methyl}-1-ethyl-1H-imidazo[4,5-c]pyridine | (d6 DMSO) 9.42 (s, 1H), 8.69 (d, J = 6.4Hz, 1H), 8.37 (d, J = 6.8Hz, 1H), 8.08 (s, 1H), 7.90 (s, 1H), 7.67-7.61 (m, 1H), 7.24 (t, J = 8.8Hz, 1H), 5.98 (s, 2H), 4.44 (q, J = 7.2Hz, 2H), 2.19 (s, 3H), 1.27 (t, J = 7.2Hz, 3H) | |
| 629 | 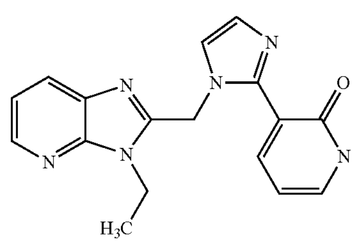 | 3-{1-(3-ethyl-3H-imidazo[4,5-b]pyridin-2-yl)methyl]-1H-imidazo-2-yl}pyridin-2(1H)-one | (d6 DMSO) 12.00 (br s, 1H), 8.28 (dd, J = 5.2, 1.2Hz, 1H), 7.93 (dd, J = 8, 1.2Hz, 1H), 7.56 (dd, J = 6.8, 2Hz, 1H), 7.45 (dd, J = 6.8, 2Hz, 1H), 7.25 (s, 1H), 7.20 (dd, J = 8, 4.8Hz, 1H), 6.98 (s, 1H), 6.19 (t, J = 5.2Hz, 1H), 5.64 (s, 2H), 4.14 (q, J = 7.2Hz, 2H), 1.07 (t, J = 7.2Hz, 3H) | m/z 319 [M − H] |
| 630 | 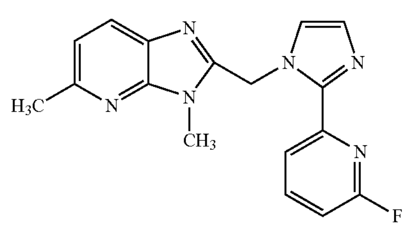 | 2-{[2-(6-fluoropyridin-2-yl)-1H-imidazol-1-yl]methyl}-3,5-dimethyl-3H-imidazo[4,5-b]pyridine | (CDCl3) 8.16 (dd, 1H), 7.88 (m, 2H), 7.16 (m, 2H), 7.06 (d, 1H), 6.85 (dd, 1H), 6.24 (s, 2H), 3.85 (s, 3H), 2.62 (s, 3H) | |

TABLE 6-continued

| Cpd # | STRUCTURE | IUPAC NAME | NMR | MS (m/z) |
|---|---|---|---|---|
| 631 | 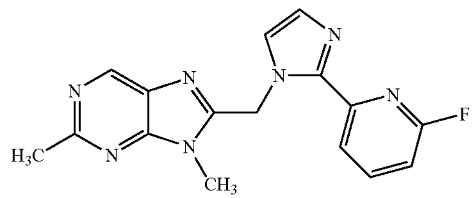 | 8-{[2-(6-fluoropyridin-2-yl)-1H-imidazol-1-yl]methyl}-2,9-dimethyl-9H-purine | (CDCl3) 8.92 (s, 1H), 8.18 (dd, 1H), 7.88 (q, 1H), 7.25 (s, 1H), 7.20 (s, 1H), 7.11 (s, 1H), 6.83 (dd, 1H), 6.22 (s, 2H), 3.89 (s, 3H), 2.8 (s, 3H) | m/z 324 [M + 1] |
| 632 | 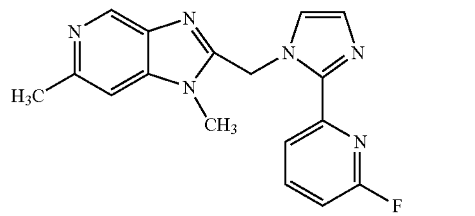 | 2-{[2-(6-fluoropyridin-2-yl)-1H-imidazol-1-yl]methyl}-1,6-dimethyl-1H-imidazo[4,5-c]pyridine | (CDCl3) 8.91 (s, 1H), 8.16 (dd, J = 7.6, 2.0 Hz, 1H), 7.85 (q, J = 8.0Hz, 1H), 7.20 (s, 1H), 7.18 (s, 1H), 7.11 (s, 1H), 6.84 (dd, J = 8.0, 2.8Hz, 1H), 6.22 (s, 2H), 3.80 (s, 3H), 2.66 (s, 3H) | m/z 323 [M + 1] |
| 633 | 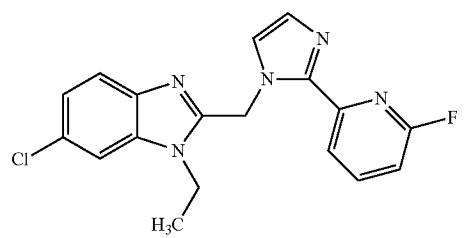 | 6-chloro-1-ethyl-2-{[2-(6-fluoropyridin-2-yl)-1H-imidazol-1-yl]methyl}-1H-benzimidazole | (CDCl3) 8.17 (dd, 1H), 7.89 (q, 1H), 7.25 (s, 1H), 7.75 (s, 1H), 7.26 (m, 2H), 7.19 (s, 1H), 7.17 (s, 1H), 6.89 (dd, 1H), 6.28 (s, 2H), 4.33 (q, 2H), 1.20 (s, 3H) | m/z 356 [M + 1] |
| 634 | 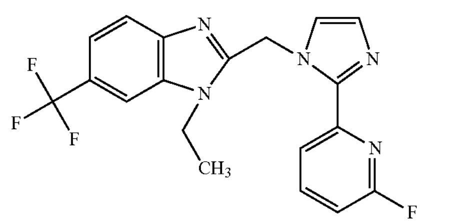 | 1-ethyl-2-{[2-(6-fluoropyridin-2-yl)-1H-imidazol-1-yl]methyl}-6-(trifluoromethyl)-1H-benzimidazole | (CDCl3) 8.20 (m, 1H), 7.87 (m, 2H), 7.63 (s, 1H), 7.48 (d, 1H), 7.20 (d, 2H), 6.85 (dd, 1H), 6.25 (s, 2H), 4.38 (q, 2H), 1.24 (t, 3H) | |

TABLE 6-continued

| Cpd # | STRUCTURE | IUPAC NAME | NMR | MS (m/z) |
|---|---|---|---|---|
| 635 | 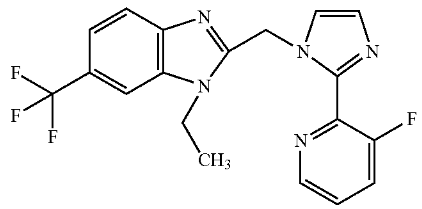 | 1-ethyl-2-{[2-(3-fluoropyridin-2-yl)-1H-imidazol-1-yl]methyl}-6-(trifluoromethyl)-1H-benzimidazole | (CDCl3) 8.46 (m, 1H), 7.84 (d, 1H), 7.60 (m, 2H), 7.52 (d, 1H), 7.38 (m, 1H), 7.25 (s, 1H), 7.10 (s, 1H), 6.14 (s, 2H), 4.35 (q, 2H), 1.14 (t, 3H) | |
| 636 | 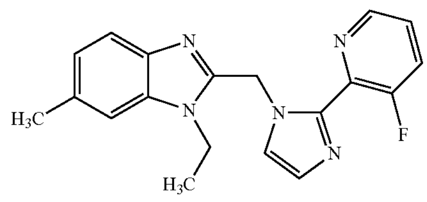 | 1-ethyl-2-{[2-(3-fluoropyridin-2-yl)-1H-imidazol-1-yl]methyl}-6-methyl-1H-benzimidazole | (CDCl3) 8.48 (dt, 1H), 7.59-7.66 (m, 2H), 7.36 (m, 1H), 7.20 (s, 1H), 7.08-7.11 (m, 3H), 6.01 (s, 2H), 4.18 (q, 2H), 2.48 (s, 3H), 1.07 (s, 3H) | |
| 637 | 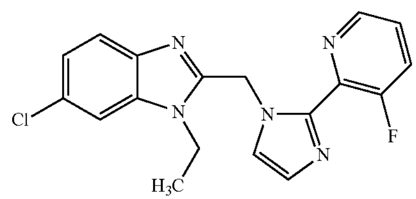 | 6-chloro-1-ethyl-2-{[2-(3-fluoropyridin-2-yl)-1H-imidazol-1-yl]methyl}-1H-benzimidazole | (CDCl3) 8.48 (dt, 1H), 7.74 (s, 1H), 7.61 (t, 1H), 7.37 (m, 1H), 7.20 (s, 1H), 7.23-7.26 (m, 3H), 7.08 (s, 1H), 6.01 (s, 2H), 4.25 (q, 2H), 1.07 (s, 3H) | |
| 638 | 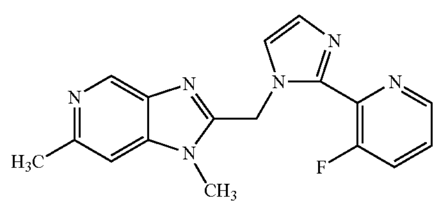 | 2-{[2-(3-fluoropyridin-2-yl)-1H-imidazol-1-yl]methyl}-1,6-dimethyl-1H-imidazo[4,5-c]pyridine | (CDCl3) 8.95 (s, 1H), 8.45 (dt, J = 5.8, 1.8Hz, 1H), 7.61 (m, 1H), 7.36 (m, 1H), 7.27 (s, 1H), 7.10 (s, 1H), 7.06 (s, 1H), 6.06 (s, 2H), 3.66 (s, 3H), 2.67 (s, 3H) | m/z 323 [M + 1] |
| 639 | 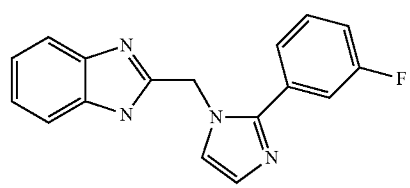 | 2-{[2-(3-fluorophenyl)-1H-imidazol-1-yl]methyl}-1H-benzimidazole | | m/z 293 [M + 1] |

TABLE 6-continued

| Cpd # | STRUCTURE | IUPAC NAME | NMR | MS (m/z) |
|---|---|---|---|---|
| 640 | 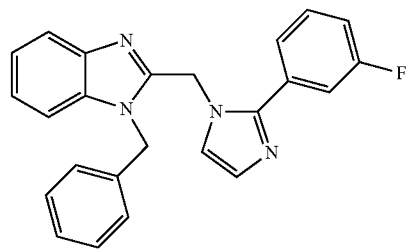 | 1-benzyl-2-{[2-(3-fluorophenyl)-1H-imidazol-1-yl]methyl}-1H-benzimidazole | | m/z 383 [M + 1] |
| 641 | 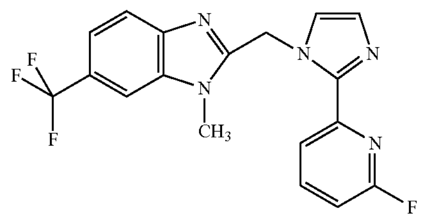 | 2-{[2-(6-fluoropyridin-2-yl)-1H-imidazol-1-yl]methyl}-1-methyl-6-(trifluoromethyl)-1H-benzimidazole | (CDCl3) 8.20 (m, 1H), 7.87 (m, 2H), 7.63 (s, 1H), 7.48 (d, 1H), 7.20 (s, 2H), 6.84 (dd, 1H), 6.25 (s, 2H), 3.92 (s, 3H) | |
| 642 | 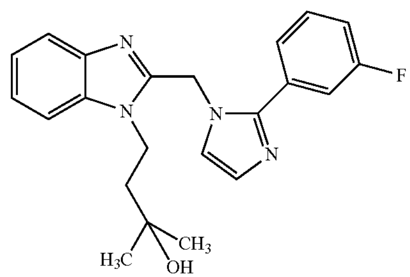 | 4-(2-{[2-(3-fluorophenyl)-1H-imidazol-1-yl]methyl}-1H-benzimidazol-1-yl)-2-methylbutan-2-ol | | m/z 379 [M + 1] |
| 643 | 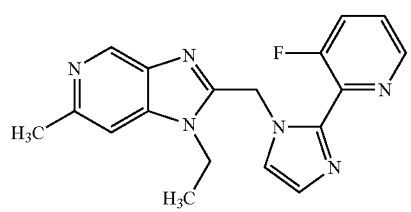 | 1-ethyl-2-{[2-(3-fluoropyridin-2-yl)-1H-imidazol-1-yl]methyl}-6-methyl-1H-imidazo[4,5-c]pyridine | (CDCl3) 8.96 (s, 1H), 8.46 (dt, 4.8, 1.4Hz, 1H), 7.61 (m, 1H), 7.37 (m, 1H), 7.24 (d, J = 1.2Hz, 1H), 7.10 (s, 1H), 7.09 (d, J = 1.2 Hz, 1H), 6.06 (s, 2H), 4.23 (q, J = 7.2Hz, 2H), 2.66 (s, 3H), 1.10 (t, J = 7.2Hz, 3H) | m/z 337 [M + 1] |

TABLE 6-continued

| Cpd # | STRUCTURE | IUPAC NAME | NMR | MS (m/z) |
|---|---|---|---|---|
| 644 | 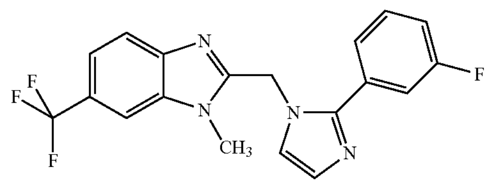 | 2-{[2-(3-fluorophenyl)-1H-imidazol-1-yl]methyl}-1-methyl-6-(trifluoromethyl)-1H-benzimidazole | | m/z 375 [M + 1] |
| 645 | 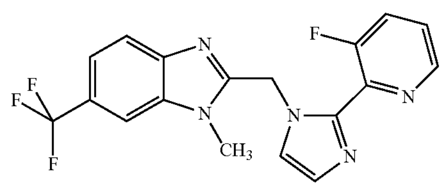 | 2-{[2-(3-fluoropyridin-2-yl)-1H-imidazol-1-yl]methyl}-1-methyl-6-(trifluoromethyl)-1H-benzimidazole | | m/z 376 [M + 1] |
| 646 | 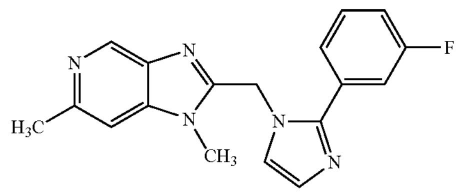 | 2-{[2-(3-fluorophenyl)-1H-imidazol-1-yl]methyl}-1,6-dimethyl-1H-imidazo[4,5-c]pyridine | (CDCl3) 8.95 (s, 1H), 7.49-7.37 (m, 3H), 7.16 (m, 2H), 7.06 (s, 1H), 6.97 (s, 1H), 5.50 (s, 2H), 3.33 (s, 3H), 2.66 (s, 3H) | m/z 322 [M + 1] |
| 647 | 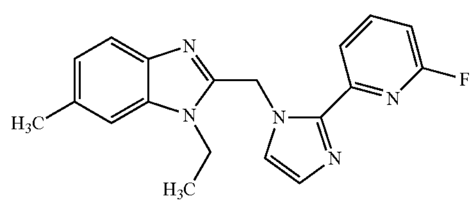 | 1-ethyl-2-{[2-(6-fluoropyridin-2-yl)-1H-imidazol-1-yl]methyl}-6-methyl-1H-benzimidazole | (CDCl3) 8.15 (dd, 1H), 7.87 (q, 1H), 7.63 (d, 1H), 7.08-7.17 (m, 4H), 6.88 (dd, 1H), 6.26 (s, 1H), 4.27 (q, 2H), 2.46 (s, 1H), 1.16 (t, 3H) | |
| 648 | 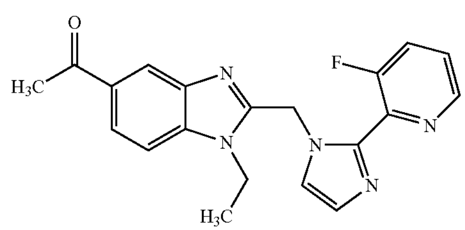 | 1-(1-ethyl-2-{[2-(3-fluoropyridin-2-yl)-1H-imidazol-1-yl]methyl}-1H-benzimidazol-5-yl)ethanone | (CDCl3) 8.45 (d, 1H), 8.38 (s, 1H), 7.98 (dd, 1H), 7.61 (t, 1H), 7.37 (m, 2H), 7.24 (s, 1H), 7.21 (s, 1H), 6.08 (s, 2H), 4.29 (q, 2H), 2.66 (s, 3H), 1.14 (t, 3H) | |

TABLE 6-continued

| Cpd # | STRUCTURE | IUPAC NAME | NMR | MS (m/z) |
|---|---|---|---|---|
| 649 | 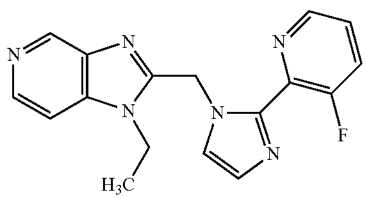 | 1-ethyl-2-{[2-(3-fluoropyridin-2-yl)-1H-imidazol-1-yl]methyl}-1H-imidazo[4,5-c]pyridine | (CDCl3) 9.12 (s, 1H), 8.45-8.49 (m, 2H), 7.620 (t, 1H), 7.35-7.41 (m, 1H), 7.30 (d, 1H), 7.27 (s, 1H), 7.11 (s, 1H), 6.13 (s, 2H), 4.30 (q, 2H), 1.12 (t, 3H) | |
| 650 | 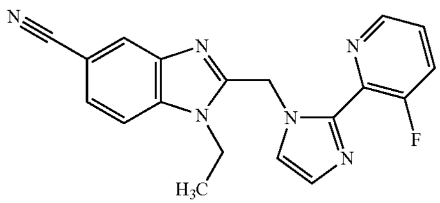 | 1-ethyl-2-{[2-(3-fluoropyridin-2-yl)-1H-imidazol-1-yl]methyl}-1H-benzimidazole-5-carbonitrile | (CDCl3) 8.45 (d, 1H), 8.09 (s, 1H), 7.62 (t, 1H), 7.58 (d, 1H), 7.42 (s, 1H), 7.35-7.40 (m, 2H), 7.09 (s, 1H), 6.10 (s, 2H), 4.32 (q, 2H), 1.12 (t, 3H) | |
| 651 | 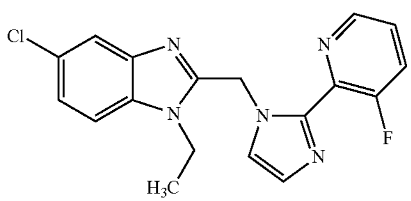 | 5-chloro-1-ethyl-2-{[2-(3-fluoropyridin-2-yl)-1H-imidazol-1-yl]methyl}-1H-benzimidazole | | m/z 356 [M + 1] |
| 652 | 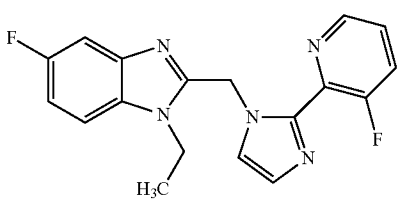 | 1-ethyl-5-fluoro-2-{[2-(3-fluoropyridin-2-yl)-1H-imidazol-1-yl]methyl}-1H-benzimidazole | | m/z 340 [M + 1] |
| 653 | 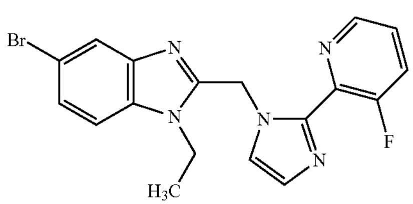 | 5-bromo-1-ethyl-2-{[2-(3-fluoropyridin-2-yl)-1H-imidazol-1-yl]methyl}-1H-benzimidazole | (CDCl3) 8.46 (s, 1H), 7.90 (s, 1H), 7.62 (t, 1H), 7.32-7.42 (m, 2H), 7.17-7.27 (m, 2H), 7.06 (s, 1H), 6.02 (s, 2H), 4.22 (q, 2H), 1.06 (t, 3H) | |

TABLE 6-continued

| Cpd # | STRUCTURE | IUPAC NAME | NMR | MS (m/z) |
|---|---|---|---|---|
| 654 | 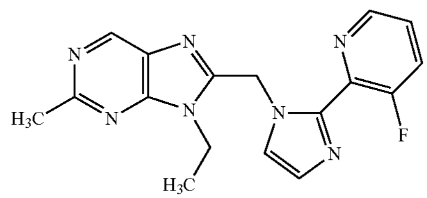 | 9-ethyl-8-{[2-(3-fluoropyridin-2-yl)-1H-imidazol-1-yl]methyl}-2-methyl-9H-purine | (CDCl3) 8.96 (s, 1H), 8.40 (d, 1H), 7.59 (m, 1H), 7.30 (m, 2H), 7.12 (s, 1H), 6.07 (s, 2H), 4.30 (q, 2H), 2.78 (s, 3H), 1.20 (t, 3H) | |
| 655 | 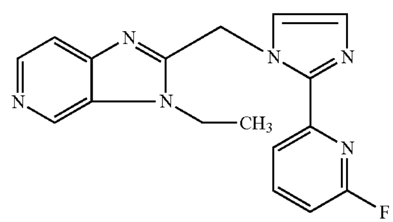 | 3-ethyl-2-{[2-(6-fluoropyridin-2-yl)-1H-imidazol-1-yl]methyl}-3H-imidazo[4,5-c]pyridine | (CDCl3) 8.84 (s, 1H), 8.47 (d, J = 5.7Hz, 1H), 8.20 (dd, J = 7.8, 3.0 Hz, 1H), 7.91 (q, J = 8.1Hz, 1H), 7.28 (s, 1H), 7.25 (d, J = 9.9 Hz, 2H), 6.91 (dd, J = 5.1, 3Hz, 1H), 6.35 (s, 2H), 4.39 (q, J = 5.4Hz, 2H), 1.49 (t, J = 5.4Hz, 3H) | m/z 323 [M + 1] |
| 656 | 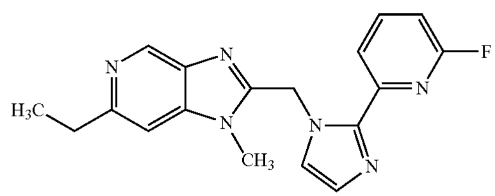 | 6-ethyl-2-{[2-(6-fluoropyridin-2-yl)-1H-imidazol-1-yl]methyl}-1-methyl-1H-imidazo[4,5-c]pyridine | (CDCl3) 8.96 (s, 1H), 8.17 (br d, J = 7.6Hz, 1H), 7.87 (q, J = 7.8 Hz, 1H), 7.21 (s, 1H), 7.19 (s, 1H), 7.12 (s, 1H), 6.87 (m, 1H), 6.24 (s, 2H), 3.83 (s, 3H), 2.95 (q, J = 7.2Hz, 2H), 1.36 (t, J = 7.2Hz 3H) | m/z 337 [M + 1] |
| 657 | 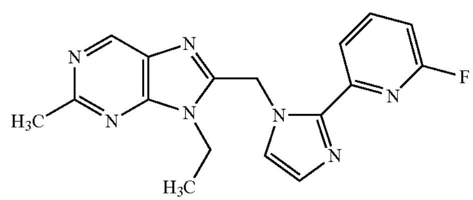 | 9-ethyl-8-{[2-(6-fluoropyridin-2-yl)-1H-imidazol-1-yl]methyl}-2-methyl-9H-purine | (CDCl3) 8.96 (s, 1H), 8.17 (br d, J = 7.6Hz, 1H), 7.87 (q, J = 7.8 Hz, 1H), 7.21 (s, 1H), 7.19 (s, 1H), 7.12 (s, 1H), 6.87 (m, 1H), 6.24 (s, 2H), 3.83 (s, 3H), 2.95 (q, J = 7.2Hz, 2H), 1.36 (t, J = 7.2Hz, 6H) | m/z 337 [M + 1] |

TABLE 6-continued

| Cpd # | STRUCTURE | IUPAC NAME | NMR | MS (m/z) |
|---|---|---|---|---|
| 658 | 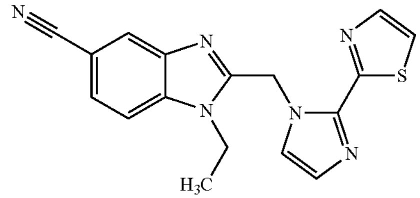 | 1-ethyl-2-{[2-(1,3-thiazol-2-yl)-1H-imidazol-1-yl]methyl}-1H-benzimidazole-5-carbonitrile | (DMSO) 8.05 (s, 1H), 7.80 (d, 1H), 7.73 (d, 1H), 7.65 (d, 1H), 7.60 (d, 1H), 7.48 (s, 1H), 7.10 (s, 1H), 6.20 (s, 2H), 4.40 (q, 2H), 1.35 (t, 3H) | |
| 659 | 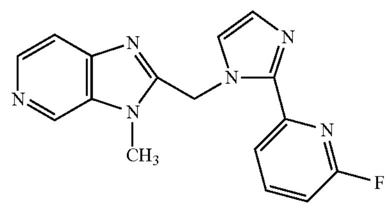 | 2-{[2-(6-fluoropyridin-2-yl)-1H-imidazol-1-yl]methyl}-3-methyl-3H-imidazo[4,5-c]pyridine | (DMSO) 8.95 (s, 1H), 8.22 (d, J = 5.4Hz, 1H), 7.99 (m, 2H), 7.54 (s, 1H), 7.43 (d, J = 5.4Hz, 1H), 7.16 (s, 1H), 7.0 (br d, J = 8.1 Hz, 1H), 6.08 (s, 2H), 4.01 (s, 3H) | m/z 309 [M + 1] |
| 660 | 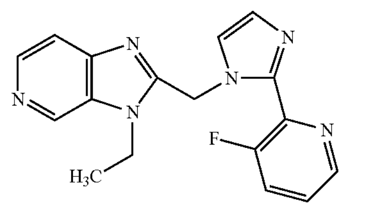 | 3-ethyl-2-{[2-(3-fluoropyridin-2-yl)-1H-imidazol-1-yl]methyl}-3H-imidazo[4,5-c]pyridine | (CDCl3) 8.81 (s, 1H), 8.46 (m, 2H), 7.64 (m, 2H), 7.36 (m, 1H), 7.25 (s, 1H), 7.12 (s, 1H), 6.11 (s, 2H), 4.38 (q, J = 7.2Hz, 2H), 1.20 (t, J = 7.2Hz, 3H) | m/z 323 [M + 1] |
| 661 | 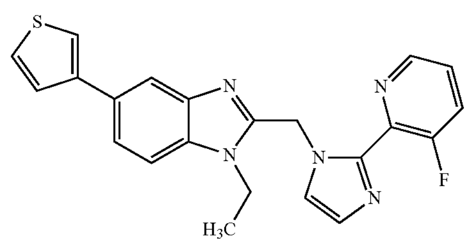 | 1-ethyl-2-{[2-(3-fluoropyridin-2-yl)-1H-imidazol-1-yl]methyl}-5-thien-3-yl-1H-benzimidazole | | 404.3 |

TABLE 6-continued

| Cpd # | STRUCTURE | IUPAC NAME | NMR | MS (m/z) |
|---|---|---|---|---|
| 662 | 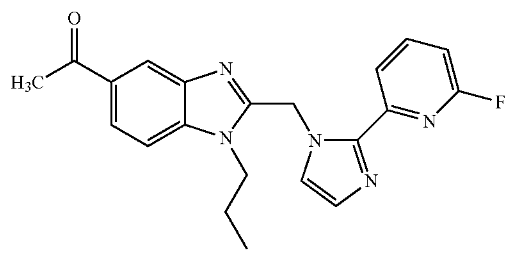 | 1-(1-propyl-2-{[2-(6-fluoropyridin-2-yl)-1H-imidazol-1-yl]methyl}-1H-benzimidazol-5-yl)ethanone | (CDCl3) 8.38 (s, 1H), 8.18 (dd, 1H), 8.00 (d, 1H), 7.91 (q, 1H), 7.39 (d, 1H), 7.24 (s, 1H), 7.18 (s, 1H), 6.89 (dd, 1H), 6.31 (s, 2H), 4.28 (t, 2H), 2.67 (s, 3H), 1.69 (q, 2H), 0.88 (t, 3H) | |
| 663 | 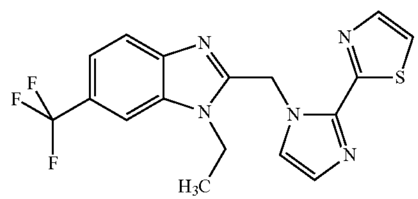 | 1-ethyl-2-{[2-(1,3-thiazol-2-yl)-1H-imidazol-1-yl]methyl}-6-(trifluoromethyl)-1H-benzimidazole | (CD3Cl) 7.87 (m, 2H), 7.62 (s, 1H), 7.55 (d, 1H), 7.41 (d, 1H), 7.18 (s, 1H), 7.15 (s, 1H), 6.37 (s, 2H), 4.30 (q, 2H), 1.14 (t, 3H) | |
| 664 | 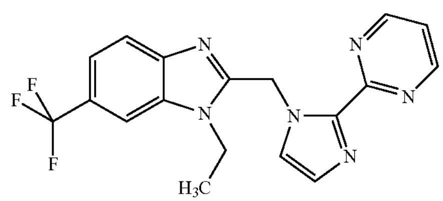 | 1-ethyl-2-[(2-pyrimidin-2-yl-1H-imidazol-1-yl)methyl]-6-(trifluoromethyl)-1H-benzimidazole | (CDCl3) 8.86 (d, 2H), 7.85 (d, 1H), 7.62 (s, 1H), 7.55 (d, 1H), 7.29 (m, 2H), 7.16 (s, 1H), 6.39 (s, 2H), 4.28 (q, 2H), 1.18 (t, 3H) | |
| 665 | 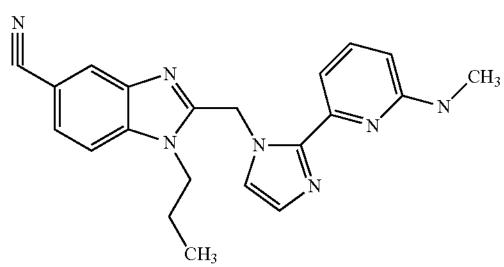 | 2-({2-[6-(methylamino)pyridin-2-yl]-1H-imidazol-1-yl}methyl)-1-propyl-1H-benzimidazole-5-carbonitrile | | m/z 372 [M + 1] |

TABLE 6-continued

| Cpd # | STRUCTURE | IUPAC NAME | NMR | MS (m/z) |
|---|---|---|---|---|
| 666 | 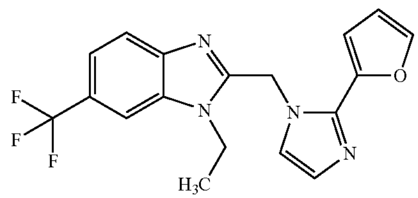 | 1-ethyl-2-{[2-(2-furyl)-1H-imidazol-1-yl]methyl}-6-(trifluoromethyl)-1H-benzimidazole | | m/z 361 [M + 1] |
| 667 | 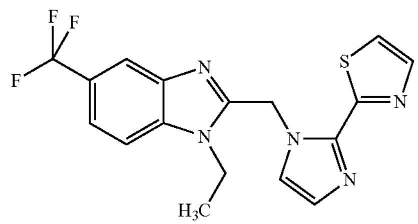 | 1-ethyl-2-{[2-(1,3-thiazol-2-yl)-1H-imidazol-1-yl]methyl}-5-(trifluoromethyl)-1H-benzimidazole | (CDCl3) 8.14 (s, 1H), 7.84 (d, 1H), 7.58 (d, 1H), 7.40 (m, 2H), 7.18 (s, 1H), 7.15 (s, 1H), 6.37 (s, 2H), 4.30 (q, 2H), 1.12 (t, 3H) | |
| 668 | 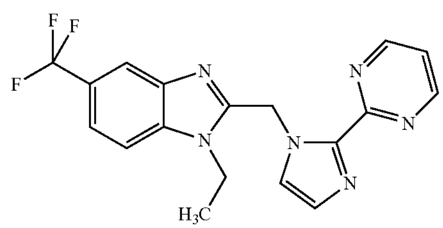 | 1-ethyl-2-[(2-pyrimidin-2-yl-1H-imidazol-1-yl)methyl]-5-(trifluoromethyl)-1H-benzimidazole | (CDCl3) 8.85 (d, 2H), 8.06 (s, 1H) <7.54 (d, 1H), 7.40 (d, 1H), 7.28 (m, 2H), 7.15 (s, 1H), 6.38 (s, 2H), 4.27 (q, 2H), 1.15 (t, 3H) | |
| 669 | 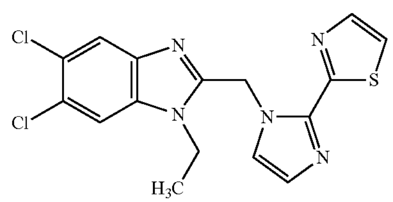 | 5,6-dichloro-1-ethyl-2-{[2-(1,3-thiazol-2-yl)-1H-imidazol-1-yl]methyl}-1H-benzimidazole | (CDCl3) 7.84 (m, 2H), 7.44 (s, 1H), 7.34 (d, 1H), 7.14 (m, 2H), 6.31 (s, 2H), 4.20 (q, 2H), 1.06 (t, 3H) | |

TABLE 6-continued

| Cpd # | STRUCTURE | IUPAC NAME | NMR | MS (m/z) |
|---|---|---|---|---|
| 670 | 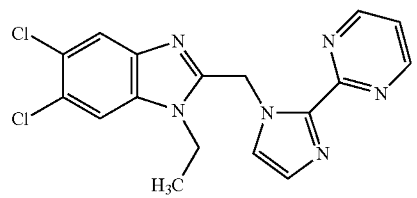 | 5,6-dichloro-1-ethyl-2-[(2-pyrimidin-2-yl-1H-imidazol-1-yl)methyl]-1H-benzimidazole | (CDCl3) 8.84 (d, 2H), 7.84 (s, 1H), 7.43 (s, 1H), 7.26 (m, 2H), 7.13 (s, 1H), 6.33 (s, 2H), 4.18 (q, 2H), 1.10 (t, 3H) | |
| 671 | 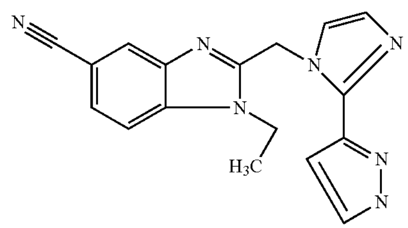 | 1-ethyl-2-{[2-(1H-pyrazol-3-yl)-1H-imidazol-1-yl]methyl}-1H-benzimidazole-5-carbonitrile | (CDCl3) 7.97 (s, 1H), 7.53 (br s, 1H), 7.46 (d, J = 8.7Hz, 1H), 7.35 (d, J = 8.1Hz, 1H), 6.97 (d, J = 6.3Hz, 2H), 6.79 (br s, 1H), 6.10 (s, 2H), 4.22 (q, J = 7.2Hz, 2H), 0.88 (t, J = 7.2Hz, 3H) | m/z 318 [M + 1] |
| 672 | 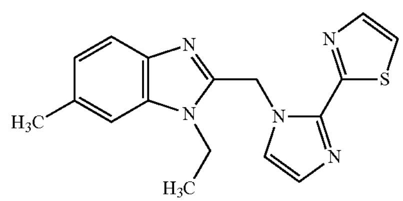 | 1-ethyl-6-methyl-2-{[2-(1,3-thiazol-2-yl)-1H-imidazol-1-yl]methyl}-1H-benzimidazole | (CDCl3) 7.86 (d, 1H), 7.65 (d, 1H), 7.39 (d, 1H), 7.14 (d, 1H), 7.11 (m, 3H), 6.31 (s, 2H), 4.16 (q, 2H), 1.02 (t, 3H) | |
| 673 | 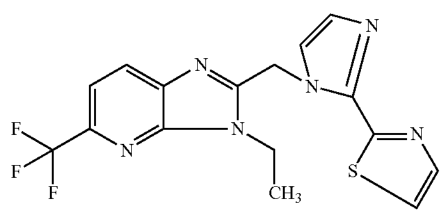 | 3-ethyl-2-{[2-(1,3-thiazol-2-yl)-1H-imidazol-1-yl]methyl}-5-(trifluoromethyl)-3H-imidazo[4,5-b]pyridine | (CD3OD) 8.03 (d, J = 8.4Hz, 1H), 7.72 (d, J = 3.3Hz, 1H), 7.65 (d, J = 8.1Hz, 1H), 7.55 (d, J = 3.3Hz, 1H), 7.46 (d, J = 1.5 Hz, 1H), 7.20 (d, J = 1.5Hz, 1H), 6.3 (s, 2H), 4.56 (q, J = 6.9Hz, 2H), 1.49 (t, J = 6.9Hz, 3H) | |

TABLE 6-continued

| Cpd # | STRUCTURE | IUPAC NAME | NMR | MS (m/z) |
|---|---|---|---|---|
| 674 | 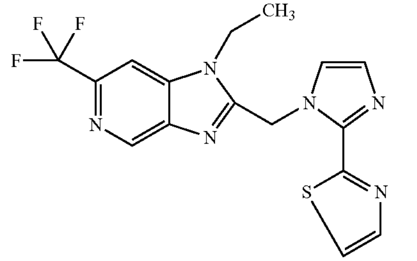 | 1-ethyl-2-{[2-(1,3-thiazol-2-yl)-1H-imidazol-1-yl]methyl}-6-(trifluoromethyl)-1H-imidazo[4,5-c]pyridine | (CD3OD) 8.83 (s, 1H), 8.14 (s, 1H), 7.71 (d, J = 2.7Hz, 1H), 7.53 (d, J = 2.7Hz, 1H), 7.45 (d, J = 0.9Hz, 1H), 7.19 (d, J = 0.9 Hz, 1H), 6.30 (s, 2H), 4.54 (q, J = 5.4Hz, 2H), 1.46 (t, J = 5.4Hz, 3H) | m/z 379 [M + 1] |
| 675 | 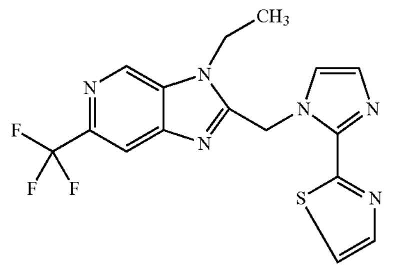 | 3-ethyl-2-{[2-(1,3-thiazol-2-yl)-1H-imidazol-1-yl]methyl}-6-(trifluoromethyl)-3H-imidazo[4,5-c]pyridine | (CD3OD) 9.02 (s, 1H), 7.89 (s, 1H), 7.70 (d, J = 3Hz, 1H), 7.52 (d, J = 3.3Hz, 1H), 7.46 (d, J = 1.5Hz, 1H), 7.19 (d, J = 1.5Hz, 1H), 6.29 (s, 2H), 4.56 (q, J = 7.5 Hz, 2H), 1.52 (t, J = 7.5Hz, 3H) | m/z 379 [M + 1] |
| 676 | 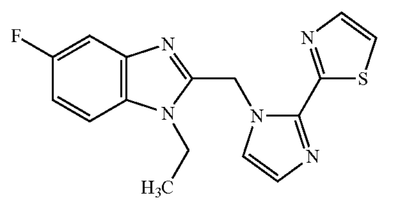 | 1-ethyl-5-fluoro-2-{[2-(1,3-thiazol-2-yl)-1H-imidazol-1-yl]methyl}-1H-benzimidazole | (CDCl3) 7.88 (d, 1H), 7.45 (dd, 1H), 7.39 (d, 1H), 7.23 (dd, 1H), 7.18 (s, 1H), 7.12 (s, 1H), 7.06 (td, 1H) | |
| 677 | 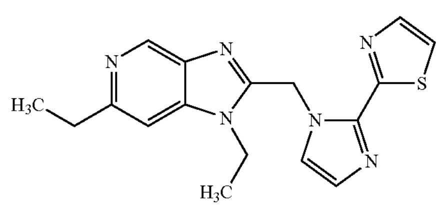 | 1,6-diethyl-2-{[2-(1,3-thiazol-2-yl)-1H-imidazol-1-yl]methyl}-1H-imidazo[4,5-c]pyridine | (CDCl3) 9.01 (d, J = 1.2Hz, 1H), 7.85 (d, J = 3.6Hz, 1H), 7.40 (d, J = 3.0 Hz, 1H), 7.16 (d, J = 1.5 Hz, 1H), 7.14 (d, J = 0.9Hz, 1H), 7.10 (s, 1H), 6.34 (s, 2H), 4.22 (q, J = 7.2Hz, 2H), 2.93 (q, J = 7.2Hz, 2H), 1.35 (t, J = 7.2Hz, 3H), 1.10 (t, J = 7.2Hz, 3H) | m/z 339 [M + 1] |

TABLE 6-continued

| Cpd # | STRUCTURE | IUPAC NAME | NMR | MS (m/z) |
|---|---|---|---|---|
| 678 | 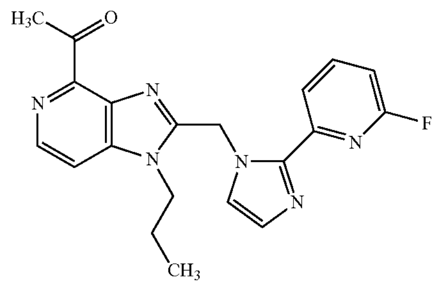 | 1-(2-{[2-(8-fluoropyridin-2-yl)-1H-imidazol-1-yl]methyl}-1-propyl-1H-imidazo[4,5-c]pyridin-4-yl)ethanone | (CDCl3) 9.01 (d, J = 1.2Hz, 1H), 7.85 (d, J = 3.6Hz, 1H), 7.40 (d, J = 3.0 Hz, 1H), 7.16 (d, J = 1.5 Hz, 1H), 7.14 (d, J = 0.9Hz, 1H), 7.10 (s, 1H), 6.34 (s, 2H), 4.22 (q, J = 7.2Hz, 2H), 2.93 (q, J = 7.2Hz, 2H), 1.35 (t, J = 7.2Hz, 3H), 1.10 (t, J = 7.2Hz, 3H) | m/z 339 [M + 1] |
| 679 | 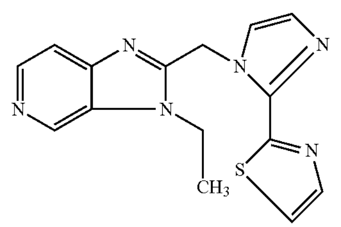 | 3-ethyl-2-{[2-(1,3-thiazol-2-yl)-1H-imidazol-1-yl]methyl}-3H-imidazo[4,5-c]pyridine | (CD3OD) 8.87 (s, 1H), 8.30 (d, J = 5.7Hz, 1H), 7.75 (d, J = 3.3 Hz, 1H), 7.57 (d, J = 4.8Hz, 1H), 7.52 (d, J = 3.3Hz, 1H), 7.39 (d, J = 1.5Hz, 1H), 7.18 (d, J = 1.5 Hz, 1H), 6.29 (s, 2H), 4.52 (q, J = 7.5Hz, 2H), 1.44 (t, J = 7.5Hz, 3H) | m/z 311 [M + 1] |
| 680 | 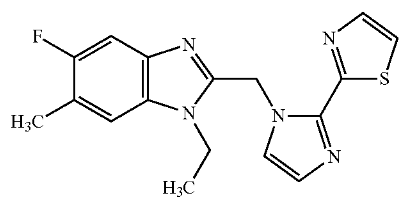 | 1-ethyl-5-fluoro-6-methyl-2-{[2-(1,3-thiazol-2-yl)-1H-imidazol-1-yl]methyl}-1H-benzimidazole | (CDCl3) 7.86 (d, 1H), 7.40 (m, 2H), 7.15 (d, 1H), 7.11 (d, 1H), 7.07 (d, 1H), 6.30 (s, 2H), 4.17 (q, 2H), 2.39 (d, 3H), 1.03 (t, 3H) | |
| 681 | 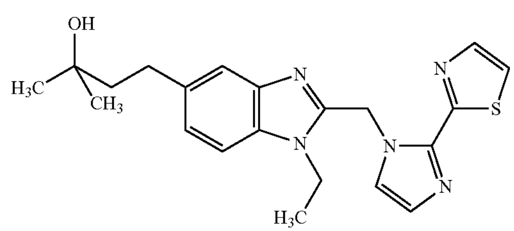 | 4-(1-ethyl-2-{[2-(1,3-thiazol-2-yl)-1H-imidazol-1-yl]methyl}-1H-benzimidazol-5-yl)-2-methylbutan-2-ol | (CDCl3) 7.85 (d, 1H), 7.60 (s, 1H), 7.38 (d, 1H), 7.22 (m, 1H), 7.15 (m, 2H), 7.09 (s, 1H), 6.31 (s, 2H), 4.17 (q, 2H), 2.80 (m, 2H), 1.81 (m, 2H), 1.22 (d, 6H), 1.01 (t, 3H) | m/z 396.3 [M + 1] |

TABLE 6-continued

| Cpd # | STRUCTURE | IUPAC NAME | NMR | MS (m/z) |
|---|---|---|---|---|
| 682 | 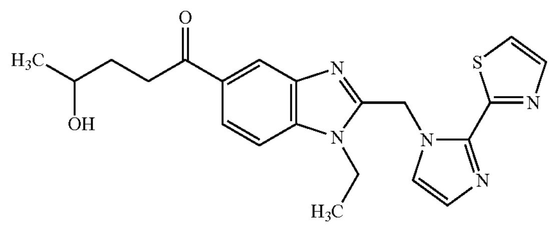 | 1-(1-ethyl-2-{[2-(1,3-thiazol-2-yl)-1H-imidazol-1-yl]methyl}-1H-benzimidazol-5-yl)-4-hydroxypentan-1-one | (CDCl3) 8.44 (d, 1H), 7.80 (dd, 1H), 7.85 (d, 1H), 7.40 (d, 1H), 7.36 (d, 1H), 7.18 (d, 1H), 7.14 (d, 1H), 6.36 (s, 2H), 4.27 (q, 2H), 3.86 (m, 1H), 3.19 (t, 2H), 1.93 (m, 2H), 1.25 (d, 3H), 1.09 (t 3H) | m/z 410.2 [M + 1] |
| 683 | 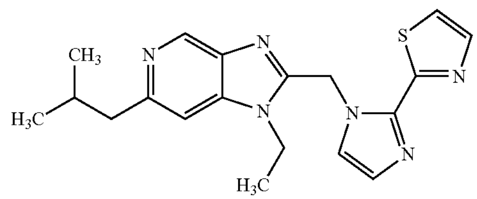 | 1-ethyl-6-isobutyl-2-{[2-(1,3-thiazol-2-yl)-1H-imidazol-1-yl]methyl}-1H-imidazo[4,5-c]pyridine | (CDCl3) 9.02 (s, 1H), 7.85 (d, 1H), 7.40 (d, 1H), 7.18 (s, 1H), 7.15 (s, 1H), 7.06 (s, 1H), 6.35 (s, 2H), 4.22 (q, 2H), 2.75 (d, 1H), 2.1 (m, 1H), 1.10 (t, 3H), 0.93 (d, 6H) | |
| 684 | 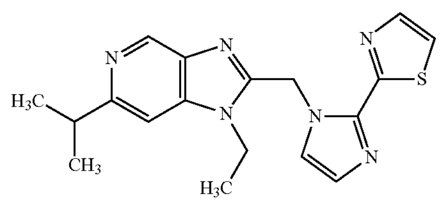 | 1-ethyl-6-isopropyl-2-{[2-(1,3-thiazol-2-yl)-1H-imidazol-1-yl]methyl}-1H-imidazo[4,5-c]pyridine | (CDCl3) 9.01 (s, 1H), 7.83 (d, J = 3.2Hz, 1H), 7.38 (d, J = 3.2Hz, 1H), 7.15 (s, 1H), 7.12 (s, 1H), 7.09 (s, 1H), 6.32 (s, 2H), 4.21 (q, J = 7.2Hz, 2H), 3.17 (sept, J = 6.8Hz, 1H), 1.34 (d, J = 6.8 Hz, 6H), 1.10 (t, J = 7.2Hz, 3H) | m/z 353 [M + 1] |
| 685 | 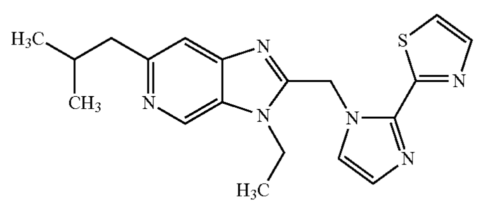 | 3-ethyl-6-isobutyl-2-{[2-(1,3-thiazol-2-yl)-1H-imidazol-1-yl]methyl}-3H-imidazo[4,5-c]pyridine | (CDCl3) 8.70 (s, 1H), 7.85 (d, 1H), 7.41 (s, 1H), 7.40 (d, 1H), 7.20 (s, 1H), 7.15 (s, 1H), 6.34 (s, 2H), 4.33 (q, 2H), 2.75 (d, 1H), 2.1 (m, 1H), 1.19 (t, 3H), 0.93 (d, 6H) | |

| Cpd # | STRUCTURE | IUPAC NAME | NMR | MS (m/z) |
|---|---|---|---|---|
| 686 | 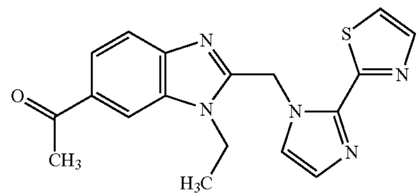 | 1-(1-ethyl-2-{[2-(1,3-thiazol-2-yl)-1H-imidazol-1-yl]methyl}-1H-benzimidazol-6-yl)ethanone | (CDCl3) 8.05 (d, 1H), 7.92 (dd, 1H), 7.87 (dd, 1H), 7.81 (dd, 1H), 7.40 (d, 1H), 7.20 (d, 1H), 7.14 (d, 1H), 6.17 (s, 2H), 4.33 (q, 2H), 2.67 (s, 3H), 1.13 (t, 3H) | |
| 687 | 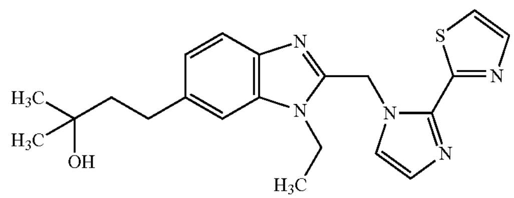 | 4-(1-ethyl-2-{[2-(1,3-thiazol-2-yl)-1H-imidazol-1-yl]methyl}-1H-benzimidazol-6-yl)-2-methylbutan-2-ol | (CDCl3) 7.88 (d, 1H), 7.68 (d, 1H), 7.39 (d, 1H), 7.12-7.18 (m, 3H), 7.09 (d, 1H), 6.13 (s, 2H), 4.19 (q, 1H), 2.80-2.89 (m, 2H), 1.80-1.89 (m, 2H), 1.31 (s, 6H), 1.06 (t, 3H) | |
| 688 | 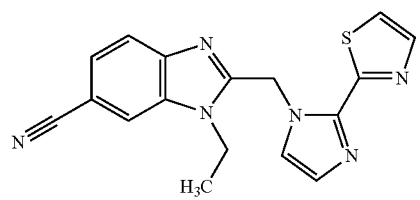 | 1-ethyl-2-{[2-(1,3-thiazol-2-yl)-1H-imidazol-1-yl]methyl}-1H-benzimidazole-6-carbonitrile | (CD3OD) (2HCl Salt) 8.38 (s, 1H), 7.98-8.01 (m, 2H), 7.95 (d, 1H), 7.87 (d, 1H), 7.71 (d, 2H), 6.50 (s, 2H), 4.62 (q, 2H), 1.62 (t, 3H) | |
| 689 | 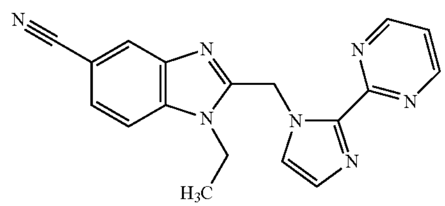 | 1-ethyl-2-[(2-pyrimidin-2-yl-1H-imidazol-1-yl)methyl]-1H-benzimidazole-5-carbonitrile | (CD3OD) (2HCl Salt) 8.88 (d, 2H), 8.08 (d, 1H), 7.95 (d, 1H), 7.93 (d, 1H), 7.90 (s, 1H), 7.73 (dd, 1H), 7.56 (t, 1H), 6.60 (s, 2H), 4.61 (q, 2H), 1.63 (t, 3H) | |
| 690 | 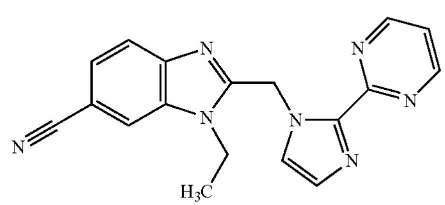 | 1-ethyl-2-[(2-pyrimidin-2-yl-1H-imidazol-1-yl)methyl]-1H-benzimidazole-6-carbonitrile | (CDCl3) 8.85 (d, 2H), 7.82 (d, 1H), 7.69 (d, 1H), 7.55 (dd, 1H), 7.26-7.30 (m, 2H), 7.18 (d, 1H), 6.39 (s, 2H), 4.29 (q, 2H), 1.09 (t, 3H) | |

TABLE 6-continued

| Cpd # | STRUCTURE | IUPAC NAME | NMR | MS (m/z) |
|---|---|---|---|---|
| 691 | 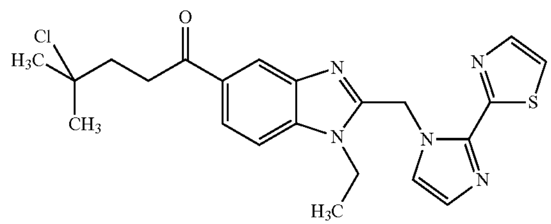 | 4-chloro-1-(1-ethyl-2-{[2-(1,3-thiazol-2-yl)methyl]-1H-imidazol-1-yl]methyl}-1H-benzimidazol-5-yl)-4-methylpentan-1-one | | m/z 442.2 [M − 1] 444.1 [M + 1] |
| 692 | 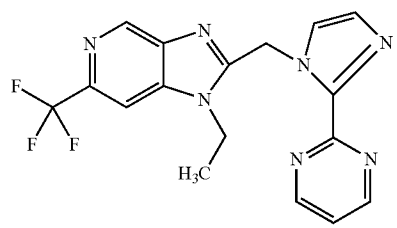 | 1-ethyl-2-[(2-pyrimidin-2-yl-1H-imidazol-1-yl)methyl]-6-(trifluoromethyl)-1H-imidazo[4,5-c]pyridine | (CD3OD) 8.79 (s, 1H), 8.70 (d, J = 5.1Hz, 1H), 8.17 (s, 1H), 7.52 (d, J = 1.2Hz, 1H), 7.31 (d, J = 1.2Hz, 1H), 7.27 (t, J = 5.1Hz, 1H), 6.63 (s, 1H), 6.32 (s, 2H), 4.57 (q, J = 7.5Hz, 2H), 1.50 (t, J = 7.5Hz, 3H) | m/z 374 [M + 1] |
| 693 | 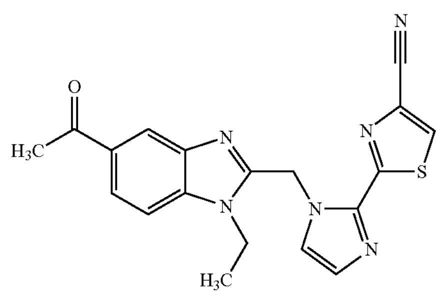 | 2-{1-[(5-acetyl-1-ethyl-1H-benzimidazol-2-yl)methyl]-1H-imidazol-2-yl}-1,3-thiazole-4-carbonitrile | (CDCl3 + CD3OD) 8.29 (s, 1H), 8.25 (d, 1H), 7.97 (dd, 1H), 7.52 (d, 1H), 7.42 (s, 1H), 7.22 (s, 1H), 6.17 (s, 2H), 4.44 (q, 2H), 2.64 (s, 3H), 1.43 (t, 3H) | |
| 694 | 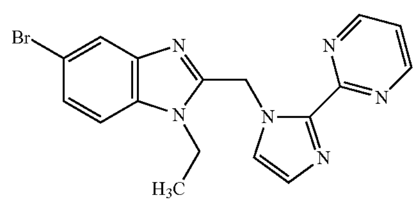 | 5-bromo-1-ethyl-2-[(2-pyrimidin-2-yl-1H-imidazol-1-yl)methyl]-1H-benzimidazole | (CDCl3) 8.85 (d, 2H), 7.91 (d, 1H), 7.39 (dd, 1H), 7.27 (t, 1H), 7.25 (m, 1H), 7.19 (d, 1H), 7.13 (d, 1H), 6.35 (s, 2H), 4.20 (q, 2H), 1.08 (t, 3H) | m/z 377 [M + 1] |

TABLE 6-continued

| Cpd # | STRUCTURE | IUPAC NAME | NMR | MS (m/z) |
|---|---|---|---|---|
| 695 | 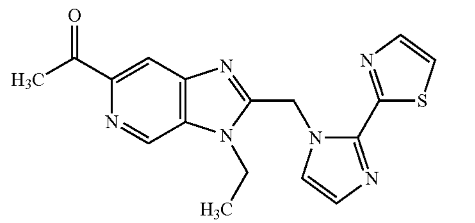 | 1-(3-ethyl-2-{[2-(1,3-thiazol-2-yl)-1H-imidazol-1-yl]methyl}-3H-imidazo[4,5-c]pyridin-6-yl)ethanone | (CDCl3) 8.79 (d, 2H), 8.47 (d, 1H), 7.83 (d, 1H), 7.40 (d, 1H), 7.19 (d, 1H), 7.15 (d, 1H), 6.39 (s, 2H), 4.02 (q, 2H), 2.77 (s, 3H), 1.86 (t, 3H) | m/z 353.2 [M + 1] |
| 696 | 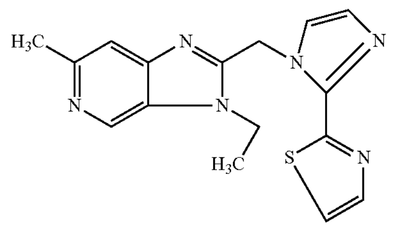 | 3-ethyl-6-methyl-2-{[2-(1,3-thiazol-2-yl)-1H-imidazol-1-yl]methyl}-3H-imidazo[4,5-c]pyridine | (CDCl3) 8.67 (s, 1H), 7.83 (d, J = 3.0 Hz, 1H), 7.5 (s, 1H), 7.38 (d, J = 3.0 Hz, 1H), 7.18 (d, J = 1.2 Hz, 1H), 7.14 (d, J = 1.2 Hz, 1H), 6.33 (s, 2H), 4.32 (q, J = 7.5Hz, 2H), 1.16 (t, J = 7.5Hz, 3H) | m/z 325 [M + 1] |
| 697 | 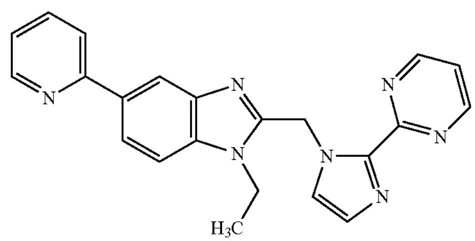 | 1-ethyl-5-pyridin-2-yl-2-[(2-pyrimidin-2-yl-1H-imidazol-1-yl)methyl]-1H-benzimidazole | | m/z 382.2 [M + 1] |
| 698 | 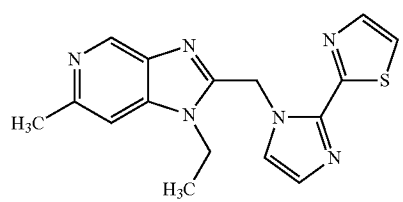 | 1-ethyl-6-methyl-2-{[2-(1,3-thiazol-2-yl)-1H-imidazol-1-yl]methyl}-1H-imidazo[4,5-c]pyridine | (CDCl3) 8.96 (d, J = 0.9Hz, 1H), 7.84 (d, J = 3.3Hz, 1H), 7.39 (d, J = 3.0 Hz, 1H), 7.16 (d, J = 0.9 Hz, 1H), 7.13 (d, J = 1.5Hz, 1H), 7.10 (s, 1H), 6.33 (s, 2H), 4.21 (q, J = 7.2Hz, 2H), 2.66, (s, 2H), 1.09 (t, J = 7.2Hz, 3H) | m/z 325 [M + 1] |

TABLE 6-continued

| Cpd # | STRUCTURE | IUPAC NAME | NMR | MS (m/z) |
|---|---|---|---|---|
| 699 | 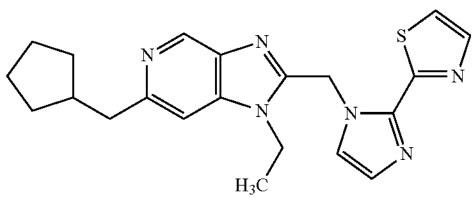 | 6-(cyclopentylmethyl)-1-ethyl-2-{[2-(1,3-thiazol-2-yl)-1H-imidazol-1-yl]methyl}-1H-imidazo[4,5-c]pyridine | (CDCl3) 9.01 (s, 1H), 7.85 (d, 1H), 7.41 (d, 1H), 7.18 (d, 1H), 7.15 (d, 1H), 7.08 (s, 1H), 6.36 (s, 2H), 4.22 (q, 2H), 2.86 (d, 2H), 2.25-2.40 (m, 1H), 1.46-1.78 (m, 6H), 1.15-1.30 (m, 2H), 1.08 (t 3H) | |
| 700 | 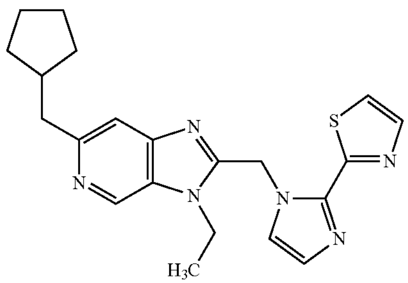 | 6-(cyclopentylmethyl)-3-ethyl-2-{[2-(1,3-thiazol-2-yl)-1H-imidazol-1-yl]methyl}-3H-imidazo[4,5-c]pyridine | (CDCl3) 8.68 (s, 1H), 7.84 (d, 1H), 7.48 (s, 1H), 7.41 (d, 1H), 7.20 (s, 1H), 7.15 (s, 1H), 6.14 (s, 2H), 4.32 (q, 2H), 2.88 (d, 2H), 2.25-2.38 (m, 1H), 1.45-72 (m, 6H), 1.16-1.33 (m, 5H) | |
| 701 | 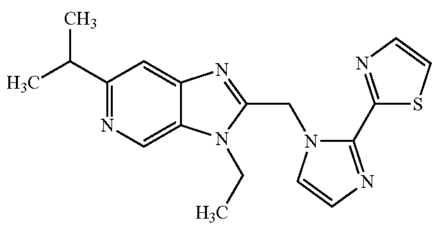 | 3-ethyl-6-isopropyl-2-{[2-(1,3-thiazol-2-yl)-1H-imidazol-1-yl]methyl}-3H-imidazo[4,5-c]pyridine | (CDCl3) 8.70 (d, J = 1.2Hz, 1H), 7.83 (d, J = 3.0 Hz, 1H), 7.53 (d, J = 0.9Hz, 1H), 7.39 (d, J = 3.0 Hz, 1H), 7.18 (d, J = 0.9Hz, 1H), 7.14 (d, J = 0.9Hz, 1H), 6.32 (s, 2H), 4.32 (q, J = 7.2Hz, 2H), 3.18 (sept, J = 6.9Hz, 1H), 1.34 (d, J = 6.9Hz, 6H), 1.17 (t, J = | m/z 353 [M + 1] |
| 702 | 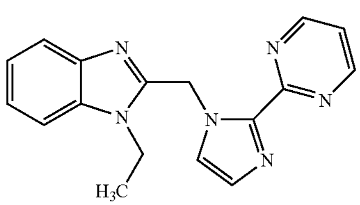 | 1-ethyl-2-[(2-pyrimidin-2-yl-1H-imidazol-1-yl)methyl]-1H-benzimidazole | | m/z 305 [M + 1] |

TABLE 6-continued

| Cpd # | STRUCTURE | IUPAC NAME | NMR | MS (m/z) |
|---|---|---|---|---|
| 703 | 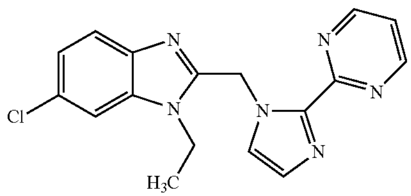 | 6-chloro-1-ethyl-2-[(2-pyrimidin-2-yl-1H-imidazol-1-yl)methyl]-1H-benzimidazole | | m/z 339 [M + 1] |
| 704 | 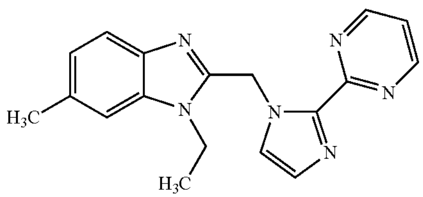 | 1-ethyl-6-methyl-2-[(2-pyrimidin-2-yl-1H-imidazol-1-yl)methyl]-1H-benzimidazole | | m/z 319 [M + 1] |
| 705 | 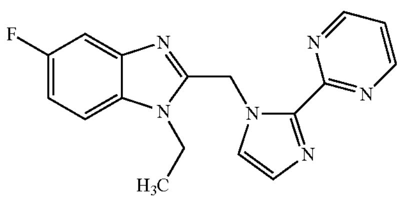 | 1-ethyl-5-fluoro-2-[(2-pyrimidin-2-yl-1H-imidazol-1-yl)methyl]-1H-benzimidazole | | m/z 323 [M + 1] |
| 706 | 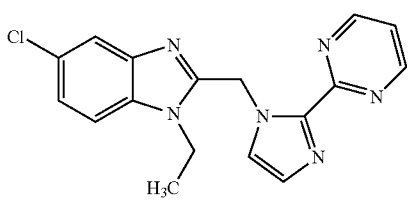 | 5-chloro-1-ethyl-2-[(2-pyrimidin-2-yl-1H-imidazol-1-yl)methyl]-1H-benzimidazole | | m/z 339 [M + 1] |
| 707 | 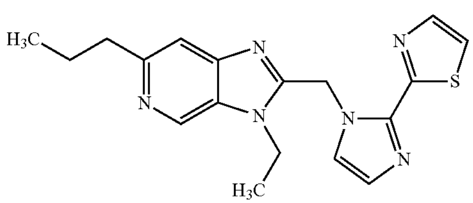 | 3-ethyl-6-propyl-2-{[2-(1,3-thiazol-2-yl)-1H-imidazol-1-yl]methyl}-3H-imidazo[4,5-c]pyridine | (CDCl3) 8.69 (d, J = 0.9Hz, 1H), 7.83 (d, J = 3.3Hz, 1H), 7.49 (d, J = 1.2Hz, 1H), 7.39 (d, J = 3.6 Hz, 1H), 7.18 (d, J = 0.9Hz, 1H), 7.14 (d, J = 1.5Hz, 1H), 6.33 (s, 2H), 4.31 (q, J = 7.2Hz, 2H), 2.86 (m, 2H), 1.78 (sext, J = 7.2 Hz, 2H), 1.17 (t, J = 7.2Hz, 3H), 0.97 (d, J = 7.2Hz, 3H) | m/z 353 [M + 1] |

TABLE 6-continued

| Cpd # | STRUCTURE | IUPAC NAME | NMR | MS (m/z) |
|---|---|---|---|---|
| 708 | 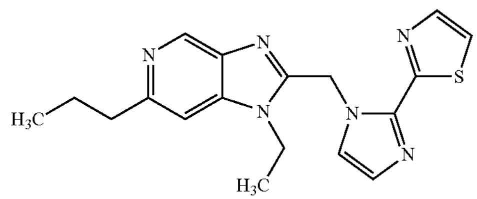 | 1-ethyl-6-propyl-2-{[2-(1,3-thiazol-2-yl)-1H-imidazol-1-yl]methyl}-1H-imidazo[4,5-c]pyridine | (CDCl3) 9.00 (d, J = 0.9Hz, 1H), 7.84 (d, J = 3.0 Hz, 1H), 7.39 (d, J = 3.3Hz, 1H), 7.16 (d, J = 1.5 Hz, 1H), 7.13 (d, J = 1.5Hz, 1H), 7.09 (s, 1H), 6.33 (s, 2H), 4.22 (q, J = 7.2Hz, 2H), 2.86 (m, 2H), 1.79 (sext, J = 7.2Hz, 2H), 1.09 (t, J = 7.2Hz, 3H), 0.96 (t, J = 7.2Hz, 3H) | m/z 353 [M + 1] |
| 709 | 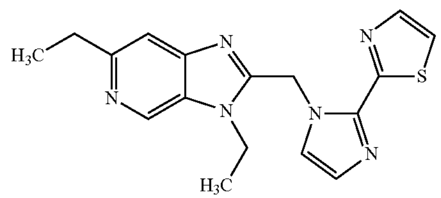 | 3,6-diethyl-2-{[2-(1,3-thiazol-2-yl)-1H-imidazol-1-yl]methyl}-3H-imidazo[4,5-c]pyridine | (CDCl3) 8.69 (d, J = 0.9Hz, 1H), 7.84 (d, J = 3.6Hz, 1H), 7.51 (s, 1H), 7.39 (d, J = 3.6Hz, 1H), 7.18 (d, J = 1.5Hz, 1H), 7.14 (d, J = 0.9Hz, 1H), 6.33 (s, 2H), 4.32 (q, J = 7.2Hz, 2H), 2.93 (q, J = 7.2Hz, 2H), 1.34 (t, J = 7.2 Hz, 3H), 1.17 (t, J = 7.2Hz, 3H) | m/z 339 [M + 1] |
| 710 | 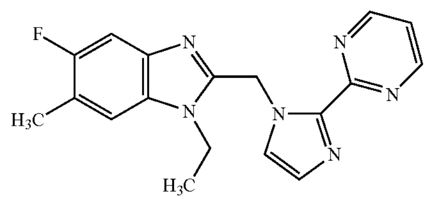 | 1-ethyl-5-fluoro-6-methyl-2-{[2-pyrimidin-2-yl-1H-imidazol-1-yl]methyl}-1H-benzimidazole | | m/z 337.4 [M + 1] |
| 711 | 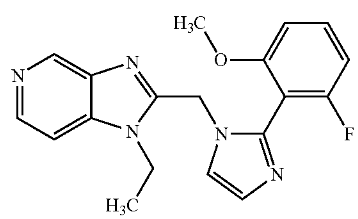 | 1-ethyl-2-{[2-(2-fluoro-6-methoxyphenyl)-1H-imidazol-1-yl]methyl}-1H-imdazo[4,5-c]pyridine | (CDCl3) 9.04 (d, J = 0.9Hz, 1H), 8.42 (d, J = 5.4Hz, 1H), 7.46-7.38 (m, 1H), 7.25-7.22 (m, 2H), 7.00 (d, J = 0.9Hz, 1H), 6.85-6.76 (m, 2H), 5.31, 5.22 (AB, J = 15.3Hz, 2H), 3.85 (q, J = 7.2Hz, 2H), 3.77 (s, 3H), 1.00 (t, J = 7.2 Hz, 3H) | m/z 352 [M + 1] |

TABLE 6-continued

| Cpd # | STRUCTURE | IUPAC NAME | NMR | MS (m/z) |
|---|---|---|---|---|
| 712 | 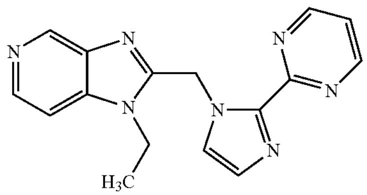 | 1-ethyl-2-[(2-pyrimidin-2-yl-1H-imidazol-1-yl)methyl]-1H-imidazo[4,5-c]pyridine | (CDCl3) 9.09 (s, 1H), 8.85 (d, 2H), 8.46 (d, 1H), 7.26–7.30 (m, 3H), 7.16 (1H), 6.39 (s, 2H), 4.25 (q, 2H), 1.15 (t, 3H) | |
| 713 | 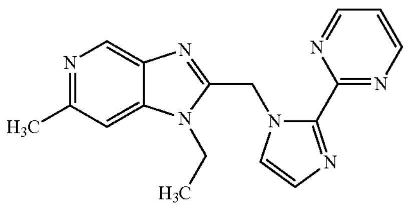 | 1-ethyl-6-methyl-2-[(2-pyrimidin-2-yl-1H-imidazol-1-yl)methyl]-1H-imidazo[4,5-c]pyridine | (CDCl3) 8.95 (d, J = 1.2Hz, 1H), 8.84 (d, J = 4.8Hz, 2H), 7.27 (t, J = 5.1Hz, 1H), 7.25 (d, J = 1.2 Hz, 1H), 7.13 (d, J = 1.2Hz, 1H), 7.10 (s, 1H), 6.35 (s, 2H), 4.19 (q, J = 7.2Hz, 2H), 2.65 (s, 3H), 1.12 (t, J = 7.2Hz, 3H) | m/z 320 [M + 1] |
| 714 | 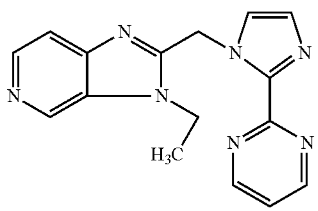 | 3-ethyl-2-[(2-pyrimidin-2-yl-1H-imidazol-1-yl)methyl]-3H-imidazo[4,5-c]pyridine | (DMSO) 8.94 (s, 1H), 8.71 (d, J = 5.1Hz, 2H), 8.22 (d, J = 5.7 Hz, 1H), 7.53 (d, J = 1.2Hz, 1H), 7.43 (d, J = 5.4Hz, 1H), 7.31 (t, J = 4.5Hz, 1H), 7.17 (d, J = 1.2 Hz, 1H), 6.22 (s, 2H), 4.46 (q, J = 7.5Hz, 2H), 1.39 (t, J = 7.5 Hz 3H) | m/z 306 [M + 1] |
| 715 | 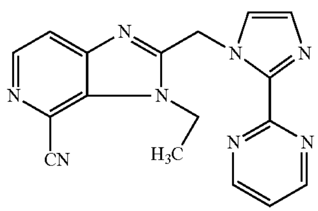 | 3-ethyl-2-[(2-pyrimidin-2-yl-1H-imidazol-1-yl)methyl]-3H-imidazo[4,5-c]pyridine-4-carbonitrile | (CD3OD) 8.70 (d, J = 5.1Hz, 2H), 8.41 (d, J = 5.4Hz, 1H), 7.73 (d, J = 5.1Hz, 1H), 7.52 (d, J = 1.2Hz, 1H) 7.31 (d, J = 1.2Hz 1H), 7.27 (t, J = 4.5Hz, 1H), 6.35 (s, 2H), 4.75 (q, J = 7.5Hz, 2H), 1.63 (t, J = 7.2Hz, 3H) | m/z 331 [M + 1] |

TABLE 6-continued

| Cpd # | STRUCTURE | IUPAC NAME | NMR | MS (m/z) |
|---|---|---|---|---|
| 716 | 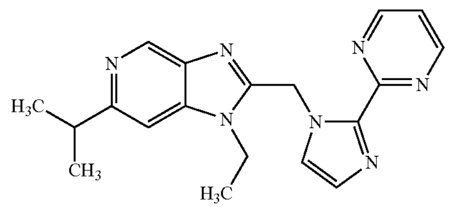 | 1-ethyl-6-isopropyl-2-[(2-pyrimidin-2-yl-1H-imidazol-1-yl)methyl]-1H-imidazo[4,5-c]pyridine | (CDCl3) 9.01 (d, J = 0.9Hz, 1H), 8.84 (d, J = 4.8Hz, 2H), 7.28 (t, J = 4.8Hz, 1H), 7.25 (d, J = 1.2 Hz, 1H), 7.13 (d, J = 0.9Hz, 1H), 7.10 (d, J = 0.9Hz, 1H), 6.35 (s, 2H), 4.21 (d, J = 7.2Hz, 2H), 3.17 (sept, J = 6.9Hz, 1H), 1.34 (d, J = 6.9Hz, 6H), 1.13 (t, J = 7.2Hz, 3H) | m/z 348 [M + 1] |
| 717 | 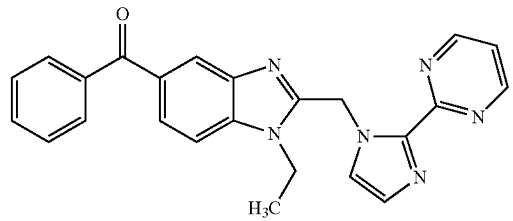 | {1-ethyl-2-[(2-pyrimidin-2-yl-1H-imidazol-1-yl)methyl]-1H-benzimidazol-5-yl}(phenyl)methanone | (CDCl3) 8.84 (d, 2H), 8.20 (s, 1H), 7.80-7.90 (m, 3H), 7.40-7.60 (m, 4H), 7.3 (m, 3H), 7.18 (s, 1H), 6.38 (s, 2H), 4.25 (q, 2H), 1.22 (t, 3H) | |
| 718 | 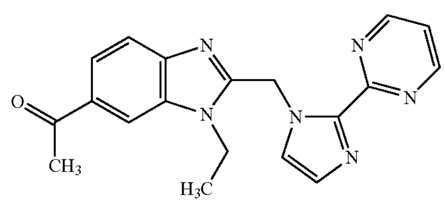 | 1-{1-ethyl-2-[(2-pyrimidin-2-yl-1H-imidazol-1-yl)methyl]-1H-benzimidazol-6-yl}ethanone | (CDCl3) 8.84 (d, 2H), 8.03 (s, 1H), 7.90 (d, 1H), 7.78 (d, 1H), 7.25-7.28 (m, 2H), 7.18 (s, 1H), 6.38 (s, 2H), 4.48 (q, 2H), 2.66 (s, 3H), 1.08 (t, 3H) | |
| 719 | 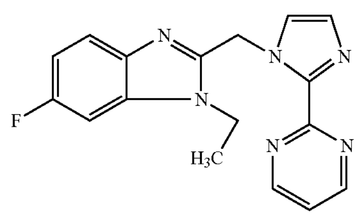 | 1-ethyl-6-fluoro-2-[(2-pyrimidin-2-yl-1H-imidazol-1-yl)methyl]-1H-benzimidazole | (CDCl3) 8.87 (d, J = 5.1Hz, 1H), 7.71 (q, J = 4.5Hz, 1H), 7.27 (m, 3H), 7.14 (s, 1H), 7.03 (m, 2H), 6.34 (s, 2H), 4.18 (q, J = 7.5 Hz, 2H), 1.11 (t,, J = 7.5Hz, 3H) | m/z 323 [M + 1] |

TABLE 6-continued

| Cpd # | STRUCTURE | IUPAC NAME | NMR | MS (m/z) |
|---|---|---|---|---|
| 720 | 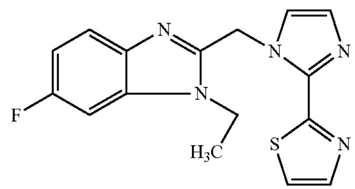 | 1-ethyl-6-fluoro-2-{[2-(1,3-thiazol-2-yl)-1H-imidazol-1-yl]methyl}-1H-benzimidazole | (CDCl3) 7.86 (d, J = 3.3Hz, 1H), 7.70 (q, J = 4.8Hz, 1H), 7.40 (d, J = 3Hz, 1H), 7.25 (s, 1H), 7.16 (d, J = 1.2Hz, 1H), 7.01 (m, 2H), 6.32 (s, 2H), 4.19 (q, J = 6.9 Hz, 2H), 1.06 (t., J = 7.5Hz, 3H) | m/z 328 [M + 1] |
| 721 | 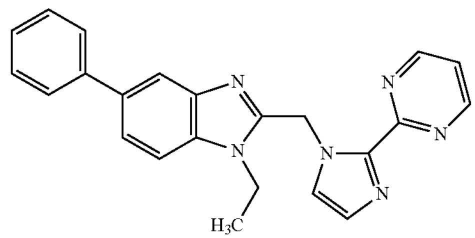 | 1-ethyl-5-phenyl-2-[(2-pyrimidin-2-yl-1H-imidazol-1-yl)methyl]-1H-benzimidazole | | m/z 381.5 [M + 1] |
| 722 | 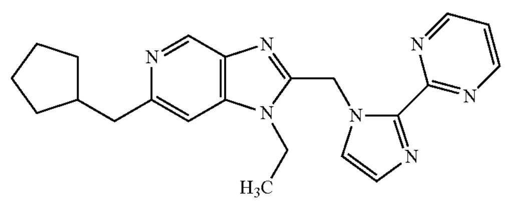 | 6-(cyclopentylmethyl)-1-ethyl-2-[(2-pyrimidin-2-yl-1H-imidazol-1-yl)methyl]-1H-imidazo[4,5-c]pyridine | (CDCl3) 9.00 (s, 1H), 8.86 (d, 2H), 7.25-7.31 (m, 2H), 7.15 (s, 1H), 7.08 (s, 1H), 6.37 (s, 2H), 4.20 (q, 2H), 2.87 (d, 2H), 2.25-2.40 (m, 1H), 1.42-1.78 (m, 6H), 1.15-1.30 (m, 2H), 1.13 (t, 3H) | |
| 723 | 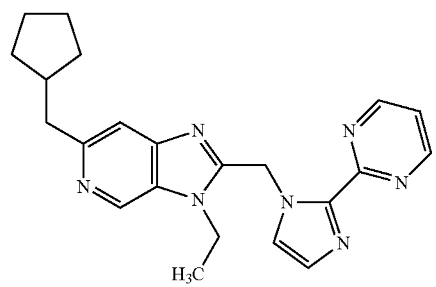 | 6-(cyclopentylmethyl)-3-ethyl-2-[(2-pyrimidin-2-yl-1H-imidazol-1-yl)methyl]-3H-imidazo[4,5-c]pyridine | (CDCl3) 8.85 (d, 2H), 8.69 (s, 1H), 7.47 (s, 1H), 7.25-7.29 (m, 2H), 7.18 (s, 1H), 6.38 (s, 2H), 4.30 (q, 2H), 2.88 (d, 2H), 2.22-2.39 (m, 1H), 1.42-1.78 (m, 6H), 1.20-1.33 (m, 5H) | |

TABLE 6-continued

| Cpd # | STRUCTURE | IUPAC NAME | NMR | MS (m/z) |
|---|---|---|---|---|
| 724 | 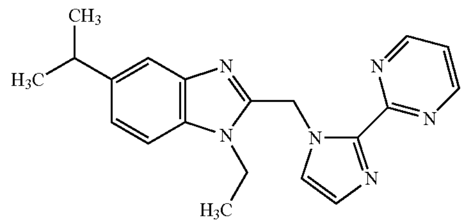 | 1-ethyl-5-isopropyl-2-[(2-pyrimidin-2-yl-1H-imidazol-1-yl)methyl]-1H-benzimidazole | (CDCl3) 8.85 (d, 2H), 7.63 (d, 1H), 7.24 (m, 2H), 7.21 (m, 2H), 7.13 (d, 1H), 6.33 (s, 2H), 4.14 (q, 2H), 3.02 (m, 1H), 1.29 (d, 6H), 1.08 (t, 3H) | |
| 725 | 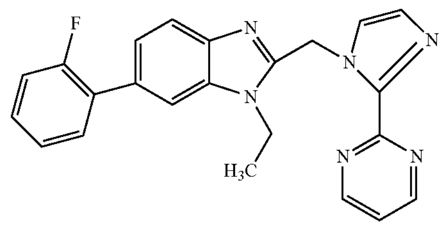 | 1-ethyl-6-(2-fluorophenyl-2-[(2-pyrimidin-2-yl-1H-imidazol-1-yl)methyl]-1H-benzimidazole | (CDCl3) 8.87 (d, J = 4.8Hz, 2H), 7.85 (d, J = 8.4Hz, 1H), 7.48 (m, 3H), 7.22 (m, 6H), 6.39 (s, 2H), 4.25 (q, J = 7.2Hz, 2H), 1.16 (t, J = 7.2Hz, 3H) | m/z 399 [M + 1] |
| 726 | 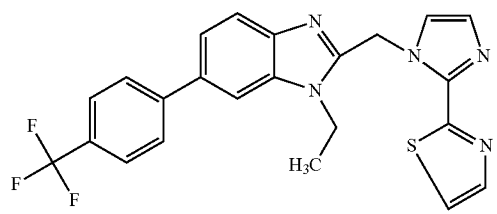 | 1-ethyl-2-[[2-(1,3-thiazol-2-yl)-1H-imidazol-1-yl]methyl]-6-[4-(trifluoromethyl)phenyl]-1H-benzimidazole | (DMSO) 7.95 (m, 3H), 7.79 (m, 3H), 7.70 (d, J = 3.3Hz, 1H), 7.59 (d, J = 8.7Hz, 1H), 7.52 (s, 1H), 7.48 (s, 1H), 6.19 (s, 2H), 4.43 (q, J = 7.2Hz, 2H), 1.34 (t, J = 7.2Hz, 3H) | m/z 454 [M + 1] |
| 727 | 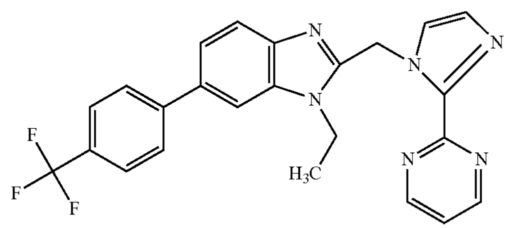 | 1-ethyl-2-[(2-pyrimidin-2-yl-1H-imidazol-1-yl)methyl]-6-[4-(trifluoromethyl)phenyl]-1H-benzimidazole | (CDCl3) 8.87 (d, J = 4.8Hz, 2H), 8.00 (s, 1H), 7.86 (d, J = 8.4Hz, 1H), 7.71 (m, 3H), 7.52 (m, 2H), 7.27 (t, J = 4.8Hz, 1H), 7.25 (s, 1H), 7.17 (s, 1H), 6.39 (s, 2H), 4.28 (q, J = 6.9Hz, 2H), 1.16 (t, J = 6.9Hz, 3H) | m/z 449 [M + 1] |

| Cpd # | STRUCTURE | IUPAC NAME | NMR | MS (m/z) |
|---|---|---|---|---|
| 728 | 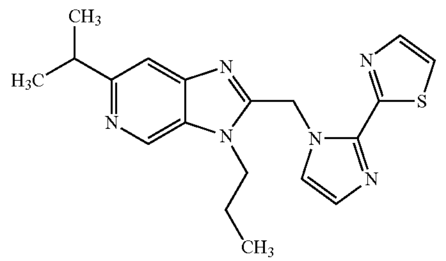 | 6-isopropyl-3-propyl-2-{[2-(1,3-thiazol-2-yl)-1H-imidazol-1-yl]methyl}-3H-imidazo[4,5-c]pyridine | (CDCl3) 8.69 (d, J = 1.2Hz, 1H), 7.83 (d, J = 3.3Hz, 1H), 7.52 (s, 1H), 7.39 (d, J = 3.0 Hz, 1H), 7.21 (d, J = 1.5Hz, 1H), 7.13 (d, J = 0.9Hz, 1H), 6.33 (s, 2H), 4.21 (m, 2H), 3.18 (sept, J = 6.9Hz, 1H), 1.61 (sext, J = 7.2Hz, 2H), 1.34 (d, J = 6.9 Hz, 6H), 0.77 (t, J = 7.2Hz, 3H) | m/z 367 [M + 1] |
| 729 | 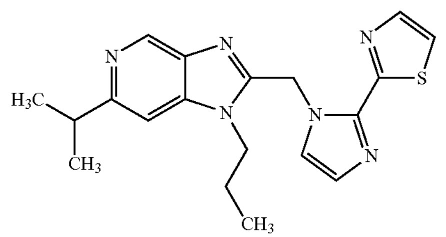 | 6-isopropyl-1-propyl-2-{[2-(1,3-thiazol-2-yl)-1H-imidazol-1-yl]methyl}-1H-imidazo[4,5-c]pyridine | (CDCl3) 9.01 (d, J = 0.9Hz, 1H), 7.85 (d, J = 3.6Hz, 1H), 7.39 (d, J = 3.6Hz, 1H), 7.18 (d, J = 0.9 Hz, 1H), 7.12 (d, J = 0.9Hz, 1H), 7.07 (s, 1H), 6.33 (s, 2H), 4.10 (m, 2H), 3.16 (sept, J = 6.9Hz, 1H), 1.52 (sext, J = 7.2Hz, 2H), 1.34 (d, J = 6.9Hz, 6H), 0.75 (t, J = 7.2Hz, 3H) | m/z 367 [M + 1] |
| 730 | 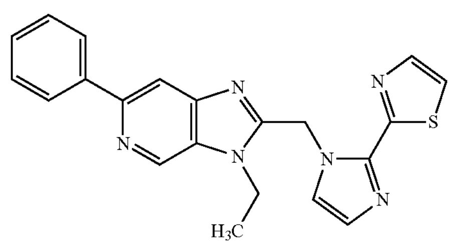 | 3-ethyl-6-phenyl-2-{[2-(1,3-thiazol-2-yl)-1H-imidazol-1-yl]methyl}-3H-imidazo[4,5-c]pyridine | (CDCl3) 8.85 (d, 1H), 8.08 (d, 1H), 8.02 (d, 1H), 7.99 (m, 1H), 7.84 (d, 1H), 7.48 (m, 2H), 7.40 (m, 2H), 7.22 (d, 1H), 7.17 (d, 1H), 6.36 (s, 2H), 4.38 (q, 2H), 1.22 (t, 3H) | m/z 387.4 [M + 1] |
| 731 | 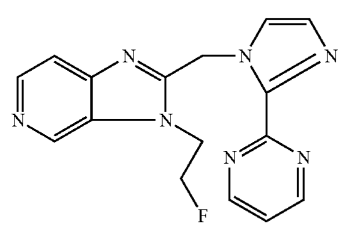 | 3-(2-fluoroethyl)-2-[(2-pyrimidin-2-yl-1H-imidazol-1-yl)methyl]-3H-imidazo[4,5-b]pyridine | (CD3OD) 8.91 (s, 1H), 8.69 (d, J = 5.1Hz, 2H), 8.28 (d, J = 5.7 Hz, 1H), 7.52 (m, 2H), 7.30 (s, 1H), 7.26 (t, J = 4.8Hz, 1H), 6.25 (s, 2H) | m/z 324 [M + 1] |

TABLE 6-continued

| Cpd # | STRUCTURE | IUPAC NAME | NMR | MS (m/z) |
|---|---|---|---|---|
| 732 | 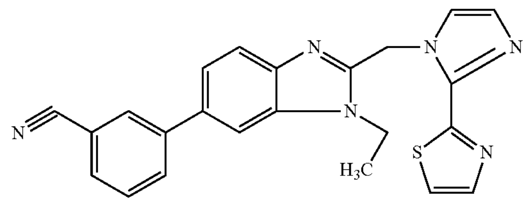 | 3-(1-ethyl-2-{[2-(1,3-thiazol-2-yl)-1H-imidazol-1-yl]methyl}-1H-benzimidazol-6-yl)benzonitrile | (DMSO) 8.24 (s, 1H), 8.09 (d, J = 7.8Hz, 1H), 8.0 (s, 1H), 7.76 (m, 2H), 7.61 (m, 5H), 7.11 (s, 1H), 6.18 (s, 2H), 4.42 (q, J = 7.5 Hz, 2H), 1.34 (t, J = 7.5Hz, 3H) | m/z 411 [M + 1] |
| 733 | 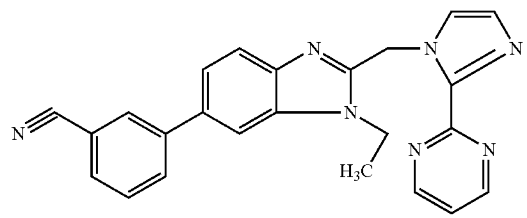 | 3-{1-ethyl-2-[(2-pyrimidin-2-yl-1H-imidazol-1-yl)methyl]-1H-benzimidazol-6-yl}benzonitrile | (DMSO) 6.76 (d, J = 5.1 Hz, 1H), 8.24 (s, 1H), 8.07 (d, J = 8.4Hz, 1H), 7.99 (s, 1H), 7.77 (d, J = 7.8 Hz, 1H), 7.64 (t, J = 8.1Hz, 1H), 7.50 (m, 3H), 7.34 (t, J = 4.8Hz, 1H), 7.17 (s, 1H), 6.17 (s, 2H), 4.42 (q, J = 6.9Hz, 2H), 1.34 (t, J = 6.0 Hz, 3H) | m/z 406 [M + 1] |
| 734 | 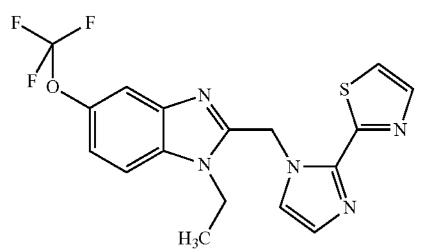 | 1-ethyl-2-{[2-(1,3-thiazol-2-yl)-1H-imidazol-1-yl]methyl}-5-(trifluoromethoxy)-1H-benzimidazole | (CDCl3) 7.86 (d, 1H), 7.66 (s, 1H), 7.40 (d, 1H), 7.33 (d, 1H), 7.26 (d, 2H), 7.14 (s, 1H), 6.34 (s, 2H), 4.26 (q, 2H), 1.10 (t, 3H) | m/z 394 [M + 1] |
| 735 | 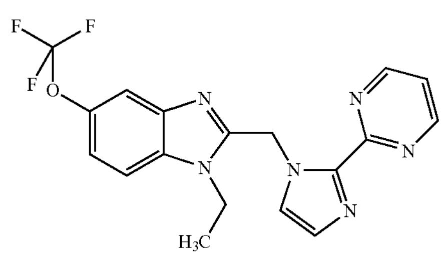 | 1-ethyl-2-[(2-pyrimidin-2-yl-1H-imidazol-1-yl)methyl]-5-(trifluoromethoxy)-1H-benzimidazole | (CDCl3) 8.84 (d, 2H), 7.63 (s, 1H), 7.25-7.28 (m, 3H), 7.15 (d, 2H), 6.35 (s, 2H), 4.22 (q, 2H), 1.13 (t, 3H) | |

TABLE 6-continued

| Cpd # | STRUCTURE | IUPAC NAME | NMR | MS (m/z) |
|---|---|---|---|---|
| 736 | 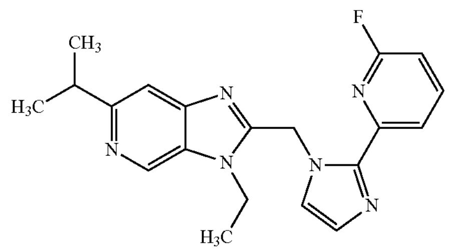 | 3-ethyl-2-{[2-(6-fluoropyridin-2-yl)-1H-imidazol-1-yl]methyl}-6-isopropyl-3H-imidazo[4,5-c]pyridine | (CDCl3) 8.71 (d, J = 1.2Hz, 1H), 8.17 (dd, J = 7.7, 1.7Hz, 1H), 7.88 (q, J = 7.9Hz, 1H), 7.51 (d, J = 0.9Hz, 1H), 7.21 (d, J = 0.9 Hz, 1H), 7.18 (d, J = 1.5Hz, 1H), 6.88 (dd, J = 8.3, 2.0 Hz, 1H), 6.26 (s, 2H), 4.42 (q, J = 7.2Hz, 2H), 3.17 (sept, J = 6.9Hz, 1H), 1.33 (d, J = 6.9Hz, 6H), 1.30 (t, J = 7.2Hz, 3H) | m/z 365 [M + 1] |
| 737 | 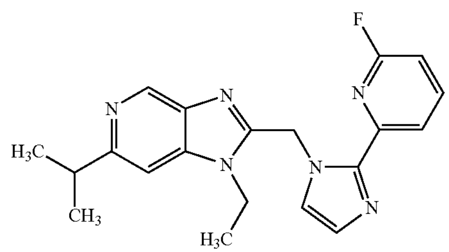 | 1-ethyl-2-{[2-(6-fluoropyridin-2-yl)-1H-imidazol-1-yl]methyl}-6-isopropyl-1H-imidazo[4,5-c]pyridine | (CDCl3) 8.99 (d, J = 0.9Hz, 1H), 8.16 (dd, J = 7.8, 1.5Hz, 1H), 7.88 (q, J = 7.8Hz, 1H), 7.18 (d, J = 0.9Hz, 1H), 7.16 (d, J = 1.5 Hz, 1H), 7.11 (d, J = 0.9Hz, 1H), 6.89 (dd, J = 7.8, 2.4Hz, 1H), 6.27 (s, 2H), 4.33 (q, J = 7.2Hz, 2H), 3.17 (sept, J = 6.9Hz, 1H), 1.35 (d, J = 6.9Hz, 6H), 1.23 (t, J = 7.2Hz, 3H) | m/z 365 [M + 1] |
| 738 | 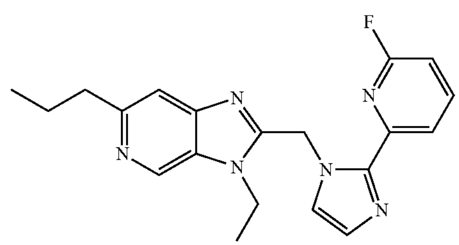 | 3-ethyl-2-{[2-(6-fluoropyridin-2-yl)-1H-imidazol-1-yl]methyl}-6-propyl-3H-imidazo[4,5-c]pyridine | (CDCl3) 8.70 (d, J = 0.9 Hz, 1H), 8.17 (dd, J = 8.0, 2.6Hz, 1H), 7.89 (q, J = 7.8Hz, 1H), 7.47 (s, 1H), 7.22 (d, J = 0.9Hz, 1H), 7.18 (d, J = 1.5Hz, 1H), 6.88 (dd, J = 8.6, 2.9Hz, 1H), 6.27 (s, 2H), 4.42 (q, J = 7.2Hz, 2H), 2.86 (m, 2H), 1.78 (sextet, J = 7.2 Hz, 2H), 1.20 (t, J = 7.2 Hz) | m/z 365 [M + 1] |
| 739 | 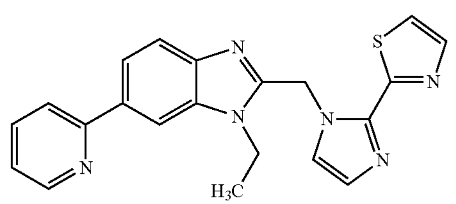 | | (CD3OD) 8.60 (d, J = 4.5Hz, 1H), 8.09 (s, 1H), 7.88 (m, 4H), 7.68 (d, J = 8.4Hz, 1H), 7.57 (d, J = 3.3Hz, 1H), 7.34 (m, 2H), 7.15 (s, 1H), 6.31 (s, 2H), 4.45 (q, J = 7.5Hz, 2H), 1.32 (t, J = 7.5Hz, 3H) | m/z 387 [M + 1] |

TABLE 6-continued

| Cpd # | STRUCTURE | IUPAC NAME | NMR | MS (m/z) |
|---|---|---|---|---|
| 740 | 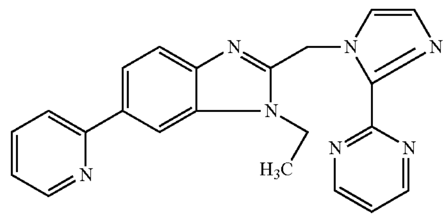 | | (CD3OD) 8.77 (m, 2H), 8.14 (s, 1H), 7.91 (m, 2H), 7.81 (d, J = 8.4Hz, 1H), 7.62 (d, J = 8.4Hz, 1H), 7.45 (s, 1H), 7.32 (m, 4H), 6.30 (s, 2H), 4.50 (q, J = 7.2Hz, 2H), 1.42 (t, J = 7.2Hz, 3H) | m/z 382 [M + 1] |
| 741 | 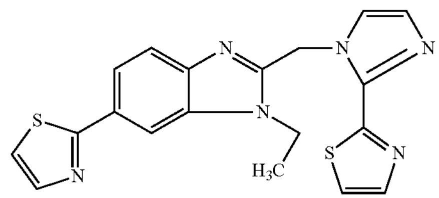 | | (CD3OD) 8.11 (s, 1H), 7.78-7.91 (m, 3H), 7.55-7.62 (m, 4H), 7.42 (d, J = 1.5Hz, 1H), 6.25 (s, 2H), 4.46 (q, J = 7.5Hz, 2H), 1.37 (t, J = 7.5Hz, 3H) | m/z 393 [M + 1] |
| 742 | 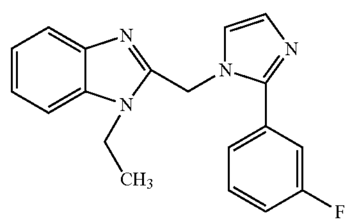 | 1-ethyl-2-{[2-(3-fluorophenyl)-1H-imidazol-1-yl]methyl}-1H-benzimidazole | | 321.3 |
| 743 | 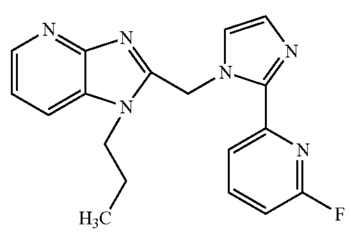 | 2-{[2-(6-fluoropyridin-2-yl)-1H-imidazol-1-yl]methyl}-1-propyl-1H-imidazo[4,5-b]pyridine | (HCl salt) H-1 NMR (dmso): 1.05 (t, 3H), 2.03 (h, 2H), 4.62 (t, 2H), 6.58 (s, 2H), 7.24 (d, 1H), 7.82 (t, 1H), 7.95 (s, 1H), 8.05 (m, 2H), 8.25 (q, 1H), 8.62 (d, 1H), 8.93 (d, 1H) | 337 [M + 1] |

TABLE 6-continued

| Cpd # | STRUCTURE | IUPAC NAME | NMR | MS (m/z) |
|---|---|---|---|---|
| 744 | 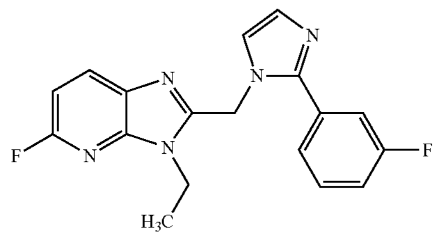 | 3-ethyl-5-fluoro-2-{[2-(3-fluorophenyl)-1H-imidazol-1-yl]methyl}-3H-imidazo[4,5-b]pyridine | dihydrochloride 1H NMR (d6 DMSO): 8.18 (1H, t), 7.99 (1H, d), 7.94 (1H, d), 7.72-7.69 (1H, m), 7.66-7.61 (1H, m), 7.58-7.50 (2H, m), 7.03 (1H, d), 5.96 (2H, s), 4.23 (2H, q), 1.31 (3H, s) | 340.2 [M + 1] |
| 745 | 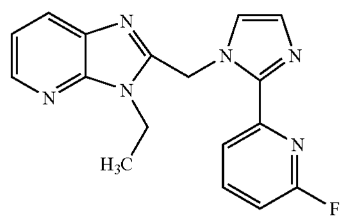 | 3-ethyl-2-{[2-(6-fluoropyridin-2-yl)-1H-imidazol-1-yl]methyl}-3H-imidazo[4,5-b]pyridine | 1H NMR, δppm (CDCl3): 8.39 (dd, 1H), 8.19 (m, 1H), 8.02 (dd, 1H), 7.89 (m, 1H), 7.20-7.26 (m, 3H), 6.89 (m, 1H), 6.32 (s, 2H), 4.47 (q, 2H), 1.30 (t, 3H) | 323.3 [M + 1] |
| 746 | 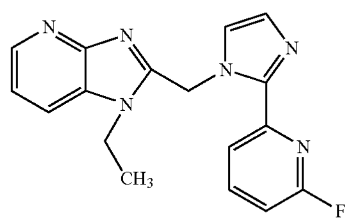 | 1-ethyl-2-{[2-(6-fluoropyridin-2-yl)-1H-imidazol-1-yl]methyl}-1H-imidazo[4,5-b]pyridine | (HCl salt) H-1 NMR (dmso): 1.63 (t, 3H), 4.72 (q, 2H), 6.58 (s, 2H), 7.30 (d, 1H), 7.82 (m, 1H), 7.96 (s, 1H), 8.03 (m, 2H), 8.24 (q, 1H), 8.90 (d, 1H), 8.90 (d, 1H) | 323 [M + 1] |
| 747 | 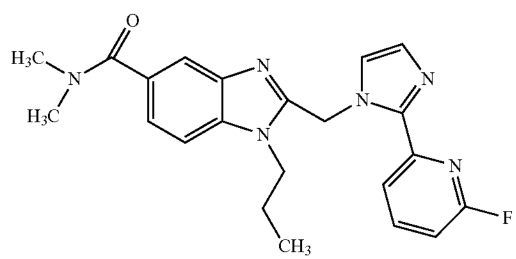 | 2-{[2-(6-fluoropyridin-2-yl)-1H-imidazol-1-yl]methyl}-N,N-dimethyl-1-propyl-1H-benzimidazole-5-carboxamide | CDCl3; 8.17 (d, J = 7.42Hz, 1H), 7.85-7.92 (m, 1H), 7.80 (s, 1H), 7.34-7.42 (m, 2H), 7.21 (s, 1H), 7.15 (s, 1H), 6.89 (d, J = 7.97Hz, 1H), 6.29 (s, 2H), 4.21-4.26 (m, 2H), 3.04-3.11 (br d, 6H), 1.61-1.69 (m, 2H), 0.80 (t, J = 7.42Hz, 3H). | |

TABLE 6-continued

| Cpd # | STRUCTURE | IUPAC NAME | NMR | MS (m/z) |
|---|---|---|---|---|
| 748 | 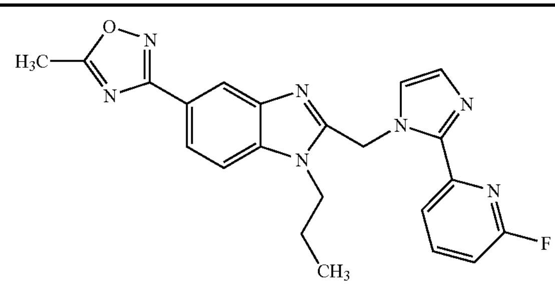 | 2-{[2-(6-fluoropyridin-2-yl)-1H-imidazol-1-yl]methyl}-5-(5-methyl-1,2,4-oxadiazol-3-yl)-1-propyl-1H-benzimidazole | d6-DMSO: 7.94-8.09 (m, 3H), 7.82 (d, 1H), 7.76 (d, 1H), 7.47 (s, 1H), 7.18 (s, 1H), 7.03 (d, 1H), 6.15 (s, 2H), 4.35 (t, 2H), 2.65 (s, 3H), 1.74-1.82 (m, 2H), 0.94 (t, 3H). | 418.3 [M + 1]; 416.2 [M − 1] |
| 749 | 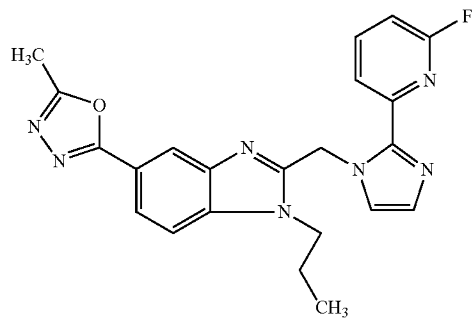 | 2-{[2-(6-fluoropyridin-2-yl)-1H-imidazol-1-yl]methyl}-5-(5-methyl-1,3,4-oxadiazol-2-yl)-1-propyl-1H-benzimidazole | CDCl₃: 8.36 (s, 1H), 8.18 (dd, 1H), 8.03 (dd, 1H), 7.89 (q, 1H), 7 44 (d, 1H), 7.25 (s, 1H), 7.17 (s, 1H), 6.90 (dd, 1H), 6.33 (s, 2H), 4.29 (t, 2H), 2.59 (s, 3H), 1.59-1.74 (m, 2H), 0.82 (t, 3H). | 418.3 [M + 1]; 416.2 [M − 1] |
| 750 | 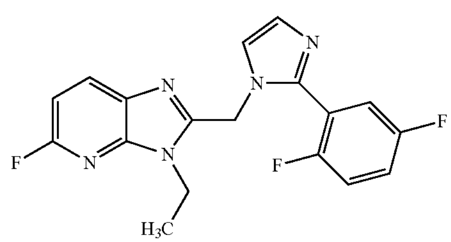 | 2-{[2-(2,5-difluorophenyl)-1H-imidazol-1-yl]methyl}-3-ethyl-5-fluoro-3H-imidazo[4,5-b]pyridine | hydrochloride 1H NMR (d6 DMSO): 8.15 (1H, t), 8.08 (1H, d), 7.99 (1H, d), 7.76-7.72 (1H, m), 7.62-7.50 (2H, m), 7.02 (1H, d), 5.92 (2H, s), 4.20 (2H, q), 1.26 (3H, t) | 358.2 [M + 1] |

TABLE 6-continued

| Cpd # | STRUCTURE | IUPAC NAME | NMR | MS (m/z) |
|---|---|---|---|---|
| 751 | 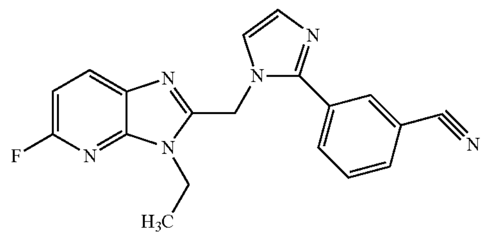 | 3-(1-[(3-ethyl-5-fluoro-3H-imidazo[4,5-b]pyridin-2-yl)methyl]-1H-imidazol-2-yl)benzonitrile | hydrochloride 1H NMR (d6 DMSO): 8.30 (1H, s), 8.16 (1H, dd), 8.11 (1H, d), 8.04 (1H, d), 8.00 (1H, d), 7.96 (1H, d), 7.74 (1H, t), 7.03 (1H, d), 5.97 (2H, s), 4.22 (2H, q), 1.30 (3H, t) | 347.3 [M + 1] |
| 752 | 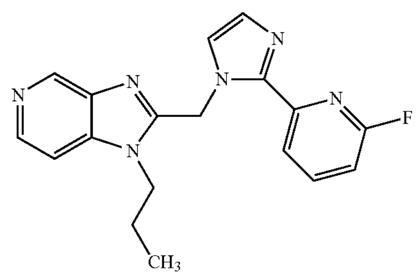 | 2-{[2-(6-fluoropyridin-2-yl)-1H-imidazol-1-yl]methyl}-1-propyl-1H-imidazo[4,5-c]pyridine | $^{1}$H NMR (CDCl3) δ 9.06 (s, 1H), 8.42 (d, 1H), 8.18 (d, 1H), 7.88 (dd, 1H), 7.28 (d, 1H), 7.22 (d, 1H), 7.18 (d, 1H), 6.88 (d, 1H), 6.29 (s, 2H), 4.26 (t, 2H), 1.69 (q, 2H), 0.84 (t, 3H) | m/e 337 |
| 753 | 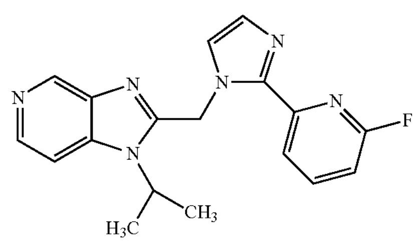 | 2-{[2-(6-fluoropyridin-2-yl)-1H-imidazol-1-yl]methyl}-1-isopropyl-1H-imidazo[4,5-c]pyridine | $^{1}$H NMR (CDCl3) δ 9.03 (s, 1H), 8.35 (d, 1H), 8.14 (d, 1H), 7.87 (dd, 1H), 7.42 (d, 1H), 7.15 (d, 1H), 7.09 (d, 1H), 6.87 (d, 1H), 6.28 (s, 2H), 5.08 (septet, 1H), 1.49 (d, 6H) | m/e 337 |
| 754 | 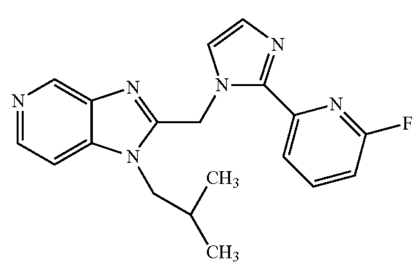 | 2-{[2-(6-fluoropyridin-2-yl)-1H-imidazol-1-yl]methyl}-1-isobutyl-1H-imidazo[4,5-c]pyridine | $^{1}$H NMR (CDCl3) δ 9.03 (s, 1H), 8.39 (d, 1H), 8.15 (d, 1H), 7.85 (dd, 1H), 7.27 (d, 1H), 7.24 (s, 1H), 7.17 (s, 1H), 6.85 (d, 1H), 6.25 (s, 2H), 4.08 (d, 2H), 2.09 (septet, 1H), 0.85 (d, 6H) | m/z 323. |

TABLE 6-continued

| Cpd # | STRUCTURE | IUPAC NAME | NMR | MS (m/z) |
|---|---|---|---|---|
| 755 | 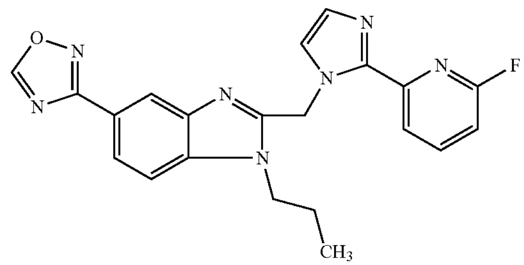 | 2-{[2-(6-fluoropyridin-2-yl)-1H-imidazol-1-yl]methyl}-5-(1,2,4-oxadiazol-3-yl)-1-propyl-1H-benzimidazole | Formate d6-DMSO: 9.62 (s, 1H), 7.99-8.09 (m, 3H), 7.90 (d, J = 8.24 Hz, 1H), 7.79 (d, J = 8.79Hz, 1H), 7.52 (s, 1H), 7.17 (s, 1H), 7.02 (d, J = 7.41Hz, 1H), 6.16 (s, 2H), 4.34-4.39 (m, 2H), 1.7-1.84 (m, 2H), 0.92 (t, J = 7.14Hz, 3H) | |
| 756 | Chiral | {(2S)-1-[(2-{[2-(6-fluoropyridin-2-yl)-1H-imidazol-1-yl]methyl}-1-propyl-1H-benzimidazol-5-yl)carbonyl]pyrrolidin-2-yl}methanol | CDCl₃: 8.18 (d, J = 7.69Hz, 1H), 7.86-7.94 (m, 2H), 7.51 (d, J = 8.52 Hz, 1H), 7.38 (d, J = 8.52Hz, 1H), 7.22 (s, 1H), 7.17 (s, 1H), 6.9 (dd, J = 2.75, 8.24Hz, 1H), 6.30 (s, 2H), 4.43-4.46 (m, 1H), 4.23-4.28 (m, 2H), 3.76-3.79 (m, 2H), 3.52-3.62 (m, 2H), 2.16-2.19 (m, 1H), 1.25-1.85 (m, 5H), 0.82 (t, J = 7.23Hz, 2H). | |
| 757 | 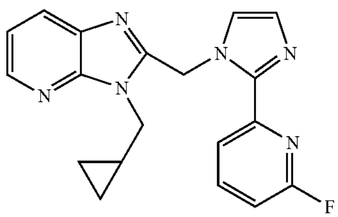 | 3-(cyclopropylmethyl)-2-{[2-(6-fluoropyridin-2-yl)-1H-imidazol-1-yl]methyl}-3H-imidazo[4,5-b]pyridine | ¹H NMR, δppm (CDCl3): 8.37 (dd, 1H), 8.18 (dd, 1H), 8.01 (dd, 1H), 7.88 (m, 1H), 7.20-7.26 (m, 3H), 6.87 (dd, 1H), 6.31 (s, 2H), 4.31 (d, 2H), 1.22 (m, 1H), 0.42-0.53 (m, 4H) | 349.3 [M + 1] |
| 758 | 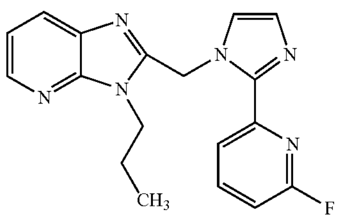 | 2-{[2-(6-fluoropyridin-2-yl)-1H-imidazol-1-yl]methyl}-3-propyl-3H-imidazo[4,5-b]pyridine | ¹H NMR, δppm (CDCl3): 8.38 (dd, 1H), 8.19 (m, 1H), 8.02 (dd, 1H), 7.89 (m, 1H), 7.20-7.26 (m, 3H), 6.88 (m, 1H), 6.32 (s, 2H), 4.35 (t, 2H), 1.74 (m, 2H), 0.85 (t, 3H) | 337.2 [M + 1] |

TABLE 6-continued

| Cpd # | STRUCTURE | IUPAC NAME | NMR | MS (m/z) |
|---|---|---|---|---|
| 759 | 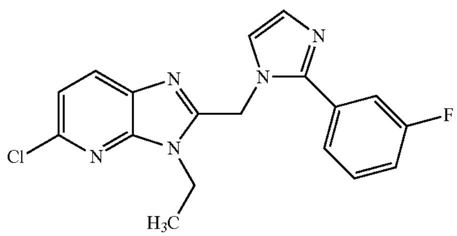 | 5-chloro-3-ethyl-2-{[2-(3-fluorophenyl)-1H-imidazol-1-yl]methyl}-3H-imidazo[4,5-b]pyridine | | 356.2 [M + 1] |
| 760 | 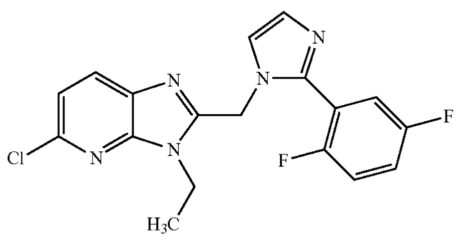 | 5-chloro-2-{[2-(2,5-difluorophenyl)-1H-imidazol-1-yl]methyl}-3-ethyl-3H-imidazo[4,5-b]pyridine | 1H NMR (CDCl3): 7.96 (1H, d), 7.38-7.34 (1H, m), 7.26-7.17 (4H, m), 7.04 (1H, d), 5.37 (1H, s), 3.96 (2H, q), 1.06 (3H, t) | 374.2 [M + 1] |
| 761 | 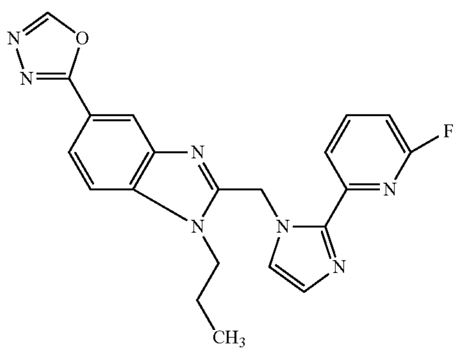 | 2-{[2-(6-fluoropyridin-2-yl)-1H-imidazol-1-yl]methyl}-5-(1,3,4-oxadiazol-2-yl)-1-propyl-1H-benzimidazole | CDCl3: 8.45 s, 1H), 8.43 (s, 1H), 8.19 (d, J = 7.14Hz, 1H), 8.10 (d, J = 8.38Hz, 1H), 7.90 (q, J = 7.96Hz, 1H), 7.48 (d, J = 8.52Hz, 1H), 7.19 (s, 1H), 6.89-6.92 (m, 1H), 6.33 (s, 2H), 4.3 (t, J = 7.42Hz, 2H), 1.67-1.749 m, 2H), 0.86 (t, J = 7.42Hz, 3H) | 404.6 [M + 1]; 402.3 [M − 1] |

TABLE 6-continued

| Cpd # | STRUCTURE | IUPAC NAME | NMR | MS (m/z) |
|---|---|---|---|---|
| 762 | 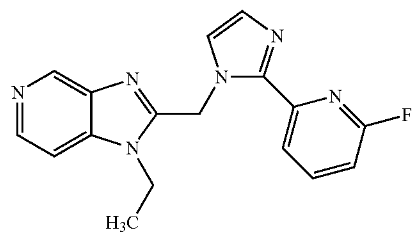 | 1-ethyl-2-{[2-(6-fluoropyridin-2-yl)-1H-imidazol-1-yl]methyl}-1H-imidazo[4,5-c]pyridine | ¹H NMR (CDCl3) δ 8.82 (s, 1H), 8.45 (d, 1H), 8.18 (d, 1H), 7.88 (dd, 1H), 7.65 (d, 1H), 7.23 (d, 1H), 7.20 (d, 1H), 6.88 (d, 1H), 6.30 (s, 2H), 4.47 (q, 2H), 1.33 (t, 3H) | m/e 323 |
| 763 | 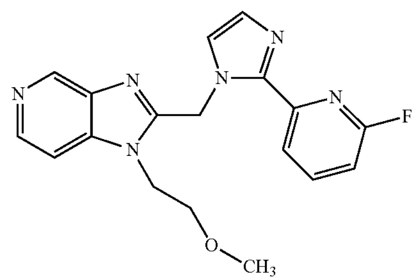 | 2-{[2-(6-fluoropyridin-2-yl)-1H-imidazol-1-yl]methyl}-1-(2-methoxyethyl)-1H-imidazo[4,5-c]pyridine | ¹H NMR (CDCl3) δ 9.02 (s, 1H), 8.41 (d, 1H), 8.16 (d, 1H), 7.84 (dd, 1H), 7.36 (d, 1H), 7.25 (d, 1H), 7.21 (d, 1H), 6.83 (d, 1H), 6.18 (s, 2H), 4.57 (t, 2H), 3.56 (t, 2H), 3.20 (s, 3H) | m/e 353 |
| 764 | 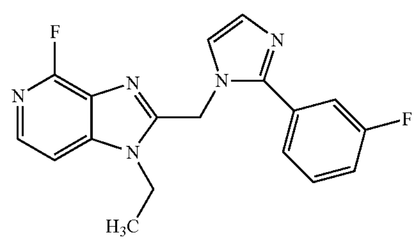 | 1-ethyl-4-fluoro-2-{[2-(3-fluorophenyl)-1H-imidazol-1-yl]methyl}-1H-imidazo[4,5-c]pyridine | 1H NMR (CDCl3): 7.97 (1H, dd), 7.53-7.48 (1H, m), 7.44-7.38 (2H, m), 7.22-7.12 (3H, m), 7.04 (1H, s), 5.55 (2H, s), 3.75 (2H, q), 0.96 (3H, t) | 340.1 [M + 1] |
| 765 | 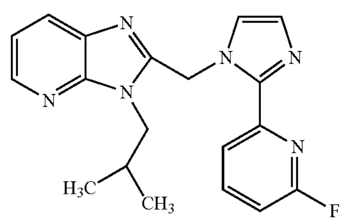 | 2-{[2-(6-fluoropyridin-2-yl)-1H-imidazol-1-yl]methyl}-3-isobutyl-3H-imidazo[4,5-b]pyridine | ¹H NMR, δppm (CDCl3): 8.38 (dd, 1H), 8.18 (dd, 1H), 8.01 (dd, 1H), 7.88 (m, 1H), 7.20-7.27 (m, 3H), 6.87 (dd, 1H), 6.29 (s, 2H), 4.21 (d, 2H), 2.27 (m, 1H), 0.87 (d, 6H) | 351.3 [M + 1] |

| Cpd # | STRUCTURE | IUPAC NAME | NMR | MS (m/z) |
|---|---|---|---|---|
| 766 | 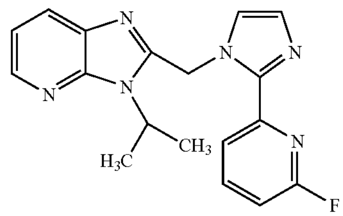 | 2-{[2-(6-fluoropyridin-2-yl)-1H-imidazol-1-yl]methyl}-3-isopropyl-3H-imidazo[4,5-b]pyridine | 1H NMR, δppm (CDCl3): 8.36 (dd, 1H), 8.18 (m, 1H), 8.00 (dd, 1H), 7.90 (m, 1H), 7.18-7.22 (m, 2H), 7.13 (d, 1H), 6.89 (m, 1H), 6.32 (s, 2H), 5.04 (m, 1H), 1.63 (d, 6H) | 337.2 [M+1] |
| 767 | 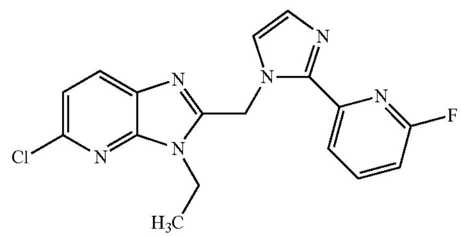 | 5-chloro-3-ethyl-2-{[2-(6-fluoropyridin-2-yl)-1H-imidazol-1-yl]methyl}-1H-imidazo[4,5-b]pyridine | 1H NMR (CDCl3): 8.17 (1H, dd), 7.94-7.84 (2H, m), 7.23-7.20 (3H, m), 6.89-6.85 (1H, m), 6.27 (2H, s), 4.45 (2H, q), 1.31 (3H, t) | 357.2 [M+1] |
| 768 | 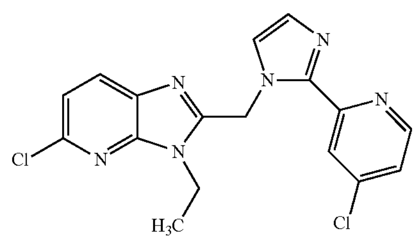 | 5-chloro-2-{[2-(4-chloropyridin-2-yl)-1H-imidazol-1-yl]methyl}-3-ethyl-3H-imidazo[4,5-b]pyridine | 1H NMR (CDCl3): 8.41 (1H, d), 8.35 (1H, dd), 7.94 (1H, d), 7.26-7.17 (4H, m), 6.36 (2H, s), 4.36 (2H, q), 1.22 (3H, t) | 373.2 (M) |
| 769 | 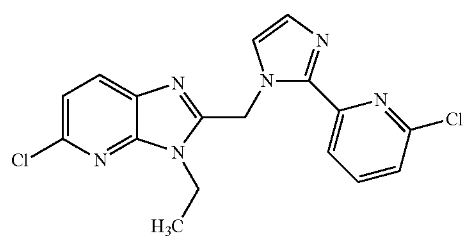 | 5-chloro-2-{[2-(6-chloropyridin-2-yl)-1H-imidazol-1-yl]methyl}-3-ethyl-3H-imidazo[4,5-b]pyridine | 1H NMR (CDCl3): 8.22 (1H, d), 7.94 (1H, d), 7.75 (1H, t), 7.29-7.20 (4H, m), 6.31 (2H, s), 4.45 (2H, q), 1.30 (3H, t) | 373.3 (M) |

TABLE 6-continued

| Cpd # | STRUCTURE | IUPAC NAME | NMR | MS (m/z) |
|---|---|---|---|---|
| 770 | 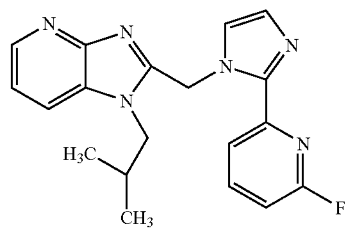 | 2-{[2-(6-fluoropyridin-2-yl)-1H-imidazol-1-yl]methyl}-1-isobutyl-1H-imidazo[4,5-b]pyridine | (HCl salt) H-1 NMR (dmso): 1.05 (d, 6H), 2.40 (h, 1H), 4.50 (d, 2H), 6.57 (s, 2H), 7.30 (d, 1H), 7.82 (m, 1H), 7.93 (s, 1H), 8.03 (m, 2H), 8.23 (q, 1H), 8.62 (d, 1H), 8.95 (d, 1H) | 351 [M + 1] |
| 771 | 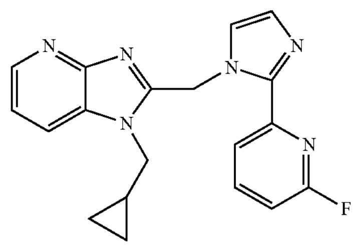 | 1-(cyclopropylmethyl)-2-{[2-(6-fluoropyridin-2-yl)-1H-imidazol-1-yl]methyl}-1H-imidazo[4,5-b]pyridine | (free base) H-1 NMR (CDCl3): 0.30 (m, 2H), 0.57 (m, 2H), 1.05 (m, 1H), 4.23 (d, 2H), 6.38 (s, 2H), 6.80 (d, 1H), 7.08 (s, 1H), 7.22 (m, 1H), 7.39 (s, 1H), 7.73 (d, 1H), 7.90 (q, 1H), 8.20 (d, 1H), 8.58 (d, 1H) | 349 [M + 1] |
| 772 | 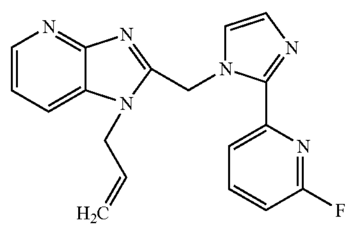 | 1-allyl-2-{[2-(6-fluoropyridin-2-yl)-1H-imidazol-1-yl]methyl}-1H-imidazo[4,5-b]pyridine | (HCl salt) Melting point: 225-231 (decompose) H-1 NMR (dmso): 5.22-5.53 (m, 4H), 6.21 (m, 1H), 6.53 (s, 2H), 7.24 (d, 1H), 7.82 (m, 1H), 7.95 (s, 1H), 8.05 (m, 2H), 8.25 (q, 1H), 8.62 (s, 1H), 8.82 (d, 1H) | 335 [M + 1] |
| 773 | 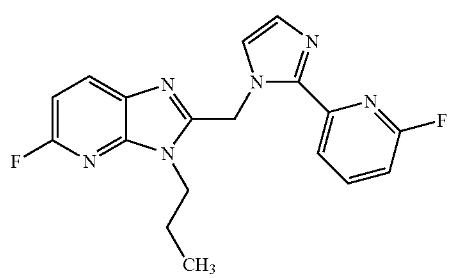 | 5-fluoro-2-{[2-(6-fluoropyridin-2-yl)-1H-imidazol-1-yl]methyl}-3-propyl-3H-imidazo[4,5-b]pyridine | hydrochloride 1H NMR (d6 DMSO): 8.42 (1H, d), 8.26 (1H, q), 8.10-8.05 (2H, m), 7.96 (1H, d), 7.36 (1H, dd), 6.97 (1H, d), 6.33 (2H, s), 4.30 (2H, t), 1.90-1.83 (2H, m), 0.93 (3H, t). | |

TABLE 6-continued

| Cpd # | STRUCTURE | IUPAC NAME | NMR | MS (m/z) |
|---|---|---|---|---|
| 774 | 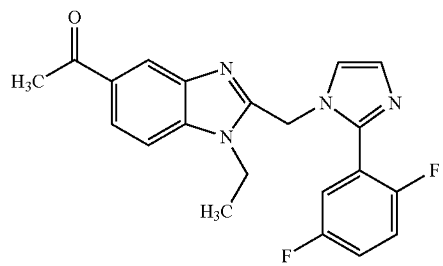 | 1-(2-{[2-(2,5-difluorophenyl)-1H-imidazol-1-yl]methyl}-1-ethyl-1H-benzimidazol-5-yl)ethanone | $^1$H NMR, δppm (CDCl3): 8.39 (dd, 1H), 8.01 (dd, 1H), 7.34-7.41 (m, 2H), 7.18-7.24 (m, 3H), 7.04 (d, 1H), 5.40 (s, 2H), 3.88 (q, 2H), 2.69 (s, 3H), 1.03 (t, 3H) | 381.4 [M + 1] |
| 775 | 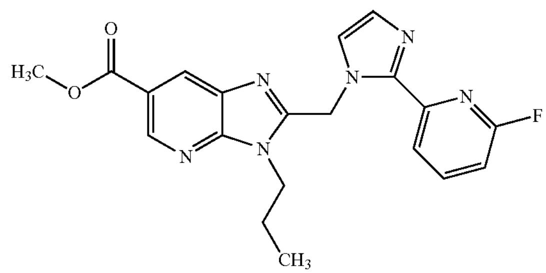 | methyl 2-{[2-(6-fluoropyridin-2-yl)-1H-imidazol-1-yl]methyl}-3-propyl-3H-imidazo[4,5-b]pyridine-6-carboxylate | 1H NMR (CDCl3): 9.05 (1H, d), 8.62 (1H, d), 8.19 (1H, dd), 7.88 (1H, q), 7.26-7.21 (2H, m), 6.89-6.85 (1H, m), 6.31 (2H, s), 4.39 (2H, t), 3.96 (3H, s), 1.79-1.72 (2H, m), 0.87 (3H, t) | 395.3 [M + 1] |
| 776 | 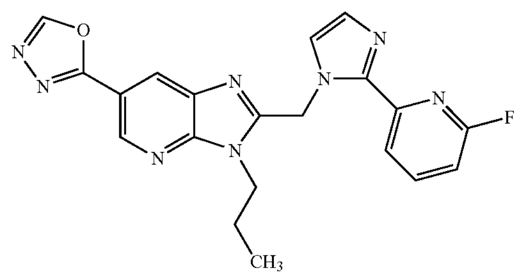 | 2-{[2-(6-fluoropyridin-2-yl)-1H-imidazol-1-yl]methyl}-6-(1,3,4-oxadiazol-2-yl)-3-propyl-3H-imidazo[4,5-b]pyridine | (KC 1084-78-2) | 405.3 [M + 1] |

| Cpd # | STRUCTURE | IUPAC NAME | NMR | MS (m/z) |
|---|---|---|---|---|
| 777 | 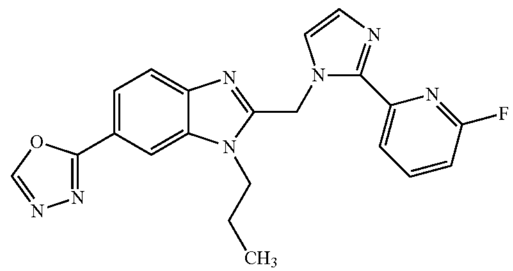 | 2-{[2-(6-fluoropyridin-2-yl)-1H-imidazol-1-yl]methyl}-6-(1,3,4-oxadiazol-2-yl)-1-propyl-1H-benzimidazole | ¹H NMR (CDCl3) δ 8.46 (s, 1H), 8.18-8.14 (m, 2H), 7.95-7.83 (m, 3H), 7.24 (d, 1H), 7.17 (d, 1H), 6.87 (d, 1H), 6.31 (s, 2H), 4.30 (t, 2H), 1.71 (q, 2H), 0.85 (t, 3H) | m/e 404 |
| 778 | 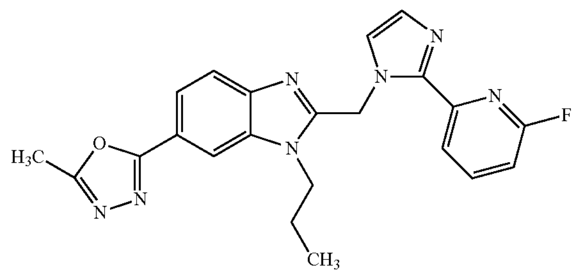 | 2-{[2-(6-fluoropyridin-2-yl)-1H-imidazol-1-yl]methyl}-6-(5-methyl-1,3,4-oxadiazol-2-yl)-1-propyl-1H-benzimidazole | ¹H NMR (CDCl3) δ 8.17 (d, 1H), 8.07 (s, 1H), 7.91-7.80 (m, 3H), 7.23 (d, 1H), 7.16 (d, 1H), 6.87 (d, 1H), 6.29 (s, 2H), 4.28 (t, 2H), 2.61 (s, 3H), 1.69 (q, 2H), 0.84 (t, 3H) | m/e 418 |
| 779 | 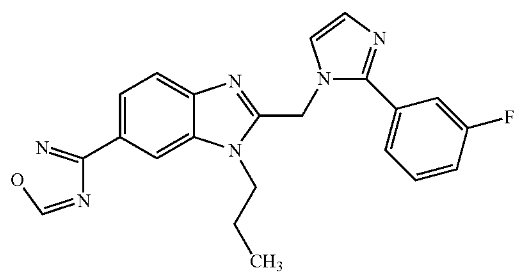 | 2-{[2-(3-fluorophenyl)-1H-imidazol-1-yl]methyl}-6-(1,2,4-oxadiazol-3-yl)-1-propyl-1H-benzimidazole | ¹H NMR (CDCl3) δ 8.89 (s, 1H), 8.15 (s, 1H), 8.12-8.03 (m, 1H), 7.81-7.73 (m, 1H), 7.40-7.02 (m, 6H), 5.47 (s, 2H), 3.82 (t, 2H), 1.55 (q, 2H), 0.79 (t, 3H) | m/e 403 |

TABLE 6-continued

| Cpd # | STRUCTURE | IUPAC NAME | NMR | MS (m/z) |
|---|---|---|---|---|
| 780 | 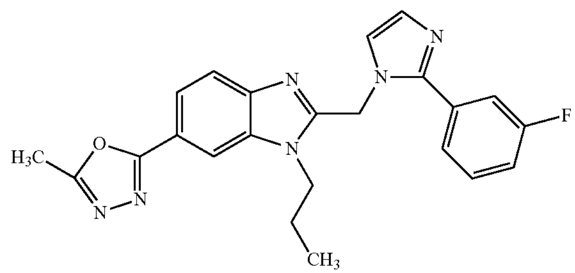 | 2-{[2-(3-fluorophenyl)-1H-imidazol-1-yl]methyl}-6-(5-methyl-1,3,4-oxadiazol-2-yl)-1-propyl-1H-benzimidazole | ¹H NMR (CDCl3) δ 8.04 (s, 1H), 7.94-7.84 (m, 2H), 7.50 (7.39 (m, 3H), 7.22-7.16 (m, 2H), 7.08 (d, 1H), 5.52 (s, 2H), 3.76 (t, 2H), 2.63 (s, 3H), 1.47 (q, 2H), 0.77 (t, 3H) | m/e 417 |
| 781 | 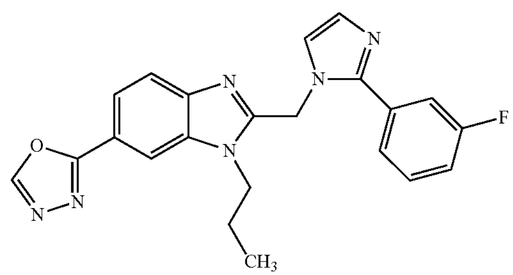 | 2-{[2-(3-fluorophenyl)-1H-imidazol-1-yl]methyl}-6-(1,3,4-oxadiazol-2-yl)-1-propyl-1H-benzimidazole | ¹H NMR (CDCl3) δ 8.50 (s, 1H), 8.15 (d, 1H), 7.98-7.89 (m, 2H), 7.56-7.39 (m, 3H), 7.24-7.05 (m, 3H), 5.57 (s, 2H), 3.78 (t, 2H), 1.47 (q, 2H), 0.80 (t, 3H) | m/e 403 |
| 782 | 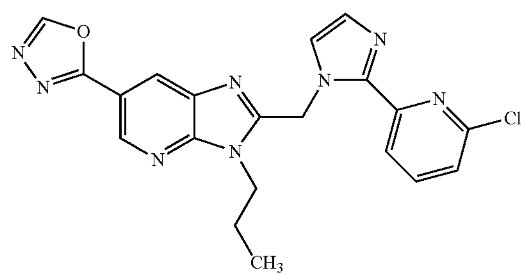 | 2-{[2-(6-chloropyridin-2-yl)-1H-imidazol-1-yl]methyl}-6-(1,3,4-oxadiazol-2-yl)-3-propyl-3H-imidazo[4,5-b]pyridine | 1H NMR (CDCl3): 9.14 (1H, d), 8.63 (1H, d), 8.51 (1H, s), 8.26 (1H, d), 7.76 (1H, t), 7.28-7.24 (3H, m), 6.36 (2H, s), 4.42 (2H, t), 1.81-1.74 (2H, m), 0.88 (3H, t) | 421.3 [M + 1] |

TABLE 6-continued

| Cpd # | STRUCTURE | IUPAC NAME | NMR | MS (m/z) |
|---|---|---|---|---|
| 783 | 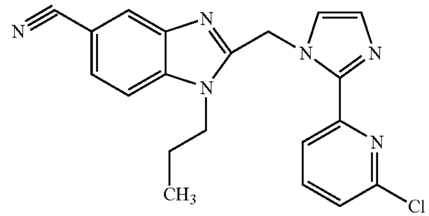 | 2-{[2-(6-chloropyridin-2-yl)-1H-imidazol-1-yl]methyl}-1-propyl-1H-benzimidazole-5-carbonitrile | 1H NMR (d6 DMSO): 8.02 (1H, d, J = 7.7Hz), 8.08 (1H, s), 7.76 (1H, t, J = 8Hz), 7.55 (1H, dd, J = 8, 1.4 Hz), 7.428 (1H, d, J = 8.5Hz), 7.18-7.32 (3H, m), 6.34 (1H, s), 4.29 (2H, t, J = 8.7Hz), 1.66 (2H, m), 0.81 (3H, t, J = 8.7Hz) | 377.3 [M + 1] |
| 784 | 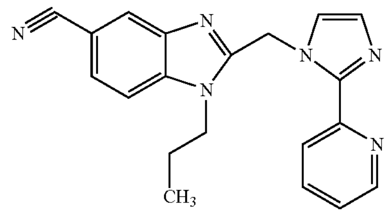 | 1-propyl-2-{[2-(2-pyridin-2-yl)-1H-imidazol-1-yl)methyl]-1H-benzimidazole-5-carbonitrile | | |
| 785 | 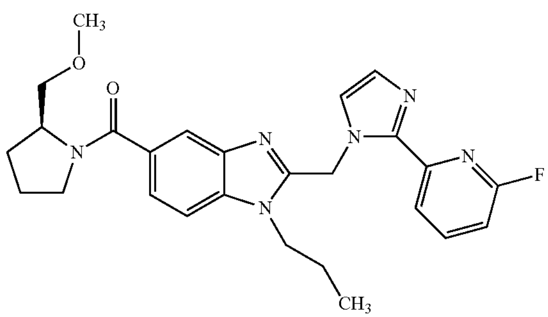 | 2-{[2-(6-fluoropyridin-2-yl)-1H-imidazol-1-yl]methyl}-5-{[(2S)-2-(methoxymethyl)pyrrolidin-1-yl]carbonyl}-1-propyl-1H-benzimidazole | CDCl3: 8.17 (d, J = 7.42Hz, 1H), 7.85-7.93 (m, 2H), 7.51-7.53 (m, 1H), 7.35 (d, J = 8.51Hz, 1H), 7.21 (s, 1H), 7.16 (s, 1H), 6.89 (dd, J = 2.47, 7.97Hz, 1H), 6.28-6.3 (m, 2H), 4.46 (bs, 1H), 4.21-4.26 (m, 2H), 3.51-3.68 (m, 4H), 3.40 (s, 3H), 1.95-2.05 (m, 4H), 1.62-1.72 (m, 2H), 0.81 (t, J = 7.42Hz, 3H). | 475.2 [M + 1]; 477.2 [M − 1] |
| 786 | 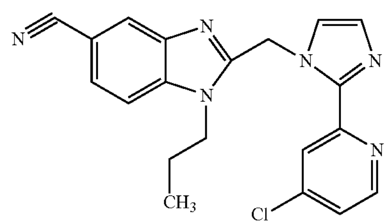 | 2-{[2-(4-chloropyridin-2-yl)-1H-imidazol-1-yl]methyl}-1-propyl-1H-benzimidazole-5-carbonitrile | 1H NMR (d6 DMSO): 8.42 (1H, d, J = 5Hz), 8.35 (1H, s), 8.08 (1H, s), 7.1-7.65 (1H, m), 6.41 (1H, s), 4.19 (2H, t, J = 7.4Hz), 1.57 (2H, m), 0.78 (3H, t, J = 7.4Hz) | 377.3 [M + 1] |

TABLE 6-continued

| Cpd # | STRUCTURE | IUPAC NAME | NMR | MS (m/z) |
|---|---|---|---|---|
| 787 | 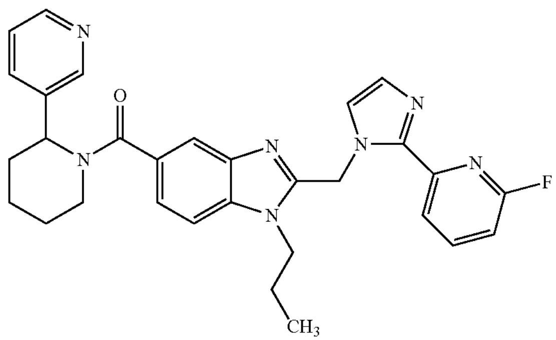 | 2-{[2-(8-fluoropyridin-2-yl)-1H-imidazol-1-yl]methyl}-1-propyl-5-[(2-pyridin-3-ylpiperidin-1-yl)carbonyl]-1H-benzimidazole | CDCl₃; 8.61 9 s, 1H), 8.52 (d, J = 4.67Hz, 1H), 8.15-8.18 (m, 1H), 7.87-7.93 (m, 1H), 7.85 (s, 1H), 7.66 (d, J = 7.69Hz, 1H), 7.30-7.45 (m, 3H), 7.21 (s, 1H), 7.16 (s, 1H), 6.88-6.91 (m, 1H), 6.29 (s, 2H), 4.25 (t, J = 7.42Hz, 2H), 2.82-2.91 | 524.0 [M + 1]; 522.4 [M − 1] |
| 788 | 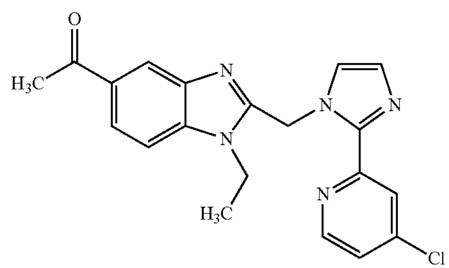 | 1-(2-{[2-(4-chloropyridin-2-yl)-1H-imidazol-1-yl]methyl}-1-ethyl-1H-benzimidazol-5-yl)ethanone | ¹H NMR, δppm (CDCl3): 8.36-8.47 (m, 3H), 8.01 (dd, 1H), 7.38 (d, 1H), 7.29 (dd, 1H), 7.16-7.18 (m, 2H), 6.43 (s, 2H), 4.30 (q, 2H), 2.68 (s, 3H), 1.14 (t, 3H) | 380.3 [M + 1] |
| 789 | 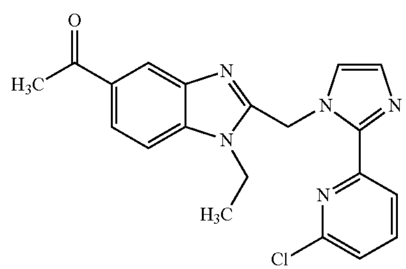 | 1-(2-{[2-(6-chloropyridin-2-yl)-1H-imidazol-1-yl]methyl}-1-ethyl-1H-benzimidazol-5-yl)ethanone | ¹H NMR, δppm (CDCl3): 8.40 (d, 1H), 8.23 (d, 1H), 8.01 (dd, 1H), 7.77 (t, 1H), 7.41 (d, 1H), 7.30 (d, 1H), 7.24 (d, 1H), 7.18 (d, 1H), 6.36 (s, 2H), 4.41 (q, 2H), 2.68 (s, 3H), 1.25 (t, 3H) | 380.3 [M + 1] |

TABLE 6-continued

| Cpd # | STRUCTURE | IUPAC NAME | NMR | MS (m/z) |
|---|---|---|---|---|
| 790 | 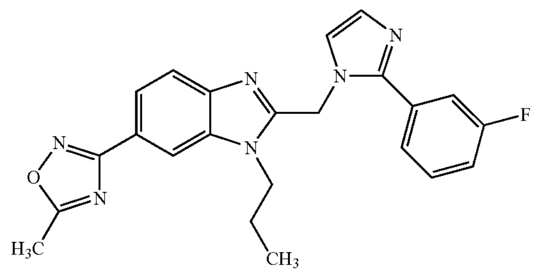 | 2-{[2-(3-fluorophenyl)-1H-imidazol-1-yl]methyl}-6-(5-methyl-1,2,4-oxadiazol-3-yl)-1-propyl-1H-benzimidazole | ¹H NMR (CDCl3) δ 8.03 (d, 1H), 8.02 (s, 1H), 7.85 (d, 1H), 7.51-7.40 (m, 3H), 7.21-7.16 (m, 2H), 7.07 (d, 1H), 5.52 (s, 2H), 3.75 (t, 2H), 2.67 (s, 3H), 1.47 (q, 2H), 0.76 (t, 3H) | m/e 417 |
| 791 | 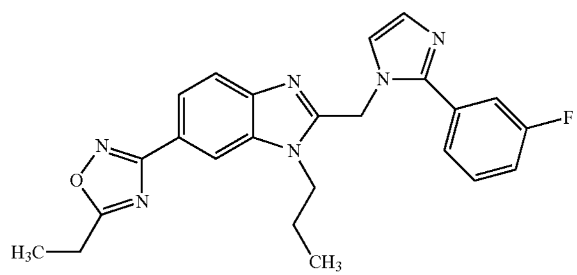 | 6-(5-ethyl-1,2,4-oxadiazol-3-yl)-2-{[2-(3-fluorophenyl)-1H-imidazol-1-yl]methyl}-1-propyl-1H-benzimidazole | ¹H NMR (CDCl3) δ 8.05 (d, 1H), 8.03 (s, 1H), 7.85 (d, 1H), 7.52-7.41 (m, 3H), 7.21-7.17 (m, 2H), 7.08 (d, 1H), 5.52 (s, 2H), 3.76 (t, 2H), 3.00 (q, 2H), 1.51-1.45 (m, 5H), 0.77 (t, 3H) | m/e 431 |
| 792 | 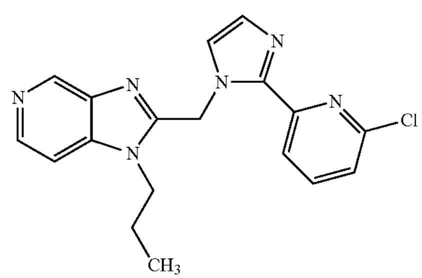 | 2-{[2-(6-chloropyridin-2-yl)-1H-imidazol-1-yl]methyl}-1-propyl-1H-imidazo[4,5-c]pyridine | dihydrochloride ¹H NMR (DMSO-d6) δ 9.32 (s, 1H), 8.68 (d, 1H), 8.47 (d, 1H), 8.45 (d, 1H), 8.09-8.03 (m, 2H), 7.80 (d, 1H), 7.54 (d, 1H), 6.45 (s, 2H), 4.61 (t, 2H), 1.88 (q, 2H), 0.95 (t, 3H) | m/e 352 |

| Cpd # | STRUCTURE | IUPAC NAME | NMR | MS (m/z) |
|---|---|---|---|---|
| 793 | 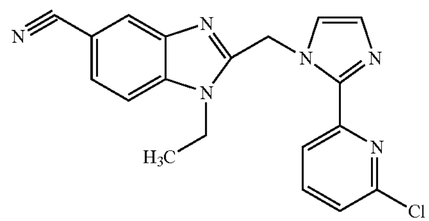 | 2-{[2-(6-chloropyridin-2-yl)-1H-imidazol-1-yl]methyl}-1-ethyl-1H-benzimidazole-5-carbonitrile | Mesylate d6-DMSO: 8.02-8.14 (m, 3H), 7.97 (s, 1H), 7.77 (s, 1H), 7.6 (d, J = 8.51Hz, 1H), 7.57 (d, J = 7.97Hz, 1H), 6.26 (s, 2H), 4.44-4.51 (m, 2H), 2.30 (s, 3H), 1.39 (t, J = 7.14 Hz, 3H) | 363.2 [M + 1] |
| 794 | 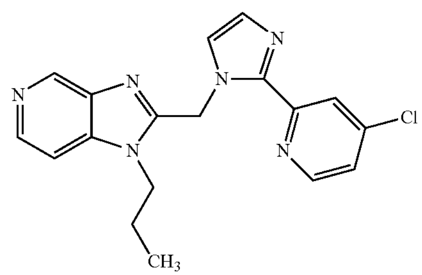 | 2-{[2-(4-chloropyridin-2-yl)-1H-imidazol-1-yl]methyl}-1-propyl-1H-imidazo[4,5-c]pyridine | dihydrochloride ¹H NMR (DMSO-d6) δ 9.31 (s, 1H), 8.66 (d, 1H), 8.45 (s, 1H), 8.41 (d, 1H), 8.32 (d, 1H), 7.86 (d, 1H), 7.63 (d, 1H), 7.52 (d, 1H), 6.42 (s, 2H), 4.55 (t, 2H), 1.91 (q, 2H), 0.97 (t, 3H) | m/e 353 |
| 795 | 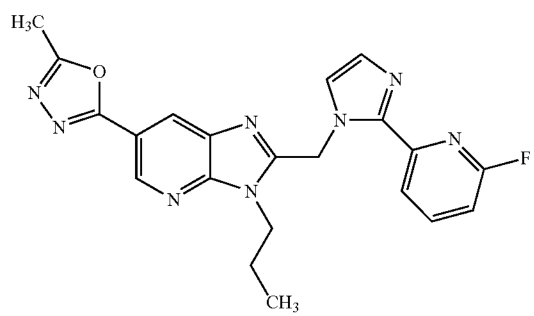 | 2-{[2-(6-fluoropyridin-2-yl)-1H-imidazol-1-yl]methyl}-6-(5-methyl-1,3,4-oxadiazol-2-yl)-3-propyl-3H-imidazo[4,5-b]pyridine | 1H NMR (CDCl3): 9.07 (1H, d), 8.56 (1H, d), 8.20 (1H, dd), 7.88 (1H, q), 7.26-7.2292H, m), 6.88 (1H, dd), 6.3292H, s), 4.40 (2H, t), 2.65 (3H, s), 1.81-1.74 (2H, m), 0.88 (3H, t) | 419.3 [M + 1] |

TABLE 6-continued

| Cpd # | STRUCTURE | IUPAC NAME | NMR | MS (m/z) |
|---|---|---|---|---|
| 796 | 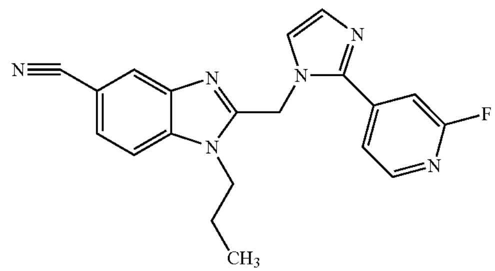 | 2-{[2-(2-fluoropyridin-4-yl)-1H-imidazol-1-yl]methyl}-1-propyl-1H-benzimidazole-5-carbonitrile | 1H NMR (CDCl3): 8.28 (1H, d), 8.04 (1H, s), 7.54-7.49 (2H, m), 7.40 (1H, d), 7.25-7.22 (2H, m), 7.11 (1H, s), 5.55 (2H, s), 3.89 (2H, t), 1.60-1.53 (2H, m), 0.83 (3H, t) | 361.2 [M + 1] |
| 797 | 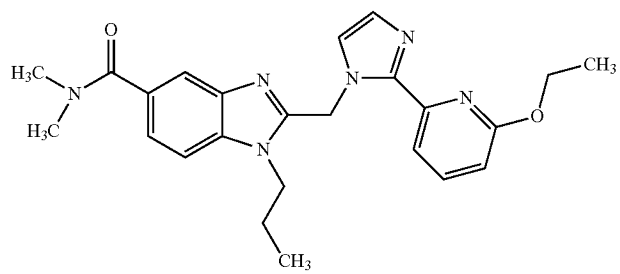 | 2-{[2-(6-ethoxypyridin-2-yl)-1H-imidazol-1-yl]methyl}-N,N-dimethyl-1-propyl-1H-benzimidazole-5-carboxamide | 1H NMR (CDCl3): 8.49 (1H, d), 8.10 (1H, d), 7.88 (1H, d), 7.71 (1H, t), 7.13 (1H, d), 7.00 (1H, d), 6.74 (1H, d), 6.45 (2H, s), 4.27 (2H, q), 4.08 (2H, t), 3.15-3.06 (6H, br d), 1.48-1.35 (5H, m), 0.67 (3H, t) | 434.6 [M + 1] |
| 798 | 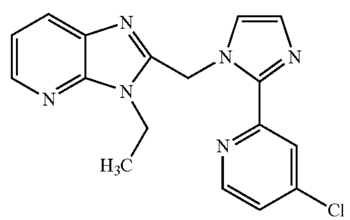 | 2-{[2-(4-chloropyridin-2-yl)-1H-imidazol-1-yl]methyl}-3-ethyl-3H-imidazo[4,5-b]pyridine | $^{1}$H NMR, δppm (CDCl3): 8.44 (dd, 1H), 8.39 (m, 1H), 8.03 (dd, 1H), 7.18-7.28 (m, 5H), 6.41 (s, 2H), 4.39 (q, 2H), 1.20 (t, 3H) | 339.2 [M + 1] |
| 799 | 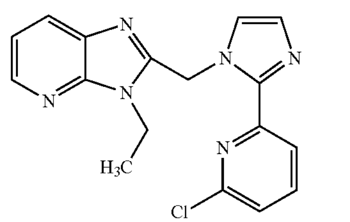 | 2-{[2-(6-chloropyridin-2-yl)-1H-imidazol-1-yl]methyl}-3-ethyl-3H-imidazo[4,5-b]pyridine | $^{1}$H NMR, δppm (CDCl3): 8.39 (dd, 1H), 8.23 (dd, 1H), 8.03 (dd, 1H), 7.76 (t, 1H), 7.19-7.29 (m, 4H), 6.36 (s, 2H), 4.48 (q, 2H), 1.29 (t, 3H) | 339.2 [M + 1] |

TABLE 6-continued

| Cpd # | STRUCTURE | IUPAC NAME | NMR | MS (m/z) |
|---|---|---|---|---|
| 800 | 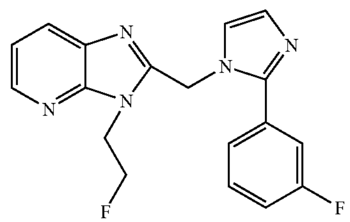 | 3-(2-fluoroethyl)-2-{[2-(3-fluorophenyl)-1H-imidazol-1-yl]methyl}-3H-imidazo[4,5-b]pyridine | H-1 NMR (CDCl3): 4.26 (t, 1H), 4.35 (t, 1H), 4.51 (t, 1H), 4.67 (t, 1H), 5.54 (s, 2H), 7.09-7.45 (m, 4H), 8.06 (d, 1H), 8.36 (d, 1H) | 340 [M + 1] |
| 801 | 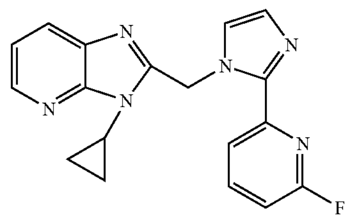 | 3-cyclopropyl-2-{[2-(6-fluoropyridin-2-yl)-1H-imidazol-1-yl]methyl}-3H-imidazo[4,5-b]pyridine | H-1 NMR (CDCl3): line list provided 1.20-1.24 (m, 4H), 3.35 (m, 1H), 6.29 (s, 2H), 6.79 (d, 1H), 7.15 (m, 3H), 7.82 (d, 1H), 7.92 (d, 1H), 8.15 (d, 1H), 8.37 (d, 1H) | 335 [M + 1] |
| 802 | 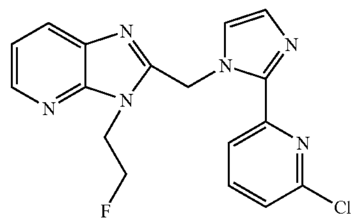 | 2-{[2-(6-chloropyridin-2-yl)-1H-imidazol-1-yl]methyl}-3-(2-fluoroethyl)-3H-imidazo[4,5-b]pyridine | HCl salt H-1 NMR (dmso): line list provided 4.77 (s, 2H), 4.90 (m, 2H), 6.28 (s, 2H), 7.24 (m, 1H), 7.62 (d, 1H), 7.93 (m, 2H), 8.12 (m, 2H), 8.36 (m, 2H) | 357 [M + 1] |
| 803 | 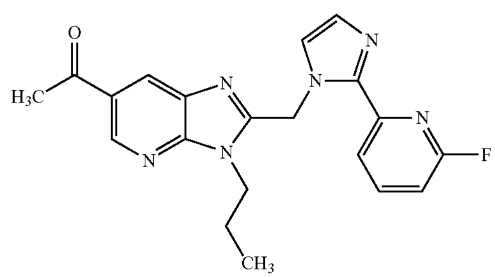 | 1-(2-{[2-(6-fluoropyridin-2-yl)-1H-imidazol-1-yl]methyl}-3-propyl-3H-imidazo[4,5-b]pyridin-6-yl)ethanone | 1H NMR (CDCl3): 9.01 (1H, d), 8.53 (1H, d), 8.20-8.17 (1H, m), 7.87 (1H, q), 7.24-7.21 (2H, m), 6.88-6.84 (1H, m), 6.30 (2H, s), 4.40 (2H, t), 2.66 (3H, s), 1.80-1.73 (2H, m), 0.88 (3H, t) | 379.3 [M + 1] |

TABLE 6-continued

| Cpd # | STRUCTURE | IUPAC NAME | NMR | MS (m/z) |
|---|---|---|---|---|
| 804 | 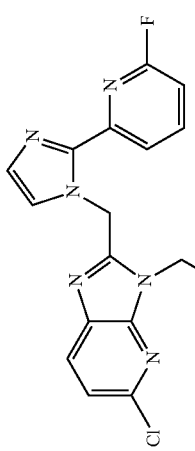 | 5-chloro-2-{[2-(6-fluoropyridin-2-yl)-1H-imidazol-1-yl]methyl}-3-propyl-3H-imidazo[4,5-b]pyridine | hydrochloride 1H NMR (d6 DMSO): 8.35 (1H, dd), 8.24 (1H, q), 8.02 (1H, s), 7.95 (1H, dd), 7.90 (1H, s), 7.33 (1H, dd), 7.28 (1H, d), 7.26 (1H, d), 6.32 (2H, s), 4.33 (2H, t), 1.90-1.85 (2H, m), 0.94 (3H, t) | 371.3 [M + 1] |
| 805 | 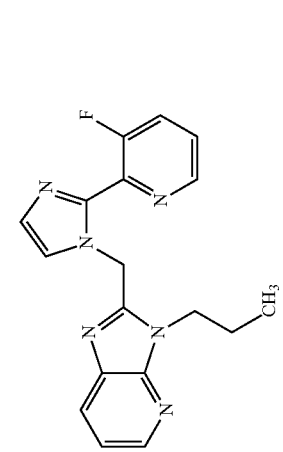 | 2-{[2-(3-fluoropyridin-2-yl)-1H-imidazol-1-yl]methyl}-3-propyl-3H-imidazo[4,5-b]pyridine | dihydrochloride 1H NMR (d6 DMSO): 8.48-8.46 (1H, m), 8.30 (1H, dd), 8.12-8.03 (2H, m), 7.96 (1H, d), 7.90 (1H, dd), 7.72-7.65 (1H, m), 7.22 (1H, dd), 6.18 (2H, s), 4.27 (2H, t), 1.83-1.75 (2H, m) 0.87 (3H, t) | 337.2 |
| 806 | 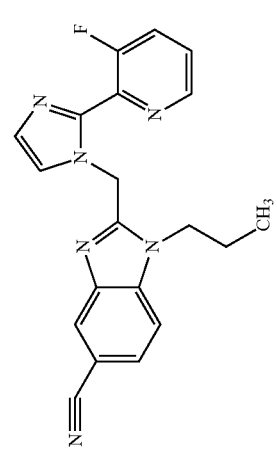 | 2-{[2-(3-fluoropyridin-2-yl)-1H-imidazol-1-yl]methyl}-1-propyl-1H-benzimidazole-5-carbonitrile | hydrochloride 1H NMR (d6 DMSO): 8.45 (1H, m), 8.08-8.02 (3H, m), 7.93 (1H, s), 7.83 (1H, d), 7.69-7.62 (2H, m), 6.16 (2H, s), 4.29 (2H, t), 1.72-1.20 (2H, m), 0.86 (3H, t) | 361.2 [M + 1] |

TABLE 6-continued

| Cpd # | STRUCTURE | IUPAC NAME | NMR | MS (m/z) |
|---|---|---|---|---|
| 807 | 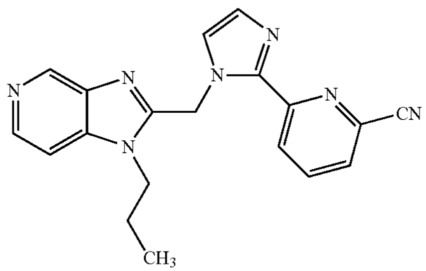 | 6-{1-[(1-propyl-1H-imidazo[4,5-c]pyridin-2-yl)methyl]-1H-imidazol-2-yl}pyridine-2-carbonitrile | $^1$H NMR (CDCl3) δ 9.03 (s, 1H), 8.56 (d, 1H), 8.44 (d, 1H), 7.91 (dd, 1H), 7.60 (d, 1H), 7.32 (d, 1H), 7.30 (d, 1H), 7.25 (d, 1H), 6.25 (s, 2H), 4.31 (t, 2H), 1.78 (q, 2H), 0.90 (t, 3H) | m/e 344 |
| 808 | 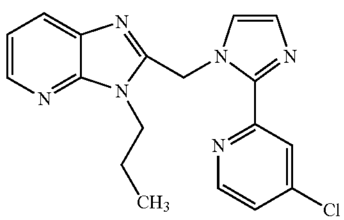 | 2-{[2-(4-chloropyridin-2-yl)-1H-imidazol-1-yl]methyl}-3-propyl-3H-imidazo[4,5-b]pyridine | $^1$H NMR, δppm (CDCl3): 8.36-8.45 (m, 3H), 8.03 (dd, 1H), 7.18-7.29 (m, 4H), 6.40 (s, 2H), 4.28 (t, 2H), 1.66 (m, 2H), 0.81 (t, 3H) | |
| 809 | 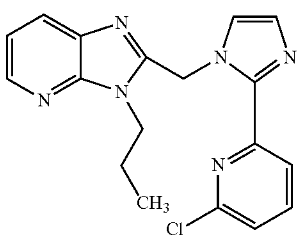 | 2-{[2-(6-chloropyridin-2-yl)-1H-imidazol-1-yl]methyl}-3-propyl-3H-imidazo[4,5-b]pyridine | $^1$H NMR, δppm (CDCl3): 8.39 (dd, 1H), 8.23 (dd, 1H), 8.02 (dd, 1H), 7.76 (t, 1H), 7.19-7.29 (m, 4H), 6.36 (s, 2H), 4.34 (t, 2H), 1.72 (m, 2H), 0.83 (t, 3H) | |
| 810 | 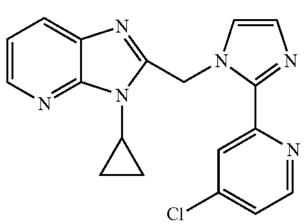 | 2-{[2-(4-chloropyridin-2-yl)-1H-imidazol-1-yl]methyl}-3-cyclopropyl-3H-imidazo[4,5-b]pyridine | HCl salt H-1 NMR (DMSO): line list provided 1.24 (m, 4H), 3.48 (m, 1H), 6.43 (s, 2H), 7.19 (m, 1H), 7.67 (m, 1H), 7.86 (d, 1H), 7.97 (s, 1H), 8.06 (s, 1H), 8.31 (d, 1H), 8.56 (d, 1H), 8.64 (m, 1H) | 351 [M + 1]; 349 [M − 1] |

TABLE 6-continued

| Cpd # | STRUCTURE | IUPAC NAME | NMR | MS (m/z) |
|---|---|---|---|---|
| 811 | 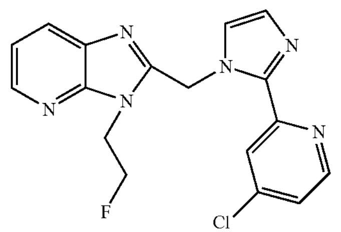 | 2-{[2-(4-chloropyridin-2-yl)-1H-imidazol-1-yl]methyl}-3-(2-fluoroethyl)-3H-imidazo[4,5-b]pyridine | H-1 NMR (CDCl3): 4.60-4.77 (m, 2H), 4.81 (s, 2H), 6.35 (s, 2H), 7.20-7.25 (m, 5H), 6.32 (s, 2H), 4.36 (t, 2H), 1.80 (m, 2H), 0.89 (t, 3H) 8.03 (d, 1H), 8.38 (m, 1H) | 357 [M + 1] |
| 812 | 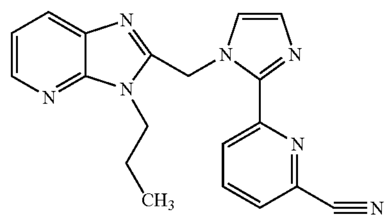 | 6-{1-[(3-propyl-3H-imidazo[4,5-b]pyridin-2-yl)methyl]-1H-imidazol-2-yl}pyridine-2-carbonitrile | 1H NMR, δppm (CDCl3): 8.56 (dd, 1H), 8.39 (dd, 1H), 8.00 (dd, 1H), 7.92 (dd, 1H), 7.63 (dd, 1H), 7.20-7.29 (m, 3H), 6.32 (s, 2H), 4.36 (t, 2H), 1.80 (m, 2H), 0.89 (t, 3H) LC-MS: calcd: 343.39, found 344.1 [M + 1] | |
| 813 | 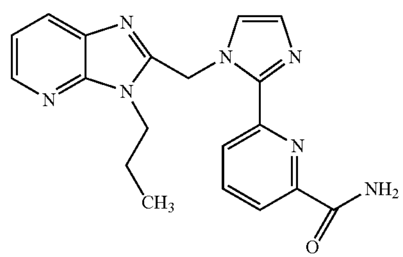 | 6-{1-[(3-propyl-3H-imidazo[4,5-b]pyridin-2-yl)methyl]-1H-imidazol-2-yl}pyridine-2-carboxamide | 1H NMR, δppm (CDCl3): 8.88 (s, 1H), 8.42 (dd, 1H), 8.38 (dd, 1H), 8.15 (dd, 1H), 7.98 (dd, 1H), 7.93 (d, 1H), 7.22-7.27 (m, 3H), 6.18 (s, 2H), 5.67 (s, 1H), 4.07 (t, 2H), 1.54 (m, 2H), 0.83 (t, 3H) | 362.2 [M + 1] |
| 814 | 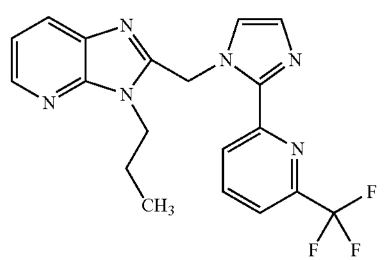 | 3-propyl-2-{[2-[6-(trifluoromethyl)pyridin-2-yl]-1H-imidazol-1-yl]methyl}-3H-imidazo[4,5-b]pyridine | 1H NMR, δppm (CDCl3): 8.53 (d, 1H), 8.39 (dd, 1H), 7.96-8.06 (m, 2H), 7.64 (dd, 1H), 7.20-7.27 (m, 3H), 6.42 (s, 2H), 4.26 (t, 2H), 1.61 (m, 2H), 0.72 (t, 3H) | 387.3 [M + 1] |

TABLE 6-continued

| Cpd # | STRUCTURE | IUPAC NAME | NMR | MS (m/z) |
|---|---|---|---|---|
| 815 | 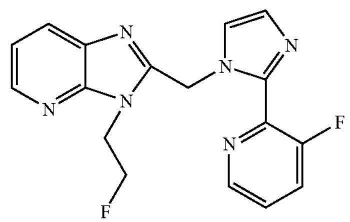 | 3-(2-fluoroethyl)-2-{[2-(3-fluoropyridin-2-yl)-1H-imidazol-1-yl]methyl}-3H-imidazo[4,5-b]pyridine | H-1 NMR (CDCl3): line list provided 4.58-4.66 (m, 2H), 4.75 (s, 2H), 6.03 (s, 2H), 7.21-7.35 (m, 4H), 7.57 (m, 1H), 8.04 (d, 1H), 8.41 (m, 1H) | 341 [M + 1] |
| 816 | 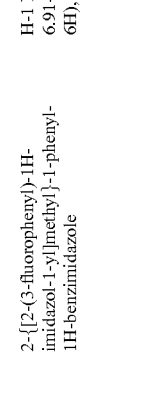 | 2-{[2-(3-fluorophenyl)-1H-imidazol-1-yl]methyl}-1-phenyl-1H-benzimidazole | H-1 NMR (CDCl3): 5.38 (s, 2H), 6.91-7.17 (m, 8H), 7.22-7.45 (m, 6H), 7.84 (d, 1H) | 369 |
| 817 | 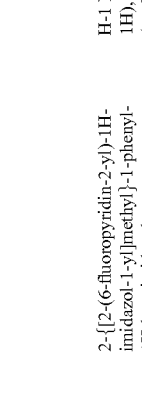 | 2-{[2-(6-fluoropyridin-2-yl)-1H-imidazol-1-yl]methyl}-1-phenyl-1H-benzimidazole | H-1 NMR: 6.22 (s, 2H), 6.78 (m, 1H), 7.03-7.37 (m, 9H), 7.65-7.92 (m, 3H) | 368 [M − 1] |
| 818 | 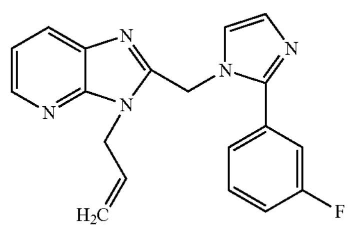 | 3-allyl-2-{[2-(3-fluorophenyl)-1H-imidazol-1-yl]methyl}-3H-imidazo[4,5-b]pyridine | H-1 NMR (CDCl3): 4.59-4.62 (m, 3H), 5.03 (d, 1H), 5.43 (s, 2H), 5.70 (m, 1H), 7.03 (s; 1H), 7.17 (m, 1H), 7.25 (m, 2H), 7.43 (m, 3H), 8.04 (d, 1H), 8.40 (d, 1H) | 334 [M + 1]; 3332 [M − 1] |

TABLE 6-continued

| Cpd # | STRUCTURE | IUPAC NAME | NMR | MS (m/z) |
|---|---|---|---|---|
| 819 | 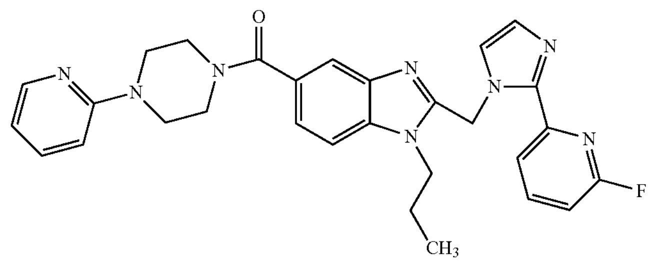 | 2-{[2-(6-fluoropyridin-2-yl)-1H-imidazol-1-yl]methyl}-1-propyl-5-[(4-pyridin-2-ylpiperazin-1-yl)carbonyl]-1H-benzimidazole | CDCl₃; 8.15-8.2 (m, 2H), 7.82-7.94 (m, 2H), 7.44-7.53 (m, 1H), 7.35-7.44 (m, 2H), 7.18 (q, 2H), 6.88 (d, 1H), 6.71 (s, 1H), 6.65 (s, 1H), 6.29 (s, 2H), 4.21-4.29 (m, 2H), 3.53-4.0 (m, 8H), 1.53-1.71 (m, 2H), 0.82 (t, 3H). | |
| 820 | 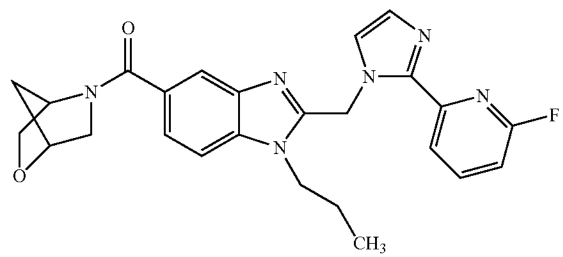 | 5-[(2-{[2-(6-fluoropyridin-2-yl)-1H-imidazol-1-yl]methyl}-1-propyl-1H-benzimidazol-5-yl)carbonyl]-2-oxa-5-azabicyclo[2.2.1]heptane | CDCl₃; 8.18 (d, 7.97Hz, 1Hz), 7.85-7.94 (m, 2H), 7.52-7.54 (m, 1H), 7.38-7.42 (m, 1H), 7.17-7.26 (m, 2H), 6.90 (d, J = 7.96Hz, 1H), 6.30 (s, 2H), 4.73-5.06 (m, 1H), 4.56 (d, 1H), 4.24-4.35 (m, 2H), 4.04-4.10 (m, 1H), 3.81-3.89 (m, 1H), 3.51-3.7 (m,12 2H), 1.96 (s, 1H), 1.86 (s, 1H), 1.64-1.71 (m, 2H), 0.83 (t, J = 7.28 Hz, 3H). | |
| 821 | 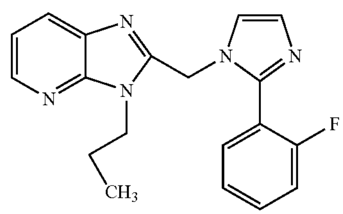 | 2-{[2-(2-fluorophenyl)-1H-imidazol-1-yl]methyl}-3-propyl-3H-imidazo[4,5-b]pyridine | ¹H NMR, δppm (CDCl3): 8.39 (dd, 1H), 8.03 (dd, 1H), 7.65 (m, 1H), 7.50 (m, 1H), 7.20-7.35 (m, 3H), 7.07 (d, 1H), 5.38 (s, 2H), 3.84 (t, 2H), 1.46 (m, 2H), 0.74 (t, 3H) | 336.2 [M + 1] |
| 822 | 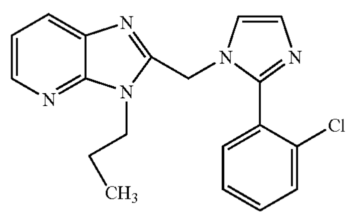 | 2-{[2-(2-chlorophenyl)-1H-imidazol-1-yl]methyl}-3-propyl-3H-imidazo[4,5-b]pyridine | ¹H NMR, δppm (CDCl3): 8.38 (dd, 1H), 8.02 (dd, 1H), 7.33-7.56 (m, 4H), 7.19-7.27 (m, 2H), 7.09 (d, 1H), 5.30 (s, 2H), 3.85 (t, 2H), 1.50 (m, 2H), 0.76 (t, 3H) | 352.2 [M + 1] |

TABLE 6-continued

| Cpd # | STRUCTURE | IUPAC NAME | NMR | MS (m/z) |
|---|---|---|---|---|
| 823 | 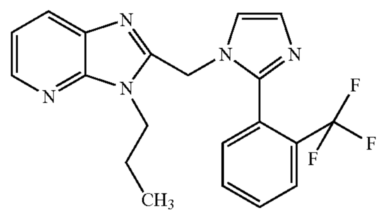 | 3-propyl-2-({2-[2-(trifluoromethyl)phenyl]-1H-imidazol-1-yl}methyl)-3H-imidazo[4,5-b]pyridine | 1H NMR, δppm (CDCl3); 8.39 (dd, 1H), 8.02 (dd, 1H), 7.84 (dd, 1H), 7.53-7.65 (m, 2H), 7.45 (m, 1H), 7.21-7.27 (m, 2H), 7.09 (d, 1H), 5.17 (s, 2H), 3.93 (t, 2H), 1.59 (m, 2H), 0.80 (t, 3H) | 386.2 [M + 1] |
| 824 | 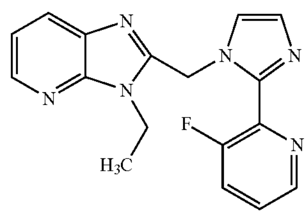 | 3-ethyl-2-{[2-(3-fluoropyridin-2-yl)-1H-imidazol-1-yl]methyl}-3H-imidazo[4,5-b]pyridine | 1H NMR, δppm (CDCl3); 8.47 (m, 1H), 8.40 (dd, 1H), 8.04 (dd, 1H), 7.62 (m, 1H), 7.36 (m, 1H), 7.23-7.28 (m, 2H), 7.16 (d, 1H), 6.10 (s, 2H), 4.37 (q, 2H), 1.19 (t, 3H) | 323.3 [M + 1] |
| 825 | 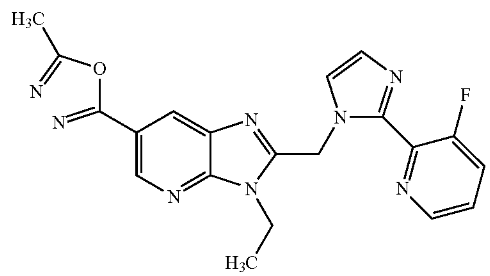 | 3-ethyl-2-{[2-(3-fluoropyridin-2-yl)-1H-imidazol-1-yl]methyl}-6-(5-methyl-1,3,4-oxadiazol-2-yl)-3H-imidazo[4,5-b]pyridine | 1H NMR (CDCl3): 9.08 (1H, d), 8.58 (1H, d), 8.45-8.43 (1H, m), 7.65-7.59 (1H, m), 7.39-7.30 (2H, m), 7.18 (1H, s), 6.14 (2H, s), 4.43 (2H, q), 2.66 (3H, s), 1.23 (3H, t) | 405.3 [M + 1] |
| 826 | 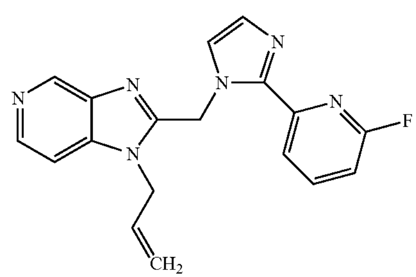 | 1-allyl-2-{[2-(6-fluoropyridin-2-yl)-1H-imidazol-1-yl]methyl}-1H-imidazo[4,5-c]pyridine | 1H NMR (CDCl3) δ 9.05 (s, 1H), 8.40 (d, 1H), 8.14 (d, 1H), 7.85 (dd, 1H), 7.26 (d, 1H), 7.22 (d, 1H), 7.17 (6.85 (d, 1H), 6.19 (s, 2H), 5.82-5.70 (m, 1H), 5.12 (d, 1H), 4.99-4.96 (m, 2H), 4.82 (d, 1H) | m/e 335 |

TABLE 6-continued

| Cpd # | STRUCTURE | IUPAC NAME | NMR | MS (m/z) |
|---|---|---|---|---|
| 827 | 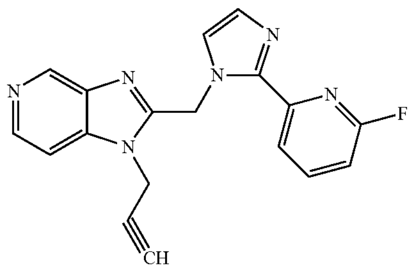 | 2-{[2-(6-fluoropyridin-2-yl)-1H-imidazol-1-yl]methyl}-1-prop-2-ynyl-1H-imidazo[4,5-c]pyridine | ¹H NMR (CDCl3) δ 9.04 (s, 1H), 8.46 (d, 1H), 8.15 (d, 1H), 7.86 (dd, 1H), 7.41 (d, 1H), 7.26 (d, 1H), 7.21 (d, 1H), 6.85 (d, 1H), 6.23 (s, 2H), 5.21 (d, 2H), 2.33–2.32 (m, 1H) | m/e 333 |
| 828 | 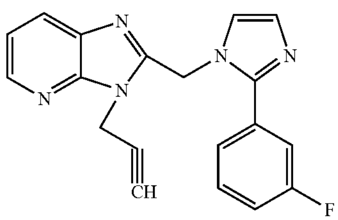 | 2-{[2-(3-fluorophenyl)-1H-imidazol-1-yl]methyl}-3-prop-2-ynyl-3H-imidazo[4,5-b]pyridine | H-1 NMR (dmso): 3.47 (s, 1H), 4.78 (s, 2H), 5.65 (s, 2H), 7.07–7.45 (m, 5H), 7.45 (m, 2H), 8.07 (m, 1H), 8.42 (m, 1H) | 332 [M + 1]; 330 [M − 1] |
| 829 | 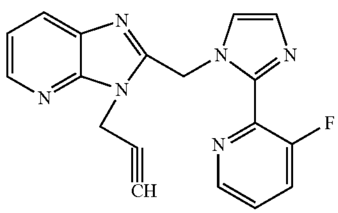 | 2-{[2-(3-fluoropyridin-2-yl)-1H-imidazol-1-yl]methyl}-3-prop-2-ynyl-3H-imidazo[4,5-b]pyridine | HCl salt H-1 NMR (dmso): line list provided 3.51 (s, 1H), 5.25 (s, 2H), 6.25 (s, 2H), 7.27 (m, 1H), 7.72 (m, 1H), 7.94–8.15 (m, 4H), 8.35 (m, 1H), 8.50 (1H) | 333 [M + 1] |
| 830 | 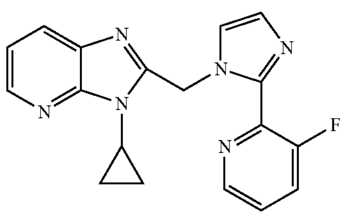 | 3-cyclopropyl-2-{[2-(3-fluoropyridin-2-yl)-1H-imidazol-1-yl]methyl}-3H-imidazo[4,5-b]pyridine | HCl salt H-1 NMR (dmso): line list provided 1.19 (m, 4H), 3.36 (m, 2H), 6.24 (s, 2H), 7.21 (m, 1H), 7.70 (m, 1H), 7.88 (d, 2H), 8.00 (s, 1H), 8.07 (m, 3H), 8.31 (d, 1H), 8.52 (d, 1H) | 335 [M + 1] |

TABLE 6-continued

| Cpd # | STRUCTURE | IUPAC NAME | NMR | MS (m/z) |
|---|---|---|---|---|
| 831 | 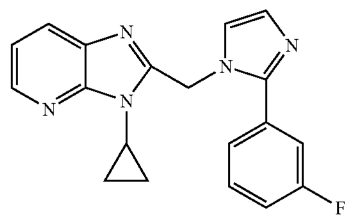 | 3-cyclopropyl-2-{[2-(3-fluorophenyl)-1H-imidazol-1-yl]methyl}-3H-imidazo[4,5-b]pyridine | HCl salt H-1 NMR (DMSO): line list provided 1.03-1.22 (m, 4H), 3.37 (m, 1H), 5.96 (s, 2H), 7.22 (m, 1H), 7.45-7.78 (m, 4H), 7.95-8.03 (m, 3H), 8.37 (d, 1H) | 334 [M + 1]; 332 [M − 1] |
| 832 | 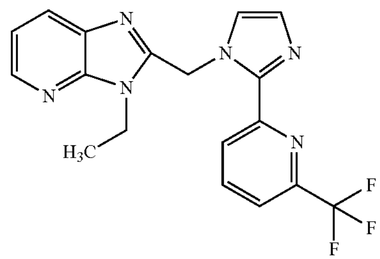 | 3-ethyl-2-({2-[6-(trifluoromethyl)pyridin-2-yl]-1H-imidazol-1-yl}methyl)-3H-imidazo[4,5-b]pyridine | $^1$H NMR, δppm (CDCl3): 8.52 (d, 1H), 8.39 (dd, 1H), 7.90-8.05 (m, 2H), 7.64 (d, 1H), 7.21-7.27 (m, 3H), 6.42 (s, 2H), 4.39 (q, 2H), 1.17 (t, 3H) | 373.3 [M + 1] |
| 833 | 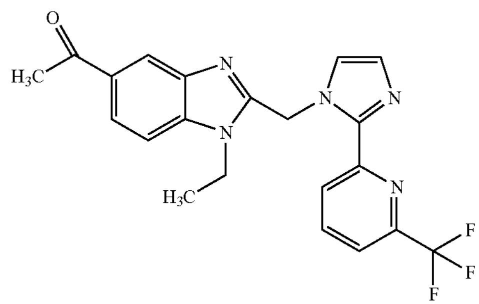 | 1-[1-ethyl-2-({2-[6-(trifluoromethyl)pyridin-2-yl]-1H-imidazol-1-yl}methyl)-1H-benzimidazol-5-yl]ethanone | $^1$H NMR, δppm (CDCl3): 8.52 (d, 1H), 8.40 (d, 1H), 7.99-8.03 (m, 2H), 7.64 (d, 1H), 7.40 (d, 1H), 7.20-7.22 (m, 2H), 6.41 (s, 2H), 4.34 (q, 2H), 2.68 (s, 3H), 1.15 (t, 3H) | 414.2 [M + 1] |

TABLE 6-continued

| Cpd # | STRUCTURE | IUPAC NAME | NMR | MS (m/z) |
|---|---|---|---|---|
| 834 | 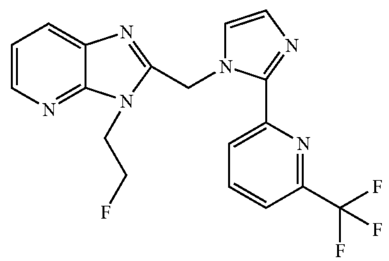 | 3-(2-fluoroethyl)-2-({2-[6-(trifluoromethyl)pyridin-2-yl]-1H-imidazol-1-yl}methyl)-3H-imidazo[4,5-b]pyridine | H-1 NMR (CDCl3): line list provided 4.60-4.81 (m, 4H), 6.30 (s, 2H), 7.18-7.30 (m, 3H), 7.54 (d, 1H), 7.88-8.00 (m, 2H), 8.33 (d, 1H), 8.49 (d, 1H) | 391 [M + 1]; 389 [M − 1] |
| 835 | 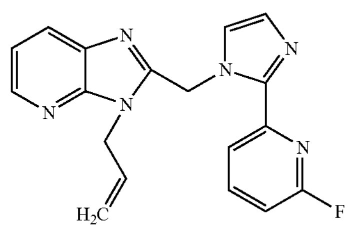 | 3-allyl-2-{[2-(6-fluoropyridin-2-yl)-1H-imidazol-1-yl]methyl}-3H-imidazo[4,5-b]pyridine | H-1 NMR (CDCl3): line list provided 4.87 (d, 1H), 5.14 (m, 3H), 5.87 (m, 1H), 6.24 (s, 2H), 6.86 (dd, 1H), 7.23 (m, 3H), 7.84 (m, 1H), 8.02 (d, 1H), 8.15 (m, 1H), 8.38 (d, 1H) | 335 [M + 1]; 333 [M − 1] |
| 836 | 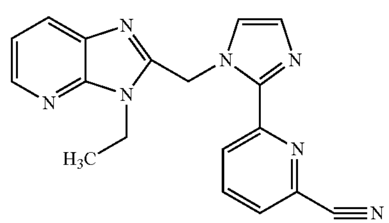 | 6-{1-[(3-ethyl-3H-imidazo[4,5-b]pyridin-2-yl)methyl]-1H-imidazol-2-yl}pyridine-2-carbonitrile | $^1$H NMR, δppm (CDCl3): 8.56 (dd, 1H), 8.40 (dd, 1H), 8.01 (dd, 1H), 7.93 (t, 1H), 7.63 (dd, 1H), 7.21-7.29 (m, 3H), 6.33 (s, 2H), 4.44 (q, 2H), 1.35 (t, 3H) | 330.1 [M + 1] |
| 837 | 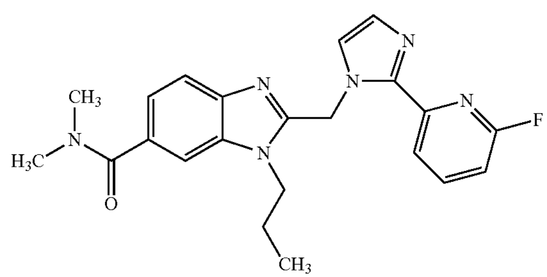 | 2-{[2-(6-fluoropyridin-2-yl)-1H-imidazol-1-yl]methyl}-N,N-dimethyl-1-propyl-1H-benzimidazole-6-carboxamide | $^1$H NMR (CDCl3) δ 8.17 (d, 1H), 7.89 (dd, 1H), 7.74 (d, 1H), 7.49 (s, 1H), 7.30 (d, 1H), 7.21 (d, 1H), 7.15 (d, 1H), 6.89 (d, 1H), 6.29 (s, 2H), 4.23 (t, 2H), 3.07 (br d, 6H), 1.66 (q, 2H), 0.81 (t, 3H) | m/e 407 |

TABLE 6-continued

| Cpd # | STRUCTURE | IUPAC NAME | NMR | MS (m/z) |
|---|---|---|---|---|
| 838 | 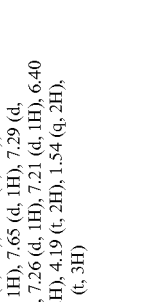 | 1-propyl-2-({2-[6-(trifluoromethyl)pyridin-2-yl]-1H-imidazol-1-yl}methyl)-1H-imidazo[4,5-c]pyridine | $^1$H NMR (CDCl3) δ 9.08 (s, 1H), 8.52 (d, 1H), 8.44 (d, 1H), 7.99 (dd, 1H), 7.65 (d, 1H), 7.29 (d, 1H), 7.26 (d, 1H), 7.21 (d, 1H), 6.40 (s, 2H), 4.19 (t, 2H), 1.54 (q, 2H), 0.71 (t, 3H) | m/e 387 |
| 839 | 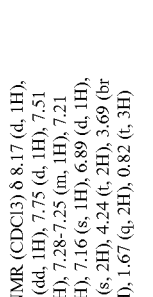 | 2-{[2-(6-fluoropyridin-2-yl)-1H-imidazol-1-yl]methyl}-6-(morpholin-4-ylcarbonyl)-1-propyl-1H-benzimidazole | $^1$H NMR (CDCl3) δ 8.17 (d, 1H), 7.88 (dd, 1H), 7.75 (d, 1H), 7.51 (s, 1H), 7.28-7.25 (m, 1H), 7.21 (s, 1H), 7.16 (s, 1H), 6.89 (d, 1H), 6.29 (s, 2H), 4.24 (t, 2H), 3.69 (br s, 8H), 1.67 (q, 2H), 0.82 (t, 3H) | m/e 449 |
| 840 | 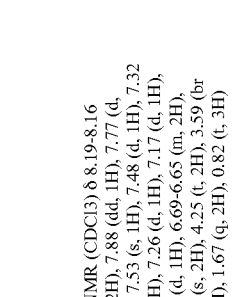 | 2-{[2-(6-fluoropyridin-2-yl)-1H-imidazol-1-yl]methyl}-1-propyl-6-[(4-pyridin-2-ylpiperazin-1-yl)carbonyl]-1H-benzimidazole | $^1$H NMR (CDCl3) δ 8.19-8.16 (m, 2H), 7.88 (dd, 1H), 7.77 (d, 1H), 7.53 (s, 1H), 7.48 (d, 1H), 7.32 (d, 1H), 7.26 (d, 1H), 7.17 (d, 1H), 6.89 (d, 1H), 6.69-6.65 (m, 2H), 6.30 (s, 2H), 4.25 (t, 2H), 3.59 (br s, 8H), 1.67 (q, 2H), 0.82 (t, 3H) | m/e 525 |

TABLE 6-continued

| Cpd # | STRUCTURE | IUPAC NAME | NMR | MS (m/z) |
|---|---|---|---|---|
| 841 | 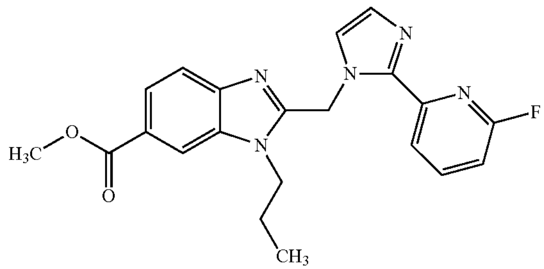 | methyl 2-{[2-(6-fluoropyridin-2-yl)-1H-imidazol-1-yl]methyl}-1-propyl-1H-benzimidazole-6-carboxylate | ¹H NMR (CDCl3) δ 8.18 (d, 1H), 8.09 (s, 1H), 7.98-7.87 (m, 2H), 7.76 (d, 1H), 7.24 (s, 1H), 7.17 (s, 1H), 6.88 (d, 1H), 6.31 (s, 2H), 4.29 (t, 2H), 3.94 (s, 3H), 1.69 (q, 2H), 0.85 (t, 3H) 4. | m/e 39 |
| 842 | 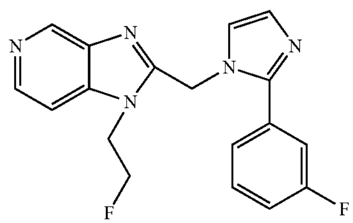 | 1-(2-fluoroethyl)-2-{[2-(3-fluorophenyl)-1H-imidazol-1-yl]methyl}-1H-imidazol[4,5-c]pyridine | H-1 NMR (CDCl3): 4.02 (t, 1H), 4.05 (t, 1H), 4.32 (t, 1H), 4.47 (t, 1H), 5.58 (s, 2H), 7.05-7.33 (m, 5H), 7.44 (m, 2H), 8.47 (d, 1H), 9.10 (s, 1H) | 340 [M + 1] |
| 843 | 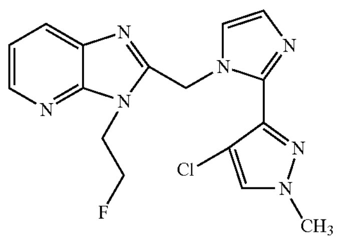 | 2-{[2-(4-chloro-1-methyl-1H-pyrazol-3-yl)-1H-imidazol-1-yl]methyl}-3-(2-fluoroethyl)-3H-imidazo[4,5-b]pyridine | H-1 NMR (CDCl3): line list provided 3.89 (s, 3H), 4.55 (s, 2H), 4.69 (m, 1H), 4.71 (m, 1H), 5.93 (s, 2H), 7.11 (s, 1H), 7.25 (m, 2H), 7.47 (s, 1H), 8.04 (d, 1H), 8.36 (d, 1H) | 360 [M + 1] |
| 844 | 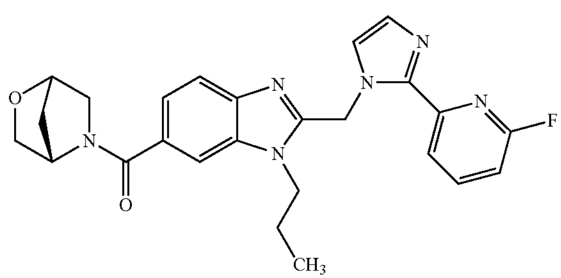 | (4S)-5-[(2-{[2-(6-fluoropyridin-2-yl)-1H-imidazol-1-yl]methyl}-1-propyl-1H-benzimidazol-6-yl)carbonyl]-2-oxa-5-azabicyclo[2.2.1]heptane | ¹H NMR (CDCl3) δ 8.18 (d, 1H), 7.89 (dd, 1H), 7.78-7.72 (m, 1H), 7.62 (s, 1H), 7.42-7.33 (m 1H), 7.22 (s, 1H), 7.17 (s, 1H), 6.89 (d, 1H), 6.30 (s, 2H), 5.06-4.51 (m 2H), 4.25 (t, 2H), 4.11-3.48 (m, 4H), 1.96-1.87 (m, 2H), 1.68 (q, 2H), 0.83 (t, 3H) | m/e 461 |

TABLE 6-continued

| Cpd # | STRUCTURE | IUPAC NAME | NMR | MS (m/z) |
|---|---|---|---|---|
| 845 | 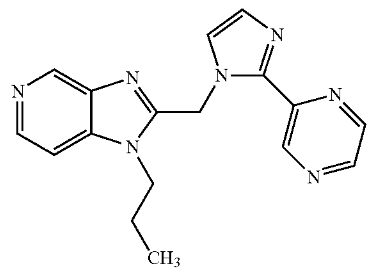 | 1-propyl-2-[(2-pyrazin-2-yl-1H-imidazol-1-yl)methyl]-1H-imidazo[4,5-c]pyridine | ¹H NMR (CDCl3) δ 9.58 (s, 1H), 9.09 (d, 1H), 8.61-8.42 (m, 3H), 7.32-7.24 (m, 3H), 6.33 (s, 2H), 4.16 (t, 2H), 1.63 (q, 2H), 0.81 (t, 3H) | m/e 320 |
| 846 | 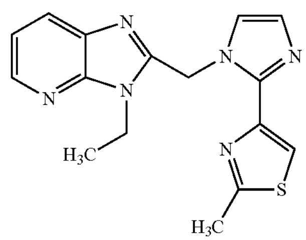 | 3-ethyl-2-{[2-(2-methyl-1,3-thiazol-4-yl)-1H-imidazol-1-yl]methyl}-3H-imidazo[4,5-b]pyridine | ¹H NMR, δppm (CDCl3): 8.40 (dd, 1H), 8.05 (dd, 1H), 7.88 (s, 1H), 7.25 (m, 1H), 7.11 (d, 1H), 7.07 (d, 1H), 6.29 (s, 2H), 4.35 (q, 2H), 2.78 (s, 3H), 1.18 (t, 3H) | 325.2 [M + 1] |
| 847 | 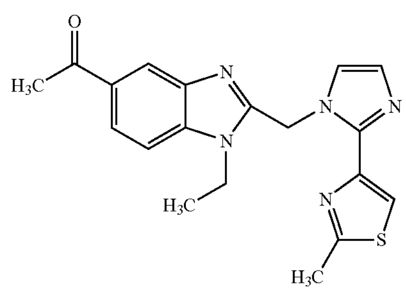 | 1-(1-ethyl-2-{[2-(2-methyl-1,3-thiazol-4-yl)-1H-imidazol-1-yl]methyl}-1H-benzimidazol-5-yl)ethanone | ¹H NMR, δppm (CDCl3): 8.41 (d, 1H), 8.01 (dd, 1H), 7.89 (s, 1H), 7.38 (d, 1H), 7.10 (d, 1H), 7.05 (d, 1H), 6.30 (s, 2H), 4.27 (q, 2H), 2.79 (s, 3H), 2.69 (s, 3H), 1.12 (t, 3H) | 366.2 [M + 1] |
| 848 | 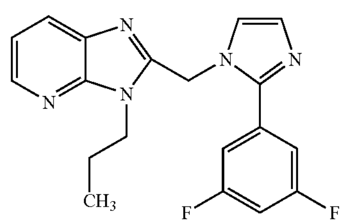 | 2-{[2-(3,5-diflourophenyl)-1H-imidazol-1-yl]methyl}-3-propyl-3H-imidazo[4,5-b]pyridine | ¹H NMR, δppm (CDCl3): 8.41 (dd, 1H), 8.06 (dd, 1H), 7.19-7.29 (m, 4H), 7.08 (d, 1H), 6.93 (m, 1H), 5.52 (s, 2H), 3.96 (t, 2H), 1.57 (m, 3H), 0.82 (t, 3H) | 354.3 [M + 1] |

TABLE 6-continued

| Cpd # | STRUCTURE | IUPAC NAME | NMR | MS (m/z) |
|---|---|---|---|---|
| 849 | 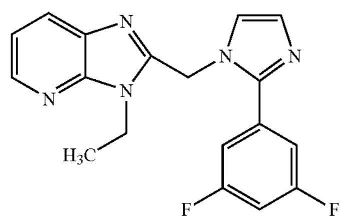 | 2-{[2-(3,5-difluorophenyl)-1H-imidazol-1-yl]methyl}-3-ethyl-3H-imidazo[4,5-b]pyridine | ¹H NMR, δppm (CDCl3): 8.41 (dd, 1H), 8.06 (dd, 1H), 7.19-7.31 (m, 4H), 7.07 (d, 1H), 6.93 (m, 1H), 5.52 (s, 2H), 4.05 (q, 2H), 1.14 (t, 3H). | 340.3 [M + 1] |
| 850 | 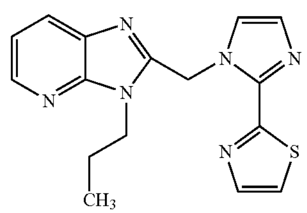 | 3-propyl-2-{[2-(1,3-thiazol-2-yl)-1H-imidazol-1-yl]methyl}-3H-imidazo[4,5-b]pyridine | ¹H NMR, δppm (CDCl3): 8.40 (dd, 1H), 8.05 (dd, 1H), 7.86 (d, 1H), 7.40 (d, 1H), 7.25 (d, 1H), 7.22 (d, 1H), 7.15 (d, 1H), 6.37 (s, 2H), 4.27 (t, 2H), 1.62 (m, 2H), 0.78 (t, 3H). | 325.3 [M + 1] |
| 851 | 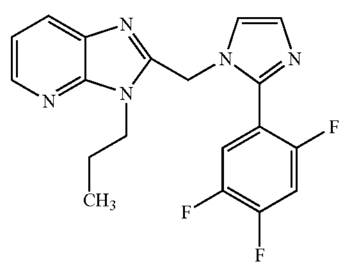 | 3-propyl-2-{[2-(2,4,5-trifluorophenyl)-1H-imidazol-1-yl]methyl}-3H-imidazo[4,5-b]pyridine | ¹H NMR, δppm (CDCl3): 8.41 (dd, 1H), 8.03 (dd, 1H), 7.50 (m, 1H), 7.22-7.29 (m, 2H), 7.07-7.15 (m, 2H), 5.37 (s, 2H), 3.93 (t, 2H), 1.53 (m, 2H), 0.82 (t, 3H). | 372.2 [M + 1] |
| 852 | 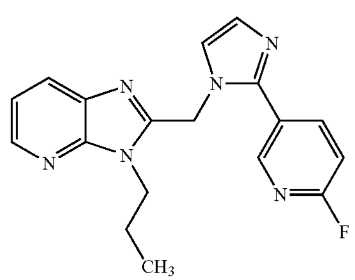 | 2-{[2-(6-fluoropyridin-3-yl)-1H-imidazol-1-yl]methyl}-3-propyl-3H-imidazo[4,5-b]pyridine | 1H NMR (CDCl3): 8.53-8.51 (1H, m), 8.40 (1H, dd), 8.16-8.14 (1H, m), 8.03 (1H, dd), 7.28-7.23 (2H, m), 7.11 (1H, d), 7.05 (1 h, dd), 5.46 (2H, s), 4.00 (2H, t), 1.65-1.59 (2H, m), 0.84 (3H, t) | 337.1 [M + 1] |

TABLE 6-continued

| Cpd # | STRUCTURE | IUPAC NAME | NMR | MS (m/z) |
|---|---|---|---|---|
| 853 | 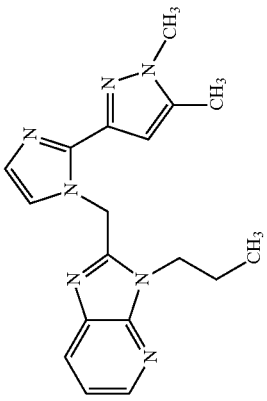 | 2-{[2-(1,5-dimethyl-1H-pyrazol-3-yl)-1H-imidazol-1-yl]methyl}-3-propyl-3H-imidazo[4,5-b]pyridine | 1H NMR (CDCl3): 8.37 (1H, dd), 8.04 (1H, dd), 7.22 (1H, dd), 7.06 (1H, d), 7.02 (1H, d), 6.66 (1H, s), 6.20 (1H, s), 4.19 (2H, t), 3.83 (3H, s), 2.33 (3H, s), 1.60-1.53 (2H, m), 0.76 (3H, t) | 336.2 [M + 1] |
| 854 | 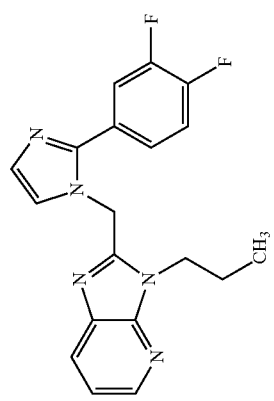 | 2-{[2-(3,4-difluorophenyl)-1H-imidazol-1-yl]methyl}-3-propyl-3H-imidazo[4,5-b]pyridine | 1H NMR (CDCl3): 8.38 (1H, dd), 8.04 (1H, dd), 7.56-7.50 (1H, m), 7.41-7.36 (1H, m), 7.30-7.21 (2H, m), 7.15 (1H, d), 7.04 (1H, d), 5.4592H, s), 3.92 (2H, t), 1.60-1.50 (2H, m), 0.80 (3H, t) | 354.3 [M + 1] |
| 855 | 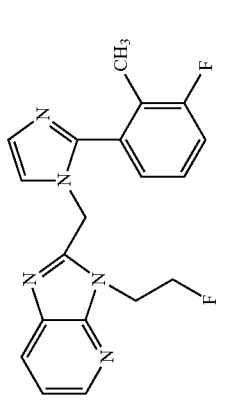 | 3-(2-fluoroethyl)-2-{[2-(3-fluoro-2-methylphenyl)-1H-imidazol-1-yl]methyl}-3H-imidazo[4,5-b]pyridine | H-1 NMR (CDCl3): 2.13 (s, 3H), 4.14 (m, 1H), 4.24 (m, 1H), 4.48 (m, 1H), 4.64 (m, 1H), 5.29 (s, 2H), 7.09-7.26 (m, 6H), 8.02 (d, 1H), 8.35 (d, 1H) | 354 [M + 1] |
| 856 | 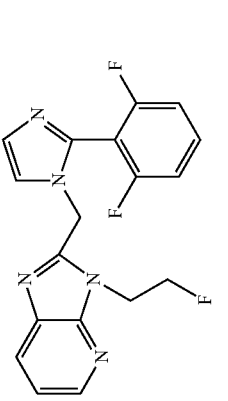 | 2-{[2-(2,6-difluorophenyl)-1H-imidazol-1-yl]methyl}-3-(2-fluoroethyl)-3H-imidazo[4,5-b]pyridine | H-1 NMR (CDCl3): line list provided 4.14 (t, 1H), 4.24 (t, 1H), 4.46 (t, 1H), 4.64 (t, 1H), 5.40 (s, 2H), 6.98 (m, 2H), 7.11 (s, 1H), 7.26-7.40 (m, 3H), 8.01 (d, 1H), 8.34 (d, 1H) | 358 [M + 1] |

TABLE 6-continued

| Cpd # | STRUCTURE | IUPAC NAME | NMR | MS (m/z) |
|---|---|---|---|---|
| 857 | 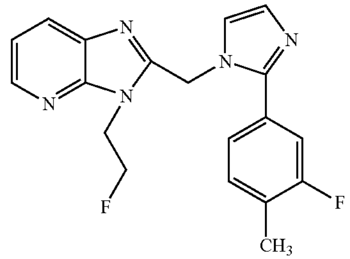 | 3-(2-fluoroethyl)-2-{[2-(3-fluoro-4-methylphenyl)-1H-imidazol-1-yl]methyl}-3H-imidazo[4,5-b]pyridine | H-1 NMR (CDCl3): line list provided 2.35 (s, 3H), 4.26 (t, 1H), 4.35 (t, 1H), 4.51 (t, 1H), 4.67 (t, 1H), 5.53 (s, 2H), 7.07 (s, 1H), 7.18 (s, 1H), 7.26-7.34 (m, 4H), 8.07 (d, 1H), 8.36 (d, 1H) | 354 [M + 1] |
| 858 | 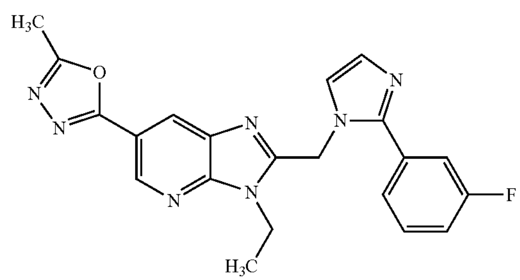 | 3-ethyl-2-{[2-(3-fluorophenyl)-1H-imidazol-1-yl]methyl}-6-(5-methyl-1,3,4-oxadiazol-2-yl)-3H-imidazo[4,5-b]pyridine | dihydrochloride 1H NMR (d6 DMSO): 9.96 (1H, d), 8.50 (1H, d), 7.98-7.91 (2H, m), 7.72-7.50 (4H, m), 6.01 (2H, s), 4.35 (2H, q), 2.58 (3H, s), 1.35 (3H, t) | 404.3 [M + 1] |
| 859 | 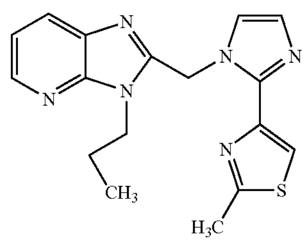 | 2-{[2-(2-methyl-1,3-thiazol-4-yl)-1H-imidazol-1-yl]methyl}-3-propyl-3H-imidazo[4,5-b]pyridine | 1H NMR, δppm (CDCl3): 8.40 (dd, 1H), 8.05 (dd, 1H), 7.91 (s, 1H), 7.24 (m, 1H), 7.11 (d, 1H), 7.07 (d, 1H), 6.30 (s, 2H), 4.22 (t, 2H), 2.78 (s, 3H), 1.62 (m, 2H), 0.79 (t, 3H) | 339.2 [M + 1] |
| 860 | 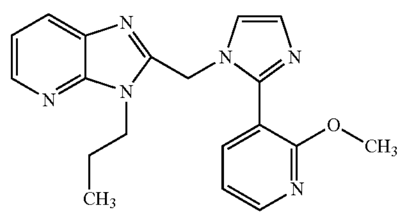 | 2-{[2-(2-methoxypyridin-3-yl)-1H-imidazol-1-yl]methyl}-3-propyl-3H-imidazo[4,5-b]pyridine | 1H NMR, δppm (CDCl3): 8.38 (dd, 1H), 8.30 (dd, 1H), 8.03 (dd, 1H), 7.87 (dd, 1H), 7.19-7.27 (m, 2H), 7.01-7.05 (m, 2H), 5.33 (s, 2H), 3.97 (s, 3H), 3.86 (t, 2H), 1.47 (m, 2H), 0.77 (t, 3H). | 349.3 [M + 1] |

TABLE 6-continued

| Cpd # | STRUCTURE | IUPAC NAME | NMR | MS (m/z) |
|---|---|---|---|---|
| 861 | 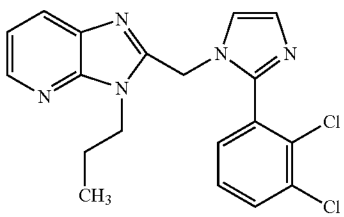 | 2-{[2-(2,3-dichlorophenyl)-1H-imidazol-1-yl]methyl}-3-propyl-3H-imidazo[4,5-b]pyridine | ¹H NMR, δppm (CDCl3): 8.38 (dd, 1H), 8.02 (dd, 1H), 7.59 (dd, 1H), 7.39 (dd, 1H), 7.21-7.29 (m, 3H), 7.10 (d, 1H), 5.29 (s, 2H), 3.90 (t, 2H), 1.53 (m, 2H), 0.79 (t, 3H). | 386.3 |
| 862 | 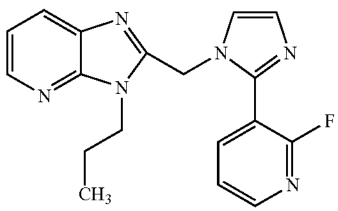 | 2-{[2-(2-fluoropyridin-3-yl)-1H-imidazol-1-yl]methyl}-3-propyl-3H-imidazo[4,5-b]pyridine | ¹H NMR, δppm (CDCl3): 8.39 (dd, 1H), 8.35 (m, 1H), 8.12 (m, 1H), 8.02 (dd, 1H), 7.35 (m, 1H), 7.22-7.29 (m, 2H), 7.10 (d, 1H), 5.43 (s, 2H), 3.95 (t, 2H), 1.54 (m, 2H), 0.80 (t, 3H). | 337.2 |
| 863 | 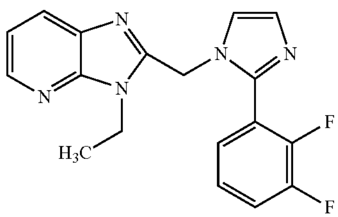 | 2-{[2-(2,3-difluorophenyl)-1H-imidazol-1-yl]methyl}-3-ethyl-3H-imidazo[4,5-b]pyridine | ¹H NMR, δppm (CDCl3): 8.40 (dd, 1H), 8.04 (dd, 1H), 7.22-7.43 (m, 5H), 7.08 (d, 1H), 5.40 (s, 2H), 3.99 (q, 2H), 1.05 (t, 3H). | 340.1 |
| 864 | 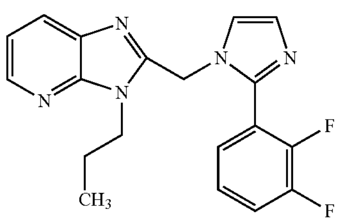 | 2-{[2-(2,3-difluorophenyl)-1H-imidazol-1-yl]methyl}-3-propyl-3H-imidazo[4,5-b]pyridine | ¹H NMR, δppm (CDCl3): 8.39 (dd, 1H), 8.03 (dd, 1H), 7.22-7.42 (m, 5H), 7.09 (d, 1H), 5.39 (s, 2H), 3.86 (t, 2H), 1.50 (m, 2H), 0.78 (t, 3H) | 354.2 |

TABLE 6-continued

| Cpd # | STRUCTURE | IUPAC NAME | NMR | MS (m/z) |
|---|---|---|---|---|
| 865 | 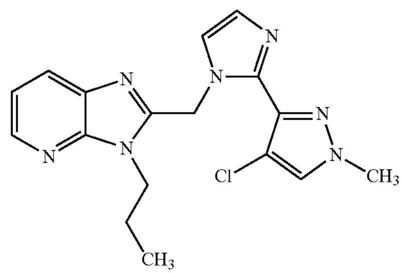 | 2-{[2-(4-chloro-1-methyl-1H-pyrazol-3-yl)-1H-imidazol-1-yl]methyl}-3-propyl-3H-imidazo[4,5-b]pyridine | 1H NMR (CDCl3): 8.38 (1H, dd), 8.04 (1H, dd), 7.52 (1H, s), 7.26-7.21 (2H, m), 7.05 (1H, d), 5.98 (2H, s), 4.15 (2H, t), 3.94 (3H, s), 1.62-1.52 (2H, m), 0.80 (3H, t) | 356.2 [M + 1] |
| 866 | 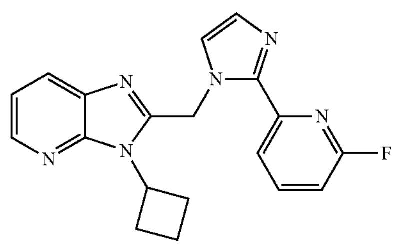 | 3-cyclobutyl-2-{[2-(6-fluoropyridin-2-yl)-1H-imidazol-1-yl]methyl}-3H-imidazo[4,5-b]pyridine | dihydrochloride 1H NMR (d6 DMSO): 8.39 (1H, dd), 8.33 (1H, dd), 8.25 (1H, q), 8.03 (1H, d), 7.95 (1H, d), 7.87 (1H, dd), 7.33 (1H, dd), 7.21 (1H, dd), 6.34 (2H, s), 5.18 (1H, m), 3.28-1.20 (2H, m), 2.58-2.42 (2H, m), 2.00-1.86 (2H, m) | 349.3 [M + 1] |
| 867 | 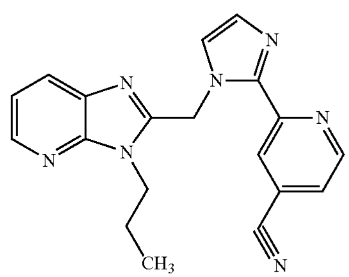 | 2-(1-{[3-propyl-3H-imidazo[4,5-b]pyridin-2-yl]methyl}-1H-imidazol-2-yl)isonicotinonitrile | dihydrochloride 1H NMR (d6 DMSO): 8.78 (1H, s), 8.72 (1H, d), 8.32 (1H, dd), 7.99 (1H, d), 7.93-7.86 (3H, m), 7.21 (1H, dd), 6.34 (2H, s), 4.37 (2H, t), 1.91-1.82 (2H, m), 0.93 (3H, t) | 344.2 [M + 1] |

TABLE 6-continued

| Cpd # | STRUCTURE | IUPAC NAME | NMR | MS (m/z) |
|---|---|---|---|---|
| 868 | 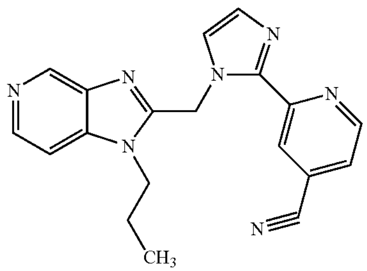 | 2-{[1-((1-propyl-1H-imidazo[4,5-c]pyridin-2-yl)methyl]-1H-imidazol-2-yl}isonicotinonitrile | 1H NMR (CDCl3) δ 9.07 (s, 1H), 8.68 (d, 1H), 8.60 (s, 1H), 8.44 (d, 1H), 7.45 (d, 1H), 7.29 (d, 1H), 7.26 (d, 1H), 7.22 (d, 1H), 6.37 (s, 2H), 4.16 (t, 2H), 1.63 (q, 2H), 0.81 (t, 3H) | m/e 344 |
| 869 | 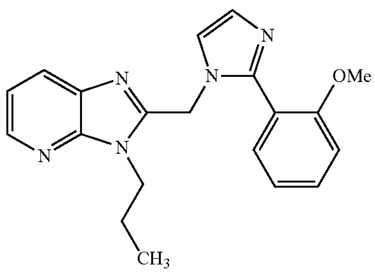 | 2-{[2-(2-methoxyphenyl)-1H-imidazol-1-yl]methyl}-3-propyl-3H-imidazo[4,5-b]pyridine | dihydrochloride 1H NMR (d6 DMSO): 8.33 (1H, dd), 8.02-7.99 (2H, m), 7.93 (1H, d), 7.65-7.59 (1H, m), 7.51-7.48 (1H, m), 7.29-7.21 (2H, m), 7.11-7.06 (1H, m), 5.75 (2H, s), 4.12 (2H, t), 3.64 (3H, s), 1.69-1.61 (2H, m), 0.74 (3H, t). | 348.3 [M + 1] |
| 870 | 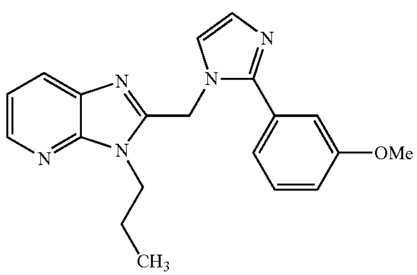 | 2-{[2-(3-methoxyphenyl)-1H-imidazol-1-yl]methyl}-3-propyl-3H-imidazo[4,5-b]pyridine | dihydrochloride 1H NMR (d6 DMSO): 8.35 (1H, dd), 8.04-7.98 (2H, m), 7.93 (1H, d), 7.48 (1H, t), 7.35-7.19 (4H, m), 5.95 (2H, s), 4.22 (2H, t), 3.69 (3H, s), 1.79-1.68 (2H, m), 0.81 (3H, t) | 348.39 [M + 1] |

TABLE 6-continued

| Cpd # | STRUCTURE | IUPAC NAME | NMR | MS (m/z) |
|---|---|---|---|---|
| 871 | 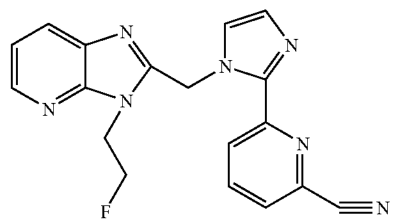 | 6-(1-{[3-(2-fluoroethyl)-3H-imidazo[4,5-b]pyridin-2-yl]methyl}-1H-imidazol-2-yl)pyridine-2-carbonitrile | H-1 NMR (CDCl3): line list provided 4.74 (m, 1H), 4.84-4.95 (m, 3H), 6.16 (s, 2H), 7.19-7.28 (m, 2H), 7.39 (s, 1H), 7.54 (d, 1H), 7.83 (t, 1H), 7.89 (d, 1H), 8.34 (m, 1H), 8.53 (d, 1H) | 348 [M + 1] |
| 872 | 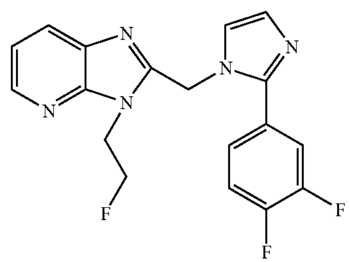 | 2-{[2-(3,4-difluorophenyl)-1H-imidazol-1-yl]methyl}-3-(2-fluoroethyl)-3H-imidazo[4,5-b]pyridine | H-1 NMR (CDCl3): line list provided 4.33 (t, 1H), 4.42 (t, 1H), 4.56 (t, 1H), 4.73 (t, 1H), 5.51 (s, 2H), 7.07 (s, 1H), 7.18-7.26 (m, 2H), 7.39 (m, 1H), 7.55 (m, 1H), 8.07 (d, 1H), 8.37 (s, 1H) | 358 [M + 1] |
| 873 | 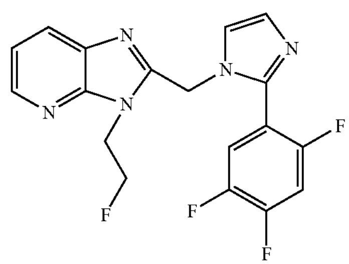 | 3-(2-fluoroethyl)-2-{[2-(2,4,5-trifluorophenyl)-1H-imidazol-1-yl]methyl}-3H-imidazo[4,5-b]pyridine | H-1 NMR (CDCl3): line list provided 4.23 (t, 1H), 4.31 (t, 1H), 4.50 (t, 1H), 4.66 (t, 1H), 5.40 (s, 2H), 7.01-7.09 (m, 2H), 7.20-7.26 (m, 2H), 7.43 (m, 1H), 7.99 (d, 1H), 8.32 (d, 1H) | 376 [M + 1] |
| 874 | 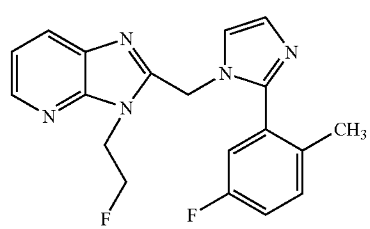 | 3-(2-fluoroethyl)-2-{[2-(5-fluoro-2-methylphenyl)-1H-imidazol-1-yl]methyl}-3H-imidazo[4,5-b]pyridine | H-1 NMR (CDCl3): line list provided 2.16 (s, 3H), 4.19 (t, 1H), 4.26 (t, 1H), 4.49 (t, 1H), 4.57 (t, 1H), 5.28 (s, 2H), 7.02-7.07 (2H), 7.14 (s, 1H), 7.21-7.26 (m, 3H), 8.02 (d, 1H), 8.35 (d, 1H) | 354 |

TABLE 6-continued

| Cpd # | STRUCTURE | IUPAC NAME | NMR | MS (m/z) |
|---|---|---|---|---|
| 875 | 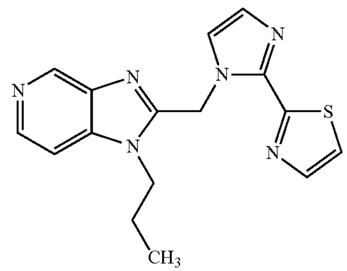 | 1-propyl-2-{[2-(1,3-thiazol-2-yl)-1H-imidazol-1-yl]methyl}-1H-imidazo[4,5-c]pyridine | 1H NMR (CDCl3) δ 9.07 (s, 1H), 8.41 (d, 1H), 7.82 (d, 1H), 7.38 (d, 1H), 7.25 (d, 1H), 7.19 (s, 1H), 7.12 (s, 1H), 6.35 (s, 2H), 4.14 (t, 2H), 1.53 (q, 2H), 0.74 (t, 3H) | m/e 325 |
| 876 | 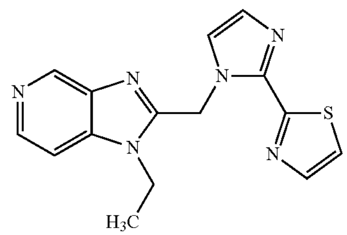 | 1-ethyl-2-{[2-(1,3-thiazol-2-yl)-1H-imidazol-1-yl]methyl}-1H-imidazo[4,5-c]pyridine | 1H NMR (CDCl3) δ 9.08 (s, 1H), 8.43 (d, 1H), 7.85 (d, 1H), 7.38 (d, 1H), 7.38-7.26 (m, 1H), 7.17 (s, 1H), 7.14 (s, 1H), 6.35 (s, 2H), 4.25 (q, 2H), 1.11 (t, 3H) | m/e 311 |
| 877 | 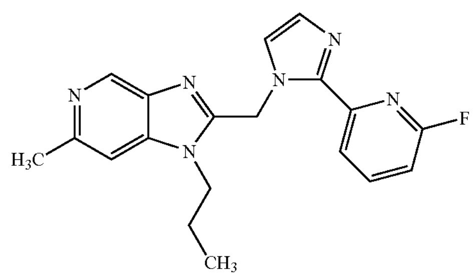 | 2-{[2-(6-fluoropyridin-2-yl)-1H-imidazol-1-yl]methyl}-6-methyl-1-propyl-1H-imidazo[4,5-c]pyridine | 1H NMR (CDCl3) δ 8.93 (s, 1H), 8.16 (d, 1H), 7.87 (dd, 1H), 7.20 (d, 1H), 7.16 (d, 1H), 7.10 (d, 1H), 6.87 (d, 1H), 6.26 (s, 2H), 4.19 (t, 2H), 2.65 (s, 3H), 1.65 (q, 2H), 0.83 (t, 3H) | m/e 351 |

TABLE 6-continued

| Cpd # | STRUCTURE | IUPAC NAME | NMR | MS (m/z) |
|---|---|---|---|---|
| 878 | 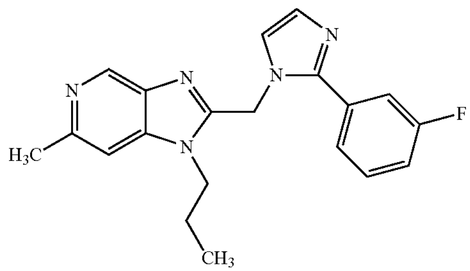 | 2-{[2-(3-fluorophenyl)-1H-imidazol-1-yl]methyl}-6-methyl-1-propyl-1H-imidazo[4,5-c]pyridine | ¹H NMR (CDCl3) δ 8.95 (s, 1H), 7.49-7.36 (m, 3H), 7.19-7.15 (m, 2H), 7.04 (m, 2H), 5.48 (s, 2H), 3.64 (t, 2H), 2.64 (s, 3H), 1.40 (q, 2H), 0.73 (t, 3H) | |
| 879 | 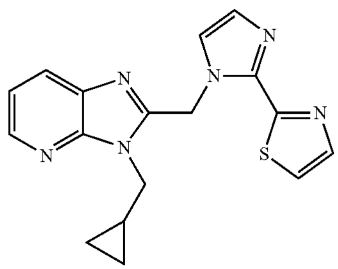 | 3-(cyclopropylmethyl)-2-{[2-(1,3-thiazol-2-yl)-1H-imidazol-1-yl]methyl}-3H-imidazo[4,5-b]pyridine | dihydrochloride 1H NMR (d6 DMSO): 8.35 (1H, dd), 7.95 (1H, dd), 7.90-7.87 (2H, m), 7.81 (1H, s), 7.52 (1H, s), 7.27 (1H, dd), 6.35 (2H, s), 4.31 (2H, d0, 1.42-1.38 (1H, m), 0.55-0.52 (4H, m) | 335.1 [M − 1] |
| 880 | 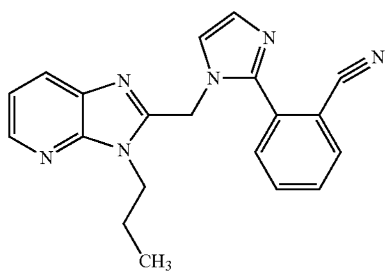 | 2-{1-[(3-propyl-3H-imidazo[4,5-b]pyridin-2-yl)methyl]-1H-imidazol-2-yl}benzonitrile | dihydrochloride 1H NMR (d6 DMSO): 8.31 (1H, d), 8.15 (1H, s), 8.05-8.03 (2H, m), 7.94-7.92 (2H, m), 7.85-7.77 (2H, m), 7.27-7.24 (1H, m), 5.97 (1H, s), 4.14 (2H, t), 1.72-1.64 (2H, m), 0.75 (3H, t) | 343.3 [M + 1] |

TABLE 6-continued

| Cpd # | STRUCTURE | IUPAC NAME | NMR | MS (m/z) |
|---|---|---|---|---|
| 881 | 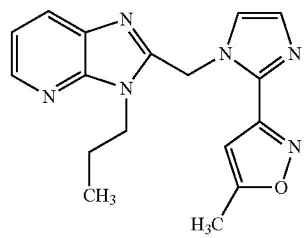 | 2-{[2-(5-methylisoxazol-3-yl)-1H-imidazol-1-yl]methyl}-3-propyl-3H-imidazo[4,5-b]pyridine | $^1$H NMR, δppm (CDCl3): 8.39 (dd, 1H), 8.04 (dd, 1H), 7.19-7.27 (m, 3H), 6.65 (d, 1H), 6.10 (s, 2H), 4.26 (t, 2H), 1.63 (m, 2H), 0.83 (t, 3H) | 323.2 |
| 882 | 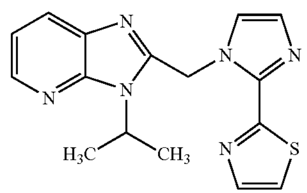 | 3-isopropyl-2-{[2-(1,3-thiazol-2-yl)-1H-imidazol-1-yl]methyl}-3H-imidazo[4,5-b]pyridine | $^1$H NMR, δppm (CDCl3): 8.37 (dd, 1H), 8.02 (dd, 1H), 7.84 (d, 1H), 7.39 (d, 1H), 7.11-7.23 (m, 3H), 6.32 (s, 2H), 4.92 (m, 1H), 1.56 (d, 6H) | 325.4 |
| 883 | 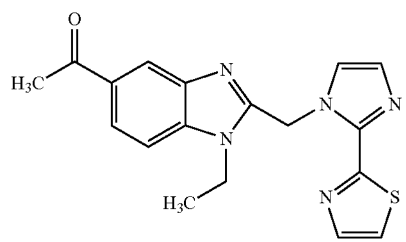 | 1-(1-ethyl-2-{[2-(1,3-thiazol-2-yl)-1H-imidazol-1-yl]methyl}-1H-benzimidazol-5-yl)ethanone | $^1$H NMR, δppm (CDCl3): 8.39 (d, 1H), 8.00 (dd, 1H), 7.84 (d, 1H), 7.39 (d, 1H), 7.37 (d, 1H), 7.18 (d, 1H), 7.13 (d, 1H), 6.35 (s, 2H), 4.27 (q, 2H), 2.67 (s, 3H), 1.12 (t, 3H) | 352.2 |
| 884 | 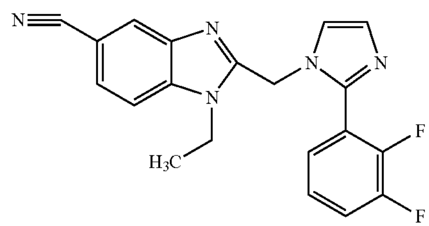 | 2-{[2-(2,3-difluorophenyl)-1H-imidazol-1-yl]methyl}-1-ethyl-1H-benzimidazole-5-carbonitrile | $^1$H NMR, δppm (CDCl3): 8.09 (dd, 1H), 7.55 (dd, 1H), 7.19-7.40 (m, 5H), 7.04 (d, 1H), 5.40 (s, 2H), 3.86 (q, 2H), 1.02 (t, 3H) | |

TABLE 6-continued

| Cpd # | STRUCTURE | IUPAC NAME | NMR | MS (m/z) |
|---|---|---|---|---|
| 885 | 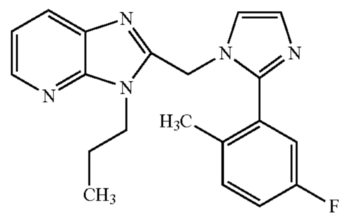 | 2-{[2-(5-fluoro-2-methylphenyl)-1H-imidazol-1-yl]methyl}-3-propyl-3H-imidazo[4,5-b]pyridine | ¹H NMR, δppm (CDCl3): 8.39 (dd, 1H), 8.03 (dd, 1H), 7.20-7.31 (m, 3H), 7.07-7.13 (m, 3H), 5.24 (s, 2H), 3.88 (t, 2H), 2.22 (s, 3H), 1.54 (m, 2H), 0.78 (t, 3H) | 350.3 |
| 886 | 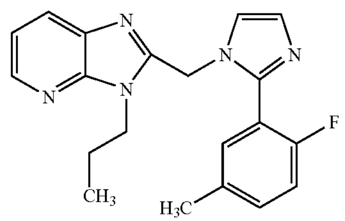 | 2-{[2-(2-fluoro-5-methylphenyl)-1H-imidazol-1-yl]methyl}-3-propyl-3H-imidazo[4,5-b]pyridine | ¹H NMR, δppm (CDCl3): 8.38 (dd, 1H), 8.04 (dd, 1H), 7.44 (dd, 1H), 7.22-7.30 (m, 2H), 7.19 (d, 1H), 7.12 (dd, 1H), 7.05 (d, 1H), 5.37 (s, 2H), 3.84 (t, 2H), 2.36 (s, 3H), 1.46 (m, 2H), 0.76 (t, 3H) | 350.3 |
| 887 | 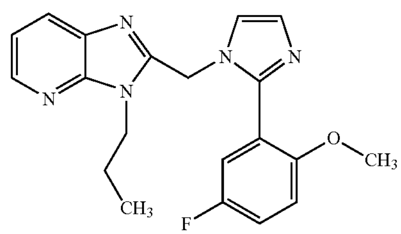 | 2-{[2-(5-fluoro-2-methoxyphenyl)-1H-imidazol-1-yl]methyl}-3-propyl-3H-imidazo[4,5-b]pyridine | ¹H NMR, δppm (CDCl3): 8.39 (dd, 1H), 8.03 (dd, 1H), 7.15-7.32 (m 4H), 7.03 (d, 1H), 6.96 (dd, 1H), 5.30 (s, 2H), 3.84 (t, 2H), 3.79 (s, 3H), 1.46 (m, 2H), 0.76 (t, 3H) | 366.2 |
| 888 | 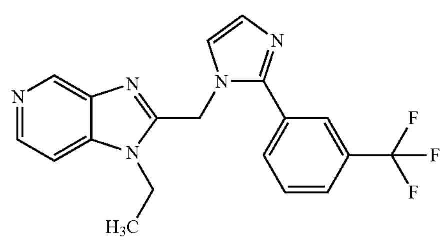 | 1-ethyl-2-({2-[3-(trifluoromethyl)phenyl]-1H-imidazol-1-yl}methyl)-1H-imidazo[4,5-c]pyridine | dihydrochloride 1H NMR (d6 DMSO): 10.02 (1H, s), 8.70 (1H, d), 8.37 (1H, d), 8.08 (1H, s), 7.97-7.94 (3H, m), 7.82 (1H, s), 7.75 (1H, t), 6.09 (2H, s), 4.45 (2H, q), 1.32 (3H, t). | |

TABLE 6-continued

| Cpd # | STRUCTURE | IUPAC NAME | NMR | MS (m/z) |
|---|---|---|---|---|
| 889 | 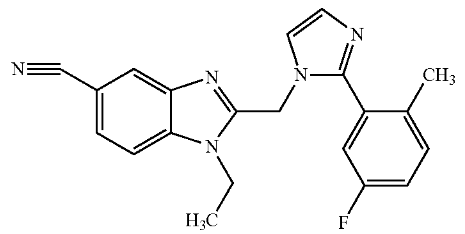 | 1-ethyl-2-{[2-(5-fluoro-2-methylphenyl)-1H-imidazol-1-yl]methyl}-1H-benzimidazole-5-carbonitrile | hydrochloride 1H NMR (d6 DMSO): 8.10 (1H, s), 8.07 (1H, d), 7.95 (1H, d), 7.78 (1H, d), 7.64 (1H, dd), 7.52 (1H, dd), 7.38-7.35 (2H, m), 5.82 (2H, s), 4.23 (2H, q), 2.17 (3H, s), 1.18 (3H, t). | |
| 890 | 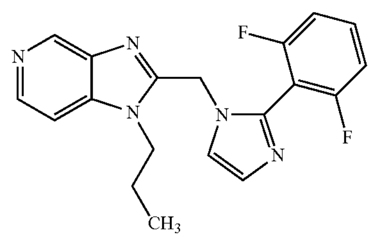 | 2-{[2-(2,6-difluorophenyl)-1H-imidazol-1-yl]methyl}-1-propyl-1H-imidazo[4,5-c]pyridine | ¹H NMR (CDCl3) δ 9.05 (s, 1H), 8.43 (d, 1H), 7.5-7.4 (m, 1H), 7.27-7.23 (m, 2H), 7.07-7.01 (m, 3H), 5.34 (s, 2H), 3.75 (t, 2H), 1.47 (q, 2H), 0.77 (t, 3H) | m/e 354 |
| 891 | 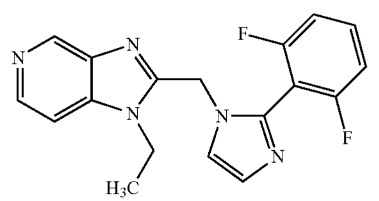 | 2-{[2-(2,6-difluorophenyl)-1H-imidazol-1-yl]methyl}-1-ethyl-1H-imidazo[4,5-c]pyridine | ¹H NMR (CDCl3) δ 9.05 (s, 1H), 8.43 (d, 1H), 7.52-7.42 (m, 1H), 7.27-7.23 (m, 2H), 7.08-7.01 (m, 3H), 5.35 (s, 2H), 3.85 (q, 2H), 1.02 (t, 3H) | m/e 340 |
| 892 | 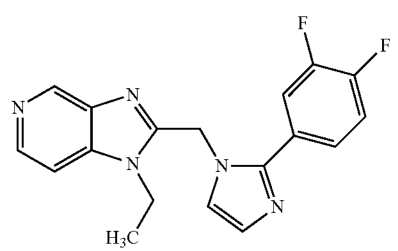 | 2-{[2-(3,4-difluorophenyl)-1H-imidazol-1-yl]methyl}-1-ethyl-1H-imidazo[4,5-c]pyridine | ¹H NMR (CDCl3) δ 9.10 (s, 1H), 8.46 (d, 1H), 7.56-7.51 (m, 1H), 7.42-7.30 (m, 1H), 7.31-7.26 (m, 2H), 7.16 (d, 1H), 7.03 (d, 1H), 5.48 (s, 2H), 3.83 (q, 2H), 1.05 (t, 3H) | m/e 340 |

TABLE 6-continued

| Cpd # | STRUCTURE | IUPAC NAME | NMR | MS (m/z) |
|---|---|---|---|---|
| 893 | 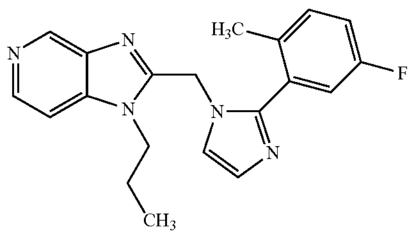 | 2-{[2-(5-fluoro-2-methylphenyl)-1H-imidazol-1-yl]methyl}-1-propyl-1H-imidazo[4,5-c]pyridine | 1H NMR (CDCl3) δ 9.07 (s, 1H), 8.43 (d, 1H), 7.31-7.23 (m, 3H), 7.12-7.04 (m, 3H), 5.24 (s, 2H), 3.73 (t, 2H), 2.21 (s, 3H), 1.49 (q, 2H), 0.75 (t, 3H) | m/e 350 |
| 894 | 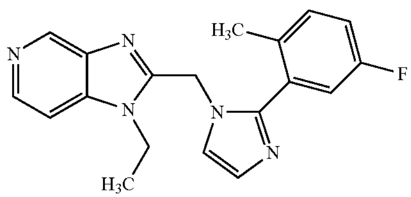 | 1-ethyl-2-{[2-(5-fluoro-2-methylphenyl)-1H-imidazol-1-yl]methyl}-1H-imidazo[4,5-c]pyridine | 1H NMR (CDCl3) δ 9.08 (s, 1H), 8.44 (d, 1H), 7.31-7.24 (m, 3H), 7.12-7.04 (m, 3H), 5.25 (s, 1H), 3.83 (q, 2H), 2.22 (s, 3H), 1.06 (t, 3H) | m/e 336 |
| 895 | 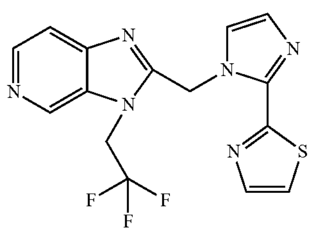 | 2-{[2-(1,3-thiazol-2-yl)-1H-imidazol-1-yl]methyl}-3-(2,2,2-trifluoroethyl)-3H-imidazo[4,5-b]pyridine | H-1 NMR (CDCl3): line list provided 5.32 (q, 2H), 6.19 (s, 2H), 7.19 (s, 1H), 7.26 (m, 2H), 7.43 (s, 1H), 7.79 (d, 1H), 8.04 (d, 1H), 8.41 (m, 1H) | 365 [M + 1] |
| 896 | 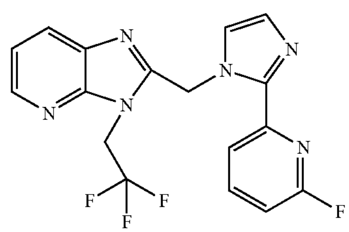 | 2-{[2-(6-fluoropyridin-2-yl)-1H-imidazol-1-yl]methyl}-3-(2,2,2-trifluoroethyl)-3H-imidazo[4,5-b]pyridine | HCl salt H-1 NMR (CD3OD): 5.42 (q, 2H), 6.40 (s, 2H), 7.24 (d, 1H), 7.37 (m, 1H), 7.90 (m, 2H), 8.03 (m, 2H), 8.22 (m, 1H), 8.43 (m, 1H) | 377 [M + 1] |

TABLE 6-continued

| Cpd # | IUPAC NAME | NMR | MS (m/z) |
|---|---|---|---|
| 897 | 2-{2-(3,4-difluorophenyl)-1H-imidazol-1-yl]methyl}6-3-ethyl-3H-imidazo[4,5-b]pyridine | $^1$H NMR, δppm (CDCl3): 8.39 (dd, 1H), 8.04 (dd, 1H), 7.54 (m 1H), 7.40 (m, 1H), 7.26-7.32 (m, 2H), 7.16 (d, 1H), 7.04 (d, 1H), 5.47 (s, 2H), 4.02 (q, 2H), 1.09 (t, 3H) | 340.2 |
| 898 | 2-{[2-(1-methyl-1H-pyrazol-3-yl)-1H-imidazol-1-yl]methyl}-3-propyl-3H-imidazo[4,5-b]pyridine | 1H NMR (CDCl3): 8.38 (1H, dd), 8.05 (1H, dd), 7.42 (1H, d), 7.23 (1H, dd), 7.09 (1H, d), 7.04 (1H, d), 6.91 (1H, d), 6.21 (2H, s), 4.19 (2H, t), 3.97 (3H, s), 1.61-1.50 (2H, m), 0.76 (3H, t) | 322.3 [M + 1] |
| 899 | 2-{[2-(2,3-difluorophenyl)-1H-imidazol-1-yl]methyl}-1-ethyl-1H-imidazo[4,5-c]pyridine | dihydrochloride 1H NMR (d6 DMSO): 9.44 (1H, s), 8.70 (1H, d), 8.37 (1H, d), 8.04 (1H, s), 7.89 (1H, s), 7.73 (1H, q), 7.49 (1H, d), 7.37 (1H, t), 6.05 (2H, s), 4.44 (2H, q), 1.30 (3H, t) | 340.2 |

TABLE 6-continued

| Cpd # | STRUCTURE | IUPAC NAME | NMR | MS (m/z) |
|---|---|---|---|---|
| 900 | 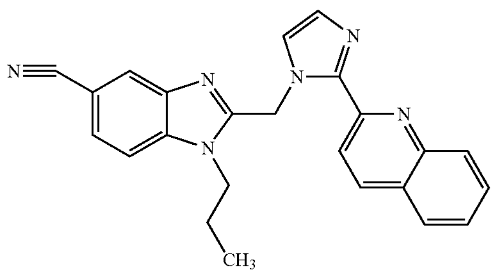 | 1-propyl-2-{[2-quinolin-2-yl-1H-imidazol-1-yl]methyl]-1H-benzimidazole-5-carbonitrile | dihydrochloride 1H NMR (d6 DMSO): 8.60 (1H, d), 8.35-91H, d), 8.02-7.99 (2H, m), 7.88-7.85 (2H, m), 7.79-7.60 (5H, m), 6.54 (2H, s), 4.47 (2H, t), 1.85-1.77 (2H, m), 0.89 (3H, t) | 393.4 [M + 1] |
| 901 | 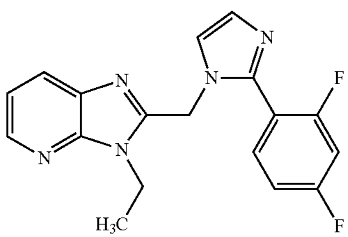 | 2-{[2-(2,4-difluorophenyl)-1H-imidazol-1-yl]methyl]-3-ethyl-3H-imidazo[4,5-b]pyridine | dihydrochloride 1H NMR (d6 DMSO): 8.35-8.33 (1H, m), 8.07-8.06 (1H, m), 7.99-7.96 (2H, m), 7.86-7.80 (1H, m), 7.63-7.57 (1H, m), 7.35-7.32 (1H, m), 7.28-7.25 (1H, m), 5.89 (2H, s), 4.27 (2H, q), 1.28 (3H, t) | 340.2 [M + 1] |
| 902 | 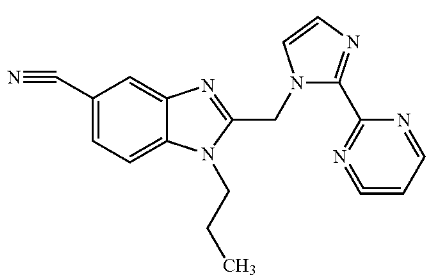 | 1-Propyl-2-(2-pyrimidin-2-yl-imidazol-1-yl)methyl)-1H-benzoimidazole-5-carbonitrile | dihydrochloride 1H NMR (d6 DMSO): 8.92 (2H, d), 8.18 (1H, d), 8.00-7.99 (2H, m), 7.88 (1H, dd), 7.65-7.62 (2H, m), 6.46 (2H, s), 4.42 (2H, t), 1.93-1.84 (2H, m), 0.97 (3H, t) | 344.2 [M + 1] |
| 903 | 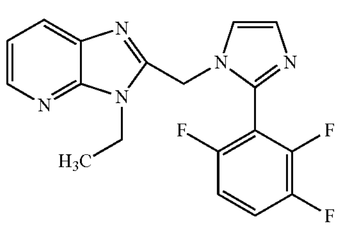 | 3-ethyl-2-{[2-(2,3,6-trifluorophenyl)-1H-imidazol-1-yl]methyl]-3H-imidazo[4,5-b]pyridine | 1H NMR, δppm (CDCl3): 8.40 (dd, 1H), 8.02 (dd, 1H), 7.24-7.32 (m, 3H), 7.11 (d, 1H), 7.00 (m, 1H), 5.36 (s, 2H), 4.02 (q, 2H), 1.09 (t, 3H) | 358.2 |

TABLE 6-continued

| Cpd # | STRUCTURE | IUPAC NAME | NMR | MS (m/z) |
|---|---|---|---|---|
| 904 | 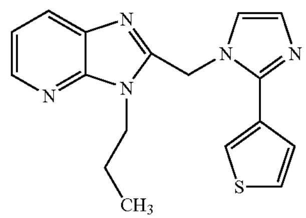 | 3-propyl-2-[(2-thien-3-yl-1H-imidazol-1-yl)methyl]-3H-imidazo[4,5-b]pyridine | ¹H NMR, δppm (CDCl3); 8.40 (dd, 1H), 8.05 (dd, 1H), 7.66 (dd, 1H), 7.43-7.49 (m, 2H), 7.25 (dd, 1H), 7.14 (d, 1H), 7.02 (d, 1H), 5.55 (s, 2H), 3.91 (t, 2H), 1.51 (m, 2H), 0.79 (t, 3H) | 324.3 |
| 905 | 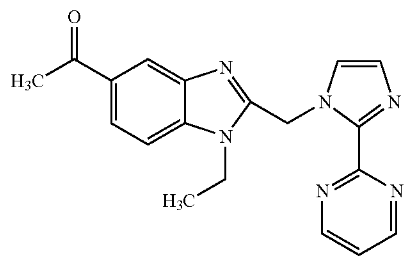 | 1-(1-ethyl-2-[(2-pyrimidin-2-yl-1H-imidazol-1-yl)methyl]-1H-benzimidazol-5-yl}ethanone | ¹H NMR, δppm (CDCl3): 8.87 (d, 2H), .8.41 (dd, 1H), 8.02 (dd, 1H), 7.40 (dd, 1H), 7.26-7.31 (m, 2H), 7.16 (d, 1H), 6.40 (s, 2H), 4.27 (q, 2H), 2.69 (s, 3H), 1.17 (t, 3H) | |
| 906 | 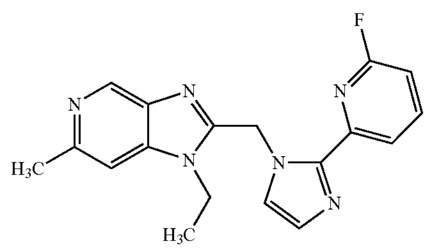 | 1-ethyl-2-{[2-(6-fluoropyridin-2-yl)-1H-imidazol-1-yl]methyl}-6-methyl-1H-imidazo[4,5-c]pyridine | ¹H NMR (CDCl3) δ 8.93 (s, 1H), 8.16 (d, 1H), 7.87 (dd, 1H), 7.18 (d, 1H), 7.12 (s, 1H), 6.87 (d, 1H), 6.26 (s, 2H), 4.30 (q, 2H), 2.65 (s, 3H), 1.22 (t, 3H) | m/e 337 |
| 907 | 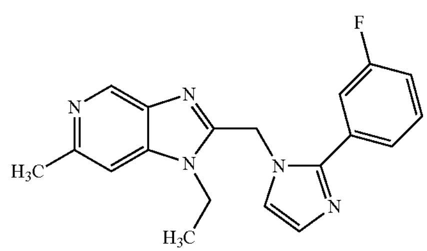 | 1-ethyl-2-{[2-(3-fluorophenyl)-1H-imidazol-1-yl]methyl}-6-methyl-1H-imidazo[4,5-c]pyridine | dihydrochloride ¹H NMR (DMSO-d6) δ 9.28 (s, 1H), 8.24 (s, 1H), 8.23 (d, 1H), 7.94 (d, 1H), 7.69-7.48 (m, 4H), 6.12 (s, 2H), 4.39 (q, 2H), 2.77 (s, 3H), 1.35 (t, 3H); | m/e 336 |

TABLE 6-continued

| Cpd # | STRUCTURE | IUPAC NAME | NMR | MS (m/z) |
|---|---|---|---|---|
| 908 | 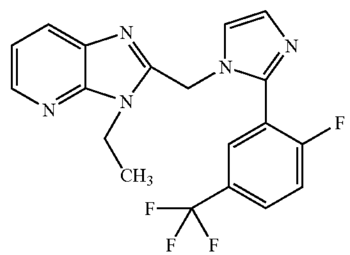 | 3-ethyl-2-({2-[2-fluoro-5-(trifluoromethyl)phenyl]-1H-imidazol-1-yl}methyl)-3H-imidazo[4,5-b]pyridine | H-1 NMR (CDCl3): line list provided 1.08 (t, 3H), 3.99 (q, 2H), 5.38 (s, 2H), 7.10 (s, 1H), 7.22-7.39 (m, 2H), 7.75 (m, 1H), 7.93 (m, 1H), 8.02 (d, 1H), 8.38 (d, 1H) | 390 (M + 1) |
| 909 | 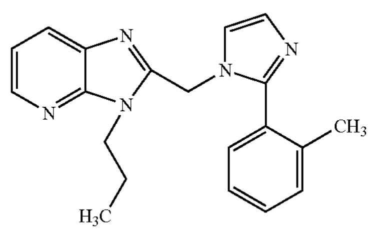 | 2-{[2-(2-methylphenyl)-1H-imidazol-1-yl]methyl}-3-propyl-3H-imidazo[4,5-b]pyridine | H-1 NMR (CDCl3): line list provided 0.73 (t, 3H), 1.49 (m, 2H), 2.24 (s, 3H), 3.81 (m, 2H), 5.22 (s, 2H), 7.10 (s, 1H), 7.18-7.36 (m, 6H), 8.02 (d, 1H), 8.37 (d, 1H) | 332 [M + 1] |
| 910 | 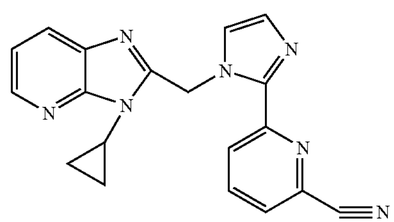 | 6-{1-[(3-cyclopropyl-3H-imidazo[4,5-b]pyridin-2-yl)methyl]-1H-imidazol-2-yl}pyridine-2-carbonitrile | H-1 NMR (CDCl3): line list provided 1.28 (m, 4H), 3.37 (m, 1H), 3.48 (s, 2H), 6.36 (s, 2H), 7.15-7.28 (m, 3H), 7.56 (d, 1H), 7.86 (m, 2H), 8.38 (m, 1H), 8.54 (d, 1H) | 342 [M + 1]; 340 [M − 1] |
| 911 | 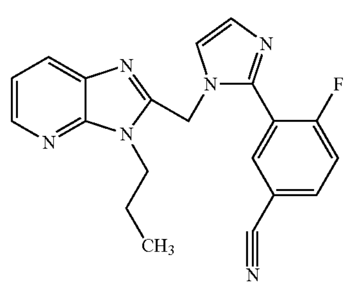 | 4-fluoro-3-{1-[(3-propyl-3H-imidazo[4,5-b]pyridin-2-yl)methyl]-1H-imidazol-2-yl}benzonitrile | CDCl; 8.38 (dd, J = 1.48, 4.8Hz, 1H), 7.98 (dt, J = 1.48, 7.35Hz, 2H), 7.72-7.78 (m, 1H), 7.35 (t, J = 9.07Hz, 1H), 7.22-7.26 (m, 2H), 7.11 (d, J = 1.1Hz, 1H), 5.37 (s, 2H), 3.93 (t, J = 7.69Hz, 2H), 1.54 (dq, J = 7.42, 7.69Hz, 2H), | 361.2 [M + 1] |

TABLE 6-continued

| Cpd # | STRUCTURE | IUPAC NAME | NMR | MS (m/z) |
|---|---|---|---|---|
| 912 | 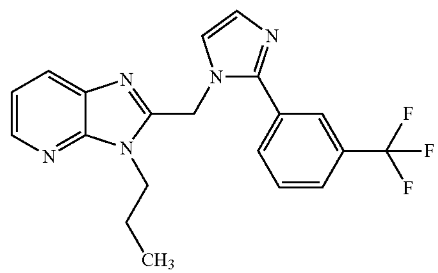 | 1-propyl-2-({2-[3-(trifluoromethyl)phenyl]-1H-imidazol-1-yl}methyl)-1H-imidazo[4,5-c]pyridine | 1H NMR (CDCl3): 9.09 (1H, s), 8.43 (1H, d), 7.93 (1H, s), 7.84 (1H, d), 7.72 (1H, d), 7.62 (1H, t), 7.25 (1H, ), 7.19 (1H, d), 7.09 (1H, d), 5.50 (2H, s), 3.63 (2H, t), 1.49-1.39 (2H, m), 0.75 (3H, t). | |
| 913 | 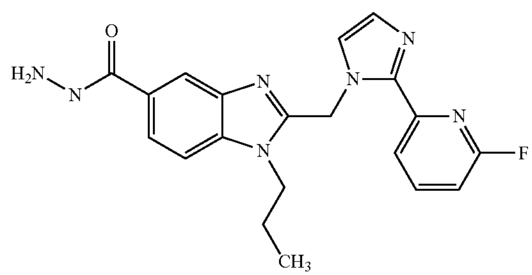 | 2-{[2-(6-fluoropyridin-2-yl)-1H-imidazol-1-yl]methyl}-1-propyl-1H-benzimidazole-6-carbohydrazide | CD3OD: 8.10-8.29 (m, 6H), 8.03 (S, 1H), 7.29 (d, 1H), 6.4 (s, 2H), 4.59-4.65 (m, 2H), 2.0-2.12 (m, 2H), 1.06-1.07 (m, 3H). | 394.3 [M + 1] |

TABLE 7

| Cmp. # | STRUCTURE | IUPAC NAME | NMR | MS (m/z) |
|---|---|---|---|---|
| 914 | 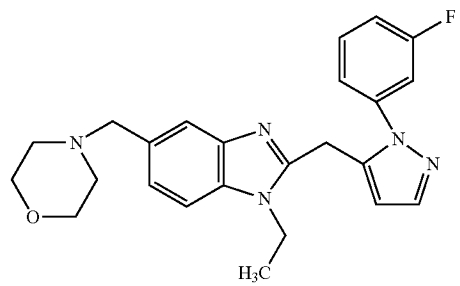 | 1-ethyl-2-{[1-(3-fluorophenyl)-1H-pyrazol-5-yl]methyl}-5-(morpholin-4-ylmethyl)-1H-benzimidazole | | 420.3 [M + 1] |
| 915 | 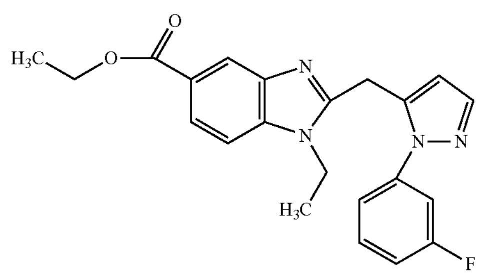 | ethyl 1-ethyl-2-{[1-(3-fluorophenyl)-1H-pyrazol-5-yl]methyl}-1H-benzimidazole-5-carboxylate | | 393.3 [M + 1] |
| 916 | 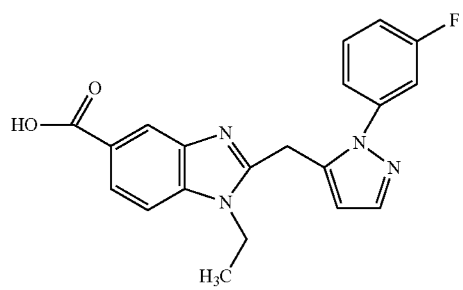 | 1-ethyl-2-{[1-(3-fluorophenyl)-1H-pyrazol-5-yl]methyl}-1H-benzimidazole-5-carboxylic acid | | 365.2 [M + 1] |

TABLE 7-continued

| Cmp. # | STRUCTURE | IUPAC NAME | NMR | MS (m/z) |
|---|---|---|---|---|
| 917 | 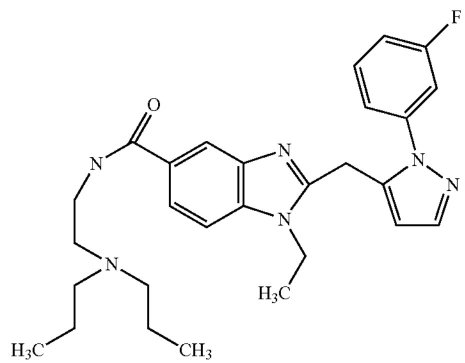 | N-[2-(dipropylamino)ethyl]-1-ethyl-2-{[1-(3-fluorophenyl)-1H-pyrazol-5-yl]methyl}-1H-benzimidazole-5-carboxamide | | 491.4 [M+1] |
| 918 | 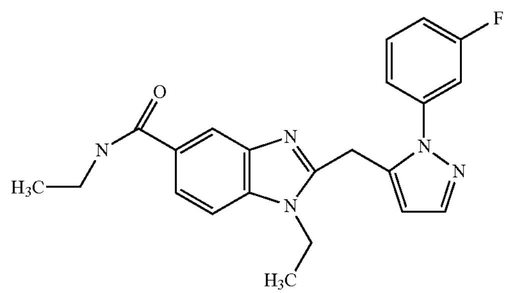 | N,1-diethyl-2-{[1-(3-fluorophenyl)-1H-pyrazol-5-yl]methyl}-1H-benzimidazole-5-carboxamide | | 392.3 [M+1] |
| 919 | 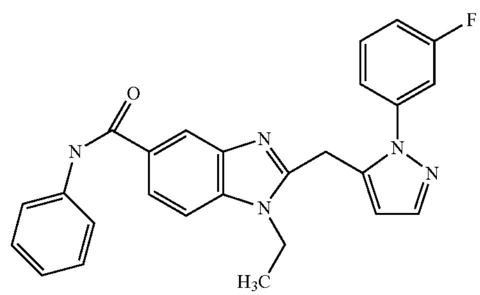 | 1-ethyl-2-{[1-(3-fluorophenyl)-1H-pyrazol-5-yl]methyl}-N-phenyl-1H-benzimidazole-5-carboxamide | | 392.3 [M+1] |

TABLE 7-continued

| Cmp. # | STRUCTURE | IUPAC NAME | NMR | MS (m/z) |
|---|---|---|---|---|
| 920 | 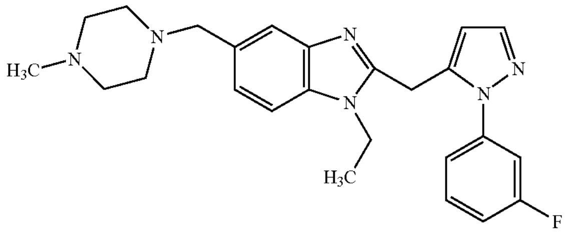 | 1-ethyl-2-{[1-(3-fluorophenyl)-1H-pyrazol-5-yl]methyl}-5-[(4-methylpiperazin-1-yl)methyl]-1H-benzimidazole | 1H NMR (CDCl3): 7.65 (d, 1H), 7.61 (d, 1H), 7.45 (m, 1H), 7.22-7.31 (m, 4H), 7.11 (m, 1H), 6.16 (d, 1H), 4.31 (s, 2H), 3.96 (q, 2H), 3.62 (s, 2H), 2.40-2.60 (m, 8H), 2.25 (s, 3H), 1.22 (t, 3H) | |
| 921 | 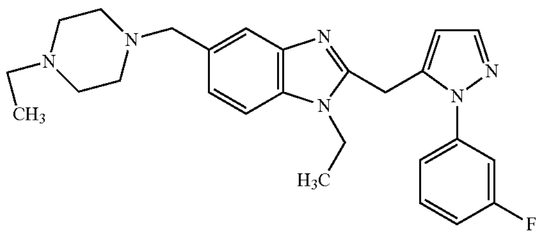 | 1-ethyl-5-[(4-ethylpiperazin-1-yl)methyl]-2-{[1-(3-fluorophenyl)-1H-pyrazol-5-yl]methyl}-1H-benzimidazole | 1H NMR (CDCl3): 7.65 (d, 1H), 7.62 (d, 1H), 7.45 (m, 1H), 7.23-7.30 (m, 4H), 7.13 (m, 1H), 6.16 (d, 1H), 4.31 (s, 2H), 3.96 (q, 2H), 3.62 (s, 2H), 2.40-2.60 (m, 10H), 1.21 (t, 3H), 1.078 (t, 3H) | |
| 922 | 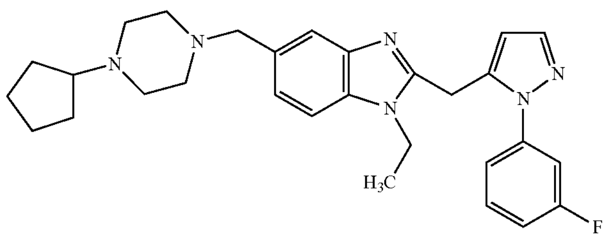 | 5-[(4-cyclopentylpiperazin-1-yl)methyl]-1-ethyl-2-{[1-(3-fluorophenyl)-1H-pyrazol-5-yl]methyl}-1H-benzimidazole | 1H NMR (CDCl3): 7.65 (d, 1H), 7.61 (d, 1H), 7.45 (m, 1H), 7.22-7.31 (m, 4H), 7.13 (m, 1H), 6.15 (d, 1H), 4.31 (s, 2H), 3.96 (q, 2H), 3.63 (s, 2H), 2.40-2.60 (m, 9H), 1.31-1.90 (m, 8H), 1.21 (t, 3H.) | |
| 923 | 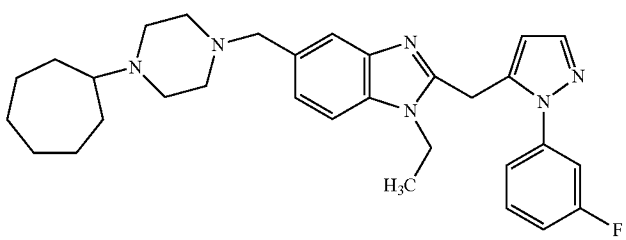 | 5-[(4-cycloheptylpiperazin-1-yl)methyl]-1-ethyl-2-{[1-(3-fluorophenyl)-1H-pyrazol-5-yl]methyl}-1H-benzimidazole | | 515.5 [M + 1] |

TABLE 7-continued

| Cmp. # | STRUCTURE | IUPAC NAME | NMR | MS (m/z) |
|---|---|---|---|---|
| 924 | 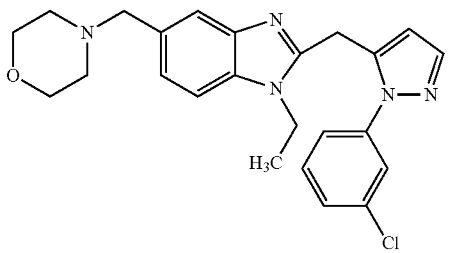 | 2-{[1-(3-chlorophenyl)-1H-pyrazol-5-yl]methyl}-1-ethyl-5-(morpholin-4-yl)methyl)-1H-benzimidazole | | 436.3 [M + 1]; 434.3 [M − 1] |
| 925 | 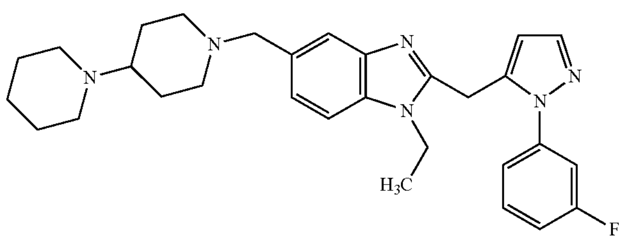 | 1'-[(1-ethyl-2-{[1-(3-fluorophenyl)-1H-pyrazol-5-yl]methyl}-1H-benzimidazol-5-yl)methyl]-1,4-bipiperidine | 1H NMR (CDCl3): 7.63 (d, 1H), 7.61 (d, 1H), 7.44 (m, 1H), 7.23-7.31 (m, 4H), 7.13 (m, 1H), 6.16 (d, 1H), 4.31 (s, 2H), 3.96 (q, 2H), 3.61 (s, 2H), 2.96 (m, 2H), 2.50 (m, 4H), 1.40-2.31 (m, 13H), 1.23 (t, 3H) | |
| 926 | 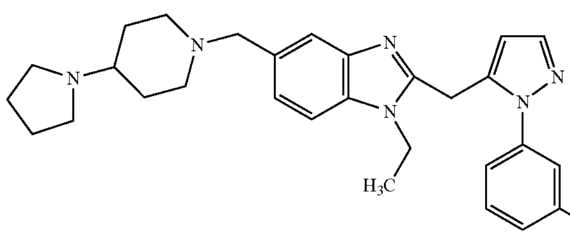 | 1-ethyl-2-{[1-(3-fluorophenyl)-1H-pyrazol-5-yl]methyl}-5-[(4-pyrrolidin-1-ylpiperidin-1-yl)methyl]-1H-benzimidazole | | |
| 927 | 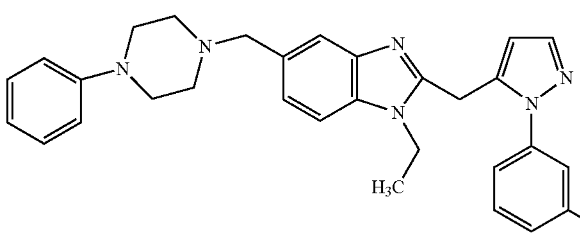 | 1-ethyl-2-{[1-(3-fluorophenyl)-1H-pyrazol-5-yl]methyl}-5-[(4-phenylpiperazin-1-yl)methyl]-1H-benzimidazole | 1H NMR (CDCl3): 7.69 (d, 1H), 7.62 (s, 1H), 7.45 (m, 1H), 7.21-7.33 (m, 6H), 7.13 (m, 1H), 6.82-6.94 (m, 3H), 6.16 (d, 1H), 4.33 (s, 2H), 3.97 (q, 2H), 3.69 (s, 2H), 3.15-3.23 (m, 4H), 2.59-2.67 (m, 4H), 1.21 (t, 3H) | |

TABLE 7-continued

| Cmp. # | STRUCTURE | IUPAC NAME | NMR | MS (m/z) |
|---|---|---|---|---|
| 928 | 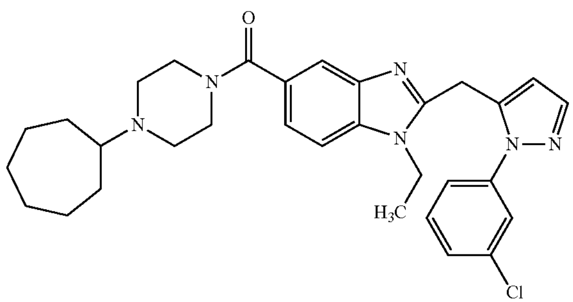 | 2-{[1-(3-chlorophenyl)-1H-pyrazol-5-yl]methyl}-5-[(4-cycloheptylpiperazin-1-yl)carbonyl]-1-ethyl-1H-benzimidazole | | 545.4 [M + 1]; 543.4 [M − 1] |
| 929 | 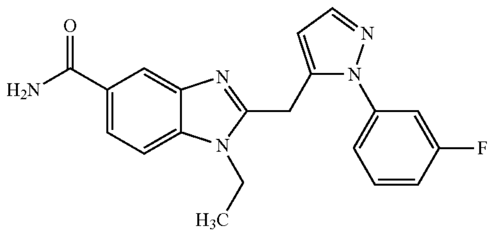 | 1-ethyl-2-{[1-(3-fluorophenyl)-1H-pyrazol-5-yl]methyl}-1H-benzimidazole-5-carboxamide | | |
| 930 | 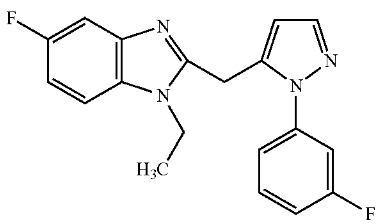 | 1-ethyl-5-fluoro-2-{[1-(3-fluorophenyl)-1H-pyrazol-5-yl]methyl}-1H-benzimidazole | (L)-Tartrate salt 1H NMR (CD3OD): 7.67 (s, 1H), 7.05-7.46 (m, 7H), 6.31 (s, 1H), 4.53 (s, 2H), 4.47 (s, 2H), 4.14 (q, 2H), 1.21 (t, 3H) | |
| 931 | 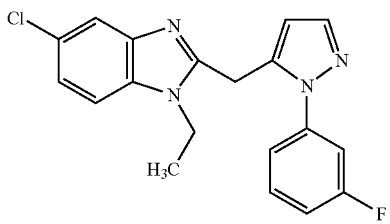 | 5-chloro-1-ethyl-2-{[1-(3-fluorophenyl)-1H-pyrazol-5-yl]methyl}-1H-benzimidazole | (L)-Tartrate salt 1H NMR (d6-DMSO): 7.65 (s, 1H), 7.21-7.58 (m, 7H), 6.26 (s, 1H), 4.48 (s, 2H), 4.30 (s, 2H), 4.16 (q, 2H), 1.15 (t, 3H) | |

| Cmp. # | STRUCTURE | IUPAC NAME | NMR | MS (m/z) |
|---|---|---|---|---|
| 932 | 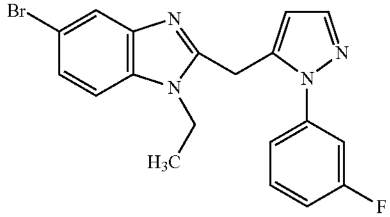 | 5-bromo-1-ethyl-2-{[1-(3-fluorophenyl)-1H-pyrazol-5-yl]methyl}-1H-benzimidazole | (L)-Tartrate salt 1H NMR (d6-DMSO): 7.72 (d, 1H), 7.65 (d, 1H), 7.21-7.53 (m, 6H), 6.26 (s, 1H), 4.48 (s, 2H), 4.30 (s, 2H), 4.16 (q, 2H), 1.14 (t, 3H) | |
| 933 | 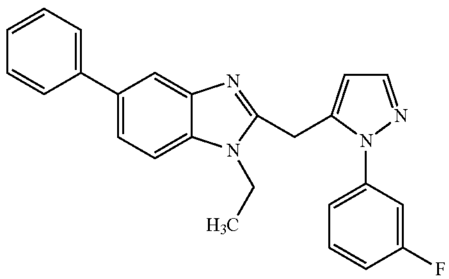 | 1-ethyl-2-{[1-(3-fluorophenyl)-1H-pyrazol-5-yl]methyl}-5-phenyl-1H-benzimidazole | 1H NMR (CDCl3): 7.96 (d, 1H), 7.27-7.66 (m, 11H), 7.14 (m, 1H), 6.21 (d, 1H), 4.38 (s, 2H), 4.01 (q, 2H), 1.25 (t, 3H) | |
| 934 | 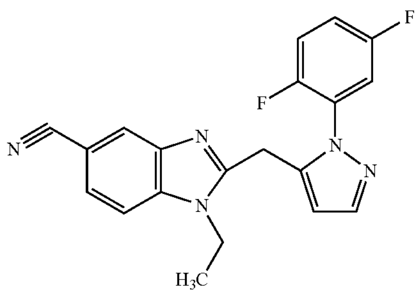 | 2-{[1-(2,5-difluorophenyl)-1H-pyrazol-5-yl]methyl}-1-ethyl-1H-benzimidazole-5-carbonitrile | | 364.2 [M + 1] |

TABLE 7-continued

| Cmp. # | STRUCTURE | IUPAC NAME | NMR | MS (m/z) |
|---|---|---|---|---|
| 935 | 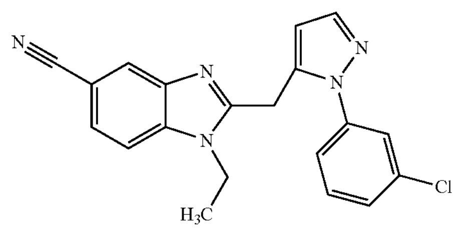 | 2-{[1-(3-chlorophenyl)-1H-pyrazol-5-yl]methyl}-1-ethyl-1H-benzimidazole-5-carbonitrile | 1H NMR (CDCl3): 8.05 (d, 1H), 7.36-7.65 (m, 7H), 6.21 (d, 1H), 4.36 (s, 2H), 4.02 (q, 2H), 1.24 (t, 3H) | |
| 936 | 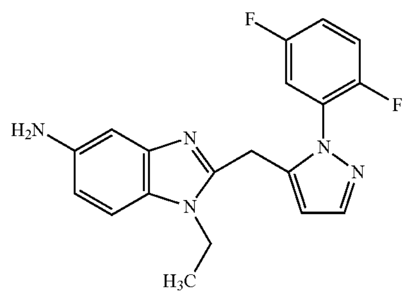 | 2-{[1-(2,5-difluorophenyl)-1H-pyrazol-5-yl]methyl}-1-ethyl-1H-benzimidazol-5-amine | | 354.2 [M + 1] |
| 937 | 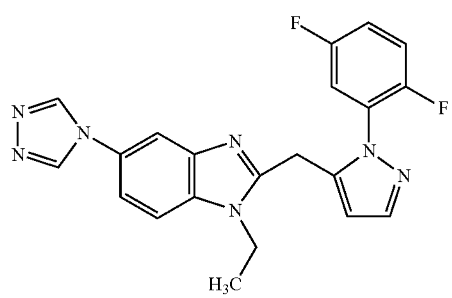 | 2-{[1-(2,5-difluorophenyl)-1H-pyrazol-5-yl]methyl}-1-ethyl-5-(4H-1,2,4-triazol-4-yl)-1H-benzimidazole | | 405.95 [M + 1] |
| 938 | 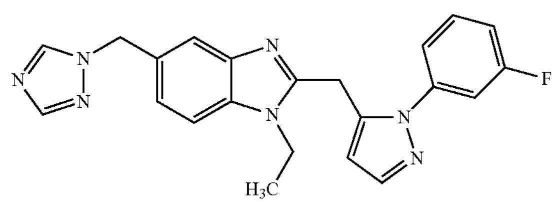 | 1-ethyl-2-{[1-(3-fluorophenyl)-1H-pyrazol-5-yl]methyl}-5-(1H-1,2,4-triazol-1-ylmethyl)-1H-benzimidazole | | 402.4 [M + 1] |

TABLE 7-continued

| Cmp. # | STRUCTURE | IUPAC NAME | NMR | MS (m/z) |
|---|---|---|---|---|
| 939 | 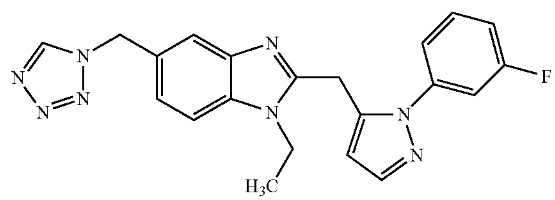 | 1-ethyl-2-{[1-(3-fluorophenyl)-1H-pyrazol-5-yl]methyl}-5-(1H-tetraazol-1-ylmethyl)-1H-benzimidazole | | 403.2 [M + 1]; 401.4 [M − 1] |
| 940 | 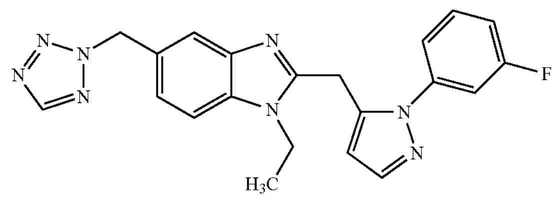 | 1-ethyl-2-{[1-(3-fluorophenyl)-1H-pyrazol-5-yl]methyl}-5-(2H-tetraazol-2-ylmethyl)-1H-benzimidazole | | 403.4 [M + 1]; 401.4 [M − 1] |
| 941 | 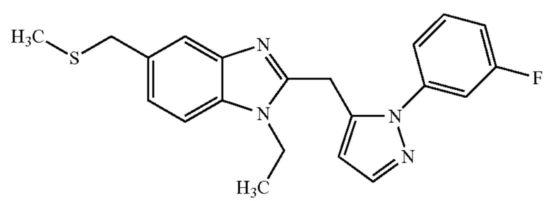 | 1-ethyl-2-{[1-(3-fluorophenyl)-1H-pyrazol-5-yl]methyl}-5-[(methylthio)methyl]-1H-benzimidazole | | 381.3 [M + 1]; 379.3 [M − 1] |
| 942 | 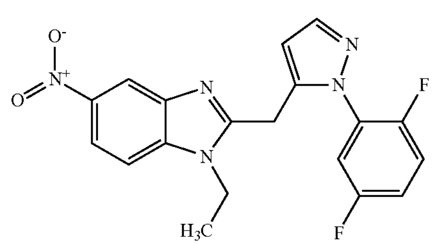 | 2-{[1-(2,5-difluorophenyl)-1H-pyrazol-5-yl]methyl}-1-ethyl-5-nitro-1H-benzimidazole | Mesylate 1H NMR (d6 DMSO) 8.38 (1H, d), 8.15-8.12 (1H, m), 7.77 (1H, d), 7.71 (1H, s), 7.51-7.34 (3H, m), 6.40 (1H, s), 4.21 (2H, q), 2.32 (3H, s), 1.11 (3H, t). | 384.2 [M + 1] |

TABLE 7-continued

| Cmp. # | STRUCTURE | IUPAC NAME | NMR | MS (m/z) |
|---|---|---|---|---|
| 943 | 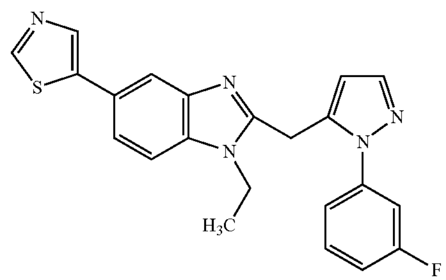 | 1-ethyl-2-{[1-(3-fluorophenyl)-1H-pyrazol-5-yl]methyl}-5-(1,3-thiazol-5-yl)-1H-benzimidazole | Hydrochloride 1H NMR (CD3OD): 9.725 (s, 1H), 8.67 (s, 1H), 8.13 (s, 1H), 8.01-8.08 (m, 2H), 7.79 (s, 1H), 7.21-7.57 (m, 4H), 6.59 (d, 1H), 4.97 (s, 2H), 4.50 (q, 2H), 1.39 (t, 3H) | |
| 944 | 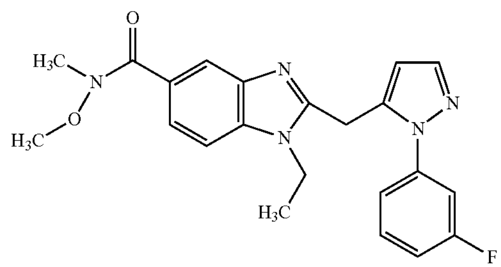 | 1-ethyl-2-{[1-(3-fluorophenyl)-1H-pyrazol-5-yl]methyl}-N-methoxy-N-methyl-1H-benzimidazole-5-carboxamide | 1H NMR (CDCl3): 8.13 (d, 1H), 7.63-7.70 (m, 2H), 7.24-7.49 (m, 4H), 7.13 (m, 1H), 6.19 (d, 1H), 4.36 (s, 2H), 4.00 (q, 2H), 3.60 (s, 3H), 3.40 (s, 3H), 1.23 (t, 3H) | |
| 945 | 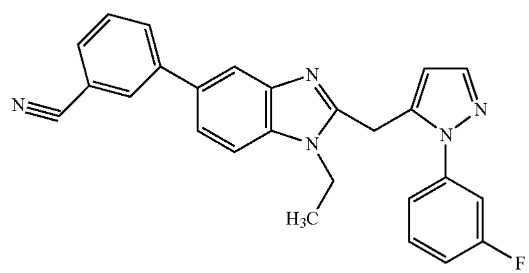 | 3-(1-ethyl-2-{[1-(3-fluorophenyl)-1H-pyrazol-5-yl]methyl}-1H-benzimidazol-5-yl)benzonitrile | 1H NMR (CDCl3): 7.84-7.92 (m, 3H), 7.40-7.64 (m, 6H), 7.26-7.33 (m, 2H), 7.14 (m, 1H), 6.21 (d, 1H), 4.37 (s, 2H), 4.03 (q, 2H), 1.26 (t, 3H) | |

TABLE 7-continued

| Cmp. # | STRUCTURE | IUPAC NAME | NMR | MS (m/z) |
|---|---|---|---|---|
| 946 | 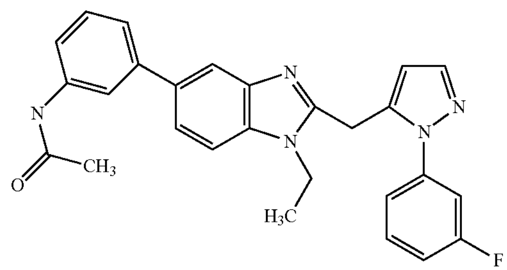 | N-[3-(1-ethyl-2-{[1-(3-fluorophenyl)-1H-pyrazol-5-yl]methyl}-1H-benzimidazol-5-yl)phenyl]acetamide | 1H NMR (CDCl3): 7.93 (d, 1H), 7.26-7.72 (m, 10H), 7.14 (m, 1H), 6.20 (d, 1H), 4.36 (s, 2H), 4.01 (q, 2H), 2.21 (s, 3H), 1.24 (t, 3H) | |
| 947 | 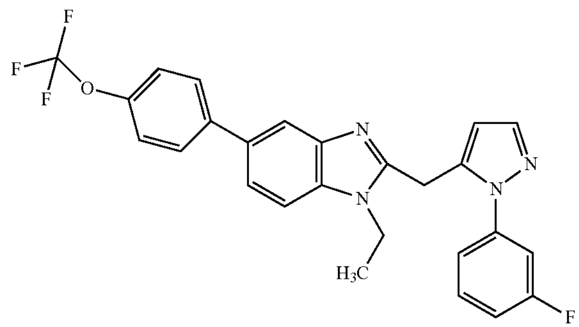 | 1-ethyl-2-{[1-(3-fluorophenyl)-1H-pyrazol-5-yl]methyl}-5-[4-(trifluoromethoxy)phenyl]-1H-benzimidazole | 1H NMR (CDCl3): 7.92 (d, 1H), 7.27-7.65 (m, 10H), 7.14 (m, 1H), 6.20 (d, 1H), 4.37 (s, 2H), 4.08 (q, 2H), 1.25 (t, 3H) | |
| 948 | 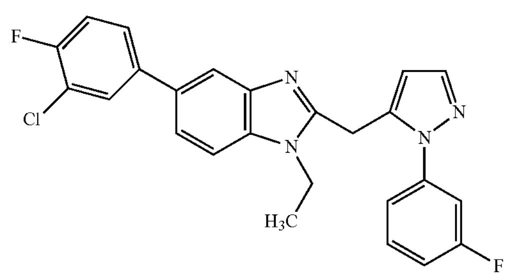 | 5-(3-chloro-4-fluorophenyl)-1-ethyl-2-{[1-(3-fluorophenyl)-1H-pyrazol-5-yl]methyl}-1H-benzimidazole | 1H NMR (CDCl3): 7.897 (d, 1H), 7.63-7.66 (m, 2H), 7.11-7.50 (m, 8H), 6.21 (d, 1H), 4.36 (s, 2H), 4.02 (q, 2H), 1.25 (t, 3H) | |

TABLE 7-continued

| Cmp. # | STRUCTURE | IUPAC NAME | NMR | MS (m/z) |
|---|---|---|---|---|
| 949 | 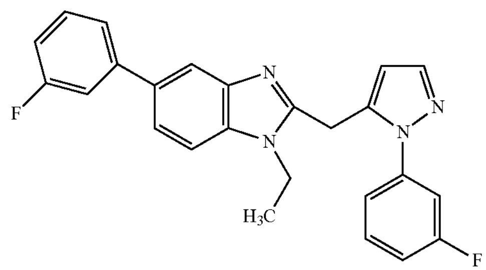 | 1-ethyl-5-(3-fluorophenyl)-2-{[1-(3-fluorophenyl)-1H-pyrazol-5-yl]methyl}-1H-benzimidazole | 1H NMR (CDCl3): 7.95 (d, 1H), 7.64 (d, 1H), 7.27-7.53 (m, 8H) 7.14 (m, 2H), 7.03 (m, 1H), 6.20 (d, 1H), 4.36 (s, 2H), 4.02 (q, 2H), 1.25 (t, 3H) | |
| 950 | 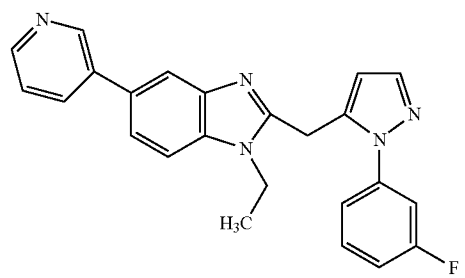 | 1-ethyl-2-{[1-(3-fluorophenyl)-1H-pyrazol-5-yl]methyl}-5-pyridin-3-yl-1H-benzimidazole | 1H NMR (CDCl3): 8.90 (d, 1H), 8.59 (m, 1H), 7.90-7.95 (m, 2H), 7.64 (d, 1H), 7.25-7.53 (m, 6H), 7.14 (m, 1H), 6.21 (d, 1H), 4.37 (s, 2H), 4.03 (q, 2H), 1.26 (t, 3H) | |
| 951 | 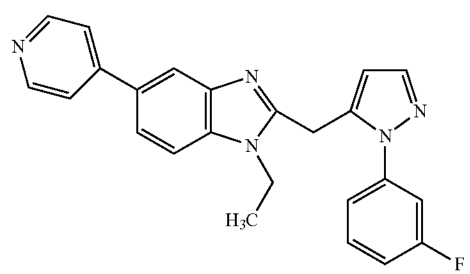 | 1-ethyl-2-{[1-(3-fluorophenyl)-1H-pyrazol-5-yl]methyl}-5-pyridin-4-yl-1H-benzimidazole | 1H NMR (CDCl3): 8.67 (d, 1H), 8.65 (d, 1H), 8.03 (d, 1H), 7.26-7.65 (m, 8H), 7.15 (m, 1H), 6.21 (d, 1H), 4.37 (s, 2H), 4.03 (q, 2H), 1.26 (t, 3H) | |

TABLE 7-continued

| Cmp. # | STRUCTURE | IUPAC NAME | NMR | MS (m/z) |
|---|---|---|---|---|
| 952 | 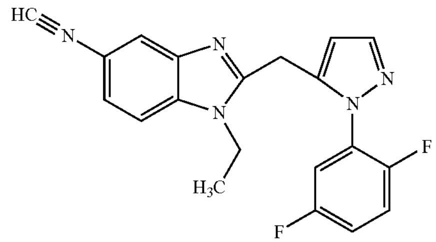 | 2-{[1-(2,5-difluorophenyl)-1H-pyrazol-5-yl]methyl}-1-ethyl-5-(methylidyne-lambda~5~-azanyl)-1H-benzimidazole | 1H NMR (CDCl3): 7.70-7.67 (2H, m), 7.31-7.14 (5H, m), 6.16 (1H, s), 4.28 (2H, s), 4.02 (2H, q), 1.22 (3H, t) | 364.1 [M + 1] |
| 953 | 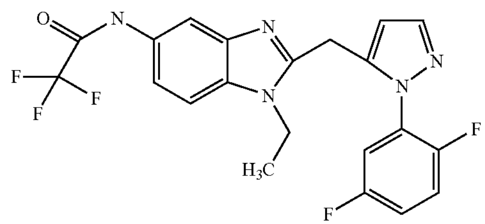 | N-(2-{[1-(2,5-difluorophenyl)-1H-pyrazol-5-yl]methyl}-1-ethyl-1H-benzimidazol-5-yl)-2,2,2-trifluoroacetamide | | 449.96 [M + 1] |
| 954 | 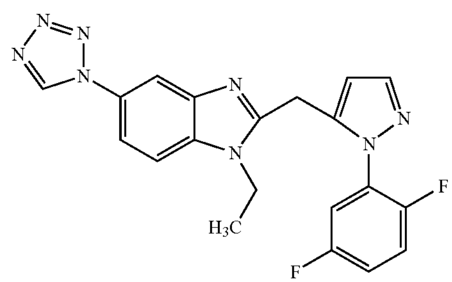 | 2-{[1-(2,5-difluorophenyl)-1H-pyrazol-5-yl]methyl}-1-ethyl-5-(1H-tetraazol-1-yl)-1H-benzimidazole | 1H NMR (DMSO): 10.07 (s, 1H 0, 8.07 (s, 1H), 7.86 (d, 1H), 7.79 (d, 1H), 7.71 (s, 1H), 7.36-7.57 (m, 3H), 6.4 (s, 2H), 4.46 (s, 2H), 4.21 (q, 2H 0, 1.14 (t, 3H) | |

TABLE 7-continued

| Cmp. # | STRUCTURE | IUPAC NAME | NMR | MS (m/z) |
|---|---|---|---|---|
| 955 | 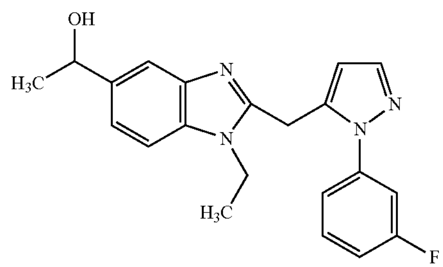 | 1-(1-ethyl-2-{[1-(3-fluorophenyl)-1H-pyrazol-5-yl]methyl}-1H-benzimidazol-5-yl)ethanol | | |
| 956 | 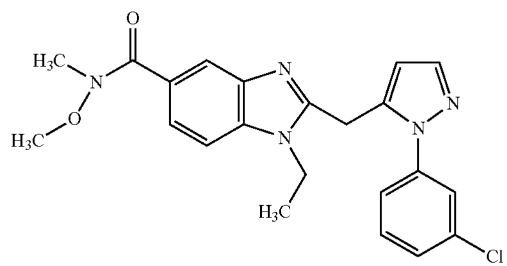 | 2-{[1-(3-chlorophenyl)-1H-pyrazol-5-yl]methyl}-1-ethyl-N-methoxy-N-methyl-1H-benzimidazole-5-carboxamide | 1H NMR (CDCl3): 8.13 (d, 1H), 7.63-7.70 (m, 2H), 7.51 (m, 1H), 7.31-7.41 (m, 4H), 6.20 (d, 1H), 4.35 (s, 2H), 4.00 (q, 2H), 3.60 (s, 3H), 3.40 (s, 3H), 1.23 (t, 3H) | |
| 957 | 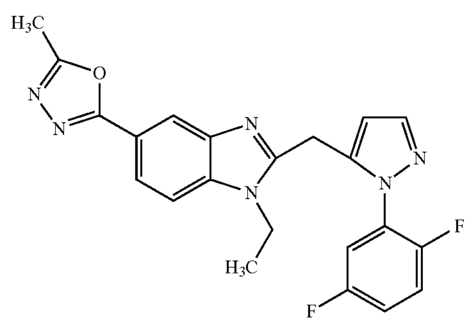 | 2-{[1-(2,5-difluorophenyl)-1H-pyrazol-5-yl]methyl}-1-ethyl-5-(5-methyl-1,3,4-oxadiazol-2-yl)-1H-benzimidazole | | 437.02 [M + 1] |

TABLE 7-continued

| Cmp. # | STRUCTURE | IUPAC NAME | NMR | MS (m/z) |
|---|---|---|---|---|
| 958 | 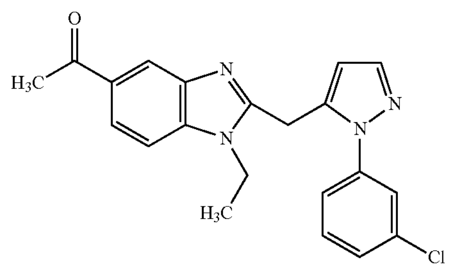 | 1-(2-{[1-(3-chlorophenyl)-1H-pyrazol-5-yl]methyl}-1-ethyl-1H-benzimidazol-5-yl)ethanone | 1H NMR (CDCl3): 8.37 (d, 1H), 8.03 (dd, 1H), 7.65 (d, 1H), 7.38-7.50 (m, 5H), 6.24 (d, 1H), 4.49 (s, 2H), 4.03 (q, 2H), 2.68 (s, 3H), 1.24 (t, 3H) | |
| 959 | 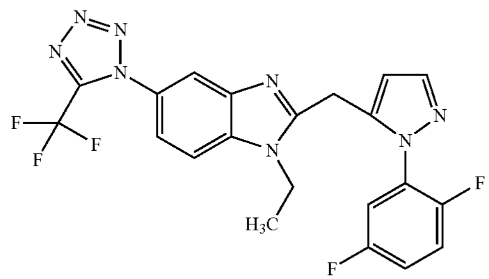 | 2-{[1-(2,5-difluorophenyl)-1H-pyrazol-5-yl]methyl}-1-ethyl-5-[5-(trifluoromethyl)-1H-tetrazol-1-yl]-1H-benzimidazole | | 474.99 [M + 1] |
| 960 | 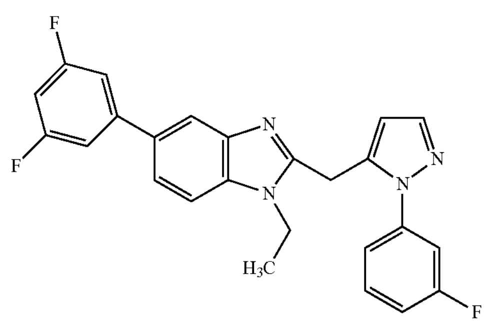 | 5-(3,5-difluorophenyl)-1-ethyl-2-{[1-(3-fluorophenyl)-1H-pyrazol-5-yl]methyl}-1H-benzimidazole | 1H NMR (CDCl3): 7.91 (d, 1H), 7.64 (d, 1H), 7.27-7.50 (m, 5H), 7.10-7.18 (m, 3H), 6.77 (m, 1H), 6.20 (d, 1H), 4.36 (s, 2H), 4.02 (q, 2H), 1.25 (t, 3H) | |

TABLE 7-continued

| Cmp. # | STRUCTURE | IUPAC NAME | NMR | MS (m/z) |
|---|---|---|---|---|
| 961 | 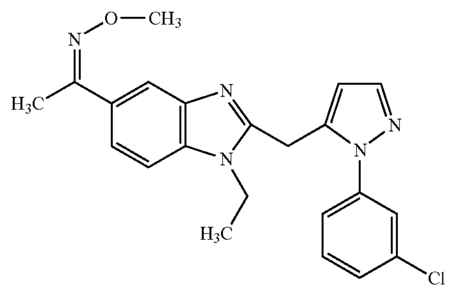 | (1Z)-1-(2-{[1-(3-chlorophenyl)-1H-pyrazol-5-yl]methyl}-1-ethyl-1H-benzimidazol-5-yl)ethanone O-methyloxime | 1H NMR (CDCl3): 7.94 (d, 1H), 7.73 (dd, 1H), 7.73 (dd, 1H), 7.63 (d, 1H), 7.52 (m, 1H), 7.38-7.40 (m, 3H), 7.27 (m, 1H), 6.19 (d, 1H), 4.32 (s, 2H), 3.87-4.10 (m, 5H), 2.30 (s, 3H), 1.22 (t, 3H.) | |
| 962 | 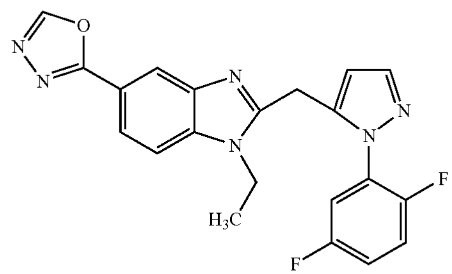 | 2-{[1-(2,5-difluorophenyl)-1H-pyrazol-5-yl]methyl}-1-ethyl-5-(1,3,4-oxadiazol-2-yl)-1H-benzimidazole | | 425.10 [M + 1] |
| 963 | 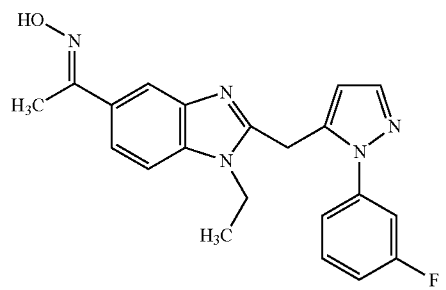 | (1E)-1-(1-ethyl-2-{[1-(3-fluorophenyl)-1H-pyrazol-5-yl]methyl}-1H-benzimidazol-5-yl)ethanone oxime | 1H NMR (CD3OD): 7.81 (d, 1H), 7.64-7.68 (m, 2H), 7.42-7.53 (m, 2H), 7.16-7.32 (m, 3H), 6.28 (d, 1H), 4.44 (s, 2H), 4.12 (q, 2H), 2.30 (s, 3H), 1.23 (t, 3H) | |

TABLE 7-continued

| Cmp. # | STRUCTURE | IUPAC NAME | NMR | MS (m/z) |
|---|---|---|---|---|
| 964 | 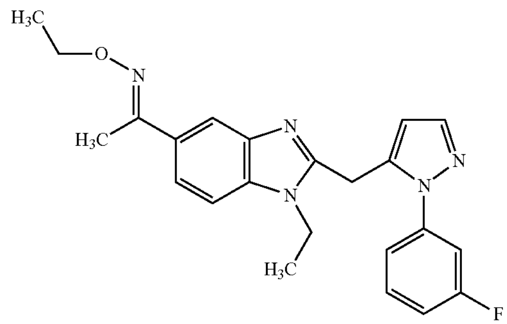 | (1E)-1-(1-ethyl-2-{[1-(3-fluorophenyl)-1H-pyrazol-5-yl]methyl}-1H-benzimidazol-5-yl)ethanone O-ethyloxime | Syn and anti 1H NMR (CDCl3): 7.95(d, 1H + H1), 7.73 (dd, 1H + H1), 7.63 (d, 1H + H1), 7.44 (m, 1H + H1), 7.24-7.33 (m, 3H + H1), [6.18 (d, 1H + H1), 7.13 (d, 1H + H1)], 4.33 (s, 2H), [4.26 (q, 2H), 4.13 (q, 2H1)], 3.98 (q, 2H + 2H1), [2.31 (s, 3H), 2.27 (s, 3H1)], [1.35 (t, 3H), 1.28 (t, 3H1)], 1.22 (t, 3H + H1)] | |
| 965 | 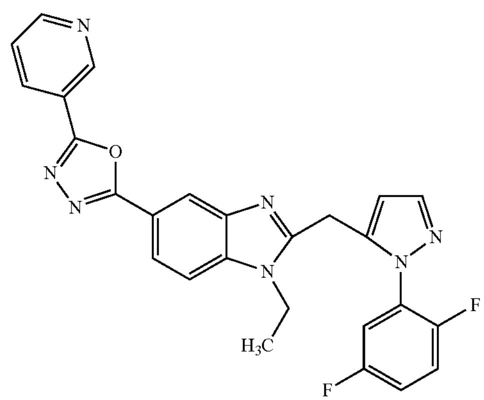 | 2-{[1-(2,5-difluorophenyl)-1H-pyrazol-5-yl]methyl}-1-ethyl-5-(5-pyridin-3-yl-1,3,4-oxadiazol-2-yl)-1H-benzimidazole | 1H NMR (d6 DMSO): 9.40 (1H, s), 8.87 (1H, s), 8.63 (1H, d), 8.41 (1H, s), 8.20 (1H, d), 8.01 (1H, d), 7.76 (2H, m), 7.59 (1H, m), 7.48-7.41 (2H, m), 6.50 (1H, s), 4.61 (2H, s), 4.31 (2H, q), 1.19 (3H, t) | 484.5 [M + 1] |

TABLE 7-continued

| Cmp. # | STRUCTURE | IUPAC NAME | NMR | MS (m/z) |
|---|---|---|---|---|
| 966 | 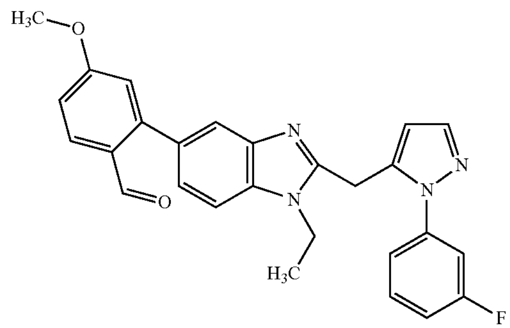 | 2-(1-ethyl-2-{[1-(3-fluorophenyl)-1H-pyrazol-5-yl]methyl}-1H-benzimidazol-5-yl)-4-methoxybenzaldehyde | 1H NMR (CDCl3): 9.86 (s, 1H), 8.03 (d, 1H), 7.26-7.78 (m, 7H), 6.94-7.18 (m, 3H), 6.22 (dd, 1H), 4.38 (s, 2H), 4.04 (q, 2H), 3.91 (s, 3H), 1.27 (t, 3H) | |
| 967 | 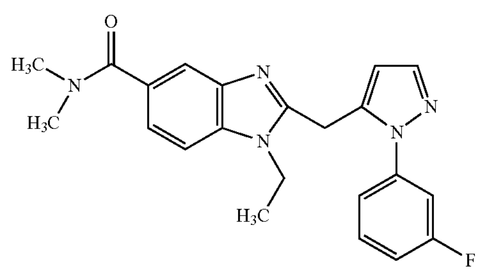 | 1-ethyl-2-{[1-(3-fluorophenyl)-1H-pyrazol-5-yl]methyl}-N,N-dimethyl-1H-benzimidazole-5-carboxamide | 1H NMR (CDCl3): 7.78 (s, 1H), 7.63 (s, 1H), 7.10-7.48 (m, 6H), 6.18 (s, 1H), 4.35 (s, 2H), 4.00 (q, 2H), 3.13 (s, 3H), 3.05 (s, 3H), 1.22 (t, 3H) | |
| 968 | 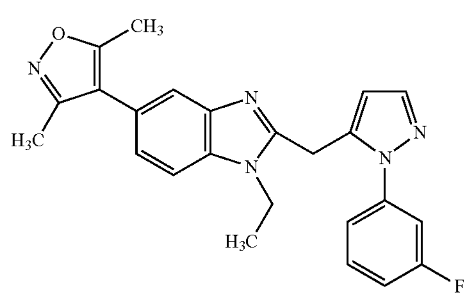 | 5-(3,5-dimethylisoxazol-4-yl)-1-ethyl-2-{[1-(3-fluorophenyl)-1H-pyrazol-5-yl]methyl}-1H-benzimidazole | 1H NMR (CDCl3): 7.62-7.64 (m, 2H), 7.25-7.50 (m, 4H), 7.11-7.18 (m, 2H), 6.21 (d, 1H), 4.36 (s, 2H), 4.02 (q, 2H), 2.42 (s, 3H), 2.29 (s, 3H), 1.26 (t, 3H) | |

TABLE 7-continued

| Cmp. # | STRUCTURE | IUPAC NAME | NMR | MS (m/z) |
|---|---|---|---|---|
| 969 | 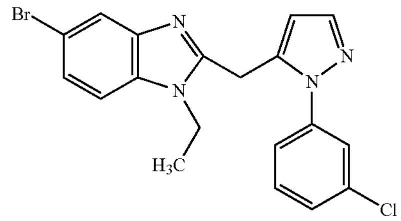 | 5-bromo-2-{[1-(3-chlorophenyl)-1H-pyrazol-5-yl]methyl}-1-ethyl-1H-benzimidazole | 1H NMR (CDCl3): 7.87 (d, 1H), 7.63 (d, 1H), 7.50 (m, 1H), 7.35-7.42 (m, 4H), 7.18 (d, 1H), 6.18 (d, 1H), 4.31 (s, 2H), 3.96 (q, 2H), 1.21 (t, 3H) | |
| 970 | 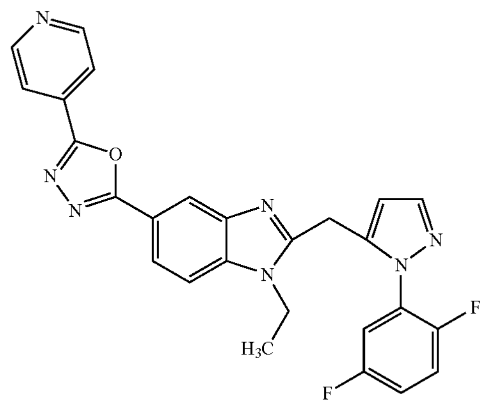 | 2-{[1-(2,5-difluorophenyl)-1H-pyrazol-5-yl]methyl}-1-ethyl-5-(5-pyridin-4-yl-1,3,4-oxadiazol-2-yl)-1H-benzimidazole | Dihydrochloride 1H NMR (d6 DMSO): 8.98 (2H, m), 8.43 (1H, s), 8.35 (2H, m), 8.19 (1H, d), 7.99 (1H, d), 7.75 (1H, d), 7.59-7.5691H, m), 7.50-7.41 (2H, m), 6.49 (1H, s), 4.58 (2H, s), 4.30 (2H, q), 1.19 (3H, t) | 484.5 [M + 1] |
| 971 | 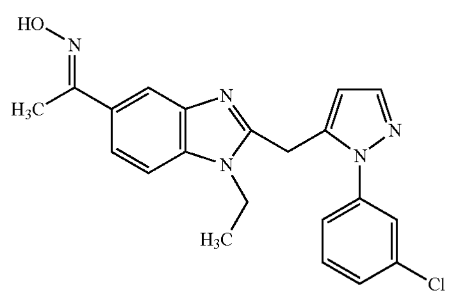 | (1E)-1-(2-{[1-(3-chlorophenyl)-1H-pyrazol-5-yl]methyl}-1-ethyl-1H-benzimidazol-5-yl)ethanone oxime | 1H NMR (CDCl3): 10.92 (br s, 1H), 8.58 (s, 1H), 7.52-7.64 (m, 3H), 7.29 (d, 1H), 6.20 (d, 1H), 4.36 (s, 2H), 3.97 (q, 2H), 2.38 (s, 3H), 1.21 (t, 3H) | |

TABLE 7-continued

| Cmp. # | STRUCTURE | IUPAC NAME | NMR | MS (m/z) |
|---|---|---|---|---|
| 972 | 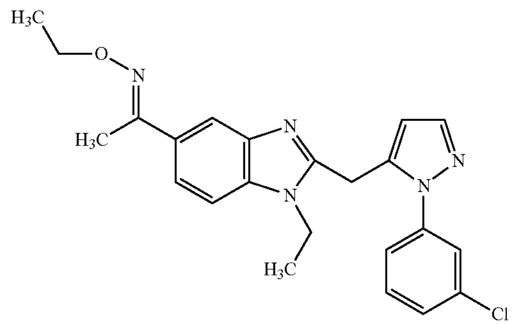 | (1E)-1-(2-{[1-(3-chlorophenyl)-1H-pyrazol-5-yl]methyl}-1-ethyl-1H-benzimidazol-5-yl)ethanone O-ethyloxime | Syn and anti 1H NMR (CDCl3): 7.95 (d, 1H + H1), 7.73 (dd, 1H + H1), 7.63 (d, 1H + H1), 7.44 (m, 1H + H1), 7.24-7.33 (m, 3H + H1), 6.18 (d, 1H + H1), 7.13 (d, 1H + H1)], 4.33 (s, 2H), [4.26 (q, 2H), 4.13 (q, 2H1)], 3.98 (q, 2H + 2H1), [2.31 (s, 3H), 2.27 (s, 3H1)], [1.35 (t, 3H), 1.28 (t, 3H1)], 1.22 (t, 3H + H1)] | |
| 973 | 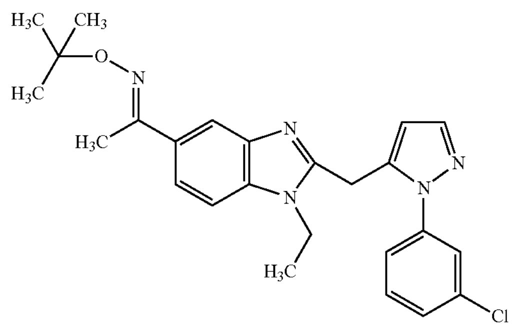 | (1E)-1-(2-{[1-(3-chlorophenyl)-1H-pyrazol-5-yl]methyl}-1-ethyl-1H-benzimidazol-5-yl)ethanone O-(tert-butyl)oxime | Syn and anti 1H NMR (CDCl3): 8.00 (d, 1H + H1), 7.75 (dd, 1H + H1), 7.63 (d, 1H + H1), 7.27 (d, 1H + H1), 7.38-7.40 (m, 3H + H1), 6.20 (d, 1H) [6.18 (d, 1H1)], 4.32 (s, 2H + H1), 3.99 (q, 2H + H1), 2.28 (s, 3H), [2.27 (s, 3H1)], 1.37 (s, 9H), [1.32 (s, 9H1)], 1.22 (t, 3H, t3H) | |
| 974 | 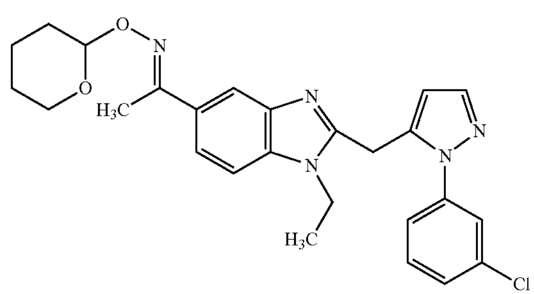 | (1E)-1-(2-{[1-(3-chlorophenyl)-1H-pyrazol-5-yl]methyl}-1-ethyl-1H-benzimidazol-5-yl)ethanone O-tetrahydro-2H-pyran-2-yloxime | 1H NMR (CDCl3): 7.95 (d, 1H), 7.79 (dd, 1H), 7.63 (d, 1H), 7.52 (m, 1H), 7.37-7.40 (m, 3H), 7.26 (dd, 1H), 6.19 (d, 1H), 5.43 (m, 1H), 4.32 (s, 2H), 3.85-4.02 (m, 4H), 3.66 (m, 2H), 1.62-1.92 (m, 4H), 1.22 (t, 3H) | |

TABLE 7-continued

| Cmp. # | STRUCTURE | IUPAC NAME | NMR | MS (m/z) |
|---|---|---|---|---|
| 975 | 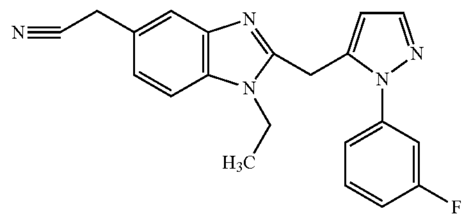 | (1-ethyl-2-{[1-(3-fluorophenyl)-1H-pyrazol-5-yl]methyl}-1H-benzimidazol-5-yl)acetonitrile | 7.66 (m, 1H), 7.63 (d, 1H), 7.24-7.49 (m, 5H), 7.13 (m, 1H), 6.17 (d, 1H), 4.34 (s, 2H), 3.99 (q, 2H), 3.87 (s, 2H), 1.22 (t, 3H) | |
| 976 | 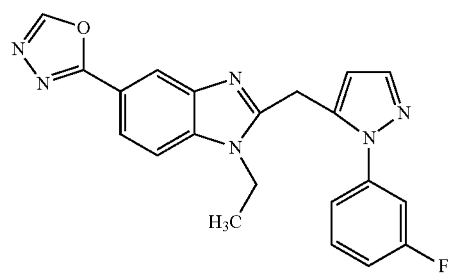 | 1-ethyl-2-{[1-(3-fluorophenyl)-1H-pyrazol-5-yl]methyl}-5-(1,3,4-oxadiazol-2-yl)-1H-benzimidazole | 1H NMR (d6 DMSO): 8.17 (1H, s), 8.04-7.98 (2H, m), 7.71 (1H, d), 7.55-7.50 (2H, m), 7.45-7.43 (1H, m), 7.29-7.24 (1H, m), 6.40 (1H, d), 4.77 (2H, s), 4.36 (2H, q), 2.58 (3H, s), 1.24 (3H, t) | 403.6 [M + 1] |
| 977 | 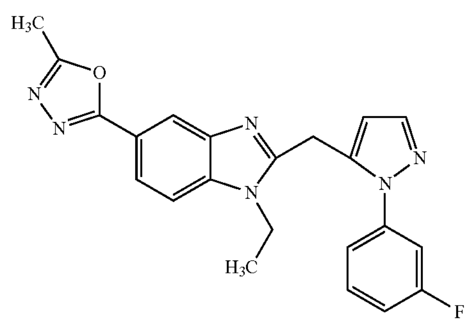 | 1-ethyl-2-{[1-(3-fluorophenyl)-1H-pyrazol-5-yl]methyl}-5-(5-methyl-1,3,4-oxadiazol-2-yl)-1H-benzimidazole | 1H NMR (CD3OD): 8.79 (s, 1H), 8.31 (d, 1H), 7.69 (s, 1H), 7.60 (d, 1H), 7.46 (dd, 1H), 7.30 (d, 2H), 7.16-7.20 (m, 1H), 6.37 (s, 1H), 4.55 (s, 2H), 4.20 (q, 2H), 1.24 (t, 3H) | |

TABLE 7-continued

| Cmp. # | STRUCTURE | IUPAC NAME | NMR | MS (m/z) |
|---|---|---|---|---|
| 978 | 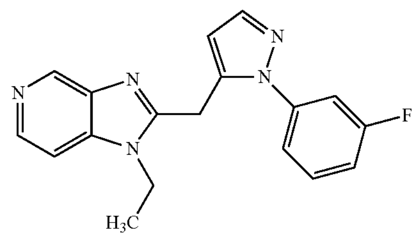 | 1-ethyl-2-{[1-(3-fluorophenyl)-1H-pyrazol-5-yl]methyl}-1H-imidazo[4,5-c]pyridine | 1H NMR (CD3OD): 8.79 (s, 1H), 8.31 (d, 1H), 7.69 (s, 1H), 7.60 (d, H), 7.46 (dd, 1H), 7.30 (d, 2H), 7.16-7.20 (m, 1H), 6.37 (s, 1H), 4.55 (s, 2H), 4.20 (q, 2H), 1.24 (t, 3H) | |
| 979 | 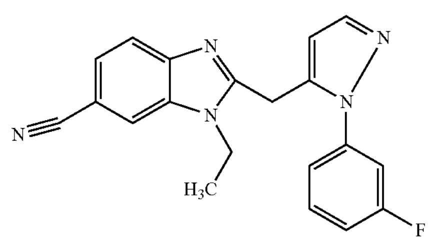 | 1-ethyl-2-{[1-(3-fluorophenyl)-1H-pyrazol-5-yl]methyl}-1H-benzimidazole-6-carbonitrile | | |
| 980 | 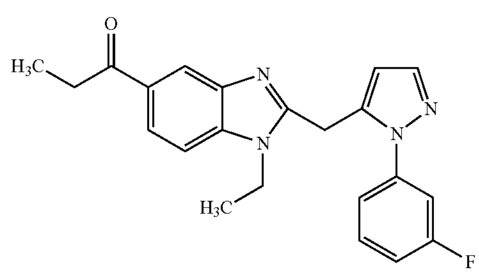 | 1-(1-ethyl-2-{[1-(3-fluorophenyl)-1H-pyrazol-5-yl]methyl}-1H-benzimidazol-5-yl)propan-1-one | | |
| 981 | 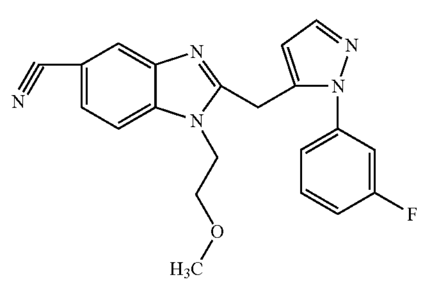 | 2-{[1-(3-fluorophenyl)-1H-pyrazol-5-yl]methyl}-1-(2-methoxyethyl)-1H-benzimidazole-5-carbonitrile | | |

TABLE 7-continued

| Cmp. # | STRUCTURE | IUPAC NAME | NMR | MS (m/z) |
|---|---|---|---|---|
| 982 | 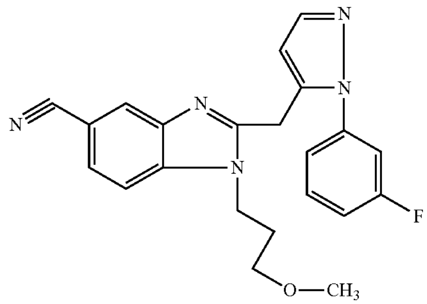 | 2-{[1-(3-fluorophenyl)-1H-pyrazol-5-yl]methyl}-1-(3-methoxypropyl)-1H-benzimidazole-5-carbonitrile | | 390.1 [M + 1]; 388.3 [M − 1] |
| 983 | 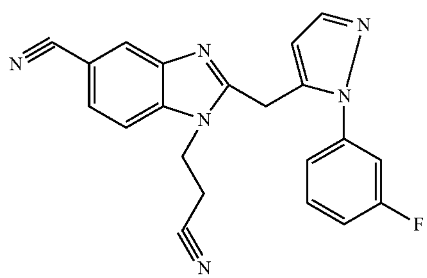 | 1-(2-cyanoethyl)-2-{[1-(3-fluorophenyl)-1H-pyrazol-5-yl]methyl}-1H-benzimidazole-5-carbonitrile | | 371.3 [M + 1] |
| 984 | 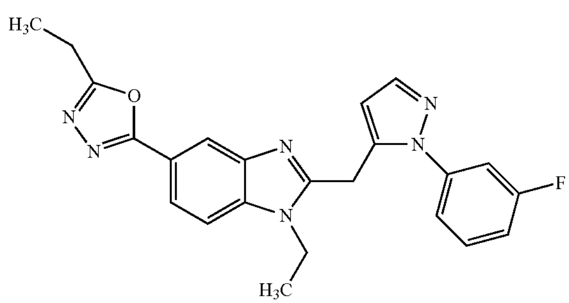 | 1-ethyl-5-(5-ethyl-1,3,4-oxadiazol-2-yl)-2-{[1-(3-fluorophenyl)-1H-pyrazol-5-yl]methyl}-1H-benzimidazole | 1H NMR (d6DMSO): 8.17 (1H, s), 8.01-7.94 (2H, m), 7.71 (1H, s), 7.53-7.51 (2H, m), 7.44-7.42 (1H, m), 7.28-7.24 (1H, m), 6.39 (1H, s), 4.73 (2H, s), 4.33 (2H, q), 2.94 (2H, q), 1.32 (3H, t), 1.23 (3H, t) | 417.5 [M + 1] |

TABLE 7-continued

| Cmp. # | STRUCTURE | IUPAC NAME | NMR | MS (m/z) |
|---|---|---|---|---|
| 985 | 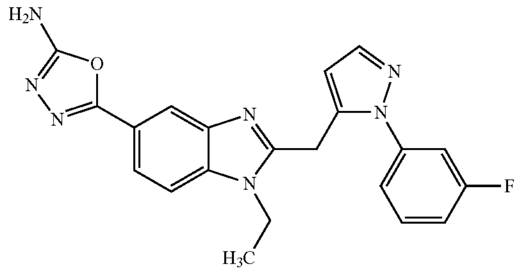 | 5-(1-ethyl-2-{[1-(3-fluorophenyl)-1H-pyrazol-5-yl]methyl}-1H-benzimidazol-5-yl)-1,3,4-oxadiazol-2-amine | 1H NMR (d6DMSO): 8.17 (1H, s), 8.01-7.94 (2H, m), 7.71 (1H, s), 7.53-7.51 (2H, m), 7.44-7.42 (1H, m), 7.28-7.24 (1H, m), 6.39 (1H, s), 4.73 (2H, s), 4.33 (2H, q), 2.94 (2H, q), 1.32 (3H, t), 1.23 (3H, t) | 417.5 [M + 1] |
| 986 | 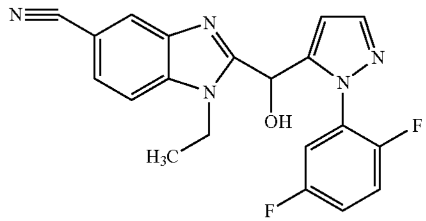 | 2-[[1-(2,5-difluorophenyl)-1H-pyrazol-5-yl](hydroxy)methyl]-1-ethyl-1H-benzimidazole-5-carbonitrile | 1H NMR (CDCl3): 7.93 (d, 1H), 7.67 (d, 1H), 7.55 (dd, 1H), 7.40 (dd, 1H), 7.24 (m, 1H), 7.10-7.15 (m, 2H), 6.20 (d, 1H), 6.01 (s, 1H), 4.98 (br, S, 1H): 4.04 (q, 2H), 1.21 (t, 3H) | |
| 987 | 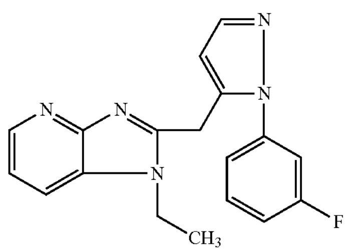 | 1-ethyl-2-{[1-(3-fluorophenyl)-1H-pyrazol-5-yl]methyl}-1H-imidazo[4,5-b]pyridine | | 322.3 [M + 1]; 320.3 [M − 1] |
| 988 | 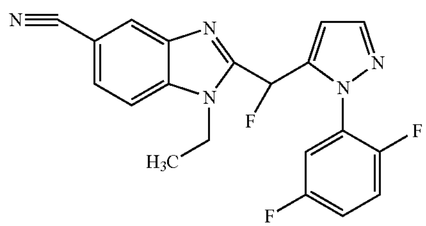 | 2-[[1-(2,5-difluorophenyl)-1H-pyrazol-5-yl](fluoro)methyl]-1-ethyl-1H-benzimidazole-5-carbonitrile | 1H NMR (CDCl3): 8.07 (d, 1H), 7.77 (d, 1H), 7.60 (dd, 1H), 7.47 (dd, 1H), 7.11-7.23 (m, 3H), 6.85 (d, 1H, J(H, F) = 47.4), 6.50 (t, 1H), 4.27 (m, 2H), 1.36 (t, 3H) | |

| Cmp. # | STRUCTURE | IUPAC NAME | NMR | MS (m/z) |
|---|---|---|---|---|
| 989 | 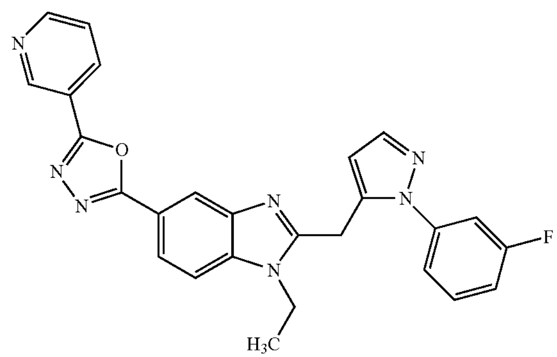 | 1-ethyl-2-{[1-(3-fluorophenyl)-1H-pyrazol-5-yl]methyl}-5-(5-pyridin-3-yl-1,3,4-oxadiazol-2-yl)-1H-benzimidazole | 1H NMR (d6DMSO): 9.41 (1H, s), 8.88 (1H, d), 8.67 (1H, d), 8.46 (1H, s), 8.25 (1H, d), 8.10 (1H, d), 7.81-7.72 (2H, m), 7.55-7.46 (3H, m), 7.30-7.26 (1H, m), 6.43 (1H, s), 4.84 (2H, s), 4.40 (2H, q), 1.27 (3H, t) | |
| 990 | 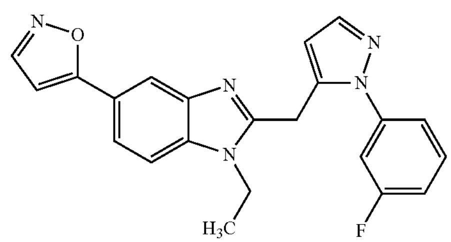 | 1-ethyl-2-{[1-(3-fluorophenyl)-1H-pyrazol-5-yl]methyl}-5-isoxazol-5-yl-1H-benzimidazole | 1H NMR (CDCl3): 8.30 (d, 1H), 8.16 (dd, 1H), 7.76 (dd, 1H), 7.64 (d, 1H), 7.38-7.50 (m, 2H), 7.25-7.32 (m, 2H), 7.14 (m, 1H), 6.52 (d, 1H), 6.21 (d, 1H), 4.37 (s, 2H), 4.01 (q, 2H), 1.25 (t, 3H) | |
| 991 | 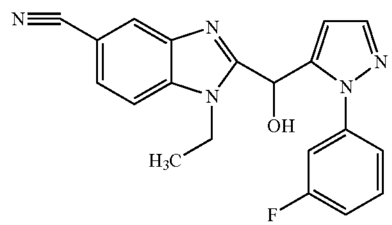 | 1-ethyl-2-[[1-(3-fluorophenyl)-1H-pyrazol-5-yl](hydroxy)methyl]-1H-benzimidazole-5-carbonitrile | 1H NMR (CDCl3): 8.02 (dd, 1H), 7.47-7.62 (m, 5H), 7.39 (d, 1H), 7.18 (m, 1H), 6.12 (d, 1H), 6.00 (s, 1H), 5.05 (brs, 1H), 3.83 (q, 2H), 1.08 (t, 3H) | |

TABLE 7-continued

| Cmp. # | STRUCTURE | IUPAC NAME | NMR | MS (m/z) |
|---|---|---|---|---|
| 992 | 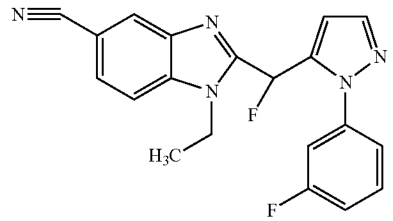 | 1-ethyl-2-{fluoro[1-(3-fluorophenyl)-1H-pyrazol-5-yl]methyl}-1H-benzimidazole-5-carbonitrile | 1H NMR (CDCl3): 8.12 (dd, 1H), 7.73 (d, 1H), 7.62 (dd, 1H), 7.44-7.53 (m, 2H), 7.31-7.39 (m, 2H), 7.17 (m, 1H), 6.83 (d, 1H, JH, F = 46.8 MZ), 4.39 (m, 2H), 1.43 (t, 3H) | |
| 993 | 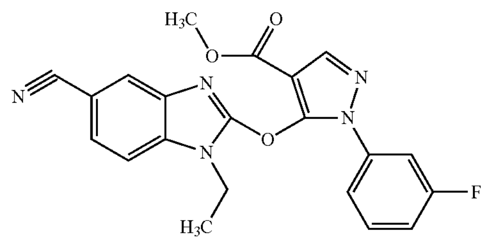 | methyl 5-[(5-cyano-1-ethyl-1H-benzimidazol-2-yl)oxy]-1-(3-fluorophenyl)-1H-pyrazole-4-carboxylate | | 406.3 [M + 1] |
| 994 | 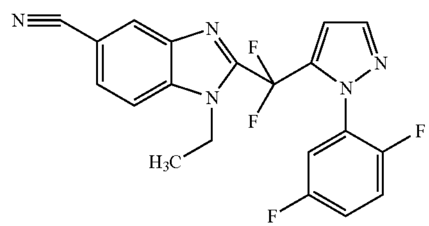 | 2-{[1-(2,5-difluorophenyl)-1H-pyrazol-5-yl](difluoromethyl)}-1-ethyl-1H-benzimidazole-5-carbonitrile | 1H NMR (CDCl3): 8.09 (m, 1H), 7.84 (M, 1H), 7.64 (dd, 1H), 7.48 (dd, 1H), 6.96-7.18 (m, 3H), 6.85 (d, 1H), 4.33 (q, 2H), 1.38 (t, 3H) | |
| 995 | 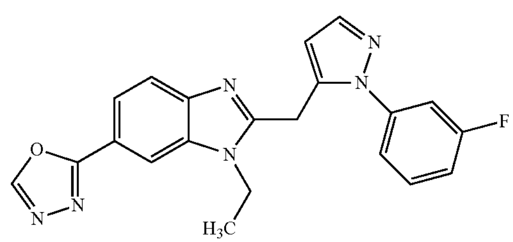 | 1-ethyl-2-{[1-(3-fluorophenyl)-1H-pyrazol-5-yl]methyl}-6-(1,3,4-oxadiazol-2-yl)-1H-benzimidazole | | 389.2 [M + 1] |

TABLE 7-continued

| Cmp. # | STRUCTURE | IUPAC NAME | NMR | MS (m/z) |
|---|---|---|---|---|
| 996 | 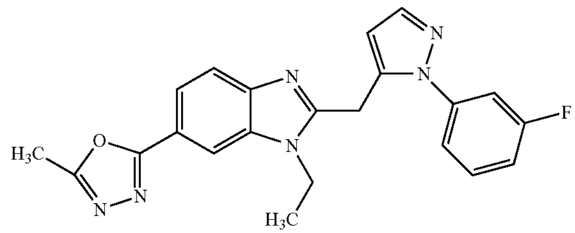 | 1-ethyl-2-{[1-(3-fluorophenyl)-1H-pyrazol-5-yl]methyl}-6-(5-methyl-1,3,4-oxadiazol-2-yl)-1H-benzimidazole | | 403.3 [M + 1] |
| 997 | 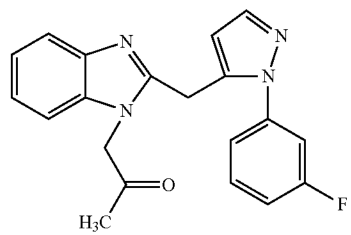 | 1-(2-{[1-(3-fluorophenyl)-1H-pyrazol-5-yl]methyl}-1H-benzimidazol-1-yl)acetone | | 349.3 [M + 1]; 347.2 [M − 1] |
| 998 | 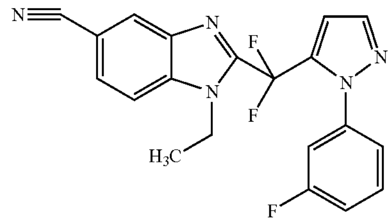 | 2-{difluoro[1-(3-fluorophenyl)-1H-pyrazol-5-yl]methyl}-1-ethyl-1H-benzimidazole-5-carbonitrile | 1H NMR (CDCl3): 8.078 (m, 1H), 7.80 (m, 1H), 7.63 (dd, 1H), 7.48 (dd, 1H), 7.13-7.28 (m, 3H), 6.99 (m, 1H), 6.81 (d, 1H), 4.35 (q, 2H), 1.39 (t, 3H) | |
| 999 | 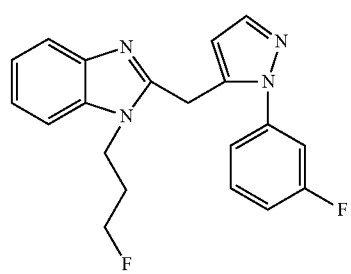 | 2-{[1-(3-fluorophenyl)-1H-pyrazol-5-yl]methyl}-1-(3-fluoropropyl)-1H-benzimidazole | | 353.2 [M + 1]; 351.2 [M − 1] |

TABLE 7-continued

| Cmp. # | STRUCTURE | IUPAC NAME | NMR | MS (m/z) |
|---|---|---|---|---|
| 1000 | 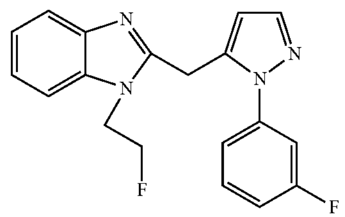 | 1-(2-fluoroethyl)-2-{[1-(3-fluorophenyl)-1H-pyrazol-5-yl]methyl}-1H-benzimidazole | | 339.2 [M + 1] |
| 1001 | 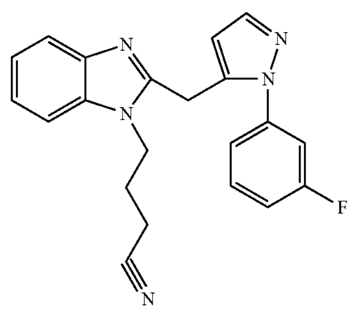 | 4-(2-{[1-(3-fluorophenyl)-1H-pyrazol-5-yl]methyl}-1H-benzimidazol-1-yl)butanenitrile | | 360.2 [M + 1]; 358.3 [M − 1] |
| 1002 | 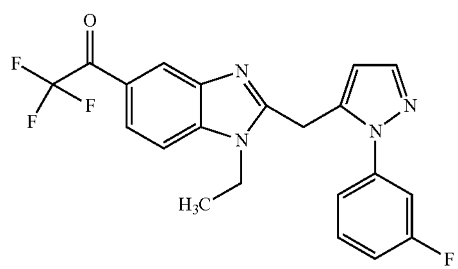 | 1-(1-ethyl-2-{[1-(3-fluorophenyl)-1H-pyrazol-5-yl]methyl}-1H-benzimidazol-5-yl)-2,2,2-trifluoroethanone | | 417.2 [M + 1] |

TABLE 7-continued

| Cmp. # | STRUCTURE | IUPAC NAME | NMR | MS (m/z) |
|---|---|---|---|---|
| 1003 | 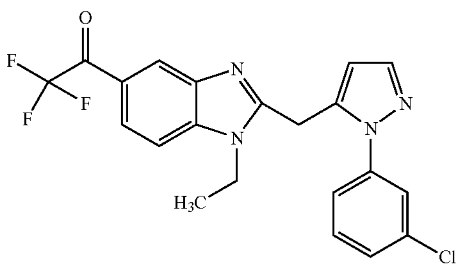 | 1-(2-{[1-(3-chlorophenyl)-1H-pyrazol-5-yl]methyl}-1-ethyl-1H-benzimidazol-5-yl)-2,2,2-trifluoroethanone | | |
| 1004 | 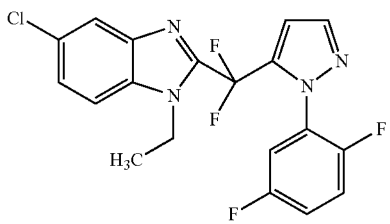 | 5-chloro-2-{[1-(2,5-difluorophenyl)-1H-pyrazol-5-yl](difluoro)methyl]-1-ethyl-1H-benzimidazole | | |
| 1005 | 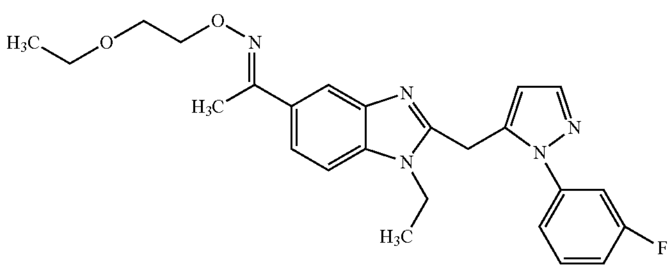 | (1E)-1-(1-ethyl-2-{[1-(3-fluorophenyl)-1H-pyrazol-5-yl]methyl}-1H-benzimidazol-5-yl)ethanone O-(2-ethoxyethyl)oxime | 1H NMR, δ ppm (CDCl3): 7.95 (m, 1H), 7.72 (dd, 1H), 7.63 (d, 1H), 7.45 (m, 1H), 7.11-7.31 (m, 4H), 6.18 (d, 1H), 4.34-4.37 (m, 4H), 3.98 (q, 2H), 3.77 (t, 2H), 3.58 (q, 2H), 2.33 (s, 3H), 1.18-1.26 (m, 6H) | |
| 1006 | 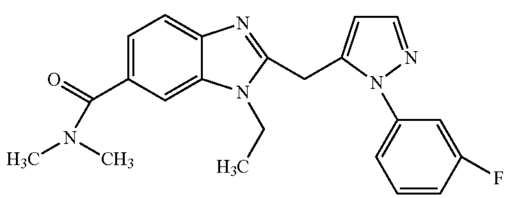 | 1-ethyl-2-{[1-(3-fluorophenyl)-1H-pyrazol-5-yl]methyl}-N,N-dimethyl-1H-benzimidazole-6-carboxamide | 1H NMR, δ ppm (CDCl3): 7.72 (dd, 1H), 7.63 (d, 1H), 7.40-7.49 (m, 2H), 7.24-7.34 (m, 3H), 7.13 (d, 1H), 6.18 (d, 1H), 4.35 (s, 2H), 3.99 (q, 2H), 3.13 (s, 2H), 3.07 (s, 3H), 1.23 (t, 3H) | |

TABLE 7-continued

| Cmp. # | STRUCTURE | IUPAC NAME | NMR | MS (m/z) |
|---|---|---|---|---|
| 1007 | 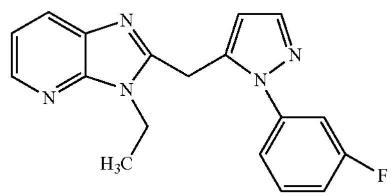 | 3-ethyl-2-{[1-(3-fluorophenyl)-1H-pyrazol-5-yl]methyl}-3H-imidazo[4,5-b]pyridine | | |
| 1008 | 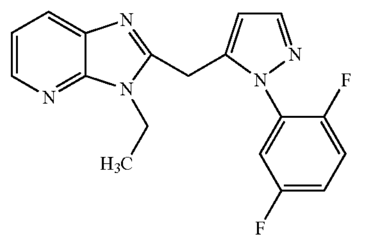 | 2-{[1-(2,5-difluorophenyl)-1H-pyrazol-5-yl]methyl}-3-ethyl-3H-imidazo[4,5-b]pyridine | 1H NMR (CDCl3): 8.19 (1H, d), 7.61 (1H, d), 7.48-7.44 (1H, m), 7.28-7.13 (4H, m), 6.14 (1H, m), 4.44 (2H, s), 3.93 (2H, q), 1.17 (3H, t), | 356.2 [M+1] |
| 1009 | 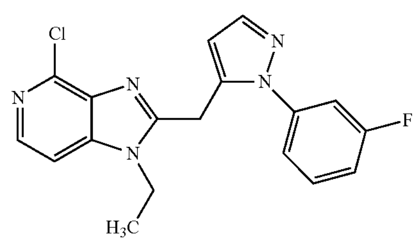 | 4-chloro-1-ethyl-2-{[1-(3-fluorophenyl)-1H-pyrazol-5-yl]methyl}-1H-imidazo[4,5-c]pyridine | 1H nmr (CDCl3): 8.19 (1H, d), 7.61 (1H, d), 7.48-7.44 (1H, m), 7.28-7.13 (4H, m), 6.14 (1H, m), 4.44 (2H, s), 3.93 (2H, q), 1.17 (3H, t) | 356.2 [M+1] |
| 1010 | 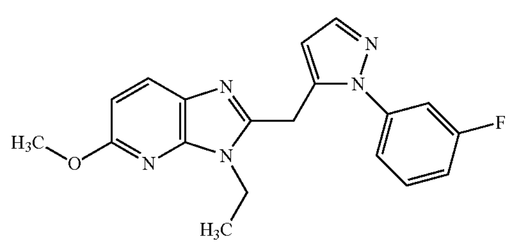 | 3-ethyl-2-{[1-(3-fluorophenyl)-1H-pyrazol-5-yl]methyl}-5-methoxy-3H-imidazo[4,5-b]pyridine | | 392.3 [M+1] |

TABLE 7-continued

| Cmp. # | STRUCTURE | IUPAC NAME | NMR | MS (m/z) |
|---|---|---|---|---|
| 1011 | 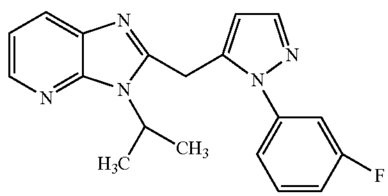 | 2-{[1-(3-fluorophenyl)-1H-pyrazol-5-yl]methyl}-3-isopropyl-3H-imidazo[4,5-b]pyridine | | |
| 1012 | 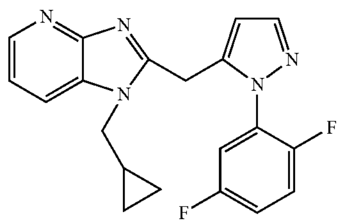 | 1-(cyclopropylmethyl)-2-{[1-(2,5-difluorophenyl)-1H-pyrazol-5-yl]methyl}-1H-imidazo[4,5-b]pyridine | H-1 NMR (CDCl3): 0.22 (m, 2H), 0.54 (m, 2H), 0.95 (m, 1H), 3.84 (d, 2H), 4.32 (s, 2H), 6.18 (s, 2H), 7.13-7.25 (m, 4H), 7.65 (m, 2H), 8.52 (d, 1H) | 366 [M + 1] |
| 1013 | 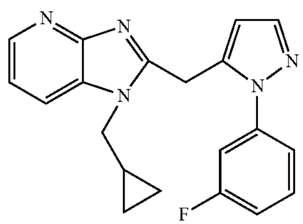 | 1-(cyclopropylmethyl)-2-{[1-(3-fluorophenyl)-1H-pyrazol-5-yl]methyl}-1H-imidazo[4,5-b]pyridine | H-1 NMR (CDCl3): 0.22 (m, 2H), 0.54 (m, 2H), 0.95 (m, 1H), 3.84 (d, 2H), 4.32 (s, 2H), 6.18 (s, 2H), 7.13-7.25 (m, 4H), 7.65 (m, 2H), 8.52 (d, 1H) | 366 [M + 1] |
| 1014 | 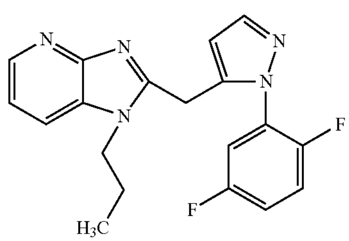 | 2-{[1-(2,5-difluorophenyl)-1H-pyrazol-5-yl]methyl}-1-propyl-1H-imidazo[4,5-b]pyridine | H-1 NMR (CDCl3): 0.82 (t, 3H), 1.62 (h, 2H), 3.85 (t, 2H), 4.33 (s, 2H), 6.20 (s, 1H), 7.05-7.25 (m, 4H), 7.82 (m, 2H), 8.53 (d, 1H) | 354 [M + 1] |

TABLE 7-continued

| Cmp. # | STRUCTURE | IUPAC NAME | NMR | MS (m/z) |
|---|---|---|---|---|
| 1015 | 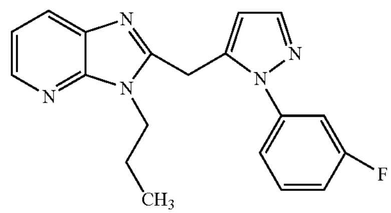 | 2-{[1-(3-fluorophenyl)-1H-pyrazol-5-yl]methyl}-3-propyl-3H-imidazo[4,5-b]pyridine | (CDCl3) 8.43 (dd, J = 4.8, 1.5 Hz, 1H), 8.10 (dd, J = 8.0, 1.4 Hz, 1H), 7.64 (d, J = 2.1Hz, 1H), 7.47 (m, 1H), 7.23-7.34 (m, 3H), 7.12 (m, 1H), 6.31 (d, J = 1.8Hz, 1H), 4.60 (s, 2H), 4.03 (t, J = 7.7Hz, 2H), 1.65 (m, 2H), 0.84 (t, J = 7.5 Hz) | m/z 366.2 [M + 1] |
| 1016 | 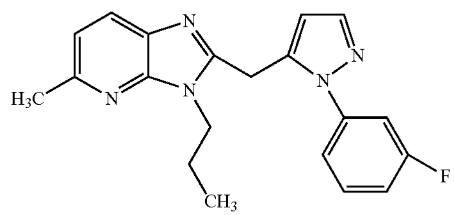 | 2-{[1-(3-fluorophenyl)-1H-pyrazol-5-yl]methyl}-5-methyl-3-propyl-3H-imidazo[4,5-b]pyridine | (CDCl3) 7.85 (d, J = 7.8Hz, 1H), 7.64 (d, J = 1.5Hz, 1H), 7.43 (m, 1H), 7.24-7.29 (m, 2H), 7.12 (m, 1H), 7.06 (d, J = 8.1Hz, 1H), 6.22 (d, J = 1.5 Hz, 1H), 4.33 (s, 2H), 4.01 (t, J = 7.5Hz, 2H), 2.64 (s, 3H), 1.67 (m, 2H), 0.84 (t, J = 7.3 Hz, 3H) | m/z 350.3 [M + 1] |
| 1017 | 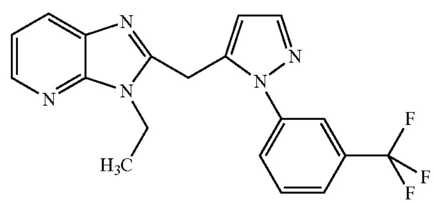 | 3-ethyl-2-({1-[3-(trifluoromethyl)phenyl]-1H-pyrazol-5-yl}methyl)-3H-imidazo[4,5-b]pyridine | (CDCl3) 8.36 (dd, J = 4.8, 1.3 Hz, 1H), 7.98 (dd, J = 8.0, 1.3 Hz, 1H), 7.78 (m, 1H), 7.56-7.72 (m, 4H), 7.22 (dd, J = 8.1, 4.8Hz, 1H), 6.29 (d, J = 1.5 Hz, 1H), 4.36 (s, 2H), 4.17 (q, J = 7.2Hz, 2H), 1.27 (t, J = 7.2 Hz, 3H) | m/z 372.2 [M + 1] |
| 1018 | 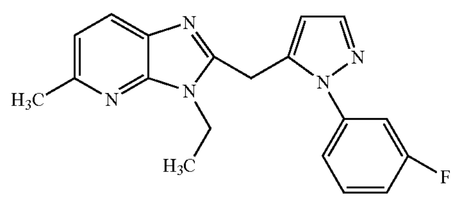 | 3-ethyl-2-{[1-(3-fluorophenyl)-1H-pyrazol-5-yl]methyl}-5-methyl-3H-imidazo[4,5-b]pyridine | (CDCl3) 7.85 (d, J = 8.1Hz, 1H), 7.64 (d, J = 1.8Hz, 1H), 7.44 (m, 1H), 7.24-7.29 (m, 2H), 7.13 (m, 1H), 7.06 (d, J = 8.1Hz, 1H), 6.21 (d, J = 1.5 Hz, 1H), 4.33 (s, 2H), 4.12 (q, J = 7.3Hz, 2H), 2.65 (s, 3H), 1.25 (t, J = 7.3Hz, 3H) | m/z 336.2 [M + 1] |

TABLE 7-continued

| Cmp. # | STRUCTURE | IUPAC NAME | NMR | MS (m/z) |
|---|---|---|---|---|
| 1019 | 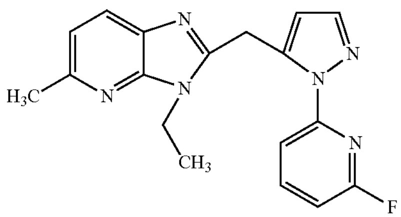 | 3-ethyl-2-{[1-(6-fluoropyridin-2-yl)-1H-pyrazol-5-yl]methyl}-5-methyl-3H-imidazo[4,5-b]pyridine | | m/z 337.2 [M + 1] |
| 1020 | 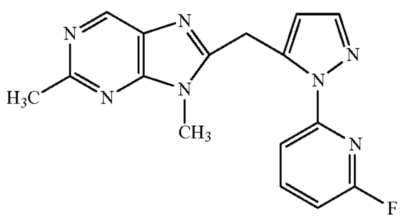 | 8-{[1-(6-fluoropyridin-2-yl)-1H-pyrazol-5-yl]methyl}-2,9-dimethyl-9H-purine | (CDCl3) 8.81 (s, 1H), 7.87 (m, 2H), 7.69 (d, 1H), 6.67 (dd, 1H), 6.33 (s, 1H), 4.86 (s, 2H), 3.90 (s, 3H), 2.79 (s, 3H) | |
| 1021 | 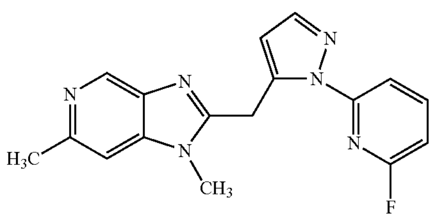 | 2-{[1-(6-fluoropyridin-2-yl)-1H-pyrazol-5-yl]methyl}-1,6-dimethyl-1H-imidazo[4,5-c]pyridine | (CDCl3) 8.82 (s, 1H), 7.88 (m, 1H), 7.84 (m, 1H), 7.67 (s, 1H), 7.11 (s, 1H), 6.69 (m, 1H), 6.27, (s, 1H), 4.85 (s, 2H), 3.81 (s, 3H), 2.66 (s, 3H) | |
| 1022 | 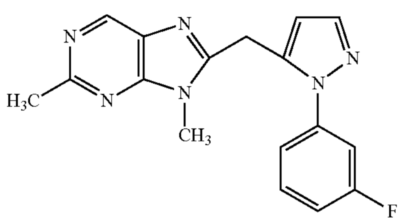 | 8-{[1-(3-fluorophenyl)-1H-pyrazol-5-yl]methyl}-2,9-dimethyl-9H-purine | (CDCl3) 8.90 (s, 1H), 7.63 (d, 1H), 7.42 (m, 1H), 7.26 (m, 2H), 7.12 (m, 1H), 6.16 (d, 1H), 4.32 (s, 2H), 3.60 (s, 3H), 2.78 (s, 3H) | m/z 323 [M + 1] |

TABLE 7-continued

| Cmp. # | STRUCTURE | IUPAC NAME | NMR | MS (m/z) |
|---|---|---|---|---|
| 1023 | 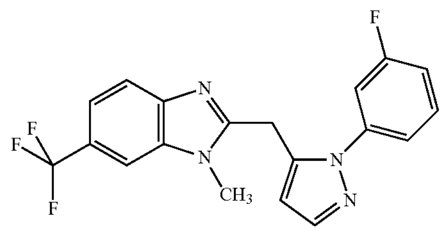 | 2-{[1-(3-fluorophenyl)-1H-pyrazol-5-yl]methyl}-1-methyl-6-(trifluoromethyl)-1H-benzimidazole | (CDCl3) 7.79 (d, 1H), 7.59 (d, 2H), 7.54 (m, 2H), 7.30 (m, 2H), 7.16 (m, 1H), 6.12 (d, 1H), 4.38 (s, 2H), 3.61 (s, 3H), | |
| 1024 | 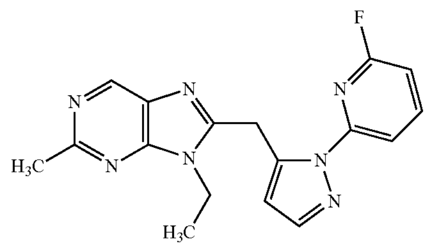 | 9-ethyl-8-{[1-(6-fluoropyridin-2-yl)-1H-pyrazol-5-yl]methyl}-2-methyl-9H-purine | (CDCl3) 8.82 (s, 1H), 7.88 (m, 1H), 7.83 (q, 1H), 7.69 (d, 1H), 6.69 (m, 1H), 6.35 (s, 1H), 4.95 (s, 2H), 4.44 (q, 2H), 2.82 (s, 3H), 1.52 (t, 3H) | |
| 1025 | 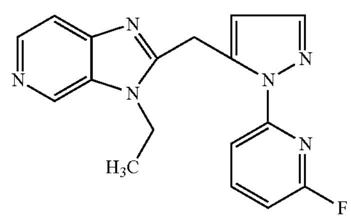 | 3-ethyl-2-{[1-(6-fluoropyridin-2-yl)-1H-pyrazol-5-yl]methyl}-3H-imidazo[4,5-c]pyridine | (CDCl3) 8.78 (s, 1H), 8.38 (d, J = 3.9Hz, 1H), 7.83-7.89 (m, 2H), 7.66 (s, 1H), 7.56 (d, J = 3.9Hz, 1H), 7.25 (d, J = 9.9 Hz, 1H), 6.70 (d, J = 9.9Hz, 1H), 4.81 (s, 2H), 4.39 (q, J = 5.4Hz, 2H), 1.49 (t, J = 5.4Hz, 3H) | m/z 323 [M + 1] |
| 1026 | 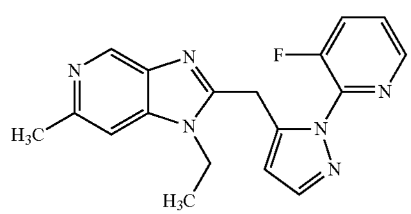 | 1-ethyl-2-{[1-(3-fluoropyridin-2-yl)-1H-pyrazol-5-yl]methyl}-6-methyl-1H-imidazo[4,5-c]pyridine | (CDCl3) 8.82 (s, 1H), 8.28 (br d, J = 4.0 Hz, 1H), 7.70 (d, J = 1.6Hz, 1H), 7.61 (m, 1H), 7.35 (m, 1H), 7.07 (s, 1H), 6.23 (s, 1H), 4.56 (s, 2H), 4.09 (q, J = 7.2Hz, 2H), 2.65 (s, 3H), 1.25 (t, J = 7.2Hz, 3H) | m/z 337 [M + 1] |

TABLE 7-continued

| Cmp. # | STRUCTURE | IUPAC NAME | NMR | MS (m/z) |
|---|---|---|---|---|
| 1027 | 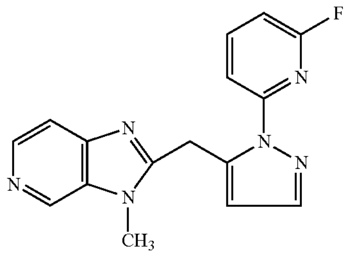 | 2-{[1-(6-fluoropyridin-2-yl)-1H-pyrazol-5-yl]methyl}-3-methyl-3H-imidazo[4,5-c]pyridine | (CDCl3) 8.78 (br s, 1H), 8.38 (br s, 1H), 7.87 (m, 2H), 7.68 (s, 1H), 7.55 (br s, 1H), 7.25 (s, 1H), 6.69 (br d, J = 7.5Hz, 1H), 6.30 (s, 2H), 4.88 (s, 3H) | m/z 309.2 [M + 1] |
| 1028 | 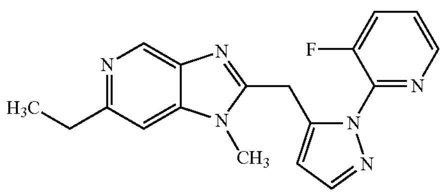 | 6-ethyl-2-{[1-(3-fluoropyridin-2-yl)-1H-pyrazol-5-yl]methyl}-1-methyl-1H-imidazo[4,5-b]pyridine | (CDCl3) 8.86 (s, 1H), 8.30 (d, J = 4.4Hz, 1H), 7.71 (s, 1H), 7.62 (m, 1H), 7.36 (m, 1H), 7.07 (s, 1H), 6.18 (s, 1H), 4.58 (s, 2H), 3.64 (s, 3H), 2.94 (q, J = 7.6Hz, 2H), 1.36 (t, J = 7.6 Hz, 3H) | m/z 337 [M + 1] |
| 1029 | 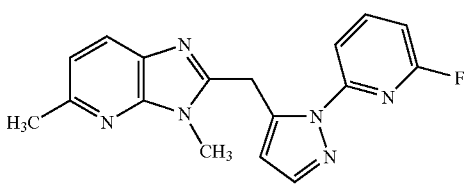 | 2-{[1-(6-fluoropyridin-2-yl)-1H-pyrazol-5-yl]methyl}-3,5-dimethyl-3H-imidazo[4,5-b]pyridine | (CDCl3) 8.86 (s, 1H), 8.30 (d, J = 4.4Hz, 1H), 7.71 (s, 1H), 7.62 (m, 1H), 7.36 (m, 1H), 7.07 (s, 1H), 6.18 (s, 1H), 4.58 (s, 2H), 3.64 (s, 3H), 2.94 (q, J = 7.6Hz, 2H), 1.36 (t, J = 7.6 Hz, 3H) | m/z 337 [M + 1] |
| 1030 | 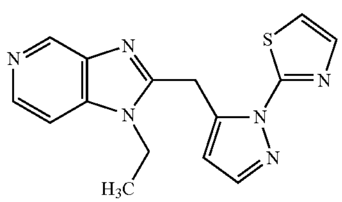 | 1-ethyl-2-{[1-(1,3-thiazol-2-yl)-1H-pyrazol-5-yl]methyl}-1H-imidazo[4,5-c]pyridine | (CDCl3) 9.00 (s, 1H 0, 8.43 (d, 1H), 7.63 (d, 1H), 7.43 (d, 1H), 7.15 (d, 1H), 7.06 (d, 1H), 6.25 (d, 1H), 4.99 (s, 2H), 4.25 (q, 2H), 1.36 (t, 3H) | |

TABLE 7-continued

| Cmp. # | STRUCTURE | IUPAC NAME | NMR | MS (m/z) |
|---|---|---|---|---|
| 1031 | 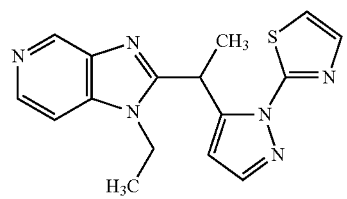 | 1-ethyl-2-{1-[1-(1,3-thiazol-2-yl)-1H-pyrazol-5-yl]ethyl}-1H-imidazo[4,5-c]pyridine | (CDCl3) 9.05 (s, 1H), 8.39 (d, 1H), 7.59 (d, 1H), 7.49 (d, 1H), 7.25 (d, 1H), 7.09 (d, 1H), 6.28 (d, 1H), 5.85 (q, 1H), 4.19 (q, 2H), 1.85 (d, 3H), 1.29 (t, 3H) | |
| 1032 | 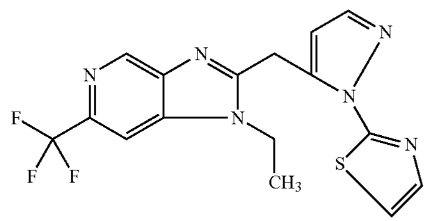 | 1-ethyl-2-{[1-(1,3-thiazol-2-yl)-1H-pyrazol-5-yl]methyl}-6-(trifluoromethyl)-1H-imidazo[4,5-c]pyridine | (CD3OD) 8.7 (s, 1H), 8.17 (s, 1H), 7.74 (d, J = 3.6Hz, 1H), 7.33 (d, J = 3.6Hz, 1H), 7.21 (d, J = 3.6Hz, 1H), 7.21 (d, J = 3.6Hz, 1H), 6.53 (s, 1H), 5.01 (s, 2H), 4.54 (q, J = 7.2Hz, 2H), 1.52 (t, J = 7.2Hz, 3H) | |
| 1033 | 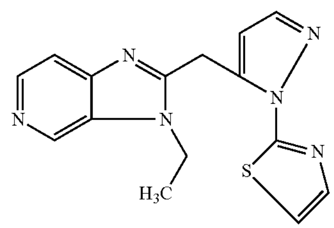 | 3-ethyl-2-{[1-(1,3-thiazol-2-yl)-1H-pyrazol-5-yl]methyl}-3H-imidazo[4,5-c]pyridine | (CD3OD) 9.42 (s, 1H), 8.44 (d, J = 6.6Hz, 1H), 7.9 (d, J = 6.3 Hz, 1H), 7.7 (s, 1H), 7.26 (d, J = 3.6Hz, 1H), 7.20 (d, J = 3.6 Hz, 1H), 6.63 (s, 1H), 5.09 (s, 2H), 4.68 (q, J = 7.5Hz, 2H), 1.62 (t, J = 7.5Hz, 3H) | m/z 311 [M + 1] |

TABLE 8

| Cmp. # | STRUCTURE | IUPAC NAME | NMR | MS (m/z) |
|---|---|---|---|---|
| 1035 | 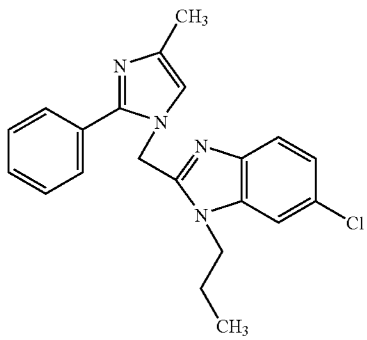 | 6-chloro-2-[(4-methyl-2-phenyl-1H-imidazol-1-yl)methyl]-1-propyl-1H-benzimidazole | 1H NMR (CDCl3): 7.62-7.71 (m, 3H), 7.45-7.53 (m, 3H), 7.23-7.27 (m, 2H), 6.74 (q, 1H), 5.42 (s, 2H), 3.59 (t, 2H), 2.21 (d, 3H), 1.37 (m, 2H), 0.70 (t, 3H) | |
| 1036 | 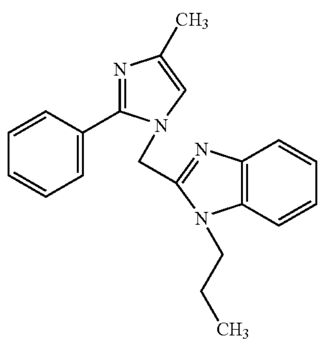 | 2-[(4-methyl-2-phenyl-1H-imidazol-1-yl)methyl]-1-propyl-1H-benzimidazole | 1H NMR (CDCl3): 7.80 (m, 1H), 7.25-7.67 (m, 8H), 6.74 (q, 1H), 5.43 (s, 2H), 3.62 (t, 2H), 2.20 (d, 3H), 1.38 (m, 2H,), 0.69 (t, 3H) | |
| 1037 | 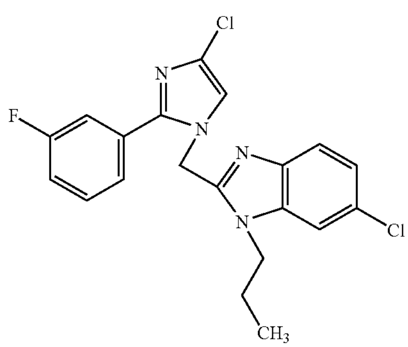 | 6-chloro-2-{[4-chloro-2-(3-fluorophenyl)-1H-imidazol-1-yl]methyl}-1-propyl-1H-benzimidazole | 1H NMR (CDCl3): 7.70 (d, 1H), 7.37-7.50 (m, 3H), 7.17-7.32 (m, 3H), 6.96 (s, 1H), 5.43 (s, 2H), 3.70 (t, 2H), 1.49 (m, 2H), 0.77 (t, 3H) | |
| 1038 | 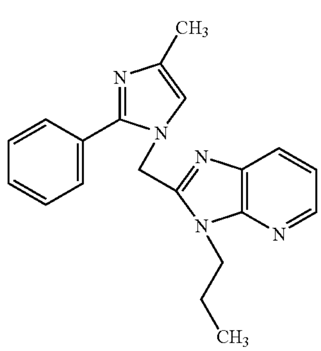 | 2-[(4-methyl-2-phenyl-1H-imidazol-1-yl)methyl]-3-propyl-3H-imidazo[4,5-b]pyridine | 1H NMR (CDCl3): 8.39 (dd, 1H), 8.06 (dd, 1H), 7.63-7.65 (m, 2H), 7.45-7.55 (m, 3H), 7.26 (m, 1H), 6.77 (q, 1H), 5.46 (s, 2H), 3.82 (t, 2H), 2.23 (d, 3H), 1.46 (m, 2H), 0.73 (t, 3H) | |

TABLE 8-continued

| Cmp. # | STRUCTURE | IUPAC NAME | NMR | MS (m/z) |
|---|---|---|---|---|
| 1039 | 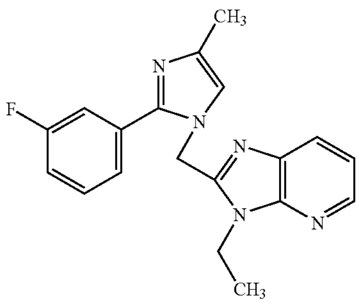 | 3-ethyl-2-{[2-(3-fluorophenyl)-4-methyl-1H-imidazol-1-yl]methyl}-3H-imidazo[4,5-b]pyridine | 1H NMR (CDCl3): 8.39 (dd, 1H), 8.06 (dd, 1H), 7.38-7.50 (m, 3H), 7.12-7.29 (m, 2H), 6.77 (q, 1H), 5.46 (s, 2H), 3.98 (q, 2H), 2.22 (d, 3H), 1.08 (t, 3H) | |
| 1040 | 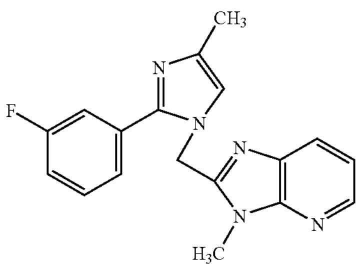 | 2-{[2-(3-fluorophenyl)-4-methyl-1H-imidazol-1-yl]methyl}-3-methyl-3H-imidazo[4,5-b]pyridine | | |
| 1041 | 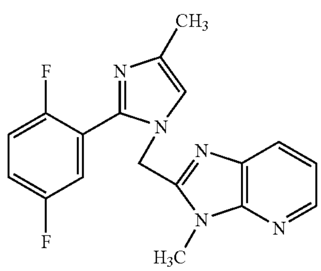 | 2-{[2-(2,5-difluorophenyl)-4-methyl-1H-imidazol-1-yl]methyl}-3-methyl-3H-imidazo[4,5-b]pyridine | | |
| 1042 | 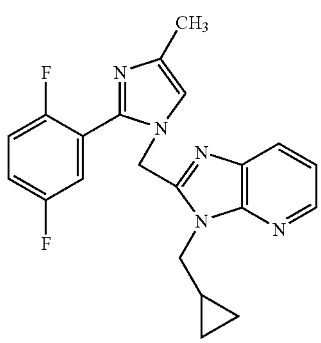 | 3-(cyclopropylmethyl)-2-{[2-(2,5-difluorophenyl)-4-methyl-1H-imidazol-1-yl]methyl}-3H-imidazo[4,5-b]pyridine | 1H NMR (CDCl3): 8.38 (dd, 1H), 8.04 (dd, 1H), 7.40 (m, 1H), 7.15-7.27 (m, 3H), 6.79 (d, 1H), 5.35 (s, 2H), 3.82 (d, 2H), 2.22 d, 3H), 0.75 (m, 1H), 0.39-0.44 (m, 2H), 0.23-0.28 (m, 2H) | |
| 1043 | 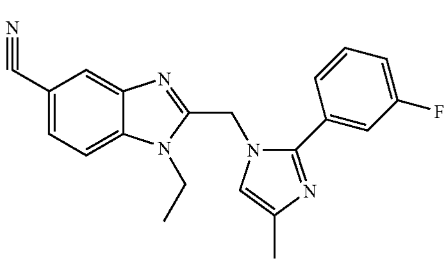 | 1-ethyl-2-{[2-(3-fluorophenyl)-4-methyl-1H-imidazol-1-yl]methyl}-1H-benzimidazole-5-carbonitrile | | m/z 360 [M + 1] |

TABLE 8-continued

| Cmp. # | STRUCTURE | IUPAC NAME | NMR | MS (m/z) |
|---|---|---|---|---|
| 1044 | 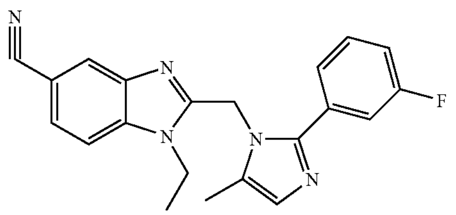 | 1-ethyl-2-{[2-(3-fluorophenyl)-5-methyl-1H-imidazol-1-yl]methyl}-1H-benzimidazole-5-carbonitrile | | m/z 360 [M + 1] |
| 1045 | 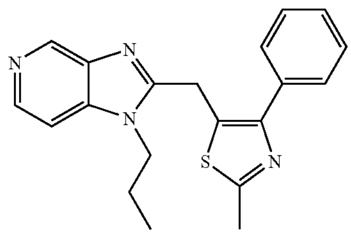 | 2-[(2-methyl-4-phenyl-1,3-thiazol-5-yl)methyl]-1-propyl-1H-imidazo[4,5-c]pyridine | (CDCl3) 9.06 (s, 1H), 8.39 (d, J = 5.6Hz, 1H), 7.61 (m, 2H), 7.47 (m, 2H), 7.41 (m, 1H), 7.20 (d, J = 5.6Hz, 1H), 4.54 (s, 2H), 3.77 (t, J = 7.6 Hz, 2H), 2.68 (s, 3H), | m/z 349 [M + 1] |
| 1046 | 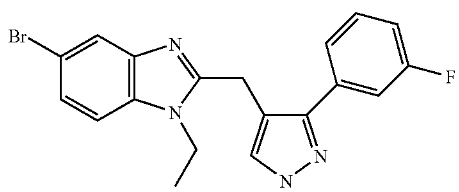 | 5-bromo-1-ethyl-2-{[3-(3-fluorophenyl)-1H-pyrazol-4-yl]methyl}-1H-benzimidazole | | 401.0 [M + 1] |
| 1047 | 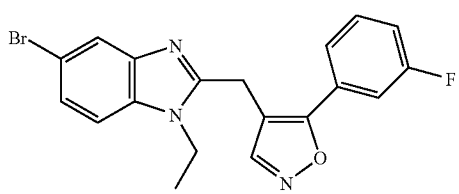 | 5-bromo-1-ethyl-2-{[5-(3-fluorophenyl)isoxazol-4-yl]methyl}-1H-benzimidazole | (CDCl3) 8.40 (s, 1H), 7.88 (s, 1H), 7.31-7.52 (m, 4H), 7.18-7.22 (m, 2H), 4.14 (s, 2H), 4.04 (q, 2H), 1.18 (t, 3H) | |
| 1048 | 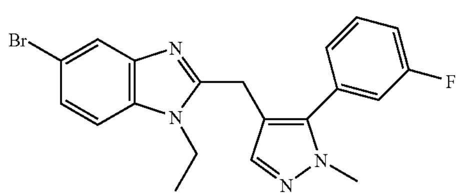 | 5-bromo-1-ethyl-2-{[5-(3-fluorophenyl)-1-methyl-1H-pyrazol-4-yl]methyl}-1H-benzimidazole | (CDCl3) 7.81 (s, 1H), 7.38-7.45 (m, 2H), 7.32 (dd, 1H), 7.00-7.18 (m, 4H), 4.00 (s, 2H), 3.90 (q, 2H), 3.78 (s, 3H), 1.15 (t, 3H) | |
| 1049 | 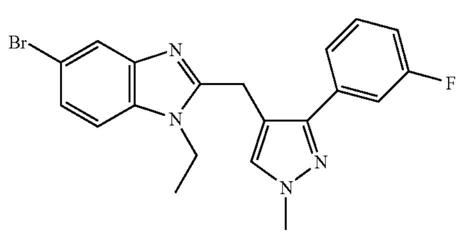 | 5-bromo-1-ethyl-2-{[3-(3-fluorophenyl)-1-methyl-1H-pyrazol-4-yl]methyl}-1H-benzimidazole | (CDCL3) 7.88 (s, 1H), 7.27-7.42 (m, 4H), 7.00-7.20 (m, 3H), 4.21 (s, 2H), 3.95 (t, 2H), 3.83 (s, 3H), 1.15 (t, 3H) | |
| 1050 | 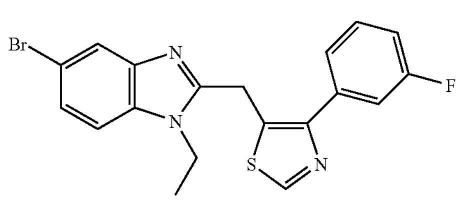 | 5-bromo-1-ethyl-2-{[4-(3-fluorophenyl)-1,3-thiazol-5-yl]methyl}-1H-benzimidazole | (CDCl3) 8.78 (s, 1H), 7.91 (s, 1H), 7.38-7.48 (m, 4H), 7.11-7.19 (m, 2H), 4.59 (s, 2H), 3.90 (q, 2H), 1.12 (t, 3H) | |

TABLE 8-continued

| Cmp. # | STRUCTURE | IUPAC NAME | NMR | MS (m/z) |
|---|---|---|---|---|
| 1051 | 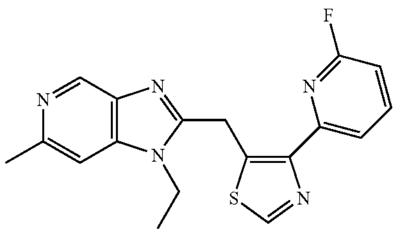 | 1-ethyl-2-{[4-(6-fluoropyridin-2-yl)-1,3-thiazol-5-yl]methyl}-6-methyl-1H-imidazo[4,5-c]pyridine | (CDCl3) 8.92 (s, 1H), 8.75 (s, 1H), 8.16 (d, 1H), 7.90 (dd, 1H), 7.08 (s, 1H), 6.87 (d, 1H), 5.28 (s, 2H 0, 4.32 (q, 2H), 2.63 (s, 3H), 1.32 (t, 3H) | |
| 1052 | 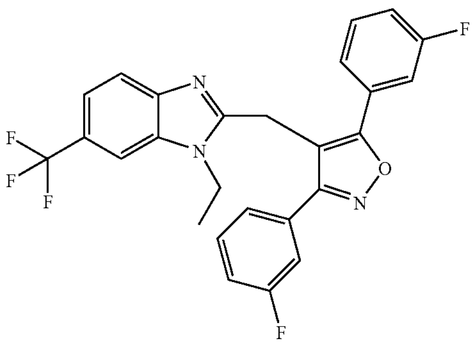 | 2-{[3,5-bis(3-fluorophenyl)isoxazol-4-yl]methyl}-1-ethyl-6-(trifluoromethyl)-1H-benzimidazole | | m/z 484 [M + 1] |
| 1053 | 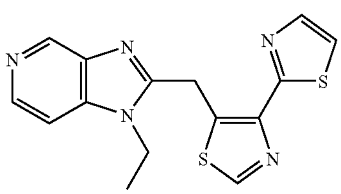 | 2-(2,4'-bi-1,3-thiazol-5'-ylmethyl)-1-ethyl-1H-imidazo[4,5-c]pyridine | (CDCl3) 9.05 (s, 1H 0, 8.76 (s, 1H), 8.41 (d, 1H), 7.88 (d, 1H), 7.41 (d, 1H), 7.25 (d, 1H), 5.35 (s, 2H), 4.26 (q, 2H), 1.25 (t, 3H) | |
| 1054 | 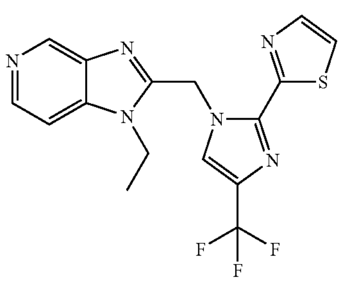 | 1-ethyl-2-{[2-(1,3-thiazol-2-yl)-4-(trifluoromethyl)-1H-imidazol-1-yl]methyl}-1H-imidazo[4,5-c]pyridine | (CDCl3) 9.10 (s, 1H), 8.47 (d, J = 6.0 Hz, 1H), 7.88 (d, J = 3.2Hz, 1H), 7.58 (s, 1H), 7.48 (d, J = 3.2Hz, 1H), 7.31 (d, J = 5.6Hz, 1H), 6.37 (s, 2H), 4.31 (q, J = 7.2Hz, 2H), 1.24 (t, J = 7.2Hz, 3H) | m/z 379 [M + 1] |
| 1055 | 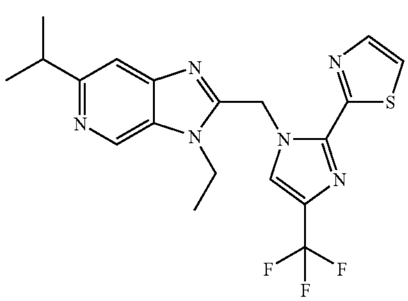 | 3-ethyl-6-isopropyl-2-{[2-(1,3-thiazol-2-yl)-4-(trifluoromethyl)-1H-imidazol-1-yl]methyl}-3H-imidazo[4,5-c]pyridine | (CDCl3) 8.75 (s, 1H), 7.87 (d, J = 3.3Hz, 1H), 7.59 (d, J = 0.9Hz, 1H), 7.54 (s, 1H), 7.47 (d, J = 3.6Hz, 1H), 6.32 (s, 2H), 4.38 (q, J = 7.2Hz, 2H), 3.21 (sept, J = 6.9Hz, 1H), 1.35 (d, J = 6.9Hz, 6H) 1.30 (t, J = 7.2Hz | m/z 421 [M + 1] |

TABLE 8-continued

| Cmp. # | STRUCTURE | IUPAC NAME | NMR | MS (m/z) |
|---|---|---|---|---|
| 1056 | 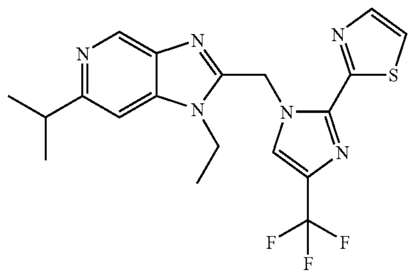 | 1-ethyl-6-isopropyl-2-{[2-(1,3-thiazol-2-yl)-4-(trifluoromethyl)-1H-imidazol-1-yl]methyl}-1H-imidazo[4,5-c]pyridine | (CDCl3) 9.02 (s, 1H), 7.88 (d, J = 2.7Hz, 1H), 7.55 (d, J = 0.9Hz, 1H), 7.48 (d, J = 3.3Hz, 1H), 7.13 (s, 1H), 6.34 (s, 2H), 4.28 (q, J = 7.2Hz, 2H), 3.20 (sept, J = 6.9Hz, 1H), 1.36 (d, J = 6.9Hz, 6H), 1.22 (t, J = 7.2Hz, | m/z 421 [M + 1] |

Example 51

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 52

Receptor Autograph

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 53

Binding Assay

The high affinity and high selectivity of preferred compounds of the invention for the benzodiazepine site of the $GABA_A$ receptor can be confirmed using the binding assay described by Thomas and Tallman (*J. Bio. Chem.* 1981; 156: 9838-9842, and *J. Neurosci.* 1983; 3:433-440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted. The resulting pellet may be stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations contain 100 μl of tissue homogenate, 100 μl of radioligand, (0.5 nM $^{3}$H-Ro15-1788 [$^{3}$H-Flumazenil], specific activity 80 Ci/mmol), and test compound or control (see below), and are brought to a total volume of 500 μl with Buffer A. Incubations are carried for 30 minutes at 4° C. and then rapidly filtered through Whatman GFE filters to separate free and bound ligand. Filters are washed twice with fresh Buffer A and counted in a liquid scintillation counter. Nonspecific binding (control) is determined by displacement of $^{3}$H Ro15-1788 with 10 μM Diazepam (Research Biochemicals International, Natick, Mass.). Data are collected in triplicate, averaged, and percent inhibition of total specific binding (Total Specific Binding=Total−Nonspecific) is calculated for each compound.

A competition binding curve may obtained with up to 11 points spanning the compound concentration range from $10^{-12}$M to $10^{-5}$M obtained per curve by the method described above for determining percent inhibition. $K_i$ values are calculated according the Cheng-Prussof equation. Each of the compounds disclosed in Tables 6-8 was tested in this fashion and each was found to have a $K_i$ of <4 μM. Preferred compounds of the invention exhibit $K_i$ values of less than 100 nM and more preferred compounds of the invention exhibit $K_i$ values of less than 10 nM.

Example 54

Electrophysiology

The following assay can be used to determine if a compound of the invention acts as an agonist, an antagonist, or an inverse agonist at the benzodiazepine site of the $GABA_A$ receptor.

Assays are carried out as described in white and Gurley (NeuroReport 6: 1313-1316, 1995) and White, Gurley, Hartnett, Stirling, and Gregory (Receptors and Channels 3: 1-5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. $X_{14766}$, human $\alpha_2$, GENBANK accession no. A28100; human $\alpha_3$, GENBANK accession no. A28102; human $\alpha_5$, GENBANK accession no. A28104; human $\beta_2$, GENBANK accession no. NM 021911; human $\beta_3$, GENBANK accession no. M82919 and accession no. Z20136; human $\gamma_2$, GENBANK accession no. $X_{15376}$; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat P2, GENBANK accession no. $X_{15467}$; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM-9 μM). Each oocyte is exposed to increasing concentrations of a compound being evaluated (test compound) in order to evaluate a concentration/effect relationship. Test compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 μM RO15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

It is to be understood that the foregoing describes preferred embodiments of the present invention and that modifications may be made therein without departing from the scope of the present invention as set forth in the following claims.

What is claimed is:

1. A compound of the formula:

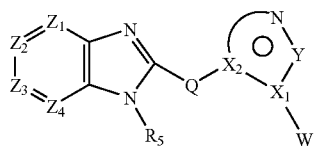

or a pharmaceutically acceptable salt thereof, wherein:
$Z_1$ is nitrogen or $CR_1$;

$Z_2$ is nitrogen or $CR_2$;
$Z_3$ is nitrogen or $CR_3$;
$Z_4$ is nitrogen or $CR_4$;
where $Z_2$ and $Z_4$ are nitrogen, $Z_1$ is $CR_1$, and $Z_3$ is $CR_3$, or $Z_1$ and $Z_3$ are nitrogen, $Z_2$ is $CR_2$, and $Z_4$ is $CR_4$;
$R_1$, $R_2$, $R_3$, and $R_4$ are independently selected from
i) hydrogen, halogen, hydroxy, nitro, cyano, amino, haloalkyl, and haloalkoxy,
ii) alkyl, alkoxy, cycloalkyl, alkenyl, alkynyl, (cycloalkyl)alkyl, —NH($R_{10}$), —N($R_{10}$)($R_{11}$), hydroxyalkyl, aminoalkyl, ($R_{10}$)NHalkyl-, ($R_{10}$)($R_{11}$)Nalkyl-, alkanoyl, alkoxycarbonyl, (heterocycloalkyl)alkyl, alkylsulfonyl, alkylthio, mono- or dialkylaminocarbonyl, heterocycloalkyl, aryl, and heteroaryl, each of which is optionally substituted with 1, 2, 3, or 4 of $R_{20}$,
   wherein $R_{10}$ and $R_{11}$ are independently selected at each occurrence from the group consisting of alkyl, alkenyl, alkynyl, alkoxy, cycloalkyl, (cycloalkyl)alkyl, aryl, arylalkyl, alkanoyl, and mono and dialkylaminoalkyl; and
iii) a group of the formula:

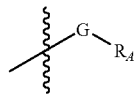

where G is a bond, alkyl, —O—, —C(=O)—, or —$CH_2$C(=O)—, and
   $R_A$ is a saturated, partially unsaturated, or aromatic carbocycle, consisting of 1 ring or 2 fused, pendant, or spiro rings, each ring containing 0, 1, or 2 heteroatoms independently chosen from N, S. and O, said saturated, partially unsaturated, or aromatic carbocycle is optionally substituted with 1, 2, 3, or 4 of $R_{20}$,
iv) a group of the formula

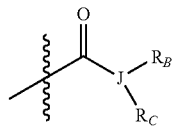

where J is N, CH, or C-alkyl, and
   $R_B$ and $R_C$ are independently selected from the group consisting of hydrogen, alkyl, alkenyl, alkynyl, alkoxy, cycloalkyl, (cycloalkyl)alkyl, heterocycloalkyl, aryl, arylalkyl, alkanoyl, heteroaryl, and mono and dialkylaminoalkyl, each of which is optionally substituted by 1 or 2 substituents independently chosen from halogen, hydroxy, cyano, amino, nitro, alkoxy, and alkyl;
$R_B$ and $R_C$ and the atom to which they are attached form a 4- to 10-membered monocyclic or bicyclic ring, which may contain:
a) one or more double bonds,
b) one or more of oxo, O, S, SO, $SO_2$, or N—$R_D$ wherein $R_D$ is hydrogen, $AR_1$, alkyl, cycloalkyl, heterocycloalkyl, or $AR_1$alkyl; wherein $AR_1$ is aryl or heteroaryl, each of which is optionally substituted by 1 or 2 substituents independently chosen from halogen, hydroxy, cyano, amino, nitro, alkoxy, and alkyl, and/or
c) one or more substituents $R_{20}$;

v) —OC(=O)R$_E$, —C(=O)OR$_E$, —C(=O)NH$_2$, —C(=O)NHR$_E$, —C(=O)NR$_E$R$_F$, —NHC(=O)R$_E$, —C(=NR$_E$)R$_F$, —HC=N—OH, —HC=N(alkoxy), —HC=N(alkyl), —NR$_E$C(=O)R$_F$, —NHS(O)$_m$R$_E$, and —NR$_E$S(O)$_m$R$_F$, where m is 0, 1 or 2, and R$_E$ and R$_F$ are independently selected at each occurrence from alkyl, cycloalkyl, heterocycloalkyl, alkoxy, mono- or dialkylamino, aryl, or heteroaryl each of which is optionally substituted by 1, 2, or 3 of R$_{30}$;

R$_{20}$ is independently selected at each occurrence from the group consisting of: halogen; hydroxy; nitro; cyano; amino; alkyl; alkoxy optionally substituted with amino or mono- or dialkylamino; cycloalkyl; cycloalkylalkyl; cycloalkylalkoxy; alkenyl; alkynyl; haloalkyl; oxo; haloalkoxy; mono- and dialkylamino; aminoalkyl; and mono- and dialkylaminoalkyl;

R$_{30}$ is independently selected at each occurrence from halogen, hydroxy, nitro, cyano, amino, alkyl, alkoxy optionally substituted with amino or mono- or dialkylamino, cycloalkyl, cycloalkylalkyl, cycloalkylalkoxy, heterocycloalkyl, alkenyl, alkynyl, haloalkyl, haloalkoxy, oxo, mono- and dialkylamino, aminoalkyl, and mono- and dialkylaminoalkyl;

R$_5$ represents hydrogen or haloalkyl; or

R$_5$ represents alkyl, cycloalkyl, or (cycloalkyl)alkyl, each of which may contain one or more double or triple bonds, and each of which is optionally substituted with 1, 2, or 3 of R$_{30}$, or R$_5$ represents aryl, arylalkyl, heteroaryl, or heteroarylalkyl each of which is optionally substituted with 1, 2, or 3 substituents selected from the group consisting of haloalkyl, amino, —NH(R$_{10}$), —N(R$_{10}$)(R$_{11}$), carboxamido, (R$_{10}$)NHcarbonyl, (R$_{10}$)(R$_{11}$)Ncarbonyl, halogen, hydroxy, nitro, cyano, amino, alkyl, alkoxy optionally substituted with amino or mono- or dialkylamino, cycloalkyl, cycloalkylalkyl, cycloalkylalkoxy, heterocycloalkyl, alkenyl, alkynyl, haloalkyl, haloalkoxy, aminoalkyl, and mono- and dialkylaminoalkyl;

Q represents —C(R$_6$)(R$_7$) or oxygen,
with the proviso that Q is not oxygen when X$_2$ is nitrogen;

R$_6$ and R$_7$ independently represent hydrogen, fluorine, or alkyl;

the group:

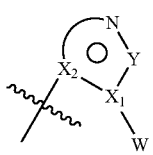

represents a 5 to 7 membered heteroaryl or heterocycloalkyl ring containing up to 4 heteroatoms independently selected from nitrogen, sulfur, and oxygen, said 5 to 7 membered heteroaryl or heterocycloalkyl ring is substituted at each carbon atom by R, and substituted at each nitrogen atom available for substitution by R', wherein R is independently chosen at each occurrence from hydrogen, halogen, amino, alkyl, alkenyl, alkynyl, alkoxy, cycloalkyl, (cycloalkyl)alkyl, haloalkyl, haloalkoxy, carboxamido, and 3- to 7-membered carbocyclic or heterocyclic groups which are saturated, unsaturated, or aromatic, which may be further substituted with one or more substituents independently selected from halogen, oxo, hydroxy, alkyl, and alkoxy, where the heterocyclic groups contain at least one carbon atom and one, two, or three heteroatoms selected from oxygen, nitrogen, and sulfur atoms;

R' is independently chosen at each occurrence from alkyl, hydrogen, cycloalkyl, cycloalkyl(alkyl), and 3- to 7-membered carbocyclic or heterocyclic groups which are saturated, unsaturated, or aromatic, which 3- to 7-membered carbocyclic or heterocyclic groups which are optionally substituted with one or more substituents independently selected from halogen, oxo, hydroxy, alkyl, and alkoxy, where the heterocyclic groups contain at least one carbon atom and one, two, or three heteroatoms selected from oxygen, nitrogen, and sulfur atoms;

X$_1$ and X$_2$ independently represent nitrogen, sulfur, carbon or CH;

Y is nitrogen, oxygen, sulfur, carbon, —OH—, —OH$_2$—, or absent; and

W represents aryl or heteroaryl, wherein the aryl or heteroaryl group is optionally substituted with up to 4 groups independently selected from R$_{30}$, —CO$_2$H, —C(=O)OR$_E$, —C(=O)NHR$_E$, —C(=O)NR$_E$R$_F$, —C(O)R$_E$, and —S(O)$_m$R$_E$, —OR$_E$, where R$_{30}$ and R$_E$ are as defined above and m is 0, 1, or 2.

2. A compound or salt according to claim 1, wherein

R$_1$, R$_2$, R$_3$, and R$_4$ are independently selected from i) hydrogen, halogen, hydroxy, nitro, cyano, amino, halo (C$_1$-C$_6$)alkyl, and halo (C$_1$-C$_6$)alkoxy, ii) (C$_1$-C$_6$)alkyl, (C$_1$-C$_6$)alkoxy, (C$_3$-C$_8$) cycloalkyl, (C$_2$-C$_6$)alkenyl, alkynyl, ((C$_3$-C$_8$)cycloalkyl) (C$_1$-C$_4$) alkyl, —NH (R$_{10}$), —N(R$_{10}$)(R$_{11}$), hydroxy(C$_1$-C$_6$) alkyl, amino (C$_1$-C$_6$)alkyl, (R$_{10}$)NH(C$_1$-C$_6$)alkyl, (R$_{10}$) (R$_{11}$)N(C$_1$-C$_6$)alkyl, (C$_1$-C$_6$)alkanoyl, (C$_1$-C$_6$) alkoxycarbonyl, (C$_1$-C$_6$)alkylsulfonyl, (C$_1$-C$_6$) alkylthio, mono- or di (C$_1$-C$_6$)alkylaminocarbonyl, heterocycloalkyl, (heterocycloalkyl)C$_1$-C$_4$ alkyl, aryl, and heteroaryl, each of which is optionally substituted with 1, 2, 3, or 4 of R$_{20}$, wherein R$_{10}$ and R$_{11}$ are independently selected from the group consisting of (C$_1$-C$_6$)alkyl, (C$_1$-C$_6$)alkenyl, (C$_1$-C$_6$) alkoxy, (C$_3$-C$_8$)cycloalkyl, (C$_3$-C$_8$)cycloalkylalkyl, aryl, aryl (C$_1$-C$_6$)alkyl, (C$_1$-C$_6$)alkanoyl, and mono and di(C$_1$-C$_6$)alkylaminoalkyl;

iii) a group of the formula:

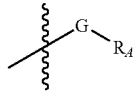

where G is (C$_1$-C$_6$)alkyl, —O—, —C (=O)—, or —CH$_2$C (=O)—, and

R$_A$ is a saturated, partially unsaturated, or aromatic carbocycle, consisting of 1 ring or 2 fused, pendant, or spiro rings, each ring consisting of from 3 to 8 ring atoms, and each ring containing 0, 1, or 2 heteroatoms independently chosen from N, S, and O; said saturated, partially unsaturated, or aromatic carbocycle is optionally substituted with 1, 2, 3, or 4 of R$_{20}$, and iv) a group of the formula

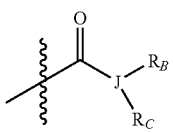

where J is N, CH, or C—($C_1$-$C_6$)alkyl and $R_B$ and $R_C$ are independently selected from the group consisting of hydrogen, ($C_1$-$C_6$)alkyl, ($C_2$-$C_6$)alkenyl, ($C_2$-$C_6$) alkynyl, ($C_1$-$C_6$)alkoxy, ($C_3$-$C_8$)cycloalkyl, ($C_1$-$C_6$cycloalkyl) ($C_1$-$C_4$)alkyl, heterocycloalkyl, aryl, aryl ($C_1$-$C_4$)alkyl, ($C_1$-$C_6$)alkanoyl, heteroaryl, and mono and di($C_1$-$C_6$)alkylamino ($C_1$-$C_6$)alkyl, each of which is optionally substituted by 1 or 2 substituents independently chosen from halogen, hydroxy, cyano, amino, nitro, $C_1$-$C_6$alkoxy, and $C_1$-$C_6$alkyl; or $R_B$ and $R_C$ and the atom to which they are attached form a 4- to 10-membered monocyclic or bicyclic ring, which may contain a) one or more double bonds;

b) one or more of oxo, O, S, SO, $SO_2$, and N—$R_D$ wherein $R_D$ is hydrogen, $Ar_1$, ($C_1$-$C_6$)alkyl, ($C_3$-$C_6$) cycloalkyl, heterocycloalkyl, or $Ar_1$($C_1$-$C_6$)alkyl; wherein $Ar_1$ is aryl or heteroaryl, each of which is optionally substituted by 1 or 2 substituents independently chosen from halogen, hydroxy, cyano, amino, nitro, $C_1$-$C_6$alkoxy, and $C_1$-$C_6$alkyl; and/or c) one or more substituents $R_{20}$;

v) —OC(=O)$R_E$, —C(=O)O$R_E$, —C(=O)$NH_2$, —C(=O)NH$R_E$, —C(=O)N$R_E R_F$, —NHC(=O)$R_E$, —C(=N$R_E$)$R_F$, —HC=N—OH, —HC=N($C_1$-$C_6$alkoxy), —HC=N($C_1$-$C_6$alkyl), —N$R_E$C(=O)$R_F$, —NHS(O)$_m R_E$, and —N$R_E$S(O)$_m R_F$, where m is 0, 1 or 2, and $R_E$ and $R_F$ are independently selected at each occurrence from ($C_1$-$C_6$)alkyl, ($C_3$-$C_8$)cycloalkyl, heterocycloalkyl, ($C_1$-$C_6$)alkoxy, mono- and di($C_1$-$C_6$)alkylamino, aryl, and heteroaryl each of which is optionally substituted by 1, 2, or 3 of $R_{30}$;

$R_{20}$ is independently selected at each occurrence from the group consisting of halogen; hydroxy; nitro; cyano; amino; ($C_1$-$C_6$)alkyl; ($C_1$-$C_6$)alkoxy optionally substituted with amino or mono- or di($C_1$-$C_6$) alkylamino; ($C_3$-$C_8$)cycloalkyl; ($C_3$-$C_8$)cycloalkyl ($C_1$-$C_4$)alkyl; ($C_3$-$C_8$)cycloalkyl($C_1$-$C_4$)alkoxy; ($C_2$-$C_6$)alkenyl; ($C_2$-$C_6$)alkynyl; halo($C_1$-$C_6$)alkyl; halo($C_1$-$C_6$) alkoxy; oxo; mono- and di($C_1$-$C_6$)alkylamino; amino($C_1$-$C_6$)alkyl; and mono- and di( $C_1$-$C_6$)alkylamino ( $C_1$-$C_6$)alkyl;

$R_{30}$ is independently selected at each occurrence from halogen, hydroxy, nitro, cyano, amino, ($C_1$-$C_6$)alkyl, ($C_1$-$C_6$)alkoxy optionally substituted with amino or mono- or di($C_1$-$C_6$)alkylamino, ($C_3$-$C_8$)cycloalkyl, ($C_3$-$C_8$)cycloalkyl($C_1$-$C_4$)alkyl, ($C_3$-$C_8$)cycloalkyl ($C_1$-$C_4$)alkoxy, heterocycloalkyl, ($C_2$-$C_6$)alkenyl, ($C_2$-$C_6$)alkynyl, halo( $C_1$-$C_6$)alkyl, halo($C_1$-$C_6$) alkoxy, oxo, mono- and di($C_1$-$C_6$)alkylamino, amino ($C_1$-$C_6$)alkyl, and mono- and di($C_1$-$C_6$)alkylamino ($C_1$-$C_6$)alkyl;

$R_5$ represents hydrogen or halo($C_1$-$C_6$)alkyl; or $R_5$ represents (C1-C6)alkyl, ($C_3$-$C_8$)cycloalkyl, or ($C_3$-$C_8$cycloalkyl) ($C_1$-$C_4$)alkyl, each of which may contain one or more double or triple bonds, and each of which is optionally substituted with 1, 2, or 3 of $R_{30}$ or $R_5$ represents aryl, aryl($C_1$-$C_4$)alkyl, heteroaryl, or heteroaryl($C_{1-4}$)alkyl each of which is optionally substituted with 1, 2, or 3 substituents selected from the group consisting of:

halo($C_1$-$C_6$)alkyl, amino, NH($R_{10}$), N($R_{10}$)($R_{11}$), carboxamido, NH($R_{10}$)carbonyl, N($R_{10}$)($R_{11}$)carbonyl, halogen, hydroxy, nitro, cyano, amino, ($C_1$-$C_6$)alkyl, ($C_1$-$C_6$)alkoxy optionally substituted with amino or mono- or di($C_1$-$C_6$)alkylamino, ($C_3$-$C_8$)cycloalkyl, ($C_3$-$C_8$)cycloalkyl($C_1$-$C_4$)alkyl, ($C_3$-$C_8$)cycloalkyl ($C_1$-$C_4$)alkoxy, heterocyclo($C_1$-$C_4$) alkyl, ($C_3$-$C_8$) alkenyl, ($C_3$-$C_8$)alkynyl, halo($C_1$-$C_6$)alkyl, halo ($C_1$-$C_6$) alkoxy, amino($C_1$-$C_6$)alkyl, and mono- and di($C_1$-$C_6$)alkylamino ($C_1$-$C_6$)alkyl;

Q represents —C($R_6$)($R_7$) or oxygen, with the proviso that Q is not oxygen when $X_2$ is nitrogen;

$R_6$ and $R_7$ independently represent hydrogen, fluorine, or $C_1$-$C_6$alkyl;

the group:

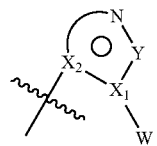

represents a 5 to 7 membered heteroaryl or heterocycloalkyl ring containing up to 4 heteroatoms selected from nitrogen, sulfur, and oxygen, said 5 to 7 membered heteroaryl or heterocycloalkyl ring is substituted at each carbon atom by R, and is substituted at each nitrogen atom available for substitution by R', wherein R is independently chosen at each occurrence from hydrogen, halogen, amino, $C_1$-$C_6$alkyl, ($C_3$-$C_8$)alkenyl, ($C_2$-$C_6$)alkynyl, $C_1$-$C_6$alkoxy, ($C_3$-$C_8$)cycloalkyl, ($C_3$-$C_8$cycloalkyl) ($C_1$-$C_4$)alkyl, halo($C_1$-$C_6$)alkyl, haloalkoxy, carboxamido, and 3- to 7-membered carbocyclic or heterocyclic groups which are saturated, unsaturated, or aromatic, which may be further substituted with one or more substituents independently selected from halogen, oxo, hydroxy, $C_{1-4}$alkyl , and —O($C_{1-4}$alkyl), where the heterocyclic groups contain at least one carbon atom and one, two, or three heteroatoms selected from oxygen, nitrogen, and sulfur atoms;

R' is independently chosen at each occurrence from hydrogen, $C_1$-$C_6$alkyl, $C_3$-$C_8$cycloalkyl, $C_3$-$C_8$cycloalkyl($C_1$-$C_4$alkyl), and 3- to 7-membered carbocyclic or heterocyclic groups which are saturated, unsaturated, or aromatic, which 3- to 7-membered carbocyclic or heterocyclic groups are optionally substituted with one or more substituents independently selected from halogen, oxo, hydroxy, $C_{1-4}$alkyl, and —O($C_{14}$alkyl), where the heterocyclic groups contain at least one carbon atom and one, two, or three heteroatoms selected from oxygen, nitrogen, and sulfur atoms; and $X_1$, $X_2$, W, and Y are as defined in claim 1.

3. A compound or salt according to claim 2 of the formula:

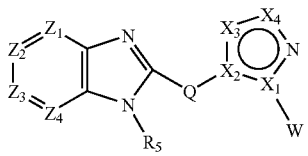

wherein $Z_1$, $Z_2$, $Z_3$, $Z_4$, $R_5$, Q, $X_1$, $X_2$, and W are as defined in claim 2;

$X_3$ and $X_4$ are independently selected from the group consisting of carbon, CR, N, O, S, NH, and $N(C_1-C_6)$alkyl;

provided that at least one of $X_1$, $X_2$, $X_3$, and X4 is carbon or CR, wherein R is independently chosen at each occurrence from hydrogen, halogen, amino, $(C_1-C_6)$alkyl, $(C_1-C_6)$alkoxy, $(C_3-_8)$cycloalkyl, $(C_3-C_8)$cycloalkyl$(C_1-C_6)$alkyl, $(C_2-C_6)$alkenyl, $(C_3-C_8)$alkynyl, halo$(C_1-C_6)$alkyl, halo$(C_1-C_6)$alkoxy, carboxamido, and 3- to 7-membered carbocyclic or heterocyclic groups which are saturated, unsaturated, or aromatic, which may be further substituted with one or more substituents independently selected from halogen, oxo, hydroxy, $C_{1-4}$alkyl, and —O($C_{1-4}$alkyl), where the heterocyclic groups contain at least one carbon atom and one, two, or three heteroatoms selected from oxygen, nitrogen, and sulfur atoms.

4. A pharmaceutical composition comprising a compound or salt according to claim 1 combined with at least one pharmaceutically acceptable carrier or excipient.

5. A method for demonstrating the presence of a $GABA_A$ receptor in a cell or tissue sample, said method comprising:

contacting a cell or tissue sample with a labeled compound or salt according to claim 1;

washing the cell or tissue sample to remove unbound labeled compound or salt; and detecting the presence of labeled compound or salt in the cell or tissue sample.

6. The method of claim 5 in which the cell or tissue sample is a tissue section.

7. The method of claim 5 in which the labeled compound or salt contains a radioactive label or a directly or indirectly luminescent label.

8. The method of claim 5 in which the cell or tissue sample is a tissue section, labeled compound or salt contains a radioactive label or a directly or indirectly luminescent label, and the labeled compound or salt is detected autoradiographically to generate an autoradiogram.

9. A method for demonstrating the presence of a $GABA_A$ receptor in a tissue section comprising:

contacting the tissue section with a radiolabeled or luminescently labeled compound or salt according to claim 1 to yield a contacted tissue section;

washing the tissue section to remove unbound labeled compound or salt;

detecting the labeled compound or salt in the tissue section; and comparing the exposure density of the tissue section with the exposure density of a second tissue section that has not been contacted with a compound or salt according to claim 1.

10. A process for preparing a compound of Formula A

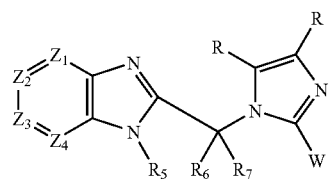

Formula A comprising reacting a compound of Formula B

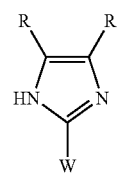

Formula B with a compound of Formula C

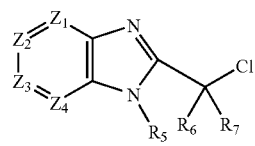

Formula C wherein:

$Z_1$ is nitrogen or $CR_1$;
$Z_2$ is nitrogen or $CR_2$;
$Z_3$ is nitrogen or $CR_3$;
$Z_4$ is nitrogen or $CR_4$;
where $Z_2$ and $Z_4$ are nitrogen, $Z_1$ is $CR_1$, and $Z_{3\ is\ CR3}$, or $Z_1$ and $Z_3$ are nitrogen, $Z_2$ is $CR_2$, and $Z_4$ is $CR_4$;
$R_1$, $R_2$, $R_3$, and $R_4$ are independently selected from
i) hydrogen, halogen, hydroxy, nitro, cyano, amino, haloalkyl, and haloalkoxy,
ii) alkyl, alkoxy, cycloalkyl, alkenyl, alkynyl, (cycloalkyl)alkyl, —NH($R_{10}$), —N($R_{10}$)($R_{11}$), hydroxyalkyl, aminoalkyl, ($R_{10}$)NHalkyl, ($R_{10}$)($R_{11}$)Nalkyl, alkanoyl, alkoxycarbonyl, (heterocycloalkyl) alkyl, alkylsulfonyl, alkylthio, mono- or dialkylaminocarbonyl, heterocycloalkyl, aryl, and heteroaryl, each of which is optionally substituted with 1, 2, 3, or 4 of $R_{20}$,
wherein $R_{10}$ and $R_{11}$ are independently selected from the group consisting of alkyl, alkenyl, alkynyl, alkoxy, cycloalkyl, (cycloalkyl)alkyl, aryl, arylalkyl, alkanoyl, and mono and dialkylaminoalkyl; and
iii) a group of the formula:

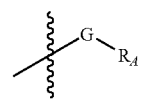

where G is a bond, alkyl, —O—, —C(=O)—, or —CH$_2$C(=O)—, and
$R_A$ is a saturated, partially unsaturated, or aromatic carbocycle, consisting of 1 ring or 2 fused, pendant, or spiro rings, each ring containing 0, 1, or 2 heteroatoms independently chosen from N, S, and O, said saturated, partially unsaturated, or aromatic carbocycle is optionally substituted with 1, 2, 3, or 4 of $R_{20}$, and iv) a group of the formula

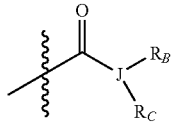

where J is N, CH, or C-alkyl, and
$R_B$ and $R_C$ are independently selected from the group consisting of hydrogen, alkyl, alkenyl, alkynyl, alkoxy, cycloalkyl, (cycloalkyl)alkyl, heterocycloalkyl, aryl, arylalkyl, alkanoyl, heteroaryl, and mono and dialkylaminoalkyl, each of which is optionally substituted by 1 or 2 substituents independently chosen from halogen, hydroxy, cyano, amino, nitro, alkoxy, and alkyl;

$R_B$ and $R_C$ and the atom to which they are attached form a 4- to 10-membered monocyclic or bicyclic ring, which may contain:
a) one or more double bonds,
b) one or more of oxo, O, S, SO, $SO_2$, or N—$R_D$ wherein $R_D$ is hydrogen, $AR_1$, alkyl, cycloalkyl, heterocycloalkyl, or $AR_1$alkyl; wherein $AR_1$ is aryl or heteroaryl, each of which is optionally substituted by 1 or 2 substituents independently chosen from halogen, hydroxy, cyano, amino, nitro, alkoxy, and alkyl, and/or
c) one or more substituents $R_{20}$;

v) —OC(=O)$R_E$, —C(=O)O$R_E$, —C(=O)$NH_2$, —C(=O)NH$R_E$—C(=O)N$R_ER_F$, —NHC(=O)$R_E$, —C(=N$R_E$)$R_F$, —HC=N—OH, —HC=N(alkoxy), —HC=N(alkyl), —N$R_E$C(=O)$R_F$, —NHS(O)$_mR_E$, and —N$R_E$S(O)$_mR_F$, where m is 0, 1 or 2, and $R_E$ and $R_F$ are independently selected at each occurrence from alkyl, cycloalkyl, heterocycloalkyl, alkoxy, mono- or dialkylamino, aryl, or heteroaryl each of which is optionally substituted by 1, 2, or 3 of $R_{30}$;

$R_{20}$ is independently selected at each occurrence from the group consisting of: halogen; hydroxy; nitro; cyano; amino; alkyl; alkoxy optionally substituted with amino or mono- or dialkylamino; cycloalkyl; cycloalkylalkyl; cycloalkylalkoxy; alkenyl; alkynyl; haloalkyl; oxo; haloalkoxy; mono- and dialkylamino; aminoalkyl; and mono- and dialkylaminoalkyl;

$R_{30}$ is independently selected at each occurrence from halogen, hydroxy, nitro, cyano, amino, alkyl, alkoxy optionally substituted with amino or mono- or dialkylamino, cycloalkyl, cycloalkylalkyl, cycloalkylalkoxy, heterocycloalkyl, alkenyl, alkynyl, haloalkyl, haloalkoxy, oxo, mono- and dialkylamino, aminoalkyl, and mono- and dialkylaminoalkyl;

$R_5$ represents hydrogen or haloalkyl; or
$R_5$ represents alkyl, cycloalkyl, or (cycloalkyl)alkyl, each of which may contain one or more double or triple bonds, and each of which is optionally substituted with 1, 2, or 3 of $R_{30}$, or
$R_5$ represents aryl, arylalkyl, heteroaryl, or heteroarylalkyl each of which is optionally substituted with 1, 2, or 3 substituents selected from the group consisting of haloalkyl, amino, —NH($R_{10}$), —N($R_{10}$)($R_{11}$), carboxamido, ($R_{10}$)NHcarbonyl, ($R_{10}$)($R_{11}$)Ncarbonyl, halogen, hydroxy, nitro, cyano, amino, alkyl, alkoxy optionally substituted with amino or mono- or dialkylamino, cycloalkyl, cycloalkylalkyl, cycloalkylalkoxy, heterocycloalkyl, alkenyl, alkynyl, haloalkyl, haloalkoxy, aminoalkyl, and mono- and dialkylaminoalkyl;

$R_6$ and $R_7$ independently represent hydrogen, fluorine, or alkyl;

R is independently chosen at each occurrence from hydrogen, halogen, amino, ($C_1$-$C_6$alkyl, ($C_2$-$C_6$)alkenyl, ($C_2$-$C_4$)alkynyl, $C_1$-$C_6$alkoxy, ($C_3$-$C_8$)cycloalkyl, ($C_3$-$C_8$cycloalkyl) ($C_1$-$C_4$) alkyl, halo($C_1$-$C_6$)alkyl, haloalkoxy, carboxamido, and 3- to 7-membered carbocyclic or heterocyclic groups which are saturated, unsaturated, or aromatic, which may be further substituted with one or more substituents independently selected from halogen, oxo, hydroxy, $C_1$-4alkyl, and —O($C_1$-$C_4$alkyl), where the heterocyclic groups contain at least one carbon atom and one, two, or three heteroatoms selected from oxygen, nitrogen, and sulfur atoms; and W represents aryl or heteroaryl, wherein the aryl or heteroaryl group is optionally substituted with up to 4 groups independently selected from $R_{30}$, —$CO_2H$, —C(=O)O$R_E$, —C(=O)NH$R_E$, —C(=O)N$R_ER_F$, —C(O)$R_E$, and —S(O)$_mR_E$, —O$R_E$, where $R_{30}$ and $R_E$ are as defined above and m is 0, 1, or 2.

11. A compound according to claim 1, which is:
8-{[2-(6-Fluoropyridin-2-yl)-1H-imidazol-1-yl]methyl}-2,9-dimethyl-9H-purine;
9-ethyl-8-{[2-(3-fluoropyridin-2-yl)-1H-imidazol-1-yl]methyl}-2-methyl-9H-purine;
9-ethyl-8-{[2-(6-fluoropyridin-2-yl)-1H-imidazol-1-yl]methyl}-2-methyl-9H-purine;
8-{[1-(6-fluoropyridin-2-yl)-1H-pyrazol-5-yl]methyl}-2,9-dimethyl-9H-purine;
8-{[1-(3-fluorophenyl)-1H-pyrazol-5-yl]methyl}-2,9-dimethyl-9H-purine;
9-ethyl-8-{[1-(6-fluoropyridin-2-yl)-1H-pyrazol-5-yl]methyl}-2-methyl-9H-purine; or
a pharmaceutically acceptable salt thereof.

12. A compound or salt according to claim 3 of the formula

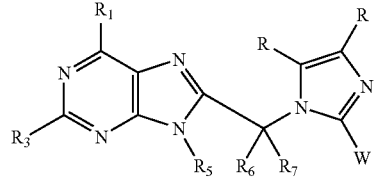

wherein R, $R_1$, $R_3$, $R_5$, $R_6$, $R_7$, and W are as defined in claim 3.

13. A compound or salt according to claim 12, wherein:
R is independently selected at each occurrence from the group consisting of
i) hydrogen, halogen, ($C_1$-$C_6$)alkyl, ($C_3$-$C_8$)cycloalkyl, ($C_3$-$C_8$)cycloalkyl($C_1$-$C_6$)alkyl, ($C_1$-$C_6$)alkoxy, halo($C_1$-$C_6$)alkyl, halo($C_1$-$C_6$)alkoxy, and
ii) phenyl and pyridyl each of which is optionally substituted with up to 3 substituents independently chosen from halogen, hydroxy, ($C_1$-$C_4$)alkyl, and —O($C_1$-$C_4$alkyl);

$R_1$ and $R_3$ are independently selected from hydrogen, halogen, hydroxy, nitro, cyano, amino, ($C_1$-$C_6$)alkyl, ($C_1$-$C_6$)alkoxy, ($C_3$-$C_8$)cycloalkyl, ($C_3$-$C_8$)cycloalkyl($C_1$-$C_6$)alkyl, ($C_2$-$C_6$)alkenyl, ($C_2$-$C_6$)alkynyl, heterocycloalkyl, halo($C_1$-$C_6$)alkyl, halo($C_1$-$C_6$)alkoxy, mono or di($C_1$-$C_6$)alkylamino, amino($C_1$-$C_6$)alkyl, and mono- and di($C_1$-$C_6$)alkylamino($C_1$-$C_6$)alkyl;

$R_5$ represents hydrogen, ($C_1$-$C_6$)alkyl, ($C_3$-$C_8$)cycloalkyl, ($C_3$-$C_8$)cycloalkyl($C_1$-C6)alkyl, phenyl, benzyl, thiophenyl, thiazoyl, pyridyl, imidazolyl, pyrazolyl, or pyrimidinyl;

$R_6$ and $R_7$ independently represent hydrogen, fluorine, or ($C_1$-$C_6$)alkyl; and W represents phenyl, pyrimidinyl, pyridyl, pyridizinyl, or pyrazinyl, each of which is optionally substituted with up to 4 $R_{30}$ groups.

14. A compound or salt according to claim 13, wherein:
R is independently selected at each occurrence from the group consisting of hydrogen, halogen, and ($C_1$-$C_2$) alkyl;
$R_1$ and $R_3$ are independently selected from hydrogen, halogen, hydroxy, nitro, cyano, amino, ($C_1$-$C_6$)alkyl, ($C_1$-$C_6$)alkoxy, ($C_3$-$C_8$)cycloalkyl, ($C_3$-$C_8$)cycloalkyl($C_1$-$C_6$)alkyl, halo ($C_1$-$C_6$)alkyl, halo($C_1$-$C_6$)alkoxy, mono or di($C_1$-$C_6$) alkylamino, amino($C_1$-$C_6$)alkyl, and mono- and di($C_1$-$C_6$)alkylamino ($C_{1-6}$)alkyl;
$R_5$ represents ($C_1$-$C_6$)alkyl;
$R_6$ and $R_7$ are hydrogen; and
W represents phenyl, pyrimidinyl, pyridyl, pyridizinyl, or pyrazinyl each of which is optionally substituted with up to 4 $R_{30}$ groups.

15. A compound or salt according to claim 14 wherein
$R_1$ and $R_3$ are independently selected from hydrogen, halogen, trifluoromethyl, ($C_1$-$C_2$)alkyl, and cyano; and
W is phenyl or pyridyl, each of which is optionally substituted by one or more substituents independently chosen from halogen, cyano, hydroxy, oxo, halo($C_1$-$C_2$)alkyl, ($C_1$-$C_2$)alkyl, and ($C_1$-$C_2$)alkoxy.

16. A compound or salt according to claim 15, wherein W is 2-pyrimidinyl, 3-fluorophenyl, or 6-fluoro-2-pyridinyl.

17. A compound or salt according to claim 3 of the formula

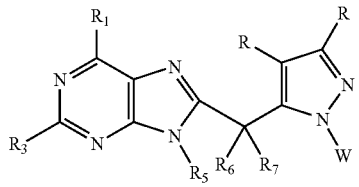

wherein R, $R_1$, $R_3$, $R_5$, $R_6$, $R_7$, and W are as defined in claim 3.

18. A compound or salt according to claim 17, wherein:
R is independently selected at each occurrence from the group consisting of i) hydrogen, halogen, ($C_1$-$C_6$)alkyl, ($C_{1\text{-}C_8}$)cycloalkyl, ($C_3$-$C_8$)cycloalkyl($C_1$-$C_6$)alkyl, ($C_1$-$C_6$)alkoxy, halo ($C_1$-$C_6$)alkyl, halo($C_1$-$C_6$)alkoxy, and
ii) phenyl and pyridyl each of which is optionally substituted with up to 3 substituents independently chosen from halogen, hydroxy, ($C_{1\text{-}4}$)alkyl, and —O($C_{1\text{-}4}$ alkyl);
$R_1$ and $R_3$ are independently selected from hydrogen, halogen, hydroxy, nitro, cyano, amino, ($C_1$-$C_6$)alkyl, ($C_1$-$C_6$)alkoxy, ($C_3$-$C_8$)cycloalkyl, ($C_3$-$C_8$)cycloalkyl($C_1$-$C_6$)alkyl, ($C_{2\text{-}6}$)alkenyl, ($C_2$-$C_6$)alkynyl, heterocycloalkyl, halo($C_1$-$C_6$)alkyl, halo ($C_1$-$C_6$)alkoxy, mono or di($C_1$-$C_6$)alkylamino, amino($C_1$-$C_6$) alkyl, and mono- and di($_1$-$_6$)alkylamino($C_1$-$C_6$) alkyl;
$R_5$ represents hydrogen, ($C_1$-$C_6$)alkyl, ($C_3$-$C_8$)cycloalkyl, ($C_3$-$C_8$)cycloalkyl($C_1$-$C_6$)alkyl, phenyl, benzyl, thiophenyl, thiazoyl, pyridyl, imidazolyl, pyrazolyl, or pyrimidinyl;
$R_6$ and $R_7$ independently represent hydrogen, fluorine, or ($C_1$-$C_6$)alkyl; and
W represents phenyl, pyrimidinyl, pyridyl, pyridizinyl, or pyrazinyl, each of which is optionally substituted with up to 4 $R_{30}$ groups.

19. A compound or salt according to claim 18, wherein:
R is independently selected at each occurrence from the group consisting of hydrogen, halogen, and ($C_1$-$C_2$) alkyl;
$R_1$ and $R_3$ are independently selected from hydrogen, halogen, hydroxy, nitro, cyano, amino, ($C_1$-$C_6$)alkyl, ($C_1$-$C_6$)alkoxy, ($C_3$-$C_8$)cycloalkyl, ($C_3$-$C_8$)cycloalkyl($C_1$-$C_6$)alkyl, halo ($C_{1\text{-}6}$)alkyl, halo($C_1$-$C_6$)alkoxy, mono or di($C_1$-$C_6$)alkylamino, amino($C_1$-$C_6$)alkyl, and mono- and di($C_1$-$C_6$)alkylamino($C_1$-$C_6$)alkyl;
$R_5$ represents ($C_1$-$C_6$)alkyl;
$R_6$ and $R_7$ are hydrogen; and
W represents phenyl, pyrimidinyl, pyridyl, pyridizinyl, or pyrazinyl each of which is optionally substituted with up to 4 $R_{30}$ groups.

20. A compound or salt according to claim 19 wherein
$R_1$ and $R_3$ are independently selected from hydrogen, halogen, trifluoromethyl, ($C_1$-$C_2$)alkyl, and cyano; and
W is phenyl or pyridyl, each of which is optionally substituted by one or more substituents independently chosen from halogen, cyano, hydroxy, oxo, halo($C_1$-$C_2$)alkyl, ($C_1$-$C_2$)alkyl, and ($C_1$-$C_2$) alkoxy.

21. A compound or salt according to claim 20, wherein W is 2-pyrimidinyl, 3-fluorophenyl, or 6-fluoro-2-pyridinyl.

* * * * *